US010059961B2

(12) United States Patent
Alphey

(10) Patent No.: US 10,059,961 B2
(45) Date of Patent: *Aug. 28, 2018

(54) EXPRESSION SYSTEMS

(71) Applicant: Oxitec Limited, Abingdon, Oxfordshire (GB)

(72) Inventor: Luke Alphey, Abingdon (GB)

(73) Assignee: Oxitec Limited, Abingdon (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/839,683

(22) Filed: Aug. 28, 2015

(65) Prior Publication Data

US 2016/0060651 A1  Mar. 3, 2016

Related U.S. Application Data

(63) Continuation of application No. 11/352,177, filed on Feb. 10, 2006, now Pat. No. 9,133,477, which is a continuation-in-part of application No. 10/566,448, filed as application No. PCT/GB2004/003263 on Jul. 28, 2004, now Pat. No. 9,121,036.

(30) Foreign Application Priority Data

Jul. 28, 2003 (GB) ................... 0317656.7

(51) Int. Cl.
*C12N 15/85* (2006.01)
*A01K 67/033* (2006.01)

(52) U.S. Cl.
CPC .......... *C12N 15/85* (2013.01); *A01K 67/0333* (2013.01); *C12N 15/8509* (2013.01); *A01K 2217/05* (2013.01); *A01K 2217/20* (2013.01); *A01K 2227/70* (2013.01); *A01K 2227/706* (2013.01); *A01K 2267/02* (2013.01); *C12N 2830/007* (2013.01); *C12N 2830/008* (2013.01)

(58) Field of Classification Search
CPC ................................................. C12N 15/8509
See application file for complete search history.

(56) References Cited

U.S. PATENT DOCUMENTS

| | | | |
|---|---|---|---|
| 5,254,801 A | 10/1993 | Dotson et al. | |
| 5,278,057 A | 1/1994 | Jorgensen | |
| 5,670,353 A | 9/1997 | Ahlquist et al. | |
| 5,674,747 A | 10/1997 | Hammock et al. | |
| 5,773,697 A | 6/1998 | Tomes et al. | |
| 5,851,796 A | 12/1998 | Schatz | |
| 5,977,441 A | 11/1999 | Oliver et al. | |
| 6,200,800 B1 | 3/2001 | Choulika et al. | |
| 6,235,278 B1 | 5/2001 | Miller et al. | |
| 6,338,040 B1 | 1/2002 | Buman et al. | |
| 6,962,810 B2 | 11/2005 | Fraser et al. | |
| 7,998,475 B2 | 8/2011 | Alphey | |
| 8,124,404 B2 | 2/2012 | Alphey | |
| 9,121,036 B2 | 9/2015 | Alphey | |
| 9,125,388 B2 | 9/2015 | Alphey | |
| 9,133,477 B2 | 9/2015 | Alphey | |
| 9,487,801 B2 | 11/2016 | Alphey et al. | |
| 2003/0015007 A1 | 8/2003 | Savakis et al. | |
| 2003/0213005 A1 | 11/2003 | Alphey et al. | |
| 2004/0082032 A1 | 4/2004 | Bovi et al. | |
| 2005/0221430 A1 | 10/2005 | Prentice | |
| 2006/0212949 A1 | 9/2006 | Alphey | |
| 2006/0242717 A1 | 10/2006 | Alphey | |
| 2006/0275276 A1 | 12/2006 | Alphey | |
| 2007/0056051 A1 | 3/2007 | Alphey | |
| 2008/0115233 A1 | 5/2008 | Alphey et al. | |
| 2009/0170793 A1 | 7/2009 | Gaur | |
| 2009/0183269 A1 | 7/2009 | Alphey | |
| 2013/0298266 A1 | 11/2013 | Alphey et al. | |

FOREIGN PATENT DOCUMENTS

| | | |
|---|---|---|
| EP | 0 636 310 | 2/1995 |
| EP | 0 955 364 | 11/1999 |
| GB | 2 355 459 | 4/2001 |
| GB | 2 404 382 | 2/2005 |
| GB | 2 443 186 | 4/2008 |
| GB | 2 500 113 | 9/2013 |
| JP | 2008-067678 | 3/2008 |
| WO | WO-90/08830 | 8/1990 |
| WO | WO-94/03619 | 2/1994 |
| WO | WO-96/04393 | 2/1996 |
| WO | WO-96/24605 | 8/1996 |
| WO | WO-97/30162 | 8/1997 |
| WO | WO-98/08960 | 3/1998 |
| WO | WO-99/10488 | 3/1999 |
| WO | WO-00/73510 | 12/2000 |
| WO | WO 01/39599 | 6/2001 |
| WO | WO-01/59088 | 8/2001 |
| WO | WO-01/91802 | 12/2001 |
| WO | WO-02/46444 | 6/2002 |
| WO | WO-02/101061 | 12/2002 |
| WO | WO-04/044150 | 5/2004 |
| WO | WO-04/098278 | 11/2004 |
| WO | WO-04/108933 | 12/2004 |
| WO | WO-05/003364 | 1/2005 |
| WO | WO-05/012534 | 2/2005 |
| WO | WO-07/091099 | 8/2007 |
| WO | WO-2008/134068 | 11/2008 |
| WO | WO-2009/016627 | 2/2009 |
| WO | WO-2009/115569 | 9/2009 |
| WO | WO-2009/157771 | 12/2009 |
| WO | WO-2013/131920 | 9/2013 |

OTHER PUBLICATIONS

Ernst et al. (1991, Inaugural-Dissertation, Aus Frankfurt/Main, BRD, pp. 1-29, 32 pages total).*

(Continued)

*Primary Examiner* — Thaian N Ton
*Assistant Examiner* — David A. Montanari
(74) *Attorney, Agent, or Firm* — Morrison & Foerster LLP

(57) ABSTRACT

A gene expression system is provided. The system comprises at least one coding sequence to be expressed in an organism, and at least one promoter operably linked thereto. It further comprises at least one splice control sequence which, in cooperation with a spliceosome, mediates alternative splicing of RNA transcripts of the coding sequence. The mediation of alternative splicing is in a sex-specific, stage-specific, germline-specific and tissue-specific manner.

26 Claims, 48 Drawing Sheets

Specification includes a Sequence Listing.

(56) References Cited

OTHER PUBLICATIONS

Horn et al. (2003, Nature Biotechnology, vol. 21, pp. 64-70).*
Guo et al. (1993, Mol. Cell. Biol., vol. 13(2), pp. 1104-1118).*
Adelman et al., "Formation and loss of large, unstable tandem arrays of the piggyBac transposable element in the yellow fever mosquito, *Aedes aegypti*," Transgenic Res (2004) 13(5):411-425.
Advisory Action for U.S. Appl. No. 11/733,737, dated Aug. 5, 2009, 4 pages.
Advisory Action for U.S. Appl. No. 11/733,737, dated Jun. 3, 2013, 7 pages.
Alignment of SEQ ID No. 22 of D1 (WO 2005/012534) with tTAV, Jul. 4, 2014.
Alphey et al. "Managing Insecticide Resistance by Mass Release of Engineered Insects" J. Econ. Entomol. (2007) 100(5):1642-1649.
Alphey et al. "Dominant Lethality and Insect Population Control," Mol Biochem Parasitol (2002)121(2):173-178.
Alphey et al., "Modeling resistance to genetic control of insects," Journal of Theoretical Biology (2011) 270:42-55.
Appeal Brief for U.S. Appl. No. 11/733,737, filed Feb. 3, 2014, 40 pages.
Appeal Brief for U.S. Appl. No. 12/278,849, filed Oct. 16, 2014, 31 pages.
Arribas et al., Biochimica et Biophysica Acta (1986) 868:119-127.
Atkinson et al. "Hermes and Other hAT Elements as Gene Vectors in Insects," Insect Transgenesis: Methods and Applications (2000) pp. 219-236.
Atkinson et al., "Genetic transformation systems in insects," Annu Rev Entomol (2001) 46:317-346.
Bello et al., "Spatial and temporal targeting of gene expression in *Drosophila* by means of a tetracycline-dependent transactivator system," Development (1998) 125(12):2193-2202.
Beullens et al., "Inactivation of nuclear inhibitory polypeptides of protein phosphatase-1 (NIPP-1) by protein kinase A," J Biol Chem (1993) 268(18):13172-13177.
Beullens et al., "Molecular determinants of nuclear protein phosphatase-1 regulation by NIPP-1," J Biol Chem (1999) 274(20):14053-14061.
Beullens et al., "The isolation of novel inhibitory polypeptides of protein phosphatase 1 from bovine thymus nuclei," J Biol Chem (1992) 267(23):16538-16544.
Bieschke et al. "Doxycycline-Induced Transgene Expression During *Drosophila* Development and Aging," Mol Gen Genet (1998) 258(6):571-579.
Blitvich et al., Insect Molecular Biology (2002) 11(5):431-442.
Boudrez et al., "Identification of MYPT1 and NIPP1 as subunits of protein phosphatase 1 in rat liver cytosol," FEBS Letters 455 (1999) pp. 175-178.
Burcin et al., "A regulatory system for target gene expression," Frontiers in Biosc. (1998) 3:c1-7.
Cabera et al. "Expression Pattern of Ga14 Enhancer Trap Insertions Into the bric a brac Locus Generated by P Element Replacement," Genesis (2002) 34:62-65.
Carriere et al., "Reversing Insect Adaptation to Transgenic Insecticidal Plants," Proc. R. Soc. Lond. B. (2001) 268:1475-1480.
Chen et al. "The Use of Modified Tetracycline Regulatory Expression System with Reduced Basal Level to Develop and In Vivo Biopesticide Expression System," Food Sci Agricult. Chem (2000) 2(4):220-225.
Chen et al., The Journal of Biological Chemistry (1996) 271(42):25735-25737.
Communication pursuant to Article 94(3) EPC for EP 07712717.3, dated Jul. 11, 2014, 8 pages.
Communication pursuant to Article 94(3) EPC for EP 07712717.3, dated Nov. 6, 2015, 4 pages.
Communication pursuant to Article 96(2) EPC for EP 00979774.7, dated Mar. 8, 2006, 4 pages.
Communication pursuant to Article 96(2) EPC for EP 00979774.7, dated Aug. 2, 2005, 4 pages.
Communication pursuant to Article 96(2) EPC for EP 00979774.7, dated Oct. 4, 2004, 4 pages.
Communication pursuant to Article 96(2) EPC for EP 00979774.7, dated Nov. 28, 2003, 5 pages.
Communication under Rule 51(4) EPC, directed to EP 00979774.7, dated May 9, 2007, 4 pages.
Davis et al. "Engineered Underdominance Allows Efficient and Economical Introgression of Traits into Pest Populations," J. Theor. Biol. (2001) 212(1):83-98.
Decision on Further Processing for EP 00979774.7, dated Jan. 29, 2007, 1 page.
Deng et al., "A targeted gene silencing technique shows that *Drosophila* myosin VI is required for egg chamber and imaginal disc morphogenesis," J Cell Science (1999) 112:3677-3690.
DeVault et al., "Biotechnology and new integrated pest management approaches," Nature Biotechnology (1996) 14:46-49.
Egloff et al., "Structural basis for the recognition of regulatory subunits by the catalytic subunit of protein phosphatase 1," EMBO J (1997) 16(8):1876-1887.
Elick et al. "Analysis of the Cis-Acting DNA Elements Required for piggyback Transposable Element Excision," Mol. Gen. Genet. (1997) 255:605-610.
Ernst, U. "Regulation of Sexual Differentiation in *Drosophila*: Alternative Splicing of the Transformer Primary Transcript Requires Masking of the Non-Specific Acceptor Site in Females," Inaugural Dissertation, Aus Frankfurt / Main, BRD (1991) (Abstract Only).
Examination Report for EP 04743590.4, dated Nov. 14, 2008, 4 pages.
Office Action for EP 04743590.4, dated Feb. 16, 2012, 8 pages.
Examination Report for NZ 519175, dated Nov. 28, 2003, 1 page.
Examination Report for NZ 519175, dated Jul. 9, 2002, 2 pages.
Examiner's Answer to Appeal Brief for U.S. Appl. No. 11/733,737, dated Jul. 18, 2014, 12 pages.
Final Office Action for U.S. Appl. No. 10/148,041, dated Mar. 7, 2006, 9 pages.
Final Office Action for U.S. Appl. No. 10/562,843, dated Feb. 3, 2010, 5 pages.
Final Office Action for U.S. Appl. No. 10/566,448, dated Nov. 10, 2009, 18 pages.
Final Office Action for U.S. Appl. No. 10/566,448, dated Feb. 2, 2011, 13 pages.
Final Office Action for U.S. Appl. No. 10/566,448, dated Aug. 14, 2014, 24 pages.
Final Office Action for U.S. Appl. No. 11/352,177, dated Oct. 14, 2014, 6 pages.
Final Office Action for U.S. Appl. No. 11/352,177, dated Mar. 16, 2011, 17 pages.
Final Office Action for U.S. Appl. No. 11/733,737, dated Apr. 17, 2009, 16 pages.
Final Office Action for U.S. Appl. No. 11/733,737, dated Aug. 4, 2010, 18 pages.
Final Office Action for U.S. Appl. No. 11/733,737, dated Jan. 7, 2013, 26 pages.
Final Office Action for U.S. Appl. No. 13/942,601, dated Jul. 31, 2014, 23 pages.
Final Office Action for U.S. Appl. No. 10/562,843, filed Aug. 25, 2011, 5 pages.
Final Office Action for U.S. Appl. No. 12/278,849, dated Mar. 17, 2014, 24 pages.
Final Office Action for U.S. Appl. No. 12/278,849, dated Jun. 6, 2013, 24 pages.
Final Office Action for U.S. Appl. No. 12/278,849, dated Oct. 9, 2015, 7 pages.
Fryxell et al., "Autocidal biological control: a general strategy for insect control based on genetic transformation with a highly conserved gene," J Econ Entomol (1995) 88(5):1221-1232.
Fu et al. "Female-specific insect lethality engineered using alternative splicing", Nature Biotechnology (2007) 25(3):353-357.
Fu et al., "Female-specific flightless phenotype for mosquito control," PNAS (2010) 107(10):4550-4554.

(56) References Cited

OTHER PUBLICATIONS

Funaguma et al. The Bmdsx transgene including trimmed introns is sex-specifically spliced in tissues of the silkworm, Bombyx moil, Journal of Insect Science (online) (2005) 5(17):1-6.
Further Search Report for GB 9928181.8, dated Apr. 30, 2001.
Fussenegger et al., "Autoregulated multiscistronic expression vectors provide one-step cloning of regulated product gene expression in mammalian cells," Biotechnol Prog (1997) 13:733-740.
Fussenegger et al., "Regulated Multicistronic Expression Technology for Mammalian Metabolic Engineering," Cytotechnology (1998) 28:111-125.
Fux et al., "Novel Macrolide-Adjustable Bidirectional Expression Modules for Coordinated Expression of Two Different Transgenes in Mice," J Gene Medicine (2003) 5:1067-1079.
"Gene Linkage and Genetic Mapping," in Essential Genetics, Daniel L. Hartl and Elizabeth W. Jones (eds.), (1999) Jones and Bartlett Publishers, Sudbury, Massachussetts, pp. 126-127.
Gloor et al. "Targeted Gene Replacement in *Drosophila* via P Element-Induced Gap Repair," Science (1991) 253:1110-1117.
Golovnin et al., "The su(Hw) insulator can disrupt enhancer-promoter interactions when located more than 20 kilobases away from the *Drosophila* achaete-scute complex," Mol Cell Biol (1999) 19(5):3443-3456.
Gong et al. "A dominant lethal genetic system for autocidal control of the Mediterranean fruitfly", Nature Biotechnology (2005) 23(4):453-456.
Gonzy-Treboul et al. "Enhancer-Trap Targeting at the Broad-Complex Locus of *Drosophila melanogaster*," Genes Dev (1995) 9:1137-1148.
Gossen et al., "Tetracyclines in the control of gene expression in eukaryotes," Tetracyclines I Biology, Chemistry and Medicine (2001) pp. 139-157.
Guo et al., "Species-specific signals for the splicing of a short *Drosophila* intron in vitro," Mol Cell Biol (1993) 13(2):1104-1118.
Handler et al. "A Current Prospective on Insect Gene Transformation," Insect Biochem. Mol. Biol. (2001) 31(2):111-128.
Handler, A. (2002) "Use of piggyback Transposon for Germ-Line Transformation of insects," Insect Biochem Mol Biol 32:1211-1220.
Harris et al., "Field performance of engineered male mosquitoes," Nature Biotechnology (2011) 29(11):1034-1039.
Heinrich et al. "A Repressible Female-Specific Lethal Genetic System for Making Transgenic Insect Strains Suitable for a Sterile-Release Program," Proc. Nat. Acad. Sci. USA (2000) 97:8229-8232.
Heslip et al. "Targeted Transposition at the vestigial Locus of *Drosophila melanogaster*," Genetics (1994) 138:1127-1135.
Hofmann et al. "Rapid Retroviral Delivery of Tetracycline-Inducible Genes in a Single Autoregulatory Cassette," Proc. Nat. Acad. Sci. USA (1996) 93:5185-5190.
Hondred et al., Plant Physiology (1999) 119:713-723.
Horn et al. "Highly sensitive, fluorescent transformation marker for Drosophil49a transgenesis" Dev Genes Evol (2000) 210:623-629.
Horn et al. "PiggyBac-Based Insertional Metagenesis and Enhancer Detection as a Tool for Functional Insect Genomics," Genetics (2003) 163(2):647-661.
Horn et al. "A Transgene-Based Embryo-Specific Lethality System for Insect Pest Management," Nat. Biotechnol (2003) 21(1):64-70.
Horn et al., "Highly sensitive, fluorescent transformation marker for *Drosophila* transgenesis," Dev Genes Evol (2000) 210:623-629.
Horn et al "Fluorescent Transformation Markers for Insect Transgenesis," Insect Biochem. Mol. Biol. (2002) 32:1221-1235.
Imai, C. "Control of Insecticide Resistance in a Field Population of Houseflies, *Musca domestica*, by Releasing Susceptible Flies," Res. Popul. Ecol. (1987) 29:129-146.
Inoue et al., "Binding of the *Drosophila* Sex-lethal gene product to the alternative splice site of transformer primary transcript," Nature (1990) 344:461-463.
International Preliminary Examination Report for PCT/GB00/04541, dated Apr. 4, 2002, 2 pages.
International Preliminary Report on Patentability for PCT/GB2004/002021, dated Nov. 18, 2005, 6 pages.
International Preliminary Report on Patentability for PCT/GB2004/002869, dated Jan. 3, 2006, 9 pages.
International Preliminary Report on Patentability for PCT/GB2004/003263, dated Jan. 30, 2006, 6 pages.
International Search Report for PCT/GB00/04541, dated Dec. 5, 2001, 4 pages.
International Search Report for PCT/GB2004/002021, dated Oct. 6, 2004, 3 pages.
International Search Report for PCT/GB2004/002869, dated Jan. 11, 2005, 5 pages.
Jagiello et al., "NIPP-1, a nuclear inhibitory subunit of protein phosphatase-1, has RNA-binding properties," J Biol Chem (1997) 272(35):22067-22071.
Jin et al., "Mapping of the RNA-binding and endoribonuclease domains of NIPP1, a nuclear targeting subunit of protein phosphatase 1," Biochem J (1999) 342:13-19.
Johnson-Schlitz et al. "P-Element-Induced Interallelic Gene Conversion of Insertions and Deletions in *Drosophila melanogaster*," Mol Cell Biol. (1993)13:70067018.
Krafsur, "Bionomics of the face fly, *Musca autumnalis*," Annu Rev Entomol (1997) 42:503-523 (Abstract).
Lankenau et al. "Comparison of Targeted-Gene Replacement Frequencies in *Drosophila melanogaster* at the Forked and White Loci," Mol. Cell Biol. (1996)16:3535-3544.
Louis et al. "A Theoretical Model for the Regulation of Sex-Lethal, a Gene That Controls Sex Determination and Dosage Compensation in *Drosophila melanogaster*," Genetics (2003) 165:1355-1384.
Loukeris et al. "Introduction of the transposable element Minos into the germ line of *Drosophila melanogaster*," Proc Natl Acad Sci (1995) 92:9485-9489.
Munoz et al. "The AeAct-4 gene is expressed in the developing flight muscles of female Aedes aegypti", Insect Molecular Biology (2004)13(5):563-568.
Namciu et al., "Human matrix attachment regions insulate transgene expression from chromosomal position effects in *Drosophila melanogaster*," Mol Cell Biol (1998) 18(4):2382-2391.
Nitasaka et al., "Repressor of P elements in *Drosophila melanogaster*: Cytotype determination by a defective P element carrying only open reading frames 0 through 2," Proc Natl Acad Sci USA (1987) 84(21):7605-7608.
Notice of Allowance for U.S. Appl. No. 10/566,448, dated Mar. 19, 2015, 10 pages.
Notice of Allowance for U.S. Appl. No. 11/352,177, dated Mar. 17, 2015, 10 pages.
Notice of Allowance for U.S. Appl. No. 11/352,177, dated Jul. 7, 2015, 9 pages.
Notice of Allowance for U.S. Appl. No. 13/942,601, dated Apr. 10, 2015, 11 pages.
Notice of Appeal for U.S. Appl. No. 10/566,448, filed Feb. 18, 2015, 4 pages.
Notice of Appeal for U.S. Appl. No. 11/733,737, filed Jul. 3, 2013, 1 page.
Notice of Appeal for U.S. Appl. No. 12/278,849, filed Jun. 17, 2014, 1 page.
Notice of Appeal for U.S. Appl. No. 13/942,601, filed Feb. 2, 2015, 1 page.
Noting of loss of rights (R. 69(1) EPC) for EP 00979774.7, dated Jul. 17, 2004, 1 page.
O'Brochta et al., "Gene vector and transposable element behavior in mosquitos," J Exp Biol (2003) 206(Pt 21):3823-3834.
Office Action for AU 17165/01, dated Jul. 13, 2004, 3 pages.
Office Action for CN 00818682.0, fax dated Feb. 4, 2005, 7 pages.
Office Action for IL 149885, dated Apr. 26, 2007, 4 pages.
Office Action for U.S. Appl. No. 10/148,041, dated Jul. 1, 2005, 14 pages.
Office Action for U.S. Appl. No. 10/148,041, dated Oct. 10, 2006, 8 pages.
Office Action in U.S. Appl. No. 10/556,804, dated Feb. 1, 2011, 4 pages.
Office Action in U.S. Appl. No. 10/556,804, dated May 12, 2010, 8 pages.

(56) References Cited

OTHER PUBLICATIONS

Office Action in U.S. Appl. No. 10/562,843, dated Nov. 12, 2008, 6 pages.
Office Action in U.S. Appl. No. 10/562,843, dated Feb. 16, 2011, 4 pages.
Office Action in U.S. Appl. No. 10/562,843, dated Jul. 30, 2010, 7 pages.
Office Action in U.S. Appl. No. 10/562,843, dated Jun. 9, 2009, 5 pages.
Office Action for U.S. Appl. No. 10/566,448, dated Nov. 22, 2013, 24 pages.
Office Action for U.S. Appl. No. 10/566,448, dated Apr. 27, 2010, 12 pages.
Office Action for U.S. Appl. No. 10/566,448, dated Jan. 7, 2009, 14 pages.
Office Action for U.S. Appl. No. 11/352,177, dated Jun. 10, 2009, 14 pages.
Office Action for U.S. Appl. No. 11/352,177, dated Jan. 30, 2014, 17 pages.
Office Action for U.S. Appl. No. 11/352,177, dated Apr. 14, 2010, 15 pages.
Office Action for U.S. Appl. No. 11/733,737, dated Oct. 1, 2009, 21 pages.
Office Action for U.S. Appl. No. 11/733,737, dated Apr. 10, 2008, 8 pages.
Office Action for U.S. Appl. No. 11/733,737, dated Mar. 27, 2012, 17 pages.
Office Action for U.S. Appl. No. 11/733,737, dated Jun. 28, 2011, 14 pages.
Office Action for U.S. Appl. No. 11/733,737, dated Feb. 8, 2011, 6 pages.
Office Action for U.S. Appl. No. 12/278,849, dated Mar. 10, 2015, 18 pages.
Office Action for U.S. Appl. No. 12/278,849, dated Dec. 5, 2014, 15 pages.
Office Action for U.S. Appl. No. 13/942,601, dated Nov. 4, 2013, 16 pages.
Office Action in U.S. Appl. No. 12/278,849, dated Aug. 9, 2013, 22 pages.
Office Action in U.S. Appl. No. 12/278,849, dated Oct. 10, 2012, 12 pages.
Oxitec Nov. 2011 Newsletter, http://www.oxitec.com/our-news/newsletters/november-2011-newsletter/, downloaded Dec. 13, 2011, 6 pages.
Pane et al. "The transformer gene in Ceratitis capitata provides a genetic basis for selecting and remembering the sexual fate" Development (2002) 129:3715-3725.
Parker et al., "Functional interaction between nuclear inhibitor of protein phosphatase type 1 (NIPP1) and protein phosphatase type 1 (PP1) in *Drosophila*: consequences of over-expression of NIPP1 in flies and suppression by co-expression of PP1," Biochem J (2002) 368:789-797.
Phuc et al., "Late-acting dominant lethal genetic systems and mosquito control," BMC Biology (2007) 5:11, 11 pages.
PiggyBac website, http://piggybac.bio.nd.edu/, Mar. 21, 2006, 5 pp.
Raton CRC Press, pp. 219-235.
Rejection for CN 00818682.0, fax dated Jan. 26, 2006, 4 pages.
Reply Brief and Request for Oral Hearing for U.S. Appl. No. 11/733,737, filed Sep. 18, 2014, 16 pages.
Request for Continued Examination for U.S. Appl. No. 10/148,041, filed Sep. 11, 2006, 8 pages.
Request for Continued Examination for U.S. Appl. No. 10/566,448, filed Aug. 2, 2011, 23 pages.
Request for Continued Examination for U.S. Appl. No. 10/566,448, filed Feb. 25, 2010, 21 pages.
Request for Continued Examination for U.S. Appl. No. 11/352,177, filed Jun. 17, 2015, 14 pages.
Request for Continued Examination for U.S. Appl. No. 11/352,177, filed Sep. 16, 2011, 14 pages.
Request for Continued Examination for U.S. Appl. No. 11/733,737, filed Aug. 14, 2009, 1 page.
Request for Continued Examination for U.S. Appl. No. 13/942,601, filed Jun. 19, 2015, 3 pages.
Request for Further Processing for EP 00979774.7, filed Jan. 4, 2007, 4 pages.
Response for U.S. Appl. No. 10/562,843, filed Feb. 24, 2009, 13 pages.
Response for U.S. Appl. No. 10/562,843, filed Nov. 30, 2010, 8 pages.
Response for U.S. Appl. No. 10/562,843, filed Oct. 5, 2009, 10 pages.
Response to Communication for EP 00979774.7, filed Apr. 14, 2005, 7 pages.
Response to Communication for EP 00979774.7, filed Sep. 20, 2004, 8 pages.
Response to Communication for EP 00979774.7, filed Feb. 13, 2006, 8 pages.
Response to Final Office Action for U.S. Appl. No. 10/566,448, filed Dec. 15, 2014, 9 pages.
Response to Final Office Action for U.S. Appl. No. 11/352,177, filed Dec. 3, 2014, 8 pages.
Response to Final Office Action for U.S. Appl. No. 11/733,737, filed Jul. 17, 2009, 26 pages.
Response to Final Office Action for U.S. Appl. No. 11/733,737, filed Dec. 6, 2010, 26 pages.
Response to Final Office Action for U.S. Appl. No. 11/733,737, filed Apr. 8, 2013, 25 pages.
Response to Final Office Action in U.S. Appl. No. 10/562,843, filed Nov. 21, 2011, 6 pages.
Response to Office Action for U.S. Appl. No. 10/148,041, filed Dec. 5, 2005, 11 pages.
Response to Office Action for U.S. Appl. No. 10/556,804, filed Nov. 12, 2010, 12 pages.
Response to Office Action for U.S. Appl. No. 10/556,804, filed Mar. 25, 2011, 9 pages.
Response to Office Action for U.S. Appl. No. 10/562,843, filed Jun. 16, 2011, 9 pages.
Response to Office Action for U.S. Appl. No. 10/566,448, filed Apr. 22, 2014, 17 pages.
Response to Office Action for U.S. Appl. No. 10/566,448, filed Oct. 27, 2010, 20 pages.
Response to Office Action for U.S. Appl. No. 10/566,448, filed Aug. 28, 2009, 15 pages.
Response to Office Action for U.S. Appl. No. 10/566,448, filed Jul. 7, 2009, 15 pages.
Response to Office Action for U.S. Appl. No. 11/352,177, filed Dec. 10, 2009, 20 pages.
Response to Office Action for U.S. Appl. No. 11/352,177, filed Oct. 14, 2010, 13 pages.
Response to Office Action for U.S. Appl. No. 11/352,177, filed May 28, 2014, 14 pages.
Response to Office Action for U.S. Appl. No. 11/733,737, filed Oct. 10, 2008, 8 pages.
Response to Office Action for U.S. Appl. No. 11/733,737, filed Feb. 18, 2011, 11 pages.
Response to Office Action for U.S. Appl. No. 11/733,737, filed Oct. 28, 2011, 27 pages.
Response to Office Action for U.S. Appl. No. 11/733,737, filed Jan. 29, 2010, 23 pages.
Response to Office Action for U.S. Appl. No. 11/733,737, filed Aug. 9, 2012, 24 pages.
Response to Office Action for U.S. Appl. No. 12/278,849, filed Aug. 7, 2015, 24 pages.
Response to Office Action for U.S. Appl. No. 12/278,849, filed Apr. 10, 2013, 19 pages.
Response to Office Action for U.S. Appl. No. 12/278,849, filed Jan. 9, 2014, 21 pages.
Response to Office Action for U.S. Appl. No. 13/942,601, filed Feb. 4, 2014, 45 pages.
Response to Restriction Requirement for U.S. Appl. No. 10/148,041, filed Apr. 13, 2005, 10 pages.

(56) References Cited

OTHER PUBLICATIONS

Response to Restriction Requirement for U.S. Appl. No. 10/556,804, filed Jun. 29, 2009, 2 pages.
Response to Restriction Requirement for U.S. Appl. No. 10/562,843, filed Jun. 27, 2008, 2 pages.
Response to Restriction Requirement for U.S. Appl. No. 10/566,448, filed Dec. 1, 2008, 9 pages.
Response to Restriction Requirement for U.S. Appl. No. 10/566,448, filed Feb. 8, 2008, 9 pages.
Response to Restriction Requirement for U.S. Appl. No. 11/352,177, filed Mar. 13, 2009, 12 pages.
Response to Restriction Requirement for U.S. Appl. No. 11/352,177, filed Nov. 3, 2008, 8 pages.
Response to Restriction Requirement for U.S. Appl. No. 11/352,177, filed Jun. 9, 2008, 9 pages.
Response to Restriction Requirement for U.S. Appl. No. 11/733,737, filed Jan. 26, 2009, 8 pages.
Response to Restriction Requirement for U.S. Appl. No. 12/278,849, filed Sep. 28, 2010, 13 pages.
Restriction Requirement for U.S. Appl. No. 10/148,041, dated Mar. 10, 2005, 5 pages.
Restriction Requirement for U.S. Appl. No. 10/556,804, dated May 28, 2009, 5 pages.
Restriction Requirement for U.S. Appl. No. 10/562,843, dated Jun. 12, 2008, 6 pages.
Restriction Requirement for U.S. Appl. No. 10/566,448, dated Aug. 29, 2008, 7 pages.
Restriction Requirement for U.S. Appl. No. 10/566,448, dated Jan. 9, 2008, 5 pages.
Restriction Requirement for U.S. Appl. No. 11/352,177, dated Jan. 13, 2009, 10 pages.
Restriction Requirement for U.S. Appl. No. 11/352,177, dated Sep. 2, 2008, 5 pages.
Restriction Requirement for U.S. Appl. No. 11/352,177, dated Mar. 31, 2008, 8 pages.
Restriction Requirement for U.S. Appl. No. 11/733,737, dated Dec. 31, 2008, 9 pages.
Restriction Requirement for U.S. Appl. No. 12/278,849, dated May 28, 2010, 7 pages.
Robinson et al. "Mutations and Their Use in Insect Control," Mutation Research (2002) 511(2):113-132.
Ronaldson et al., "Two independent cis-acting elements regulate the sex- and tissue-specific expression of yp3 in *Drosophila melanogaster*," Genet Res. (1995) 66(1):9-17.
Rong et al. "Gene Targeting by Homologous Recombination in *Drosophila*," Science (2000) 288:2013-2018.
Rong et al. "A Targeted Gene Knockout in *Drosophila*," Genetics (2001)157:1307-1312.
Russ et al. "Self-Deleting Retrovirus Vectors for Gene Therapy," J. Virol. (1996) 70:4927-4932.
Saccone et al., Genetica (2002) 116:15-23.
Saccone et al. "Sex Determination in Medfly: A Molecular Approach," In; Area-Wide Control of Fruit Flies and Other Pest Insects, Tan, K.H. ed., Penerbit USM, Penag, (2000) pp. 491-496.
Scali et al. "Identification of sex-specific transcripts of the Anopheles gambiae doublesex gene", Journal of Experimental Biology (2005) 208(19):3701-3709.
Schwechheimer et al., "Transactivation of a target gene through feedforward loop activation in plants," Funct Integr Genomics (2000) 1:35-43.
Search Report Corresponding to Great Britain Patent Application No. GB 0317656.7, Date of Search Nov. 25, 2003.
Search Report Corresponding to Great Britain Patent Application No. GB 0621234.4, Date of Search Feb. 21, 2007.
Search Report corresponding to International Application No. PCT/GB2007/000488, dated Jun. 6, 2007, 3 pages.
Search Report Corresponding to International Application No. PCT/GB2004/003263, dated Nov. 5, 2004, 3 pages.
Second Office Action for AU 17165/01, dated Mar. 21, 2006, 2 pages.
Second Office Action for CN 00818682.0, dated Jul. 28, 2006, 4 pages.
Sepp et al. "Conversion of lacZ Enhanced Trap Lines to GAL4 Lines Using Targeted Transposition in *Drosophila melanogaster*," Genetics (1999)151:1093-1101.
Shelton et al. "Field Tests on Managing Resistance to Bt-Engineered Plants", Nature Biotechnology (2000) 18(3):339-342.
Shockett et al. "A Modified Tetracycline-Regulated System Provides Autoregulatory, Inducible Gene Expression in Cultured Cells and Transgenic Mice," Proc Nat Acad Sci USA (1995) 92:6522-6526.
Sondergaard et al., "Nutritional response in a *Drosophila* yolk protein gene promoter," Mol Gen Genet (1995) 248(1):25-32.
Spradling et al., "Transposition of cloned P elements into *Drosophila* germ line chromosomes," Science (1982) 218(4570):341-347.
Stadtfeld et al., "Without a trace? PiggyBac-ing toward pluripotency," Nat Methods (2009) 6(5):329-330.
Stebbins et al. "Adaptable Doxycycline-Regulated Gene Expression Systems for *Drosophila*," Gene (2001) 270:103-111.
Stebbins et al. "Tetracycline-Inducible Systems for *Drosophila*," Proc Nat Acad Sci USA (2001) 98:10775-10780.
Steiner et al. "Homologous Recombination as the Main Mechanism for DNA Integration and Cause of Rearrangements in the Filamentous Ascomycete Ashbya gossypii," Genetics (1995)140:973-987.
Summary of Office Action for MX PA/a/2002/005337, dated Jan. 3, 2007, 2 pages.
Supplemental response to Office Action for U.S. Appl. No. 11/352,177, dated Oct. 21, 2010, 15 pages.
Thomas et al. "Insect Population Control Using Dominant, Repressible, Lethal Genetic System," Science (2000) 287:2474-2476.
Van Eynde et al., "Molecular cloning of NIPP-1, a nuclear inhibitor of protein phosphatase-1, reveals homology with polypeptides involved in RNA processing," J Biol Chem (1995) 270(47):28068-28074.
Van Eynde et al., "Organization and alternate splice products of the gene encoding nuclear inhibitor of protein phosphatase-1 (NIPP-1)," Eur J Biochem (1999) 261(1):291-300.
Vulsteke et al., "Properties and phosphorylation sites of baculovirus-expressed nuclear inhibitor of protein phosphatase-1 (NIPP-1)," J Biol Chem (1997) 272(52):32972-32978.
Weinmann et al., "A chimeric transactivator allows tetracycline-responsive gene expression in whole plants," Plant J (1994) 5(4):559-569.
Wera et al., "Inhibition of translation by mRNA encoding NIPP-1, a nuclear inhibitor of protein phosphatase-1," Eur J Biochem (1997) 247(1):411-415.
Wharton et al., "CNS midline enhancers of the *Drosophila* slit and Toll genes," Mech Dev (1993) 40(3):141-154.
Wimmer, "Eco-friendly insect management," Nat Biotechnology (2005) 23(4):432-433.
Wise De Valdez et al., "Genetic elimination of dengue vector mosquitoes," Proc Natl Acad Sci USA (2011) 108(12):4772-4775.
Wobus et al. "A New Transposable Element in Chironomus thummi," Mol General Genet (1990) 222:311-316.
Woltjen et al., "PiggyBac transposition reprograms fibroblasts to induced pluripotent stem cells," Nature (2009) 458(7239):766-770.
Wool et al., "Genetically-Induced Susceptibility to Malathion in Tribolium Castaneum Despite Selection for Resistance," Ent. Exp. & Appl (1980) 28:183190.
Written Opinion corresponding to International Application No. PCT/GB2007/000488, parent of the present application.
Written Opinion for PCT/GB2004/002021, received Oct. 4, 2004, 5 pages.
Written Opinion for PCT/GB2004/002869, received Jan. 12, 2005, 8 pages.
Written Opinion for PCT/GB2004/003263, received Nov. 5, 2004, 5 pages.
Wu et al. "Expression of Highly Controllable Genes in Insect Cells Using a Modified Tetracycline-Regulated Gene Expression System," J. Biotechnol. (2000) 80(1):7583.
Notice of Allowance for U.S. Appl. No. 10/566,448, dated Jul. 13, 2015, 10 pages.

(56) References Cited

OTHER PUBLICATIONS

Response to Communication pursuant to Article 94(3) EPC, filed Mar. 16, 2016, 5 pages.
Communication under Rule 71(3) EPC for EP 07 712 717.3, dated Jun. 20, 2016, 7 pages.
Formal Report (translation) for BR PI0707579-0, dated Jun. 21, 2016, 2 pages.
Formal Report (translation) for BR PI0413024-3, dated Jun. 7, 2016, 10 pages.
Allen et al., "Flight muscle-specific expression of act88F: GFP in transgenic Culex quinquefasciatus Say (Diptera: Culicidae)," Parasitology Int (2004) 53(4):307-314.
Allen et al., "PiggyBac transformation of the New World screwworm, *Cochliomyia hominivorax*, produces multiple distinct mutant strains," Med. Vet. Entomol (2004) 18:1-9.
Allen et al., "Stable, germ-line transformation of Culex quinquefasciatus (Diptera: Culicidae)," J Med Entomol (2001) 38(5):701-710.
Alphey et al., "Malaria control with genetically manipulated insect vectors," Science (2002) 298:119-21.
Alphey, "Engineering Insects for the Sterile Insect Technique," in: Area-wide Control of Insect Pests: from Research to Field Implementation, Vreysen et al., (eds.), Dordrecht, The Netherlands, Springer (2007) pp. 51-60.
Ant et al., "Control of the olive fruit fly using genetics-enhanced sterile insect technique," BMC Biology (2012) 10:51, 8 pages.
Arama et al., "Caspase activity and a specific cytochrome C are required for sperm differentiation in *Drosophila*," Dev Cell (2003) 4(5):687-97.
Barreau et al., "Post-meiotic transcription in *Drosophila* testes," Development (2008) 135(11):1897-1902.
Bauer Dumont et al., "Recurrent positive selection at bgcn, a key determinant of germ line differentiation, does not appear to be driven by simple coevolution with its partner protein bam," Mol Biol Evol (2007) 24(1):182-191.
Beall et al., "Discovery of tMAC: a *Drosophila* testis-specific meiotic arrest complex paralogous to Myb-Muv B," Genes Dev (2007) 21(8):904-919.
Berghammer et al., "A universal marker for transgenic insects," Nature (1999) 402(6760):370-371.
Beumer et al., "Efficient gene targeting in *Drosophila* with zinc-finger nucleases," Genetics (2006)172(4):2391-2403.
Bibikova et al., "Targeted chromosomal cleavage and mutagenesis in *Drosophila* using zinc-finger nucleases," Genetics (2002)161(3):1169-1175.
Black et al., "Why RIDL is not SIT," Trends Parasitol (2011) 27(8):362-370.
Brand et al., "Ectopic expression in *Drosophila*," Methods Cell Biol (1994)44:635-654.
Brand et al., "Targeted gene expression as a means of altering cell fates and generating dominant phenotypes," Development (1993) 118(2):401-415.
Burn et al., "Alternative 5C actin transcripts are localized in different patterns during *Drosophila* embryogenesis," Dev Biol (1989) 131(2):345-355.
Burt et al., "Site-specific selfish genes as tools for the control and genetic engineering of natural populations," Proc Biol Sci (2003) 270:921-928.
Caceres et al., "Mass rearing of temperature sensitive genetic sexing strains in the Mediterranean fruit fly (*Ceratitis capitata*)," Genetica (2002) 115(1):107-116.
Cagan et al., "Spermatogenesis: Borrowing the Apoptotic Machinery," Curr Biol (2003)13:R600-R602.
Catteruccia et al., "An Anopheles transgenic sexing strain for vector control," Nat Biotechnol, (2005) 23(11):1414-1417.
Catteruccia et al., "Impact of genetic manipulation on the fitness of *Anopheles stephensi* mosquitoes," Science (2003) 299(5610):1225-1227.
Catteruccia et al., "Stable germline transformation of the malaria mosquito *Anopheles stephensi*," Nature (2000) 405(6789):959-962.
Catteruccia et al., "Transgenic technologies to induce sterility," Malaria Journal (2009)8 (Supp2)S7.
Cenik et al., "Genome analysis reveals interplay between 5'UTR introns and nuclear mRNA export for secretory and mitochondrial genes," PLoS Genet (2011) 794:e1001366.
Cha et al., "Expression of green fluorescent protein in insect larvae and its application for heterologous protein production," Biotechnol Bioeng (1997) 56(3):239-247.
Chalfie et al., "Green fluorescent protein as a marker for gene expression," Science (1994) 263(5148):802-805.
Cheng et al., "Cellular transformation by Simian Virus 40 and Murine Polyoma Virus T antigens," Semin Cancer Biol (2009) 19(4):218-228.
Chintapalli et al., "Using FlyAtlas to identify better *Drosophila melanogaster* models of human disease," Nature Genetics (2007) 39(6)715-720.
Cho, "Enhancers," WIREs Dev Biol (2012) 1:469-478.
Definition of "pest" from the Concise Oxford American Dictionary (2006) p. 661.
Deredec et al., "The population genetics of using homing endonuclease genes in vector and pest management," Genetics (2008) 179(4):2013-2026.
Dhillon et al., "The melon fruit fly, *Bactrocera cucurbitae*: A review of its biology and management," J Insect Sci (2005) 5:40.
Flaminia et al., "Transgenic technologies to induce sterility," Malar J. (2009) 8 Suppl 2:S7.
Franz, "Genetic sexing strains in the Mediterranean Fruit Fly, an example for other species amenable to large-scale rearing for the sterile insect technique" in:Sterile Insect Technique, Principles and Practice in Area-Wide Integrated Pest Management, Dyck et al., (eds), The Netherlands, Springer (2005) pp. 427-451.
Franz, "Recombination between homologous autosomes in medfly (*Ceratitis capitata*) males: type-1 recombination and the implications for the stability of genetic sexing strains," Genetica (2002) 116(1):73-84.
Fraser,"Insect transgenesis: current applications and future prospects," Annu Rev Entomol (2012) 57:267-289.
Fuller, "Spermatogenesis," in: The Development of *Drosophila melanogaster*, Bate et al., Cold Spring Harbor Laboratory Press (1993) pp. 71-147.
Fussenegger et al., "Streptogramin-based gene regulation systems for mammalian cells," Nat Biotechnol (2000) 18(11):1203-1208.
Fussenegger et al., "The impact of mammalian gene regulation concepts on functional genomic research, metabolic engineering, and advanced gene therapies," Biotechnol Prog (2001) 17(1):1-51.
Ghosh et al., "Transcription factor binding and induced transcription alter chromosomal c-myc replicator activity," Mol Cell Biol (2004) 24(23):10193-10207.
Gonczy et al., "Bag-of-marbles and benign gonial cell neoplasm act in the germline to restrict proliferation during *Drosophila* spermatogenesis," Development (1997) 124(21):4361-4371.
Gong et al., "Ends-out, or replacement, gene targeting in *Drosophila*," Proc Natl Acad Sci (USA) (2003) 100(5):2556-2561.
Gossen et al., "Studying gene function in eukaryotes by conditional gene inactivation," Annu Rev Genet (2002) 36:153-173.
Gossen et al., "Tight control of gene expression in mammalian cells by tetracycline-responsive promoters," Proc Natl Acad Sci (USA) (1992) 89(12):5547-5551.
Graham et al., "Larval diets containing dyes for tagging pink bollworm moth internally," J Econ Entomol (1971) 64:376-379.
Great Britain Application No. 1303932.6, filed Mar. 5, 2013, 42 pages.
Hagler et al., "Methods for marking insects: current techniques and future prospects," Annu. Rev. Entomol. (2001) 46:511-543.
Hagler et al., "An Alternative to conventional insect marking procedures; detection of a protein mark on pink bollworm by ELISA," Entomol Exp Appl (2002) 103(1):1-9.
Han et al., PNAS (2011) 108:9673-9678.
Handler et al., "Germline transformation of *Drosophila melanogaster* with the piggyBac transposon vector," Insect Mol Biol (1999) 8(4):449-457.
Handler et al., "Polyubiquitin-regulated DsRed marker for transgenic insects," BioTechniques (2001) 31:820-828.

(56) References Cited

OTHER PUBLICATIONS

Handler et al., "Prospects for using genetic transformation for improved SIT and new biocontrol methods," Genetics (2002) 116:137-149.
Handler et al., "The lepidopteran transposon vector, piggyBac, mediates germ-line transformation in the Mediterranean fruit fly," PNAS (1998) 95:7520-7525.
He et al., "The actin gene family in the oriental fruit fly *Bactrocera dorsalis*. Muscle specific actins," Insect Biochem Mol Biol (1994) 24(9):891-906.
Hiller et al., "Testis-specific TAF homologs collaborate to control a tissue-specific transcription program," Development (2004) 131:5297-5308.
Hockemeyer et al., "Genetic engineering of human pluripotent cells using TALE nucleases," Nat Biotechnol (2011) 29(8):731-734.
International Preliminary Report on Patentability for PCT/EP2014/054290, dated Sep. 8, 2015, 7 pages.
International Preliminary Report on Patentability for PCT/GB2007/000488, date of search May 5, 2008, 11 pages.
International Search Report and Written Opinion for PCT/EP2013/054417, dated Jul. 12, 2013, 14 pages.
International Search Report and Written Opinion for PCT/EP2014/054290, dated Jun. 18, 2014, 11 pages.
International Search Report and Written Opinion for PCT/GB2015/051633, dated Oct. 8, 2015, 11 pages.
International Search Report for PCT/GB2000/04541, dated Nov. 19, 2001.
Irvin et al., "Assessing fitness costs for transgenic Aedes aegypti expressing the GFP marker and transposase genes," Proc Natl Acad Sci U.S.A. (2004) 101(3):891-896.
Jattani et al., "Deficiency screen identifies a novel role for beta 2 tubulin in salivary gland and myoblast migration in the *Drosophila* embryo," Dev Dyn (2009) 238(4):853-863.
Jiang et al., "Tombola, a tesmin/TSO1-family protein, regulates transcriptional activation in the *Drosophila* male germline and physically interacts with always early," Development (2007) 134(8):1549-1559.
Jiang et al., "Transcriptional activation in *Drosophila* spermatogenesis involves the mutually dependent function of aly and a novel meiotic arrest gene cookie monster," Development (2003) 130(3):563-573.
Jin et al., "Engineered female-specific lethality for control of pest lepidoptera," ACS Synthetic Biology, ACS (2013) 1(3):160-66.
Kawase et al., "Gbb/Bmp signaling is essential for maintaining germline stem cells and for repressing bam transcription in the *Drosophila* testis," Development (2004) 131(6):1365-1375.
Kelly et al., "*Drosophila* MEF2 is a direct regulator of Actin57B transcription in cardiac, skeletal, and visceral muscle lineages," Mech Dev (2002) 110(1-2):39-50.
Kim et al., "Hybrid restriction enzymes: zinc finger fusions to Fok I cleavage domain," Proc Natl Acad Sci (USA) (1996) 93:1156-1160.
Klassen, "History of the Sterile Insect Technique," in: Sterile Insect Technique, Principles and Practice in Area-Wide Integrated Pest Management, Curits et al., (eds) The Netherlands, Springer (2005) pp. 3-36.
Knipling et al., "Possibilities of Insect Control or Eradication Through the Use of Sexually Sterile Males," J Econ Entomol (1955) 48:459-462.
Koukidou et al., "Germ line transformation of the olive fly *Bactrocera oleae* using a versatile transgenesis marker," Insect Mol Biol (2006) 15(1):95-103.
Loew et al., "Improved tet-responsive promoters with minimized background expression," BMC Biotechnology (2010) 10:81.
Loukeris et al., "Gene transfer into the medfly, *Ceratitis capitata*, with a *Drosophila hydei* transposable element," Science (1999) 270(5244):2002-2005.
Lycett et al., "Conditional expression in the malaria mosquito *Anopheles stephensi* with Tet-On and Tet-Off systems," Genetics (2004) 167(4):1781-1790.

Mahfouz et al., "De novo-engineered transcription activator-like effector (TALE) hybrid nuclease with novel DNA binding specificity creates double-strand breaks," Proc Natl Acad Sci (USA) (2011) 101(6):2623-2628.
Malacrida et al., "A transgenic sperm marking system in the medfly, as a tool for pest control strategies and sperm use analysis," Entomological Research (2007) 37:A56.
Marrelli et al., "Mosquito transgenesis: what is the fitness cost?" Trends Parasitol (2006) 22(5):197-202.
Mattox et al., "Alternative splicing of the sex determination gene transformer-2 is sex-specific in tile germ line but not in the soma," Genes & Development (1990) 4(5):789-805.
Mattox et al., "Autoregulation of the splicing of transcripts from the transformer-2 gene of *Drosophila*," Genes & Development (1991) 5:786-796.
Matz et al., "Fluorescent proteins from nonbioluminescent Anthozoa species," Nat Biotechnol (1999) 17(10):969-973.
Maynard-Smith et al., "A directed approach for engineering conditional protein stability using biologically silent small molecules," J Biol Chem (2007) 282(34):24866-24872.
Miller et al., "A TALE nuclease architecture for efficient genome editing," Nat Biotechnol (2011) 29(2):143-148.
Miller., "An improved zinc-finger nuclease architecture for highly specific genome editing," Nat Biotechnol (2007) 25(7):778-785.
Mishra, "Understanding Forest Biology," Discovery publishing house (2009) 3 pages.
Morrison et al., "Genetic Improvements to the sterile insect technique for agricultural pests," Asia Pacific J Mol Biol and Biotechnol (2010) 18(2):275-295.
Mounier et al., "Insect muscle actins differ distinctly from invertebrate and vertebrate cytoplasmic actins," J Mol Evol (1992) 34(5):406-415.
Nielsen et al., "Axoneme-specific beta-tubulin specialization: a conserved C-terminal motif specifies the central pair," Curr Biol (2001) 11(7):529-533.
Nongthomba et al., "Expression and function of the *Drosophila* ACT88F actin isoform is not restricted to the indirect flight muscles," Journal of Muscle Research and Cell Motility (2001) 22:111-119.
Ohshima et al., "Reassessment of 79B actin gene expression in the abdomen of adult *Drosphila melanogaster*," Instect Molecular Biology (1997) 6(3):227-231.
Osanai-Futahasi et al., "A visible dominant marker for insect transgenesis," Nature Communications (2012) 3:1295.
Osterwalder et al., "A conditional tissue-specific transgene expression system using inducible GAL4," Proc Natl Acad Sci (USA) (2001) 98(22):12596-12601.
Papathanos et al., "Sex separation strategies: past experience and new approaches," Malar J. (2009) 8 Supp 2:S5.
Parker, "Mass-rearing for sterile insect release," The Netherlands, Springer (2005) pp. 209-232.
Peloquin et al., "Germ-line transformation of pink bollworm (*Lepidoptera: gelechiidae*) mediated by the piggyBac transposable element," Insect Mol Biol (2000) 9(3):323-333.
Perera et al., "Germ-line transformation of the South American malaria vector, Anopheles albimanus, with a piggyBac/EGFP transposon vector is routine and highly efficient," Insect Mol Biol (2002) 11(4):291-297.
Perezgasga et al., "Regulation of transcription of meiotic cell cycle and terminal differentiation genes by the testis-specific Zn-finger protein matotopetli," Development (2004) 131(8):1691-1702.
Perrin et al., "The actin gene family: function follows isoform," Cytoskeleton (2010) 67(10):630-634.
Pinkerton et al., "Green fluorescent protein as a genetic marker in transgenic Aedes aegypti," Insect Mol Biol (2000) 9(1):1-10.
Prasher et al., "Primary structure of the Aequorea victoria green-fluorescent protein," Gene (1992) 111(2):229-233.
Qin et al., "Systematic comparison of constitutive promoters and the Doxycycline-inducible promoter," PLOS One (2010) 5(5):e10611.
Raja et al., "Replacement by *Drosophila melanogaster* Protamines and Mst77F of Histones during Chromatin Condensation in Late

(56) References Cited

OTHER PUBLICATIONS

Spermatids and Role of Sesame in the Removal of These Proteins from the Male Pronucleus," (2005) Mol Cell Biol 25(14):6165-6177.
Remy et al., "Zinc-finger nucleases: a powerful tool for genetic engineering of animals," Transgenic Res (2010) 19:363-371.
Rendon et al., "Medfly (*Diptera: tephritidae*) genetic sexing: large-scale field comparison of males-only and bisexual sterile fly releases in Guatemala," J Econ Entomol (2004) 97(5):1547-1553.
Robinson et al., "*Ceratitis capitata*—a suitable case for genetic sexing," Genetica (1982) 58(3):229-237.
Robinson et al., "Prospects for the future development and application of the sterile insect technique," The Netherlands, Springer (2005) pp. 727-760.
Robinson, "Genetic Basis of the Sterile Insect Technique," in: Sterile Insect Technique, Principles and Practice in Area-Wide Integrated Pest Management, Dyck et al., (eds.), The Netherland, Springer (2005) pp. 95-114.
Rong et al., "Targeted mutagenesis by homologous recombination in *D. melanogaster*," Genes Dev (2002) 16:1568-1581.
Roper et al., "Contribution of sequence variation in *Drosophila* actins to their incorporation into actin-based structures in vivo," Journal of Cell Science (2005) 118:3937-3948.
Rossler, "The genetics of the Mediterranean fruit fly: a "white pupae" mutant," Annals of the Entomological Society of America (1979) 72:583-585.
Rubin et al., "Genetic transformation of *Drosophila* with transposable element vectors," Science (1982) 218(4570):348-353.
Santel et al., "The *Drosophila* don Juan (dj) gene encodes a novel sperm specific protein component characterized by an unusual domain of a repetitive amino acid motif," Mech Dev (1997) 64(1-2):19-30.
Schetelig et al., "Strategy for enhanced transgenic strain development for embryonic conditional lethality in *Anastrepha suspensa*," Pro Natl Acad Sci (USA) (2012) 24: 9348-9353.
Shah et al., "Cardiac remodeling in *Drosophila* arises from changes in actin gene expression and from a contribution of lymph gland-like cells to the heart musculature," Mech Dev (2011) 128(3-4):222-233.
Simmons et al., "Field Performance of a Genetically Engineered Strain of Pink Bollworm," PLoS ONE (2011) 6(9):1-11.

Smith et al., "Testis-specific expression of the beta2 tubulin promoter of *Aedes aegypti* and its application as a genetic sex-separation marker," Insect Mol Bid (2007) 16(1):16-71.
Spradling et al., "P element-mediated transformation," *Drosophila* a practical approach (1986) Chapter 8:175-197.
Tamura et al., "Germline transformation of the silkworm *Bombyx mori* L. using a piggyBac transposon-derived vector," Nat Biotechnol (2000) 18(1):81-84.
Theodoraki et al., "cDNA cloning, heat shock regulation and developmental expression of the hsp83 gene in the Mediterranean fruit fly *Ceratitis capitata*," Insect Mol Biol (2006) 15(6):839-852.
Urnov et al., "Highly efficient endogenous human gene correction using designed zinc-finger nucleases," Nature (2005) 435:646-651.
Viktorinova et al., "Comparative analysis of binary expression systems for directed gene expression in transgenic insects," Insect Biochem Mol Biol (2007) 37:246-254.
Vivinus et al., Eur. J. Biochem. (2001) 268:1908-1917.
Webster et al., Cell (1988) 52:169-178.
White-Cooper et al., "Transcription of meiotic cell cycle and terminal differentiation genes depends on a conserved chromatin associated protein, whose nuclear localisation is regulated," Development (2000) 127:5463-5473.
Wilson et al., "Position effects on eukaryotic gene expression," Annu Rev Cell Biol (1990) 6:679-714.
Wilson et al., "Sperm plasma membrane breakdown during *Drosophila* fertilization requires sneaky, an acrosomal membrane protein," Development (2006) 133(24):4871-4879.
Windbichler et al., "A synthetic homing endonuclease-based gene drive system in the human malaria mosquito," Nature (2011) 473(7346):212-215.
Windbichler et al., "Homing endonuclease mediated gene targeting in Anopheles gambiae cells and embryos," Nucleic Acids Res (2007) 35:5922-5933.
Windbichler et al., "Targeting the X chromosome during spermatogenesis induces Y chromosome transmission ratio distortion and early dominant embryo lethality in Anopheles gambiae," PLoS Genet (2008) 4(12):e1000291.
Zhao et al., "Male germ cell specification and differentiation," Dev Cell (2002) 2(5):537-547.
Zimowska et al., "The beta2-tubulin gene from three tephritid fruit fly species and use of its promoter for sperm marking," Insect Biochem Mol Biol (2009) 39(8):508-515.

* cited by examiner

Potential PCR products generated:
1. If intron is not excised → ~1550 bp
2. If intron is spliced in male form (M1 or M2) → ~600 bp
3. If intron is spliced in female form → ~200 bp

```
Native:  CGTAGATTTG|GT..intron..AG|GTGAAGGCTC
LA1188:  CTACTG|GCACGT..intron..AG|GTGAAGAATA
LA3077:  AACGAAGTTG|GT..intron..AG|GTATTGAGGG
LA3097:  AGCCACCATG|GT..intron..AG|GTCAGCCGCC
```

Figure 33

|  | NT Males | NT Females | TET Males | TET Females |
|---|---|---|---|---|
| 3077A | 111 | 32 | 73 | 44 |
| 3077B | 314 | 157 | 132 | 121 |
| 3077C | 161 | 116 | 60 | 84 |
| 3077D | 445 | 85 | 194 | 190 |
|  |  |  |  |  |
| 3097A | 179 | 5 | 89 | 90 |
| 3097B | 440 | 0 | 59 | 27 |
| 3097C | 172 | 0 | 46 | 44 |
|  |  |  |  |  |
| 3233A | 457 | 1 | 79 | 58 |
| 3233B | 171 | 0 | 14 | 13 |
|  |  |  |  |  |
| 3014;1217 | 136 | 0 | 48 | 10 |
| 3166;1217 | 64 | 0 | 5 | 7 |

Figure 35

|       | NT males | NT females | TET males | TET females |
|-------|----------|------------|-----------|-------------|
| 3097A | 136      | 0          | 21        | 19          |
| 3097B | 295      | 11         | 14        | 11          |
| 3097C | 96       | 12         | 22        | 21          |
| 3097D | 103      | 15         | 82        | 67          |
| 3233A | 78       | 6          | 32        | 5           |

Figure 38

SEQUENCE LISTING

```
<160> NUMBER OF SEQ ID NOS: 106

<210> SEQ ID NO 1
<211> LENGTH: 44
<212> TYPE: DNA
<213> ORGANISM: Drosophila sp.

<400> SEQUENCE: 1
cacagcgcat gatgagcaca ttaacaaaat gtagtaaaat agga                     44

<210> SEQ ID NO 2
<211> LENGTH: 44
<212> TYPE: DNA
<213> ORGANISM: Drosophila sp.

<400> SEQUENCE: 2
gtttcgataa atattgctat ttaaaatgct tattttcaat gcta                     44

<210> SEQ ID NO 3
<211> LENGTH: 44
<212> TYPE: DNA
<213> ORGANISM: Drosophila sp.

<400> SEQUENCE: 3
tttgttttct aacgttaaag ttaaagagag tccagccaca tttt                     44

<210> SEQ ID NO 4
<211> LENGTH: 21
<212> TYPE: DNA
<213> ORGANISM: Artificial Sequence
```

```
<220> FEATURE:
<223> OTHER INFORMATION: Synthetic construct, Oligonucleotide useful as
      PCR Primer

<400> SEQUENCE: 4
acgcgagagg tgaaattctt g                                                  21

<210> SEQ ID NO 5
<211> LENGTH: 23
<212> TYPE: DNA
<213> ORGANISM: Artificial Sequence
<220> FEATURE:
<223> OTHER INFORMATION: Synthetic construct, Oligonucleotide useful as
      PCR Primer

<400> SEQUENCE: 5
gaaaacatct ttggcaaatg ctt                                                23

<210> SEQ ID NO 6
<211> LENGTH: 16
<212> TYPE: DNA
<213> ORGANISM: Artificial Sequence
<220> FEATURE:
<223> OTHER INFORMATION: Synthetic construct, nucleotide portion of
      TaqMan MGB probe

<400> SEQUENCE: 6
ccgtcgtaag actaac                                                        16

<210> SEQ ID NO 7
<211> LENGTH: 17
<212> TYPE: DNA
<213> ORGANISM: Artificial Sequence
<220> FEATURE:
<223> OTHER INFORMATION: Synthetic construct, Oligonucleotide useful as
      PCR Primer

<400> SEQUENCE: 7
catgccgacg cgctaga                                                       17

<210> SEQ ID NO 8
<211> LENGTH: 26
<212> TYPE: DNA
<213> ORGANISM: Artificial Sequence
<220> FEATURE:
<223> OTHER INFORMATION: Synthetic construct, Oligonucleotide useful as
      PCR Primer

<400> SEQUENCE: 8
gtaaacatct gctcaaactc gaagtc                                             26

<210> SEQ ID NO 9
<211> LENGTH: 18
<212> TYPE: DNA
<213> ORGANISM: Artificial Sequence
<220> FEATURE:
<223> OTHER INFORMATION: Synthetic construct, nucleotide portion of
      TaqMan MGB probe

<400> SEQUENCE: 9
tcgatctgga catgttgg                                                      18

<210> SEQ ID NO 10
<211> LENGTH: 25
<212> TYPE: DNA
<213> ORGANISM: Artificial Sequence
<220> FEATURE:
```

<223> OTHER INFORMATION: Synthetic construct, Oligonucleotide useful as
      PCR Primer

<400> SEQUENCE: 10
gccctcgatg gtagacccgt aattg                                          25

<210> SEQ ID NO 11
<211> LENGTH: 27
<212> TYPE: DNA
<213> ORGANISM: Artificial Sequence
<220> FEATURE:
<223> OTHER INFORMATION: Synthetic construct, Oligonucleotide useful as
      PCR Primer

<400> SEQUENCE: 11
gctaaacaat ctgcaggtac cctggcg                                        27

<210> SEQ ID NO 12
<211> LENGTH: 20
<212> TYPE: DNA
<213> ORGANISM: Artificial Sequence
<220> FEATURE:
<223> OTHER INFORMATION: Synthetic construct, Oligonucleotide useful as
      PCR Primer

<400> SEQUENCE: 12
cctgccagga ctcgccttcc                                                20

<210> SEQ ID NO 13
<211> LENGTH: 22
<212> TYPE: DNA
<213> ORGANISM: Artificial Sequence
<220> FEATURE:
<223> OTHER INFORMATION: Synthetic construct, Oligonucleotide useful as
      PCR Primer

<400> SEQUENCE: 13
gtcatcaact ccgcgttgga gc                                             22

<210> SEQ ID NO 14
<211> LENGTH: 2556
<212> TYPE: DNA
<213> ORGANISM: Artificial Sequence
<220> FEATURE:
<223> OTHER INFORMATION: Synthetic construct, Sequence of the tetO7-tTA
      region of JY2004-tTA

<400> SEQUENCE: 14
gcggccgcat agtcgacatt tcgagtttac cactccctat cagtgataga gaaaagtgaa      60
agtcgagttt accactccct atcagtgata gagaaaagtg aaagtcgagt ttaccactcc     120
ctatcagtga tagagaaaag tgaaagtcga gtttaccact ccctatcagt gatagagaaa     180
agtgaaagtc gagtttacca ctccctatca gtgatagaga aaagtgaaag tcgagtttac     240
cactccctat cagtgataga gaaaagtgaa agtcgagttt accactccct atcagtgata     300
gagaaaagtg aaagtcgagc tcggtacccg gtcgaggta ggcgtgtacg gtgggaggcc     360
tatataagca gagctcgttt agtgaaccgt cagatcgcct ggagacgcca tccacgctgt     420
tttgacctcc atagaagaca ccgggaccga tccagcctcc gcggccccga attcgagctc     480
ggtacccggg gatccccgct cgagctgaat agggaattgg gaattggagc agaggtgggt     540
tcttcgcatt acactgttcg ccacaatctt gttattcat tcgccttgca ggttgccacc     600
atggaattga gattagataa agtaaagtg attaacagcg cattagagct gcttaatgag     660

-continued

| | |
|---|---|
| gtcggaatcg aaggtttaac aacccgtaaa ctcgcccaga agctaggtgt agagcagcct | 720 |
| acattgtatt ggcatgtaaa aaataagcgg gctttgctcg acgccttagc cattgagatg | 780 |
| ttagataggc accatactca cttttgccct ttagaagggg aaagctggca agatttttta | 840 |
| cgtaataacg ctaaaagttt tagatgtgct ttactaagtc atcgcgatgg agcaaaagta | 900 |
| catttaggta cacggcctac agaaaaacag tatgaaactc tcgaaaatca attagccttt | 960 |
| ttatgccaac aagttttttc actagagaat gcattatatg cactcagcgc tgtgggcat | 1020 |
| tttactttag gttgcgtatt ggaagatcaa gagcatcaag tcgctaaaga agaaagggaa | 1080 |
| acacctacta ctgatagtat gccgccatta ttacgacaag ctatcgaatt atttgatcac | 1140 |
| caaggtgcag agccagcctt cttattcggc cttgaattga tcatatgcgg attagaaaaa | 1200 |
| caacttaaat gtgaaagtgg gtccgcgtac agccgcgcgc gtacgaaaaa caattacggg | 1260 |
| tctaccatcg agggcctgct cgatctcccg gacgacgacg cccccgaaga ggcggggctg | 1320 |
| gcggctccgc gcctgtcctt tctccccgcg ggacacacgc gcagactgtc gacggccccc | 1380 |
| ccgaccgatg tcagcctggg ggacgagctc cacttagacg gcgaggacgt ggcgatggcg | 1440 |
| catgccgacg cgctagacga tttcgatctg gacatgttgg gggacgggga ttccccgggt | 1500 |
| ccgggattta cccccacga ctccgccccc tacgcgctc tggatatggc cgacttcgag | 1560 |
| tttgagcaga tgtttaccga tgcccttgga attgacgagt acggtgggta gtgaaacgcg | 1620 |
| tctagagctg agaacttcag ggtgagtttg ggacccttg attgttcttt cttttttcgct | 1680 |
| attgtaaaat tcatgttata tggaggggc aaagttttca gggtgttgtt tagaatggga | 1740 |
| agatgtccct tgtatcacca tggaccctca tgataatttt gtttctttca ctttctactc | 1800 |
| tgttgacaac cattgtctcc tcttatttc tttcatttt ctgtaacttt ttcgttaaac | 1860 |
| tttagcttgc atttgtaacg aattttaaa ttcactttg tttatttgtc agattgtaag | 1920 |
| tactttctct aatcacttt tttcaaggc aatcagggta tattatattg tacttcagca | 1980 |
| cagttttaga gaacaattgt tataattaaa tgataaggta gaatatttct gcatataaat | 2040 |
| tctggctggc gtggaaatat tcttattggt agaaacaact acaccctggt catcatcctg | 2100 |
| cctttctctt tatggttaca atgatataca ctgtttgaga tgaggataaa atactctgag | 2160 |
| tccaaaccgg gcccctctgc taaccatgtt catgccttct tctctttcct acagctcctg | 2220 |
| ggcaacgtgc tggttgttgt gctgtctcat cattttggca aagaattcac tcctcaggtg | 2280 |
| caggctgcct atcagaaggt ggtggctggt gtggccaatg ccctggctca caaataccac | 2340 |
| tgagatcttt ttccctctgc caaaaattat ggggacatca tgaagcccct tgagcatctg | 2400 |
| acttctggct aataaaggaa atttatttc attgcaatag tgtgttggaa ttttttgtgt | 2460 |
| ctctcactcg gaaggacata tgggagggca aatcatttaa aacatcagaa tgagtatttg | 2520 |
| gtttagagtt tggcaacata tgcccatagc ggccgc | 2556 |

<210> SEQ ID NO 15
<211> LENGTH: 12087
<212> TYPE: DNA
<213> ORGANISM: Artificial Sequence
<220> FEATURE:
<223> OTHER INFORMATION: Synthetic construct, plasmid pP[Casper-Act5C-tTA]

<400> SEQUENCE: 15

| | |
|---|---|
| gatccatgag caattagcat gaacgttctg aaaagcgcgt ttagctctcc actacttaca | 60 |
| catattctat gctgcaatat tgaaaatcta ataaacaaaa ctaatgtaca ttaattcttc | 120 |

```
agttttgaat atccttctcc tgactttctt atttagaatt aatataatac tgcatacatt    180
aatactgtaa atatgataag tacctgcaaa acactgcagc tcaagtctta atgaggttct    240
gcgatagctt agcataatta gtaacttatc gcgcagaatt ccctaatgtt cccgacctac    300
atgtacttct gatagttgcc gaggtcaaat gttgttgtat ttgtattata cctcaatatt    360
ggtatattca atatctaata gtacccaatt caattgcaaa gatagtcatt aaaaaaacct    420
aaatcacttg caaattgact tttctgccgg aaaagcaacc ttgacacaca agttaatta     480 gtttatctgg aagtcatgtg agaaatttgt aaataaaatt tttcgcagta atttaagtgg    540
gcctaatccc ttttaagcat cttggtttta cgatgacacc gcaataaggt acaactttat    600 attgttttg caatcagctt gagtctttat taggcatcag tctttctctc taagtttctt     660
cgtgcaataa atgaggttcc aaactccgta gattttcct tctttgttga atccagatcc     720
tgcaaagaaa aaagagcaaa cccctaggtc tgtccaggaa tgtattttcg tgtttgtcga    780
tcgaccatgg tctcgagagg ccttgcagcc aagctttgcg tactcgcaaa ttattaaaaa    840
taaaacttta aaataatttt cgtctaatta atattatgag ttaattcaaa ccccacggac    900
atgctaaggg ttaatcaaca atcatatcgc tgtctcactc agactcaata cgacactcag    960
aatactattc ctttcactcg cacttattgc aagcatacgt taagtggatg tctcttgccg   1020
acgggaccac cttatgttat ttcatcatgg tctggccatt ctcatcgtga gcttccgggt   1080
gctcgcatat ctggctctaa gacttcgggc ccgacgcaag gagtagccga catatatccg   1140
aaataactgc ttgtttttt ttttaccatt attaccatcg tgtttactgt ttattgcccc    1200
ctcaaaaagc taatgtaatt atatttgtgc caataaaaac aagatatgac ctatagaata   1260
caagtatttc cccttcgaac atccccacaa gtagactttg gatttgtctt ctaaccaaaa   1320
gacttacaca cctgcatacc ttacatcaaa aactcgttta tcgctacata aaacaccggg   1380
atatattttt tatatacata cttttcaaat cgcgcgccct cttcataatt cacctccacc   1440
acaccacgtt tcgtagttgc tctttcgctg tctcccaccc gctctccgca acacattcac   1500
cttttgttcg acgaccttgg agcgactgtc gttagttccg cgcgattcgg tgcggtattt   1560
cacaccgcat atggtgcact ctcagtacaa tctgctctga tgccgcatag ttaagccagc   1620
cccgacaccc gccaacaccc gctgacgcgc cctgacgggc ttgtctgctc ccggcatccg   1680
cttacagaca agctgtgacc gtctccggga gctgcatgtg tcagaggttt tcaccgtcat   1740
caccgaaacg cgcgagacga aagggcctcg tgatacgcct atttttatag gttaatgtca   1800
tgataataat ggtttcttag acgtcaggtg gcacttttcg gggaaatgtg cgcggaaccc   1860
ctatttgttt attttctaa atacattcaa atatgtatcc gctcatgaga caataaccct    1920
gataaatgct tcaataatat tgaaaaagga agagtatgag tattcaacat ttccgtgtcg   1980
cccttattcc ctttttttgcg gcattttgcc ttcctgtttt tgctcaccca gaaacgctgg   2040
tgaaagtaaa agatgctgaa gatcagttgg gtgcacgagt gggttacatc gaactggatc   2100
tcaacagcgg taagatcctt gagagttttc gccccgaaga acgttttcca atgatgagca   2160
cttttaaagt tctgctatgt ggcgcggtat tatcccgtat tgacgccggg caagagcaac   2220
tcggtcgccg catacactat tctcagaatg acttggttga gtactcacca gtcacagaaa   2280
agcatcttac ggatggcatg acagtaagag aattatgcag tgctgccata accatgagtg   2340
ataacactgc ggccaactta cttctgacaa cgatcggagg accgaaggag ctaaccgctt   2400
ttttgcacaa catgggggat catgtaactc gccttgatcg ttgggaaccg gagctgaatg   2460
aagccatacc aaacgacgag cgtgacacca cgatgcctgt agcaatggca acaacgttgc   2520
```

```
gcaaactatt aactggcgaa ctacttactc tagcttcccg gcaacaatta atagactgga      2580
tggaggcgga taaagttgca ggaccacttc tgcgctcggc ccttccggct ggctggttta      2640
ttgctgataa atctggagcc ggtgagcgtg ggtctcgcgg tatcattgca gcactggggc      2700
cagatggtaa gccctcccgt atcgtagtta tctacacgac ggggagtcag gcaactatgg      2760
atgaacgaaa tagacagatc gctgagatag gtgcctcact gattaagcat tggtaactgt      2820
cagaccaagt ttactcatat atactttaga ttgatttaaa acttcatttt taatttaaaa      2880
ggatctaggt gaagatcctt tttgataatc tcatgaccaa aatcccttaa cgtgagtttt      2940
cgttccactg agcgtcagac cccgtagaaa agatcaaagg atcttcttga gatccttttt      3000
ttctgcgcgt aatctgctgc ttgcaaacaa aaaaaccacc gctaccagcg gtggtttgtt      3060
tgccggatca agagctacca actcttttc cgaaggtaac tggcttcagc agagcgcaga      3120
taccaaatac tgtccttcta gtgtagccgt agttaggcca ccacttcaag aactctgtag      3180
caccgcctac atacctcgct ctgctaatcc tgttaccagt ggctgctgcc agtggcgata      3240
agtcgtgtct taccgggttg gactcaagac gatagttacc ggataaggcg cagcggtcgg      3300
gctgaacggg gggttcgtgc acacagccca gcttggagcg aacgacctac accgaactga      3360
gatacctaca gcgtgagcta tgagaaagcg ccacgcttcc cgaagggaga aaggcggaca      3420
ggtatccggt aagcggcagg gtcggaacag gagagcgcac gagggagctt ccaggggaa      3480 acgcctggta tctttatagt cctgtcgggt ttcgccacct ctgacttgag cgtcgatttt      3540
tgtgatgctc gtcaggggg cggagcctat ggaaaaacgc cttcttcttg aactcgggct      3600
cggtgccagt atacctcaaa tggttgtcgt acctctcatg gttccgttac gccaacgagg      3660
gtctgctgat taaccaatgg gcggacgtgg agcgggcga aattagctgc acatcgtcga      3720
acaccacgtg ccccagttcg ggcaaggtca tcctggagac gcttaacttc tccgccgccg      3780
atctgccgct ggactacgtg ggtctggccc atgatgaaat aacataaggt ggtcccgtcg      3840
aaagccgaag cttaccgaag tatacactta aattcagtgc acgtttgctt gttgagagga      3900
aaggttgtgt gcggacgaat ttttttttga aaacattaac ccttacgtgg aataaaaaaa      3960
aatgaaatat tgcaaatttt gctgcaaagc tgtgactgga gtaaaattaa ttcacgtgcc      4020
gaagtgtgct attaagagaa aattgtggga gcagagcctt gggtgcagcc ttggtgaaaa      4080
ctcccaaatt tgtgataccc actttaatga ttcgcagtgg aaggctgcac ctgcaaaagg      4140
tcagacattt aaaaggaggc gactcaacgc agatgccgta cctagtaaag tgatagagcc      4200
tgaaccagaa aagataaaag aaggctatac cagtgggagt acacaaacag agtaagtttg      4260
aatagtaaaa aaaatcattt atgtaaacaa taacgtgact gtgcgttagg tcctgttcat      4320
tgtttaatga aaataagagc ttgagggaaa aaattcgtac tttggagtac gaaatgcgtc      4380
gtttagagca gcagccgaat taattctagt tccagtgaaa tccaagcatt ttctaaatta      4440
aatgtattct tattattata gttgttattt ttgatatata taaacaacac tattatgccc      4500
accatttttt tgagatgcat ctacacaagg aacaaacact ggatgtcact ttcagttcaa      4560
attgtaacgc taatcactcc gaacaggtca caaaaaatta ccttaaaaag tcataatatt      4620
aaattagaat aaatatagct gtgagggaaa tatatacaaa tatattggag caaataaatt      4680
gtacatacaa atatttatta ctaatttcta ttgagacgaa atgaaccact cggaaccatt      4740
tgagcgaacc gaatcgcgcg gaactaacga cagtcgctcc aaggtcgtcg aacaaaaggt      4800
gaatgtgttg cggagagcgg gtgggagaca gcgaaagagc aactacgaaa cgtggtgtgg      4860
```

```
tggaggtgaa ttatgaagag ggcgcgcgat ttgaaaagta tgtatataaa aaatatatcc    4920 cggtgttttta tgtagcgata aacgagttttt tgatgtaagg tatgcaggtg tgtaagtctt    4980
ttggttagaa gacaaatcca aagtctactt gtggggatgt tcgaagggga aatacttgta    5040
ttctataggt catatcttgt ttttattggc acaaatataa ttacattagc tttttgaggg    5100
ggcaataaac agtaaacacg atggtaataa tggtaaaaaa aaaaaacaag cagttatttc    5160
ggatatatgt cggctactcc ttgcgtcggg cccgaagtct tagagccaga tatgcgagca    5220
cccggaagct cacgatgaga atggccagac ccacgtagtc cagcggcaga tcggcggcgg    5280
agaagttaag cgtctccagg atgaccttgc ccgaactggg gcacgtggtg ttcgacgatg    5340
tgcagctaat ttcgcccggc tccacgtccg cccattggtt aatcagcaga ccctcgttgg    5400
cgtaacggaa ccatgagagg tacgacaacc atttgaggta tactggcacc gagcccgagt    5460
tcaagaagaa gccgccaaag agcaggaatg gtatgataac cggcggaccc acagacagcg    5520
ccatcgaggt cgaggagctg gcgcaggata ttagatatcc gaaggacgtt gacacattgg    5580
ccaccagagt gaccagcgcc aggcagttga agaagtgcag cactccggcc gcagtccga    5640 tcatcggata ggcaatcgcc gtgaagacca gtggcactgt gagaaaaagc ggcaattcgg    5700
caatcgtttt gcccagaaag tatgtgtcac agcgataaag tcgacttcgg gcctccctca    5760
taaaaactgg cagctctgag gtgaacacct aaatcgaatc gattcattag aaagttagta    5820
aattattgaa atgcaaatgt attctaaaca tgacttacat ttatcgtggc aaagacgttt    5880
tgaaaggtca tgttggtcag gaagaggaag atggctccgt tgatattcat cacacccact    5940
tgcgtgagtt gttggcccaa aaagatgagg ccaatcaaga tggcaaccat ctgcaaatta    6000
aaatgttact cgcatctcat taatattcgc gagttaaatg aaatttattt atcttctgca    6060
aaactataaa ctatacatct cattgaaaaa aactaagaag ggtgtggaat caggcaattc    6120
tatctaaaat ctagcgaatt tgtttccaag aattgtaagc gttatatcat ttgtttccac    6180
tggaaccact caccgttgtc tgaataagtc gcacttttac gaggagtggt tccttgagca    6240
ccgacagcca ggatcgccac aggaccgccc ggaactgcat gaaccaggtg gccttgtagg    6300
tgtacccatt ctccggctgc tccagtggct tctccagatt tttggtggcc aacaactgct    6360
ccatatcccg ggctactttg ctaatggcaa aattgtcgcc atatcttggc gatccgatca    6420
cgggactcga tctcccgtcc gggcacaacg gccaacacct gtacgtaaaa gtccgccgga    6480 tgtagttgg taggacactg ggcacccacg ctggatagga gttgagatgt aatgtaatgc    6540 tagatacct taataaacac atcgaactca ctaggaaaag aagtcgacgg cttcgctggg    6600
agtgcccaag aaagctaccc tgccctcggc catcagaagg atcttgtcaa agagctcaaa    6660
cagctcggaa gacggctgat gaatggtcag gatgacggtc ttgcccttct gcgacagctt    6720
cttcagcacc tggacgacgc tgtgggcggt aaatgagtcc agtccggagg tgggctcatc    6780
gcagatcaga agcggcggat cggttagtgc ctcggaggcg aatgccagac gcttcctttc    6840
tccgccggac agacctttca ccctgccggg cacaccgatg atcgtgtgct gacatttgct    6900
gagcgaaagc tcctggatca cctgatccac gcgggccact cgctgccgat aggtcagatg    6960
tcgtggcatc cgcaccatgg cttggaaaat caggtgttcc ctggccgtta gggagccgat    7020
aaagaggtca tcctgctgga cataggcgca cctggcctgc atctccttgg cgtccacagg    7080
ttggccattg agcagtcgca tcccggatgg cgatacttgg atgccctgcg gcgatcgaaa    7140
ggcaagggca ttcagcaggg tcgtctttcc ggcaccggaa ctgcccatca cggccaaaag    7200
ttcgcccgga taggccacgc cgcaaactga gttcaaatt ggtaattgga ccctttatta    7260
```

```
agatttcaca cagatcagcc gactgcgaat agaaactcac cgttcttgag caaatgtttc    7320
ctgggcgccg gtatgtgtcg ctcgttgcag aatagtccgc gtgtccggtt gaccagctgc    7380
cgccatccgg agcccggctg attgaccgcc ccaaagatgt ccatattgtg ccaggcatag    7440
gtgaggttct cggctagttg gccgctccct gaaccggagt cctccggcgg actgggtggc    7500
aggagcgtgc cgtagttttt ggcctgcccg aagccctggt taatgcagct ctgcgaagcg    7560
tccgctgtca ccctgcaatg atagggatc tcaaatatca actacaagcg ttatgctcat    7620
ctaaccccga acaaaacgaa gtatcctacg aagtaggttt atacttttat ttatttttg    7680 tgcatagctt aaaatatctg gttgttatat tttttgtaaa aaagaatgta gtcgaaaatg    7740
aatgccttta gatgtcttga tcatgatatg atcttaaaaa ttgtcttata tagcgagcac    7800
agctaccaga ataatctgtt tcgtgtcact atttgtttgt gcgattgcgg tttgggattt    7860
ttgtgggtcg cagttctcac gccgcagaca atttgatgtt gcaatcgcag ttcctataga    7920
tcaagtgaac ttaagatgta tgcacatgta ctactcacat tgttcagatg ctcggcagat    7980
gggtgtttgc tgcctccgcg aattaatagc tcctgatcct cttggcccat tgccgggatt    8040
tttcacactt tcccctgctt acccacccaa aaccaatcac cacccaatc actcaaaaaa    8100 caaacaaaaa taagaagcga gaggagtttt ggcacagcac tttgtgttta attgatggcg    8160
taaaccgctt ggagcttcgt cacgaaaccg ctgacaaagt gcaactgaag gcggacattg    8220
acgctaggta acgctacaaa cggtggcgaa agagatagcg gacgcagcgg cgaaagagac    8280
ggcgatattt ctgtggacag agaaggaggc aaacagcgct gactttgagt ggaatgtcat    8340
tttgagtgag aggtaatcga agaacctgg tacatcaaat acccttggat cgaagtaaat    8400
ttaaaactga tcagataagt tcaatgatat ccagtgcagt aaaaaaaaaa aatgttttt    8460 ttatctactt tccgcaaaaa tgggtttat taacttacat acatactaga attctaaaaa    8520
aaatcatgaa tggcatcaac tctgaatcaa atctttgcag atgcacctac ttctcatttc    8580
cactgtcaca tcatttttcc agatctcgct gcctgttatg tgcccacaa accaagacac    8640 gttttatggc cattaaagct ggctgatcgt cgccaaacac caaatacata tcaatatgta    8700
cattcgagaa agaagcgatc aaagaagcgt cttcgggcga gtaggagaat gcggaggaga    8760
aggagaacga gctgatctag tatctctcca caatccaatg ccaactgacc aactggccat    8820
attcggagca atttgaagcc aatttccatc gcctggcgat cgctccattc ttggctatat    8880 gttttcacc gttcccgggg ccattttcaa agactcgtcg gtaagataag attgtgtcac    8940
tcgctgtctc tcttcatttg tcgaagaatg ctgaggaatt tcgcgatgac gtcggcgagt    9000
attttgaaga atgagaataa tttgtattta tacgaaaatc agttagtgga atttctaca    9060 aaaacatgtt atctatagat aatttgttg caaaatatgt tgactatgac aaagattgta    9120
tgtatatacc tttaatgtat tctcattttc ttatgtattt ataatggcaa tgatgatact    9180
gatgatattt taagatgatg ccagaccaca ggctgatttc tgcgtcttt gccgaacgca    9240 gtgcatgtgc ggttgttgtt ttttggaata gtttcaattt tcggactgtc cgctttgatt    9300
tcagtttctt ggcttattca aaaagcaaag taaagccaaa aaagcgagat ggcaatacca    9360
aatgcggcaa aacggtagtg gaaggaaagg ggtgcggggc agcggaagga agggtggggc    9420
ggggcgtggc ggggtctgtg gctgggcgcg acgtcaccga cgttggagcc actcctttga    9480
ccatgtgtgc gtgtgtgtat tattcgtgtc tcgccactcg ccggttgttt ttttctttt    9540 atctcgctct ctctagcgcc atctcgtacg catgctcaac gcaccgcatg ttgccgtgtc    9600
```

```
ctttatgcgt cattttggct cgaaataggc aattatttaa acaaagatta gtcaacgaaa    9660
acgctaaaat aaataagtct acaatatggt tacttattgc catgtgtgtg cagccaacga    9720
tagcaacaaa agcaacaaca cagtggcttt ccctctttca cttttgttt gcaagcgcgt     9780 gcgagcaaga cggcacgacc ggcaaacgca attacgctga caaagagcag acgaagtttt    9840
ggccgaaaaa catcaaggcg cctgatacga atgcatttgc aataacaatt gcgatattta    9900
atattgttta tgaagctgtt tgacttcaaa acacacaaaa aaaaaataa aacaaattat     9960 ttgaaagaga attaggaatc ggacagctta tcgttacggg ctaacagcac accgagacga   10020
aatagcttac ctgacgtcac agcctctgga agaactgccg ccaagcagac gatgcagagg   10080
acgacacata gagtagcgga gtaggccagc gtagtacgca tgtgcttgtg tgtgaggcgt   10140
ctctctcttc gtctcctgtt tgcgcaaacg catagactgc actgagaaaa tcgattacct   10200 atttttatg aatgaatatt tgcactatta ctattcaaaa ctattaagat agcaatcaca    10260
ttcaatagcc aaatactata ccacctgagc gatgcaacga aatgatcaat ttgagcaaaa   10320
atgctgcata tttaggacgg catcattata gaaatgcttc ttgctgtgta cttttctctc   10380
gtctggcagc tgtttcgccg ttattgttaa aaccggctta agttaggtgt gttttctacg   10440
actagtgatg cccctactag aagatgtgtg ttgcacaaat gtccctgaat aaccaatttg   10500
aagtgcagat agcagtaaac gtaagctaat atgaatatta tttaactgta atgttttaat   10560
atcgctggac attactaata aacccactat aaacacatgt acatatgtat gttttggcat   10620
acaatgagta gttggggaaa aaatgtgtaa aagcaccgtg accatcacag cataaagata   10680
accagctgaa gtatcgaata tgagtaaccc ccaaattgaa tcacatgccg caactgatag   10740
gacccatgga agtacactct tcatggcgat atacaagaca cacacaagca cgaacaccca   10800
gttgcggagg aaattctccg taaatgaaaa cccaatcggc gaacaattca tacccatata   10860
tggtaaaagt tttgaacgcg acttgagagc ggagagcatt gcggctgata aggttttagc   10920
gctaagcggg ctttataaaa cgggctgcgg gaccagtttt catatcacta ccgtttgagt   10980
tcttgtgctg tgtggatact cctcccgaca caaagccgct ccatcagcca gcagtcgtct   11040
aatccagaga ccccggatct agaaccaaaa tggctagatt agataaaagt aaagtgatta   11100
acagcgcatt agagctgctt aatgaggtcg gaatcgaagg tttaacaacc cgtaaactcg   11160
cccagaagct aggtgtagag cagcctacat tgtattggca tgtaaaaaat aagcgggctt   11220
tgctcgacgc cttagccatt gagatgttag ataggcacca tactcacttt tgcccttag    11280 aaggggaaag ctggcaagat tttttacgta ataacgctaa aagttttaga tgtgctttac   11340
taagtcatcg cgatggagca aaagtacatt taggtacacg gcctacagaa aaacagtatg   11400
aaactctcga aaatcaatta gccttttttat gccaacaagg ttttcacta gagaatgcat    11460 tatatgcact cagcgctgtg gggcatttta ctttaggttg cgtattggaa gatcaagagc   11520
atcaagtcgc taagaagaa agggaaacac ctactactga tagtatgccg ccattattac    11580
gacaagctat cgaattattt gatcaccaag gtgcagagcc agccttctta ttcggccttg   11640
aattgatcat atgcggatta gaaaaacaac ttaaatgtga aagtgggtcc gcgtacagcc   11700
gcgcgcgtac gaaaaacaat tacgggtcta ccatcgaggg cctgctcgat ctcccggacg   11760
acgacgcccc cgaagaggcg gggctggcgg ctccgcgcct gtccttttctc cccgcgggac   11820 acacgcgcag actgtcgacg gccccccgca ccgatgtcag cctggggggac gagctccact   11880 tagacgcgcga ggacgtggcg atggcgcatg ccgacgcgct agacgatttc gatctggaca   11940 tgttgggga cggggattcc ccgggtccgg gatttacccc ccacgactcc gcccctacg    12000
```

```
gcgctctgga tatggccgac ttcgagtttg agcagatgtt taccgatgcc cttggaattg    12060
acgagtacgg tgggtagggg gcgcgag                                        12087

<210> SEQ ID NO 16
<211> LENGTH: 11920
<212> TYPE: DNA
<213> ORGANISM: Artificial Sequence
<220> FEATURE:
<223> OTHER INFORMATION: Synthetic construct, plasmid pLA513

<400> SEQUENCE: 16
gggccgatct gacaatgttc agtgcagaga ctcggctacg cctcgtggac tttgaagttg      60
accaacaatg tttattctta cctctaatag tcctctgtgg caaggtcaag attctgttag     120
aagccaatga agaacctggt tgttcaataa cattttgttc gtctaatatt tcactaccgc     180
ttgacgttgg ctgcacttca tgtacctcat ctataaacgc ttcttctgta tcgctctgga     240
cgtcatcttc acttacgtga tctgatattt cactgtcaga atcctcacca acaagctcgt     300
catcgctttg cagaagagca gagaggatat gctcatcgtc taaagaacta cccattttat     360
tatatattag tcacgatatc tataacaaga aaatatatat ataataagtt atcacgtaag     420
tagaacatga ataacaata taattatcgt atgagttaaa tcttaaaagt cacgtaaaag     480
ataatcatgc gtcattttga ctcacgcggt cgttatagtt caaaatcagt gacacttacc     540
gcattgacaa gcacgcctca cgggagctcc aagcggcgac tgagatgtcc taaatgcaca     600
gcgacggatt cgcgctattt agaaagagag agcaatattt caagaatgca tgcgtcaatt     660
ttacgcagac tatctttcta gggttaaaaa agatttgcgc tttactcgac ctaaacttta     720
aacacgtcat agaatcttcg tttgacaaaa accacattgt ggccaagctg tgtgacgcga     780
cgcgcgctaa agaatggcaa accaagtcgc gcgagcgtcg acctgcaggc atgcaagctt     840
gcatgcctgc aggtcgaaat tcgtaatcat ggtcatagct gtttcctgtg tgaaattgtt     900
atccgctcac aattccacac aacatacgag ccggaagcat aaagtgtaaa gcctggggtg     960
cctaatgagt gagctaactc acattaattg cgttgcgctc actgcccgct ttccagtcgg    1020
gaaacctgtc gtgccagctg cattaatgaa tcggccaacg cgcggggaga ggcggtttgc    1080
gtattgggcg ctcttccgct tcctcgctca ctgactcgct gcgctcggtc gttcggctgc    1140
ggcgagcggt atcagctcac tcaaaggcgg taatacggtt atccacagaa tcaggggata    1200
acgcaggaaa gaacatgtga gcaaaaggcc agcaaaaggc caggaaccgt aaaaaggccg    1260
cgttgctggc gtttttccat aggctccgcc cccctgacga gcatcacaaa aatcgacgct    1320
caagtcagag gtggcgaaac ccgacaggac tataaagata ccaggcgttt ccccctggaa    1380
gctccctcgt gcgctctcct gttccgaccc tgccgcttac cggatacctg tccgcctttc    1440
tcccttcggg aagcgtggcg ctttctcaat gctcacgctg taggtatctc agttcggtgt    1500
aggtcgttcg ctccaagctg ggctgtgtgc acgaaccccc cgttcagccc gaccgctgcg    1560
ccttatccgg taactatcgt cttgagtcca acccggtaag acacgactta tcgccactgg    1620
cagcagccac tggtaacagg attagcagag cgaggtatgt aggcggtgct acagagttct    1680
tgaagtggtg gcctaactac ggctacacta gaaggacagt atttggtatc tgcgctctgc    1740
tgaagccagt taccttcgga aaaagagttg gtagctcttg atccggcaaa caaaccaccg    1800
ctggtagcgg tggttttttt gtttgcaagc agcagattac gcgcagaaaa aaggatctc     1860 aagaagatcc tttgatcttt tctacggggt ctgacgctca gtggaacgaa aactcacgtt    1920
```

```
aagggattttt ggtcatgaga ttatcaaaaa ggatcttcac ctagatcctt ttaaattaaa    1980
aatgaagttt taaatcaatc taaagtatat atgagtaaac ttggtctgac agttaccaat    2040
gcttaatcag tgaggcacct atctcagcga tctgtctatt tcgttcatcc atagttgcct    2100
gactccccgt cgtgtagata actacgatac gggagggctt accatctggc cccagtgctg    2160
caatgatacc gcgagaccca cgctcaccgg ctccagattt atcagcaata aaccagccag    2220
ccggaagggc cgagcgcaga agtggtcctg caactttatc cgcctccatc cagtctatta    2280
attgttgccg ggaagctaga gtaagtagtt cgccagttaa tagtttgcgc aacgttgttg    2340
ccattgctac aggcatcgtg gtgtcacgct cgtcgtttgg tatggcttca ttcagctccg    2400
gttcccaacg atcaaggcga gttacatgat cccccatgtt gtgcaaaaaa gcggttagct    2460
ccttcggtcc tccgatcgtt gtcagaagta agttggccgc agtgttatca ctcatggtta    2520
tggcagcact gcataattct cttactgtca tgccatccgt aagatgcttt tctgtgactg    2580
gtgagtactc aaccaagtca ttctgagaat agtgtatgcg cgaccgagt tgctcttgcc    2640
cggcgtcaat acgggataat accgcgccac atagcagaac tttaaaagtg ctcatcattg    2700
gaaaacgttc ttcggggcga aaactctcaa ggatcttacc gctgttgaga tccagttcga    2760
tgtaacccac tcgtgcaccc aactgatctt cagcatcttt tactttcacc agcgtttctg    2820
ggtgagcaaa aacaggaagg caaaatgccg caaaaaaggg aataagggcg acacggaaat    2880
gttgaatact catactcttc ctttttcaat attattgaag catttatcag gttattgtc    2940
tcatgagcgg atacatattt gaatgtattt agaaaaataa acaatagggg ttccgcgca    3000
catttccccg aaaagtgcca cctgacgtct aagaaaccat tattatcatg acattaacct    3060
ataaaaatag gcgtatcacg aggccctttc gtctcgcgcg tttcggtgat gacggtgaaa    3120
acctctgaca catgcagctc ccggagacgg tcacagcttg tctgtaagcg gatgccggga    3180
gcagacaagc ccgtcagggc gcgtcagcgg gtgttggcgg gtgtcggggc tggcttaact    3240
atgcggcatc agagcagatt gtactgagag tgcaccatat gcggtgtgaa ataccgcaca    3300
gatgcgtaag gagaaaatac cgcatcaggc gccattcgcc attcaggctg cgcaactgtt    3360
gggaagggcg atcggtgcgg gcctcttcgc tattacgcca gctggcgaaa gggggatgtg    3420
ctgcaaggcg attaagttgg gtaacgccag ggttttccca gtcacgacgt tgtaaaacga    3480
cggccagtgc caagctttgt ttaaaatata acaaaattgt gatcccacaa aatgaagtgg    3540
ggcaaaatca ataattaat agtgtccgta aacttgttgg tcttcaactt tttgaggaac    3600
acgttggacg gcaaatccgt gactataaca caagttgatt taataatttt agccaacacg    3660
tcgggctgcg tgttttttgc cgacgcgtct gtgtacacgt tgattaactg gtcgattaaa    3720
ctgttgaaat aatttaattt ttggttcttc tttaaatctg tgatgaaatt ttttaaaata    3780
actttaaatt cttcattggt aaaaaatgcc acgttttgca acttgtgagg gtctaatatg    3840
aggtcaaact cagtaggagt tttatccaaa aagaaaaca tgattacgtc tgtacacgaa    3900
cgcgtattaa cgcagagtgc aaagtataag agggttaaaa aatatatttt acgcaccata    3960
tacgcatcgg gttgatatcg ttaatatgga tcaatttgaa cagttgatta acgtgtctct    4020
gctcaagtct ttgatcaaaa cgcaaatcga cgaaaatgtg tcggacaata tcaagtcgat    4080
gagcgaaaaa ctaaaaaggc tagaatacga caatctcaca gacagcgttg agatatacgg    4140
tattcacgac agcaggctga ataataaaaa aattagaaac tattatttaa ccctagaaag    4200
ataatcatat tgtgacgtac gttaaagata atcatgcgta aaattgacgc atgtgtttta    4260
tcggtctgta tatcgaggtt tatttattaa tttgaataga tattaagttt tattatattt    4320
```

```
acacttacat actaataata aattcaacaa acaatttatt tatgtttatt tatttattaa    4380
aaaaaaacaa aaactcaaaa tttcttctat aaagtaacaa aacttttaaa cattctctct    4440
tttacaaaaa taaacttatt ttgtacttta aaaacagtca tgttgtatta taaaataagt    4500
aattagctta acttatacat aatagaaaca aattatactt attagtcagt cagaaacaac    4560
tttggcacat atcaatatta tgctctcgac aaataacttt tttgcatttt ttgcacgatg    4620
catttgcctt tcgccttatt ttagaggggc agtaagtaca gtaagtacgt tttttcatta    4680
ctggctcttc agtactgtca tctgatgtac caggcacttc atttggcaaa atattagaga    4740
tattatcgcg caaatatctc ttcaaagtag gagcttctaa acgcttacgc ataaacgatg    4800
acgtcaggct catgtaaagg tttctcataa attttttgcg actttggacc ttttctccct    4860
tgctactgac attatggctg tatataataa aagaatttat gcaggcaatg tttatcattc    4920
cgtacaataa tgccataggc cacctattcg tcttcctact gcaggtcatc acagaacaca    4980
tttggtctag cgtgtccact ccgcctttag tttgattata atacataacc atttgcggtt    5040
taccggtact ttcgttgata gaagcatcct catcacaaga tgataataag tataccatct    5100
tagctggctt cggtttatat gagacgagag taagggtcc gtcaaaacaa aacatcgatg     5160
ttcccactgg cctggagcga ctgttttcca gtacttccgg tatctcgcgt ttgtttgatc    5220
gcacggttcc cacaatggtt gcggccggcc agatttaaat gagcggccgc agatatccag    5280
tgcagtaaaa aaaaaaaatg tttttttat ctactttccg caaaaatggg ttttattaac     5340
ttacatacat actagaattc tatattctaa aaacacaaat gatacttcta aaaaaaatca    5400
tgaatggcat caactctgaa tcaaatcttt gcagatgcac ctacttctca tttccactgt    5460
cacatcattt ttccagatct cgctgcctgt tatgtggccc acaaaccaag acacgtttta    5520
tggccattaa agctggctga tcgtcgccaa acaccaaata catatcaata tgtacattcg    5580
agaaagaagc gatcaaagaa gcgtcttcgg gcgagtagga gaatgcggag gagaaggaga    5640
acgagctgat ctagtatctc tccacaatcc aatgccaact gaccaactgg ccatattcgg    5700
agcaatttga agccaatttc catcgcctgg cgatcgctcc attcttggct atatgttttt    5760
caccgttccc ggggccattt tcaaagactc gtcggtaaga taagattgtg tcactcgctg    5820
tctctcttca tttgtcgaag aatgctgagg aatttcgcga tgacgtcggc gagtattttg    5880
aagaatgaga ataatttgta tttatacgaa aatcagttag tggaattttc tacaaaaaca    5940
tgttatctat agataatttt gttgcaaaat atgttgacta tgacaaagat tgtatgtata    6000
tacctttaat gtattctcat tttcttatgt atttataatg gcaatgatga tactgatgat    6060
attttaagat gatgccagac cacaggctga tttctgcgtc ttttgccgaa cgcagtgcat    6120
gtgcggttgt tgttttttgg aatagtttca attttcggac tgtccgcttt gatttcagtt    6180
tcttggctta ttcaaaaagc aaagtaaagc caaaaaagcg agatggcaat accaaatgcg    6240
gcaaaacggt agtggaagga aagggtgcg gggcagcgga aggaagggtg gggcggggcg     6300
tggcggggtc tgtggctggg cgcgacgtca ccgacgttgg agccactcct ttgaccatgt    6360
gtgcgtgtgt gtattattcg tgtctcgcca ctcgccggtt gttttttct ttttatctcg     6420
ctctctctag cgccatctcg tacgcatgct caacgcaccg catgttgccg tgtcctttat    6480
gcgtcatttt ggctcgaaat aggcaattat ttaaacaaag attagtcaac gaaaacgcta    6540
aaataaataa gtctacaata tggttactta ttgccatgtg tgtgcagcca acgatagcaa    6600
caaaagcaac aacacagtgg ctttccctct ttcacttttt gtttgcaagc gcgtgcgagc    6660
```

```
aagacggcac gaccggcaaa cgcaattacg ctgacaaaga gcagacgaag ttttggccga    6720
aaaacatcaa ggcgcctgat acgaatgcat ttgcaataac aattgcgata tttaatattg    6780
tttatgaagc tgtttgactt caaaacacac aaaaaaaaaa ataaaacaaa ttatttgaaa    6840
gagaattagg aatcggacag cttatcgtta cgggctaaca gcacaccgag acgaaatagc    6900
ttacctgacg tcacagcctc tggaagaact gccgccaagc agacgatgca gaggacgaca    6960
catagagtag cggagtaggc cagcgtagta cgcatgtgct tgtgtgtgag gcgtctctct    7020
cttcgtctcc tgtttgcgca aacgcataga ctgcactgag aaaatcgatt acctattttt    7080
tatgaatgaa tatttgcact attactattc aaaactatta agatagcaat cacattcaat    7140
agccaaatac tataccacct gagcgatgca acgaaatgat caatttgagc aaaaatgctg    7200
catatttagg acggcatcat tatagaaatg cttcttgctg tgtacttttc tctcgtctgg    7260
cagctgtttc gccgttattg ttaaaaccgg cttaagttag gtgtgttttc tacgactagt    7320
gatgccccta ctagaagatg tgtgttgcac aaatgtccct gaataaccaa tttgaagtgc    7380
agatagcagt aaacgtaagc taatatgaat attatttaac tgtaatgttt taatatcgct    7440
ggacattact aataaaccca ctataaacac atgtacatat gtatgttttg gcatacaatg    7500
agtagttggg gaaaaaatgt gtaaaagcac cgtgaccatc acagcataaa gataaccagc    7560
tgaagtatcg aatatgagta acccccaaat tgaatcacat gccgcaactg ataggaccca    7620
tggaagtaca ctcttcatgg cgatatacaa gacacacaca agcacgaaca cccagttgcg    7680
gaggaaattc tccgtaaatg aaaacccaat cggcgaacaa ttcatacccca tatatggtaa    7740 aagttttgaa cgcgacttga gagcggagag cattgcggct gataaggttt tagcgctaag    7800
cgggctttat aaaacgggct gcgggaccag ttttcatatc actaccgttt gagttcttgt    7860
gctgtgtgga tactcctccc gacacaaagc cgctccatca gccagcagtc gtctaatcca    7920
gagaccccgg atctagaacc aaaatggcta gaatggcctc ctccgagaac gtcatcaccg    7980
agttcatgcg cttcaaggtg cgcatggagg gcaccgtgaa cggccacgag ttcgagatcg    8040
agggcgaggg cgagggccgc ccctacgagg gccacaacac cgtgaagctg aaggtgacca    8100
agggcggccc cctgcccttc gcctgggaca tcctgtcccc ccagttccag tacggctcca    8160
aggtgtacgt gaagcacccc gccgacatcc ccgactacaa gaagctgtcc ttccccgagg    8220
gcttcaagtg ggagcgcgtg atgaacttcg aggacggcgg cgtggcgacc gtgacccagg    8280
actcctccct gcaggacggc tgcttcatct acaaggtgaa gttcatcggc gtgaacttcc    8340
cctccgacgg ccccgtgatg cagaagaaga ccatgggctg ggaggcctcc accgagcgcc    8400 tgtaccccg cgacggcgtg ctgaagggcg agacccacaa ggccctgaag ctgaaggacg    8460
gcggccacta cctggtggag ttcaagtcca tctacatggc caagaagccc gtgcagctgc    8520
ccggctacta ctacgtggac gccaagctgg acatcacctc ccacaacgag gactacacca    8580
tcgtggagca gtacgagcgc accgagggcc gccaccacct gttcctgtga gatccatgag    8640
caattagcat gaacgttctg aaaagcgcgt ttagctctcc actacttaca catattctat    8700
gctgcaatat tgaaaatcta ataaacaaaa ctaatgtaca ttaattcttc agttttgaat    8760
atccttctcc tgactttctt atttagaatt aatataatac tgcatacatt aatactgtaa    8820
atatgataag tacctgcaaa acactgcagc tcaagtctta atgaggttct gcgatagctt    8880
agcataatta gtaacttatc gcgcagaatt ccctaatgtt cccgacctac atgtacttct    8940
gatagttgcc gaggtcaaat gttgttgtat ttgtattata cctcaatatt ggtatattca    9000
atatctaata gtacccaatt caattgcaaa gatagtcatt aaaaaaacct aaatcacttg    9060
```

```
caaattgact tttctgccgg aaaagcaacc ttgacacaca aagttaatta gtttatctgg   9120
aagtcatgtg agaaatttgt aaataaaatt tttcgcagta atttaagtgg gcctaatccc   9180
ttttaagcat cttggtttta cgatgacacc gcaataaggt acaactttat attgttttg   9240 caatcagctt gagtctttat taggcatcag tctttctctc taagtttctt cgtgcaataa   9300
atgaggttcc aaactccgta gattttcct tctttgttga atccagatcc tgcaaagaaa   9360
aaagagcaaa cccctaggtc tgtccaggaa tgtattttcg tgtttgtcga tcgaccatgg   9420
tctcgagggg gggccttaat taagaggcgc gccaggtttc gactttcact tttctctatc   9480
actgataggg agtggtaaac tcgactttca cttttctcta tcactgatag ggagtggtaa   9540
actcgacttt cacttttctc tatcactgat agggagtggt aaactcgact ttcacttttc   9600
tctatcactg atagggagtg gtaaactcga ctttcacttt tctctatcac tgataggagg   9660
tggtaaactc gactttcact tttctctatc actgataggg agtggtaaac tcgactttca   9720
cttttctcta tcactgatag ggagtggtaa actcgaaaac gagcgccgga gtataaatag   9780
aggcgcttcg tctacggagc gacaattcaa ttcaaacaag caaagtgaac acgtcgctaa   9840
gcgaaagcta agcaaataaa caagcgcagc tgaacaagct aaacaatctg cggtaccctg   9900
gcggtaagtt gatcaaagga aacgcaaagt tttcaagaaa aacaaaact aatttgattt   9960 ataacccctt tagaaaccac catgggcagc cgcctggata agtccaaagt catcaactcc   10020
gcgttggagc tgttgaacga agttggcatt gagggactga cgacccgcaa gttggcgcag   10080
aagctgggcg tggagcagcc caccctctac tggcacgtga agaataagcg ggcgctgctg   10140
gatgccctgg ccatcgagat gctcgaccgc caccacacgc attttttgccc gttggaaggc   10200 gagtcctggc aggacttcct ccgcaataac gccaagtcgt tccgctgcgc tctgctgtcc   10260
caccgagacg gtgccaaagt ccatctcggc acgcgcccga ccgaaaagca atacgagaca   10320
ctggagaacc agctcgcgtt cctgtgccag caaggcttca gcctgaaaa tgctctctac   10380 gctctgagcg ccgtcggtca ctttaccctg gctgcgtgc tggaggacca agagcatcaa   10440
gtcgcaaaag aggagcgcga gaccccaaca accgattcga tgcccccact gctgcgtcag   10500
gcaatcgagc tgttcgatca tcaaggagcc gagccggcat tcctgttcgg cttggagctg   10560
attatctgcg gattggaaaa gcaactgaaa tgcgagtcgg gctcgggccc cgcgtacagc   10620
cgcgcgcgta cgaaaaacaa ttacgggtct accatcgagg gcctgctcga tctcccggac   10680
gacgacgccc ccgaagaggc ggggctggcg gctccgcgcc tgtcctttct ccccgcggga   10740
cacacgcgca gactgtcgac ggccccccg accgatgtca gctgggggga cgagctccac   10800
ttagacggcg aggacgtggc gatggcgcat gccgacgcgc tagacgattt cgatctggac   10860
atgttggggg acgggattc cccgggtccg ggatttaccc ccacgactc cgcccccta   10920 ggcgctctgg atatggccga cttcgagttt gagcagatgt ttaccgatgc ccttggaatt   10980
gacgagtacg tgggtagtt ctagagtcga cctcgaacgt taacgttaac gtaacgttaa   11040
ctcgaggagc ttgataacat tatacctaaa cccatggtca agagtaaaca tttctgcctt   11100
tgaagttgag aacacaatta agcatcccct ggttaaacct gacattcata cttgttaata   11160
gcgccataaa catagcacca atttcgaaga aatcagttaa aagcaattag caattagcaa   11220
ttagcaataa ctctgctgac ttcaaaacga gaagagttgc aagtatttgt aaggcacagt   11280
ttatagacca ccgacggctc attagggctc gtcatgtaac taagcgcggt gaaacccaat   11340
tgaacatata gtggaattat tattatcaat ggggaagatt taaccctcag gtagcaaagt   11400
```

| | |
|---|---|
| aatttaattg caaatagaga gtcctaagac taaataatat atttaaaaat ctggcccttt | 11460 |
| gaccttgctt gtcaggtgca tttgggttca atcgtaagtt gcttctatat aaacactttc | 11520 |
| cccatccccg caataatgaa gaataccgca gaataaagag agatttgcaa caaaaaataa | 11580 |
| aggcattgcg aaaactttt atgggggatc attacactcg ggcctacggt tacaattccc | 11640 |
| agccacttaa gcgacaagtt tggccaacaa tccatctaat agctaatagc gcaatcactg | 11700 |
| gtaatcgcaa gagtatatag gcaatagaac ccatggattt gaccaaaggt aaccgagaca | 11760 |
| atggagaagc aagaggattt caaactgaac acccacagta ctgtgtacta ccactggcgc | 11820 |
| gtttgggagc tccaagcggc gactgagatg tcctaaatgc acagcgacgg attcgcgcta | 11880 |
| tttagaaaga gagagcaata tttcaagaaa aacggcgccc | 11920 |

<210> SEQ ID NO 17
<211> LENGTH: 11570
<212> TYPE: DNA
<213> ORGANISM: Artificial Sequence
<220> FEATURE:
<223> OTHER INFORMATION: Synthetic construct, plasmid pLA517

<400> SEQUENCE: 17

| | |
|---|---|
| ggccgctcat ttaaatctgg ccggccgcaa ccattgtggg aaccgtgcga tcaaacaaac | 60 |
| gcgagatacc ggaagtactg aaaaacagtc gctccaggcc agtgggaaca tcgatgtttt | 120 |
| gttttgacgg accccttact ctcgtctcat ataaaccgaa gccagctaag atggtatact | 180 |
| tattatcatc ttgtgatgag gatgcttcta tcaacgaaag taccggtaaa ccgcaaatgg | 240 |
| ttatgtatta taatcaaact aaaggcggag tggacacgct agaccaaatg tgttctgtga | 300 |
| tgacctgcag taggaagacg aataggtggc ctatggcatt attgtacgga atgataaaca | 360 |
| ttgcctgcat aaattctttt attatataca gccataatgt cagtagcaag ggagaaaagg | 420 |
| tccaaagtcg caaaaaattt atgagaaacc tttacatgag cctgacgtca tcgtttatgc | 480 |
| gtaagcgttt agaagctcct actttgaaga gatatttgcg cgataatatc tctaatattt | 540 |
| tgccaaatga agtgcctggt acatcagatg acagtactga agagccagta atgaaaaaac | 600 |
| gtacttactg tacttactgc ccctctaaaa taaggcgaaa ggcaaatgca tcgtgcaaaa | 660 |
| aatgcaaaaa agttatttgt cgagagcata atattgatat gtgccaaagt tgtttctgac | 720 |
| tgactaataa gtaaatttg tttctattat gtataagtta agctaattac ttattttata | 780 |
| atacaacatg actgttttta aagtacaaaa taagtttatt tttgtaaaag agagaatgtt | 840 |
| taaaagtttt gttactttat agaagaaatt ttgagttttt gttttttttt aataaataaa | 900 |
| taaacataaa taaattgttt gttgaattta ttattagtat gtaagtgtaa atataataaa | 960 |
| acttaatatc tattcaaatt aataaataaa cctcgatata cagaccgata aaacacatgc | 1020 |
| gtcaattta cgcatgatta tctttaacgt acgtcacaat atgattatct ttctagggtt | 1080 |
| aaataatagt ttctaatttt tttattattc agcctgctgt cgtgaatacc gtatatctca | 1140 |
| acgctgtctg tgagattgtc gtattctagc cttttagtt tttcgctcat cgacttgata | 1200 |
| ttgtccgaca cattttcgtc gatttgcgtt ttgatcaaag acttgagcag agacacgtta | 1260 |
| atcaactgtt caaattgatc catattaacg atatcaaccc gatgcgtata tggtgcgtaa | 1320 |
| aatatatttt ttaaccctct tatactttgc actctgcgtt aatacgcgtt cgtgtacaga | 1380 |
| cgtaatcatg ttttcttttt tggataaaac tcctactgag tttgacctca tattagaccc | 1440 |
| tcacaagttg caaaacgtgg catttttac caatgaagaa tttaaagtta ttttaaaaaa | 1500 |
| tttcatcaca gatttaaaga agaaccaaaa attaaattat ttcaacagtt taatcgacca | 1560 |

```
gttaatcaac gtgtacacag acgcgtcggc aaaaaacacg cagcccgacg tgttggctaa   1620
aattattaaa tcaacttgtg ttatagtcac ggatttgccg tccaacgtgt tcctcaaaaa   1680
gttgaagacc aacaagttta cggacactat taattatttg attttgcccc acttcatttt   1740
gtgggatcac aattttgtta tattttaaac aaagcttggc actggccgtc gttttacaac   1800
gtcgtgactg ggaaaaccct ggcgttaccc aacttaatcg ccttgcagca catcccccttt  1860 tcgccagctg gcgtaatagc gaagaggccc gcaccgatcg cccttcccaa cagttgcgca   1920
gcctgaatgg cgaatggcgc ctgatgcggt attttctcct tacgcatctg tgcggtattt   1980
cacaccgcat atggtgcact ctcagtacaa tctgctctga tgccgcatag ttaagccagc   2040
cccgacaccc gccaacaccc gctgacgcgc cctgacgggc ttgtctgctc ccggcatccg   2100
cttacagaca gctgtgaccg tctccgggag ctgcatgtg tcagaggttt tcaccgtcat    2160
caccgaaacg cgcgagacga agggcctcg tgatacgcct atttttatag gttaatgtca    2220
tgataataat ggtttcttag acgtcaggtg cacttttcg gggaaatgtg cgcggaaccc    2280
ctatttgttt attttttctaa atacattcaa atatgtatcc gctcatgaga caataaccct   2340
gataaatgct tcaataatat tgaaaaagga agagtatgag tattcaacat ttccgtgtcg   2400
cccttattcc cttttttgcg gcattttgcc ttcctgtttt tgctcaccca gaaacgctgg   2460
tgaaagtaaa agatgctgaa gatcagttgg gtgcacgagt gggttacatc gaactggatc   2520
tcaacagcgg taagatcctt gagagttttc gccccgaaga acgttttcca atgatgagca   2580
cttttaaagt tctgctatgt ggcgcggtat tatcccgtat tgacgccggg caagagcaac   2640
tcggtcgccg catacactat tctcagaatg acttggttga gtactcacca gtcacagaaa   2700
agcatcttac ggatggcatg acagtaagag aattatgcag tgctgccata accatgagtg   2760
ataacactgc ggccaactta cttctgacaa cgatcggagg accgaaggag ctaaccgctt   2820
ttttgcacaa catgggggat catgtaactc gccttgatcg ttgggaaccg gagctgaatg   2880
aagccatacc aaacgacgag cgtgacacca cgatgcctgt agcaatggca acaacgttgc   2940
gcaaactatt aactggcgaa ctacttactc tagcttcccg gcaacaatta atagactgga   3000
tggaggcgga taaagttgca ggaccacttc tgcgctcggc ccttccggct ggctggttta   3060
ttgctgataa atctggagcc ggtgagcgtg ggtctcgcgg tatcattgca gcactggggc   3120
cagatggtaa gccctcccgt atcgtagtta tctacacgac ggggagtcag gcaactatgg   3180
atgaacgaaa tagacagatc gctgagatag gtgcctcact gattaagcat tggtaactgt   3240
cagaccaagt ttactcatat atactttaga ttgatttaaa acttcatttt taatttaaaa   3300
ggatctaggt gaagatcctt tttgataatc tcatgaccaa aatcccttaa cgtgagtttt   3360
cgttccactg agcgtcagac cccgtagaaa agatcaaagg atcttcttga gatccttttt   3420
ttctgcgcgt aatctgctgc ttgcaaacaa aaaaaccacc gctaccagcg gtggtttgtt   3480
tgccggatca agagctacca actctttttc cgaaggtaac tggcttcagc agagcgcaga   3540
taccaaatac tgtccttcta gtgtagccgt agttaggcca ccacttcaag aactctgtag   3600
caccgcctac atacctcgct ctgctaatcc tgttaccagt ggctgctgcc agtggcgata   3660
agtcgtgtct taccgggttg gactcaagac gatagttacc ggataaggcg cagcggtcgg   3720
gctgaacggg gggttcgtgc acacagccca gcttggagcg aacgacctac accgaactga   3780
gatacctaca gcgtgagcat tgagaaagcg ccacgcttcc cgaagggaga aaggcggaca   3840
ggtatccggt aagcggcagg gtcggaacag gagagcgcac gagggagctt ccaggggaa    3900
```

```
acgcctggta tctttatagt cctgtcgggt ttcgccacct ctgacttgag cgtcgatttt   3960
tgtgatgctc gtcagggggg cggagcctat ggaaaaacgc cagcaacgcg gccttttac    4020 ggttcctggc cttttgctgg ccttttgctc acatgttctt tcctgcgtta tcccctgatt   4080
ctgtggataa ccgtattacc gcctttgagt gagctgatac cgctcgccgc agccgaacga   4140
ccgagcgcag cgagtcagtg agcgaggaag cggaagagcg cccaatacgc aaaccgcctc   4200
tccccgcgcg ttggccgatt cattaatgca gctggcacga caggtttccc gactggaaag   4260
cgggcagtga gcgcaacgca attaatgtga gttagctcac tcattaggca ccccaggctt   4320
tacactttat gcttccggct cgtatgttgt gtggaattgt gagcggataa caatttcaca   4380
caggaaacag ctatgaccat gattacgaat tcgacctgc aggcatgcaa gcttgcatgc    4440
ctgcaggtcg acgctcgcgc gacttggttt gccattcttt agcgcgcgtc gcgtcacaca   4500
gcttggccac aatgtggttt tgtcaaacg aagattctat gacgtgttta agtttaggt     4560 cgagtaaagc gcaaatcttt tttaacccta gaaagatagt ctgcgtaaaa ttgacgcatg   4620
cattcttgaa atattgctct ctcttctaa atagcgcgaa tccgtcgctg tgcatttagg    4680
acatctcagt cgccgcttgg agctcccgtg aggcgtgctt gtcaatgcgg taagtgtcac   4740
tgattttgaa ctataacgac cgcgtgagtc aaaatgacgc atgattatct tttacgtgac   4800
ttttaagatt taactcatac gataattata ttgttatttc atgttctact acgtgataa    4860 cttattatat atatattttc ttgttataga tatcgtgact aatatataat aaaatgggta   4920
gttctttaga cgatgagcat atcctctctg ctcttctgca aagcgatgac gagcttgttg   4980
gtgaggattc tgacagtgaa atatcagatc acgtaagtga agatgacgtc cagagcgata   5040
cagaagaagc gtttatagat gaggtacatg aagtgcagcc aacgtcaagc ggtagtgaaa   5100 tattagcga acaaaatgtt attgaacaac caggttcttc attggcttct aacagaatct    5160
tgaccttgcc acagaggact attagaggta agaataaaca ttgttggtca acttcaaagt   5220
ccacgaggcg tagccgagtc tctgcactga acattgtcag atcggcccgg gcgccgtttc   5280
ccaaacgcgc cagtggtagt acacagtact gtgggtgttc agtttgaaat cctcttgctt   5340
ctccattgtc tcggttacct ttggtcaaat ccatgggttc tattgcctat atactcttgc   5400
gattaccagt gattgcgcta ttagctatta gatggattgt tggccaaact tgtcgcttaa   5460
gtggctggga attgtaaccg taggcccgag tgtaatgatc ccccataaaa agttttcgca   5520
atgcctttat ttttttgttgc aaatctctct ttattctgcg gtattcttca ttattgcggg   5580
gatggggaaa gtgtttatat agaagcaact tacgattgaa cccaaatgca cctgacaagc   5640
aaggtcaaag ggccagattt ttaaatatat tatttagtct taggactctc tatttgcaat   5700
taaattactt tgctacctga gggttaaatc ttccccattg ataataataa ttccactata   5760
tgttcaattg ggtttcaccg cgcttagtta catgacgagc cctaatgagc cgtcggtggt   5820
ctataaactg tgccttacaa atacttgcaa ctcttctcgt tttgaagtca gcagagttat   5880
tgctaattgc taattgctaa ttgcttttaa ctgatttctt cgaaattggt gctatgttta   5940
tggcgctatt aacaagtatg aatgtcaggt ttaaccaggg gatgcttaat tgtgttctca   6000
acttcaaagg cagaaatgtt tactcttgac catgggttta ggtataatgt tatcaagctc   6060
ctcgagttaa cgttacgtta acgttaacgt tcgaggtcga ctctagatta ttacagcatg   6120
tcgagatcaa agtcgtccaa agcatcagcg ggcaacatat ccaagtcaaa atcatcgaga   6180
gcgtccgccg gcagcatatc caggtcgaag tcatccaggg catcggcggg gcccgagccc   6240
gactcgcatt tcagttgctt ttccaatccg cagataatca gctccaagcc gaacaggaat   6300
```

```
gccggctcgg ctccttgatg atcgaacagc tcgattgcct gacgcagcag tgggggcatc   6360
gaatcggttg ttggggtctc gcgctcctct tttgcgactt gatgctcttg gtcctccagc   6420
acgcagccca gggtaaagtg accgacggcg ctcagagcgt agagagcatt tccaggctg    6480 aagccttgct ggcacaggaa cgcgagctgg ttctccagtg tctcgtattg cttttcggtc   6540
gggcgcgtgc cgagatggac tttggcaccg tctcggtggg acagcagagc gcagcggaac   6600
gacttggcgt tattgcggag gaagtcctgc caggactcgc cttccaacgg gcaaaaatgc   6660
gtgtggtggc ggtcgagcat ctcgatggcc agggcatcca gcagcgcccg cttattcttc   6720
acgtgccagt agagggtggg ctgctccacg cccagcttct gcgccaactt gcgggtcgtc   6780
agtccctcaa tgccaacttc gttcaacagc tccaacgcgg agttgatgac tttggactta   6840
tccaggcggt gcccatggt ggtttctaaa ggtgttataa atcaaattag ttttgttttt    6900
tcttgaaaac tttgcgtttc ctttgatcaa cttaccgcca gggtaccgca gattgtttag   6960
cttgttcagc tgcgcttgtt tatttgctta gctttcgctt agcgacgtgt tcactttgct   7020
tgtttgaatt gaattgtcgc tccgtagacg aagcgcctct atttatactc cggcgctcgt   7080
tttcgagttt accactccct atcagtgata gagaaaagtg aaagtcgagt ttaccactcc   7140
ctatcagtga tagagaaaag tgaaagtcga gtttaccact ccctatcagt gatagagaaa   7200
agtgaaagtc gagtttacca ctccctatca gtgatagaga aagtgaaag tcgagtttac   7260 cactccctat cagtgataga gaaagtgaa agtcgagttt accactccct atcagtgata   7320
gagaaaagtg aaagtcgagt ttaccactcc ctatcagtga tagagaaaag tgaaagtcga   7380
aacctggcgc gcctcttaat taaggccccc cctcgagacc atggtcgatc gacaaacacg   7440
aaaatacatt cctggacaga cctaggggtt tgctcttttt tctttgcagg atctggattc   7500 aacaagaag gaaaaatcta cggagtttgg aacctcattt attgcacgaa gaaacttaga   7560
gagaaagact gatgcctaat aaagactcaa gctgattgca aaacaatat aaagttgtac   7620 cttattgcgg tgtcatcgta aaaccaagat gcttaaaagg gattaggccc acttaaatta   7680
ctgcgaaaaa ttttatttac aaatttctca catgacttcc agataaacta attaactttg   7740
tgtgtcaagg ttgcttttcc ggcagaaaag tcaatttgca agtgatttag gtttttttaa   7800
tgactatctt tgcaattgaa ttgggtacta ttagatattg aatataccaa tattgaggta   7860
taatacaaat acaacaacat ttgacctcgg caactatcag aagtacatgt aggtcgggaa   7920
cattagggaa ttctgcgcga taagttacta attatgctaa gctatcgcag aacctcatta   7980
agacttgagc tgcagtgttt tgcaggtact tatcatattt acagtattaa tgtatgcagt   8040
attatattaa ttctaaataa gaaagtcagg agaaggatat tcaaaactga agaattaatg   8100
tacattagtt ttgtttatta gattttcaat attgcagcat agaatatgtg taagtagtgg   8160
agagctaaac gcgcttttca gaacgttcat gctaattgct catggatctc acaggaacag   8220
gtggtggcgg ccctcggtgc gctcgtactg ctccacgatg gtgtagtcct cgttgtggga   8280
ggtgatgtcc agcttggcgt ccacgtagta gtagccgggc agctgcacgg gcttcttggc   8340
catgtagatg gacttgaact ccaccaggta gtggccgccg tccttcagct tcagggcctt   8400
gtgggtctcg cccttcagca cgccgtcgcg ggggtacagg cgctcggtgg aggcctccca   8460
gcccatggtc ttcttctgca tcacggggcc gtcggagggg aagttcacgc cgatgaactt   8520
caccttgtag atgaagcagc cgtcctgcag ggaggagtcc tgggtcacgg tcgccacgcc   8580
gccgtcctcg aagttcatca cgcgctccca cttgaagccc tcggggaagg acagcttctt   8640
```

```
gtagtcgggg atgtcggcgg ggtgcttcac gtacaccttg gagccgtact ggaactgggg    8700
ggacaggatg tcccaggcga agggcagggg gccgcccttg gtcaccttca gcttcacggt    8760
gttgtggccc tcgtaggggc ggccctcgcc ctcgccctcg atctcgaact cgtggccgtt    8820
cacggtgccc tccatgcgca ccttgaagcg catgaactcg gtgatgacgt tctcggagga    8880
ggccattcta gccattttgg ttctagatcc ggggtctctg gattagacga ctgctggctg    8940
atggagcggc tttgtgtcgg gaggagtatc cacacagcac aagaactcaa acggtagtga    9000
tatgaaaact ggtcccgcag cccgttttat aaagcccgct tagcgctaaa accttatcag    9060
ccgcaatgct ctccgctctc aagtcgcgtt caaaacttt t accatatatg ggtatgaatt    9120
gttcgccgat tgggttttca tttacggaga atttcctccg caactgggtg ttcgtgcttg    9180
tgtgtgtctt gtatatcgcc atgaagagtg tacttccatg ggtcctatca gttgcggcat    9240
gtgattcaat ttgggggtta ctcatattcg atacttcagc tggttatctt tatgctgtga    9300
tggtcacggt gcttttacac atttttttccc caactactca ttgtatgcca aaacatacat    9360
atgtacatgt gtttatagtg ggtttattag taatgtccag cgatattaaa acattacagt    9420
taaataatat tcatattagc ttacgtttac tgctatctgc acttcaaatt ggttattcag    9480
ggacatttgt gcaacacaca tcttctagta ggggcatcac tagtcgtaga aaacacacct    9540
aacttaagcc ggttttaaca ataacggcga acagctgcc agacgagaga aaagtacaca    9600
gcaagaagca tttctataat gatgccgtcc taaatatgca gcattttgc tcaaattgat    9660 catttcgttg catcgctcag gtggtatagt atttggctat tgaatgtgat tgctatctta    9720
atagttttga atagtaatag tgcaaatatt cattcataaa aaataggtaa tcgatttttct    9780 cagtgcagtc tatgcgtttg cgcaaacagg agacgaagag agagacgcct cacacacaag    9840
cacatgcgta ctacgctggc ctactccgct actctatgtg tcgtcctctg catcgtctgc    9900
ttggcggcag ttcttccaga ggctgtgacg tcaggtaagc tatttcgtct cggtgtgctg    9960
ttagcccgta acgataagct gtccgattcc taattctctt tcaaataatt tgttttattt    10020
ttttttttgt gtgttttgaa gtcaaacagc ttcataaaca atattaaata tcgcaattgt    10080
tattgcaaat gcattcgtat caggcgcctt gatgttttc ggccaaaact tcgtctgctc    10140
tttgtcagcg taattgcgtt tgccggtcgt gccgtcttgc tcgcacgcgc ttgcaaacaa    10200
aaagtgaaag agggaaagcc actgtgttgt tgcttttgtt gctatcgttg gctgcacaca    10260
catggcaata agtaaccata ttgtagactt atttattta gcgttttcgt tgactaatct    10320 ttgttttaaat aattgcctat ttcgagccaa aatgacgcat aaaggacacg gcaacatgcg    10380
gtgcgttgag catgcgtacg agatggcgct agagagagcg agataaaaag aaaaaaacaa    10440
ccggcgagtg gcgagacacg aataatacac acacgcacac atggtcaaag gagtggctcc    10500
aacgtcggtg acgtcgcgcc cagccacaga ccccgccacg ccccgcccca cccttccttc    10560
cgctgccccg caccccttt c cttccactac cgttttgccg catttggtat tgccatctcg    10620
cttttttggc tttactttgc ttttttgaata agccaagaaa ctgaaatcaa agcggacagt    10680
ccgaaaattg aaactattcc aaaaaacaac aaccgcacat gcactgcgtt cggcaaaaga    10740
cgcagaaatc agcctgtggt ctggcatcat cttaaaatat catcagtatc atcattgcca    10800
ttataaatac ataagaaaat gagaatacat taaaggtata tacatacaat ctttgtcata    10860
gtcaacatat tttgcaacaa aattatctat agataacatg ttttttgtaga aaattccact    10920 aactgatttt cgtataaata caaattattc tcattcttca aaatactcgc cgacgtcatc    10980
gcgaaattcc tcagcattct tcgacaaatg aagagagaca gcgagtgaca caatcttatc    11040
```

```
ttaccgacga gtctttgaaa atggccccgg gaacggtgaa aaacatatag ccaagaatgg    11100
agcgatcgcc aggcgatgga aattggcttc aaattgctcc gaatatggcc agttggtcag    11160
ttggcattgg attgtggaga gatactagat cagctcgttc tccttctcct ccgcattctc    11220
ctactcgccc gaagacgctt ctttgatcgc ttctttctcg aatgtacata ttgatatgta    11280
tttggtgttt ggcgacgatc agccagcttt aatggccata aaacgtgtct tggtttgtgg    11340
gccacataac aggcagcgag atctggaaaa atgatgtgac agtggaaatg agaagtaggt    11400
gcatctgcaa agatttgatt cagagttgat gccattcatg atttttttta gaagtatcat    11460
ttgtgttttt agaatataga attctagtat gtatgtaagt taataaaacc cattttttgcg    11520 gaaagtagat aaaaaaaaca tttttttttt ttactgcact ggatatctgc                11570

<210> SEQ ID NO 18
<211> LENGTH: 11251
<212> TYPE: DNA
<213> ORGANISM: Artificial Sequence
<220> FEATURE:
<223> OTHER INFORMATION: Synthetic construct, plasmid pLA656

<400> SEQUENCE: 18
cgccaggcga tggaaattgg cttcaaattg ctccgaatat ggccagttgg tcagttggca       60
ttggattgtg gagagatact agatcagctc gttctccttc tcctccgcat tctcctactc      120
gcccgaagac gcttctttga tcgcttcttt ctcgaatgta catattgata tgtatttggt      180
gtttggcgac gatcagccag ctttaatggc cataaaacgt gtcttggttt gtgggccaca      240
taacaggcag cgagatctgg aaaaatgatg tgacagtgga aatgagaagt aggtgcatct      300
gcaaagattt gattcagagt tgatgccatt catgattttt tttagaagta tcatttgtgt      360
ttttagaata tagaattcta gtatgtatgt aagttaataa aacccatttt tgcggaaagt      420
agataaaaaa aacatttttt ttttttactg cactggatat ctgcggccgc tcatttaaat      480
ctggccggcc gcaaccattg tgggaaccgt gcgatcaaac aaacgcgaga taccggaagt      540
actgaaaaac agtcgctcca ggccagtggg aacatcgatg tttttgtttttg acggacccct      600 tactctcgtc tcatataaac cgaagccagc taagatggta tacttattat catcttgtga      660
tgaggatgct tctatcaacg aaagtaccgg taaaccgcaa atggttatgt attataatca      720
aactaaaggc ggagtggaca cgctagacca aatgtgttct gtgatgacct gcagtaggaa      780
gacgaatagg tggcctatgg cattattgta cggaatgata acattgcct  gcataaattc      840 tttttattata tacagccata atgtcagtag caagggagaa aaggtccaaa gtcgcaaaaa      900
atttatgaga aacctttaca tgagcctgac gtcatcgttt atgcgtaagc gtttagaagc      960
tcctactttg aagagatatt tgcgcgataa tatctctaat attttgccaa atgaagtgcc      1020
tggtacatca gatgacagta ctgaagagcc agtaatgaaa aaacgtactt actgtactta      1080
ctgcccctct aaaataaggc gaaaggcaaa tgcatcgtgc aaaaaatgca aaaaagttat      1140
ttgtcgagag cataatattg atatgtgcca agttgtttc tgactgacta ataagtataa      1200
tttgtttcta ttatgtataa gttaagctaa ttacttatttt tataatacaa catgactgtt      1260
tttaaagtac aaaataagtt tatttttgta aagagagaa tgtttaaaag ttttgttact      1320
ttatagaaga aattttgagt ttttgttttt ttttaataaa taaataaaca taaatataaatt      1380 gtttgttgaa tttattatta gtatgtaagt gtaaatataa taaaacttaa tatctattca      1440
aattaataaa taaacctcga tatacagacc gataaaacac atgcgtcaat tttacgcatg      1500
```

```
attatcttta acgtacgtca caatatgatt atctttctag ggttaaataa tagtttctaa    1560 ttttttatt attcagcctg ctgtcgtgaa taccgtatat ctcaacgctg tctgtgagat    1620
tgtcgtattc tagccttttt agttttccgc tcatcgactt gatattgtcc gacacatttt    1680
cgtcgatttg cgttttgatc aaagacttga gcagagacac gttaatcaac tgttcaaatt    1740
gatccatatt aacgatatca acccgatgcg tatatggtgc gtaaaatata tttttaacc    1800 ctcttatact ttgcactctg cgttaatacg cgttcgtgta cagacgtaat catgttttct    1860
tttttggata aaactcctac tgagtttgac ctcatattag accctcacaa gttgcaaaac    1920
gtggcatttt ttaccaatga agaatttaaa gttattttaa aaaatttcat cacagattta    1980
aagaagaacc aaaaattaaa ttatttcaac agtttaatcg accagttaat caacgtgtac    2040
acagacgcgt cggcaaaaaa cacgcagccc gacgtgttgg ctaaaattat taaatcaact    2100
tgtgttatag tcacggattt gccgtccaac gtgttcctca aaaagttgaa gaccaacaag    2160
tttacggaca ctattaatta tttgattttg ccccacttca ttttgtggga tcacaatttt    2220
gttatatttt aaacaaagct tggcactggc cgtcgtttta caacgtcgtg actgggaaaa    2280
ccctggcgtt acccaactta atcgccttgc agcacatccc cctttcgcca gctggcgtaa    2340
tagcgaagag gcccgcaccg atcgcccttc ccaacagttg cgcagcctga atggcgaatg    2400
gcgcctgatg cggtattttc tccttacgca tctgtgcggt atttcacacc gcatatggtg    2460
cactctcagt acaatctgct ctgatgccgc atagttaagc cagccccgac acccgccaac    2520
acccgctgac gcgccctgac gggcttgtct gctcccggca tccgcttaca gacaagctgt    2580
gaccgtctcc gggagctgca tgtgtcagag gttttcaccg tcatcaccga aacgcgcgag    2640
acgaaagggc ctcgtgatac gcctattttt ataggttaat gtcatgataa taatggtttc    2700
ttagacgtca ggtggcactt ttcggggaaa tgtgcgcgga accccttatt gtttatttt    2760 ctaaatacat tcaaatatgt atccgctcat gagacaataa ccctgataaa tgcttcaata    2820
atattgaaaa aggaagagta tgagtattca acatttccgt gtcgccctta ttccctttt    2880 tgcggcattt tgccttcctg ttttgctca cccagaaacg ctggtgaaag taaaagatgc    2940
tgaagatcag ttgggtgcac gagtgggtta catcgaactg gatctcaaca gcggtaagat    3000
ccttgagagt tttcgccccg aagaacgttt tccaatgatg agcactttta aagttctgct    3060
atgtggcgcg gtattatccc gtattgacgc cgggcaagag caactcggtc gccgcataca    3120
ctattctcag aatgacttgg ttgagtactc accagtcaca gaaaagcatc ttacggatgg    3180
catgacagta agagaattat gcagtgctgc cataaccatg agtgataaca ctgcggccaa    3240
cttacttctg acaacgatcg gaggaccgaa ggagctaacc gcttttttgc acaacatggg    3300
ggatcatgta actcgccttg atcgttggga accggagctg aatgaagcca taccaaacga    3360
cgagcgtgac accacgatgc ctgtagcaat ggcaacaacg ttgcgcaaac tattaactgg    3420
cgaactactt actctagctt cccggcaaca attaatagac tggatggagg cggataaagt    3480
tgcaggacca cttctgcgct cggcccttcc ggctggctgg tttattgctg ataaatctgg    3540
agccggtgag cgtgggtctc gcggtatcat tgcagcactg gggccagatg gtaagccctc    3600
ccgtatcgta gttatctaca cgacggggag tcaggcaact atggatgaac gaaatagaca    3660
gatcgctgag ataggtgcct cactgattaa gcattggtaa ctgtcagacc aagtttactc    3720
atatatactt tagattgatt taaaacttca ttttaatttt aaaaggatct aggtgaagat    3780
cctttttgat aatctcatga ccaaaatccc ttaacgtgag ttttcgttcc actgagcgtc    3840
agaccccgta gaaaagatca aaggatcttc ttgagatcct tttttctgc gcgtaatctg    3900
```

```
ctgcttgcaa acaaaaaaac caccgctacc agcggtggtt tgtttgccgg atcaagagct    3960
accaactctt tttccgaagg taactggctt cagcagagcg cagataccaa atactgtcct    4020
tctagtgtag ccgtagttag gccaccactt caagaactct gtagcaccgc ctacatacct    4080
cgctctgcta atcctgttac cagtggctgc tgccagtggc gataagtcgt gtcttaccgg    4140
gttggactca agacgatagt taccggataa ggcgcagcgg tcgggctgaa cggggggttc    4200
gtgcacacag cccagcttgg agcgaacgac ctacaccgaa ctgagatacc tacagcgtga    4260
gcattgagaa agcgccacgc ttcccgaagg gagaaaggcg gacaggtatc cggtaagcgg    4320
cagggtcgga acaggagagc gcacgaggga gcttccaggg ggaaacgcct ggtatcttta    4380
tagtcctgtc gggtttcgcc acctctgact tgagcgtcga ttttttgtgat gctcgtcagg    4440
ggggcggagc ctatggaaaa acgccagcaa cgcggccttt ttacggttcc tggccttttg    4500
ctggcctttt gctcacatgt tctttcctgc gttatcccct gattctgtgg ataaccgtat    4560
taccgccttt gagtgagctg ataccgctcg ccgcagccga acgaccgagc gcagcgagtc    4620
agtgagcgag gaagcggaag agcgcccaat acgcaaaccg cctctccccg cgcgttggcc    4680
gattcattaa tgcagctggc acgacaggtt cccgactgg aaagcgggca gtgagcgcaa    4740
cgcaattaat gtgagttagc tcactcatta ggcaccccag gctttacact ttatgcttcc    4800
ggctcgtatg ttgtgtggaa ttgtgagcgg ataacaattt cacacaggaa acagctatga    4860
ccatgattac gaatttcgac ctgcaggcat gcaagcttgc atgcctgcag gtcgacgctc    4920
gcgcgacttg gtttgccatt ctttagcgcg cgtcgcgtca cacagcttgg ccacaatgtg    4980
gttttttgtca acgaagatt ctatgacgtg tttaaagttt aggtcgagta aagcgcaaat    5040
cttttttaac cctagaaaga tagtctgcgt aaaattgacg catgcattct gaaatattg    5100
ctctctcttt ctaaatagcg cgaatccgtc gctgtgcatt taggacatct cagtcgccgc    5160
ttggagctcc cgtgaggcgt gcttgtcaat gcggtaagtg tcactgattt tgaactataa    5220
cgaccgcgtg agtcaaaatg acgcatgatt atcttttacg tgacttttaa gatttaactc    5280
atacgataat tatattgtta tttcatgttc tacttacgtg ataacttatt atatatatat    5340
tttcttgtta tagatatcgt gactaatata taataaaatg ggtagttctt tagacgatga    5400
gcatatcctc tctgctcttc tgcaaagcga tgacgagctt gttggtgagg attctgacag    5460
tgaaatatca gatcacgtaa gtgaagatga cgtccgagagc gatacagaag aagcgtttat    5520
agatgaggta catgaagtgc agccaacgtc aagcggtagt gaaatattag acgaacaaaa    5580
tgttattgaa caaccaggtt cttcattggc ttctaacaga atcttgacct tgccacagag    5640
gactattaga ggtaagaata aacattgttg gtcaacttca aagtccacga ggcgtagccg    5700
agtctctgca ctgaacattg tcagatcggc ccgggcgccg ttttcttga aatattgctc    5760
tctctttcta aatagcgcga atccgtcgct gtgcatttag gacatctcag tcgccgcttg    5820
gagctcccaa acgcgccagt ggtagtacac agtactgtgg gtgttcagtt tgaaatcctc    5880
ttgcttctcc attgtctcgg ttaccttggg tcaaatccat gggttctatt gcctatatac    5940
tcttgcgatt accagtgatt gcgctattag ctattagatg gattgttggc caaacttgtc    6000
gcttaagtgg ctgggaattg taaccgtagg cccgagtgta atgatccccc ataaaaagtt    6060
ttcgcaatgc ctttatttt tgttgcaaat ctctctttat tctgcggtat tcttcattat    6120
tgcggggatg gggaaagtgt ttatatagaa gcaacttacg attgaaccca aatgcacctg    6180
acaagcaagg tcaaagggcc agattttaa atatattatt tagtcttagg actctctatt    6240
```

-continued

```
tgcaattaaa ttactttgct acctgagggt taaatcttcc ccattgataa taataattcc    6300
actatatgtt caattgggtt tcaccgcgct tagttacatg acgagcccta atgagccgtc    6360
ggtggtctat aaactgtgcc ttacaaatac ttgcaactct tctcgttttg aagtcagcag    6420
agttattgct aattgctaat tgctaattgc ttttaactga tttcttcgaa attggtgcta    6480
tgtttatggc gctattaaca agtatgaatg tcaggtttaa ccaggggatg cttaattgtg    6540
ttctcaactt caaaggcaga aatgtttact cttgaccatg ggtttaggta taatgttatc    6600
aagctcctcg agttaacgtt acgttaacgt taacgttcga ggtcgactct agaactaccc    6660
accgtactcg tcaattccaa ggcatcggt  aaacatctgc tcaaactcga agtcggccat    6720
atccagagcg ccgtaggggg cggagtcgtg gggggtaaat cccggacccg ggaatcccc     6780 gtcccccaac atgtccagat cgaaatcgtc tagcgcgtcg gcatgcgcca tcgccacgtc    6840
ctcgccgtct aagtggagct cgtcccccag gctgacatcg gtcgggggggg ccgtcgacag   6900 tctgcgcgtg tgtcccgcgg ggagaaagga caggcgcgga gccgccagcc ccgcctcttc    6960
gggggcgtcg tcgtccggga gatcgagcag gccctcgatg gtagaccggt aattgttttt    7020
cgtacgcgcg cggctgtacg cggggcccga gcccgactcg catttcagtt gcttttccaa    7080
tccgcagata atcagctcca agccaacag  gaatgccggc tcggctcctt gatgatcgaa    7140
cagctcgatt gcctgacgca gcagtggggg catcgaatcg gttgttgggg tctcgcgctc    7200
ctcttttgcg acttgatgct cttggtcctc cagcacgcag cccagggtaa agtgaccgac    7260
ggcgctcaga gcgtagagag cattttccag gctgaagcct tgctggcaca ggaacgcgag    7320
ctggttctcc agtgtctcgt attgcttttc ggtcgggcgc gtgccgagat ggactttggc    7380
accgtctcgg tgggacagca gagcgcagcg gaacgacttg gcgttattgc ggaggaagtc    7440
ctgccaggac tcgccttcca acgggcaaaa atgcgtgtgg tggcggtcga gcatctcgat    7500
ggccagggca tccagcagcg cccgcttatt cttcacgtgc cagtagaggg tgggctgctc    7560
cacgcccagc ttctgcgcca acttgcgggt cgtcagtccc tcaatgccaa cttcgttcaa    7620
cagctccaac gcggagttga tgactttgga cttatccagg cggctgccca tggtggtttc    7680
taaaggtgtt ataaatcaaa ttagttttgt tttttcttga aaactttgcg tttcctttga    7740
tcaacttacc gccagggtac cgcagattgt ttagcttgtt cagctgcgct tgtttatttg    7800
cttagctttc gcttagcgac gtgttcactt tgcttgtttg aattgaattg tcgctccgta    7860
gacgaagcgc ctctatttat actccggcgc tcgttttcga gtttaccact ccctatcagt    7920
gatagagaaa agtgaaagtc gagtttacca ctccctatca gtgatagaga aaagtgaaag    7980
tcgagtttac cactccctat cagtgataga gaaaagtgaa agtcgagttt accactccct    8040
atcagtgata gagaaaagtg aaagtcgagt ttaccactcc ctatcagtga tagagaaaag    8100
tgaaagtcga gtttaccact ccctatcagt gatagagaaa agtgaaagtc gagtttacca    8160
ctccctatca gtgatagaga aaagtgaaag tcgaaacctg gcgcgcctct taattaactc    8220
gcgttaagat acattgatga gtttggacaa accacaacta gaatgcagtg aaaaaaatgc    8280
tttatttgtg aaatttgtga tgctattgct ttatttgtaa ccattataag ctgcaataaa    8340
caagttaaca acaacaattg cattcatttt atgtttcagg ttcaggggga ggtgtgggag    8400
gttttttaaa gcaagtaaaa cctctacaaa tgtggtatgg ctgattatga tcagttatct    8460
agatccggtg gatcttacgg gtcctccacc ttccgctttt tcttgggtcg agatctcagg    8520
aacaggtggt ggcggccctc ggtgcgctcg tactgctcca cgatggtgta gtcctcgttg    8580
tgggaggtga tgtccagctt ggcgtccacg tagtagtagc cgggcagctg cacgggcttc    8640
```

```
ttggccatgt agatggactt gaactccacc aggtagtggc cgccgtcctt cagcttcagg   8700
gccttgtggg tctcgccctt cagcacgccg tcgcggggt acaggcgctc ggtggaggcc    8760
tcccagccca tggtcttctt ctgcatcacg gggccgtcgg aggggaagtt cacgccgatg   8820
aacttcacct tgtagatgaa gcagccgtcc tgcaggagg agtcctgggt cacggtcgcc    8880
acgccgccgt cctcgaagtt catcacgcgc tcccacttga agccctcggg gaaggacagc   8940
ttcttgtagt cggggatgtc ggcggggtgc ttcacgtaca ccttggagcc gtactggaac   9000 tgggggaca ggatgtccca ggcgaagggc aggggccgc ccttggtcac cttcagcttc     9060
acggtgttgt ggccctcgta ggggcggcc tcgccctcgc cctcgatctc gaactcgtgg    9120
ccgttcacgg tgccctccat gcgcaccttg aagcgcatga actcggtgat gacgttctcg   9180
gaggaggcca tggtggcgac cggtttgcgc ttcttcttgg gtggggtggg atccccgatc   9240
tgcattttgg attattctgc gggtcaaaat agagatgtgg aaaattagta cgaaatcaaa   9300
tgagtttcgt tgaaattaca aaactattga aactaacttc ctggctgggg aataaaaatg   9360
ggaaacttat ttatcgacgc caactttgtt gagaaacccc tattaaccct ctacgaatat   9420
tggaacaaag gaaagcgaag aaacaggaac aaaggtagtt gagaaacctg ttccgttgct   9480
cgtcatcgtt ttcataatgc gagtgtgtgc atgtatatat acacagctga aacgcatgca   9540
tacacattat tttgtgtgta tatggtgacg tcacaactac taagcaataa gaaattttcc   9600
agacgtggct ttcgtttcaa gcaacctact ctatttcagc taaaaataag tggatttcgt   9660
tggtaaaata cttcaattaa gcaaagaact aactaactaa taacatgcac acaaatgctc   9720
gagtgcgttc gtgatttctc gaattttcaa atgcgtcact gcgaatttca caatttgcca   9780
ataaatcttg gcgaaaatca acacgcaagt tttatttata gatttgtttg cgttttgatg   9840
ccaattgatt gggaaaacaa gatgcgtggc tgccaatttc ttatttttgta attacgtaga   9900 gcgttgaata aaaaaaaat ggccgaacaa agaccttgaa atgcagtttt tcttgaaatt    9960
actcaacgtc ttgttgctct tattactaat tggtaacagc gagttaaaaa cttacgtttc  10020
ttgtgacttt cgagaatgtt cttttaattg tactttaatc accaacaatt aagtatataaat 10080 ttttcgctga ttgcgcttta ctttctgctt gtacttgctg ctgcaaatgt caattggttt  10140
tgaaggcgac cgttcgcgaa cgctgtttat ataccttcgg tgtccgttga aaatcactaa  10200
aaaataccgt agtgttcgta acactttagt acagagaaaa aaaattgtgc cgaaatgttt  10260
ttgatacgta cgaataccttt gtattaaaat ttttatgat ttctgtgtat cacttttttt   10320
ttgtgttttt cgtttaaact caccacagta caaaacaata aatatttttt aagacaattt   10380
caaattgaga cctttctcgt actgacttga ccggctgaat gaggatttct acctagacga  10440
cctacttctt accatgacat tgaatgcaat gccacctttg atctaaactt acaaaagtcc   10500
aaggcttgtt aggattggtg tttatttagt ttgcttttga aatagcactg tcttctctac   10560
cggctataat tttgaaactc gcagcttgac tggaaattta aaagtaatt ctgtgtaggt    10620 aaagggtgtt ttaaagtgt gatgtgttga gcgttgcggc aacgactgct atttatgtat   10680
atattttcaa aacttattgt ttttgaagtg ttttaaatgg agctatctgg caacgctgcg   10740
cataatctta cacaagcttt tcttaatcca ttttaagtg aaatttgttt ttactctttc    10800
ggcaaataat tgttaaatcg ctttaagtgg gcttacatct ggataagtaa tgaaaacctg  10860
catattataa tattaaaaca tataatccac tgtgcttttcc ccgtgtgtgg ccatataccct 10920 aaaaaagttt attttcgcag agccccgcac ggtcacacta cggttcggcg attttcgatt   10980
```

-continued

```
ttggacagta ctgattgcaa gcgcaccgaa agcaaaatgg agctggagat tttgaacgcg     11040
aagaacagca agccgtacgg caaggtgaag gtgccctccg cgccacgcc catcggcgat      11100 ctgcgcgccc taattcacaa gaccctgaag cagaccccac acgcgaatcg ccagtcgctt     11160
cgtctggaac tgaagggcaa aagcctgaaa gatacggaca cattggaatc tctgtcgctg     11220
cgttccggcg acaagatcgg ggtaccgcga t                                     11251
```

<210> SEQ ID NO 19
<211> LENGTH: 9468
<212> TYPE: DNA
<213> ORGANISM: Artificial Sequence
<220> FEATURE:
<223> OTHER INFORMATION: Synthetic construct, plasmid pLA710

<400> SEQUENCE: 19

```
ggccgctcat ttaaatctgg ccggccgcaa ccattgtggg aaccgtgcga tcaaacaaac       60
gcgagatacc ggaagtactg aaaaacagtc gctccaggcc agtgggaaca tcgatgtttt      120
gttttgacgg accccttact ctcgtctcat ataaaccgaa gccagctaag atggtatact      180
tattatcatc ttgtgatgag gatgcttcta tcaacgaaag taccggtaaa ccgcaaatgg      240
ttatgtatta taatcaaact aaaggcggag tggacacgct agaccaaatg tgttctgtga      300
tgacctgcag taggaagacg aataggtggc ctatggcatt attgtacgga atgataaaca      360
ttgcctgcat aaattctttt attatataca gccataatgt cagtagcaag ggagaaaagg      420
tccaaagtcg caaaaaattt atgagaaacc tttacatgag cctgacgtca tcgtttatgc      480
gtaagcgttt agaagctcct actttgaaga gatatttgcg cgataatatc tctaatattt      540
tgccaaatga agtgcctggt acatcagatg acagtactga agagccagta atgaaaaaac      600
gtacttactg tacttactgc ccctctaaaa taaggcgaaa ggcaaatgca tcgtgcaaaa      660
aatgcaaaaa agttatttgt cgagagcata atattgatat gtgccaaagt gtttctgac       720 tgactaataa gtataatttg tttctattat gtataagtta agctaattac ttatttata       780 atacaacatg actgttttta aagtacaaaa taagtttatt tttgtaaaag agagaatgtt      840
taaaagtttt gttactttat agaagaaatt ttgagttttt gttttttttt aataaataaa      900
taaacataaa taaattgttt gttgaattta ttattagtat gtaagtgtaa atataataaa      960
acttaatatc tattcaaatt aataaataaa cctcgatata cagaccgata aaacacatgc     1020
gtcaatttta cgcatgatta tctttaacgt acgtcacaat atgattatct ttctagggtt     1080
aaataatagt ttctaatttt tttattattc agcctgctgt cgtgaatacc gtatatctca     1140
acgctgtctg tgagattgtc gtattctagc ctttttagtt tttcgctcat cgacttgata     1200
ttgtccgaca cattttcgtc gatttgcgtt ttgatcaaag acttgagcag agacacgtta     1260
atcaactgtt caaattgatc catattaacg atatcaaccc gatgcgtata tggtgcgtaa     1320
aatatatttt ttaaccctct tatactttgc actctgcgtt aatacgcgtt cgtgtacaga     1380
cgtaatcatg ttttcttttt tggataaaac tcctactgag tttgacctca tattagaccc     1440
tcacaagttg caaaacgtgg cattttttac caatgaagaa tttaaagtta ttttaaaaaa     1500
tttcatcaca gatttaaaga agaaccaaaa attaaattat tcaacagttt aatcgacca      1560 gttaatcaac gtgtacacag acgcgtcggc aaaaaacacg cagcccgacg tgttggctaa     1620
aattattaaa tcaacttgtg ttatagtcac ggatttgccg tccaacgtgt tcctcaaaaa     1680
gttgaagacc aacaagttta cggacactat taattatttg attttgcccc acttcatttt     1740
gtgggatcac aatttttgtta tattttaaac aaagcttggc actggccgtc gttttacaac     1800
```

```
gtcgtgactg ggaaaaccct ggcgttaccc aacttaatcg ccttgcagca catcccccctt   1860 tcgccagctg gcgtaatagc gaagaggccc gcaccgatcg cccttcccaa cagttgcgca   1920
gcctgaatgg cgaatggcgc ctgatgcggt attttctcct tacgcatctg tgcggtattt   1980
cacaccgcat atggtgcact ctcagtacaa tctgctctga tgccgcatag ttaagccagc   2040
cccgacaccc gccaacaccc gctgacgcgc cctgacgggc ttgtctgctc ccggcatccg   2100
cttacagaca agctgtgacc gtctccggga gctgcatgtg tcagaggttt tcaccgtcat   2160
caccgaaacg cgcgagacga aagggcctcg tgatacgcct atttttatag gttaatgtca   2220
tgataataat ggtttcttag acgtcaggtg cacttttcg gggaaatgtg cgcggaaccc   2280
ctatttgttt attttctaa atacattcaa atatgtatcc gctcatgaga caataaccct   2340
gataaatgct tcaataatat tgaaaaagga gagtatgag tattcaacat ttccgtgtcg   2400
cccttattcc cttttttgcg gcattttgcc ttcctgtttt tgctcaccca gaaacgctgg   2460
tgaaagtaaa agatgctgaa gatcagttgg gtgcacgagt gggttacatc gaactggatc   2520
tcaacagcgg taagatcctt gagagttttc gccccgaaga acgttttcca atgatgagca   2580
cttttaaagt tctgctatgt ggcgcggtat tatcccgtat tgacgccggg caagagcaac   2640
tcggtcgccg catacactat tctcagaatg acttggttga gtactcacca gtcacagaaa   2700
agcatcttac ggatggcatg acagtaagag aattatgcag tgctgccata accatgagtg   2760
ataacactgc ggccaactta cttctgacaa cgatcggagg accgaaggag ctaaccgctt   2820
ttttgcacaa catgggggat catgtaactc gccttgatcg ttgggaaccg gagctgaatg   2880
aagccatacc aaacgacgag cgtgacacca cgatgcctgt agcaatggca acaacgttgc   2940
gcaaactatt aactggcgaa ctacttactc tagcttcccg gcaacaatta atagactgga   3000
tggaggcgga taaagttgca ggaccacttc tgcgctcggc ccttccggct ggctggttta   3060
ttgctgataa atctggagcc ggtgagcgtg ggtctcgcgg tatcattgca gcactggggc   3120
cagatggtaa gccctcccgt atcgtagtta tctacacgac ggggagtcag gcaactatgg   3180
atgaacgaaa tagacagatc gctgagatag gtgcctcact gattaagcat tggtaactgt   3240
cagaccaagt ttactcatat atactttaga ttgatttaaa acttcatttt taatttaaaa   3300
ggatctaggt gaagatcctt tttgataatc tcatgaccaa aatcccttaa cgtgagtttt   3360
cgttccactg agcgtcagac cccgtagaaa agatcaaagg atcttcttga gatcctttt   3420 ttctgcgcgt aatctgctgc ttgcaaacaa aaaaaccacc gctaccagcg gtggtttgtt   3480
tgccggatca agagctacca actctttttc cgaaggtaac tggcttcagc agagcgcaga   3540
taccaaatac tgtccttcta gtgtagccgt agttaggcca ccacttcaag aactctgtag   3600
caccgcctac atacctcgct ctgctaatcc tgttaccagt ggctgctgcc agtggcgata   3660
agtcgtgtct taccgggttg gactcaagac gatagttacc ggataaggcg cagcggtcgg   3720
gctgaacggg gggttcgtgc acacagccca gcttggagcg aacgacctac accgaactga   3780
gatacctaca gcgtgagcat tgagaaagcg ccacgcttcc cgaagggaga aaggcggaca   3840
ggtatccggt aagcggcagg gtcggaacag gagagcgcac gagggagctt ccaggggaa   3900 acgcctggta tctttatagt cctgtcgggt ttcgccacct ctgacttgag cgtcgatttt   3960
tgtgatgctc gtcagggggg cggagcctat ggaaaaacgc cagcaacgcg gcctttttac   4020
ggttcctggc cttttgctgg ccttttgctc acatgttctt tcctgcgtta tcccctgatt   4080
ctgtggataa ccgtattacc gcctttgagt gagctgatac cgctcgccgc agccgaacga   4140
```

```
ccgagcgcag cgagtcagtg agcgaggaag cggaagagcg cccaatacgc aaaccgcctc    4200
tccccgcgcg ttggccgatt cattaatgca gctggcacga caggtttccc gactggaaag    4260
cgggcagtga gcgcaacgca attaatgtga gttagctcac tcattaggca ccccaggctt    4320
tacactttat gcttccggct cgtatgttgt gtggaattgt gagcggataa caatttcaca    4380
caggaaacag ctatgaccat gattacgaat tcgacctgc aggcatgcaa gcttgcatgc     4440
ctgcaggtcg acgctcgcgc gacttggttt gccattcttt agcgcgcgtc gcgtcacaca    4500
gcttggccac aatgtggttt ttgtcaaacg aagattctat gacgtgttta agtttaggt     4560 cgagtaaagc gcaaatcttt tttaaccta gaaagatagt ctgcgtaaaa ttgacgcatg     4620
cattcttgaa atattgctct ctctttctaa atagcgcgaa tccgtcgctg tgcatttagg    4680
acatctcagt cgccgcttgg agctcccgtg aggcgtgctt gtcaatgcgg taagtgtcac    4740
tgattttgaa ctataacgac cgcgtgagtc aaaatgacgc atgattatct tttacgtgac    4800
ttttaagatt taactcatac gataattata ttgttatttc atgttctact tacgtgataa    4860
cttattatat atatattttc ttgttataga tatcgtgact aatatataat aaaatgggta    4920
gttctttaga cgatgagcat atcctctctg ctcttctgca aagcgatgac gagcttgttg    4980
gtgaggattc tgacagtgaa atatcagatc acgtaagtga agatgacgtc cagagcgata    5040
cagaagaagc gtttatagat gaggtacatg aagtgcagcc aacgtcaagc ggtagtgaaa    5100 tattagcga acaaaatgtt attgaacaac caggttcttc attggcttct aacagaatct     5160
tgaccttgcc acagaggact attagaggta agaataaaca ttgttggtca acttcaaagt    5220
ccacgaggcg tagccgagtc tctgcactga acattgtcag atcggcccgg gcgccgtttt    5280
tcttgaaata ttgctctctc tttctaaata gcgcgaatcc gtcgctgtgc atttaggaca    5340
tctcagtcgc cgcttggagc tcccaaacgc gccagtggta gtacacagta ctgtgggtgt    5400
tcagtttgaa atcctcttgc ttctccattg tctcggttac cttggtcaa atccatgggt     5460 tctattgcct atatactctt gcgattacca gtgattgcgc tattagctat tagatggatt    5520
gttggccaaa cttgtcgctt aagtggctgg gaattgtaac cgtaggcccg agtgtaatga    5580
tcccccataa aaagttttcg caatgccttt atttttgtt gcaaatctct ctttattctg     5640
cggtattctt cattattgcg gggatgggga aagtgtttat atagaagcaa cttacgattg    5700
aacccaaatg cacctgacaa gcaaggtcaa agggccagat ttttaaatat attatttagt    5760
cttaggactc tctatttgca attaaattac tttgctacct gagggttaaa tcttccccat    5820
tgataataat aattccacta tatgttcaat tgggtttcac cgcgcttagt tacatgacga    5880
gccctaatga gccgtcggtg gtctataaac tgtgccttac aaatacttgc aactcttctc    5940
gttttgaagt cagcagagtt attgctaatt gctaattgct aattgctttt aactgatttc    6000
ttcgaaattg gtgctatgtt tatggcgcta ttaacaagta tgaatgtcag gtttaaccag    6060
gggatgctta attgtgttct caacttcaaa ggcagaaatg tttactcttg accatgggtt    6120
taggtataat gttatcaagc ccctcgagtt aacgttacgt taacgttaac gttcgaggtc    6180
gactctagaa ctacccaccg tactcgtcaa ttccaagggc atcggtaaac atctgctcaa    6240
actcgaagtc ggccatatcc agagcgccgt aggggggcga gtcgtggggg gtaaatcccg    6300
gacccgggga atccccgtcc cccaacatgt ccagatcgaa atcgtctagc gcgtcggcat    6360
gcgccatcgc cacgtcctcg ccgtctaagt ggagctcgtc ccccaggctg acatcggtcg    6420
ggggggccgt cgacagtctg cgcgtgtgtc ccgcggggag aaaggacagg cgcggagccg    6480
ccagccccgc ctcttcgggg gcgtcgtcgt ccgggagatc gagcaggccc tcgatggtag    6540
```

-continued

```
acccgtaatt gtttttcgta cgcgcgcggc tgtacgcggg gcccgagccc gactcgcatt    6600
tcagttgctt ttccaatccg cagataatca gctccaagcc gaacaggaat gccggctcgg    6660
ctccttgatg atcgaacagc tcgattgcct gacgcagcag tggggcatc gaatcggttg     6720 ttggggtctc gcgctcctct tttgcgactt gatgctcttg gtcctccagc acgcagccca    6780
gggtaaagtg accgacggcg ctcagagcgt agagagcatt ttccaggctg aagccttgct    6840
ggcacaggaa cgcgagctgg ttctccagtg tctcgtattg cttttcggtc gggcgcgtgc    6900
cgagatggac tttggcaccg tctcggtggg acagcagagc gcagcggaac gacttggcgt    6960
tattgcggag gaagtcctgc caggactcgc cttccaacgg gcaaaaatgc gtgtggtggc    7020
ggtcgagcat ctcgatggcc agggcatcca gcagcgcccg cttattcttc acgtgccagt    7080
agagggtggg ctgctccacg cccagcttct gcgccaactt gcgggtcgtc agtccctcaa    7140
tgccaacttc gttcaacagc tccaacgcgg agttgatgac tttggactta tccaggcggc    7200
tgcccatggt ggtttctaaa ggtgttataa atcaaattag ttttgttttt tcttgaaaac    7260
tttgcgtttc ctttgatcaa cttaccgcca gggtaccgca gattgtttag cttgttcagc    7320
tgcgcttgtt tatttgctta gctttcgctt agcgacgtgt tcactttgct tgtttgaatt    7380
gaattgtcgc tccgtagacg aagcgcctct atttatactc cggcgctcgt tttcgagttt    7440
accactccct atcagtgata gagaaaagtg aaagtcgagt ttaccactcc ctatcagtga    7500
tagagaaaag tgaaagtcga gtttaccact ccctatcagt gatagagaaa agtgaaagtc    7560
gagtttacca ctccctatca gtgatagaga aagtgaaag tcgagtttac cactccctat     7620
cagtgataga gaaagtgaa agtcgagttt accactccct atcagtgata gagaaagtg      7680 aaagtcgagt ttaccactcc ctatcagtga tagagaaaag tgaaagtcga acctggcgc     7740 gcctcttaat taactcgcgt taagatacat tgatgagttt ggacaaacca caactagaat    7800
gcagtgaaaa aaatgcttta tttgtgaaat ttgtgatgct attgctttat ttgtaaccat    7860
tataagctgc aataaacaag ttaacaacaa caattgcatt cattttatgt ttcaggttca    7920 ggggaggtg tgggaggttt tttaaagcaa gtaaaacctc tacaaatgtg gtatggctga    7980
ttatgatcag ttatctagat ccggtggatc ttacgggtcc tccaccttcc gcttttctt    8040 gggtcgagat ctcaggaaca ggtggtggcg gccctcggtg cgctcgtact gctccacgat    8100
ggtgtagtcc tcgttgtggg aggtgatgtc cagcttggcg tccacgtagt agtagccggg    8160
cagctgcacg ggcttcttgg ccatgtagat ggacttgaac tccaccaggt agtggccgcc    8220
gtccttcagc ttcagggcct tgtgggtctc gcccttcagc acgccgtcgc gggggtacag    8280
gcgctcggtg gaggcctccc agcccatggt cttcttctgc atcacggggc cgtcggaggg    8340
gaagttcacc ccgatgaact tcaccttgta gatgaagcag ccgtcctgca gggaggagtc    8400
ctgggtcacg gtcgccacgc cgccgtcctc gaagttcatc acgcgctccc acttgaagcc    8460
ctcggggaag gacagcttct tgtagtcggg gatgtcggcg ggtgcttca cgtacaccttt    8520 ggagccgtac tggaactggg gggacaggat gtcccaggcg aagggcaggg ggccgccctt    8580
ggtcaccttc agcttcacgg tgttgtggcc ctcgtagggg cggccctcgc cctcgccctc    8640
gatctcgaac tcgtggccgt tcacggtgcc ctccatgcgc accttgaagc gcatgaactc    8700
ggtgatgacg ttctcggagg aggccatggt ggcgaccggt ttgcgcttct tcttgggtgg    8760
ggtgggatcc tcgtcgcaca tcttgaatta gtctgcaaga aaagaaaaaa aacaattcaa    8820
actacattct cattccatac attatactaa gtaaacgaca aatttatttg cgtccatcta    8880
```

```
tttagtgacg ttaaagaaaa ctgtataaga ttcataattc actgttccca atttctgttt   8940
ccgaattgat cgatgcgagt ggacactttg aaatgtgcgt ccaataaact tatttcttat   9000
ttagtagtgt ttattaacat ctgcagtaca ctaaattccg aaaaatgttt ttttttataa   9060
aaaatttcac ttcactagtt atgcaacaat tatgtaacgt aacacgttat cattagcgta   9120
ttattaaaaa aaaaaaacac tcaaacatat gtaatactta aaggtaaagg gacggagaac   9180
cttcgaaatt caaattttac aaataaataa atatgttttt ttttctttcg caattttaaa   9240
attaaaactt acatagtatt attaaataag tgacaagtac gtagatgcga atgcgcactg   9300
ttcgagcaca ccttagtaaa tgagaaccga ctcgtgagga taaactatat aaaagagccg   9360
ttatcacaat ttacacagta tcggctccag tttgttttc caccaatcgc gggctgactc    9420
agttttgtc accatatatg gtaacgcgca cgctatcagg taccatgc                 9468
```

<210> SEQ ID NO 20
<211> LENGTH: 10140
<212> TYPE: DNA
<213> ORGANISM: Artificial Sequence
<220> FEATURE:
<223> OTHER INFORMATION: Synthetic construct, plasmid pLA928

<400> SEQUENCE: 20

```
ggccgctcat ttaaatctgg ccggccgcaa ccattgtggg aaccgtgcga tcaaacaaac     60
gcgagatacc ggaagtactg aaaaacagtc gctccaggcc agtgggaaca tcgatgtttt    120
gttttgacgg accccttact ctcgtctcat ataaaccgaa gccagctaag atggtatact    180
tattatcatc ttgtgatgag gatgcttcta tcaacgaaag taccggtaaa ccgcaaatgg    240
ttatgtatta taatcaaact aaaggcggag tggacacgct agaccaaatg tgttctgtga    300
tgacctgcag taggaagacg aataggtggc ctatggcatt attgtacgga atgataaaca    360
ttgcctgcat aaaattcttt tattatataca gccataatgt cagtagcaag ggagaaaagg    420
tccaaagtcg caaaaaattt atgagaaacc tttacatgag cctgacgtca tcgtttatgc    480
gtaagcgttt agaagctcct actttgaaga gatatttgcg cgataatatc tctaatatt    540
tgccaaatga agtgcctggt acatcagatg acagtactga agagccagta atgaaaaaac    600
gtacttactg tacttactgc ccctctaaaa taaggcgaaa ggcaaatgca tcgtgcaaaa    660
aatgcaaaaa agttatttgt cgagagcata atattgatat gtgccaaagt tgtttctgac    720
tgactaataa gtataatttg tttctattat gtataagtta agctaattac ttatttata    780
atacaacatg actgttttta aagtacaaaa taagtttatt tttgtaaaag agagaatgtt    840
taaaagtttt gttactttat agaagaaatt ttgagttttt gttttttttt aataaataaa   900
taaacataaa taaattgttt gttgaattta ttattagtat gtaagtgtaa atataataaa    960
acttaatatc tattcaaatt aataaataaa cctcgatata cagaccgata aaacacatgc   1020
gtcaattta cgcatgatta tctttaacgt acgtcacaat atgattatct ttctagggtt    1080
aaataatagt ttctaatttt tttattattc agcctgctgt cgtgaatacc gtatatctca   1140
acgctgtctg tgagattgtc gtattctagc ctttttagtt tttcgctcat cgacttgata   1200
ttgtccgaca catttttcgtc gatttgcgtt ttgatcaaag acttgagcag agacacgtta   1260
atcaactgtt caaattgatc catattaacg atatcaaccc gatgcgtata tggtgcgtaa   1320
aatatatttt taaccctct tatactttgc actctgcgtt aatacgcgtt cgtgtacaga   1380
cgtaatcatg ttttctttt tggataaaac tcctactgag tttgacctca tattagaccc    1440
tcacaagttg caaaacgtgg catttttac caatgaagaa tttaaagtta tttttaaaaaa    1500
```

```
tttcatcaca gatttaaaga agaaccaaaa attaaattat ttcaacagtt taatcgacca   1560
gttaatcaac gtgtacacag acgcgtcggc aaaaaacacg cagcccgacg tgttggctaa   1620
aattattaaa tcaacttgtg ttatagtcac ggatttgccg tccaacgtgt tcctcaaaaa   1680
gttgaagacc aacaagttta cggacactat taattatttg attttgcccc acttcatttt   1740
gtgggatcac aattttgtta tattttaaac aaagcttggc actggccgtc gttttacaac   1800
gtcgtgactg ggaaacccct ggcgttaccc aacttaatcg ccttgcagca catcccctt   1860 tcgccagctg gcgtaatagc gaagaggccc gcaccgatcg cccttcccaa cagttgcgca   1920
gcctgaatgg cgaatggcgc ctgatgcggt attttctcct tacgcatctg tgcggtattt   1980
cacaccgcat atggtgcact ctcagtacaa tctgctctga tgccgcatag ttaagccagc   2040
cccgacaccc gccaacaccc gctgacgcgc cctgacgggc ttgtctgctc ccggcatccg   2100
cttacagaca agctgtgacc gtctccggga gctgcatgtg tcagaggttt tcaccgtcat   2160
caccgaaacg cgcgagacga agggcctcg tgatacgcct attttatag gttaatgtca   2220 tgataataat ggtttcttag acgtcaggtg gcacttttcg gggaaatgtg cgcggaaccc   2280
ctatttgttt attttttctaa atacattcaa atatgtatcc gctcatgaga caataaccct   2340
gataaatgct tcaataatat tgaaaaagga agagtatgag tattcaacat ttccgtgtcg   2400
cccttattcc cttttttgcg gcattttgcc ttcctgtttt tgctcaccca gaaacgctgg   2460
tgaaagtaaa agatgctgaa gatcagttgg gtgcacgagt gggttacatc gaactggatc   2520
tcaacagcgg taagatccct gagagttttc gccccgaaga acgttttcca atgatgagca   2580
cttttaaagt tctgctatgt ggcgcggtat tatcccgtat tgacgccggg caagagcaac   2640
tcggtcgccg catacactat tctcagaatg acttggttga gtactcacca gtcacagaaa   2700
agcatcttac ggatggcatg acagtaagag aattatgcag tgctgccata accatgagtg   2760
ataacactgc ggccaactta cttctgacaa cgatcggagg accgaaggag ctaaccgctt   2820
ttttgcacaa catgggggat catgtaactc gccttgatcg ttgggaaccg gagctgaatg   2880
aagccatacc aaacgacgag cgtgacacca cgatgcctgt agcaatggca acaacgttgc   2940
gcaaactatt aactggcgaa ctacttactc tagcttcccg gcaacaatta atagactgga   3000
tggaggcgga taaagttgca ggaccacttc tgcgctcggc ccttccggct ggctggttta   3060
ttgctgataa atctggagcc ggtgagcgtg gtctcgcgg tatcattgca gcactggggc   3120
cagatggtaa gccctcccgt atcgtagtta tctacacgac ggggagtcag gcaactatgg   3180
atgaacgaaa tagacagatc gctgagatag gtgcctcact gattaagcat tggtaactgt   3240
cagaccaagt ttactcatat atactttaga ttgatttaaa acttcatttt taatttaaaa   3300
ggatctaggt gaagatcctt tttgataatc tcatgaccaa aatcccttaa cgtgagtttt   3360
cgttccactg agcgtcagac cccgtagaaa agatcaaagg atcttcttga gatcctttt   3420 ttctgcgcgt aatctgctgc ttgcaaacaa aaaaaccacc gctaccagcg gtggtttgtt   3480
tgccggatca agagctacca actctttttc cgaaggtaac tggcttcagc agagcgcaga   3540
taccaaatac tgtccttcta gtgtagccgt agttaggcca ccacttcaag aactctgtag   3600
caccgcctac atacctcgct ctgctaatcc tgttaccagt ggctgctgcc agtggcgata   3660
agtcgtgtct taccgggttg gactcaagac gatagttacc ggataaggcg cagcggtcgg   3720
gctgaacggg gggttcgtgc acacagccca gcttggagcg aacgacctac accgaactga   3780
gatacctaca gcgtgagcat tgagaaagcg ccacgcttcc cgaagggaga aaggcggaca   3840
```

```
ggtatccggt aagcggcagg gtcggaacag gagagcgcac gagggagctt ccagggggaa    3900
acgcctggta tctttatagt cctgtcgggt ttcgccacct ctgacttgag cgtcgatttt    3960
tgtgatgctc gtcaggggg cggagcctat ggaaaaacgc cagcaacgcg gccttttttac   4020 ggttcctggc cttttgctgg ccttttgctc acatgttctt tcctgcgtta tcccctgatt    4080
ctgtggataa ccgtattacc gcctttgagt gagctgatac cgctcgccgc agccgaacga    4140
ccgagcgcag cgagtcagtg agcgaggaag cggaagagcg cccaatacgc aaaccgcctc    4200
tccccgcgcg ttggccgatt cattaatgca gctggcacga caggtttccc gactggaaag    4260
cgggcagtga gcgcaacgca attaatgtga gttagctcac tcattaggca ccccaggctt    4320
tacactttat gcttccggct cgtatgttgt gtggaattgt gagcggataa caatttcaca    4380
caggaaacag ctatgaccat gattacgaat tcgacctgc aggcatgcaa gcttgcatgc    4440
ctgcaggtcg acgctcgcgc gacttggttt gccattcttt agcgcgcgtc gcgtcacaca    4500
gcttggccac aatgtggttt ttgtcaaacg aagattctat gacgtgttta agtttaggt     4560 cgagtaaagc gcaaatcttt tttaacccta gaaagatagt ctgcgtaaaa ttgacgcatg    4620
cattcttgaa atattgctct ctcttttctaa atagcgcgaa tccgtcgctg tgcatttagg    4680
acatctcagt cgccgcttgg agctcccgtg aggcgtgctt gtcaatgcgg taagtgtcac    4740
tgattttgaa ctataacgac cgcgtgagtc aaaatgacgc atgattatct tttacgtgac    4800
ttttaagatt taactcatac gataattata ttgttatttc atgttctact tacgtgataa    4860
cttattatat atatattttc ttgttataga tatcgtgact aatatataat aaaatgggta    4920
gttctttaga cgatgagcat atcctctctg ctcttctgca aagcgatgac gagcttgttg    4980
gtgaggattc tgacagtgaa atatcagatc acgtaagtga agatgacgtc cagagcgata    5040
cagaagaagc gtttatagat gaggtacatg aagtgcagcc aacgtcaagc ggtagtgaaa    5100
tattagacga acaaaatgtt attgaacaac caggttcttc attggcttct aacagaatct    5160
tgaccttgcc acagaggact attagaggta agaataaaca ttgttggtca acttcaaagt    5220
ccacgaggcg tagccgagtc tctgcactga acattgtcag atcggcccgg gcgccgtttt    5280
tcttgaaata ttgctctctc tttctaaata gcgcgaatcc gtcgctgtgc atttaggaca    5340
tctcagtcgc cgcttggagc tcccaaacgc gccagtggta gtacacagta ctgtgggtgt    5400
tcagtttgaa atcctcttgc ttctccattg tctcggttac ctttggtcaa atccatgggt    5460
tctattgcct atatactctt gcgattacca gtgattgcgc tattagctat tagatggatt    5520
gttggccaaa cttgtcgctt aagtggctgg gaattgtaac cgtaggcccg agtgtaatga    5580
tcccccataa aaagttttcg caatgccttt atttttttgtt gcaaatctct ctttattctg    5640
cggtattctt cattattgcg gggatgggga aagtgtttat atagaagcaa cttacgattg    5700
aacccaaatg cacctgacaa gcaaggtcaa agggccagat ttttaaatat attatttagt    5760
cttaggactc tctatttgca attaaattac tttgctacct gagggttaaa tcttccccat    5820
tgataataat aattccacta tatgttcaat tgggtttcac cgcgcttagt tacatgacga    5880
gccctaatga gccgtcggtg gtctataaac tgtgccttac aaatacttgc aactcttctc    5940
gttttgaagt cagcagagtt attgctaatt gctaattgct aattgctttt aactgatttc    6000
ttcgaaattg gtgctatgtt tatggcgcta ttaacaagta tgaatgtcag gtttaaccag    6060
gggatgctta attgtgttct caacttcaaa ggcagaaatg tttactcttg accatgggtt    6120
taggtataat gttatcaagc tcctcgagtt aacgttacgt taacgttaac gttcgaggtc    6180
gactctagaa ctacccaccg tactcgtcaa ttccaagggc atcggtaaac atctgctcaa    6240
```

```
actcgaagtc ggccatatcc agagcgccgt aggggcgga gtcgtggggg gtaaatcccg    6300
gacccgggga atccccgtcc cccaacatgt ccagatcgaa atcgtctagc gcgtcggcat    6360
gcgccatcgc cacgtcctcg ccgtctaagt ggagctcgtc ccccaggctg acatcggtcg    6420 gggggccgt cgacagtctg cgcgtgtgtc ccgcggggag aaaggacagg cgcggagccg      6480
ccagccccgc ctcttcgggg gcgtcgtcgt ccgggagatc gagcaggccc tcgatggtag    6540
acccgtaatt gtttttcgta cgcgcgcggc tgtacgcggg gcccgagccc gactcgcatt    6600
tcagttgctt ttccaatccg cagataatca gctccaagcc gaacaggaat gccggctcgg    6660
ctccttgatg atcgaacagc tcgattgcct gacgcagcag tgggggcatc gaatcggttg    6720
ttggggtctc gcgctcctct tttgcgactt gatgctcttg gtcctccagc acgcagccca    6780
gggtaaagtg accgacggcg ctcagagcgt agagagcatt ttccaggctg aagccttgct    6840
ggcacaggaa cgcgagctgg ttctccagtg tctcgtattg cttttcggtc gggcgcgtgc    6900
cgagatggac tttggcaccg tctcggtggg acagcagagc gcagcggaac gacttggcgt    6960
tattgcggag gaagtcctgc caggactcgc cttccaacgg gcaaaaatgc gtgtggtggc    7020
ggtcgagcat ctcgatggcc agggcatcca gcagcgcccg cttattcttc acgtgccagt    7080
agagggtggg ctgctccacg cccagcttct gcgccaactt gcggtcgtc agtccctcaa     7140 tgccaacttc gttcaacagc tccaacgcgg agttgatgac tttggactta tccaggcggc    7200
tgcccatggt ggtttctaaa ggtgttataa atcaaattag ttttgttttt tcttgaaaac    7260
tttgcgtttc ctttgatcaa cttaccgcca gggtaccgca gattgtttag cttgttcagc    7320
tgcgcttgtt tatttgctta gctttcgctt agcgacgtgt tcactttgct tgtttgaatt    7380
gaattgtcgc tccgtagacg aagcgcctct atttatactc cggcgctcgt tttcgagttt    7440
accactccct atcagtgata gagaaaagtg aaagtcgagt ttaccactcc ctatcagtga    7500
tagagaaaag tgaaagtcga gtttaccact ccctatcagt gatagagaaa agtgaaagtc    7560
gagtttacca ctccctatca gtgatagaga aaagtgaaag tcgagtttac cactccctat    7620
cagtgataga gaaagtgaa agtcgagttt accactccct atcagtgata gagaaaagtg     7680
aaagtcgagt ttaccactcc ctatcagtga tagagaaaag tgaaagtcga acctggcgc     7740 gcctcttaat taactcgcgt taagatacat tgatgagttt ggacaaacca caactagaat    7800
gcagtgaaaa aaatgcttta tttgtgaaat tgtgatgct attgctttat ttgtaaccat      7860
tataagctgc aataaacaag ttaacaacaa caattgcatt cattttatgt ttcaggttca    7920
gggggaggtg tgggaggttt tttaaagcaa gtaaaacctc tacaaatgtg gtatggctga    7980
ttatgatcag ttatctagat ccggtggatc ttacgggtcc tccaccttcc gcttttctt     8040 gggtcgagat ctcaggaaca ggtggtggcg gccctcggtg cgctcgtact gctccacgat    8100
ggtgtagtcc tcgttgtggg aggtgatgtc cagcttggcg tccacgtagt agtagccggg    8160
cagctgcacg gcttcttgg ccatgtgat ggacttgaac tccaccaggt agtggccgcc     8220
gtccttcagc ttcagggcct tgtgggtctc gcccttcagc acgccgtcgc ggggtacag    8280 gcgctcggtg gaggcctccc agcccatggt cttcttctgc atcacggggc cgtcggaggg    8340
gaagttcacg ccgatgaact tcaccttgta gatgaagcag ccgtcctgca gggaggagtc    8400
ctgggtcacg gtcgccacgc cgccgtcctc gaagttcatc acgcgctccc acttgaagcc    8460
ctcggggaag acagcttct tgtagtcggg gatgtcggcg gggtgcttca cgtacacctt    8520
ggagccgtac tggaactggg gggacaggat gtcccaggcg aagggcaggg ggccgcccctt   8580
```

| | |
|---|---:|
| ggtcaccttc agcttcacgg tgttgtggcc ctcgtagggg cggccctcgc cctcgccctc | 8640 |
| gatctcgaac tcgtggccgt tcacggtgcc ctccatgcgc accttgaagc gcatgaactc | 8700 |
| ggtgatgacg ttctcggagg aggccatggt ggcgaccggt ttgcgcttct tcttgggtgg | 8760 |
| ggtgggatct cccatggtgg cctgaatctc aacttgcacc tgaaggtagt gcagcaagga | 8820 |
| tgagcaaaag ggaagaaccc agaaaagaac gggaaaactt accccaatta gaattgcttg | 8880 |
| tcgccgccag tgtcaacttg caactgaaac aatatccaac atgaacgtca atttatactg | 8940 |
| ccctaatggc gaacacgata caatatttc ttttattatg ccctctaaaa ccaacgcggt | 9000 |
| tatcgtttat ttattcaaat tagatataga acatccgccg acatacaatg ttaatgcaaa | 9060 |
| aacgcgtttg gtgagcggat acgaaaacag tcggccgata acattaatc tgaggtcgat | 9120 |
| aacaccgtcc ttgaacggaa cacgaggagc gtacgtgatc agctgcattc gcgcgccgcg | 9180 |
| cctttatcga gatttatttg catacaacaa gtacactgcg ccgttgggat tgtggtaac | 9240 |
| gcgcacacat gcagagctgc aagtgtggca cattttgtct gtgcgcaaaa cctttgaagc | 9300 |
| caaaagtacg aggtccgtta cgggcatgct agcgcacacg gacaatggac ccgacaaatt | 9360 |
| ctacgccaag gatttaatga taatgtcggg caacgtatcc gttcatttta tcaataacct | 9420 |
| acaaaaatgt cgcgcgcatc acaaagacat cgatatattt aaacatttat gtcccgaact | 9480 |
| gcaaatcgat aatagtgttg tgcaacctcg agcgtccgtt tgatttaacg tatagcttgc | 9540 |
| aaatgaatta tttaattatc aatcatgttt tacgcgtaga attctacccg taaagcgagt | 9600 |
| ttagttatga gccatgtgca aaacatgaca tcagctttta tttttataac aaatgacatc | 9660 |
| atttcttgat tgtgttttac acgtagaatt ctactcgtaa agcgagttca gttttgaaaa | 9720 |
| acaaatgaca tcatcttttt gattgtgctt tacaagtaga attctacccg taaatcaagt | 9780 |
| tcggttttga aaaacaaatg agtcatattg tatgatatca tattgcaaaa caatgactc | 9840 |
| atcaatcgat cgtgcgttac acgtagaatt ctactcgtaa agcgagttta tgagccgtgt | 9900 |
| gcaaaacatg acatcatctc gatttgaaaa acaaatgaca tcatccactg atcgtgcatt | 9960 |
| acaagtagaa ttctactcgt aaagccagtt cggttatgag ccgtgtacaa acatgacat | 10020 |
| cagattatga ctcatacttg attgtgtttt acgcgtagaa ttctactcgt aaagccagtt | 10080 |
| caattttaaa aacaaatgac atcatccaaa ttaataaatg acaagcaatg ggtaccatgc | 10140 |

<210> SEQ ID NO 21
<211> LENGTH: 10522
<212> TYPE: DNA
<213> ORGANISM: Artificial Sequence
<220> FEATURE:
<223> OTHER INFORMATION: Synthetic construct, plasmid pLA1124

<400> SEQUENCE: 21

| | |
|---|---:|
| gtggttttg tcaaacgaag attctatgac gtgtttaaag tttaggtcga gtaaagcgca | 60 |
| aatctttttt aaccctagaa agatagtctg cgtaaaattg acgcatgcat tcttgaaata | 120 |
| ttgctctctc tttctaaata gcgcgaatcc gtcgctgtgc atttaggaca tctcagtcgc | 180 |
| cgcttggagc tcccgtgagg cgtgcttgtc aatgcggtaa gtgtcactga ttttgaacta | 240 |
| taacgaccgc gtgagtcaaa atgacgcatg attatctttt acgtgacttt taagatttaa | 300 |
| ctcatacgat aattatattg ttatttcatg ttctacttac gtgataactt attatatata | 360 |
| tattttcttg ttatagatat cgtgactaat atataataaa atgggtagtt ctttagacga | 420 |
| tgagcatatc ctctctgctc ttctgcaaag cgatgacgag cttgttggtg aggattctga | 480 |
| cagtgaaata tcagatcacg taagtgaaga tgacgtccag agcgatacag aagaagcgtt | 540 |

```
tatagatgag gtacatgaag tgcagccaac gtcaagcggt agtgaaatat tagacgaaca    600
aaatgttatt gaacaaccag gttcttcatt ggcttctaac agaatcttga ccttgccaca    660
gaggactatt agaggtaaga ataaacattg ttggtcaact tcaaagtcca cgaggcgtag    720
ccgagtctct gcactgaaca ttgtcagatc ggcccgggcg ccgttttcct tgaaatattg    780
ctctctcttt ctaaatagcg cgaatccgtc gctgtgcatt taggacatct cagtcgccgc    840
ttggagctcc caaacgcgcc agtggtagta cacagtactg tgggtgttca gtttgaaatc    900
ctcttgcttc tccattgtct cggttacctt tggtcaaatc catgggttct attgcctata    960
tactcttgcg attaccagtg attgcgctat tagctattag atggattgtt ggccaaactt   1020
gtcgcttaag tggctgggaa ttgtaaccgt aggcccgagt gtaatgatcc cccataaaaa   1080
gttttcgcaa tgcctttatt ttttgttgca aatctctctt tattctgcgg tattcttcat   1140
tattgcgggg atggggaaag tgtttatata gaagcaactt acgattgaac ccaaatgcac   1200
ctgacaagca aggtcaaagg gccagatttt taaatatatt atttagtctt aggactctct   1260
atttgcaatt aaattacttt gctacctgag ggttaaatct tccccattga taataataat   1320
tccactatat gttcaattgg gtttcaccgc gcttagttac atgacgagcc ctaatgagcc   1380
gtcggtggtc tataaactgt gccttacaaa tacttgcaac tcttctcgtt ttgaagtcag   1440
cagagttatt gctaattgct aattgctaat tgcttttaac tgatttcttc gaaattggtg   1500
ctatgtttat ggcgctatta acaagtatga atgtcaggtt taaccagggg atgcttaatt   1560
gtgttctcaa cttcaaaggc agaaatgttt actcttgacc atgggtttag gtataatgtt   1620
atcaagctcc tcgagttaac gttacgttaa cgttaacgtt cgaggtcgac tctagaacta   1680
cccaccgtac tcgtcaattc caagggcatc ggtaaacatc tgctcaaact cgaagtcggc   1740
catatccaga gcgccgtagg gggcggagtc gtgggggta aatcccggac ccggggaatc   1800
cccgtccccc aacatgtcca gatcgaaatc gtctagcgcg tcggcatgcg ccatcgccac   1860
gtcctcgccg tctaagtgga gctcgtcccc caggctgaca tcggtcgggg gggccgtcga   1920
cagtctgcgc gtgtgtcccg cggggagaaa ggacaggcgc ggagccgcca gccccgcctc   1980
ttcggggcg tcgtcgtccg ggagatcgag caggccctcg atggtagacc cgtaattgtt   2040
tttcgtacgc gcgcggctgt acgcggggcc cgagcccgac tcgcatttca gttgcttttc   2100
caatccgcag ataatcagct ccaagccgaa caggaatgcc ggctcggctc cttgatgatc   2160
gaacagctcg attgcctgac gcagcagtgg gggcatcgaa tcggttgttg gggtctcgcg   2220
ctcctctttt gcgacttgat gctcttggtc ctccagcacg cagcccaggg taaagtgacc   2280
gacggcgctc agagcgtaga gagcattttc caggctgaag ccttgctggc acaggaacgc   2340
gagctggttc tccagtgtct cgtattgctt ttcggtcggg cgcgtgccga gatggacttt   2400
ggcaccgtct cggtgggaca gcagagcgca gcggaacgac ttggcgttat gcggaggaa   2460
gtcctgccag gactcgcctt ccaacgggca aaaatgcgtg tggtggcggt cgagcatctc   2520
gatggccagg gcatccagca gcgcccgctt attcttcacg tgccagtaga gggtgggctg   2580
ctccacgccc agcttctgcg ccaacttgcg ggtcgtcagt ccctcaatgc caacttcgtt   2640
caacagctcc aacgcggagt tgatgacttt ggacttatcc aggcggctgc ccatggtggt   2700
ttctaaaggt gttataaatc aaattagttt tgttttttct tgaaaacttt gcgtttcctt   2760
tgatcaactt accgccaggg taccgcagat tgtttagctt gttcagctgc gcttgtttat   2820
ttgcttagct ttcgcttagc gacgtgttca ctttgcttgt ttgaattgaa ttgtcgctcc   2880
```

```
gtagacgaag cgcctctatt tatactccgg cgctcgtttt cgagtttacc actccctatc    2940
agtgatagag aaaagtgaaa gtcgagttta ccactcccta tcagtgatag agaaaagtga    3000
aagtcgagtt taccactccc tatcagtgat agagaaaagt gaaagtcgag tttaccactc    3060
cctatcagtg atagagaaaa gtgaaagtcg agtttaccac tccctatcag tgatagagaa    3120
aagtgaaagt cgagtttacc actccctatc agtgatagag aaaagtgaaa gtcgagttta    3180
ccactcccta tcagtgatag agaaaagtga agtcgaaac ctggcgcgcc ccggccatcg     3240
agaaagagag agagaagaga agagagagaa cattcgagaa agagagagag aagagaagag    3300
agagaacata ctccctatca gtgatagaga agtccctatc agtgatagag atgtccctat    3360
cagtgataga gagttcccta tcagtgatag agacgtccct atcagtgata gagaagtccc    3420
tatcagtgat agagagatcc ctatcagtga tagagatttc cctatcagtg atagagaggt    3480
ccctatcagt gatagagact tccctatcag tgatagagaa atccctatca gtgatagaga    3540
catccctatc agtgatagag aactccctat cagtgataga gacctcccta tcagtgatag    3600
agatcgatgc ggccgcatgg tacccattgc ttgtcattta ttaatttgga tgatgtcatt    3660
tgtttttaaa attgaactgg ctttacgagt agaattctac gcgtaaaaca caatcaagta    3720
tgagtcataa tctgatgtca tgttttgtac acggctcata accgaactgg ctttacgagt    3780
agaattctac ttgtaatgca cgatcagtgg atgatgtcat tgttttttca aatcgagatg    3840
atgtcatgtt ttgcacacgg ctcataaact cgctttacga gtagaattct acgtgtaacg    3900
cacgatcgat tgatgagtca tttgttttgc aatatgatat catacaatat gactcatttg    3960
tttttcaaaa ccgaacttga tttacgggta gaattctact tgtaaagcac aatcaaaaag    4020
atgatgtcat tgttttttca aaactgaact cgctttacga gtagaattct acgtgtaaaa    4080
cacaatcaag aaatgatgtc atttgttata aaaataaaag ctgatgtcat gttttgcaca    4140
tggctcataa ctaaactcgc tttacgggta gaattctacg cgtaaaacat gattgataat    4200
taaataattc atttgcaagc tatacgttaa atcaaacgga cgctcgaggt tgcacaacac    4260
tattatcgat ttgcagttcg ggacataaat gtttaaatat atcgatgtct ttgtgatgcg    4320
cgcgacattt ttgtaggtta ttgataaaat gaacggatac gttgcccgac attatcatta    4380
aatccttggc gtagaatttg tcgggtccat tgtccgtgtg cgctagcatg cccgtaacgg    4440
acctcgtact tttggcttca aaggttttgc gcacagacaa aatgtgccac acttgcagct    4500
ctgcatgtgt gcgcgttacc acaaatccca acggcgcagt gtacttgttg tatgcaaata    4560
aatctcgata aaggcgcggc gcgcgaatgc agctgatcac gtacgctcct cgtgttccgt    4620
tcaaggacgg tgttatcgac ctcagattaa tgtttatcgg ccgactgttt tcgtatccgc    4680
tcaccaaacg cgttttttgca ttaacattgt atgtcggcgg atgttctata tctaatttga    4740
ataaataaac gataaccgcg ttggttttag agggcataat aaaagaaata ttgttatcgt    4800
gttcgccatt agggcagtat aaattgacgt tcatgttgga tattgtttca gttgcaagtt    4860
gacactggcg gcgacaagca attctaattg gggtaagttt cccgttcttt tctgggttc     4920 ttccctttg ctcatccttg ctgcactacc ttcaggtgca agttgagatt caggccacca     4980
tgggagatcc cacccaccc aagaagaagc gcaaaccggt cgccaccatg gcctcctccg     5040
agaacgtcat caccgagttc atgcgcttca aggtgcgcat ggagggcacc gtgaacggcc    5100
acgagttcga gatcgagggc gagggcgagg gccgccccta cgagggccac aacaccgtga    5160
agctgaaggt gaccaagggc ggccccctgc ccttcgcctg ggacatcctg tcccccagt     5220 tccagtacgg ctccaaggtg tacgtgaagc accccgccga catccccgac tacaagaagc    5280
```

```
tgtccttccc cgagggcttc aagtgggagc gcgtgatgaa cttcgaggac ggcggcgtgg    5340
cgaccgtgac ccaggactcc tccctgcagg acggctgctt catctacaag gtgaagttca    5400
tcggcgtgaa cttcccctcc gacggccccg tgatgcagaa gaagaccatg ggctgggagg    5460
cctccaccga gcgcctgtac ccccgcgacg gcgtgctgaa gggcgagacc cacaaggccc    5520
tgaagctgaa ggacggcggc cactacctgg tggagttcaa gtccatctac atggccaaga    5580
agcccgtgca gctgcccggc tactactacg tggacgccaa gctggacatc acctcccaca    5640
acgaggacta caccatcgtg gagcagtacg agcgcaccga gggccgccac cacctgttcc    5700
tgagatctcg acccaagaaa aagcggaagg tggaggaccc gtaagatcca ccggatctag    5760
ataactgatc ataatcagcc ataccacatt tgtagaggtt ttacttgctt taaaaaacct    5820
cccacacctc cccctgaacc tgaaacataa aatgaatgca attgttgttg ttaacttgtt    5880
tattgcagct tataatggtt acaaataaag caatagcatc acaaatttca caaataaagc    5940
atttttttca ctgcattcta gttgtggttt gtccaaactc atcaatgtat cttaacgcga    6000
gttaattaag gccgctcatt taaatctggc cggccgcaac cattgtggga accgtgcgat    6060
caaacaaacg cgagataccg gaagtactga aaaacagtcg ctccaggcca gtgggaacat    6120
cgatgttttg ttttgacgga ccccttactc tcgtctcata taaaccgaag ccagctaaga    6180
tggtatactt attatcatct tgtgatgagg atgcttctat caacgaaagt accggtaaac    6240
cgcaaatggt tatgtattat aatcaaacta aaggcggagt ggacacgcta gaccaaatgt    6300
gttctgtgat gacctgcagt aggaagacga ataggtggcc tatggcatta ttgtacggaa    6360
tgataaacat tgcctgcata aattctttta ttatatacag ccataatgtc agtagcaagg    6420
gagaaaaggt ccaaagtcgc aaaaaattta tgagaaacct ttacatgagc ctgacgtcat    6480
cgtttatgcg taagcgttta gaagctccta cttttgaagag atatttgcgc gataatatct    6540
ctaatatttt gccaaatgaa gtgcctggta catcagatga cagtactgaa gagccagtaa    6600
tgaaaaaacg tacttactgt acttactgcc cctctaaaat aaggcgaaag gcaaatgcat    6660
cgtgcaaaaa atgcaaaaaa gttatttgtc gagagcataa tattgatatg tgccaaagtt    6720
gtttctgact gactaataag tataatttgt ttctattatg tataagttaa gctaattact    6780
tattttataa tacaacatga ctgttttaa agtacaaaat aagtttattt ttgtaaaaga    6840
gagaatgttt aaaagttttg ttactttata gaagaaattt tgagttttg ttttttttta    6900 ataaataaat aaacataaat aaattgtttg ttgaatttat tattagtatg taagtgtaaa    6960
tataataaaa cttaatatct attcaaatta ataaataaac ctcgatatac agaccgataa    7020
aacacatgcg tcaattttac gcatgattat ctttaacgta cgtcacaata tgattatctt    7080
tctagggtta ataatagtt tctaattttt ttattattca gcctgctgtc gtgaataccg    7140
tatatctcaa cgctgtctgt gagattgtcg tattctagcc ttttagttt ttcgctcatc    7200 gacttgatat tgtccgacac attttcgtcg atttgcgttt tgatcaaaga cttgagcaga    7260
gacacgttaa tcaactgttc aaattgatcc atattaacga tatcaacccg atgcgtatat    7320
ggtgcgtaaa atatattttt taaccctctt atactttgca ctctgcgtta atacgcgttc    7380
gtgtacagac gtaatcatgt tttctttttt ggataaaact cctactgagt ttgacctcat    7440
attagaccct cacaagttgc aaaacgtggc attttttacc aatgaagaat ttaaagttat    7500
tttaaaaaat ttcatcacag atttaaagaa gaaccaaaaa ttaaattatt tcaacagttt    7560
aatcgaccag ttaatcaacg tgtacacaga cgcgtcggca aaaacacgc agcccgacgt    7620
```

```
gttggctaaa attattaaat caacttgtgt tatagtcacg gatttgccgt ccaacgtgtt   7680
cctcaaaaag ttgaagacca acaagtttac ggacactatt aattatttga ttttgcccca   7740
cttcattttg tgggatcaca attttgttat attttaaaca aagcttggca ctggccgtcg   7800
ttttacaacg tcgtgactgg gaaaaccctg gcgttaccca acttaatcgc cttgcagcac   7860
atcccccttt cgccagctgg cgtaatagcg aagaggcccg caccgatcgc ccttcccaac   7920
agttgcgcag cctgaatggc gaatggcgcc tgatgcggta ttttctcctt acgcatctgt   7980
gcggtatttc acaccgcata tggtgcactc tcagtacaat ctgctctgat gccgcatagt   8040
taagccagcc ccgacacccg ccaacacccg ctgacgcgcc ctgacgggct tgtctgctcc   8100
cggcatccgc ttacagacaa gctgtgaccg tctccgggag ctgcatgtgt cagaggtttt   8160
caccgtcatc accgaaacgc gcgagacgaa agggcctcgt gatacgccta ttttttatagg   8220 ttaatgtcat gataataatg gtttcttaga cgtcaggtgg cacttttcgg ggaaatgtgc   8280
gcggaacccc tatttgttta tttttctaaa tacattcaaa tatgtatccg ctcatgagac   8340
aataaccctg ataaatgctt caataatatt gaaaaaggaa gagtatgagt attcaacatt   8400
tccgtgtcgc ccttattccc ttttttgcgg cattttgcct tcctgttttt gctcacccag   8460
aaacgctggt gaaagtaaaa gatgctgaag atcagttggg tgcacgagtg ggttacatcg   8520
aactggatct caacagcggt aagatccttg agagttttcg ccccgaagaa cgttttccaa   8580
tgatgagcac ttttaaagtt ctgctatgtg gcgcggtatt atcccgtatt gacgccgggc   8640
aagagcaact cggtcgccgc atacactatt ctcagaatga cttggttgag tactcaccag   8700
tcacagaaaa gcatcttacg gatggcatga cagtaagaga attatgcagt gctgccataa   8760
ccatgagtga taacactgcg gccaacttac ttctgacaac gatcggagga ccgaaggagc   8820
taaccgcttt tttgcacaac atgggggatc atgtaactcg ccttgatcgt tgggaaccgg   8880
agctgaatga agccatacca aacgacgagc gtgacaccac gatgcctgta gcaatggcaa   8940
caacgttgcg caaactatta actggcgaac tacttactct agcttcccgg caacaattaa   9000
tagactggat ggaggcggat aaagttgcag gaccacttct gcgctcggcc cttccggctg   9060
gctggtttat tgctgataaa tctggagccg gtgagcgtgg gtctcgcggt atcattgcag   9120
cactggggcc agatggtaag ccctcccgta tcgtagttat ctacacgacg gggagtcagg   9180
caactatgga tgaacgaaat agacagatcg ctgagatagg tgcctcactg attaagcatt   9240
ggtaactgtc agaccaagtt tactcatata ctttagat tgatttaaaa cttcattttt   9300
aatttaaaag gatctaggtg aagatccttt ttgataatct catgaccaaa atcccttaac   9360
gtgagttttc gttccactga gcgtcagacc ccgtagaaaa gatcaaagga tcttcttgag   9420
atcctttttt tctgcgcgta atctgctgct tgcaaacaaa aaaaccaccg ctaccagcgg   9480
tggtttgttt gccggatcaa gagctaccaa ctctttttcc gaaggtaact ggcttcagca   9540
gagcgcagat accaaatact gtccttctag tgtagccgta gttaggccac cacttcaaga   9600
actctgtagc accgcctaca tacctcgctc tgctaatcct gttaccagtg gctgctgcca   9660
gtggcgataa gtcgtgtctt accgggttgg actcaagacg atagttaccg gataaggcgc   9720
agcggtcggg ctgaacgggg ggttcgtgca cacagcccag cttggagcga acgacctaca   9780
ccgaactgag atacctacag cgtgagcatt gagaaagcgc cacgcttccc gaagggagaa   9840
aggcggacag gtatccggta agcggcaggg tcggaacagg agagcgcacg agggagcttc   9900
cagggggaaa cgcctggtat ctttatagtc ctgtcgggtt tcgccacctc tgacttgagc   9960
gtcgattttt gtgatgctcg tcaggggggc ggagcctatg gaaaaacgcc agcaacgcgg  10020
```

```
ccttttacg gttcctggcc ttttgctggc cttttgctca catgttcttt cctgcgttat    10080
cccctgattc tgtggataac cgtattaccg cctttgagtg agctgatacc gctcgccgca    10140
gccgaacgac cgagcgcagc gagtcagtga gcgaggaagc ggaagagcgc ccaatacgca    10200
aaccgcctct ccccgcgcgt tggccgattc attaatgcag ctggcacgac aggtttcccg    10260
actggaaagc gggcagtgag cgcaacgcaa ttaatgtgag ttagctcact cattaggcac    10320
cccaggcttt acactttatg cttccggctc gtatgttgtg tggaattgtg agcggataac    10380
aatttcacac aggaaacagc tatgaccatg attacgaatt cgacctgca ggcatgcaag    10440 cttgcatgcc tgcaggtcga cgctcgcgcg acttggtttg ccattcttta gcgcgcgtcg    10500
cgtcacacag cttggccaca at                                             10522

<210> SEQ ID NO 22
<211> LENGTH: 11867
<212> TYPE: DNA
<213> ORGANISM: Artificial Sequence
<220> FEATURE:
<223> OTHER INFORMATION: Synthetic construct, plasmid pLA1188

<400> SEQUENCE: 22 gtggttttg tcaaacgaag attctatgac gtgtttaaag tttaggtcga gtaaagcgca       60 aatcttttt aaccctagaa agatagtctg cgtaaaattg acgcatgcat tcttgaaata      120
ttgctctctc tttctaaata gcgcgaatcc gtcgctgtgc atttaggaca tctcagtcgc      180
cgcttggagc tcccgtgagg cgtgcttgtc aatgcggtaa gtgtcactga ttttgaacta      240
taacgaccgc gtgagtcaaa atgacgcatg attatctttt acgtgacttt taagatttaa      300
ctcatacgat aattatattg ttatttcatg ttctacttac gtgataactt attatatata      360
tattttcttg ttatagatat cgtgactaat atataataaa atgggtagtt ctttagacga      420
tgagcatatc ctctctgctc ttctgcaaag cgatgacgag cttgttggtg aggattctga      480
cagtgaaata tcagatcacg taagtgaaga tgacgtccag agcgatacag aagaagcgtt      540
tatagatgag gtacatgaag tgcagccaac gtcaagcggt agtgaaatat tagacgaaca      600
aaatgttatt gaacaaccag gttcttcatt ggcttctaac agaatcttga ccttgccaca      660
gaggactatt agaggtaaga ataaacattg ttggtcaact tcaaagtcca cgaggcgtag      720
ccgagtctct gcactgaaca ttgtcagatc ggcccgggcg ccgttttct tgaaatattg      780 ctctctcttt ctaaatagcg cgaatccgtc gctgtgcatt taggacatct cagtcgccgc      840
ttggagctcc caaacgcgcc agtggtagta cacagtactg tgggtgttca gtttgaaatc      900
ctcttgcttc tccattgtct cggttacctt tggtcaaatc catgggtct attgcctata      960 tactcttgcg attaccagtg attgcgctat tagctattag atggattgtt ggccaaactt     1020
gtcgcttaag tggctgggaa ttgtaaccgt aggcccgagt gtaatgatcc cccataaaaa     1080
gttttcgcaa tgcctttatt ttttgttgca aatctctctt tattctgcgg tattcttcat     1140
tattgcgggg atggggaaag tgtttatata gaagcaactt acgattgaac ccaaatgcac     1200
ctgacaagca aggtcaaagg gccagatttt taaatatatt atttagtctt aggactctct     1260
atttgcaatt aaattacttt gctacctgag ggttaaatct tccccattga taataataat     1320
tccactatat gttcaattgg gtttcaccgc gcttagttac atgacgagcc ctaatgagcc     1380
gtcggtggtc tataaactgt gccttacaaa tacttgcaac tcttctcgtt ttgaagtcag     1440
cagagttatt gctaattgct aattgctaat tgcttttaac tgatttcttc gaaattggtg     1500
```

```
ctatgtttat ggcgctatta caagtatga atgtcaggtt taaccagggg atgcttaatt    1560
gtgttctcaa cttcaaaggc agaaatgttt actcttgacc atgggtttag gtataatgtt    1620
atcaagctcc tcgagttaac gttacgttaa cgttaacgtt cgaggtcgac tctagaacta    1680
cccaccgtac tcgtcaattc caagggcatc ggtaaacatc tgctcaaact cgaagtcggc    1740
catatccaga gcgccgtagg gggcggagtc gtgggggta  aatcccggac ccggggaatc    1800
cccgtccccc aacatgtcca gatcgaaatc gtctagcgcg tcggcatgcg ccatcgccac    1860
gtcctcgccg tctaagtgga gctcgtcccc caggctgaca tcggtcgggg gggccgtcga    1920
cagtctgcgc gtgtgtcccg cggggagaaa ggacaggcgc ggagccgcca gccccgcctc    1980
ttcggggcg  tcgtcgtccg ggagatcgag caggccctcg atggtagacc cgtaattgtt    2040
tttcgtacgc gcgcggctgt acgcggggcc cgagcccgac tcgcatttca gttgcttttc    2100
caatccgcag ataatcagct ccaagccgaa caggaatgcc ggctcggctc cttgatgatc    2160
gaacagctcg attgcctgac gcagcagtgg gggcatcgaa tcggttgttg gggtctcgcg    2220
ctcctctttt gcgacttgat gctcttggtc ctccagcacg cagcccaggg taaagtgacc    2280
gacggcgctc agagcgtaga gagcattttc caggctgaag ccttgctggc acaggaacgc    2340
gagctggttc tccagtgtct cgtattgctt ttcggtcggg cgcgtgccga gatggacttt    2400
ggcaccgtct cggtgggaca gcagagcgca gcggaacgac ttggcgttat tgcggaggaa    2460
gtcctgccag gactcgcctt ccaacgggca aaaatgcgtg tggtggcggt cgagcatctc    2520
gatggccagg gcatccagca gcgcccgctt attcttcacc tatagatacc atagatgtat    2580
ggattagtat catatacata caaaggctat ttttgggaca tattaatatt aacaatttcc    2640
gtgatagttt tcaccatttt tgttgaatgt tacgttgaaa atttaaattt gttttaaatt    2700
aattttacca gtcatgtgtt cttaaaagtt tttatgattg aaacggcata agtggttca    2760
aaaatttatc aagaaaggct ttccttttt  aaatcttatc ttttctctt  aaaaatcact    2820
agtcaattca ttattaattt gttaacttga atttggaatg tctatttact ttcagataaa    2880
ttaaagcaag aaacttaata ttcgaaaaaa attgattcta aatggaattt cacttgatct    2940
tcatgtatgc atatcaattt ttatttacat tgtataataa gtttcgagtt gattgttgta    3000
atccacaggt gtcccagaga attaaattcc aaattaccca agtttattga atgttgattg    3060
tagtttcagt tgctttgttg ctgcaacaat ggcttgttga ttgtagatat tttcccttc     3120
cttggtttac ttattacata gactgaaaaa gaggtttact ttttttgatac ttatgaaaaa    3180
tttctattag tgattactaa ccaatcgcta tatgttact  agaaaacaaa taaactcttt    3240
acattaacat tcaataatgt ttgctctgta accgacaatt gaaggcgtta cagcaacagt    3300
aatataacta gcttcttaac cctcatctat taacccatc  gtttaaaaca ctatgttaaa    3360
tggtctaaca aatctagata ctaatagatg tcttattact tagcagccac agctgcaaca    3420
tccaagacaa ttttttgaaac ttcttattga gctcttggca gcagaaatgt tggtatttt    3480
cacagctttc tgaaagaccg gcaccttcct ccggttcccg tttctgaatt caagaggatt    3540
tccgaccccc aattaatccc gaaacaaata aggtatattc aaaatgatgg aaaagtcatg    3600
gctgctgacc ttattttat  tcctattgat agaatattat tcccctttta aatacactgt    3660
actaagaggt ccggctataa ttttactcac ttgtcgatta tcccatagaa tgttgattgt    3720
agttggttgc ttttccaggt gagagttgat caagtcacaa agttagcgt  gtgttgattg    3780
tagatttgaa ggtaaaataa ttttttgcacc cattcatcgg gtaaaacgtt ctccatagaa    3840
tacatttcca tcgataattg ataacttatg aatttcaaag aaaaaaatat gcttttaaaa    3900
```

```
ttacgtgcca gtagagggtg ggctgctcca cgcccagctt ctgcgccaac ttgcgggtcg    3960
tcagtccctc aatgccaact tcgttcaaca gctccaacgc ggagttgatg actttggact    4020
tatccaggcg gctgcccatg gtggtttcta aaggtgttat aaatcaaatt agttttgttt    4080
tttcttgaaa actttgcgtt tcctttgatc aacttaccgc cagggtaccg cagattgttt    4140
agcttgttca gctgcgcttg tttatttgct tagctttcgc ttagcgacgt gttcactttg    4200
cttgtttgaa ttgaattgtc gctccgtaga cgaagcgcct ctatttatac tccggcgctc    4260
gttttcgagt ttaccactcc ctatcagtga tagagaaaag tgaaagtcga gtttaccact    4320
ccctatcagt gatagagaaa agtgaaagtc gagtttacca ctccctatca gtgatagaga    4380
aaagtgaaag tcgagtttac cactccctat cagtgataga gaaagtgaa agtcgagttt    4440 accactccct atcagtgata gagaaaagtg aagtcgagt ttaccactcc ctatcagtga    4500
tagagaaaag tgaaagtcga gtttaccact ccctatcagt gatagagaaa agtgaaagtc    4560
gaaacctggc gcgccccggc catcgagaaa gagagagaga agagaagaga gagaacattc    4620
gagaaagaga gagagaagag aagagagaga acatactccc tatcagtgat agagaagtcc    4680
ctatcagtga tagagatgtc cctatcagtg atagagagtt ccctatcagt gatagagacg    4740
tccctatcag tgatagagaa gtccctatca gtgatagaga gatccctatc agtgatagag    4800
atttccctat cagtgataga gaggtcccta tcagtgatag agacttccct atcagtgata    4860
gagaaatccc tatcagtgat agagacatcc ctatcagtga tagagaactc cctatcagtg    4920
atagagacct ccctatcagt gatagagatc gatgcggccg catggtaccc attgcttgtc    4980
atttattaat ttggatgatg tcatttgttt ttaaaattga actggcttta cgagtagaat    5040
tctacgcgta aaacacaatc aagtatgagt cataatctga tgtcatgttt tgtacacggc    5100
tcataaccga actggcttta cgagtagaat tctacttgta atgcacgatc agtggatgat    5160
gtcatttgtt tttcaaatcg agatgatgtc atgttttgca cacggctcat aaactcgctt    5220
tacgagtaga attctacgtg taacgcacga tcgattgatg agtcatttgt tttgcaatat    5280
gatatcatac aatatgactc atttgttttt caaaaccgaa cttgatttac gggtagaatt    5340
ctacttgtaa agcacaatca aaaagatgat gtcatttgtt tttcaaaact gaactcgctt    5400
tacgagtaga attctacgtg taaaacacaa tcaagaaatg atgtcatttg ttataaaaat    5460
aaaagctgat gtcatgtttt gcacatggct cataactaaa ctcgctttac gggtagaatt    5520
ctacgcgtaa aacatgattg ataattaaat aattcatttg caagctatac gttaaatcaa    5580
acggacgctc gaggttgcac aacactatta tcgatttgca gttcgggaca taatgttta    5640 aatatatcga tgtctttgtg atgcgcgcga cattttgta ggttattgat aaaatgaacg    5700
gatacgttgc ccgacattat cattaaatcc ttggcgtaga atttgtcggg tccattgtcc    5760
gtgtgcgcta gcatgcccgt aacggacctc gtacttttgg cttcaaaggt tttgcgcaca    5820
gacaaaatgt gccacacttg cagctctgca tgtgtgcgcg ttaccacaaa tcccaacggc    5880
gcagtgtact tgttgtatgc aaataaatct cgataaaggc gcggcgcgcg aatgcagctg    5940
atcacgtacg ctcctcgtgt tccgttcaag gacggtgtta tcgacctcag attaatgttt    6000
atcggccgac tgttttcgta tccgctcacc aaacgcgttt ttgcattaac attgtatgtc    6060
ggcggatgtt ctatatctaa tttgaataaa taaacgataa ccgcgttggt tttagagggc    6120
ataataaaag aaatattgtt atcgtgttcg ccattagggc agtataaatt gacgttcatg    6180
ttggatattg tttcagttgc aagttgacac tggcggcgac aagcaattct aattggggta    6240
```

```
agttttcccg ttcttttctg ggttcttccc ttttgctcat ccttgctgca ctaccttcag    6300
gtgcaagttg agattcaggc caccatggga gatcccaccc cacccaagaa gaagcgcaaa    6360
ccggtcgcca ccatggcctc ctccgagaac gtcatcaccg agttcatgcg cttcaaggtg    6420
cgcatggagg gcaccgtgaa cggccacgag ttcgagatcg agggcgaggg cgagggccgc    6480
ccctacgagg gccacaacac cgtgaagctg aaggtgacca agggcggccc cctgcccttc    6540
gcctgggaca tcctgtcccc ccagttccag tacggctcca aggtgtacgt gaagcacccc    6600
gccgacatcc ccgactacaa gaagctgtcc ttccccgagg gcttcaagtg ggagcgcgtg    6660
atgaacttcg aggacggcgg cgtggcgacc gtgacccagg actcctccct gcaggacggc    6720
tgcttcatct acaaggtgaa gttcatcggc gtgaacttcc cctccgacgg ccccgtgatg    6780
cagaagaaga ccatgggctg ggaggcctcc accgagcgcc tgtaccccg cgacggcgtg     6840 ctgaagggcg agacccacaa ggccctgaag ctgaaggacg gcggccacta cctggtggag    6900
ttcaagtcca tctacatggc caagaagccc gtgcagctgc ccggctacta ctacgtggac    6960 gccagctgg acatcacctc ccacaacgag gactacacca cgtggagca gtacgagcgc      7020 accgagggcc gccaccacct gttcctgaga tctcgaccca agaaaaagcg aaggtggag     7080 gacccgtaag atccaccgga tctagataac tgatcataat cagccatacc acatttgtag    7140
aggttttact tgctttaaaa aacctcccac acctccccct gaacctgaaa cataaaatga    7200
atgcaattgt tgttgttaac ttgtttattg cagcttataa tggttacaaa taagcaata    7260 gcatcacaaa tttcacaaat aaagcatttt tttcactgca ttctagttgt ggtttgtcca    7320
aactcatcaa tgtatcttaa cgcgagttaa ttaaggccgc tcatttaaat ctggccggcc    7380
gcaaccattg tgggaaccgt gcgatcaaac aaacgcgaga taccggaagt actgaaaaac    7440
agtcgctcca ggcagtgggg aacatcgatg ttttgttttg acggacccct tactctcgtc    7500
tcatataaac cgaagccagc taagatggta tacttattat catcttgtga tgaggatgct    7560
tctatcaacg aaagtaccgg taaaccgcaa atggttatgt attataatca aactaaaggc    7620
ggagtggaca cgctagacca aatgtgttct gtgatgacct gcagtaggaa gacgaatagg    7680
tggcctatgg cattattgta cggaatgata acattgcct gcataaattc ttttattata     7740
tacagccata atgtcagtag caagggagaa aaggtccaaa gtcgcaaaaa atttatgaga    7800
aacctttaca tgagcctgac gtcatcgttt atgcgtaagc gtttagaagc tcctactttg    7860
aagagatatt tgcgcgataa tatctctaat attttgccaa atgaagtgcc tggtacatca    7920
gatgacagta ctgaagagcc agtaatgaaa aaacgtactt actgtactta ctgcccctct    7980
aaaataaggc gaaaggcaaa tgcatcgtgc aaaaaatgca aaaagttat tgtcgagag      8040 cataatattg atatgtgcca aagttgtttc tgactgacta ataagtataa tttgtttcta    8100
ttatgtataa gttaagctaa ttacttattt tataatacaa catgactgtt tttaaagtac    8160
aaaataagtt tattttttgta aaagagagaa tgtttaaaag ttttgttact ttatagaaga    8220
aattttgagt ttttgttttt ttttaataaa taaataaaca taaataaatt gtttgttgaa    8280
tttattatta gtatgtaagt gtaaatataa taaaacttaa tatctattca aattaataaa    8340
taaacctcga tatacagacc gataaaacac atgcgtcaat tttacgcatg attatcttta    8400
acgtacgtca caatatgatt atctttctag ggttaaataa tagtttctaa tttttttatt    8460
attcagcctg ctgtcgtgaa taccgtatat ctcaacgctg tctgtgagat tgtcgtattc    8520
tagccttttt agtttttcgc tcatcgactt gatattgtcc gacacatttt cgtcgatttg    8580
cgttttgatc aaagacttga gcagagacac gttaatcaac tgttcaaatt gatccatatt    8640
```

```
aacgatatca acccgatgcg tatatggtgc gtaaaatata ttttttaacc ctcttatact    8700
ttgcactctg cgttaatacg cgttcgtgta cagacgtaat catgttttct tttttggata    8760
aaactcctac tgagtttgac ctcatattag accctcacaa gttgcaaaac gtggcatttt    8820
ttaccaatga agaatttaaa gttattttaa aaaatttcat cacagattta agaagaacc     8880
aaaaattaaa ttatttcaac agtttaatcg accagttaat caacgtgtac acagacgcgt    8940
cggcaaaaaa cacgcagccc gacgtgttgg ctaaaattat taaatcaact tgtgttatag    9000
tcacggattt gccgtccaac gtgttcctca aaaagttgaa gaccaacaag tttacggaca    9060
ctattaatta tttgattttg ccccacttca ttttgtggga tcacaatttt gttatatttt    9120
aaacaaagct tggcactggc cgtcgtttta caacgtcgtg actgggaaaa ccctggcgtt    9180
acccaactta atcgccttgc agcacatccc cctttcgcca gctggcgtaa tagcgaagag    9240
gcccgcaccg atcgcccttc ccaacagttg cgcagcctga atggcgaatg cgcctgatg     9300
cggtatttc tccttacgca tctgtgcggt atttcacacc gcatatggtg cactctcagt     9360
acaatctgct ctgatgccgc atagttaagc cagccccgac acccgccaac acccgctgac    9420
gcgccctgac gggcttgtct gctcccggca tccgcttaca gacaagctgt gaccgtctcc    9480
gggagctgca tgtgtcagag gttttcaccg tcatcaccga aacgcgcgag acgaaagggc    9540
ctcgtgatac gcctattttt ataggttaat gtcatgataa taatggtttc ttagacgtca    9600
ggtggcactt ttcggggaaa tgtgcgcgga acccctattt gtttattttt ctaaatacat    9660
tcaaatatgt atccgctcat gagacaataa ccctgataaa tgcttcaata atattgaaaa    9720
aggaagagta tgagtattca acatttccgt gtcgccctta ttccctttt tgcggcattt    9780
tgccttcctg ttttttgctca cccagaaacg ctggtgaaag taaaagatgc tgaagatcag    9840
ttgggtgcac gagtgggtta catcgaactg gatctcaaca gcggtaagat ccttgagagt    9900
tttcgccccg aagaacgttt tccaatgatg agcactttta aagttctgct atgtggcgcg    9960
gtattatccc gtattgacgc cgggcaagag caactcggtc gccgcataca ctattctcag   10020
aatgacttgg ttgagtactc accagtcaca gaaaagcatc ttacggatgg catgacagta   10080
agagaattat gcagtgctgc cataaccatg agtgataaca ctgcggccaa cttacttctg   10140
acaacgatcg gaggaccgaa ggagctaacc gcttttttgc acaacatggg ggatcatgta   10200
actcgccttg atcgttggga accggagctg aatgaagcca taccaaacga cgagcgtgac   10260
accacgatgc ctgtagcaat ggcaacaacg ttgcgcaaac tattaactgg cgaactactt   10320
actctagctt cccggcaaca attaatagac tggatggagg cggataaagt tgcaggacca   10380
cttctgcgct cggcccttcc ggctggctgg tttattgctg ataaatctgg agccggtgag   10440
cgtgggtctc gcggtatcat tgcagcactg gggccagatg gtaagccctc ccgtatcgta   10500
gttatctaca cgacggggag tcaggcaact atggatgaac gaaatagaca gatcgctgag   10560
ataggtgcct cactgattaa gcattggtaa ctgtcagacc aagttactc atatatactt    10620
tagattgatt taaaacttca ttttttaattt aaaaggatct aggtgaagat cctttttgat   10680
aatctcatga ccaaaatccc ttaacgtgag ttttcgttcc actgagcgtc agaccccgta    10740
gaaaagatca aaggatcttc ttgagatcct ttttttctgc gcgtaatctg ctgcttgcaa    10800
acaaaaaaac caccgctacc agcggtggtt tgtttgccgg atcaagagct accaactctt    10860
tttccgaagg taactggctt cagcagagcg cagataccaa atactgtcct tctagtgtag    10920
ccgtagttag gccaccactt caagaactct gtagcaccgc ctacatacct cgctctgcta    10980
```

-continued

| | |
|---|---|
| atcctgttac cagtggctgc tgccagtggc gataagtcgt gtcttaccgg gttggactca | 11040 |
| agacgatagt taccggataa ggcgcagcgg tcgggctgaa cggggggttc gtgcacacag | 11100 |
| cccagcttgg agcgaacgac ctacaccgaa ctgagatacc tacagcgtga gcattgagaa | 11160 |
| agcgccacgc ttcccgaagg gagaaaggcg gacaggtatc cggtaagcgg cagggtcgga | 11220 |
| acaggagagc gcacgaggga gcttccaggg ggaaacgcct ggtatcttta tagtcctgtc | 11280 |
| gggtttcgcc acctctgact tgagcgtcga ttttgtgat gctcgtcagg ggggcggagc | 11340 |
| ctatggaaaa acgccagcaa cgcggccttt ttacggttcc tggccttttg ctggccttt | 11400 |
| gctcacatgt tctttcctgc gttatcccct gattctgtgg ataaccgtat taccgccttt | 11460 |
| gagtgagctg ataccgctcg ccgcagccga acgaccgagc gcagcgagtc agtgagcgag | 11520 |
| gaagcggaag agcgcccaat acgcaaaccg cctctccccg cgcgttggcc gattcattaa | 11580 |
| tgcagctggc acgacaggtt tcccgactgg aaagcgggca gtgagcgcaa cgcaattaat | 11640 |
| gtgagttagc tcactcatta ggcaccccag gctttacact ttatgcttcc ggctcgtatg | 11700 |
| ttgtgtggaa ttgtgagcgg ataacaattt cacacaggaa acagctatga ccatgattac | 11760 |
| gaatttcgac ctgcaggcat gcaagcttgc atgcctgcag gtcgacgctc gcgcgacttg | 11820 |
| gtttgccatt ctttagcgcg cgtcgcgtca cacagcttgg ccacaat | 11867 |

<210> SEQ ID NO 23
<211> LENGTH: 10786
<212> TYPE: DNA
<213> ORGANISM: Artificial Sequence
<220> FEATURE:
<223> OTHER INFORMATION: Synthetic construct, plasmid pLA670

<400> SEQUENCE: 23

| | |
|---|---|
| ggccgctcat ttaaatctgg ccggccgcaa ccattgtggg aaccgtgcga tcaaacaaac | 60 |
| gcgagatacc ggaagtactg aaaaacagtc gctccaggcc agtgggaaca tcgatgtttt | 120 |
| gttttgacgg accccttact ctcgtctcat ataaaccgaa gccagctaag atggtatact | 180 |
| tattatcatc ttgtgatgag gatgcttcta tcaacgaaag taccggtaaa ccgcaaatgg | 240 |
| ttatgtatta taatcaaact aaaggcggag tggacacgct agaccaaatg tgttctgtga | 300 |
| tgacctgcag taggaagacg aataggtggc ctatggcatt attgtacgga atgataaaca | 360 |
| ttgcctgcat aaattctttt attatataca gccataatgt cagtagcaag ggagaaaagg | 420 |
| tccaaagtcg caaaaaattt atgagaaacc tttacatgag cctgacgtca tcgtttatgc | 480 |
| gtaagcgttt agaagctcct actttgaaga gatatttgcg cgataatatc tctaatattt | 540 |
| tgccaaatga agtgcctggt acatcagatg acagtactga agagccagta atgaaaaaac | 600 |
| gtacttactg tacttactgc ccctctaaaa taaggcgaaa ggcaaatgca tcgtgcaaaa | 660 |
| aatgcaaaaa agttatttgt cgagagcata atattgatat gtgccaaagt tgtttctgac | 720 |
| tgactaataa gtataatttg tttctattat gtataagtta agctaattac ttatttata | 780 |
| atacaacatg actgttttta agtacaaaa taagtttatt tttgtaaaag agagaatgtt | 840 |
| taaaagtttt gttactttat agaagaaatt ttgagttttt gttttttttt aataaataaa | 900 |
| taaacataaa taaattgttt gttgaattta ttattagtat gtaagtgtaa atataataaa | 960 |
| acttaatatc tattcaaatt aataaataaa cctcgatata cagaccgata aaacacatgc | 1020 |
| gtcaatttta cgcatgatta tctttaacgt acgtcacaat atgattatct ttctagggtt | 1080 |
| aaataatagt ttctaatttt tttattattc agctgctgt cgtgaatacc gtatatctca | 1140 |
| acgctgtctg tgagattgtc gtattctagc cttttagtt tttcgctcat cgacttgata | 1200 |

```
ttgtccgaca cattttcgtc gatttgcgtt ttgatcaaag acttgagcag agacacgtta   1260
atcaactgtt caaattgatc catattaacg atatcaaccc gatgcgtata tggtgcgtaa   1320
aatatatttt ttaaccctct tatactttgc actctgcgtt aatacgcgtt cgtgtacaga   1380
cgtaatcatg ttttcttttt tggataaaac tcctactgag tttgacctca tattagaccc   1440
tcacaagttg caaaacgtgg catttttttac caatgaagaa tttaaagtta tttttaaaaaa   1500
tttcatcaca gatttaaaga agaaccaaaa attaaattat ttcaacagtt taatcgacca   1560
gttaatcaac gtgtacacag acgcgtcggc aaaaaacacg cagcccgacg tgttggctaa   1620
aattattaaa tcaacttgtg ttatagtcac ggatttgccg tccaacgtgt tcctcaaaaa   1680
gttgaagacc aacaagttta cggacactat taattatttg attttgcccc acttcatttt   1740
gtgggatcac aattttgtta tattttaaac aaagcttggc actggccgtc gttttacaac   1800
gtcgtgactg ggaaaaccct ggcgttaccc aacttaatcg ccttgcagca catccccctt   1860
tcgccagctg gcgtaatagc gaagaggccc gcaccgatcg cccttcccaa cagttgcgca   1920
gcctgaatgg cgaatggcgc ctgatgcggt attttctcct tacgcatctg tgcggtattt   1980
cacaccgcat atggtgcact ctcagtacaa tctgctctga tgccgcatag ttaagccagc   2040
cccgacaccc gccaacaccc gctgacgcgc cctgacgggc ttgtctgctc ccggcatccg   2100
cttacagaca agctgtgacc gtctccggga gctgcatgtg tcagaggttt tcaccgtcat   2160
caccgaaacg cgcgagacga agggcctcg tgatacgcct attttatag gttaatgtca   2220
tgataataat ggtttcttag acgtcaggtg cacttttcg gggaaatgtg cgcggaaccc   2280
ctatttgttt attttttctaa atacattcaa atatgtatcc gctcatgaga caataaccct   2340
gataaatgct tcaataatat tgaaaaagga gagtatgag tattcaacat ttccgtgtcg   2400
cccttattcc cttttttgcg gcattttgcc ttcctgtttt tgctcaccca gaaacgctgg   2460
tgaaagtaaa agatgctgaa gatcagttgg gtgcacgagt gggttacatc gaactggatc   2520
tcaacagcgg taagatcctt gagagttttc gccccgaaga acgttttcca atgatgagca   2580
cttttaaagt tctgctatgt ggcgcggtat tatcccgtat tgacgccggg caagagcaac   2640
tcggtcgccg catacactat tctcagaatg acttggttga gtactcacca gtcacagaaa   2700
agcatcttac ggatggcatg acagtaagag aattatgcag tgctgccata accatgagtg   2760
ataacactgc ggccaactta cttctgacaa cgatcggagg accgaaggag ctaaccgctt   2820
ttttgcacaa catggggat catgtaactc gccttgatcg ttgggaaccg gagctgaatg   2880
aagccatacc aaacgacgag cgtgacacca cgatgcctgt agcaatggca acaacgttgc   2940
gcaaactatt aactggcgaa ctacttactc tagcttcccg gcaacaatta atagactgga   3000
tggaggcgga taaagttgca ggaccacttc tgcgctcggc ccttccggct ggctggttta   3060
ttgctgataa atctggagcc ggtgagcgtg ggtctcgcgg tatcattgca gcactgggc   3120
cagatggtaa gccctcccgt atcgtagtta tctacacgac ggggagtcag gcaactatgg   3180
atgaacgaaa tagacagatc gctgagatag gtgcctcact gattaagcat tggtaactgt   3240
cagaccaagt ttactcatat atactttaga ttgatttaaa acttcatttt taatttaaaa   3300
ggatctaggt gaagatcctt tttgataatc tcatgaccaa atcccttaa cgtgagtttt   3360
cgttccactg agcgtcagac cccgtagaaa agatcaaagg atcttcttga tccttttt   3420
ttctgcgcgt aatctgctgc ttgcaaacaa aaaaaccacc gctaccagcg gtggtttgtt   3480
tgccggatca agagctacca actctttttc cgaaggtaac tggcttcagc agagcgcaga   3540
```

```
taccaaatac tgtccttcta gtgtagccgt agttaggcca ccacttcaag aactctgtag    3600
caccgcctac atacctcgct ctgctaatcc tgttaccagt ggctgctgcc agtggcgata    3660
agtcgtgtct taccggggttg gactcaagac gatagttacc ggataaggcg cagcggtcgg   3720
gctgaacggg gggttcgtgc acacagccca gcttggagcg aacgacctac accgaactga    3780
gatacctaca gcgtgagcat tgagaaagcg ccacgcttcc cgaagggaga aaggcggaca    3840
ggtatccggt aagcggcagg gtcggaacag gagagcgcac gagggagctt ccaggggggaa   3900 acgcctggta tctttatagt cctgtcgggt ttcgccacct ctgacttgag cgtcgatttt    3960
tgtgatgctc gtcagggggg cggagcctat ggaaaaacgc cagcaacgcg ccttttttac    4020
ggttcctggc cttttgctgg ccttttgctc acatgttctt tcctgcgtta tcccctgatt    4080
ctgtggataa ccgtattacc gcctttgagt gagctgatac cgctcgccgc agccgaacga    4140
ccgagcgcag cgagtcagtg agcgaggaag cggaagagcg cccaatacgc aaaccgcctc    4200
tccccgcgcg ttggccgatt cattaatgca gctggcacga caggtttccc gactggaaag    4260
cgggcagtga gcgcaacgca attaatgtga gttagctcac tcattaggca cccagggctt    4320
tacactttat gcttccggct cgtatgttgt gtggaattgt gagcggataa caatttcaca    4380
caggaaacag ctatgaccat gattacgaat tcgacctgc aggcatgcaa gcttgcatgc     4440
ctgcaggtcg acgctcgcgc gacttggttt gccattcttt agcgcgcgtc gcgtcacaca    4500
gcttggccac aatgtggttt ttgtcaaacg aagattctat gacgtgttta agtttaggt     4560 cgagtaaagc gcaaatcttt tttaaccta gaaagatagt ctgcgtaaaa ttgacgcatg     4620
cattcttgaa atattgctct ctctttctaa atagcgcgaa tccgtcgctg tgcatttagg    4680
acatctcagt cgccgcttgg agctcccgtg aggcgtgctt gtcaatgcgg taagtgtcac    4740
tgattttgaa ctataacgac cgcgtgagtc aaaatgacgc atgattatct tttacgtgac    4800
ttttaagatt taactcatac gataattata ttgttatttc atgttctact acgtgataa     4860 cttattatat atatatttc ttgttataga tatcgtgact aatatataat aaaatgggta    4920
gttctttaga cgatgagcat atcctctctg ctcttctgca aagcgatgac gagcttgttg    4980
gtgaggattc tgacagtgaa atatcagatc acgtaagtga agatgacgtc cagagcgata    5040
cagaagaagc gtttatagat gaggtacatg aagtgcagcc aacgtcaagc ggtagtgaaa    5100
tattagacga acaaaatgtt attgaacaac caggttcttc attggcttct aacagaatct    5160
tgaccttgcc acagaggact attagaggta agaataaaca ttgttggtca acttcaaagt    5220
ccacgaggcg tagccgagtc tctgcactga acattgtcag atcggcccgg gcgccgtttt    5280
tcttgaaata ttgctctctc tttctaaata gcgcgaatcc gtcgctgtgc atttaggaca    5340
tctcagtcgc cgcttggagc tcccaaacgc gccagtggta gtacacagta ctgtgggtgt    5400
tcagtttgaa atcctcttgc ttctccattg tctcggttac ctttggtcaa atccatgggt    5460
tctattgcct atatactctt gcgattacca gtgattgcgc tattagctat tagatggatt    5520
gttggccaaa cttgtcgctt aagtggctgg gaattgtaac cgtaggcccg agtgtaatga    5580
tcccccataa aaagttttcg caatgccttt atttttttgtt gcaaatctct ctttattctg    5640
cggtattctt cattattgcg gggatgggga aagtgtttat atagaagcaa cttacgattg    5700
aacccaaatg cacctgacaa gcaaggtcaa agggccagat ttttaaatat attatttagt    5760
cttaggactc tctatttgca attaaattac tttgctacct gagggttaaa tcttccccat    5820
tgataataat aattccacta tatgttcaat tgggtttcac cgcgcttagt tacatgacga    5880
gccctaatga gccgtcggtg gtctataaac tgtgccttac aaatacttgc aactcttctc    5940
```

```
gttttgaagt cagcagagtt attgctaatt gctaattgct aattgctttt aactgatttc    6000
ttcgaaattg gtgctatgtt tatggcgcta ttaacaagta tgaatgtcag gtttaaccag    6060
gggatgctta attgtgttct caacttcaaa ggcagaaatg tttactcttg accatgggtt    6120
taggtataat gttatcaagc tcctcgagtt aacgttacgt taacgttaac gttcgaggtc    6180
gactctagaa ctacccaccg tactcgtcaa ttccaagggc atcggtaaac atctgctcaa    6240
actcgaagtc ggccatatcc agagcgccgt aggggggcgga gtcgtgggggg gtaaatcccg    6300 gacccgggga atccccgtcc cccaacatgt ccagatcgaa atcgtctagc gcgtcggcat    6360
gcgccatcgc cacgtcctcg ccgtctaagt ggagctcgtc ccccaggctg acatcggtcg    6420
ggggggccgt cgacagtctg cgcgtgtgtc ccgcggggag aaaggacagg cgcggagccg    6480
ccagccccgc ctcttcgggg gcgtcgtcgt ccgggagatc gagcaggccc tcgatggtag    6540
acccgtaatt gttttcgta cgcgcgcggc tgtacgcggg gcccgagccc gactcgcatt    6600
tcagttgctt ttccaatccg cagataatca gctccaagcc gaacaggaat gccggctcgg    6660
ctccttgatg atcgaacagc tcgattgcct gacgcagcag tgggggcatc gaatcggttg    6720
ttggggtctc gcgctcctct tttgcgactt gatgctcttg gtcctccagc acgcagccca    6780
gggtaaagtg accgacggcg ctcagagcgt agagagcatt ttccaggctg aagccttgct    6840
ggcacaggaa cgcgagctgg ttctccagtg tctcgtattg cttttcggtc gggcgcgtgc    6900
cgagatggac tttggcaccg tctcggtggg acagcagagc gcagcggaac gacttggcgt    6960
tattgcggag gaagtcctgc caggactcgc cttccaacgg gcaaaaatgc gtgtggtggc    7020
ggtcgagcat ctcgatggcc agggcatcca gcagcgcccg cttattcttc acgtgccagt    7080
agagggtggg ctgctccacg cccagcttct gcgccaactt gcgggtcgtc agtccctcaa    7140
tgccaacttc gttcaacagc tccaacgcgg agttgatgac tttggactta tccaggcggc    7200
tgcccatggt ggtttctaaa ggtgttataa atcaaattag ttttgttttt tcttgaaaac    7260
tttgcgtttc ctttgatcaa cttaccgcca gggtaccgca gattgtttag cttgttcagc    7320
tgcgcttgtt tatttgctta gctttcgctt agcgacgtgt tcactttgct tgtttgaatt    7380
gaattgtcgc tccgtagacg aagcgcctct atttatactc cggcgctcgt tttcgagttt    7440
accactccct atcagtgata gagaaaagtg aaagtcgagt ttaccactcc ctatcagtga    7500
tagagaaaag tgaaagtcga gtttaccact ccctatcagt gatagagaaa agtgaaagtc    7560
gagtttacca ctccctatca gtgatagaga aagtgaaag tcgagtttac cactccctat    7620
cagtgataga gaaaagtgaa agtcgagttt accactccct atcagtgata gagaaaagtg    7680
aaagtcgagt ttaccactcc ctatcagtga tagagaaaag tgaaagtcga acctggcgc    7740 gcctcttaat taactcgcgt taagatacat tgatgagttt ggacaaacca caactagaat    7800
gcagtgaaaa aaatgcttta tttgtgaaat ttgtgatgct attgctttat ttgtaaccat    7860
tataagctgc aataaacaag ttaacaacaa caattgcatt catttatgt ttcaggttca    7920 gggggaggtg tgggaggttt tttaaagcaa gtaaaacctc tacaaatgtg gtatggctga    7980
ttatgatcag ttatctagat ccggtggatc ttacgggtcc tccaccttcc gcttttctt    8040 gggtcgagat ctcaggaaca ggtggtgcg ccctcggtg cgctcgtact gctccacgat    8100
ggtgtagtcc tcgttgtggg aggtgatgtc cagcttggcg tccacgtagt agtagccggg    8160
cagctgcacg ggcttcttgg ccatgtgat ggacttgaac tccaccaggt agtggccgcc    8220
gtccttcagc ttcagggcct tgtgggtctc gcccttcagc acgccgtcgc gggggtacag    8280
```

```
gcgctcggtg gaggcctccc agcccatggt cttcttctgc atcacggggc cgtcggaggg    8340
gaagttcacg ccgatgaact tcaccttgta gatgaagcag ccgtcctgca gggaggagtc    8400
ctgggtcacg gtcgccacgc cgccgtcctc gaagttcatc acgcgctccc acttgaagcc    8460
ctcggggaag gacagcttct tgtagtcggg gatgtcggcg gggtgcttca cgtacacctt    8520
ggagccgtac tggaactggg gggacaggat gtcccaggcg aagggcaggg ggccgccctt    8580
ggtcaccttc agcttcacgg tgttgtggcc ctcgtagggg cggccctcgc cctcgccctc    8640
gatctcgaac tcgtggccgt tcacggtgcc ctccatgcgc accttgaagc gcatgaactc    8700
ggtgatgacg ttctcggagg aggccatggt ggcgaccggt tgcgcttct tcttgggtgg     8760 ggtgggatcc ccgatctgca ttttggatta ttctgcgggt caaaatagag atgtggaaaa    8820
ttagtacgaa atcaaatgag tttcgttgaa attacaaaac tattgaaact aacttcctgg    8880
ctggggaata aaaatgggaa acttatttat cgacgccaac tttgttgaga aaccctatt     8940 aaccctctac gaatattgga acaaaggaaa gcgaagaaac aggaacaaag gtagttgaga    9000
aacctgttcc gttgctcgtc atcgttttca taatgcgagt gtgtgcatgt atatatacac    9060
agctgaaacg catgcataca cattattttg tgtgtatatg gtgacgtcac aactactaag    9120
caataagaaa ttttccagac gtggctttcg tttcaagcaa cctactctat ttcagctaaa    9180 ataagtgga tttcgttggt aaaatacttc aattaagcaa agaactaact aactaataac     9240
atgcacacaa atgctcgagt gcgttcgtga tttctcgaat tttcaaatgc gtcactgcga    9300
atttcacaat ttgccaataa atcttggcga aaatcaacac gcaagtttta tttatagatt    9360
tgtttgcgtt ttgatgccaa ttgattggga aaacaagatg cgtggctgcc aatttcttat    9420
tttgtaatta cgtagagcgt tgaataaaaa aaaatggcc gaacaaagac cttgaaatgc     9480 agttttctt gaaattactc aacgtcttgt tgctcttatt actaattggt aacagcgagt     9540
taaaaactta cgtttcttgt gactttcgag aatgttcttt taattgtact ttaatcacca    9600
acaattaagt ataaattttt cgctgattgc gctttacttt ctgcttgtac ttgctgctgc    9660
aaatgtcaat tggttttgaa ggcgaccgtt cgcgaacgct gtttatatac cttcggtgtc    9720
cgttgaaaat cactaaaaaa taccgtagtg ttcgtaacac tttagtacag agaaaaaaaa    9780
ttgtgccgaa atgttttga tacgtacgaa taccttgtat taaaattttt tatgatttct     9840
gtgtatcact ttttttttgt gttttcgtt taaactcacc acagtacaaa acaataaaat     9900 attttaaga caatttcaaa ttgagaccct tctcgtactg acttgaccgg ctgaatgagg     9960
atttctacct agacgaccta cttcttacca tgacattgaa tgcaatgcca cctttgatct   10020
aaacttacaa aagtccaagg cttgttagga ttggtgttta tttagtttgc ttttgaaata   10080
gcactgtctt ctctaccggc tataattttg aaactcgcag cttgactgga aatttaaaaa   10140
gtaattctgt gtaggtaaag ggtgttttaa aagtgtgatg tgttgagcgt tgcggcaacg   10200
actgctattt atgtatatat tttcaaaact tattgttttt gaagtgtttt aaatggagct   10260
atctggcaac gctgcgcata atcttacaca agcttttctt aatccatttt taagtgaaat   10320 ttgttttttac tctttcggca ataattgtt aaatcgcttt aagtgggctt acatctggat    10380
aagtaatgaa aacctgcata ttataatatt aaaacatata atccactgtg ctttccccgt   10440
gtgtggccat atacctaaaa aagtttattt tcgcagagcc ccgcacggtc acactacggt   10500
tcggcgattt tcgatttttgg acagtactga ttgcaagcgc accgaaagca aaatggagct   10560
ggagattttg aacgcgaaga acagcaagcc gtacggcaag gtgaaggtgc cctccggcgc   10620
cacgcccatc ggcgatctgc gcgccctaat tcacaagacc ctgaagcaga ccccacacgc   10680
```

```
gaatcgccag tcgcttcgtc tggaactgaa gggcaaaagc ctgaaagata cggacacatt    10740
ggaatctctg tcgctgcgtt ccggcgacaa gatcggggta ccatgc                  10786

<210> SEQ ID NO 24
<211> LENGTH: 14720
<212> TYPE: DNA
<213> ORGANISM: Artificial Sequence
<220> FEATURE:
<223> OTHER INFORMATION: Synthetic construct, plasmid pLA1038

<400> SEQUENCE: 24
gggctatggc gcgccggacg cggcaagtct gcgagcttat atttacgtgg atctccggtg      60
tgtccatgat tcggcatcat atcataaacg acgaattcca ataaaaactt tgcttgttga     120
taacacctga tgttcagaga tgcccgataa aatcacagct gttctggttc acagtcacca     180
gaaataaaaa atattggaat tgagatgtac acaattaacg atatttataa atatcttccg     240
atagtctatc gtccggttaa tcaaaataaa gtgcgacgaa ttaacatatt ttcaaaatta     300
agacgctttg atagatgtat ttgtatagag atagaaatta aggttaaaat aacataaatg     360
ccaaagttta gagcactatt caataattct cttgatttca aattgaaata atacacaata     420
taacattttc taacactaca aagtcacgat attcttccac caaccgatag tatcgcacac     480
ttgccattcg cctcatcacg cacacgcccg cttcacaatt caaacgaacg gcattttatt     540
ttcacaggat cccgggagtc gtgaatgttt tacccaatat cgactttcat tgttaactga     600
ccaaaattgt aatctgttct gttagttgtc gagtgcctgt gccgcgatcg ctatgggcat     660
atgttgccaa actctaaacc aaatactcat tctgatgttt taaatgattt gccctcccat     720
atgtccttcc gagtgagaga cacaaaaaat tccaacacac tattgcaatg aaaataaatt     780
tcctttatta gccagaagtc agatgctcaa ggggcttcat gatgtcccca taattttgg      840 cagagggaaa aagatctcag tggtatttgt gagccagggc attggccaca ccagccacca     900
ccttctgata ggcagcctgc acctgaggag tgaattcttt gccaaaatga tgagacagca     960
caacaaccag cacgttgccc aggagctgta ggaaagagaa gaaggcatga acatggttag    1020
cagaggggcc cggtttggac tcagagtatt ttatcctcat ctcaaacagt gtatatcatt    1080
gtaaccataa agagaaaggc aggatgatga ccagggtgta gttgtttcta ccaataagaa    1140
tatttccacg ccagccagaa tttatatgca gaaatattct accttatcat ttaattataa    1200
caattgttct ctaaaactgt gctgaagtac aatataatat accctgattg ccttgaaaaa    1260
aaagtgatta gagaaagtac ttacaatctg acaaataaac aaaagtgaat ttaaaaattc    1320
gttacaaatg caagctaaag tttaacgaaa aagttacaga aatgaaaag aaaataagag     1380 gagacaatgg ttgtcaacag agtagaaagt gaaagaaaca aaattatcat gagggtccat    1440
ggtgatacaa gggacatctt cccattctaa acaacaccct gaaaactttg cccctccat     1500 ataacatgaa ttttacaata gcgaaaaaga agaacaatc aagggtcccc aaactcaccc     1560
tgaagttctc agctctagac gcgtttcact acccaccgta ctcgtcaatt ccaagggcat    1620
cggtaaacat ctgctcaaac tcgaagtcgg ccatatccag agcgccgtag ggggcggagt    1680 cgtgggggt aaatcccgga cccgggaat ccccgtcccc caacatgtcc agatcgaaat      1740
cgtctagcgc gtcggcatgc gccatcgcca cgtcctcgcc gtctaagtgg agctcgtccc    1800
ccaggctgac atcggtcggg ggggccgtcg acagtctgcg cgtgtgtccc gcggggagaa    1860
aggacaggcg cggagccgcc agccccgcct cttcgggggc gtcgtcgtcc gggagatcga    1920
```

```
gcaggccctc gatggtagac ccgtaattgt ttttcgtacg cgcgcggctg tacgcggacc    1980
cactttcaca tttaagttgt ttttctaatc cgcatatgat caattcaagg ccgaataaga    2040
aggctggctc tgcaccttgg tgatcaaata attcgatagc ttgtcgtaat aatggcggca    2100
tactatcagt agtaggtgtt tccctttctt ctttagcgac ttgatgctct tgatcttcca    2160
atacgcaacc taaagtaaaa tgccccacag cgctgagtgc atataatgca ttctctagtg    2220
aaaaaccttg ttggcataaa aaggctaatt gattttcgag agtttcatac tgttttttctg   2280
taggccgtgt acctaaatgt acttttgctc catcgcgatg acttagtaaa gcacatctaa    2340
aactttagc gttattacgt aaaaaatctt gccagctttc cccttctaaa gggcaaaagt     2400
gagtatggtg cctatctaac atctcaatgg ctaaggcgtc gagcaaagcc cgcttatttt    2460
ttacatgcca atacaatgta ggctgctcta cacctagctt ctgggcgagt ttacgggttg    2520
ttaaaccttc gattccgacc tcattaagca gctctaatgc gctgttaatc actttacttt   2580
tatctaatct caattccatg gtggcaacct gcaaggcgaa tgaataaaca agattgtggc    2640
gaacagtgta atgcgaagaa cccacctctg ctccaattcc caattcccta ttcagctcga    2700
gcggggatcc ccgggtaccg agctcgaatt cggggccgcg gaggctggat cggtcccggt    2760
gtcttctatg gaggtcaaaa cagcgtggat ggcgtctcca ggcgatctga cggttcacta    2820
aacgagctct gcttatatag gcctcccacc gtacacgcct acctcgaccc gggtaccgag    2880
ctcgactttc acttttctct atcactgata gggagtggta aactcgactt tcacttttct    2940
ctatcactga tagggagtgg taaactcgac tttcacttttt ctctatcact gatagggagt   3000
ggtaaactcg actttcactt ttctctatca ctgataggga gtggtaaact cgactttcac    3060
ttttctctat cactgatagg gagtggtaaa ctcgactttc acttttctct atcactgata    3120
gggagtggta aactcgactt tcacttttct ctatcactga tagggagtgg taaactcgaa    3180
atgtcgacta tgcggaccga gcgccggagt ataaatagag gcgcttcgtc tacggagcga    3240
caattcaatt caaacaagca aagtgaacac gtcgctaagc gaaagctaag caaataaaca    3300
agcgcagctg aacaagctaa acaatctgcg ctagccacca tggttgttat taaacgtaga    3360
tttggtaatt ttaaaagcat atttttttct ttgaaattca taagttatca attatcgatg    3420
gaaatgtatt ctatggagaa cgttttaccc gatgaatggg tgcaaaaatt attttacctt    3480
caaatctaca atcaacacac gctaacttttt gtgacttgat caactctcac ctggaaaagc   3540
aaccaactac aatcaacatt ctatgggata atcgacaagt gagtaaaatt atagccggac    3600
ctcttagtac agtgtattta aaagggggaat aatattctat caataggaat aaaaataagg   3660
tcagcagcca tgacttttcc atcatttgaa atatacctta tttgtttcgg gattaattgg    3720
gggtcggaaa tcctcttgaa ttcagaaacg ggaaccggag gaaggtgccg gtctttcaga    3780
aagctgtgaa aaataccaac atttctgctg ccaagagctc aataagaagt ttcaaaaatt    3840
gtcttggatg ttgcagctgt ggctgctaag taataagaca tctattagta tctagatttg    3900
ttagaccatt taacatagtg ttttaaacga tgggtttaat agatgagggt taagaagcta    3960
gttatattac tgttgctgta acgccttcaa ttgtcggtta cagagcaaac attattgaat    4020
gttaatgtaa agagtttatt tgttttctag taaacatata gcgattggtt agtaatcact    4080
aatagaaatt tttcataagt atcaaaaaag taaacctctt tttcagtcta tgtaataagt    4140
aaaccaagga aagggaaaat atctacaatc aacaagccat tgttgcagca acaaagcaac    4200
tgaaactaca atcaacattc aataaacttg ggtaattttgg aatttaattc tctgggacac   4260
ctgtggatta caacaatcaa ctcgaaactt attatacaat gtaaataaaa attgatatgc    4320
```

```
atacatgaag atcaagtgaa attccattta gaatcaattt ttttcgaata ttaagtttct    4380
tgctttaatt tatctgaaag taaatagaca ttccaaattc aagttaacaa attaataatg    4440
aattgactag tgattttta gagaaaaaga taagatttaa aaaggaaag cctttcttga    4500 taaattttg aaccacttta tgccgtttca atcataaaaa cttttaagaa cacatgactg    4560
gtaaaattaa tttaaaacaa atttaaattt tcaacgtaac attcaacaaa aatggtgaaa    4620
actatcacgg aaattgttaa tattaatatg tcccaaaaat agcctttgta tgtatatgat    4680
actaatccat acatctatgg tatctatagg tgaaggctca aagcctctgg gcgctctcct    4740
gggcctgccc gaaagccaaa cggagcttga taatcttaca gaatacaaca cggcccacaa    4800
tcggcgcatc tcaatgctgg gcatcgatga tgataccaat atgcgaaagc aaaacgcctt    4860
gaaacaggga cggcgcactc gaaatgtcac atttaacgat gaggagattg tcatcaatcc    4920
tgaggatgtg gatcctaatg tgggacgctt caggaacttg gtacaaacca ctgtggtgcc    4980
cgccaagagg gctcgctgcg acgtcaacca ttagtgataa cgcgtctaga gctgagaact    5040
tcagggtgag tttggggacc cttgattgtt ctttcttttt cgctattgta aaattcatgt    5100
tatatggagg gggcaaagtt ttcagggtgt tgtttagaat gggaagatgt cccttgtatc    5160
accggtgatc ataatcagcc ataccacatt tgtagaggtt ttacttgctt taaaaaacct    5220
cccacacctc cccctgaacc tgaaacataa aatgaatgca attgttgttg ttaacttgtt    5280
tattgcagct tataatggtt acaaataaag caatagcatc acaaatttca caaataaagc    5340 attttttttca ctgcattcta gttgtggttt gtccaaactc atcaatgtat cttaacgcga    5400
gtttaaacgc gtccgcatac gtccgctcac gttaagttcc gcagagagaa gttgttgaaa    5460
acataaacag aatcacttgt tgcactcttt gagaaaactg gggctattgc ggaaaaaacc    5520
aactaaaaat attgcaggtt aggggtacta cgctcgattg gcgtacggcc accactttg    5580 cgacttcact gttaaccgct accttcatag agacttttac ccgataaatg ttatgtagtt    5640
tgactttctc tgttaatcac aagaaaaaat attgtggaaa ttaaaattat ctcaaactca    5700
ataaggaaat aataatatat acacctatgt tttatagaag tcaacagtaa ataagttatt    5760
tggaaaacca ttgtagccgt ttaaataaat ctccttgagt gtgttttaaa taacggtcat    5820
taagtatatt acttggccct ctgaatttct tgaattacac cattttttga aataaatcaa    5880
tccaaaagac tactttttgg tggcaaatga actgcataaa aagtaacaaa agaaatatgt    5940
ttttgaaata acagtatagc tgaagtgtat taaaaaatac cgtcatatga gcgacccgct    6000
gttaccgctt cgctgcgaat gacaaaacgg gctgagcaag aaaatggcgt agaaggcgac    6060
gaaaattcgt ttcactcgtg aagaaaacct cgataactga ggaatacagc tgggatttaa    6120
agagcatatt cgaactacaa gcagagatgt ttcctggtgg aaacggaaac gccgatttgg    6180
gctacaacaa gcatgcccac gtccatggac ttggacaaca tggccatggg cacaaccata    6240
atcacaatca gttcctgcgc agcccccacc accccccaca catttttcac tgccctccgg    6300
gggcggtcag ggcatggtga cgcccatggt agccgccggc ctgccgctcg ccatgcaggg    6360
tggcgttggc atcgattggc gcagctcgcc cagcaatgga ttaattaact cgcgttaaga    6420
tacattgatg agtttggaca aaccacaact agaatgcagt gaaaaaaatg ctttatttgt    6480
gaaatttgtg atgctattgc tttatttgta accattataa gctgcaataa acaagttaac    6540
aacaacaatt gcattcattt tatgtttcag gttcagggg aggtgtggga ggttttttaa    6600
agcaagtaaa acctctacaa atgtggtatg gctgattatg atcagttatc tagatccggt    6660
```

```
ggatcttacg ggtcctccac cttccgcttt ttcttgggtc gagatctcag gaacaggtgg    6720
tggcggccct cggtgcgctc gtactgctcc acgatggtgt agtcctcgtt gtgggaggtg    6780
atgtccagct tggcgtccac gtagtagtag ccgggcagct gcacgggctt cttggccatg    6840
tagatggact tgaactccac caggtagtgg ccgccgtcct tcagcttcag ggccttgtgg    6900
gtctcgccct tcagcacgcc gtcgcggggg tacaggcgct cggtggaggc ctcccagccc    6960
atggtcttct tctgcatcac ggggccgtcg gaggggaagt tcacgccgat gaacttcacc    7020
ttgtagatga agcagccgtc ctgcagggag gagtcctggg tcacggtcgc cacgccgccg    7080
tcctcgaagt tcatcacgcg ctcccacttg aagccctcgg ggaaggacag cttcttgtag    7140
tcggggatgt cggcggggtg cttcacgtac accttggagc cgtactggaa ctgggggac     7200
aggatgtccc aggcgaaggg caggggccg cccttggtca ccttcagctt cacggtgttg     7260
tggccctcgt aggggcggcc ctcgccctcg ccctcgatct cgaactcgtg gccgttcacg    7320
gtgccctcca tgcgcacctt gaagcgcatg aactcggtga tgacgttctc ggaggaggcc    7380
atggtggcga ccggtttgcg cttcttcttg ggtggggtgg gatccccgat ctgcattttg    7440
gattattctg cgggtcaaaa tagagatgtg gaaaattagt acgaaatcaa atgagtttcg    7500
ttgaaattac aaaactattg aaactaactt cctggctggg gaataaaaat gggaaactta    7560
tttatcgacg ccaactttgt tgagaaaccc ctattaaccc tctacgaata ttggaacaaa    7620
ggaaagcgaa gaaacaggaa caaaggtagt tgagaaacct gttccgttgc tcgtcatcgt    7680
tttcataatg cgagtgtgtg catgtatata tacacagctg aaacgcatgc atacacatta    7740
ttttgtgtgt atatggtgac gtcacaacta ctaagcaata agaaattttc cagacgtggc    7800
tttcgtttca agcaacctac tctatttcag ctaaaaataa gtggatttcg ttggtaaaat    7860
acttcaatta agcaaagaac taactaacta ataacatgca cacaaatgct cgagtgcgtt    7920
cgtgatttct cgaattttca aatgcgtcac tgcgaatttc acaatttgcc aataaatctt    7980
ggcgaaaatc aacacgcaag tttttatttat agatttgttt gcgttttgat gccaattgat    8040
tgggaaaaca agatgcgtgg ctgccaattt cttattttgt aattacgtag agcgttgaat    8100
aaaaaaaaa tggccgaaca aagaccttga aatgcagttt ttcttgaaat tactcaacgt    8160
cttgttgctc ttattactaa ttggtaacag cgagttaaaa acttacgttt cttgtgactt    8220
tcgagaatgt tctttttaatt gtactttaat caccaacaat taagtataaa tttttcgctg    8280
attgcgcttt actttctgct tgtacttgct gctgcaaatg tcaattggtt ttgaaggcga    8340
ccgttcgcga acgctgttta tataccttcg gtgtccgttg aaaatcacta aaaaataccg    8400
tagtgttcgt aacactttag tacagagaaa aaaaattgtg ccgaaatgtt tttgatacgt    8460
acgaatacct tgtattaaaa tttttttatga tttctgtgta tcactttttt tttgtgtttt    8520
tcgtttaaac tcaccacagt acaaaacaat aaaatatttt taagacaatt tcaaattgag    8580
acctttctcg tactgacttg accggctgaa tgaggatttc tacctagacg acctacttct    8640
taccatgaca ttgaatgcaa tgccaccttt gatctaaact tacaaaagtc caaggcttgt    8700
taggattggt gtttatttag tttgcttttg aaatagcact gtcttctcta ccggctataa    8760
ttttgaaact cgcagcttga ctggaaattt aaaaagtaat tctgtgtagg taaagggtgt    8820
tttaaaagtg tgatgtgttg agcgttgcgg caacgactgc tatttatgta tatatttca     8880
aaacttattg ttttttgaagt gttttaaatg gagctatctg gcaacgctgc gcataatctt    8940
acacaagctt ttcttaatcc attttttaagt gaaatttgtt tttactcttt cggcaaataa    9000
ttgttaaatc gctttaagtg ggcttacatc tggataagta atgaaaacct gcatattata    9060
```

```
atattaaaac atataatcca ctgtgctttc cccgtgtgtg gccatatacc taaaaaagtt   9120
tattttcgca gagccccgca cggtcacact acggttcggc gattttcgat tttggacagt   9180
actgattgca agcgcaccga aagcaaaatg gagctggaga ttttgaacgc gaagaacagc   9240
aagccgtacg gcaaggtgaa ggtgccctcc ggcgccacgc ccatcggcga tctgcgcgcc   9300
ctaattcaca agaccctgaa gcagacccca cacgcgaatc gccagtcgct tcgtctggaa   9360
ctgaagggca aaagcctgaa agatacggac acattggaat ctctgtcgct gcgttccggc   9420
gacaagatcg gggtaccatg cggccgctca tttaaatctg gccggcctgg ccgatctgac   9480
aatgttcagt gcagagactc ggctacgcct cgtggacttt gaagttgacc aacaatgttt   9540
attcttacct ctaatagtcc tctgtggcaa ggtcaagatt ctgttagaag ccaatgaaga   9600
acctggttgt tcaataacat tttgttcgtc taatatttca ctaccgcttg acgttggctg   9660
cacttcatgt acctcatcta taaacgcttc ttctgtatcg ctctggacgt catcttcact   9720
tacgtgatct gatatttcac tgtcagaatc ctcaccaaca agctcgtcat cgctttgcag   9780
aagagcagag aggatatgct catcgtctaa agaactaccc attttattat atattagtca   9840
cgatatctat aacaagaaaa tatatatata ataagttatc acgtaagtag aacatgaaat   9900
aacaatataa ttatcgtatg agttaaatct taaaagtcac gtaaaagata atcatgcgtc   9960
attttgactc acgcggtcgt tatagttcaa aatcagtgac acttaccgca ttgacaagca  10020
cgcctcacgg gagctccaag cggcgactga gatgtcctaa atgcacagcg acggattcgc  10080
gctatttaga aagagagagc aatatttcaa gaatgcatgc gtcaatttta cgcagactat  10140 cttctaggg ttaaaaaga tttgcgcttt actcgaccta aactttaaac acgtcataga  10200
atcttcgttt gacaaaaacc acattgtggc caagctgtgt gacgcgacgc gcgctaaaga  10260
atggcaaacc aagtcgcgcg agcgtcgacc tgcaggcatg caagcttgca tgcctgcagg  10320
tcgaaattcg taatcatggt catagctgtt tcctgtgtga aattgttatc cgctcacaat  10380
tccacacaac atacgagccg gaagcataaa gtgtaaagcc tggggtgcct aatgagtgag  10440
ctaactcaca ttaattgcgt tgcgctcact gcccgctttc cagtcgggaa acctgtcgtg  10500
ccagctgcat taatgaatcg gccaacgcgc ggggagaggc ggtttgcgta ttgggcgctc  10560
ttccgcttcc tcgctcactg actcgctgcg ctcggtcgtt cggctgcggc gagcggtatc  10620
agctcactca aaggcggtaa tacggttatc cacagaatca ggggataacg caggaaagaa  10680
catgtgagca aaaggccagc aaaaggccag gaaccgtaaa aaggccgcgt tgctggcgtt  10740
tttccatagg ctccgccccc ctgacgagca tcacaaaaat cgacgctcaa gtcagaggtg  10800
gcgaaacccg acaggactat aaagatacca ggcgtttccc cctggaagct ccctcgtgcg  10860
ctctcctgtt ccgaccctgc cgcttaccgg atacctgtcc gcctttctcc cttcgggaag  10920
cgtggcgctt tctcaatgct cacgctgtag gtatctcagt tcggtgtagg tcgttcgctc  10980
caagctgggc tgtgtgcacg aaccccccgt tcagcccgac cgctgcgcct tatccggtaa  11040
ctatcgtctt gagtccaacc cggtaagaca cgacttatcg ccactggcag cagccactgg  11100
taacaggatt agcagagcga ggtatgtagg cggtgctaca gagttcttga agtggtggcc  11160
taactacggc tacactagaa ggacagtatt tggtatctgc gctctgctga gccagttac  11220 cttcggaaaa agagttggta gctcttgatc cggcaaacaa accaccgctg gtagcggtgg  11280 ttttttttgtt tgcaagcagc agattacgcg cagaaaaaaa ggatctcaag aagatccttt  11340
gatcttttct acgggtgctg acgctcagtg gaacgaaaac tcacgttaag ggattttggt  11400
```

```
catgagatta tcaaaaagga tcttcaccta gatccttta aattaaaaat gaagttttaa    11460
atcaatctaa agtatatatg agtaaacttg gtctgacagt taccaatgct taatcagtga    11520
ggcacctatc tcagcgatct gtctatttcg ttcatccata gttgcctgac tccccgtcgt    11580
gtagataact acgatacggg agggcttacc atctggcccc agtgctgcaa tgataccgcg    11640
agacccacgc tcaccggctc cagatttatc agcaataaac cagccagccg aagggccga     11700
gcgcagaagt ggtcctgcaa ctttatccgc ctccatccag tctattaatt gttgccggga    11760
agctagagta agtagttcgc cagttaatag tttgcgcaac gttgttgcca ttgctacagg    11820
catcgtggtg tcacgctcgt cgtttggtat ggcttcattc agctccggtt cccaacgatc    11880
aaggcgagtt acatgatccc ccatgttgtg caaaaaagcg gttagctcct tcggtcctcc    11940
gatcgttgtc agaagtaagt tggccgcagt gttatcactc atggttatgg cagcactgca    12000
taattctctt actgtcatgc catccgtaag atgcttttct gtgactggtg agtactcaac    12060
caagtcattc tgagaatagt gtatgcggcg accgagttgc tcttgcccgg cgtcaatacg    12120
ggataatacc gcgccacata gcagaacttt aaaagtgctc atcattggaa aacgttcttc    12180
ggggcgaaaa ctctcaagga tcttaccgct gttgagatcc agttcgatgt aacccactcg    12240
tgcacccaac tgatcttcag catctttac tttcaccagc gtttctgggt gagcaaaaac    12300
aggaaggcaa aatgccgcaa aaaagggaat aagggcgaca cggaaatgtt gaatactcat    12360
actcttcctt tttcaatatt attgaagcat ttatcagggt tattgtctca tgagcggata    12420
catatttgaa tgtatttaga aaaataaaca ataggggtt ccgcgcacat tccccgaaaa    12480
agtgccacct gacgtctaag aaaccattat tatcatgaca ttaacctata aaaataggcg    12540
tatcacgagg ccctttcgtc tcgcgcgttt cggtgatgac ggtgaaaacc tctgacacat    12600
gcagctcccg gagacggtca cagcttgtct gtaagcggat gccgggagca gacaagcccg    12660
tcagggcgcg tcagcgggtg ttggcgggtg tcggggctgg cttaactatg cggcatcaga    12720
gcagattgta ctgagagtgc accatatatg cggtgtgaaa taccgcacag atgcgtaagg    12780
agaaaatacc gcatcaggcg ccattcgcca ttcaggctgc gcaactgttg ggaagggcga    12840
tcggtgcggg cctcttcgct attacgccag ctggcgaaag gggatgtgc tgcaaggcga    12900
ttaagttggg taacgccagg gttttcccag tcacgacgtt gtaaaacgac ggccagtgcc    12960
aagctttgtt taaatataa caaaattgtg atcccacaaa atgaagtggg gcaaaatcaa    13020
ataattaata gtgtccgtaa acttgttggt cttcaacttt ttgaggaaca cgttggacgg    13080
caaatccgtg actataacac aagttgattt aataattta gccaacacgt cgggctgcgt    13140
gtttttgcc gacgcgtctg tgtacacgtt gattaactgg tcgattaaac tgttgaaata    13200
atttaattt tggttcttct ttaaatctgt gatgaaattt tttaaaataa ctttaaattc    13260
ttcattggta aaaaatgcca cgttttgcaa cttgtgaggg tctaatatga ggtcaaactc    13320
agtaggagtt ttatccaaaa aagaaaacat gattacgtct gtacacgaac gcgtattaac    13380
gcagagtgca aagtataaga gggttaaaaa atatatttta cgcaccatat acgcatcggg    13440
ttgatatcgt taatatggat caatttgaac agttgattaa cgtgtctctg ctcaagtctt    13500
tgatcaaaac gcaaatcgac gaaaatgtgt cggacaatat caagtcgatg agcgaaaaac    13560
taaaaaggct agaatacgac aatctcacag acagcgttga gatatacggt attcacgaca    13620
gcaggctgaa taataaaaaa attagaaact attatttaac cctagaaaga taatcatatt    13680
gtgacgtacg ttaagataa tcatgcgtaa aattgacgca tgtgttttat cggtctgtat    13740
atcgaggttt atttattaat ttgaatagat attaagtttt attatattta cacttacata    13800
```

```
ctaataataa attcaacaaa caatttattt atgtttattt atttattaaa aaaaaacaaa    13860
aactcaaaat ttcttctata aagtaacaaa acttttaaac attctctctt ttacaaaaat    13920
aaacttattt tgtactttaa aaacagtcat gttgtattat aaaataagta attagcttaa    13980
cttatacata atagaaacaa attatactta ttagtcagtc agaaacaact ttggcacata    14040
tcaatattat gctctcgaca aataactttt ttgcattttt tgcacgatgc atttgccttt    14100
cgccttattt tagaggggca gtaagtacag taagtacgtt ttttcattac tggctcttca    14160
gtactgtcat ctgatgtacc aggcacttca tttggcaaaa tattagagat attatcgcgc    14220
aaatatctct tcaaagtagg agcttctaaa cgcttacgca taaacgatga cgtcaggctc    14280
atgtaaaggt ttctcataaa tttttttgcga ctttggacct tttctcccctt gctactgaca    14340 ttatggctgt atataataaa agaatttatg caggcaatgt ttatcattcc gtacaataat    14400
gccataggcc acctattcgt cttcctactg caggtcatca cagaacacat ttggtctagc    14460
gtgtccactc cgcctttagt ttgattataa tacataacca tttgcggttt accggtactt    14520
tcgttgatag aagcatcctc atcacaagat gataataagt ataccatctt agctggcttc    14580
ggtttatatg agacgagagt aagggggtccg tcaaaacaaa acatcgatgt tcccactggc    14640
ctggagcgac tgttttttcag tacttccggt atctcgcgtt tgtttgatcg cacggttccc    14700
acaatggttg cggccagccc                                               14720
```

<210> SEQ ID NO 25
<211> LENGTH: 23
<212> TYPE: DNA
<213> ORGANISM: Artificial Sequence
<220> FEATURE:
<223> OTHER INFORMATION: Synthetic construct, Oligonucleotide useful as
      PCR Primer

<400> SEQUENCE: 25

```
catcgatgcc cagcattgag atg                                              23
```

<210> SEQ ID NO 26
<211> LENGTH: 34
<212> TYPE: DNA
<213> ORGANISM: Artificial Sequence
<220> FEATURE:
<223> OTHER INFORMATION: Synthetic construct, Oligonucleotide useful as
      PCR Primer

<400> SEQUENCE: 26

```
caagcaaagt gaacacgtcg ctaagcgaaa gcta                                  34
```

<210> SEQ ID NO 27
<211> LENGTH: 28
<212> TYPE: DNA
<213> ORGANISM: Artificial Sequence
<220> FEATURE:
<223> OTHER INFORMATION: Synthetic construct, Oligonucleotide useful as
      PCR Primer

<400> SEQUENCE: 27

```
gccatccacg ctgttttgac ctccatag                                         28
```

<210> SEQ ID NO 28
<211> LENGTH: 27
<212> TYPE: DNA
<213> ORGANISM: Artificial Sequence
<220> FEATURE:
<223> OTHER INFORMATION: Synthetic construct, Oligonucleotide useful as PCR Primer

<400> SEQUENCE: 28
gccaatacaa tgtaggctgc tctacac                                           27

<210> SEQ ID NO 29
<211> LENGTH: 1005
<212> TYPE: DNA
<213> ORGANISM: Artificial Sequence
<220> FEATURE:
<223> OTHER INFORMATION: Synthetic construct, coding region of tTA from
      pUHD15-1

<400> SEQUENCE: 29

```
atgtctagat tagataaaag taaagtgatt aacagcgcat tagagctgct taatgaggtc      60
ggaatcgaag gtttaacaac ccgtaaactc gcccagaagc taggtgtaga gcagcctaca     120
ttgtattggc atgtaaaaaa taagcgggct ttgctcgacg ccttagccat tgagatgtta     180
gataggcacc atactcactt ttgccccttta aagggggaaa gctggcaaga ttttttacgt     240
aataacgcta aagttttag atgtgcttta ctaagtcatc gcgatggagc aaaagtacat      300
ttaggtacac ggcctacaga aaaacagtat gaaactctcg aaaatcaatt agccttttta     360
tgccaacaag gttttttcact agagaatgca ttatatgcac tcagcgctgt ggggcatttt     420
actttaggtt gcgtattgga agatcaagag catcaagtcg ctaaagaaga agggaaaca      480
cctactactg atagtatgcc gccattatta cgacaagcta tcgaattatt tgatcaccaa     540
ggtgcagagc cagccttctt attcggcctt gaattgatca tatgcggatt agaaaaacaa     600
cttaaatgtg aaagtgggtc cgcgtacagc cgcgcgcgta cgaaaaacaa ttacgggtct     660
accatcgagg cctgctcga tctcccggac gacgacgccc ccgaagaggc ggggctggcg     720
gctccgcgcc tgtcctttct ccccgcggga cacacgcgca gactgtcgac ggcccccccg     780
accgatgtca gcctggggga cgagctccac ttagacggcg aggacgtggc gatggcgcat     840
gccgacgcgc tagacgattt cgatctggac atgttggggg acggggattc cccgggtccg     900
ggatttaccc ccacgactc cgccccctac ggcgctctgg atatggccga cttcgagttt     960
gagcagatgt ttaccgatgc ccttggaatt gacgagtacg gtggg                   1005
```

<210> SEQ ID NO 30
<211> LENGTH: 336
<212> TYPE: PRT
<213> ORGANISM: Artificial Sequence
<220> FEATURE:
<223> OTHER INFORMATION: Synthetic construct, tTA

<400> SEQUENCE: 30

```
Met Gly Ser Arg Leu Asp Lys Ser Lys Val Ile Asn Ser Ala Leu Glu
1               5                   10                  15

Leu Leu Asn Glu Val Gly Ile Glu Gly Leu Thr Thr Arg Lys Leu Ala
            20                  25                  30

Gln Lys Leu Gly Val Glu Gln Pro Thr Leu Tyr Trp His Val Lys Asn
        35                  40                  45

Lys Arg Ala Leu Leu Asp Ala Leu Ala Ile Glu Met Leu Asp Arg His
    50                  55                  60

His Thr His Phe Cys Pro Leu Glu Gly Glu Ser Trp Gln Asp Phe Leu
65                  70                  75                  80

Arg Asn Asn Ala Lys Ser Phe Arg Cys Ala Leu Leu Ser His Arg Asp
                85                  90                  95
```

Gly Ala Lys Val His Leu Gly Thr Arg Pro Thr Glu Lys Gln Tyr Glu
            100                 105                 110

Thr Leu Glu Asn Gln Leu Ala Phe Leu Cys Gln Gln Gly Phe Ser Leu
        115                 120                 125

Glu Asn Ala Leu Tyr Ala Leu Ser Ala Val Gly His Phe Thr Leu Gly
    130                 135                 140

Cys Val Leu Glu Asp Gln Glu His Gln Val Ala Lys Glu Glu Arg Glu
145                 150                 155                 160

Thr Pro Thr Thr Asp Ser Met Pro Pro Leu Arg Gln Ala Ile Glu
                165                 170                 175

Leu Phe Asp His Gln Gly Ala Glu Pro Ala Phe Leu Phe Gly Leu Glu
            180                 185                 190

Leu Ile Ile Cys Gly Leu Glu Lys Gln Leu Lys Cys Glu Ser Gly Ser
        195                 200                 205

Ala Tyr Ser Arg Ala Arg Thr Lys Asn Asn Tyr Gly Ser Thr Ile Glu
    210                 215                 220

Gly Leu Leu Asp Leu Pro Asp Asp Ala Pro Glu Glu Ala Gly Leu
225                 230                 235                 240

Ala Ala Pro Arg Leu Ser Phe Leu Pro Ala Gly His Thr Arg Arg Leu
                245                 250                 255

Ser Thr Ala Pro Pro Thr Asp Val Ser Leu Gly Asp Glu Leu His Leu
            260                 265                 270

Asp Gly Glu Asp Val Ala Met Ala His Ala Asp Ala Leu Asp Asp Phe
        275                 280                 285

Asp Leu Asp Met Leu Gly Asp Gly Asp Ser Pro Gly Pro Gly Phe Thr
    290                 295                 300

Pro His Asp Ser Ala Pro Tyr Gly Ala Leu Asp Met Ala Asp Phe Glu
305                 310                 315                 320

Phe Glu Gln Met Phe Thr Asp Ala Leu Gly Ile Asp Glu Tyr Gly Gly
                325                 330                 335

<210> SEQ ID NO 31
<211> LENGTH: 1017
<212> TYPE: DNA
<213> ORGANISM: Artificial Sequence
<220> FEATURE:
<223> OTHER INFORMATION: Synthetic construct, DNA sequence of tTAV

<400> SEQUENCE: 31

| | | |
|---|---|---|
| atgggcagcc gcctggataa gtccaaagtc atcaactccg cgttggagct gttgaacgaa | 60 |
| gttggcattg agggactgac gacccgcaag ttggcgcaga agctgggcgt ggagcagccc | 120 |
| accctctact ggcacgtgaa gaataagcgg gcgctgctgg atgccctggc catcgagatg | 180 |
| ctcgaccgcc accacacgca tttttgcccg ttggaaggcg agtcctggca ggacttcctc | 240 |
| cgcaataacg ccaagtcgtt ccgctgcgct ctgctgtccc accgagacgg tgccaaagtc | 300 |
| catctcggca cgcgcccgac cgaaaagcaa tacgagacac tggagaacca gctcgcgttc | 360 |
| ctgtgccagc aaggcttcag cctggaaaat gctctctacg ctctgagcgc cgtcggtcac | 420 |
| tttaccctgg gctgcgtgct ggaggaccaa gagcatcaag tcgcaaaaga ggagcgcgag | 480 |
| accccaacaa ccgattcgat gcccccactg ctgcgtcagg caatcgagct gttcgatcat | 540 |
| caaggagccg agccggcatt cctgttcggc ttggagctga ttatctgcgg attggaaaag | 600 |
| caactgaaat gcgagtcggg ctcgggcccc gcgtacagcc gcgcgcgtac gaaaaacaat | 660 |
| tacgggtcta ccatcgaggg cctgctcgat ctcccggacg acgacgcccc cgaagaggcg | 720 |

```
gggctggcgg ctccgcgcct gtcctttctc cccgcgggac acacgcgcag actgtcgacg    780
gcccccccga ccgatgtcag cctgggggac gagctccact tagacggcga ggacgtggcg    840
atggcgcatg ccgacgcgct agacgatttc gatctggaca tgttggggga cggggattcc    900
ccgggtccgg gatttacccc ccacgactcc gcccctacg gcgctctgga tatggccgac     960
ttcgagtttg agcagatgtt taccgatgcc cttggaattg acgagtacgg tgggtag     1017
```

<210> SEQ ID NO 32
<211> LENGTH: 338
<212> TYPE: PRT
<213> ORGANISM: Artificial Sequence
<220> FEATURE:
<223> OTHER INFORMATION: Synthetic construct, amino acid sequence of tTAV protein

<400> SEQUENCE: 32

```
Met Gly Ser Arg Leu Asp Lys Ser Lys Val Ile Asn Ser Ala Leu Glu
1               5                   10                  15

Leu Leu Asn Glu Val Gly Ile Glu Gly Leu Thr Thr Arg Lys Leu Ala
            20                  25                  30

Gln Lys Leu Gly Val Glu Gln Pro Thr Leu Tyr Trp His Val Lys Asn
        35                  40                  45

Lys Arg Ala Leu Leu Asp Ala Leu Ala Ile Glu Met Leu Asp Arg His
    50                  55                  60

His Thr His Phe Cys Pro Leu Glu Gly Glu Ser Trp Gln Asp Phe Leu
65                  70                  75                  80

Arg Asn Asn Ala Lys Ser Phe Arg Cys Ala Leu Leu Ser His Arg Asp
                85                  90                  95

Gly Ala Lys Val His Leu Gly Thr Arg Pro Thr Glu Lys Gln Tyr Glu
            100                 105                 110

Thr Leu Glu Asn Gln Leu Ala Phe Leu Cys Gln Gln Gly Phe Ser Leu
        115                 120                 125

Glu Asn Ala Leu Tyr Ala Leu Ser Ala Val Gly His Phe Thr Leu Gly
    130                 135                 140

Cys Val Leu Glu Asp Gln Glu His Gln Val Ala Lys Glu Glu Arg Glu
145                 150                 155                 160

Thr Pro Thr Thr Asp Ser Met Pro Pro Leu Leu Arg Gln Ala Ile Glu
                165                 170                 175

Leu Phe Asp His Gln Gly Ala Glu Pro Ala Phe Leu Phe Gly Leu Glu
            180                 185                 190

Leu Ile Ile Cys Gly Leu Glu Lys Gln Leu Lys Cys Glu Ser Gly Ser
        195                 200                 205

Gly Pro Ala Tyr Ser Arg Ala Arg Thr Lys Asn Asn Tyr Gly Ser Thr
    210                 215                 220

Ile Glu Gly Leu Leu Asp Leu Pro Asp Asp Ala Pro Glu Glu Ala
225                 230                 235                 240

Gly Leu Ala Ala Pro Arg Leu Ser Phe Leu Pro Ala Gly His Thr Arg
                245                 250                 255

Arg Leu Ser Thr Ala Pro Pro Thr Asp Val Ser Leu Gly Asp Glu Leu
            260                 265                 270

His Leu Asp Gly Glu Asp Val Ala Met Ala His Ala Asp Ala Leu Asp
        275                 280                 285

Asp Phe Asp Leu Asp Met Leu Gly Asp Gly Asp Ser Pro Gly Pro Gly
    290                 295                 300

Phe Thr Pro His Asp Ser Ala Pro Tyr Gly Ala Leu Asp Met Ala Asp
```

```
                305                 310                 315                 320
Phe Glu Phe Glu Gln Met Phe Thr Asp Ala Leu Gly Ile Asp Glu Tyr
                    325                 330                 335
Gly Gly

<210> SEQ ID NO 33
<211> LENGTH: 4455
<212> TYPE: DNA
<213> ORGANISM: Artificial Sequence
<220> FEATURE:
<223> OTHER INFORMATION: Synthetic construct, plasmid pUHD15-1

<400> SEQUENCE: 33
ctcgaggagc ttggcccatt gcatacgttg tatccatatc ataatatgta catttatatt      60
ggctcatgtc caacattacc gccatgttga cattgattat tgactagtta ttaatagtaa     120
tcaattacgg ggtcattagt tcatagccca tatatggagt tccgcgttac ataacttacg     180
gtaaatggcc cgcctggctg accgcccaac gacccccgcc cattgacgtc aataatgacg     240
tatgttccca tagtaacgcc aatagggact ttccattgac gtcaatgggt ggagtattta     300
cgctaaactg cccacttggc agtacatcaa gtgtatcata tgccaagtac gccccctatt     360
gacgtcaatg acggtaaatg gcccgcctgg cattatgccc agtacatgac cttatgggac     420
tttcctactt ggcagtacat ctacgtatta gtcatcgcta ttaccatggt gatgcggttt     480
tggcagtaca tcaatgggcg tggatagcgg tttgactcac ggggatttcc aagtctccac     540
cccattgacg tcaatgggag tttgttttgg caccaaaatc aacgggactt tccaaaatgt     600
cgtaacaact ccgccccatt gacgcaaatg ggcggtaggc gtgtacggtg gaggtctat      660
ataagcagag ctcgtttagt gaaccgtcag atcgcctgga gacgccatcc acgctgtttt     720
gacctccata agacaccgg accgatcc agcctccgcg gccccgaatt catatgtcta      780
gattagataa agtaaagtg attaacagcg cattagagct gcttaatgag gtcggaatcg     840
aaggtttaac aacccgtaaa ctcgcccaga agctaggtgt agagcagcct acattgtatt     900
ggcatgtaaa aaataagcgg gctttgctcg acgccttagc cattgagatg ttagataggc     960
accatactca cttttgccct ttagaagggg aaagctggca agattttta cgtaataacg     1020
ctaaaagttt tagatgtgct ttactaagtc atcgcgatgg agcaaaagta catttaggta    1080
cacggcctac agaaaacag tatgaaactc tcgaaaatca attagccttt ttatgccaac    1140
aaggttttc actagagaat gcattatatg cactcagcgc tgtggggcat tttactttag    1200
gttgcgtatt ggaagatcaa gagcatcaag tcgctaaaga agaaagggaa acacctacta    1260
ctgatagtat gccgccatta ttacgacaag ctatcgaatt atttgatcac caaggtgcag    1320
agccagcctt cttattcggc cttgaattga tcatatgcgg attagaaaaa caacttaaat    1380
gtgaaagtgg gtccgcgtac agccgcgcgc gtacgaaaaa caattacggg tctaccatcg    1440
agggcctgct cgatctcccg gacgacgacg ccccgaaga ggcggggctg gcggctccgc    1500
gcctgtcctt tctccccgcg ggacacacgc gcagactgtc gacggccccc cgaccgatg     1560
tcagcctggg ggacgagctc cacttagacg gcgaggacgt ggcgatggcg catgccgacg    1620
cgctagacga tttcgatctg gacatgttgg gggacgggga ttccccgggt ccggatttta    1680
ccccccacga ctccgccccc tacggcgctc tggatatggc cgacttcgag tttgagcaga    1740
tgtttaccga tgcccttgga attgacgagt acggtgggta gggggcgcga ggatccagac    1800
atgataagat acattgatga gtttggacaa accacaacta gaatgcagtg aaaaaaatgc    1860
```

```
tttatttgtg aaatttgtga tgctattgct ttatttgtaa ccattataag ctgcaataaa    1920
caagttaaca acaacaattg cattcatttt atgtttcagg ttcagggga ggtgtgggag     1980
gttttttaaa gcaagtaaaa cctctacaaa tgtggtatgg ctgattatga tcctgcaagc   2040
ctcgtcgtct ggccggacca cgctatctgt gcaaggtccc cggacgcgcg ctccatgagc   2100
agagcgcccg ccgccgaggc aagactcggg cggcgccctg cccgtcccac caggtcaaca   2160
ggcggtaacc ggcctcttca tcgggaatgc gcgcgacctt cagcatcgcc ggcatgtccc   2220
ctggcggacg ggaagtatca gctcgaccaa gcttggcgag attttcagga gctaaggaag   2280
ctaaaatgga gaaaaaaatc actggatata ccaccgttga tatatcccaa tggcatcgta   2340
aagaacattt tgaggcattt cagtcagttg ctcaatgtac ctataaccag accgttcagc   2400
tgcattaatg aatcggccaa cgcgcgggga gaggcggttt gcgtattggg cgctcttccg   2460
cttcctcgct cactgactcg ctgcgctcgg tcgttcggct gcggcgagcg gtatcagctc   2520
actcaaaggc ggtaatacgg ttatccacag aatcagggga taacgcagga aagaacatgt   2580
gagcaaaagg ccagcaaaag gccaggaacc gtaaaaaggc cgcgttgctg gcgttttttcc  2640
ataggctccg ccccctgac gagcatcaca aaaatcgacg ctcaagtcag aggtggcgaa    2700
acccgacagg actataaaga taccaggcgt ttccccctgg aagctccctc gtgcgctctc   2760
ctgttccgac cctgccgctt accggatacc tgtccgcctt tctcccttcg ggaagcgtgg   2820
cgctttctca atgctcacgc tgtaggtatc tcagttcggt gtaggtcgtt cgctccaagc   2880
tgggctgtgt gcacgaaccc cccgttcagc ccgaccgctg cgccttatcc ggtaactatc   2940
gtcttgagtc caacccggta agacacgact tatcgccact ggcagcagcc actggtaaca   3000
ggattagcag agcgaggtat gtaggcggtg ctacagagtt cttgaagtgg tggcctaact   3060
acggctacac tagaaggaca gtattttggta tctgcgctct gctgaagcca gttaccttcg   3120
gaaaaagagt ggtagctctt gatccggca aacaaaccac cgctggtagc ggtggttttt    3180
ttgtttgcaa gcagcagatt acgcgcagaa aaaaaggatc tcaagaagat cctttgatct   3240
tttctacggg gtctgacgct cagtggaacg aaaactcacg ttaagggatt ttggtcatga   3300
gattatcaaa aaggatcttc acctagatcc ttttaaatta aaaatgaagt tttaaatcaa   3360
tctaaagtat atatgagtaa acttggtctg acagttacca atgcttaatc agtgaggcac   3420
ctatctcagc gatctgtcta tttcgttcat ccatagttgc ctgactcccc gtcgtgtaga   3480
taactacgat acgggagggc ttaccatctg gccccagtgc tgcaatgata ccgcgagacc   3540
cacgctcacc ggctccagat ttatcagcaa taaaccagcc agccggaagg gccgagcgca   3600
gaagtggtcc tgcaacttta tccgcctcca tccagtctat taattgttgc cgggaagcta   3660
gagtaagtag ttcgccagtt aatagtttgc gcaacgttgt tgccattgct acaggcatcg   3720
tggtgtcacg ctcgtcgttt ggtatggctt cattcagctc cggttcccaa cgatcaaggc   3780
gagttacatg atccccatg ttgtgcaaaa aagcggttag ctccttcggt cctccgatcg    3840
ttgtcagaag taagttggcc gcagtgttat cactcatggt tatggcagca ctgcataatt   3900
ctcttactgt catgccatcc gtaagatgct tttctgtgac tggtgagtac tcaaccaagt   3960
cattctgaga atagtgtatg cggcgaccga gttgctcttg cccggcgtca atacgggata   4020
ataccgcgcc acatagcaga actttaaaag tgctcatcat tggaaaacgt tcttcggggc   4080
gaaaactctc aaggatctta ccgctgttga gatccagttc gatgtaaccc actcgtgcac   4140
ccaactgatc ttcagcatct tttactttca ccagcgtttc tgggtgagca aaaacaggaa   4200
ggcaaaatgc cgcaaaaaag ggaataaggg cgacacggaa atgttgaata ctcatactct   4260
```

```
tcctttttca atattattga agcatttatc agggttattg tctcatgagc ggatacatat    4320
ttgaatgtat ttagaaaaat aaacaaatag gggttccgcg cacatttccc cgaaaagtgc    4380
cacctgacgt ctaagaaacc attattatca tgacattaac ctataaaaat aggcgtatca    4440
cgaggccctt tcgtc                                                    4455

<210> SEQ ID NO 34
<211> LENGTH: 1014
<212> TYPE: DNA
<213> ORGANISM: Artificial Sequence
<220> FEATURE:
<223> OTHER INFORMATION: Synthetic construct, open reading frame of
      tTAV construct

<400> SEQUENCE: 34
atgggcagcc gcctggataa gtccaaagtc atcaactccg cgttggagct gttgaacgaa      60
gttggcattg agggactgac gacccgcaag ttggcgcaga agctgggcgt ggagcagccc     120
accctctact ggcacgtgaa gaataagcgg gcgctgctgg atgccctggc catcgagatg     180
ctcgaccgcc accacacgca ttttttgcccg ttggaaggcg agtcctggca ggacttcctc     240
cgcaataacg ccaagtcgtt ccgctgcgct ctgctgtccc accagacgg tgccaaagtc     300 catctcggca cgcgcccgac cgaaaagcaa tacgagacac tggagaacca gctcgcgttc     360
ctgtgccagc aaggcttcag cctggaaaat gctctctacg ctctgagcgc cgtcggtcac     420
tttaccctgg gctgcgtgct ggaggaccaa gagcatcaag tcgcaaaaga ggagcgcgag     480
accccaacaa ccgattcgat gccccactg ctgcgtcagg caatcgagct gttcgatcat     540
caaggagccg agccggcatt cctgttcggc ttggagctga ttatctgcgg attggaaaag     600
caactgaaat gcgagtcggg ctcgggcccc gcgtacagcc gcgcgcgtac gaaaaacaat     660
tacgggtcta ccatcgaggg cctgctcgat ctcccggacg acgacgcccc cgaagaggcg     720
gggctggcgg ctccgcgcct gtcctttctc cccgcgggac acacgcgcag actgtcgacg     780
gcccccccga ccgatgtcag cctggggggac gagctccact agacggcga ggacgtggcg     840 atggcgcatg ccgacgcgct agacgatttc gatctggaca tgttggggga cggggattcc     900
ccgggtccgg gatttacccc ccacgactcc gcccctacg gcgctctgga tatggccgac     960
ttcgagtttg agcagatgtt taccgatgcc cttggaattg acgagtacgg tggg           1014

<210> SEQ ID NO 35
<211> LENGTH: 338
<212> TYPE: PRT
<213> ORGANISM: Artificial Sequence
<220> FEATURE:
<223> OTHER INFORMATION: Synthetic construct, Protein sequence of tTAV

<400> SEQUENCE: 35

Met Gly Ser Arg Leu Asp Lys Ser Lys Val Ile Asn Ser Ala Leu Glu
1               5                   10                  15

Leu Leu Asn Glu Val Gly Ile Glu Gly Leu Thr Thr Arg Lys Leu Ala
                20                  25                  30

Gln Lys Leu Gly Val Glu Gln Pro Thr Leu Tyr Trp His Val Lys Asn
            35                  40                  45

Lys Arg Ala Leu Leu Asp Ala Leu Ala Ile Glu Met Leu Asp Arg His
        50                  55                  60

His Thr His Phe Cys Pro Leu Glu Gly Glu Ser Trp Gln Asp Phe Leu
65                  70                  75                  80
```

Arg Asn Asn Ala Lys Ser Phe Arg Cys Ala Leu Leu Ser His Arg Asp
            85                  90                  95

Gly Ala Lys Val His Leu Gly Thr Arg Pro Thr Glu Lys Gln Tyr Glu
        100                 105                 110

Thr Leu Glu Asn Gln Leu Ala Phe Leu Cys Gln Gln Gly Phe Ser Leu
            115                 120                 125

Glu Asn Ala Leu Tyr Ala Leu Ser Ala Val Gly His Phe Thr Leu Gly
            130                 135                 140

Cys Val Leu Glu Asp Gln Glu His Gln Val Ala Lys Glu Glu Arg Glu
145                 150                 155                 160

Thr Pro Thr Thr Asp Ser Met Pro Pro Leu Leu Arg Gln Ala Ile Glu
                165                 170                 175

Leu Phe Asp His Gln Gly Ala Glu Pro Ala Phe Leu Phe Gly Leu Glu
            180                 185                 190

Leu Ile Ile Cys Gly Leu Glu Lys Gln Leu Lys Cys Glu Ser Gly Ser
            195                 200                 205

Gly Pro Ala Tyr Ser Arg Ala Arg Thr Lys Asn Asn Tyr Gly Ser Thr
        210                 215                 220

Ile Glu Gly Leu Leu Asp Leu Pro Asp Asp Ala Pro Glu Glu Ala
225                 230                 235                 240

Gly Leu Ala Ala Pro Arg Leu Ser Phe Leu Pro Ala Gly His Thr Arg
                245                 250                 255

Arg Leu Ser Thr Ala Pro Pro Thr Asp Val Ser Leu Gly Asp Glu Leu
            260                 265                 270

His Leu Asp Gly Glu Asp Val Ala Met Ala His Ala Asp Ala Leu Asp
        275                 280                 285

Asp Phe Asp Leu Asp Met Leu Gly Asp Gly Asp Ser Pro Gly Pro Gly
290                 295                 300

Phe Thr Pro His Asp Ser Ala Pro Tyr Gly Ala Leu Asp Met Ala Asp
305                 310                 315                 320

Phe Glu Phe Glu Gln Met Phe Thr Asp Ala Leu Gly Ile Asp Glu Tyr
                325                 330                 335

Gly Gly

<210> SEQ ID NO 36
<211> LENGTH: 1014
<212> TYPE: DNA
<213> ORGANISM: Artificial Sequence
<220> FEATURE:
<223> OTHER INFORMATION: Synthetic construct, open reading frame of
      tTAV2

<400> SEQUENCE: 36
atgagccgcc tggataagtc caaagtcatc aactccgcgt tggagctgtt gaacgaagtt      60
ggcattgagg gactgacgac ccgcaagttg gcgcagaagc tgggcgtgga gcagcccacc     120
ctctactggc acgtgaagaa taagcgggcg ctgctggatg ccctggccat cgagatgctc     180
gaccgccacc acacgcattt tgcccgttg gaaggcgagt cctggcagga cttcctccgc     240
aataacgcca gtcgttccg ctgcgctctg ctgtcccacc gagacggtgc caaagtccat     300
ctcggcacgc gcccgaccga aaagcaatac gagacactgg agaaccagct cgcgttcctg     360
tgccagcaag gcttcagcct ggaaaatgct ctctacgctc tgagcgccgt cggtcacttt     420
accctgggct gcgtgctgga ggaccaagag catcaagtcg caaagaggag gcgcgagacc     480
ccaacaaccg attcgatgcc cccactgctg cgtcaggcaa tcgagctgtt cgatcatcaa     540

```
ggagccgagc cggcattcct gttcggcttg agctgatta tctgcggatt ggaaaagcaa    600
ctgaaatgcg agtcgggctc gggccccgcc tacagccgcg cccgcaccaa gaacaactac   660
ggcagcacca tcgagggcct gctggatctg ccggatgatg atgccccgga ggaggcgggc   720
ctggccgccc cgcgcctgag cttcctgccg gccggacaca cccgccgcct gtcgaccgcc   780
ccgccgaccg acgtgagcct gggcgatgag ctgcacctgg atggcgagga tgtggcgatg   840
gcccacgccg atgccctgga cgacttcgac ctggacatgc tgggcgatgg cgatagcccg   900
ggaccgggat tcaccccgca cgatagcgcc ccctacggcg ccctggatat ggccgatttc   960
gagttcgagc agatgttcac cgacgccctg ggcatcgatg agtacggcgg ctaa        1014
```

<210> SEQ ID NO 37
<211> LENGTH: 337
<212> TYPE: PRT
<213> ORGANISM: Artificial Sequence
<220> FEATURE:
<223> OTHER INFORMATION: Synthetic construct, Protein sequence of tTAV2

<400> SEQUENCE: 37

```
Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
                20                  25                  30

Lys Leu Gly Val Glu Gln Pro Thr Leu Tyr Trp His Val Lys Asn Lys
            35                  40                  45

Arg Ala Leu Leu Asp Ala Leu Ala Ile Glu Met Leu Asp Arg His His
        50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser Gly
        195                 200                 205

Pro Ala Tyr Ser Arg Ala Arg Thr Lys Asn Asn Tyr Gly Ser Thr Ile
    210                 215                 220

Glu Gly Leu Leu Asp Leu Pro Asp Asp Asp Ala Pro Glu Glu Ala Gly
225                 230                 235                 240

Leu Ala Ala Pro Arg Leu Ser Phe Leu Pro Ala Gly His Thr Arg Arg
                245                 250                 255

Leu Ser Thr Ala Pro Pro Thr Asp Val Ser Leu Gly Asp Glu Leu His
            260                 265                 270

Leu Asp Gly Glu Asp Val Ala Met Ala His Ala Asp Ala Leu Asp Asp
        275                 280                 285
```

```
Phe Asp Leu Asp Met Leu Gly Asp Gly Asp Ser Pro Gly Pro Gly Phe
    290                 295                 300

Thr Pro His Asp Ser Ala Pro Tyr Gly Ala Leu Asp Met Ala Asp Phe
305                 310                 315                 320

Glu Phe Glu Gln Met Phe Thr Asp Ala Leu Gly Ile Asp Glu Tyr Gly
                325                 330                 335

Gly

<210> SEQ ID NO 38
<211> LENGTH: 1011
<212> TYPE: DNA
<213> ORGANISM: Artificial sequence
<220> FEATURE:
<223> OTHER INFORMATION: Synthetic construct, open reading frame of
      tTAV3

<400> SEQUENCE: 38
atgggcagcc gcctggacaa gagcaaggtg atcaacagcg ccctggagct gctgaacgaa      60
gttggtatcg agggcctgac cacccgcaag ctggcccaga gctgggcgt ggaacagccg      120 accctgtact ggcacgtgaa gaacaagcgc gccctgctgg acgccctggc catcgaaatg      180
ctggatcgcc accacaccca cttctgcccg ctggagggcg agagctggca ggatttcctg      240
cgcaacaacg ccaagagctt ccgctgcgcc ctgctgtcgc accgcgatgg cgccaaggtg      300
cacctgggca cccgcccgac cgagaagcag tacgagaccc tggagaacca gctggccttc      360
ctgtgccagc agggcttcag cctggagaac gccctgtacg ccctgagcgc cgtgggccac      420
ttcaccctgg gctgtgtgct ggaggatcag gagcaccagg tggccaagga ggagcgcgag      480
accccgacca ccgatagcat gccgccgctg ctgcgccagg ccatcgagct gttcgatcac      540
cagggcgccg agccggcctt cctgttcggc ctggagctga tcatctgcgg cctggaaaag      600
cagctgaagt gcgagagcgg cagcgcctac agccgcgccc gtaccaagaa caactatggc      660
agcaccatcg agggactgct ggacctgccg gatgacgatg ccccggagga agccggcctg      720 gccgccccc gcctgagctt cctgcccgcc ggacacacgc gccgcctgag caccgccccg      780
ccgaccgatg tgagcctggg cgacgagctg cacctggatg gagaggatgt ggcaatggcc      840
cacgccgacg ccctggacga tttcgacctg gatatgctgg gcgatggaga tagcccggga      900
ccgggcttca cgccccacga tagcgccccg tacggcgccc tggacatggc cgacttcgag      960
ttcgagcaaa tgttcaccga cgcgctgggc atcgatgagt atggcgggta g              1011

<210> SEQ ID NO 39
<211> LENGTH: 336
<212> TYPE: PRT
<213> ORGANISM: Artificial Sequence
<220> FEATURE:
<223> OTHER INFORMATION: Synthetic construct, Protein sequence of tTAV3

<400> SEQUENCE: 39

Met Gly Ser Arg Leu Asp Lys Ser Lys Val Ile Asn Ser Ala Leu Glu
1               5                   10                  15

Leu Leu Asn Glu Val Gly Ile Glu Gly Leu Thr Thr Arg Lys Leu Ala
            20                  25                  30

Gln Lys Leu Gly Val Glu Gln Pro Thr Leu Tyr Trp His Val Lys Asn
        35                  40                  45

Lys Arg Ala Leu Leu Asp Ala Leu Ala Ile Glu Met Leu Asp Arg His
    50                  55                  60
```

His Thr His Phe Cys Pro Leu Glu Gly Glu Ser Trp Gln Asp Phe Leu
 65                  70                  75                  80

Arg Asn Asn Ala Lys Ser Phe Arg Cys Ala Leu Leu Ser His Arg Asp
                 85                  90                  95

Gly Ala Lys Val His Leu Gly Thr Arg Pro Thr Glu Lys Gln Tyr Glu
            100                 105                 110

Thr Leu Glu Asn Gln Leu Ala Phe Leu Cys Gln Gln Gly Phe Ser Leu
        115                 120                 125

Glu Asn Ala Leu Tyr Ala Leu Ser Ala Val Gly His Phe Thr Leu Gly
    130                 135                 140

Cys Val Leu Glu Asp Gln Glu His Gln Val Ala Lys Glu Glu Arg Glu
145                 150                 155                 160

Thr Pro Thr Thr Asp Ser Met Pro Pro Leu Leu Arg Gln Ala Ile Glu
                165                 170                 175

Leu Phe Asp His Gln Gly Ala Glu Pro Ala Phe Leu Phe Gly Leu Glu
            180                 185                 190

Leu Ile Ile Cys Gly Leu Glu Lys Gln Leu Lys Cys Glu Ser Gly Ser
        195                 200                 205

Ala Tyr Ser Arg Ala Arg Thr Lys Asn Asn Tyr Gly Ser Thr Ile Glu
    210                 215                 220

Gly Leu Leu Asp Leu Pro Asp Asp Ala Pro Glu Glu Ala Gly Leu
225                 230                 235                 240

Ala Ala Pro Arg Leu Ser Phe Leu Pro Ala Gly His Thr Arg Arg Leu
                245                 250                 255

Ser Thr Ala Pro Pro Thr Asp Val Ser Leu Gly Asp Glu Leu His Leu
            260                 265                 270

Asp Gly Glu Asp Val Ala Met Ala His Ala Asp Ala Leu Asp Phe
        275                 280                 285

Asp Leu Asp Met Leu Gly Asp Gly Asp Ser Pro Gly Pro Gly Phe Thr
    290                 295                 300

Pro His Asp Ser Ala Pro Tyr Gly Ala Leu Asp Met Ala Asp Phe Glu
305                 310                 315                 320

Phe Glu Gln Met Phe Thr Asp Ala Leu Gly Ile Asp Glu Tyr Gly Gly
                325                 330                 335

<210> SEQ ID NO 40
<211> LENGTH: 568
<212> TYPE: DNA
<213> ORGANISM: Pectinophora gossypiella

<400> SEQUENCE: 40
gctagtggag aactgccaca aactgctgga aaagttccac tactcctggg aaatgatgcc      60
cctggtgctg gtcattctaa actacgccgg ctccgacctc gacgaggctt ctagaaaaat     120
tgatgaaggg aagatgatca tcaacgagta cgcgaggaag cacaatctga acatcttcga     180
tggccacgag ctaaggaact cgactcgcca gtacggactt aatacagta atattagttt     240 tctccaacaa cactaaacac gacataacac gctacacgca aaaatacac gagtctttaa     300 tgttttacac gctcagtaaa ttattcactt acacgcttaa ctaaaatttt acacaatcgg     360 taaaaaata caacaattta ttatcgtaaa aattacacaa aataaatgag atttaaatgt     420
cgtttaataa aataaaataa aaatagcatc gggaatatct tttcacctat tgccggagaa     480
cagtttaaat ggatactctc atttgaatca ttttaattgt agtagcattt tatttttta     540 ttaatagcaa taagtacaca aacataaa                                        568

<210> SEQ ID NO 41
<211> LENGTH: 610
<212> TYPE: DNA
<213> ORGANISM: Pectinophora gossypiella

<400> SEQUENCE: 41

| | | | | |
|---|---|---|---|---|
| gtagtggaga | actgccacaa | actgctggaa | aagttccact | actcctggga aatgatgccc | 60 |
| ctggtgctgg | tcattctaaa | ctacgccggc | tccgacctcg | acgaggcttc tagaaaaatt | 120 |
| gatgaaggga | agatgatcat | caacgagtac | gcgaggaagc | acaatctgaa catcttcgat | 180 |
| ggccacgagc | tgaggaactc | gactcgccag | tacggacttt | aatacagaaa atgctgagcg | 240 |
| aaattaataa | tataagtggt | gtactatcgt | cgtccatgaa | gttattttgc gaatgatact | 300 |
| ttgttttgta | tgtgctgtgt | gttgtgtgga | cttttgctgt | gcgttgctgt ttgcgatgga | 360 |
| aggactattg | tgtcgtcgcc | acgctggact | attcgcacat | tgggtggtcc accagtggcg | 420 |
| gatgtacgag | cggtcgctgt | gctcgctcct | ggagctgcaa | gcgcgcaaag gacgtactc | 480 |
| ggtgtgctgc | tcaccccgct | acgtcatcgc | gcccgagtac | gcgtcacacc tgttgcctct | 540 |
| gccgcttacc | acgcagagat | catccccgcc | gcccgcgcac | ttgtagcgat gcgaacctgc | 600 |
| gccgcgggaa | | | | | 610 |

<210> SEQ ID NO 42
<211> LENGTH: 449
<212> TYPE: DNA
<213> ORGANISM: Pectinophora gossypiella
<220> FEATURE:
<221> NAME/KEY: misc_feature
<222> LOCATION: (26)..(26)
<223> OTHER INFORMATION: At position 26, n is a, c, g, or t

<400> SEQUENCE: 42

| | | | | |
|---|---|---|---|---|
| gctagtggag | aactgccaca | aactgntgga | aaagttccac | tactcctggg aaatgatgcc | 60 |
| cctggtgctg | gtcattctaa | actacgccgg | ctccgacctc | gacgaggctt ctagaaaaat | 120 |
| tgatgaagca | cattgggtgg | tccaccagtg | gcggatgtac | gagcggtcgc tgtgctcgct | 180 |
| cctggagctg | caagcgcgca | aagggacgta | ctcggtgtgc | tgctcacccc gctacgtcat | 240 |
| cgcgcccgag | tgcgcgtcac | acctgttgcc | tctgccgctt | accacgcaga gatcatcccc | 300 |
| gccgcccgcg | cacttgtagc | gatgcgaacc | tgcgccgcgg | gaagtaagta ctatttcatt | 360 |
| tattattctt | tttattttg | gttttaaggt | gctgacagac | ttgaatttca agcaaatagt | 420 |
| gtctgacaaa | gagctcaaaa | tagacatgt | | | 449 |

<210> SEQ ID NO 43
<211> LENGTH: 28774
<212> TYPE: DNA
<213> ORGANISM: Aedes aegypti

<400> SEQUENCE: 43

| | | | | |
|---|---|---|---|---|
| acagtgaaat | ttgatcgatc | actcatcgaa | acgagatcac | tttcgattga tcgtgacaat | 60 |
| ttttagaat | ccatttcaca | gtcgttggga | ctgttgaccc | tgtcacttta aactagctag | 120 |
| tgagtagctt | tgctctagtg | aaagctaact | agcactgtta | aaaaatctta ggtaaagtgt | 180 |
| cagcaaccct | gacaactggg | ccacctcttg | ccgaccataa | gcaaatgaaa tcaaatggtt | 240 |
| cgctacgaag | gttaattggg | tttcgatcta | cttcgtccta | agcgctattt ttcgtcatac | 300 |
| ggtggagaac | ggctggtatt | cgtttacttt | agtttaccaa | gcgatgcttc caattaaccc | 360 |
| aaagctagat | gaagcaggat | tcgcgataaa | aagcagtatg | cgaacttaaa atgttctact | 420 |

-continued

| | |
|---|---|
| acattacggc gggtattcaa atttacctgc cacataaatt tattttccaa gtataatttg | 480 |
| cgaaagctgc aatggttcat gcttgaattt tacaagatga tgtaatgccg cccataagtt | 540 |
| taaatggacg gtgtatttaa ataaaaggtt catattaaac gctttcgacg ttaccaagta | 600 |
| ccatttgtac acaaacatgt aataaaacta ttgtatttct ataaataact tcagttcaat | 660 |
| catccacttt gcacattttc accgaaatcg catggacgaa ggtaaacatg tgtttgtaca | 720 |
| ttattttgat aacataaaga tatttattga agtcaagtta gtaggtgaaa cgtgtaaaag | 780 |
| tggctttagc gtacctgctt gacgtaccga gcgaaatctg attagcggtc gactaagcca | 840 |
| taaaacttct acaattcaca aaattttgaa aaattccctc gctgccacga tactaatgca | 900 |
| ctgcatggct cgctttagac taatcgccag ctgattcggt attttgaaga tgttaagtgt | 960 |
| tttaaaactt tttaagggag cgacggtgct atgattacg aatcaaatgt tctttctttt | 1020 |
| actttcagac caattgcaga acaagcttta tcctaatcca tctcattttg ggaacagcac | 1080 |
| tagccgcgac cattagccgt ttagtttaca agaaagaaaa tgaaagtctg gttaacgtct | 1140 |
| tgttcgaaat aggattaggt agagtaaaac ccttgtcgtg atcggcgctg gtaatcggca | 1200 |
| tctgcgtaga gaacatgttg tacttcctcg aggacgattg ctcgcgctcg cacggttctt | 1260 |
| attgctacca tggtgaaacc actagcgccg aggaagtgct agacgcatct cttgtacaac | 1320 |
| atgaaggagc tcctgctaac gagcgcgagc gtgccaagaa taacgatggt accactttgg | 1380 |
| tgatcgcggc tccttcacga taccgttgtg aaggttttct gaattgcgca tcgtctccga | 1440 |
| agggtgtgtc caggtgcatt gtctcccaac tgacctgttc ccgacaatat cgagcactaa | 1500 |
| atggcaacac ttccaaaaga cttaacgcgt agcagaggct tcccacacag gtccacgtaa | 1560 |
| cagagggttg actggacaag ggctgttata gctcgtgatt ggtttccatt agagagcagt | 1620 |
| atctcgtagt agcgtaggag agtccattag agtgcgatat tccgtgagtt tgtgtgaccg | 1680 |
| gcgatagaga agccctgacg ccaaaggtaa tctctcgtca tagagcatca tcgcatcctc | 1740 |
| tcaggtaatc tcacgctata aggcactcaa acacactggc cgctatctct tcgggactgc | 1800 |
| cgcgcttcaa gacgattgta actcggaaac tgacctgatt agtacataaa aagagaccta | 1860 |
| ttgcgtaagc ttataagaaa cgagtttgtc cacacggttg gcgcgaagtt ctgctaacat | 1920 |
| tgagcctttg actggactaa tcatgtattt ttctctggat aacgcattcg aatattcttt | 1980 |
| gctcaaacag gtgtgccaac atggtttcgc aagatcgctg gatggtaaag atgtccgagg | 2040 |
| cagggtacga taaccgggcg gatggcagtg gagcttccag cagcagcctg aacccgcgaa | 2100 |
| taccaaagcg ttctagcgac ctaccatttc tacaggctcc gtcccatgct attggcccgc | 2160 |
| ctaccgtcac ctcgaaggtc gtcgtcggac ttgggcgctt cgccgccgaa ctgtgcccgc | 2220 |
| tgccggaacc acggtcacaa gatcggcctg aagggacaca agcgctattg taagtatcgc | 2280 |
| aattgtacct gcgaaaagtg gcggcggctt gacacgggcg acggccttgg tgccagtgtt | 2340 |
| ctagccggac ttccctgtgt tcgcgataac attcatagcg ttaacatgga cgcttttcac | 2400 |
| ctgcctgacg gccgaacggc agcgggtcat ggccctgcag acggctctcc gaagggcgca | 2460 |
| aacccaggac gaacagcggt tgctggtaga cggagaggtg gacggactgc cggcttgccg | 2520 |
| tcgcccagta ccgggacgtc tgccgagagg cttcccgcgt ttgggtcctg cttgtcgcca | 2580 |
| acgaccatct gcctctccac cccgccgaac cggtacatag ccttcaaata ccaaaattgt | 2640 |
| ctgacctaaa agagatgatc cataattctc agcagaggtc gttgatcgac tgcgactcgt | 2700 |
| gggcggcttg gccatgtatc ggaagtttat ggttttaaca gactggattt tctctactag | 2760 |

```
gtattaagag tcgtctccag caactagctg acgctgagca ccaccggctc gatgaactcc    2820
accccgggca gctcgttggt aacgctgtcc cagcaccgaa gatcaccctg ctccgccgcg    2880
tcggtccacc ccagcgaggc ggtggccgag ctacttgagg tggggcccgt cgagcaacca    2940
ttgcgacagg gtcgtggctt ctagtgggac gaggcggcgc agccaggtgg ggtcgctccg    3000
tcagcaaaac gttgcaggta ggtgtgaggc atatctattt cgttattctc tcaatgtttg    3060
tggagaaccg gccggaattc aacatcgaag tcggttttctg agtcgttttg caacgtccat    3120
ccacactccg tatagataaa gcaataagag agttacaaac acctcttggc cggccttaag    3180
ttgtagcttc agccaaagac ttctattgat ttatgataaa tttctctcaa atgtttgcgc    3240
ggagggtgga ttttttgagag ctgagtggtg tagaaacgaa atgggcatca aacgttatgc    3300
aagataacta atactatttt aaagagagtt tacaaacgcg cctcccacct aaaaactctc    3360
gactcaccac atctttgctt tacccgtagt ttgcaatacg ggcgctgctt gaaacaggtt    3420
tatgttaggg gtttcctgtg tttcatacag tcaccccatt gttatgtata gcacacagat    3480
atggataaaa gttggattaa ccgcgacgaa ctttgtccaa atacaatccc caaggacac    3540 aaagtatgtc agtggggtaa caatacatat cgtgtgtcta tacctatttt caacctaatt    3600
gcagtgaata tcccatcaaa tagagttgca attgagtaga acacatttta ccaacgtata    3660
aagcatcgta atcaattata atatacttaa gcaaaataca cgtcacttat agggtagttt    3720
atctcaacgt taactcatct tgtgtaaaat ggttgcatat ttcgtagcat tagttaatat    3780
tatatgaatt cgttttatgt atggggaaat aatttgtcaa ccacatttct agaaaagttg    3840
attcatacat gtgtgctttt gaaagccata taccacatta tgtttgattc atatctctta    3900
taccccttta ttaaacagtt ggtgtaaaga tctttttcaac taagtatgta cacacgaaaa    3960
ctttcggtat atggtgtaat acaaactaag tatagagaat taatatgagt cgatttatcg    4020
cgaaattttt caaaatgtcc tatgtaccaa tgaaagatac tctcttatct cgctctgttt    4080
tgaacataac aactgaaact attatactca gctaaatagc gctttaaaaa gttttacagg    4140
atacatggtt actttctatg agagaataga gcgagacaaa acttgtattg ttgactttga    4200
tttgggaagt ttttcactat agataaaaaa atgtccttga ctagcgtttc atacaaaaaa    4260
aaaaaaaaac gcaaccaaaa atgttaatgt ggttcagtga aaaccccttca aaagtgata    4320 tctattttttt tacaggaact gatcgcaaag tatgttttttt ttttttttttg cgttggtttt    4380 tacaattaca ccaagtcact ttgattaaag aggaagtaaa ctaagatagt gtctcaatgt    4440
tggataggtc atttagaaaa ggtccgcgag attggatcca taataatgat tctcctctct    4500
aactaatttc tccttcattt gattctatca cagagttaca acctatccag taaatctttt    4560
ccaggcgctc taacctaggt attattacta agaggagaga cactgatccg catctgtggg    4620
atggacaacg tttgtaattt ctatcggtat cgaaaataat cgcgcatttt cgggcgtatt    4680
ccagaaaaca acaatgaaat gtgactaggc gtagacaccc tacctgttgc aaacattaaa    4740
gatagccata gctttttatta gcgcgtaaaa gcccgcataa ggtctttttgt tgttacttta    4800 atactgaagc aaatgtgcac aattttcatt acatgatatt attcaatggg gtaggtgggc    4860
gacaaaatag attcattaat gttggataat aggggcgttt tatgacttcg tttacacgtg    4920
ttaaaagtaa tgtactataa taagttaccc catccacccg ctgtttttatc taagtaatta    4980 caacctatta tccccgcaaa gtcattatcc ctaaatgctc cacctcagct ggtggccccg    5040
tcagtcagtt gatcgggaaa gcagcaatca atccggagac aggtcgacct ccatcgaaca    5100
cagtaatagg gatttacgag gtggagtcga ccaccggggc agtcagtcaa ctagcccttt    5160
```

```
cgtcgttagt taggcctctg tccagctgga ggtagcttgt ggaaccgaac aacactagat    5220
gttcgatttc taacgaccga ctaagaacat cgtcggaagc gtctggttca ttcgacgagc    5280 cggaagggt  tcatctttcg ccttggcttg ttgtgatcta caagctaaag attgctggct    5340
gattcttgta gcagccttcg cagaccaagt aagctgctcg gccttcccca agtagaaagc    5400
ctcgtcgtcg aacgaatagc tgctgctaca cttcgcgtcg ttatcgtcgt cggggggattg   5460 gtgtttgtaa ctgcgcactc gtttatacat tgttgtttgc gagcagcagc ttgcttatcg    5520
acgacgatgt gaagcgcagc aatagcagca gcccctaac cacaaacatt gacgcgtgag     5580
caaatatgta acaacaaacg cgatcggcgg gcgctgtaac tgcctgcagt cacgcgttca    5640
ttcgcagtcg ttgtcgtagt catacacacg ccgtcgttcc tttgtatcag ctgtgtagca    5700
gctagccgcc cgcgacattg acggacgtca gtgcgcaagt aagcgtcagc aacagcatca    5760
gtatgtgtgc ggcagcaagg aaacatagtc gacacatcgt tttagtggtg ttacaacatt    5820
gagctacttt ttgcgtttcg ctttcgtgct cggcggcgg cggcgggact tcgctgcact     5880
gataggaacg gaatgcatgc aaatcaccac aatgttgtaa ctcgatgaaa aacgcaaagc    5940
gaaagcacga cgccgccgcc gccgccctga agcgacgtga ctatccttgc cttacgtacg    6000
tgctccggtt gaagagagct ctgcgccact tgtggcgggt ttcactcaaa aggcatcgtc    6060
gcgtcgcaac aaagtgcgca cattcgacgc gtaactgtaa acgaggccaa cttctctcga    6120
gacgcggtga acaccgccca agtgagtttt ccgtagcag cgcagcgttg tttcacgcgt     6180
gtaagctgcg cattgacatt gtaaatagaa agactttggt gcgtttagaa aaagggtcac    6240
aaagggtggc aagtgagtat gtatgtgagc tcatttcatt ctcgatggca ttgagacgta    6300
catttatctt tctgaaacca cgcaaatctt tttcccagtg tttcccaccg ttcactcata    6360
catacactcg agtaaagtaa gagctaccgt aactctgcat atctattctg agaacgaaag    6420
ttcaatggat gcattttatg caatgccacc ggaattttcc tatgaactgc tttcacactt    6480
cttttaagaa aattttgcag tagataagac tcttgctttc aagttaccta cgtaaaatac    6540
gttacggtgg ccttaaaagg atacttgacg aaagtgtgaa gaaaattctt ttaaaacgtc    6600
atttaattta ttcactccat ttagttctga cgtaacattc cagataacac acttcaaagt    6660
catggtcagt tcatgttgaa cgaatgtgca ccgcgatcca taaattaaat aagtgaggta    6720
aatcaagact gcattgtaag gtctattgtg tgaagtttca gtaccagtca agtacaactt    6780
gcttacacgt ggcgctaggt cgcagaacga ttccatgtct taatgtcgtc acttatcata    6840
taatcaccca gttttttgccc cacttaaaaa aacgatgtcc acttttttatc tgagtttctt    6900 gcgtcttgct aaggtacaga attacagcag tgaatagtat attagtgggt caaaacggg     6960 gtgaattttt ttgctacagg tgaaaaatag actcaaagaa tctcctctct tttcagccaa    7020
ccactccagc ggaacccctg aacccggaaa catggtacca ggtgagttcg ctgttgaaat    7080
actaatttgc agaaaacata agaggagaga aaagtcggtt ggtgaggtcg ccttggggac    7140
ttgggccttt gtaccatggt ccactcaagc gacaacttta tgattaaacg tcttttgtat    7200
agaaattttg ctaccgattt accataactg gaatcgaaga caatatgact tcatcacacc    7260
agcagtaaac acggcgtaaa aatgattcat caggacccgc tctttaaaac gatggctaaa    7320
tggtattgac cttagcttct gttatactga agtagtgtgg tcgtcatttg tgccgcattt    7380
ttactaagta gtcctgggcg tcaatagccc tgttttttcca cgctcatctt gggtttcaca    7440
tcggtgaaca ccacttggag acgttttcac acaatgttca tgttcttctt tgagtaaatg    7500
```

```
agttatcggg acaaaaaggt gcgagtagaa cccaaagtgt agccacttgt ggtgaacctc   7560
tgcaaaagtg tgttacaagt acaagaagaa actcatttac aagttatgcg tggtcccgtg   7620
ctcatcaaga tagtgtgcca cacataagaa ttatcttaat tgaggccttc tgcgggccgt   7680
gagcttgttt gctacgccct ttcaatacgc accagggcac gagtagttct atcacacggt   7740
gtgtattctt aatagaatta actccggaag acgcccggca ctcgaacaaa cgatgcggga   7800
tccttggcgt tgagttttag tttctttgac agagaaagac ttttgataat ctactttctg   7860
cagctacgac ctttctctga actatttgga aaattataac aggaaccgca actcaaaatc   7920
aaagaaactg tctcttctg aaaactatta tgatgaaagac gtcgatgctg aaagagact   7980 tgataaacct tttaatattg ttatgttgac aatatttatc ccttcgatta caaaaaact   8040 tcaagccagg gaaacatcca gtgtgaaaac actaagcggc gcactttggt tcatttcatt   8100
aatacaactg ttataaatag ggaagctaat tgttttttga agttcggtcc ctttgtaggt   8160
cacacttttg tgattcgccg cgtgaaacca agtaaagtaa cgtatcgatc actcttaatt   8220
caagatgaca aagtggttga gtagtagagt acgtggctca caatcggaag gttcttggct   8280
cgaatctcaa tgtatgctat gcatagctag tgagaattaa gttctactgt ttcaccaact   8340
catcatctca tgcaccgagt gttagccttc caagaaccga gcttagagtt acatacgata   8400
ttttaacttt tttttttattt tgtcgatcat aaacggatgc gcgactcagc attttggca   8460 tttgaatcat gattccgagt aatcagctac aaaaacctaa aaaattgaaa aaaaaataaa   8520
acagctagta tttgcctacg cgctgagtcg taaaaaccgt aaacttagta ctaaggctca   8580
ttagtcgatg tttttggatt cgcgtgtgtt gcgttacggc aatctgactc atgatatcat   8640
gagtccaaat catggtgtat tttcataaga cgaaaacacg ctggaatcat gatatcatga   8700
gcgcacacaa cgcaatgccg ttagactgag tactatagta ctcaggttta gtaccacata   8760
aaagtattct gcttttgtgc gaccttagta ctatagtact gtaataatct tgttttgga   8820 ttctgatttc tacccgtgca tttctaaagt ttgcaaagaa ggaagcttca aaaaacttcc   8880
aaaagcttat gttacagaag cattattaga acaaaaacct aagactaaag atgggcacgt   8940
aaagatttca aacgtttctt ccttcgaagt tttttgaagg ttttcgaata caatgtcttc   9000
cttggaaagc ttaagttaca gcagtttccg taccagaacg ttggaaagct tatattacga   9060
aacagtaata gggtttctat gcggtggaag tgctgtttata gaacctttcg aattcaatgt   9120
cgtcaaaggc atggtcttgc aacctttcga atataatgct ttgtcattat cccaaagata   9180
cgccaccttc acgacaatat tggcgtgtaa gcatttataa tacatctggg tatcatcgaa   9240
atcattagaa aaaatgcggt ataagtttca cttgaattca gatcagtgat cgattgttac   9300
accgcacatt cgtaaatatt atgtagaccc atagtagctt tagtaatctt ttttacgcca   9360
tattcaaagt gaacttaagt ctagtcacta gctaacaatg agttcaaata gatccaaata   9420
tatgagggtg aaacgtcatt gcgatccact gtgaactgca gttgattggc cgcaatttca   9480
aaatatgtac acccgagtga tcaagtttat ctaggtttat atactcccac tttgcagtaa   9540
cgctaggtga cacttgacgt caactaaccg gcgttaaagt tttatacatg tgggctcact   9600
tctgcacggc tgttcagctg acatccttca ttgtcccagt cgttcataca aacttgcccg   9660
tcaagatcaa ggaagttggc gcttgatcaa tgttctgttt agacgtgccg acaagtcgac   9720
tgtaggaagt aacagggtca gcaagtatgt ttgaacgggc agttctagtt ccttcaaccg   9780
cgaactagtt acaagacaaa catttctttt ttccttaagta gtattgggcg ctgcggtcac   9840
ctcatttatc ttttttgaaat tgtttcggaa ataatgcacg agatgcaata acggttcttg   9900
```

```
gtaaagaaaa aagaattcat cataacccgc gacgccagtg gagtaaatag aaaaacttta   9960
acaaagcctt tattacgtgc tctacgttat tgccaagaac aacatagtca tgtagaacct  10020
tacaaatgat cagaattgat ttgatcaatt catttccagc tttcaaactg acgatcgccc  10080
aatgctaccg tccatcacga ttgtatcagt acatcttgga atgtttacta gtcttaacta  10140
aactagttaa gtaaaggtcg aaagtttgac tgctagcggg ttacgatggc aggtagtgct  10200
tattccacgc actggctgtc atgttccctg ccagatttac gtagtgttct tttgtaaagg  10260
caacactgct gcactgctcc aagtcactcc aagcttcatc ataaggtgcg tgaccgacag  10320
tacaagggac ggtctaaatg catcacaaga aaacatttcc gttgtgacga cgtgacgagg  10380
ttcagtgagg ttcgaagtag tgcgagttga agcaaactgt gaaggattga tattttgaat  10440
taaatcaagc tctcgcgttg caggcagctg taacttgcca ccaagtatga tcggtcttcc  10500
acgctcaact tcgtttgaca cttcctaact ataaaactta atttagttcg agagcgcaac  10560
gtccgtcgac attgaacggt ggttcatact agccagaagg gacttcgttc cataaaaagt  10620
ggaatgctcc tcgtccgatt tccagaaaca gtcggttatg caataaaaca ggatcaggtt  10680
cgatgactct tggcgatatc ctgaagcaag gtattttca ccttacgagg agcaggctaa  10740
aggtctttgt cagccaatac gttatttgt cctagtccaa gctactgaga accgctatag  10800
tgaattggag tcgttaccta tccccgata aagatatcct ctcgcaattc gaggggggatt  10860 aggattagaa accgtttgct gatatttgcg agatataaaa acttaacctc agcaatggat  10920
agggggctat ttctatagga gagcgttaag ctcccctaa tcctaatctt tggcaaacga  10980
ctataaacgc tctatatttt actaataaaa tcttcaattc gctaaaagca cttcaattct  11040
tgttttctct tctggtttca gttgacccc atatgcgagt gcagcatcac ggaccggact  11100
tgattatttt agaagttaag cgattttcgt gaagttaaga acaaaagaga agaccaaagt  11160
caactggggg tatacgctca cgtcgtagtg cctggcctga caggaacagg tgcgtacttc  11220
cttaacttca ctatcaataa aaccgtacct cctccagtcc atcgaaacaa caataaaata  11280
ctgcaccgat cagctggaat gtccttgtcc acgcatgaag gaattgaagt gatagttatt  11340
ttggcatgga ggaggtcagg tagctttgtt gttatttat gacgtggcta gtcgaccta  11400 ttctatcccg ggaggtccaa tcgctacaat ttatgcacat ttaattccac tggagccatg  11460
tgcgttcggg catcttatca ggcgttcggg aattgaaact aagataggc cctccaggtt  11520 agcgatgtta aatacgtgta aattaaggtg acctcggtac acgcaagccc gtagaatagt  11580
ccgcaagccc ttaactttga ttacgacctc atttgtcatt aacgggatgc attcgtacgc  11640
agtcagcgtc ttatcggcat atatgcggta gcccccgag tgacaattaa accatggagc  11700
aatgctggag taaacagtaa ttgccctacg taagcatgcg tcagtcgcag aatagccgta  11760
tatacgccat cgggggggctc actgttaatt tggtacctcg cgaaaccaat ttcacagcgg  11820
tccaccaact accgaatgcg atgcattttt atacgacagt ggcgttacta ggtgcttaac  11880
atatcaaaac ttggaagctt gctttggtta aagtgtcgcc aggtggttga tggcttacgc  11940
tacgtaaaaa tatgctgtca ccgcaatgat ccacgaattg tatagttttg aaccttcgaa  12000
cctttcaaaa gcttgcaaag cttccttcca ggagcttgga aagcttcctt ccaggagctt  12060
ggaaagcttc cttccaggag cttggaaagc ttccttccag ggaaagtttt cgaacgtttc  12120
gaaggaaggt cctcgaacct ttcgaaggaa ggtcctcgaa cctttcgaag gaaggtcctc  12180
gaacctttcg aaggaaggtc gagcttggaa agcttccttc caggagcttg gaaagcttcc  12240
```

```
ttccagtagc ttggaaagct tccttccagg agcttggaaa gcttccttcc aggagcttgg    12300
ctcgaacctt tcgaaggaag gtcctcgaac ctttcgaagg aaggtcatcg aacctttcga    12360
aggaaggtcc tcgaaccttt cgaaggaagg tcctcgaacc aaagcttcct tccaggagct    12420
tggaaagctt ccttccagga gcttggaaag cttccttcca ggagcttgga aagcttcctt    12480
ccaggagctt ggaaagcttc tttcgaagga aggtcctcga acctttcgaa ggaaggtcct    12540
cgaacctttc gaaggaaggt cctcgaacct ttcgaaggaa ggtcctcgaa cctttcgaag    12600
cttccaggag cttggaaagc ttccttccag gagcttggaa agcttccttc aggagcttg     12660
gaaagcttcc ttccaggagc ttggaaagct tccttccagg gaaggtcctc gaacctttcg    12720
aaggaaggtc ctcgaacctt tcgaaggaag gtcctcgaac ctttcgaagg aaggtcctcg    12780
aacctttcga aggaaggtcc agcttggaaa gcttccttcc aggagcttgg aaagcttcct    12840
tccaggagct tggaaagctt ccttccagga gcttggaaag cttccttcca ggagcttgga    12900
tcgaaccttt cgaaggaagg tcctcgaacc tttcgaagga aggtcctcga acctttcgaa    12960
ggaaggtcct cgaaccttc gaaggaaggt cctcgaacct aagcttcctt ccaggagctt     13020
ggaaagcttc cttccaggag cttggaaagc ttccttccag gagcttggaa agcttccttc    13080
caggagcttg aaagcttcc ttcgaaggaa ggtcctcgaa cctttcgaag gaaggtcct      13140
gaacctttcg aaggaaggtc ctcgaacctt tcgaaggaag gtcctcgaac ctttcgaagg    13200
ttccaggagt ggaaaagatt cctgaaagt acttggagaa attcctcgag ttatttcagt    13260
aaagattata ctggaggaac caatggtgga atcacttgag aaggtcctca ccttttctaa    13320
ggactttca tgaacctctt taaggagctc aataaagtca tttctaatat gacctccttg    13380
gttaccacct tagtgaactc gcatttcggc agaaatccct ggcaaaatcg ctatggaaaa    13440
atccctgcaa aaaatcctgg aataatcctt gccggaatct catgaggaac tcctggtaaa    13500
cgtaaagccg tctttaggga ccgttttagc gatacctttt tagggacgtt ttttaggacc    13560
ttattaggaa cggccttaga gtactccttg aggaccattt attctttaac aaatttctgt    13620
ttattttctc tacaaagtta cagctccttt accgtgccga ttggccagaa atgaccccaa    13680
agactcatgg ggtacgatct taagaaattg tttaaagaca aataaaagag atgtttcaat    13740
gtcgaggaaa tggcacggct aaccggtctt tactgggtt tctgagtacc ccatgctaga     13800
tatttctgcc aaatatactg tatgtttgtt tcttctgat atgcttttaa gctcaatttt      13860
ctttggaatg gtggagattt gttttggcct ccaatatact ataaagacgg tttatatgac    13920
atacaaacaa agaagactg tacgaaaatt cgagttaaaa gaaaccttac cacctctaaa    13980
caaaaccgga ggttatatga tgctagctcg tagttcgtac ctgaagtcaa ctcctcaatt    14040
cctaaatgct acaataatat ataaaatttt aggaaataac tgcaaaatat tctgaaggcc    14100
acgatcgagc atcaagcatg gacttcagtt gaggagttaa ggatttacga tgttattata    14160
tattttaaaa tccttttattg acgttttata agacttccgg atgtcttgat ctatcttgat    14220
gtatctaata tgtaatccca gaagcattct agttttttct gataatctgt gaaataagtt    14280
gtttttacga actttgactt tacagaacta gatagaacta catagattat acattagggt    14340
cttcgtaaga tcaaaaaga ctattagaca ctttattcaa caaaaatgct tgaaactgaa     14400
ttcgggattt gaggtacaag cttcaaata tattggaggt tctgcgatat aacttcaat     14460
gaattattgg aaattagaaa tcgtcttgtg catacgggtt aagccctaaa ctccatgttc    14520
gaaagtttat ataacctcca agacgctata attgaagtta cttaataacc tttaatctttt   14580
agcagaacac gtatgcccaa aatcgatttt agtctctggt agatttcgag agggaatgtc    14640
```

```
tgaagaaatt ttctgaccta catgtgaagt attgtctgtc aaattcaaaa tattttctgt    14700
ttagctaaaa tcagagacca tctaaagctc tcccttacag acttctttaa aagactggat    14760
gtacacttca taacagacag tttaagtttt ataaaagaca aggaaattaa aattttttgg    14820
ggaaaactcg aaactccttg gatatccaag gaaacaaaaa aaaagaaat atctgaagaa    14880 gtgcatcgtc cttttccctt tcctttaatt ttaaaaaacc cctttgagc tttgaggaac    14940 ctataggttc ctttgttttt ttttctttta tagacttctt cacgtagcag gaaaaaggaa    15000
aattattgtt ttaattaact aatagttctg ctagaaaggt ttttggcaga accccaaaat    15060
gatattcaaa gcaactaaca gctcgatttc ccctcgtttc ttaataacaa aattaattga    15120
ttatcaagac gatcttcca aaaccgtct tggggtttta ctataagttt cgttgattgt    15180
cgagctaaag gggagcaaag caatttcaga cgacgaactt gtcaaacgat ctcaatggct    15240
cctggagaag ctgcgatacc cctgggagat gatgcccctg atgtacgtga tactgaaagg    15300
gttaaagtct gctgcttgaa cagtttgcta gagttaccga ggacctcttc gacgctatgg    15360
ggaccctcta ctacggggac tacatgcact atgactttcc cgccgacgga gacgtcaata    15420
aagcgcgcca acggattgac gaaggtatgg gggttcttac cggttgggac tgtttccgag    15480
gtatcgatcg ggtgtcactc gcggctgcct ctgcagttat ttcgcgcggt tgcctaactg    15540
cttccatacc cccaagaatg gccaaccctg acaaaggctc catgctagc ccacagtgag    15600 acttcctggg tgctcccatt ttgtaactgc taacgcttat tattgagttt caggacatct    15660
gggatcttcg gtcgacggag tctattccca acagtgccct tgaaggaccc acgagggtaa    15720
aacattgacg attgcgaata ataactcaaa gtcctgtaga ccctagaagc cagctgcctc    15780
agataagggt tgtcacggga ggatcaaaca ctgccatcat gcagtttccg tagcctgttg    15840
ggctacgctc cccgacttga catcccccat tcttatcaaa caacaactca aggcctgaga    15900
cctagtttgt gacggtagta cgtcaaaggc atcggacaac ccgatgcgag gggctgaact    15960 gtaggggta agaatagttt gttgttgagt tccggactct caacgagtgg tggaatttgc    16020
gcacgaagtc attggtttgt cctggtaaaa gttaaagggg ttaactggag ggttaattga    16080
cacggtttca actgatggcc gttgctcacc accttaaacg cgtgcttcag taaccaaaca    16140
ggaccatttt caattttccc aattgacctc ccaattaact gtgccaaagt tgactaccgg    16200
ttattgacac acgatgaaa gacttgcacg cttgaccttc tgtctgtact aataaaagtt    16260
acgttggctg ggttttgggg tcataatggc cccaaaatcg aataactgtg tgcctacttt    16320
ctgaacgtgc gaactggaag acagacatga ttattttcaa tgcaaccgac ccaaaacccc    16380
agtattaccg gggttttagc aatcgtcata acttcttgaa atacaactca cgtttaagac    16440
cattcaagag tattagatca tcgtctataa tagcagattt gaaatttact tcacatttcg    16500
ttagcagtat tgaagaactt tatgttgagt gcaaattctg gtaagttctc ataatctagt    16560
agcagatatt atcgtctaaa ctttaaatga agtgtaaagc gtattgcagt gcccccttgct    16620 tccacaatgg aattagttaa agtttcgaga gcattgtcaa tatcaagtgt tgttagcaaa    16680
caaatgctaa catcaagatt cataacgtca cggggaacga aggtgttacc ttaatcaatt    16740
tcaaagctct cgtaacagtt atagttcaca acaatcgttt gtttacgatt gtagttctaa    16800
actatcgatg tttgattcac atgtattcca atcagctcgt aaaaatgga aagtggagct    16860 gatagggttg agaatcgctt catgggataa ttggaaacag tgatagctac aaactaagtg    16920
tacataaggt tagtcgagca tttttacct ttcacctcga ctatcccaac tcttagcgaa    16980
```

```
gtaccctatt aacctttgtc ggacatgatc agaatgaaaa tcagcgtgag taaccagttg    17040
actacaaaga tgactagagt cggttaagaa aaattcaagt agggctatca ggttattgaa    17100
cctgtactag tcttactttt agtcgcactc attggtcaac tgatgtttct actgatctca    17160
gccaattctt tttaagttca tcccgatagt ccataacctt ttgaaaaata tcccgaaggg    17220
ccctcatcaa ttaaaatttt gcctttggaa atgtttggca ttcaagtagc aaattttaac    17280
atactgcgat tcgatttccg aacttttat agggcttccc gggagtagtt aattttaaaa    17340
cggaaacctt tacaaaccgt aagttcatcg tttaaaattg tatgacgcta agctaaaggc    17400
caagttagtt tgaaacaaat taacttgcta cccagtgcat taaaaaggca agtaggcagc    17460
tttggaagta taaacttagc tgtgttttaa cagaagcact gttcaatcaa actttgttta    17520
attgaacgat gggtcacgta attttccgt tcatccgtcg aaaccttcat atttgaatcg     17580
acacaaaatt gtcttcgtga cgcaagtttc aaaaattttg gtttcgaatg acaaaaaaag    17640
ttgatgttat atacgcctat tgaatgatga ttccagttga tcatttcgac aaacaaaaaa    17700
gcgttcaaag tttttaaaac caaagcttac tgttttttc aactacaata tatgcggata     17760
acttactact aaggtcaact agtaaagctg tttgttttt gaatctcttt tgatttcaga     17820
tccaggattc aaataacatt ccgttatcag ataaggggtt aatgccacaa tcgtgtggtc    17880
cattatcccc ggaaacttca cttagagaaa actaaagtct aggtcctaag tttattgtaa    17940
ggcaatagtc tatttcccaa ttacggtgtt agcacaccag gtaataggggg cctttgaagt   18000 caccgtcaca ctcgatccag atctgatgtg atctctgccg tcgggcgcct cagaagcgaa    18060
aaccacattc gcccgcgctc tccggaatta tgtcgtaaaa gtggcagtgt gagctaggtc    18120
tagactacac tagagacggc agcccgcgga gtcttcgctt ttggtgtaag cgggcgcgag    18180 aggcctaat acagcatttt taaaacttta caaccataat tattcagaac ttcgacgact     18240
gcgcgatgac ttggccgcgg tgtgcctgct tgggatggac ctccgagcac tgaaagcagt    18300
attttgaaat gttggtatta ataagtcttg aagctgctga cgcgctactg aaccggcgcc    18360
acacggacga accctacctg gaggctcgtg actttcgtca ggtttgtaca aattgaatgg    18420
gctatttgaa attaattggg ctgcgataac ttcaaagtgt gacatcaaaa tggtgtgagt    18480
tttttactgc acaaattcca ccaaacatgt ttaacttacc cgataaactt taattaaccc    18540
gacgctattg aagtttcaca ctgtagtttt accacactca aaaatgacg tgtttaaggt     18600 agttatttcc tacttcatat caatcggagc tccaggagtg aagatccaaa ttaccaagct    18660
tggccatttc gtatgaaaaa cggcaaaatg atcttttttt tcaataaagg atgaagtata    18720
gttagcctcg aggtcctcac ttctaggttt aatggttcga accggtaaag catacttttt    18780
gccgttttac tagaaaaaaa cgccagtcac tgtatctcat gatccagatg agataaaaaa    18840
gttcgagtct tcgacaaagt tgttttggaa gtcatggaca ttcttaagca aacaacttag    18900
gcggtcagtg acatagagta ctaggtctac tctatttttt caagctcaga agctgtttca    18960
acaaaacctt cagtacctgt aagaattcgt ttgttgaatc ttttgccact aggtggcgcc    19020
agtaagcata ttcgtcatca aacgtcaaca tcccaccgca aaatcgctag tgtttggagg    19080
ggattttaac ctccaaattg aaaacggtga tccaccgcgg tcattcgtat aagcagtagt    19140
ttgcagttgt agggtggcgt tttagcgatc acaaacctcc cctaaaattg gaggtttaac    19200
ccaaataacc tccaaatcat cacctccaag ttagttctaa tacactccgt tatatgaaat    19260
atggtggtgc gtcgatcgtc gcaagttat cgttaaacag ggtttattgg aggtttagta    19320
gtggaggttc aatcaagatt atgtgaggca atatacttta taccaccacg cagctagcag    19380
```

```
cgttcaaata gcaatttgtc tcaataaaat gagcatttta tatcgtgata catatgagaa  19440
gatagaggtt tcaattaaaa caaatccaca tggtgtcgct aataaaattg tgcattttaa  19500
agttattta ctcgtaaaat atagcactat gtatactctt ctatctccaa agttaatttt   19560
gtttaggtgt accacagcga ttattttaac acgtaaaatt gcgagttata tcctctgatc  19620
aagataaaat agaaaattcg attttttgaat attcaattat aagagcctga ataactacaa 19680
catgtagtga atcgaaactg cgctcaatat aggagactag ttctatttta tcttttaagc  19740
taaaaactta taagttaata ttctcggact tattgatgtt gtacatcact tagctttgac  19800
atttatgacg gtttgtgaag gttacacgtc ctaagcattt ggattcaaga aaagcaagag  19860
atatgacgaa tgtaaacttt atcgtatcaa tgaagtaact taaatactgc caaacacttc  19920
caatgtgcag gattcgtaaa cctaagttct tttcgttctc tatactgctt acatttgaaa  19980
tagcatagtt acttcattga agcgtccaga acagtacaaa ccaacatcgt accgtcgtat  20040
tccactccgg tcgttgcaat atctctaggt ccaccgaaaa acactcatga ccaagatcgt  20100
tcgcaggtct tgtcatgttt ggttgtagca tggcagcata aggtgaggcc agcaacgtta  20160
tagagatcca ggtggctttt tgtgagtact ggttctagca gtcgtcgatc ttggtccacc  20220
gaaacaccga tgtccatatc gtttcgtcga acttggacca acgattcatg caactgatga  20280
caacgcggcc cccgggtcgt cagcagctag aaccaggtgg ctttgtggct acaggtatag  20340
caaagcagct tgaacctggt tgctaagtac gttgactact gttgcgccgg gggcccagca  20400
accaatatcc gaaaaatcca actgttcttc tctgcctcgc aggtcaagcc gtggtcaatg  20460
aatactcacg attgcacaat ctgaacatgt tcgacggtgt tggttatagg cttttaggt   20520
tgacaagaag agacggagcg tccagttcgg caccagttac ttatgagtgc taacgtgtta  20580
gacttgtaca agctgccaca agagttgcgc agtacgacgc gccagtccgg atgatagact  20640
ttttacacga tcagcacgac ccactgcgct gcggcaaagg tcgaaccgaa acaagaataa  20700
tctcaacgcg tcatgctgcg cggtcaggcc tactatctga aaaatgtgct agtcgtgctg  20760
ggtgacgcga cgccgtttcc agcttggctt tgttcttatt accacgaaga tcagatcgat  20820
tcgacggaag aagcaatcga atgcaaagaa gaatcggaac gaagaaaact ctaaagcatc  20880
gcatatttac aaagcataac tggtgcttct agtctagcta agctgccttc ttcgttagct  20940
tacgtttctt cttagccttg cttctttga gatttcgtag cgtataaatg tttcgtattg  21000
ggaaaacccg caagttcaaa ctagtgatta gtgtaagatg aagcaaagca gaaatgtagt  21060
atctagattt ttcgacgtta gtttacaaag ataaaaaatg cctttgggc gttcaagttt  21120
gatcactaat cacattctac ttcgtttcgt ctttacatca tagatctaaa agctgcaat  21180
caaatgtttc tatttttac aggttggaca tacaatcgtg ggtattcgtc tgagttcgtc  21240
acaactgcac cggaaactgt gaaacagaat agagccaacc tgtgcgcgga gaatgttgag  21300
tccaacctgt atgttagcac ccataagcag actcaagcag tgttgacgtg cctttgaca   21360
ctttgtctta tctcggttgg acacgcgcct cttacaactc gtcattataa gcttccttag  21420
catccacggg tgaaagtcga tcgacggaag cctgcaagac tctgtcgatg ggctttcgtc  21480
ctagaagaat aagattaaac cagtaatatt cgaaggaatc gtaggtgccc actttcagct  21540
agctgccttc ggacgttctg agacagctac ccgaaagcag gatcttctta ttctaatttg  21600
ctgaaatgta ttctcccgtg gaatggtttc atttgagtaa ttctgtatct tctccttccc  21660
aattccacga acgcgacgaa ctctaataca aacaacataa gactttacat aagagggcac  21720
```

-continued

```
cttaccaaag taaactcatt aagacataga agaggaaggg ttaaggtgct tgcgctgctt    21780
gagattatgt ttgttgtatt tgaccacagt gcaaatgctg tttaacgata atagcgacat    21840
gcagccattc tggggctacc acgtgtagct ctacttgtga gacagcgttc ctaaagagtg    21900
actggtgtca cgtttacgac aaattgctat tatcgctgta cgtcggtaag accccgatgg    21960
tgcacatcga gatgaacact ctgtcgcaag gatttctcac tgaaagtgca aacaagtgat    22020
gaaaccaata gtgcaaagca agtttagagg gaaaatttaa aaaatgcaaa acagcagtag    22080
tacttaactt ttaagattgt actttcacgt ttgttcacta ctttggttat cacgtttcgt    22140
tcaaatctcc cttttaaatt ttttacgttt tgtcgtcatc atgaattgaa aattctaaca    22200
gtttcgaaag ccgaagtgtg ttccatctgc caccggaaaa aaacgacgac agcagaatca    22260
tcaacaagca acatccatcc gaaaaaatcc gggaaaccgg caaagctttc ggcttcacac    22320
aaggtagacg gtggcctttt tttgctgctg tcgtcttagt agttgttcgt tgtaggtagg    22380
cttttttagg ccctttggcc atcttcaacc aaccatccta caatctacaa accagagatt    22440
atatctcttc aatcgtttcc gacatcggtc ggtttcggtg cccaaaatga tctgataaac    22500
tagaagttgg ttggtaggat gttagatgtt tggtctctaa tatagagaag ttagcaaagg    22560
ctgtagccag ccaaagccac gggttttact agactatttg acttatctct ctgtagcttg    22620
catgccattg cgagcgtatt ttggtagctg gccgttgcca aacggctccg acaggtactg    22680
ctattggagg ttgtgcacga tgaatagaga gacatcgaac gtacggtaac gctcgcataa    22740
aaccatcgac cggcaacggt ttgccgaggc tgtccatgac gataacctcc aacacgtgct    22800
ccacgttgag tttgccttt gagttggaga gtgtgtcttt tcgtcatata tttggccttt    22860
tcaagggtga ttttcaggct gcgtaaagat tgtatagttt ggtgcaactc aaacggaaaa    22920
ctcaacctct cacacagaaa agcagtatat aaaccgaaaa agttcccact aaaagtccga    22980
cgcatttcta acatatcaaa aaccagctaa aacatattga tgacaagttc tatttcagca    23040
ccacaaacaa gcctgttaat gtctctcacc gcaaccattg ttctgcgcgc gttataatca    23100
ttggtcgatt ttgtataact actgttcaag ataaagtcgt ggtgtttgtt cggacaatta    23160
cagagagtgg cgttggtaac aagacgcgcg caatattagt gcatagaagt ttattttctt    23220
tgggatgatt caaatattac gtgacgcaaa gtttgccaat tttagaaccc ctccctcctc    23280
cacgtaacgg cttttgtgtg cgtatcttca aataaagaa accctactaa gtttataatg    23340
cactgcgttt caaacggtta aaatcttggg gagggaggag gtgcattgcc gaaaacacac    23400
aaaaatttaa attttgtgta tagaccgtag catttcggaa gaccccctcc cttactctgt    23460
tgagttacgt aaaatttcaa cgatcctttt gtagttctga tttttaaatt taaaacacat    23520
atctggcatc gtaaagcctt ctgggggagg gaatgagaca actcaatgca ttttaaagtt    23580
gctaggaaaa catcaagact atttttatatc agcgtgcagt gttatgaaga tatccacagt    23640
ataaaatatt atttttatttt aaattctatg ctgattatca atgtgttact agtggctttt    23700
taaaatatag tcgcacgtca caatacttct ataggtgtca tattttataa taaaataaaa    23760
tttaagatac gactaatagt tacacaatga tcaccgaaaa catactcatg ttgcgagctc    23820
gatttggcgc acgggtcat ctacacctga taccttagg gtcgttgggg gaccacttag    23880
cgtgcacgta cggacattca gtatgagtac aacgctcgag ctaaaccgcg tgccccagta    23940
gatgtggact atggaaatcc cagcaacccc ctggtgaatc gcacgtgcat gcctgtaagt    24000
aaatgttgtt caaattttttt tcttaccaag acgagcactt tacaatgaca aactctggct    24060
ctgctctggc tctgctctgg ctctgctctg gctctgctct tttacaacaa gtttaaaaaa    24120
```

```
agaatggttc tgctcgtgaa atgttactgt ttgagaccga gacgagaccg agacgagacc   24180
gagacgagac cgagacgaga ggctctgctc tggctctgct ctggctctgc tctggctctg   24240
ctctggctct gctctggctc tgctctggct ctgctctggc tctgctctgg ctctgctctg   24300
ccgagacgag accgagacga gaccgagacg agaccgagac gagaccgaga cgagaccgag   24360
acgagaccga gacgagaccg agacgagacc gagacgagac gctctgctct ggctctgctc   24420
tggctctgct ctggctctgc tctggctctg ctctggctct gctctggctc tgctctggct   24480
ctgctctggc tctgctctgg cgagacgaga ccgagacgag accgagacga gaccgagacg   24540
agaccgagac gagaccgaga cgaccgag acgagaccga gacgagaccg agacgagacc   24600
ctctgctctg caaaatgctc tggattaatt tattgctcac actcttttgc tgttggacca   24660
ctattcattt caaatcttca atatgttcct attacccccca gagacgagac gttttacgag   24720
acctaattaa ataacgagtg tgagaaaacg acaacctggt gataagtaaa gtttagaagt   24780
tatacaagga taatgggggt aacacggtcc acacggatcg atttcaacta actccactct   24840
cgtatgcata ttttgtgtat aaattttgaa taatcgaaaa gggttgctgc aaatgttaat   24900
ttgtgccagg tgtgcctagc taaagttgat tgaggtgaga gcatacgtat aaaacacata   24960
tttaaaactt attagctttt cccaacgacg tttacaatta attttttccc tctacccccct   25020 cactctgtcg ttggcgttgg aaaaaaatca ccactgcata caaaacactc attggttggg   25080
tggaaggacg gtttagcaga taaaaaaggg agatggggga gtgagacagc aaccgcaacc   25140 ttttttttagt ggtgacgtat gttttgtgag taaccaaccc accttcctgc caaatcgtct   25200
gttgctaaat tttccatatc acgctgattg atttgtgatt aaaaataaat ataaatagaa   25260
aatgaataat tcccacatgt gtttcggtat taggcaccgg caacgattta aaaggtatag   25320
tgcgactaac taaacactaa tttttatta tatttatctt ttacttatta agggtgtaca   25380
caaagccata atccgtggcc catggggcgg cgaagtgcag acggttctag ttctcattat   25440
ttggcatcga ttggcggtca aactacaacc tccatggaga aacaggcccc atccgtactt   25500
gtaccccgcc gcttcacgtc tgccaagatc aagagtaata aaccgtagct aaccgccagt   25560
ttgatgttgg aggtacctct ttgtccgggg taggcatgaa agttattaat aaataacaat   25620
gatttgaatt tgaatcattc atgctgcggc gtggctgatt tcggtgaatt gttgttctct   25680
tagagaaaga ggggggatttg tcaataatta tttattgtta ctaaacttaa acttagtaag   25740
tacgacgccg caccgactaa agccacttaa caacaagaga atctctttct ccccctaaac   25800
aatttggacg agtaaataac attgaatatt acactttatg actaatcacc agtaatgaaa   25860
caacacgggt gatgatttca aaagcttcat tctaaatgca ttaaacctgc tcatttattg   25920
taacttataa tgtgaaatac tgattagtgg tcattacttt tgttgtgccca ctactaaagt   25980 tttcgaagta agatttacgt tggttcactt ttggtggcag atttaaaact cttatcttcc   26040
tcttttcttc aacaggtttc acgccatcaa agacgcttgg cagccgcttc catttgcgta   26100
accaagtgaa aaccaccgtc taaattttga gaatagaagg agaaaagaag ttgtccaaag   26160
tgcggtagtt tctgcgaacc gtcggcgaag gtaaacgcat gcaaacgtat gttaaccta   26220 ggttttaatg ttaaaagtat caccaaaaat caagtcccaa gacttctgca agaatggttt   26280
atgctgaatt tattcgaaat cgtttgcata caattggaat ccaaaattac aattttcata   26340
gtggttttta gttcagggtt ctgaagacgt tcttaccaaa tacgacttaa ataagcttta   26400
ggttttattt tcatcgaaac atgtgtgatg taggctacta ttttggtaaa accgttggca   26460
```

```
acgactgtat ttaaactcac aaaatttgaa ccaaacttat ccaaaataaa agtagctttg   26520
tacacactac atccgatgat aaaccatttt tggcaaccgt tgctgacata aatttgagtg   26580
ttttaaactt ggtttgaata aattgtaact tttaattgag taaacatagg cgaaagagag   26640
tgattcaaat gggattcgga atcgaacggt tcttctaagt aagacaaacg aaaaaaacaa   26700
ttaacattga aaattaactc atttgtatcc gctttctctc actaagttta ccctaagcct   26760
tagcttgcca agaagattca ttctgttttgc ttttttttgtt ccaaacgagt caaagctgca   26820
aaaacttcaa gtttgaactg tgatatcaat gaaattaaat acgaactatg tatcaagatt   26880
acagtaaaat ttaaagaaga ggtttgctca gtttcgacgt ttttgaagtt caaacttgac   26940
actatagtta cttaatttta tgcttgatac atagttctaa tgtcatttta aatttcttct   27000
ctttcaacgc atgaaacagg agggtggcaa ccgaaaagtg actgaatcaa ttgcgggtta   27060
tcattcgaga tatccagggg ttgaattgtg agaaaacttc gaaagttgcg tactttgtcc   27120
tcccaccgtt ggcttttcac tgacttagtt aacgcccaat agtaagctct ataggtcccc   27180
aacttaacac tcttttgaag ttcttcttct tattcttggc aatacgtcct cactgggata   27240
gagtctgctt cctaacttca tgttcaatga ccacttccac agttattaac tgagagcttt   27300
aagaagaaga ataagaaccg ttatgcagga gtgaccctat ctcagacgaa ggattgaagt   27360
acaagttact ggtgaaggtg tcaataattg actctcgaaa ctttgccaaa gttgccattt   27420
tcgcattcgt atatcgtgtg gcagcagtgt tgtgaaaaac tcaatttctc ataactaacg   27480
cttgagattt ttcatgcgtg gaaacggttt caacggtaaa agcgtaagca tatagcacac   27540
cgtcgtcaca acacttttg agttaaagag tattgattgc gaactctaaa aagtacgcac    27600
agttgtcaat cacgcaactc agcagtcaaa attttccaca gtatacttac acacggcaat   27660
aatttcttgc tagtctggta aaattatagt aatcttttct tcaacagtta gtgcgttgag   27720
tcgtcagttt taaaggtgt catatgaatg tgtgccgtta ttaaagaacg atcagaccat    27780
tttaatatca ttagaaaaga aacgtaaaca acaaaaattcg ggtttcaaga gttttgacg    27840
ggagcaagca aaataggatt tagaattttg catgagacga agtttgaaaa ttttattgtc   27900
ttgcatttgt tgttttaagc ccaaagttct caaaaactgc cctcgttcgt tttatcctaa   27960
atcttaaaac gtactctgct tcaaactttt aaaataacag aaatttagta tcggttcaat   28020
cgaattttcg aacacaattg taggctctat ataaactaca tttattccct tattttgcca   28080
gatacaatac tcgcataact tttaaatcat agccaagtta gcttaaaagc ttgtgttaac   28140
atccgagata tatttgatgt aaataaggga ataaacggt ctatgttatg agcgtattga    28200
tgagatctcg cctaaaaagc cattggtaac cgagtgtgta gctctttgtt tctaagccaa   28260
ttaatggacc tggatgaaaa ctatcatcac tgggaaatag actctagagc ggatttttcg   28320
gtaaccattg gctcacacat cgagaaacaa agattcggtt aattacctgg acctacttt    28380
gatagtagtg acccctttatc aggaggaact tgtcttttatc gtagcattgt taaataacgt  28440
gtaaacccat ttgtttcctc ggtagctgca agctacacac tcgattacca atggctttta   28500
tcctccttga acagaaatag catcgtaaca atttattgca catttgggta aacaaggag    28560
ccatcgacgt tcgatgtgtg agctaatggt taccgaaaat gggcgagatc acaagttatg   28620
cgagaatact tcccgaaatc accaccttt acccttttaa ataacgaaat tactacaaac    28680
ttcgttaccc gctctagtgt tcaatacgct cttatgaagg gctttagtgg tggaaaatgg   28740
gaaaatttat tgctttaatg atgtttgaag caat                               28774
```

<210> SEQ ID NO 44
<211> LENGTH: 3399
<212> TYPE: DNA
<213> ORGANISM: Cydia pomonella
<220> FEATURE:
<221> NAME/KEY: misc_feature
<222> LOCATION: (1179)..(1184)
<223> OTHER INFORMATION: At positions 1179-1184, n, at each occurrence, is a or c or g or t

<400> SEQUENCE: 44

```
catcagacgg gcccaggctc aggatgaagc tagagcgcgg gcggcggacg cagggctcca      60
ccctcccggg atcgagctag atcggcctga gccgccagtg gtgaaagcgc cgaggagtcc     120
cgtgatcccg ccgccgccgc cgcgctccat gggatcggcg agctgcgact ccgttccggg     180
atcgcccggg gtatcgccgt atgcgccgaa cccgccgtcc gctccgcctc cgccgatgcc     240
gccgctcccg cctccgcaac cagtggccct ggactccctg gtagaaaact gccacaagct     300
gctggaaaaa ttccactaca gttgggagat gatgccgctc gtgctggtca tcctcaacta     360
cgccggctcc gacctggagg aggcctcgcg gaagattgac gaaggtaagt ttaaatttaa     420
gtacataaca atgcttacag acgaattgaa agggaatgtg actcggctaa tccaccagga     480
tataattttg tagagtgcgc taaagaattc tagcaacgga cgctgttatt ctgccaccgc     540
cgttgatgcc gccgtcttct gatagtgata ctttaagatc cgtatactac gctcacttcc     600
attcacttat gtcgtacgga gtattaatat gggtaaactc gcggacacga aacgattacg     660
aaaacgcaga gtacttagat tggagcaaag cccagggatt cgccgagact tttttgttac     720
ggaagattga tgaaggtaag caagtttggga ctgtggcgag ttgacacatg aaacaagtca     780
aggtcacagc tggagttcca ttaaagctgg atgctaccgc tagtcatcct gaggccggct     840
ccgacttcgt gcaatgaggt attaagctgc tggaattgaa tggaatatag tggtgaaaca     900
ctactactag gtttaagcgt ttagttatat ggttgttttc ttatttttaa tttttaaatg     960
ctctgctaag ctaaaacggc waatgtctat ttttgattat aaagacttat ataaacaac    1020
ttgtttagct tcttttkacgt cttttttgtta agctgtgccc tggttttaaa wkgggcgaac    1080
acytcacgaa taagacgtaa ttttaaaaag aaaatagata tcggccctct tggttcgcat    1140
ttatacatat gtattgctgc ccgtgcgaat gttggggann nnnnaaacag tacccctagt    1200
gtaartaaat tcgatttcga aacgtgacgt acgcgtttgc gtttagtctc mwtttgtatt    1260
ggatttagaa agagcgcgcc aagcgggacg ttttggaaac tcaaatcct atacaaaatg    1320
agacttaacg caaasgcgtt tcgtcacgtt atgatgtcga tcaaatttac actaggggta    1380
cagaggtatt gcagtaactg tacaaatact aaactaaatt aataaattag ctaaatctaa    1440
aatataccct tcaggcattg tactaaggat gctggcggaa ttacttgtgc gaggaagccg    1500
ccagctttc ggtcaccatt tacgagtacg tataccaaac gcttcgttgc tgcaaaaaag    1560
tttcaacgcc aaatggtaca aaatgcttta tattgttctc tatatattat attaacacat    1620
cgttattta acctaggtct tagttatgta caaggttaca taaaatagat gttcctagtc    1680
cattcctccg tgtatgttgt gtctattata aagcaaggct gcattttgta atcagtcaat    1740
ttcaatataa aaaagttgca tcgttttttt ttactkttcg acaattaaat tcaagtagca    1800
aaaaataacc caccttaatt tgtcatggtc ataatgaaac aatgacaarg tttttttat    1860
cgcccgatac atgtacgtgt tctccaaaat gcagtctccg cgccgccaag cgaacgttca    1920
aactgtgcga tttccgttgt ccccaggcaa aatgatcatc aacgattacg ccaggaagca    1980
taatctgaac atcttcgacg ggctcgagct gaggaactcg acacgccact ccatttcgga    2040
```

```
tggcgatgaa aaacgcccac cgcaacctaa gcaagtctca aagtaaggtt ccatttaaat    2100
catctcaaaa ccgttagaaa cactcaaaaa gaaaccaaaa ttctgttcgg aaaccgacct    2160
ttgttttta cacacactta gaccgaattt gcaaatttta acccttatt cctaaaacta    2220
gcaatggtaa gctcggctga atttcacata caaacggagt ttcgttctca ttataaaact    2280
gcgtgttgga ttgtaatgga actttgcaca tacaatgaca tgaggtatgt ctagggctga    2340
aattagttta tacttggtat ctgaggctac ataaactaat tacagcctta gacttggagg    2400
atttaacaac tggaaacacc ttgtctgtaa ttctctgtac aacgatttta cggggagga    2460
gcaaatatgt cagttaaacg tcagtccaaa caatacatat gactattggc cgtggtattt    2520
cgacggaggg gtaataagct cttaaaggcg actccgatat gcctaatcct attgttagta    2580
caaagtttca gagcaattta gctagtcgtt ttaaaatgag agcgtaacta cgttagcttg    2640
ctcttcttcc tcctgctctt atcccacgtt atgtggggtc ggcacaacat gttcctctct    2700
tctcactcct ttcttctca tatcctcttt cacacaatcc atccatcgtt tacttacaac    2760
cgagcttgct ggggaccgtt aaggcgccgc gagttcaggt tcttctctca ctctcactct    2820
cactggtgtg agcggagcga gacagcgttt tattttcgcc ttatcgaggt tccactgtat    2880
tataaataac ttacatttat aaagacgctg taatcgataa gaagttgagt cacgcttacg    2940
tcgcttacgt actacgtata gtaacgtagc ctgccgttta caaacaatgt acggagctac    3000
aacgttgcaa gttcggtccc cacacaacac aatgtgtcat aacacattaa caacattgtt    3060
acacacccac acatacaaat ttgctaagtt gataaaagag tggtgtgtcc gacgaatcag    3120
aacatcacta acccagtcgt gatttcattt ccacagtgac cggacgaagg tggagaagtt    3180
cgaaatttaa aaaagtgac cacattttat ttaatagtga tgtgcaagtg atactatttt    3240
tattttgttt ttcttttgta ggaaaatgct gagcgaaata aataatttta gtggtgtgct    3300
atcgtcatcg atgaagttgt tttgcgaatg atactatgtt cttcaagtgc tgtgttttgt    3360
ggactgtggg gtgactgttc ctgtaaataa gcttcgttg                          3399
```

<210> SEQ ID NO 45
<211> LENGTH: 996
<212> TYPE: DNA
<213> ORGANISM: Cydia pomonella

<400> SEQUENCE: 45

```
catcagacgg gcccaggctc aggatgaagc tagagcgcgg gcggcggacg cagggctcca     60
ccctcccggg atcgagctag atcggcctga gccgccagtg gtgaaagcgc cgaggagtcc    120
cgtgatcccg ccgccgccgc cgcgctccat gggatcggcg agctgcgact ccgttccggg    180
atcgcccggg gtatcgccgt atgcgccgca cccgccgtcc gctccgcctc cgccgatgcc    240
gccgctcccg cctccgcaac cagtggcctt ggactccctg gtagaaaact gccacaagct    300
gctggaaaaa ttccactaca gttgggagat gatgccgctc gtgctggtca tcctcaacta    360
cgccggctcc gacctggagg aggcctcgcg gaagattgac gaagcctcct gggtggtgca    420
ccagtggcgg ctgtacgagc gctcactgtg ctcgctgctg gagctgcaag cgcgcaaaga    480
gtcgttttgc tgctcgccgc gctatgtgct gtcgcgcgag tacgcgccgc acctgcccgt    540
gccgctcatg cgctcgccgc cgccagcgca cttgtagccc cacaccgcgc cgcgacagac    600
ggcgcacgag cccactgagc catctacttc ggccaaaccc gagtaggccc gaggccgacc    660
cgagcccgac ccgagaggac ccgagtgggc tattccggac tttacctagt tttatatgtg    720
```

```
ctatacgtgt tacaacacgc atatttgtat attatcacgg acattaagtt ggagagcggt    780
taccttatct tgttaacccg gtccttgaag taattattcc cagatatatt aagaaaacca    840
gtgaatactt tgcctgatgt ataattaaca gttgttaagc aaccatgaga attatggtat    900
ttcttgtgga catgttgcag ctagaaattt catatcatcg gtgataaaat ttaaccacac    960
tgtggttggc ggaaaaccac attgtttgta atattg                              996
```

<210> SEQ ID NO 46
<211> LENGTH: 6751
<212> TYPE: DNA
<213> ORGANISM: Artificial Sequence
<220> FEATURE:
<223> OTHER INFORMATION: Synthetic construct, pLA3435-Bombyx mori-dsx
      construct/plasmid.
<220> FEATURE:
<221> NAME/KEY: misc_feature
<222> LOCATION: (1617)..(1622)
<223> OTHER INFORMATION: At positions 1617-1622, n, at each occurrence,
      is a, c, g, or t

<400> SEQUENCE: 46

```
ggccgcatgg tacccattgc ttgtcattta ttaatttgga tgatgtcatt tgttttaaa     60 attgaactgg ctttacgagt agaattctac gcgtaaaaca caatcaagta tgagtcataa    120
tctgatgtca tgttttgtac acggctcata accgaactgg ctttacgagt agaattctac    180
ttgtaatgca cgatcagtgg atgatgtcat ttgttttca aatcgagatg atgtcatgtt    240
ttgcacacgg ctcataaact cgctttacga gtagaattct acgtgtaacg cacgatcgat    300
tgatgagtca tttgttttgc aatatgatat catacaatat gactcatttg ttttcaaaa    360 ccgaacttga tttacgggta gaattctact tgtaaagcac aatcaaaag atgatgtcat    420 ttgttttca aaactgaact cgctttacga gtagaattct acgtgtaaaa cacaatcaag    480
aaatgatgtc atttgttata aaaataaaag ctgatgtcat gttttgcaca tggctcataa    540
ctaaactcgc tttacgggta gaattctacg cgtaaaacat gattgataat taaataattc    600
atttgcaagc tatacgttaa atcaaacgga cgctcgaggt tgcacaacac tattatcgat    660
ttgcagttcg ggacataaat gtttaaatat atcgatgtct ttgtgatgcg cgcgacattt    720
ttgtaggtta ttgataaaat gaacggatac gttgcccgac attatcatta aatccttggc    780
gtagaatttg tcgggtccat tgtccgtgtg cgctagcatg cccgtaacgg acctcgtact    840
tttggcttca aaggttttgc gcacagacaa aatgtgccac acttgcagct ctgcatgtgt    900
gcgcgttacc acaaatccca acggcgcagt gtacttgttg tatgcaaata atctcgata    960 aaggcgcggc gcgcgaatgc agctgatcac gtacgctcct cgtgttccgt tcaaggacgg   1020
tgttatcgac ctcagattaa tgtttatcgg ccgactgttt tcgtatccgc tcaccaaacg   1080
cgtttttgca ttaacattgt atgtcggcgg atgttctata tctaatttga ataaataaac   1140
gataaccgcg ttggtttag agggcataat aaaagaaata ttgttatcgt gttcgccatt   1200
agggcagtat aaattgacgt tcatgttgga tattgtttca gttgcaagtt gacactggcg   1260
gcgacaagca attctaattg gggtaagttt tcccgttctt ttctgggttc ttccctttg    1320 ctcatccttg ctgcactacc ttcaggtgca agttgagatt caggccacca tgggagatcc   1380
caccccaccc aagaagaagc gcaaaccggt ccgtcccctc ggagacgctt gtggagaact   1440
gtcacagact cctcgagaag ttccattact cgtgggagat gatgccgctt gtgctcgtca   1500
tcatgaacta cgcccgcagc gacttggatg aggcttcaag gaaaatctac gaaggtaccg   1560
aatgtgtaaa tacgagtgta gcgttgatta gaaaacggac attgttcgtg agtttannnn   1620
```

```
nnggtctctc tggccagcaa gacatttgaa acactgtaaa aaaattcatt gaaaaaaaag   1680
aacactgtaa tgaaaatatt ctgaatgctt aatctggtat ttcagggatt aaactgattg   1740
tgatgaaaag tgattaaact attttctttta agtaccaaat taaccgaaca ggtttgggtc   1800
tttcctttca gtaacaaaca aaatctatcg aaggtaagaa ataaacaaca ggatattttc   1860
ttttactaaa aatcaataag gagactgcac tatttcaatg ttcaacttcc tttatcgaat   1920
gcatgaaaaa tttaattgtc taaaaatcta aattactaat taacgcaaag gaacctttgc   1980
ctaaaaaaaa aaataagcta ttaaacgaat gcctaaaata cgtaacagtg ttgccagttg   2040
taaaaattgc gaatccgaga agtgcagttt cctgaaatgc ccagcgatac gaatttccta   2100
tgttagagtc ttgtccgcag ggaagatgat cgtcgacgag tacgcgagga agcacaactt   2160
gaacgtgttc gacggactag aactaaggaa ctcgacacgc caggcgcgcc ggatccggcc   2220
ggccgaaaat gctggaaatt aataatataa gtggtgtact gtcttcgtca atgaagttat   2280
tttgcgaatg atacttagtt ttacaagtgc cgtggtgtgt gttgacactt gctgtgcgat   2340
gctgtgcgaa tttcaacgga aatatttgtt gtcgtaacat tggatctatg ggtaagttta   2400
gtataataac tttactctgt tcacattagt gaaacataca tttgtaaaat ttgtgtttta   2460
ctaatgtgaa atttattttt ggaaattcac gttaacacta ttgaataaaa aaaaatcgat   2520
aatgtaattt aaaaaaaata caaaaatata gttttcgctt attgttagaa agaaaatttt   2580
acatacgcca ttttgaataa ttccttccgg gtacattggg ccctaaacca gcgatcgggg   2640
aacttttta attattaccc taaaatattt ttatgtaagt tgatattacc gatggcgaag   2700
aacaacaaaa aaaaaaacga aatcgcttct ttttagcatc tttcatatta tagacccac   2760
gataattta aatcacaacg attataaaga agtttcactt caatatatac tttttactca   2820
caaaagtttc attttacccc catttgggat aatttagccc ggttccccc ccgaccgctg   2880
gcctaaacgt atcaccgaca atagctaaaa taacaaggta cgttcgattt gccgagctga   2940
actaacatta cacagctttg cattattcat atgtacattg cgactgaaac gtccggaccg   3000
ttacaggtta ttggatgatg catcaatggc gattgcagca gtattcgttg tgctacggag   3060
cgctggagtt gtcggcgcgc aaggatgtgg ccgcgctatg ttgcctccga gatacgtgct   3120
ggcgcccgag gtcccgccgc gtctggtgcc cctccagctg atctagataa ctgatcataa   3180
tcagccatac cacatttgta gaggttttac ttgcttaaaa aaacctccca cacctccccc   3240
tgaacctgaa acataaaatg aatgcaattg ttgttgttaa cttgtttatt gcagcttata   3300
atggttacaa ataaagcaat agcatcacaa atttcacaaa taaagcattt ttttcactgc   3360
attctagttg tggtttgtcc aaactcatca atgtatctta acgcgagtta attaagtgcg   3420
cgtaaattgt aagcgttaat attttgttaa aattcgcgtt aaattttgt taaatcagct   3480
cattttttaa ccaataggcc gaaatcggca aaatccctta taaatcaaaa gaatagaccg   3540
agatagggtt gagtgttgtt ccagtttgga acaagagtcc actattaaag aacgtggact   3600
ccaacgtcaa agggcgaaaa accgtctatc agggcgatgg cccactacgt gaaccatcac   3660
cctaatcaag ttttttgggg tcgaggtgcc gtaaagcact aaatcggaac cctaagggga   3720
gccccccgatt tagagcttga cggggaaagc cggcgaacgt ggcgagaaag gaagggaaga   3780
aagcgaaagg agcgggcgct agggcgctgg caagtgtagc ggtcacgctg cgcgtaacca   3840
ccacacccgc cgcgcttaat gcgccgctac agggcgcgtc aggtggcact ttcggggaa   3900
atgtgcgcgg aacccctatt tgtttatttt tctaaataca ttcaaatatg tatccgctca   3960
```

-continued

```
tgagacaata accctgataa atgcttcaat aatattgaaa aaggaagagt cctgaggcgg      4020
aaagaaccag ctgtggaatg tgtgtcagtt agggtgtgga aagtcccag gctccccagc       4080
aggcagaagt atgcaaagca tgcatctcaa ttagtcagca accaggtgtg aaagtcccc       4140
aggctcccca gcaggcagaa gtatgcaaag catgcatctc aattagtcag caaccatagt      4200
cccgccccta actccgccca tcccgcccct aactccgccc agttccgccc attctccgcc      4260
ccatggctga ctaattttt ttatttatgc agaggccgag gccgcctcgg cctctgagct       4320
attccagaag tagtgaggag ctttttggg aggcctaggc ttttgcaaag atcgatcaag       4380
agacaggatg aggatcgttt cgcatgattg aacaagatgg attgcacgca ggttctccgg      4440
ccgcttgggt ggagaggcta ttcggctatg actgggcaca acagacaatc ggctgctctg      4500
atgccgccgt gttccggctg tcagcgcagg ggcgcccggt tctttttgtc aagaccgacc      4560
tgtccggtgc cctgaatgaa ctgcaagacg aggcagcgcg gctatcgtgg ctggccacga      4620
cgggcgttcc ttgcgcagct gtgctcgacg ttgtcactga agcgggaagg gactggctgc      4680
tattgggcga agtgccgggg caggatctcc tgtcatctca ccttgctcct gccgagaaag      4740
tatccatcat ggctgatgca atgcggcggc tgcatacgct tgatccggct acctgcccat      4800
tcgaccacca agcgaaacat cgcatcgagc gagcacgtac tcggatggaa gccggtcttg      4860
tcgatcagga tgatctggac gaagagcatc aggggctcgc gccagccgaa ctgttcgcca      4920
ggctcaaggc gagcatgccc gacggcgagg atctcgtcgt gacccatggc gatgcctgct      4980
tgccgaatat catggtggaa aatggccgct tttctggatt catcgactgt ggccggctgg      5040
gtgtggcgga ccgctatcag gacatagcgt tggctacccg tgatattgct gaagagcttg      5100
gcggcgaatg ggctgaccgc ttcctcgtgc tttacggtat cgccgctccc gattcgcagc      5160
gcatcgcctt ctatcgcctt cttgacgagt tcttctgagc gggactctgg ggttcgaaat      5220
gaccgaccaa gcgacgccca acctgccatc acgagatttc gattccaccg ccgccttcta      5280
tgaaaggttg ggcttcggaa tcgttttccg gacgccggc tggatgatcc tccagcgcgg      5340
ggatctcatg ctggagttct cgcccaccc taggggagg ctaactgaaa cacggaagga       5400
gacaataccg gaaggaaccc gcgctatgac ggcaataaaa agacagaata aaacgcacgg      5460
tgttgggtcg tttgttcata acgcggggt tcggtcccag ggctggcact ctgtcgatac       5520
cccaccgaga ccccattggg gccaatacgc ccgcgtttct tccttttccc cacccccaccc    5580
cccaagttcg ggtgaaggcc cagggctcgc agccaacgtc ggggcggcag gccctgccat     5640
agcctcaggt tactcatata actttagat tgatttaaaa cttcatttt aatttaaaag       5700
gatctaggtg aagatccttt tgataatct catgaccaaa atcccttaac gtgagttttc      5760
gttccactga gcgtcagacc ccgtagaaaa gatcaaagga tcttcttgag atccttttt      5820
tctgcgcgta atctgctgct tgcaaacaaa aaaaccaccg ctaccagcgg tggtttgttt     5880
gccggatcaa gagctaccaa ctcttttcc gaaggtaact ggcttcagca gagcgcagat      5940
accaaatact gtccttctag tgtagccgta gttaggccac cacttcaaga actctgtagc     6000
accgcctaca tacctcgctc tgctaatcct gttaccagtg ctgctgcca gtggcgataa      6060
gtcgtgtctt accggttgg actcaagacg atagttaccg gataaggcgc agcggtcggg      6120
ctgaacgggg ggttcgtgca cacagcccag cttggagcga acgacctaca ccgaactgag     6180
atacctacag cgtgagctat gagaaagcgc cacgcttccc gaagggagaa aggcggacag    6240
gtatccggta agcggcaggg tcggaacagg agagcgcacg agggagcttc caggggaaa     6300
cgcctggtat cttatagtc ctgtcgggtt tcgccacctc tgacttgagc gtcgattttt      6360
```

| | |
|---|---|
| gtgatgctcg tcagggggc ggagcctatg gaaaaacgcc agcaacgcgg ccttttacg | 6420 |
| gttcctggcc ttttgctggc cttttgctca catgttcttt cctgcgttat ccctgattc | 6480 |
| tgtggataac cgtattaccg ccatgcatta gttattaata gtaatcaatt acggggtcat | 6540 |
| tagttcatag cccatatatg gagttccgcg ttacataact tacggtaaat ggcccgcctg | 6600 |
| gctgaccgcc aacgacccc cgcccattga cgtcaataat gacgtatgtt cccatagtaa | 6660 |
| cgccaatagg gactttccat tgacgtcaat gggtggagta tttacggtaa actgcccact | 6720 |
| tggcagtaca tcaagtgtat catagcgatg c | 6751 |

<210> SEQ ID NO 47
<211> LENGTH: 8183
<212> TYPE: DNA
<213> ORGANISM: Artificial Sequence
<220> FEATURE:
<223> OTHER INFORMATION: Synthetic construct, pLA3359-Anopheles gambiae dsx construct

<400> SEQUENCE: 47

| | |
|---|---|
| ccggtgctgc tgttgctgat gctacgatcc tcgacagtga ttggaaacgc ctggagatgg | 60 |
| tgggaaaaaa tcaaacacaa aaacggtcct aatgaacatc gtgtgttctc attcgctgcc | 120 |
| acgattgaca ccttcgataa gacgcacata atgagctaaa ggagagggga cagggtcttg | 180 |
| tctttgccac gagcgataag attgcaatca ctcgtgagcg tgtgctgctg ggctgaagaa | 240 |
| gaaacacttt ccacagcagt aggtgggaag tgggattgtg gaacgtggca ttgaaaagaa | 300 |
| cctatttct aaagcccgag agcccgttct cgaactggaa aacgagatgc agaagttttt | 360 |
| tattgtcccc cgccaggaaa acaaatgtat ttaatgcttt ctctgccttt tccgccccgt | 420 |
| ttcagacgac gagctagtga agcgagccca atggctgttg agaaaactcg gctaccgtg | 480 |
| ggagatgatg cccctgatgt acgtcatact gaagagcgcc gatggcgatg tacaaaaagc | 540 |
| acaccagcgg atcgacgaag gtaagctggc gatgatggtt cgttcgaca tcactttcat | 600 |
| caccgtgtca gacatctact gtgcctagca ccggtccagt ggtcacaggg tgtagcaaaa | 660 |
| acgtgttctt ttttgcgaga gactctacct catgatgcag ctgttaagga aaggtttcag | 720 |
| atgaagacaa ttttttcctag gataatatga tcttaagtta cctgcgtatg agtgtttaac | 780 |
| attgtcgtct caactccaag gaatgtttta accgtctagg gctagtttat ttatactgtt | 840 |
| ctcattgaaa tgtcgttaaa tccaacatgt taagttagct agctcagaca cgagaagtta | 900 |
| ggagtatctg catcttgaag gtagcggcat atggtgttat gccacgttca ctgacttcaa | 960 |
| aattcgatac aaaaaaaaac aaaatcaaaa acaaaattgt gaattccgtc agccagcagc | 1020 |
| agtgaccttc aaagccttac ctttccattc atttatgttt aacacaggtc aagcggtggt | 1080 |
| caacgaatac tcacgattgc ataatctgaa catgtttgat ggcgtggagt tgcgcaatac | 1140 |
| cacccgtcag agtggatgat aaactttccg caccactgta actgtccgta tctttgtatg | 1200 |
| tgggtgtgtg tatgtgtgtt tggtgaaacg aattcaattg ttctgtgcta ttttaaatca | 1260 |
| agccgcgtgc gcaactgatg ccgataagtt caaactagtg tttaaggagt ggagagagag | 1320 |
| agccgcacca cggtacagaa gggcagcaga atgggtcggc agcctagctg cactggtgcg | 1380 |
| gtgcgtccgg cgtctcgggg ggagggcggg gaaattctag tgttaaatcg gagcagcaaa | 1440 |
| aacaaaacag tggtcgtccc gttcaagaaa cggcctgtac acacacagaa aacactgcag | 1500 |
| catgtttgta catagtagat cctagagcag gtggtcgttg ctcctcgaac gctctggacg | 1560 |
| cacggcttcg cgcgtacttg cgtagcgttc caccgatcgt gggtattcgt actgccacaa | 1620 |

```
gcccgctttc tcccatgcaa tctctgcaac caaaccaaca aacaacaaca aaataccaat    1680
cgacacaatg aatcacaccc cttttgtatc atctgtatat tcttgttctt tgcgttcttt    1740
tccatgtggc ccacgcccg gcgggtacgt aattgcgtcg aaaacccga aaacccggc       1800
acatacagtg tacatacggt ttgaggacaa ctttgacctg cagcccttct ggggctgcca    1860
cgtgtagcta tacttgtgag atcgggcgcc gacggtgtaa agcgcgaatg ccgccacac     1920
agtgtgtcca ctccaacact acccctctgg aactaccccg tccagggatg caccggctcg    1980
gctcatgccc ctgcaaaaca gtccgggctc cactgtagta gctccggcgt tgctctgaga    2040
gaaggatgcc cttcgaagtg tcgaaagcgt gcattgggcg ttcaagtgtg tgtctgtgtt    2100
aggtttagcg agaaacagca gcagttgcgt gtgctgaaaa gcgaaggagt aatagagtgc    2160
ataatgaaaa tgaaaatgaa aatgaagcaa agtagaagg cggaggagag caacctgtgt     2220
tccactagta gcgaatagtt tagtctagtt tcgtcaccaa tcaaccttcc aaccatcgtt    2280
caaccaatac ctgagtcaac atcgtcatcg ttatcgtgcc acaactttat taaaaatgaa    2340
ccttgtccgc gccaccgtag ggtgatctga ggcgaccttt cttacgggcg cgactcacat    2400
gccatcgtca ccttctccaa tcaaaaccaa cagcctgtac cgatggtgtg caattgtgcg    2460
tgcgtgtgtg ttattagcaa aaaaagagaa agagacggcg agagagagat agatcgagat    2520
cgagagtaca aaagagcagt agaaatgttc gttgtttgtt ttccgtaaca cagttgttta    2580
gccaaaatgg gaatttccaa taatcccggg ggcggggaaa tgcgggaata ctgcgtacac    2640
acatacatca atcaaaaaga aaaatccttg cgctacatca ctaccgtttg cgcggtgctg    2700
atctagagca gaccactttc cacgccattc tacaatcaat caatctgtgc agaaggtatg    2760
gtaagacggc ctttgagcga gtcacggtcg ccaccataac gccgtccgac gagggctgaa    2820
tgcgaacttt gctaatcgat tttccgcttt cttttatcc caccccctt tctctctctc      2880
tcttttgcac cgcccttgt aaccccaaa aaggtaaacg acacattaag acctacgaag      2940
cgctggtgaa gtcatcgctc gatccgaaca gcgaccggct gacggaagac gacgacgagg    3000
acgagaacat ctcggtgacc cgcaccaact ccaccattcg gtcgaggtcc agctcgctgt    3060
cgcggtcccg gtcctgctcg cgccaggccg aaactccccg ggccgacgat cgggccctga    3120
accttgacac caaatagatc tcgacccaag aaaaagcgga aggtggagga cccgtaagat    3180
ccaccggatc tagataactg atcataatca gccataccac atttgtagag gttttacttg    3240
ctttaaaaaa cctcccacac ctcccccctga acctgaaaca taaaatgaat gcaattgttg    3300
ttgttaactt gtttattgca gcttataatg gttacaaata aagcaatagc atcacaaatt    3360
tcacaaataa agcattttttt tcactgcatt ctagttgtgg tttgtccaaa ctcatcaatg    3420
tatcttaacg cgagttaatt aagtgcgcgt aaattgtaag cgttaatatt ttgttaaaat    3480
tcgcgttaaa ttttttgttaa atcagctcat tttttaacca ataggccgaa atcggcaaaa    3540
tcccttataa atcaaaagaa tagaccgaga taggggttgag tgttgttcca gtttggaaca    3600
agagtccact attaaagaac gtggactcca acgtcaaagg gcgaaaaacc gtctatcagg    3660
gcgatgcccc actacgtgaa ccatcaccct aatcaagttt tttggggtcg aggtgccgta    3720
aagcactaaa tcggaaccct aaagggagcc cccgatttag agcttgacgg ggaaagccgg    3780
cgaacgtggc gagaaaggaa gggaagaaag cgaaaggagc gggcgctagg gcgctggcaa    3840
gtgtagcggt cacgctgcgc gtaaccacca cacccgccgc gcttaatgcg ccgctacagg    3900
gcgcgtcagg tggcactttt cggggaaatg tgcgcggaac ccctatttgt ttatttttct    3960
```

```
aaatacattc aaatatgtat ccgctcatga gacaataacc ctgataaatg cttcaataat    4020
attgaaaaag gaagagtcct gaggcggaaa gaaccagctg tggaatgtgt gtcagttagg    4080
gtgtggaaag tccccaggct ccccagcagg cagaagtatg caaagcatgc atctcaatta    4140
gtcagcaacc aggtgtggaa agtccccagg ctccccagca ggcagaagta tgcaaagcat    4200
gcatctcaat tagtcagcaa ccatagtccc gcccctaact ccgcccatcc cgcccctaac    4260
tccgcccagt tccgcccatt ctccgcccca tggctgacta atttttttta tttatgcaga    4320
ggccgaggcc gcctcggcct ctgagctatt ccagaagtag tgaggaggct tttttggagg    4380
cctaggcttt tgcaaagatc gatcaagaga caggatgagg atcgtttcgc atgattgaac    4440
aagatggatt gcacgcaggt tctccggccg cttgggtgga gaggctattc ggctatgact    4500
gggcacaaca gacaatcggc tgctctgatg ccgccgtgtt ccggctgtca gcgcaggggc    4560
gcccggttct ttttgtcaag accgacctgt ccggtgccct gaatgaactg caagacgagg    4620
cagcgcggct atcgtggctg gccacgacgg gcgttccttg cgcagctgtg ctcgacgttg    4680
tcactgaagc gggaagggac tggctgctat tgggcgaagt gccggggcag gatctcctgt    4740
catctcacct tgctcctgcc gagaaagtat ccatcatggc tgatgcaatg cggcggctgc    4800
atacgcttga tccggctacc tgcccattcg accaccaagc gaaacatcgc atcgagcgag    4860
cacgtactcg gatggaagcc ggtcttgtcg atcaggatga tctggacgaa gagcatcagg    4920
ggctcgcgcc agccgaactg ttcgccaggc tcaaggcgag catgcccgac ggcgaggatc    4980
tcgtcgtgac ccatggcgat gcctgcttgc cgaatatcat ggtggaaaat ggccgctttt    5040
ctggattcat cgactgtggc cggctgggtg tggcggaccg ctatcaggac atagcgttgg    5100
ctacccgtga tattgctgaa gagcttggcg gcgaatgggc tgaccgcttc ctcgtgcttt    5160
acggtatcgc cgctcccgat tcgcagcgca tcgccttcta tcgccttctt gacgagttct    5220
tctgagcggg actctggggt tcgaaatgac cgaccaagcg acgcccaacc tgccatcacg    5280
agatttcgat tccaccgccg ccttctatga aggttgggc ttcggaatcg ttttccggga    5340
cgccggctgg atgatcctcc agcgcgggga tctcatgctg gagttcttcg cccacccta g    5400
ggggaggcta actgaaacac ggaaggagac aataccggaa ggaacccgcg ctatgacggc    5460
aataaaaaga cagaataaaa cgcacggtgt tgggtcgttt gttcataaac gcggggttcg    5520
gtcccagggc tggcactctg tcgataccccc accgagaccc cattgggcc aatacgcccg    5580
cgtttcttcc ttttcccac cccaccccccc aagttcgggt gaaggcccag ggctcgcagc    5640
caacgtcggg gcggcaggcc ctgccatagc ctcaggttac tcatatatac tttagattga    5700
tttaaaactt catttttaat ttaaaaggat ctaggtgaag atcctttttg ataatctcat    5760
gaccaaaatc ccttaacgtg agttttcgtt ccactgagcg tcagacccccg tagaaaagat    5820
caaaggatct tcttgagatc cttttttttct gcgcgtaatc tgctgcttgc aaacaaaaaa    5880
accaccgcta ccagcggtgg tttgtttgcc ggatcaagag ctaccaactc ttttccgaa    5940
ggtaactggc ttcagcagag cgcagatacc aaatactgtc cttctagtgt agccgtagtt    6000
aggccaccac ttcaagaact ctgtagcacc gcctacatac ctcgctctgc taatcctgtt    6060
accagtggct gctgccagtg gcgataagtc gtgtcttacc gggttggact caagacgata    6120
gttaccggat aaggcgcagc ggtcgggctg aacggggggt tcgtgcacac agcccagctt    6180
ggagcgaacg acctacaccg aactgagata cctacagcgt gagctatgag aaagcgccac    6240
gcttcccgaa gggagaaagg cggacaggta tccggtaagc ggcagggtcg gaacaggaga    6300
gcgcacgagg gagcttccag ggggaaacgc ctggtatctt tatagtcctg tcgggtttcg    6360
```

```
ccacctctga cttgagcgtc gattttgtg atgctcgtca gggggcgga gcctatggaa    6420 aaacgccagc aacgcggcct ttttacggtt cctggccttt tgctggcctt ttgctcacat    6480
gttctttcct gcgttatccc ctgattctgt ggataaccgt attaccgcca tgcattagtt    6540
attaatagta atcaattacg gggtcattag ttcatagccc atatatggag ttccgcgtta    6600
cataacttac ggtaaatggc ccgcctggct gaccgcccaa cgacccccgc ccattgacgt    6660
caataatgac gtatgttccc atagtaacgc caatagggac tttccattga cgtcaatggg    6720
tggagtattt acggtaaact gcccacttgg cagtacatca agtgtatcat agcgatgcgg    6780
ccgcatggta cccattgctt gtcatttatt aatttggatg atgtcatttg tttttaaaat    6840
tgaactggct ttacgagtag aattctacgc gtaaaacaca atcaagtatg agtcataatc    6900
tgatgtcatg ttttgtacac ggctcataac cgaactggct ttacgagtag aattctactt    6960
gtaatgcacg atcagtggat gatgtcattt gttttttcaaa tcgagatgat gtcatgtttt    7020
gcacacggct cataaactcg ctttacgagt agaattctac gtgtaacgca cgatcgattg    7080
atgagtcatt tgttttgcaa tatgatatca tacaatatga ctcatttgtt tttcaaaacc    7140
gaacttgatt tacgggtaga attctacttg taaagcacaa tcaaaaagat gatgtcattt    7200
gtttttcaaa actgaactcg ctttacgagt agaattctac gtgtaaaaca caatcaagaa    7260
atgatgtcat ttgttataaa aataaaagct gatgtcatgt tttgcacatg gctcataact    7320
aaactcgctt tacgggtaga attctacgcg taaaacatga ttgataatta aataattcat    7380
ttgcaagcta tacgttaaat caaacggacg ctcgaggttg cacaacacta ttatcgattt    7440
gcagttcggg acataaatgt ttaaatatat cgatgtcttt gtgatgcgcg cgacattttt    7500
gtaggttatt gataaaatga acggatacgt tgcccgacat tatcattaaa tccttggcgt    7560
agaatttgtc gggtccattg tccgtgtgcg ctagcatgcc cgtaacggac ctcgtacttt    7620
tggcttcaaa ggttttgcgc acagacaaaa tgtgccacac ttgcagctct gcatgtgtgc    7680
gcgttaccac aaatcccaac ggcgcagtgt acttgttgta tgcaaataaa tctcgataaa    7740
ggcgcggcgc gcgaatgcag ctgatcacgt acgctcctcg tgttccgttc aaggacggtg    7800
ttatcgacct cagattaatg tttatcggcc gactgttttc gtatccgctc accaaacgcg    7860
tttttgcatt aacattgtat gtcggcggat gttctatatc taatttgaat aaataaacga    7920
taaccgcgtt ggttttagag ggcataataa aagaaatatt gttatcgtgt cgccattag    7980 ggcagtataa attgacgttc atgttggata ttgtttcagt tgcaagttga cactggcggc    8040
gacaagcaat tctaattggg gtaagttttc ccgttctttt ctgggttctt ccctttttgct    8100 catccttgct gcactacctt caggtgcaag ttgagattca ggccaccatg ggagatccca    8160
ccccacccaa gaagaagcgc aaa                                           8183
```

<210> SEQ ID NO 48
<211> LENGTH: 7342
<212> TYPE: DNA
<213> ORGANISM: Artificial Sequence
<220> FEATURE:
<223> OTHER INFORMATION: Synthetic construct, pLA3433-Agdsx (Anopheles gambiae) construct with exon 2 included

<400> SEQUENCE: 48

```
ctagtgtcga cgatgtaggt cacggtctcg aagccgcggt gcgggtgcca ggccgtgccc    60
ttgggctccc cgggcgcgta ctccacctca cccatctggt ccatcatgat gaacgggtcg    120
aggtggcggt agttgatccc ggcgaacgcg cggcgcaccg ggaagccctc gccctcgaaa    180
```

-continued

```
ccgctgggcg cggtggtcac ggtgagcacg ggacgtgcga cggcgtcggc gggtgcggat      240
acgcggggca gcgtcagcgg gttctcgacg gtcacggcgg gcatgtcgac cgccggcgcc      300
ttaattaact cgcgttaaga tacattgatg agtttggaca aaccacaact agaatgcagt      360
gaaaaaaatg ctttatttgt gaaatttgtg atgctattgc tttatttgta accattataa      420
gctgcaataa acaagttaac aacaacaatt gcattcattt tatgtttcag gttcaggggg      480
aggtgtggga ggttttttaa agcaagtaaa acctctacaa atgtggtatg ctgattatg       540 atcagttatc tagatccggt ggatcttacg ggtcctccac cttccgcttt ttcttgggtc      600
gagatctgag tccggaatcc tcgtcgctac cgatggcgct ggtgatgcgg ggcacgctgt      660
gggcgtaggt cacctcgcgc tggcacacgt ggtcgcgctt gtcgctggtg tccctcatct      720
gcttggtgat gatggtcacg aagtgggggc cggggatctt gatggcgcgg ctgccgttga      780
aggtcatctt gctgtcgaag tggcccatca tcaggccgcc gtcggcggtg gtgaagccga      840
tgaaggccag ctggcgcacg cgttgggc cgtggggaa catgtgggtc tcgttgggca         900
ggatgtccac cagctggtcg cgcatgatgg ggccgtcggg ctggaagccg tcgcagttca      960
cggtgatgcg gctgaccacg caggtgccgt ccagctcgta ggtgtggtgg ctggtcatgg     1020
tgccgtcgtt ctcgaagcgc acggtgcggt cgatgctcag gccctcgggg aagcactcct     1080
gggcgaagtg gctgatgccg ttggggtagc gggcgaagaa gggctcgccg tactggatca     1140
ggtggcagat gggcttccag ctcatgggca gcttgccggt ctcgcacacg gcgtgcacgt     1200
tgaagtcgcc gtgggggaac ttgctgctgc cgtcggccac gatggtgaac ttctggccgt     1260
tcacctcgcc gtcgatgaag attttgaagg tcatgtcgct ctggaacagg gcggggccgc     1320
cctctgaacc atcctcgtcc atggtggcga ccggtttgcg cttcttcttg ggtgggtgg      1380 gatccaccag agacaggttg cggcggcggt tggatggcgt gggcgcgttg gcgttgttgg     1440
accggctcat gttgtgtcgc tgtaacagat gctgttcaac tgtgtttacc agatcgttgc     1500
gggctgtatt tataggcgcg ataagcggga cgggcgcctc gtgtccggtc acgcgcatga     1560
gataacgcgc ggctgatatg gaggcgcgtc ctgttccgat aaggagttgc gtccggctgc     1620
ggttagcaac acaggaagct ggcgtcctgt cacgataaga caacactcgt ccggtccgat     1680
aatgtgattc gtacgtgaca ggacgcgacc cgataaggcc ggcctacgtg actgccgaca     1740
cgtacttttt tgcactgcaa aaaggttcaa tgtgtggtag tgtatttgga gcgtatacaa     1800
cggtgtagac tatttatgta aaatagtcta cgaaacgtag agtttgtact atgtatgggc     1860
ccgcgtgcaa aagcgtgttt ttttgcagtg caaaaaagtt ggtggtgggg aggccaccga     1920
gtatggtacc atgcggccgc gtacgcgccc ggggagccca agggcacgcc ctggcacccg     1980
tccggtgctt atctagagcg cgcttggcgt aatcatggtc atagctgttt cctgtgtgaa     2040
attgttatcc gctcacaatt ccacacaaca tacgagccgg aagcataaag tgtaaagcct     2100
ggggtgccta atgagtgagc taactcacat taattgcgtt gcgctcactg cccgctttcc     2160
agtcgggaaa cctgtcgtgc cagctgcatt aatgaatcgg ccaacgcgcg gggagaggcg     2220
gtttgcgtat tgggcgctct tccgcttcct cgctcactga ctcgctgcgc tcggtcgttc     2280
ggctgcggcg agcggtatca gctcactcaa aggcggtaat acggttatcc acagaatcag     2340
gggataacgc aggaaagaac atgtgagcaa aaggccagca aaaggccagg aaccgtaaaa     2400
aggccgcgtt gctggcgttt ttccataggc tccgcccccc tgacgagcat cacaaaaatc     2460
gacgctcaag tcagaggtgg cgaaacccga caggactata aagataccag gcgtttcccc     2520
```

```
ctggaagctc cctcgtgcgc tctcctgttc cgaccctgcc gcttaccgga tacctgtccg   2580
cctttctccc ttcgggaagc gtggcgcttt ctcatagctc acgctgtagg tatctcagtt   2640
cggtgtaggt cgttcgctcc aagctgggct gtgtgcacga accccccgtt cagcccgacc   2700
gctgcgcctt atccggtaac tatcgtcttg agtccaaccc ggtaagacac gacttatcgc   2760
cactggcagc agccactggt aacaggatta gcagagcgag gtatgtaggc ggtgctacag   2820
agttcttgaa gtggtggcct aactacggct acactagaag gacagtattt ggtatctgcg   2880
ctctgctgaa gccagttacc ttcggaaaaa gagttggtag ctcttgatcc ggcaaacaaa   2940
ccaccgctgg tagcggtggt ttttttgttt gcaagcagca gattacgcgc agaaaaaaag   3000
gatctcaaga agatcctttg atcttttcta cggggtctga cgctcagtgg aacgaaaact   3060
cacgttaagg gattttggtc atgagattat caaaaaggat cttcacctag atccttttaa   3120
attaaaaatg aagttttaaa tcaatctaaa gtatatatga gtaaacttgg tctgacagtt   3180
accaatgctt aatcagtgag gcacctatct cagcgatctg tctatttcgt tcatccatag   3240
ttgcctgact ccccgtcgtg tagataacta cgatacggga gggcttacca tctggcccca   3300
gtgctgcaat gataccgcga gacccacgct caccggctcc agatttatca gcaataaacc   3360
agccagccgg aagggccgag cgcagaagtg gtcctgcaac tttatccgcc tccatccagt   3420
ctattaattg ttgccgggaa gctagagtaa gtagttcgcc agttaatagt ttgcgcaacg   3480
ttgttgccat tgctacaggc atcgtggtgt cacgctcgtc gtttggtatg gcttcattca   3540
gctccggttc ccaacgatca aggcgagtta catgatcccc catgttgtgc aaaaaagcgg   3600
ttagctcctt cggtcctccg atcgttgtca gaagtaagtt ggccgcagtg ttatcactca   3660
tggttatggc agcactgcat aattctctta ctgtcatgcc atccgtaaga tgcttttctg   3720
tgactggtga gtactcaacc aagtcattct gagaatagtg tatgcggcga ccgagttgct   3780
cttgcccggc gtcaatacgg gataataccg cgccacatag cagaacttta aaagtgctca   3840
tcattggaaa acgttcttcg gggcgaaaac tctcaaggat cttaccgctg ttgagatcca   3900
gttcgatgta acccactcgt gcacccaact gatcttcagc atcttttact ttcaccagcg   3960
tttctgggtg agcaaaaaca ggaaggcaaa atgccgcaaa aaagggaata agggcgacac   4020
ggaaatgttg aatactcata ctcttccttt ttcaatatta ttgaagcatt tatcagggtt   4080
attgtctcat gagcggatac atatttgaat gtatttagaa aaataaacaa ataggggttc   4140
cgcgcacatt tccccgaaaa gtgccaccta aattgtaagc gttaatattt tgttaaaatt   4200
cgcgttaaat ttttgttaaa tcagctcatt ttttaaccaa taggccgaaa tcggcaaaat   4260
cccttataaa tcaaaagaat agaccgagat agggttgagt gttgttccag tttggaacaa   4320
gagtccacta ttaaagaacg tggactccaa cgtcaaaggg cgaaaaaccg tctatcaggg   4380
cgatggccca ctacgtgaac catcacccta atcaagtttt tggggtcga ggtgccgtaa   4440
agcactaaat cggaacccta agggagcccc cgatttaga gcttgacggg gaaagccggc   4500
gaacgtggcg agaaaggaag ggaagaaagc gaaaggagcg ggcgctaggg cgctggcaag   4560
tgtagcggtc acgctgcgcg taaccaccac acccgccgcg cttaatgcgc cgctacaggg   4620
cgcgtcccat tcgccattca ggctgcgcaa ctgttgggaa gggcgatcgg tgcgggcctc   4680
ttcgctatta cgccagctgg cgaaaggggg atgtgctgca aggcgattaa gttgggtaac   4740
gccagggttt tcccagtcac gacgttgtaa aacgacggcc agtgagcgcg ctagcgttta   4800
aacgagctct aagatacatt gatgagtttg gacaaaccac aactagaatg cagtgaaaaa   4860
aatgctttat ttgtgaaatt tgtgatgcta ttgctttatt tgtaaccatt ataagctgca   4920
```

| | |
|---|---|
| ataaacaagt taacaacaac aattgcattc attttatgtt tcaggttcag ggggaggtgt | 4980 |
| gggaggtttt ttaaagcaag taaaacctct acaaatgtgg tatggctgat tatgatcctg | 5040 |
| cagctacgcc gctacgtctt ccgtgccgtc ctgggcgtcg tcttcgtcgt cgtcggtcgg | 5100 |
| cggcttcgcc cacgtgatcg aagcgcgctt ctcgatgggc gttccctgcc ccctgcccgt | 5160 |
| agtcgacttc gtgacaacga tcttgtctac gaagagcccg acgaacacgc gcttgtcgtc | 5220 |
| tactgacgcg cgcccccacc acgacttagg gccggtcggg tcagcgtcgg cgtcttcggg | 5280 |
| gaaccattgg tcaaggggaa gcttcggggc ttcggcggct tcaagttcgg caagccgctc | 5340 |
| ttccgccccct gctgccgga gcgtcagcgc tgcctgttgc ttccggaagt gcttcctgcc | 5400 |
| aacgggtccg tcgtacgcgc ctgccgcgcg gtcttcgtac agctcttcaa gggcgttcag | 5460 |
| ggcgtcggcg cgctccgcaa caaggttcgc ccgttcgccg ctcttctcag gcgcctcagt | 5520 |
| gagcttgccg aagcgtcggg cggcttccca cagaagcgcc aacgtctctt cgtcgccttc | 5580 |
| ggcgtgcctg atcttgttga agatgcgttc cgcaacgaac ttgtcgagtg ccgccatgct | 5640 |
| gacgttgcac gtgccttcgt gctgcccagg tgcggacggg tcgaccacct tccggcgacg | 5700 |
| gcagcggtaa gagtccttga tcgattcttc cccgcgcttc gaagtcatga cggcgccaca | 5760 |
| ctcgcagtac agcttgtcca tggcggacag aatggcttgc ccccgggaaa gccccttgcc | 5820 |
| gcgcccccctg ccgtccaacc acgcctgaag ctcataccac tcagcgggct cgatgatcgg | 5880 |
| tccgcaatca agctcgaccg gccggagcgt gatcgggtcg cgctgaatgc ggtaaccctc | 5940 |
| aatcttcgtg gtcggcgtgc cgtccggctt cttcttgtag atcacctcag cggcgaagcc | 6000 |
| cgcaatacgc gggtcccgaa ggattcgcat aacggttgcc gggtcccagg cgcttgaagc | 6060 |
| ggtcttcttc ccaatcgtct cgccccgggt cggcacggcg tcagcgtcca tgcgcttaca | 6120 |
| aagcccgtg atgctgcccg ggtgaatggc ggcttgactg cccggcttga agggaaggtg | 6180 |
| tttgtgcgtc ttgatctcac gccaccacca ccggattacg tcgggctcga actcgaaggg | 6240 |
| tccggtaagg ggagtggtcg agtgcgcaag cttgttgatg acgacattga ccattcggcc | 6300 |
| gttgcgcgtg atctccttcg tctccgaaac aagctcgaag ccgtaaggcg ccttcccgcc | 6360 |
| gacgtacccg cccaattcgc gctgaaggtt cttcgtgtcg agaatcttcg ccgacttcag | 6420 |
| cgaagattct ttgtgcgacg cgtcgagccg cataatcagg tgaatcaggt ccatgacgtt | 6480 |
| tccctgccgg aagacgcctt cctgagtgga acaatcgtc acgcccaggg cgagcaattc | 6540 |
| cgagacaatc ggaatcgcgt ccatgaccdt caggcgcgag aagcgcgaca cgtcatagac | 6600 |
| aatgatcatg ttgagccgcc cggcgcggca ttcgttcagg atgcgttcga actccgggcg | 6660 |
| ctccgccgtc ccgaacgccg acgtgcccgg cgcttcgctg aaatgcccga cgaacctgaa | 6720 |
| ccggcccccg tcgcgctcga cttcgcgctg aaggtcggcc gccttgtctt cgttggcgct | 6780 |
| acgctgtgtc gctgggcttg ctgcgctcga attctcgcgc tcgcgcgact gacggtcgta | 6840 |
| agcacccgcg tacgtgtcca tggcggatcc gtgtcgctgt aacagatgct gttcaactgt | 6900 |
| gtttaccaga tcgttgcggg ctgtatttat aggcgcgata agcgggacgg gcgcctcgtg | 6960 |
| tccggtcacg cgcatgagat aacgcgcggc tgatatggag gcgcgtcctg ttccgataag | 7020 |
| gagttgcgtc cggctgcggt tagcaacaca ggaagctggc gtcctgtcac gataagacaa | 7080 |
| cactcgtccg gtccgataat gtgattcgta cgtgacagga cgcgacccga taaggccggc | 7140 |
| ctacgtgact gccgacacgt acttttttgc actgcaaaaa ggttcaatgt gtggtagtgt | 7200 |
| atttggagcg tatacaacgg tgtagactat ttatgtaaaa tagtctacga aacgtagagt | 7260 |

```
ttgtactatg tatgggcccg cgtgcaaaag cgtgtttttt tgcagtgcaa aaagttggt    7320 ggtggggagg ccaccgagta ta                                           7342
```

<210> SEQ ID NO 49
<211> LENGTH: 11868
<212> TYPE: DNA
<213> ORGANISM: Artificial Sequence
<220> FEATURE:
<223> OTHER INFORMATION: Synthetic construct, pLA1188-cctra intron
      construct

<400> SEQUENCE: 49

```
gtggttttttg tcaaacgaag attctatgac gtgtttaaag tttaggtcga gtaaagcgca     60 aatcttttttt aaccctagaa agatagtctg cgtaaaattg acgcatgcat tcttgaaata    120
ttgctctctc tttctaaata gcgcgaatcc gtcgctgtgc atttaggaca tctcagtcgc    180
cgcttggagc tcccgtgagg cgtgcttgtc aatgcggtaa gtgtcactga ttttgaacta    240
taacgaccgc gtgagtcaaa atgacgcatg attatctttt acgtgacttt taagatttaa    300
ctcatacgat aattatattg ttatttcatg ttctacttac gtgataactt attatatata    360
tattttcttg ttatagatat cgtgactaat atataataaa atgggtagtt ctttagacga    420
tgagcatatc ctctctgctc ttctgcaaag cgatgacgag cttgttggtg aggattctga    480
cagtgaaata tcagatcacg taagtgaaga tgacgtccag agcgatacag aagaagcgtt    540
tatagatgag gtacatgaag tgcagccaac gtcaagcggt agtgaaatat tagacgaaca    600
aaatgttatt gaacaaccag gttcttcatt ggcttctaac agaatcttga ccttgccaca    660
gaggactatt agaggtaaga ataaacattg ttggtcaact tcaaagtcca cgaggcgtag    720
ccgagtctct gcactgaaca ttgtcagatc ggcccgggcg ccgttttttc ttgaaatatt    780
gctctctctt tctaaatagc gcgaatccgt cgctgtgcat ttaggacatc tcagtcgccg    840
cttggagctc ccaaacgcgc cagtggtagt acacagtact gtgggtgttc agtttgaaat    900
cctcttgctt ctccattgtc tcggttacct ttggtcaaat ccatgggttc tattgcctat    960
atactcttgc gattaccagt gattgcgcta ttagctatta gatggattgt tggccaaact    1020
tgtcgcttaa gtggctggga attgtaaccg taggcccgag tgtaatgatc ccccataaaa    1080
agttttcgca atgcctttat tttttgttgc aaatctctct ttattctgcg gtattcttca    1140
ttattgcggg gatggggaaa gtgttatat agaagcaact tacgattgaa cccaaatgca     1200
cctgacaagc aaggtcaaag gccagatttt taaatatat tatttagtct taggactctc     1260
tatttgcaat taaattactt tgctacctga gggttaaatc ttccccattg ataataataa    1320
ttccactata tgttcaattg ggtttcaccg cgcttagtta catgacgagc cctaatgagc    1380
cgtcggtggt ctataaactg tgccttacaa atacttgcaa ctcttctcgt tttgaagtca    1440
gcagagttat tgctaattgc taattgctaa ttgcttttaa ctgatttctt cgaaattggt    1500
gctatgttta tggcgctatt aacaagtatg aatgtcaggt ttaaccaggg gatgcttaat    1560
tgtgttctca acttcaaagg cagaaatgtt tactcttgac catgggttta ggtataatgt    1620
tatcaagctc ctcgagttaa cgttacgtta acgttaacgt tcgaggtcga ctctagaact    1680
acccaccgta ctcgtcaatt ccaagggcat cggtaaacat ctgctcaaac tcgaagtcgg    1740
ccatatccag agcgccgtag ggggcggagt cgtgggggt aaatcccgga cccggggaat     1800
ccccgtcccc caacatgtcc agatcgaaat cgtctagcgc gtcggcatgc gccatcgcca    1860
cgtcctcgcc gtctaagtgg agctcgtccc ccaggctgac atcggtcggg ggggccgtcg    1920
```

```
acagtctgcg cgtgtgtccc gcggggagaa aggacaggcg cggagccgcc agccccgcct    1980
cttcgggggc gtcgtcgtcc gggagatcga gcaggccctc gatggtagac ccgtaattgt    2040
ttttcgtacg cgcgcggctg tacgcggggc ccgagcccga ctcgcatttc agttgctttt    2100
ccaatccgca gataatcagc tccaagccga acaggaatgc cggctcggct ccttgatgat    2160
cgaacagctc gattgcctga cgcagcagtg ggggcatcga atcggttgtt ggggtctcgc    2220
gctcctcttt tgcgacttga tgctcttggt cctccagcac gcagcccagg gtaaagtgac    2280
cgacggcgct cagagcgtag agagcatttt ccaggctgaa gccttgctgg cacaggaacg    2340
cgagctggtt ctccagtgtc tcgtattgct tttcggtcgg gcgcgtgccg agatggactt    2400
tggcaccgtc tcggtgggac agcagagcgc agcggaacga cttggcgtta ttgcggagga    2460
agtcctgcca ggactcgcct tccaacgggc aaaaatgcgt gtggtggcgg tcgagcatct    2520
cgatggccag ggcatccagc agcgcccgct tattcttcac ctatagatac catagatgta    2580
tggattagta tcatatacat acaaaggcta ttttttgggac atattaatat taacaatttc    2640
cgtgatagtt ttcaccattt tgttgaatg ttacgttgaa atttaaatt tgttttaaat    2700
taattttacc agtcatgtgt tcttaaaagt tttatgatt gaaacggcat aaagtggttc    2760
aaaaatttat caagaaaggc tttccttttt taaatcttat cttttctct taaaaatcac    2820
tagtcaattc attattaatt tgttaacttg aatttggaat gtctatttac tttcagataa    2880
attaaagcaa gaaacttaat attcgaaaaa aattgattct aaatgaatt tcacttgatc    2940
ttcatgtatg catatcaatt tttatttaca ttgtataata gtttcgagt tgattgttgt    3000
aatccacagg tgtcccagag aattaaattc caaattaccc aagtttattg aatgttgatt    3060
gtagtttcag ttgctttgtt gctgcaacaa tggcttgttg attgtagata ttttcccttt    3120
ccttggttta cttattacat agactgaaaa agaggtttac tttttgata cttatgaaaa    3180
atttctatta gtgattacta accaatcgct atatgtttac tagaaaacaa ataaactctt    3240
tacattaaca ttcaataatg tttgctctgt aaccgacaat tgaaggcgtt acagcaacag    3300
taatataact agcttcttaa ccctcatcta ttaaccccat cgtttaaaac actatgttaa    3360
atggtctaac aaatctagat actaatagat gtcttattac ttagcagcca cagctgcaac    3420
atccaagaca atttttgaaa cttcttattg agctcttggc agcagaaatg ttggtatttt    3480
tcacagcttt ctgaaagacc ggcaccttcc tccggttccc gtttctgaat tcaagaggat    3540
ttccgacccc caattaatcc cgaaacaaat aaggtatatt caaaatgatg gaaaagtcat    3600
ggctgctgac cttatttta ttcctattga tagaatatta ttcccctttt aaatacactg    3660
tactaagagg tccggctata attttactca cttgtcgatt atcccataga atgttgattg    3720
tagttggttg cttttccagg tgagagttga tcaagtcaca aaagttagcg tgtgttgatt    3780
gtagatttga aggtaaaata attttttgcac ccattcatcg ggtaaaacgt tctccataga    3840
atacattttcc atcgataatt gataacttat gaatttcaaa gaaaaaata tgcttttaaa    3900
attacgtgcc agtagagggt gggctgctcc acgcccagct tctgcgccaa cttgcgggtc    3960
gtcagtccct caatgccaac ttcgttcaac agctccaacg cggagttgat gactttggac    4020
ttatccaggc ggctgcccat ggtggttct aaaggtgtta taaatcaaat tagttttgtt    4080
ttttcttgaa aactttgcgt ttcctttgat caacttaccg ccagggtacc gcagattgtt    4140
tagcttgttc agctgcgctt gtttatttgc ttagctttcg cttagcgacg tgttcacttt    4200
gcttgtttga attgaattgt cgctccgtag acgaagcgcc tctatttata ctccggcgct    4260
cgttttcgag tttaccactc cctatcagtg atagagaaaa gtgaaagtcg agtttaccac    4320
```

```
tccctatcag tgatagagaa aagtgaaagt cgagtttacc actccctatc agtgatagag    4380
aaaagtgaaa gtcgagttta ccactcccta tcagtgatag agaaagtgaa agtcgagtt     4440 taccactccc tatcagtgat agagaaaagt gaaagtcgag tttaccactc cctatcagtg    4500
atagagaaaa gtgaaagtcg agtttaccac tccctatcag tgatagagaa aagtgaaagt    4560
cgaaacctgg cgcgccccgg ccatcgagaa agagagagag aagagaagag agagaacatt    4620
cgagaaagag agagagaaga gaagagagag aacatactcc ctatcagtga tagagaagtc    4680
cctatcagtg atagagatgt ccctatcagt gatagagagt tccctatcag tgatagagac    4740
gtccctatca gtgatagaga agtccctatc agtgatagag agatccctat cagtgataga    4800
gatttcccta tcagtgatag agaggtccct atcagtgata gagacttccc tatcagtgat    4860
agagaaatcc ctatcagtga tagagacatc cctatcagtg atagagaact ccctatcagt    4920
gatagagacc tccctatcag tgatagagat cgatgcggcc gcatggtacc cattgcttgt    4980
catttattaa tttggatgat gtcatttgtt tttaaaattg aactggcttt acgagtagaa    5040
ttctacgcgt aaaacacaat caagtatgag tcataatctg atgtcatgtt ttgtacacgg    5100
ctcataaccg aactggcttt acgagtgaaa ttctacttgt aatgcacgat cagtggatga    5160
tgtcatttgt ttttcaaatc gagatgatgt catgttttgc acacggctca taaactcgct    5220
ttacgagtag aattctacgt gtaacgcacg atcgattgat gagtcatttg ttttgcaata    5280
tgatatcata caatatgact catttgtttt tcaaaaccga acttgattta cgggtagaat    5340
tctacttgta aagcacaatc aaaaagatga tgtcatttgt ttttcaaaac tgaactcgct    5400
ttacgagtag aattctacgt gtaaaacaca atcaagaaat gatgtcattt gttataaaaa    5460
taaaagctga tgtcatgttt tgcacatggc tcataactaa actcgcttta cgggtagaat    5520
tctacgcgta aaacatgatt gataattaaa taattcattt gcaagctata cgttaaatca    5580
aacggacgct cgaggttgca caacactatt atcgatttgc agttcgggac ataaatgttt    5640
aaatatatcg atgtctttgt gatgcgcgcg acattttgt aggttattga taaaatgaac    5700
ggatacgttg cccgacatta tcattaaatc cttggcgtag aatttgtcgg gtccattgtc    5760
cgtgtgcgct agcatgcccg taacggacct cgtacttttg gcttcaaagg ttttgcgcac    5820
agacaaaatg tgccacactt gcagctctgc atgtgtgcgc gttaccacaa atcccaacgg    5880
cgcagtgtac ttgttgtatg caaataaatc tcgataaagg cgcggcgcgc gaatgcagct    5940
gatcacgtac gctcctcgtg ttccgttcaa ggacggtgtt atcgacctca gattaatgtt    6000
tatcggccga ctgttttcgt atccgctcac caaacgcgtt tttgcattaa cattgtatgt    6060
cggcggatgt tctatatcta atttgaataa ataaacgata accgcgttgg ttttagaggg    6120
cataataaaa gaaatattgt tatcgtgttc gccattaggg cagtataaat tgacgttcat    6180
gttggatatt gtttcagttg caagttgaca ctggcggcga caagcaattc taattggggt    6240
aagttttccc gttcttttct gggttcttcc cttttgctca tccttgctgc actaccttca    6300
ggtgcaagtt gagattcagg ccaccatggg agatcccacc ccacccaaga agaagcgcaa    6360
accggtcgcc accatggcct cctccgagaa cgtcatcacc gagttcatgc gcttcaaggt    6420
gcgcatggag ggcaccgtga acggccacga gttcgagatc gagggcgagg gcgagggccg    6480
cccctacgag ggccacaaca ccgtgaagct gaaggtgacc aagggcggcc cctgccctt     6540 cgcctgggac atcctgtccc ccagttcca gtacggctcc aaggtgtacg tgaagcaccc    6600
cgccgacatc cccgactaca agaagctgtc cttccccgag ggcttcaagt gggagcgcgt    6660
```

```
gatgaacttc gaggacggcg gcgtggcgac cgtgacccag gactcctccc tgcaggacgg    6720
ctgcttcatc tacaaggtga agttcatcgg cgtgaacttc ccctccgacg gccccgtgat    6780
gcagaagaag accatgggct gggaggcctc caccgagcgc ctgtaccccc gcgacggcgt    6840
gctgaagggc gagacccaca aggccctgaa gctgaaggac ggcggccact acctggtgga    6900
gttcaagtcc atctacatgg ccaagaagcc cgtgcagctg cccggctact actacgtgga    6960
cgccaagctg gacatcacct cccacaacga ggactacacc atcgtggagc agtacgagcg    7020
caccgagggc cgccaccacc tgttcctgag atctcgaccc aagaaaaagc ggaaggtgga    7080
ggacccgtaa gatccaccgg atctagataa ctgatcataa tcagccatac cacatttgta    7140
gaggttttac ttgctttaaa aacctcccca cacctccccc tgaacctgaa acataaaatg    7200
aatgcaattg ttgttgttaa cttgtttatt gcagcttata atggttacaa ataaagcaat    7260
agcatcacaa atttcacaaa taaagcattt ttttcactgc attctagttg tggtttgtcc    7320
aaactcatca atgtatctta cgcgagtta attaaggccg ctcatttaaa tctggccggc    7380
cgcaaccatt gtgggaaccg tgcgatcaaa caaacgcgag ataccggaag tactgaaaaa    7440
cagtcgctcc aggccagtgg gaacatcgat gttttgtttt gacggacccc ttactctcgt    7500
ctcatataaa ccgaagccag ctaagatggt atacttatta tcatcttgtg atgaggatgc    7560
ttctatcaac gaaagtaccg gtaaaccgca aatggttatg tattataatc aaactaaagg    7620
cggagtggac acgctagacc aaatgtgttc tgtgatgacc tgcagtagga agacgaatag    7680
gtggcctatg gcattattgt acggaatgat aaacattgcc tgcataaatt ctttattat    7740
atacagccat aatgtcagta gcaagggaga aaaggtccaa agtcgcaaaa aatttatgag    7800
aaacctttac atgagcctga cgtcatcgtt tatgcgtaag cgtttagaag ctcctacttt    7860
gaagagatat ttgcgcgata atatctctaa tattttgcca aatgaagtgc ctggtacatc    7920
agatgacagt actgaagagc cagtaatgaa aaaacgtact tactgtactt actgccctc    7980
taaaataagg cgaaaggcaa atgcatcgtg caaaaaatgc aaaaagtta tttgtcgaga    8040
gcataatatt gatatgtgcc aaagttgttt ctgactgact aataagtata atttgtttct    8100
attatgtata agttaagcta attacttatt ttataataca acatgactgt ttttaaagta    8160
caaaataagt ttattttgt aaagagaga atgtttaaaa gttttgttac tttatagaag    8220
aaattttgag ttttgtttt ttttaataa ataaataaac ataaataaat tgtttgttga    8280
atttattatt agtatgtaag tgtaaatata ataaaactta atatctattc aaattaataa    8340
ataaacctcg atatacagac cgataaaaca catgcgtcaa ttttacgcat gattatcttt    8400
aacgtacgtc acaatatgat tatctttcta gggttaaata atagtttcta atttttttat    8460
tattcagcct gctgtcgtga ataccgtata tctcaacgct gtctgtgaga ttgtcgtatt    8520
ctagcctttt tagtttttcg ctcatcgact tgatattgtc cgacacattt tcgtcgattt    8580
gcgttttgat caaagacttg agcagagaca cgttaatcaa ctgttcaaat tgatccatat    8640
taacgatatc aacccgatgc gtatatggtg cgtaaaatat atttttaac cctcttatac    8700
tttgcactct gcgttaatac gcgttcgtgt acagacgtaa tcatgttttc tttttttggat   8760
aaaactccta ctgagtttga cctcatatta gaccctcaca agttgcaaaa cgtggcatttt   8820
tttaccaatg aagaatttaa agttatttta aaaaatttca tcacagattt aaagaagaac    8880
caaaaattaa attatttcaa cagtttaatc gaccagttaa tcaacgtgta cacagacgcg    8940
tcggcaaaaa acacgcagcc cgacgtgttg gctaaaatta ttaaatcaac ttgtgttata    9000
gtcacggatt tgccgtccaa cgtgttcctc aaaaagttga agaccaacaa gtttacggac    9060
```

| | |
|---|---|
| actattaatt atttgatttt gccccacttc attttgtggg atcacaattt tgttatattt | 9120 |
| taaacaaagc ttggcactgg ccgtcgtttt acaacgtcgt gactgggaaa accctggcgt | 9180 |
| tacccaactt aatcgccttg cagcacatcc ccctttcgcc agctggcgta atagcgaaga | 9240 |
| ggcccgcacc gatcgccctt cccaacagtt gcgcagcctg aatggcgaat ggcgcctgat | 9300 |
| gcggtatttt ctccttacgc atctgtgcgg tatttcacac cgcatatggt gcactctcag | 9360 |
| tacaatctgc tctgatgccg catagttaag ccagccccga cacccgccaa cacccgctga | 9420 |
| cgcgccctga cgggcttgtc tgctcccggc atccgcttac agacaagctg tgaccgtctc | 9480 |
| cgggagctga tgtgtcaga ggttttcacc gtcatcaccg aaacgcgcga gacgaaaggg | 9540 |
| cctcgtgata cgcctatttt tataggttaa tgtcatgata ataatggttt cttagacgtc | 9600 |
| aggtggcact tttcggggaa atgtgcgcgg aaccccctat tgtttatttt tctaaataca | 9660 |
| ttcaaatatg tatccgctca tgagacaata accctgataa atgcttcaat aatattgaaa | 9720 |
| aaggaagagt atgagtattc aacatttccg tgtcgccctt attcccttt ttgcggcatt | 9780 |
| ttgccttcct gttttgctc acccagaaac gctggtgaaa gtaaagatg ctgaagatca | 9840 |
| gttgggtgca cgagtgggtt acatcgaact ggatctcaac agcggtaaga tccttgagag | 9900 |
| ttttcgcccc gaagaacgtt ttccaatgat gagcactttt aaagttctgc tatgtggcgc | 9960 |
| ggtattatcc cgtattgacg ccgggcaaga gcaactcggt cgccgcatac actattctca | 10020 |
| gaatgacttg gttgagtact caccagtcac agaaaagcat cttacggatg gcatgacagt | 10080 |
| aagagaatta tgcagtgctg ccataaccat gagtgataac actgcggcca acttacttct | 10140 |
| gacaacgatc ggaggaccga aggagctaac cgcttttttg cacaacatgg gggatcatgt | 10200 |
| aactcgcctt gatcgttggg aaccggagct gaatgaagcc ataccaaacg acgagcgtga | 10260 |
| caccacgatg cctgtagcaa tggcaacaac gttgcgcaaa ctattaactg gcgaactact | 10320 |
| tactctagct tcccggcaac aattaataga ctggatggag gcggataaag ttgcaggacc | 10380 |
| acttctgcgc tcggcccttc cggctggctg gtttattgct gataaatctg gagccggtga | 10440 |
| gcgtgggtct cgcggtatca ttgcagcact ggggccagat ggtaagccct cccgtatcgt | 10500 |
| agttatctac acgacgggga gtcaggcaac tatggatgaa cgaaatagac agatcgctga | 10560 |
| gataggtgcc tcactgatta agcattggta actgtcagac caagtttact catatatact | 10620 |
| ttagattgat ttaaaacttc atttttaatt taaaaggatc taggtgaaga tcctttttga | 10680 |
| taatctcatg accaaaatcc cttaacgtga gttttcgttc cactgagcgt cagacccgt | 10740 |
| agaaaagatc aaaggatctt cttgagatcc tttttttctg cgcgtaatct gctgcttgca | 10800 |
| aacaaaaaaa ccaccgctac cagcggtggt ttgtttgccg gatcaagagc taccaactct | 10860 |
| ttttccgaag gtaactggct tcagcagagc gcagatacca aatactgtcc ttctagtgta | 10920 |
| gccgtagtta ggccaccact tcaagaactc tgtagcaccg cctacatacc tcgctctgct | 10980 |
| aatcctgtta ccagtggctg ctgccagtgg cgataagtcg tgtcttaccg ggttggactc | 11040 |
| aagacgatag ttaccggata aggcgcagcg gtcgggctga acggggggtt cgtgcacaca | 11100 |
| gcccagcttg gagcgaacga cctacaccga actgagatac ctacagcgtg agcattgaga | 11160 |
| aagcgccacg cttcccgaag ggagaaaggc ggacaggtat ccggtaagcg gcagggtcgg | 11220 |
| aacaggagag cgcacgaggg agcttccagg gggaaacgcc tggtatcttt atagtcctgt | 11280 |
| cgggtttcgc cacctctgac ttgagcgtcg attttgtga tgctcgtcag ggggcgag | 11340 |
| cctatggaaa aacgccagca acgcggcctt tttacggttc ctggccttt gctggccttt | 11400 |

```
tgctcacatg ttctttcctg cgttatcccc tgattctgtg gataaccgta ttaccgcctt   11460
tgagtgagct gataccgctc gccgcagccg aacgaccgag cgcagcgagt cagtgagcga   11520
ggaagcggaa gagcgcccaa tacgcaaacc gcctctcccc gcgcgttggc cgattcatta   11580
atgcagctgg cacgacaggt ttcccgactg gaaagcgggc agtgagcgca acgcaattaa   11640
tgtgagttag ctcactcatt aggcacccca ggctttacac tttatgcttc cggctcgtat   11700
gttgtgtgga attgtgagcg gataacaatt tcacacagga aacagctatg accatgatta   11760
cgaatttcga cctgcaggca tgcaagcttg catgcctgca ggtcgacgct cgcgcgactt   11820
ggtttgccat tctttagcgc gcgtcgcgtc acacagcttg ccacaat                 11868
```

<210> SEQ ID NO 50
<211> LENGTH: 11868
<212> TYPE: DNA
<213> ORGANISM: Artificial Sequence
<220> FEATURE:
<223> OTHER INFORMATION: Synthetic construct, pLA3077-a Cctra
      intron-tTAV construct.

<400> SEQUENCE: 50

```
gtggttttg tcaaacgaag attctatgac gtgtttaaag tttaggtcga gtaaagcgca     60 aatcttttt aaccctagaa agatagtctg cgtaaaattg acgcatgcat tcttgaaata    120
ttgctctctc tttctaaata gcgcgaatcc gtcgctgtgc atttaggaca tctcagtcgc   180
cgcttggagc tcccgtgagg cgtgcttgtc aatgcggtaa gtgtcactga ttttgaacta   240
taacgaccgc gtgagtcaaa atgacgcatg attatctttt acgtgacttt taagatttaa   300
ctcatacgat aattatattg ttatttcatg ttctacttac gtgataactt attatatata   360
tatttttctg ttatagatat cgtgactaat atataataaa atgggtagtt ctttagacga   420
tgagcatatc ctctctgctc ttctgcaaag cgatgacgag cttgttggtg aggattctga   480
cagtgaaata tcagatcacg taagtgaaga tgacgtccag agcgatacag aagaagcgtt   540
tatagatgag gtacatgaag tgcagccaac gtcaagcggt agtgaaatat tagacgaaca   600
aaatgttatt gaacaaccag gttcttcatt ggcttctaac agaatcttga ccttgccaca   660
gaggactatt agaggtaaga ataaacattg ttggtcaact tcaaagtcca cgaggcgtag   720
ccgagtctct gcactgaaca ttgtcagatc ggcccgggcg ccgttttct tgaaatattg    780 ctctctcttt ctaaatagcg cgaatccgtc gctgtgcatt taggacatct cagtcgccgc   840
ttggagctcc caaacgcgcc agtggtagta cacagtactg tgggtgttca gtttgaaatc   900
ctcttgcttc tccattgtct cggttacctt tggtcaaatc catgggttct attgcctata   960
tactcttgcg attaccagtg attgcgctat tagctattag atggattgtt ggccaaactt   1020
gtcgcttaag tggctgggaa ttgtaaccgt aggcccgagt gtaatgatcc cccataaaaa   1080
gttttcgcaa tgccttttatt ttttgttgca aatctctctt tattctgcgg tattcttcat  1140
tattgcgggg atggggaaag tgtttatata gaagcaactc acgattgaac ccaaatgcac   1200
ctgacaagca aggtcaaagg gccagatttt taaatatatt atttagtctt aggactctct   1260
atttgcaatt aaattacttt gctacctgag ggttaaatct tccccattga taataataat   1320
tccactatat gttcaattgg gtttcaccgc gcttagttac atgacgagcc ctaatgagcc   1380
gtcggtggtc tataaactgt gccttacaaa tacttgcaac tcttctcgtt ttgaagtcag   1440
cagagttatt gctaattgct aattgctaat tgcttttaac tgattcttc gaaattggtg    1500 ctatgtttat ggcgctatta acaagtatga atgtcaggtt taaccagggg atgcttaatt   1560
```

```
gtgttctcaa cttcaaaggc agaaatgttt actcttgacc atgggtttag gtataatgtt    1620
atcaagctcc tcgagttaac gttacgttaa cgttaacgtt cgaggtcgac tctagaacta    1680
cccaccgtac tcgtcaattc caagggcatc ggtaaacatc tgctcaaact cgaagtcggc    1740
catatccaga gcgccgtagg gggcggagtc gtgggggggta atcccggac ccggggaatc     1800 cccgtccccc aacatgtcca gatcgaaatc gtctagcgcg tcggcatgcg ccatcgccac    1860
gtcctcgccg tctaagtgga gctcgtcccc caggctgaca tcggtcgggg gggccgtcga    1920
cagtctgcgc gtgtgtcccg cggggagaaa ggacaggcgc ggagccgcca gccccgcctc    1980 ttcggggggcg tcgtcgtccg ggagatcgag caggccctcg atggtagacc cgtaattgtt    2040
tttcgtacgc gcgcggctgt acgcggggcc cgagcccgac tcgcatttca gttgcttttc    2100
caatccgcag ataatcagct ccaagccgaa caggaatgcc ggctcggctc cttgatgatc    2160
gaacagctcg attgcctgac gcagcagtgg gggcatcgaa tcggttgttg gggtctcgcg    2220
ctcctctttt gcgacttgat gctcttggtc ctccagcacg cagcccaggg taaagtgacc     2280
gacggcgctc agagcgtaga gagcattttc caggctgaag ccttgctggc acaggaacgc    2340
gagctggttc tccagtgtct cgtattgctt ttcggtcggg gcgtgccga atggacttt      2400 ggcaccgtct cggtgggaca gcagagcgca gcggaacgca ttggcgttat tgcggaggaa    2460
gtcctgccag gactcgcctt ccaacgggca aaaatgcgtg tggtggcggt cgagcatctc    2520
gatggccagg gcatccagca gcgcccgctt attcttcacg tgccagtaga gggtgggctg    2580
ctccacgccc agcttctgcg ccaacttgcg ggtcgtcagt ccctcaatac ctatagatac    2640
catagatgta tggattagta tcatatacat acaaaggcta ttttttgggac atattaatat   2700 taacaatttc cgtgatagtt ttcaccattt tgttgaatg ttacgttgaa aatttaaatt     2760
tgttttaaat taattttacc agtcatgtgt tcttaaaagt ttttatgatt gaaacggcat    2820
aaagtggttc aaaaatttat caagaaggc tttccttttt taaatcttat cttttttctct    2880 taaaaatcac tagtcaattc attattaatt tgttaacttg aatttggaat gtctatttac    2940
tttcagataa attaaagcaa gaaacttaat attcgaaaaa aattgattct aaatggaatt    3000
tcacttgatc ttcatgtatg catatcaatt tttatttaca ttgtataata agtttcgagt    3060
tgattgttgt aatccacagg tgtcccagag aattaaattc caaattaccc aagtttattg    3120
aatgttgatt gtagtttcag ttgctttgtt gctgcaacaa tggcttgttg attgtagata    3180
ttttcccttt ccttggttta cttattacat agactgaaaa agaggtttac ttttttgata    3240
cttatgaaaa atttctatta gtgattacta accaatcgct atatgttac tagaaaacaa     3300 ataaactctt tacattaaca ttcaataatg tttgctctgt aaccgacaat tgaaggcgtt    3360
acagcaacag taatataact agcttcttaa ccctcatcta ttaacccat cgtttaaaac     3420 actatgttaa atggtctaac aaatctagat actaatagat gtcttattac ttagcagcca    3480
cagctgcaac atccaagaca attttttgaaa cttcttattg agctcttggc agcagaaatg    3540
ttggtatttt tcacagcttt ctgaaagacc ggcaccttcc tccggttccc gtttctgaat    3600
tcaagaggat ttccgacccc caattaatcc cgaaacaaat aaggtatatt caaaatgatg    3660
gaaaagtcat ggctgctgac cttatttta ttcctattga tagaatatta ttcccctttt     3720
aaatacactg tactaagagg tccggctata atttttactca cttgtcgatt atcccataga   3780
atgttgattg tagttggttg cttttccagg tgagagttga tcaagtcaca aaagttagcg    3840
tgtgttgatt gtagatttga aggtaaaata attttttgcac ccattcatcg ggtaaaacgt   3900
tctccataga atacatttcc atcgataatt gataacttat gaatttcaaa gaaaaaaata    3960
```

```
tgcttttaaa attaccaact tcgttcaaca gctccaacgc ggagttgatg actttggact    4020
tatccaggcg gctgcccatg gtggtttcta aaggtgttat aaatcaaatt agttttgttt    4080
tttcttgaaa actttgcgtt tcctttgatc aacttaccgc cagggtacct gcagattgtt    4140
tagcttgttc agctgcgctt gtttatttgc ttagctttcg cttagcgacg tgttcacttt    4200
gcttgtttga attgaattgt cgctccgtag acgaagcgcc tctatttata ctccggcgct    4260
cgttttcgag tttaccactc cctatcagtg atagagaaaa gtgaaagtcg agtttaccac    4320
tccctatcag tgatagagaa aagtgaaagt cgagtttacc actccctatc agtgatagag    4380
aaaagtgaaa gtcgagttta ccactcccta tcagtgatag agaaagtga agtcgagtt    4440 taccactccc tatcagtgat agagaaaagt gaaagtcgag tttaccactc cctatcagtg    4500
atagagaaaa gtgaaagtcg agtttaccac tccctatcag tgatagagaa aagtgaaagt    4560
cgaaacctgg cgcgccccgg ccatcgagaa agagagagag aagagaagag agagaacatt    4620
cgagaaagag agagagaaga gaagagagag aacatactcc ctatcagtga tagagaagtc    4680
cctatcagtg atagagatgt ccctatcagt gatagagagt tccctatcag tgatagagac    4740
gtccctatca gtgatagaga agtccctatc agtgatagag agatccctat cagtgataga    4800
gatttcccta tcagtgatag agaggtccct atcagtgata gagacttccc tatcagtgat    4860
agagaaatcc ctatcagtga tagagacatc cctatcagtg atagagaact ccctatcagt    4920
gatagagacc tccctatcag tgatagagat cgatgcggcc gcatggtacc cattgcttgt    4980
catttattaa tttggatgat gtcatttgtt tttaaaattg aactggcttt acgagtagaa    5040
ttctacgcgt aaaacacaat caagtatgag tcataatctg atgtcatgtt ttgtacacgg    5100
ctcataaccg aactggcttt acgagtagaa ttctacttgt aatgcacgat cagtggatga    5160
tgtcatttgt ttttcaaatc gagatgatgt catgttttgc acacggctca taaactcgct    5220
ttacgagtag aattctacgt gtaacgcacg atcgattgat gagtcatttg ttttgcaata    5280
tgatatcata caatatgact catttgtttt tcaaaaccga acttgattta cgggtagaat    5340
tctacttgta aagcacaatc aaaaagatga tgtcatttgt ttttcaaaac tgaactcgct    5400
ttacgagtag aattctacgt gtaaaacaca atcaagaaat gatgtcattt gttataaaaa    5460
taaaagctga tgtcatgttt tgcacatggc tcataactaa actcgcttta cgggtagaat    5520
tctacgcgta aaacatgatt gataattaaa taattcattt gcaagctata cgttaaatca    5580
aacggacgct cgaggttgca caacactatt atcgatttgc agttcgggac ataaatgttt    5640
aaatatatcg atgtctttgt gatgcgcgcg acatttttgt aggttattga taaatgaac    5700 ggatacgttg cccgacatta tcattaaatc cttggcgtag aatttgtcgg gtccattgtc    5760
cgtgtgcgca gcatgcccg taacggacct cgtactttg gcttcaaagg ttttgcgcac    5820
agacaaaatg tgccacactt gcagctctgc atgtgtgcgc gttaccacaa atcccaacgg    5880
cgcagtgtac ttgttgtatg caaataaatc tcgataaagg cgcggcgcgc gaatgcagct    5940
gatcacgtac gctcctcgtg ttccgttcaa ggacggtgtt atcgacctca gattaatgtt    6000
tatcggccga ctgttttcgt atccgctcac caaacgcgtt tttgcattaa cattgtatgt    6060
cggcggatgt tctatatcta atttgaataa ataaacgata accgcgttgg ttttagaggg    6120
cataataaaa gaaatattgt tatcgtgttc gccattaggg cagtataaat tgacgttcat    6180
gttggatatt gtttcagttg caagttgaca ctggcggcga caagcaattc taattggggt    6240
aagttttccc gttcttttct gggttcttcc cttttgctca tccttgctgc actaccttca    6300
```

```
ggtgcaagtt gagattcagg ccaccatggg agatcccacc ccacccaaga agaagcgcaa      6360
accggtcgcc accatggcct cctccgagaa cgtcatcacc gagttcatgc gcttcaaggt      6420
gcgcatggag ggcaccgtga acggccacga gttcgagatc gagggcgagg gcgagggccg      6480
cccctacgag ggccacaaca ccgtgaagct gaaggtgacc aagggcggcc ccctgccctt      6540
cgcctgggac atcctgtccc cccagttcca gtacggctcc aaggtgtacg tgaagcaccc      6600
cgccgacatc cccgactaca agaagctgtc cttccccgag ggcttcaagt gggagcgcgt      6660
gatgaacttc gaggacggcg gcgtggcgac cgtgacccag gactcctccc tgcaggacgg      6720
ctgcttcatc tacaaggtga agttcatcgg cgtgaacttc ccctccgacg gccccgtgat      6780
gcagaagaag accatgggct gggaggcctc caccgagcgc ctgtacccccc gcgacggcgt      6840 gctgaagggc gagacccaca aggccctgaa gctgaaggac ggcggccact acctggtgga      6900
gttcaagtcc atctacatgg ccaagaagcc cgtgcagctg cccggctact actacgtgga      6960
cgccaagctg gacatcaccc tccacaacga ggactacacc atcgtggagc agtacgagcg      7020
caccgagggc cgccaccacc tgttcctgag atctcgaccc aagaaaaagc ggaaggtgga      7080
ggacccgtaa gatccaccgg atctagataa ctgatcataa tcagccatac cacatttgta      7140
gaggttttac ttgctttaaa aaacctccca cacctccccc tgaacctgaa acataaaatg      7200
aatgcaattg ttgttgttaa cttgtttatt gcagcttata atggttacaa ataaagcaat      7260
agcatcacaa atttcacaaa taaagcattt ttttcactgc attctagttg tggtttgtcc      7320
aaactcatca atgtatctta acgcgagtta attaaggccg ctcatttaaa tctggccggc      7380
cgcaaccatt gtgggaaccg tgcgatcaaa caaacgcgag ataccggaag tactgaaaaa      7440
cagtcgctcc aggccagtgg gaacatcgat gttttgtttt gacggacccc ttactctcgt      7500
ctcatataaa ccgaagccag ctaagatggt atacttatta tcatcttgtg atgaggatgc      7560
ttctatcaac gaaagtaccg gtaaaccgca atggttatg tattataatc aaactaaagg      7620
cggagtggac acgctagacc aaatgtgttc tgtgatgacc tgcagtagga agacgaatag      7680
gtggcctatg gcattattgt acggaatgat aaacattgcc tgcataaatt cttttattat      7740
atacagccat aatgtcagta gcaagggaga aaaggtccaa agtcgcaaaa aatttatgag      7800
aaacctttac atgagcctga cgtcatcgtt tatgcgtaag cgtttagaag ctcctacttt      7860
gaagagatat ttgcgcgata atatctctaa tattttgcca aatgaagtgc ctggtacatc      7920
agatgacagt actgaagagc cagtaatgaa aaaacgtact tactgtactt actgccctc      7980 taaaataagg cgaaaggcaa atgcatcgtg caaaaaatgc aaaaaagtta tttgtcgaga      8040
gcataatatt gatatgtgcc aaagttgttt ctgactgact aataagtata atttgtttct      8100
attatgtata agttaagcta attacttatt ttataataca acatgactgt ttttaaagta      8160
caaaataagt ttatttttgt aaaagagaga atgtttaaaa gttttgttac tttatagaag      8220 aaatttgag tttttgtttt tttttaataa ataaataaac ataaataat tgtttgttga      8280 atttattatt agtatgtaag tgtaaatata ataaacttta atatctattc aaattaataa      8340
ataaacctcg atatacagac cgataaaaca catgcgtcaa ttttacgcat gattatcttt      8400
aacgtacgtc acaatatgat tatcttccta gggttaaata tagtttccta attttttttat     8460 tattcagcct gctgtcgtga ataccgtata tctcaacgct gtctgtgaga ttgtcgtatt      8520
ctagcctttt tagttttttcg ctcatcgact tgatattgtc cgacacattt tcgtcgattt     8580
gcgttttgat caaagacttg agcagagaca cgttaatcaa ctgttcaaat tgatccatat      8640
taacgatatc aacccgatgc gtatatggtg cgtaaaatat atttttaac cctcttatac      8700
```

```
tttgcactct gcgttaatac gcgttcgtgt acagacgtaa tcatgttttc tttttttggat   8760
aaaactccta ctgagtttga cctcatatta gaccctcaca agttgcaaaa cgtggcattt   8820
tttaccaatg aagaatttaa agttattttta aaaaatttca tcacagattt aaagaagaac  8880
caaaaattaa attatttcaa cagtttaatc gaccagttaa tcaacgtgta cacagacgcg   8940
tcggcaaaaa acacgcagcc cgacgtgttg gctaaaatta ttaaatcaac ttgtgttata   9000
gtcacggatt tgccgtccaa cgtgttcctc aaaaagttga agaccaacaa gtttacggac   9060
actattaatt atttgatttt gccccacttc attttgtggg atcacaattt tgttatattt   9120
taaacaaagc ttggcactgg ccgtcgtttt acaacgtcgt gactgggaaa accctggcgt   9180
tacccaactt aatcgccttg cagcacatcc cctttcgcc agctggcgta atagcgaaga   9240
ggcccgcacc gatcgccctt cccaacagtt gcgcagcctg aatggcgaat ggcgcctgat   9300
gcggtatttt ctccttacgc atctgtgcgg tatttcacac cgcatatggt gcactctcag   9360
tacaatctgc tctgatgccg catagttaag ccagccccga cacccgccaa cacccgctga   9420
cgcgccctga cgggcttgtc tgctcccggc atccgcttac agacaagctg tgaccgtctc   9480
cgggagctgc atgtgtcaga ggttttcacc gtcatcaccg aaacgcgcga dacgaaaggg   9540
cctcgtgata cgcctatttt tataggttaa tgtcatgata ataatggttt cttagacgtc   9600
aggtggcact tttcggggaa atgtgcgcgg aaccctatt tgtttatttt tctaaataca   9660
ttcaaatatg tatccgctca tgagacaata accctgataa atgcttcaat aatattgaaa   9720
aaggaagagt atgagtattc aacatttccg tgtcgccctt attcccttt ttgcggcatt   9780
ttgccttcct gtttttgctc acccagaaac gctggtgaaa gtaaagatg ctgaagatca    9840
gttgggtgca cgagtgggtt acatcgaact ggatctcaac agcggtaaga tccttgagag   9900
ttttcgcccc gaagaacgtt ttccaatgat gagcactttt aaagttctgc tatgtggcgc    9960
ggtattatcc cgtattgacg ccgggcaaga gcaactcggt cgccgcatac actattctca  10020
gaatgacttg gttgagtact caccagtcac agaaaagcat cttacggatg gcatgacagt  10080
aagagaatta tgcagtgctg ccataaccat gagtgataac actgcggcca acttacttct  10140
gacaacgatc ggaggaccga aggagctaac cgcttttttg cacaacatgg ggatcatgt   10200
aactcgcctt gatcgttggg aaccggagct gaatgaagcc ataccaaacg acgagcgtga  10260
caccacgatg cctgtagcaa tggcaacaac gttgcgcaaa ctattaactg gcgaactact  10320
tactctagct tcccggcaac aattaataga ctggatggag gcggataaag ttgcaggacc  10380
acttctgcgc tcggcccttc cggctggctg gtttattgct gataaatctg gagccggtga  10440
gcgtgggtct cgcggtatca ttgcagcact ggggccagat ggtaagccct cccgtatcgt  10500
agttatctac acgacgggga gtcaggcaac tatggatgaa cgaaatagac agatcgctga  10560
gataggtgcc tcactgatta agcattggta actgtcagac caagtttact catatatact  10620
ttagattgat ttaaaacttc atttttaatt taaaaggatc taggtgaaga tccttttga   10680
taatctcatg accaaaatcc cttaacgtga gttttcgttc cactgagcgt cagacccccgt  10740
agaaaagatc aaaggatctt cttgagatcc tttttttctg cgcgtaatct gctgcttgca  10800
aacaaaaaaa ccaccgctac cagcggtggt ttgtttgccg gatcaagagc taccaactct  10860
ttttccgaag gtaactggct tcagcagagc gcagatacca aatactgtcc ttctagtgta  10920
gccgtagtta ggccaccact tcaagaactc tgtagcaccg cctacatacc tcgctctgct  10980
aatcctgtta ccagtggctg ctgccagtgg cgataagtcg tgtcttaccg ggttggactc  11040
```

| | | | |
|---|---|---|---|
| aagacgatag | ttaccggata aggcgcagcg gtcgggctga acgggggggtt cgtgcacaca | 11100 | |
| gcccagcttg | gagcgaacga cctacaccga actgagatac ctacagcgtg agcattgaga | 11160 | |
| aagcgccacg | cttcccgaag ggagaaaggc ggacaggtat ccggtaagcg gcagggtcgg | 11220 | |
| aacaggagag | cgcacgaggg agcttccagg gggaaacgcc tggtatcttt atagtcctgt | 11280 | |
| cgggtttcgc | cacctctgac ttgagcgtcg attttgtga tgctcgtcag gggggcggag | 11340 | |
| cctatggaaa | aacgccagca acgcggcctt tttacggttc ctggcctttt gctggccttt | 11400 | |
| tgctcacatg | ttctttcctg cgttatcccc tgattctgtg ataaccgta ttaccgcctt | 11460 | |
| tgagtgagct | gataccgctc gccgcagccg aacgaccgag cgcagcgagt cagtgagcga | 11520 | |
| ggaagcggaa | gagcgcccaa tacgcaaacc gcctctcccc gcgcgttggc cgattcatta | 11580 | |
| atgcagctgg | cacgcacaggt ttcccgactg gaaagcgggc agtgagcgca acgcaattaa | 11640 | |
| tgtgagttag | ctcactcatt aggcaccccca ggctttacac tttatgcttc cggctcgtat | 11700 | |
| gttgtgtgga | attgtgagcg gataacaatt tcacacagga aacagctatg accatgatta | 11760 | |
| cgaatttcga | cctgcaggca tgcaagcttg catgcctgca ggtcgacgct cgcgcgactt | 11820 | |
| ggtttgccat | tctttagcgc gcgtcgcgtc acacagcttg gccacaat | 11868 | |

<210> SEQ ID NO 51
<211> LENGTH: 11788
<212> TYPE: DNA
<213> ORGANISM: Artificial Sequence
<220> FEATURE:
<223> OTHER INFORMATION: Synthetic construct, pLA3097-a Cctra
      intron-tTAV construct.

<400> SEQUENCE: 51

| | | |
|---|---|---|
| gggcggccgt | ttttcttgaa atattgctct ctctttctaa atagcgcgaa tccgtcgctg | 60 |
| tgcatttagg | acatctcagt cgccgcttgg agctcccaaa cgcgccagtg gtagtacaca | 120 |
| gtactgtggg | tgttcagttt gaaatcctct tgcttctcca ttgtctcggt tacctttggt | 180 |
| caaatccatg | ggttctattg cctatatact cttgcgatta ccagtgattg cgctattagc | 240 |
| tattagatgg | attgttggcc aaacttgtcg cttaagtggc tgggaattgt aaccgtaggc | 300 |
| ccgagtgtaa | tgatccccca taaaaagttt tcgcaatgcc tttattttt gttgcaaatc | 360 |
| tctctttatt | ctgcggtatt cttcattatt gcggggatgg ggaaagtgtt tatatagaag | 420 |
| caacttacga | ttgaacccaa atgcacctga caagcaaggt caaagggcca gattttaaa | 480 |
| tatattattt | agtcttagga ctctctattt gcaattaaat tactttgcta cctgagggtt | 540 |
| aaatcttccc | cattgataat aataattcca ctatatgttc aattgggttt caccgcgctt | 600 |
| agttacatga | cgagccctaa tgagccgtcg gtggtctata aactgtgcct tacaaatact | 660 |
| tgcaactctt | ctcgttttga agtcagcaga gttattgcta attgctaatt gctaattgct | 720 |
| tttaactgat | ttcttcgaaa ttggtgctat gtttatggcg ctattaacaa gtatgaatgt | 780 |
| caggtttaac | caggggatgc ttaattgtgt tctcaacttc aaaggcagaa atgtttactc | 840 |
| ttgaccatgg | gtttaggtat aatgttatca agctcctcga gttaacgtta cgttaacgtt | 900 |
| aacgttcgag | gtcgactcta gaactaccca ccgtactcgt caattccaag gcatcggta | 960 |
| aacatctgct | caaactcgaa gtcggccata tccagagcgc cgtagggggc ggagtcgtgg | 1020 |
| ggggtaaatc | ccggacccgg ggaatcccg tcccccaaca tgtccagatc gaaatcgtct | 1080 |
| agcgcgtcgg | catgcgccat cgccacgtcc tcgccgtcta agtggagctc gtcccccagg | 1140 |
| ctgacatcgg | tcgggggggc cgtcgacagt ctgcgcgtgt gtcccgcggg gagaaaggac | 1200 |

```
aggcgcggag ccgccagccc cgcctcttcg ggggcgtcgt cgtccgggag atcgagcagg    1260
ccctcgatgg tagacccgta attgtttttc gtacgcgcgc ggctgtacgc ggggcccgag    1320
cccgactcgc atttcagttg cttttccaat ccgcagataa tcagctccaa gccgaacagg    1380
aatgccggct cggctccttg atgatcgaac agctcgattg cctgacgcag cagtgggggc    1440
atcgaatcgg ttgttggggt ctcgcgctcc tcttttgcga cttgatgctc ttggtcctcc    1500
agcacgcagc ccagggtaaa gtgaccgacg gcgctcagag cgtagagagc attttccagg    1560
ctgaagcctt gctggcacag aacgcgagc tggttctcca gtgtctcgta ttgcttttcg     1620
gtcgggcgcg tgccgagatg gactttggca ccgtctcggt gggacagcag agcgcagcgg    1680
aacgacttgg cgttattgcg gaggaagtcc tgccaggact cgccttccaa cgggcaaaaa    1740
tgcgtgtggt ggcggtcgag catctcgatg ccagggcat ccagcagcgc ccgcttattc      1800
ttcacgtgcc agtagagggt gggctgctcc acgcccagct tctgcgccaa cttgcgggtc    1860
gtcagtccct caatgccaac ttcgttcaac agctccaacg cggagttgat gactttggac    1920
ttatccaggc ggctgaccta tagataccat agatgtatgg attagtatca tatacataca    1980
aaggctattt ttgggacata ttaatattaa caatttccgt gatagttttc accatttttg    2040
ttgaatgtta cgttgaaaat ttaaatttgt tttaaattaa ttttaccagt catgtgttct    2100
taaaagtttt tatgattgaa acggcataaa gtggttcaaa aatttatcaa gaaaggcttt    2160
ccttttttaa atcttatctt tttctcttaa aaatcactag tcaattcatt attaatttgt    2220
taacttgaat ttggaatgtc tatttacttt cagataaatt aaagcaagaa acttaatatt    2280 cgaaaaaat tgattctaaa tggaatttca cttgatcttc atgtatgcat atcaatttttt     2340 atttacattg tataataagt ttcgagttga ttgttgtaat ccacaggtgt cccagagaat    2400
taaattccaa attcccaag tttattgaat gttgattgta gtttcagttg ctttgttgct      2460
gcaacaatgg cttgttgatt gtagatattt tcccttttcct tggtttactt attacataga    2520
ctgaaaaaga ggtttacttt tttgatactt atgaaaaatt tctattagtg attactaacc    2580
aatcgctata tgtttactag aaaacaaata aactctttac attaacattc aataatgttt    2640
gctctgtaac cgacaattga aggcgttaca gcaacagtaa tataactagc ttcttaaccc    2700
tcatctatta accccatcgt ttaaaacact atgttaaatg gtctaacaaa tctagatact    2760
aatagatgtc ttattactta gcagccacag ctgcaacatc caagacaatt tttgaaactt    2820
cttattgagc tcttggcagc agaaatgttg gtattttca cagctttctg aaagaccggc     2880
accttcctcc ggttcccgtt tctgaattca agaggatttc cgaccccaa ttaatcccga     2940 aacaaataag gtatattcaa aatgatggaa aagtcatggc tgctgacctt attttattc     3000 ctattgatag aatattattc cccttttaaa tacactgtac taagaggtcc ggctataatt    3060
ttactcactt gtcgattatc ccatagaatg ttgattgtag ttggttgctt ttccaggtga    3120
gagttgatca agtcacaaaa gttagcgtgt gttgattgta gatttgaagg taaaataatt    3180
tttgcaccca ttcatcgggt aaaacgttct ccatagaata catttccatc gataattgat    3240
aacttatgaa tttcaaagaa aaaaatatgc ttttaaaatt accatggtgg ctagcgcaga    3300
ttgtttagct tgttcagctg cgcttgttta tttgcttagc tttcgcttag cgacgtgttc    3360
actttgcttg tttgaattga attgtcgctc cgtagacgaa gcgcctctat ttatactccg    3420
gcgctcgttt tcgagtttac cactcccat cagtgataga aaaagtgaa agtcgagttt      3480 accactccct atcagtgata gagaaaagtg aaagtcgagt ttaccactcc ctatcagtga    3540
tagagaaaag tgaaagtcga gtttaccact ccctatcagt gatagagaaa agtgaaagtc    3600
```

```
gagtttacca ctccctatca gtgatagaga aaagtgaaag tcgagtttac cactccctat    3660
cagtgataga gaaaagtgaa agtcgagttt accactccct atcagtgata gagaaaagtg    3720
aaagtcgaaa cctggcgcgc cccggccatc gagaaagaga gagagaagag aagagagaga    3780
acattcgaga aagagagaga gaagagaaga gagagaacat actccctatc agtgatagag    3840
aagtccctat cagtgataga gatgtcccta tcagtgatag agagttccct atcagtgata    3900
gagacgtccc tatcagtgat agagaagtcc ctatcagtga tagagagatc cctatcagtg    3960
atagagattt ccctatcagt gatagagagg tccctatcag tgatagagac ttccctatca    4020
gtgatagaga atccctatc agtgatagag acatccctat cagtgataga gaactcccta    4080
tcagtgatag agacctccct atcagtgata gagatcgatg cggccgcatg gtacccattg    4140
cttgtcattt attaatttgg atgatgtcat ttgttttaa aattgaactg gctttacgag    4200
tagaattcta cgcgtaaaac acaatcaagt atgagtcata atctgatgtc atgttttgta    4260
cacggctcat aaccgaactg gctttacgag tagaattcta cttgtaatgc acgatcagtg    4320
gatgatgtca tttgttttc aaatcgagat gatgtcatgt tttgcacacg gctcataaac    4380
tcgctttacg agtagaattc tacgtgtaac gcacgatcga ttgatgagtc atttgttttg    4440
caatatgata tcatacaata tgactcattt gttttcaaa accgaacttg atttacgggt    4500
agaattctac ttgtaaagca caatcaaaaa gatgatgtca tttgttttc aaaactgaac    4560 tcgctttacg agtagaattc tacgtgtaaa acacaatcaa gaaatgatgt catttgttat    4620
aaaaataaaa gctgatgtca tgttttgcac atggctcata actaaactcg ctttacgggt    4680
agaattctac gcgtaaaaca tgattgataa ttaaataatt catttgcaag ctatacgtta    4740
aatcaaacgg acgctcgagg ttgcacaaca ctattatcga tttgcagttc gggacataaa    4800
tgtttaaata tatcgatgtc tttgtgatgc gcgcgacatt tttgtaggtt attgataaaa    4860
tgaacggata cgttgcccga cattatcatt aaatccttgg cgtagaattt gtcgggtcca    4920
ttgtccgtgt gcgctagcat gcccgtaacg gacctcgtac ttttggcttc aaaggttttg    4980
cgcacagaca aaatgtgcca cacttgcagc tctgcatgtg tgcgcgttac cacaaatccc    5040
aacggcgcag tgtacttgtt gtatgcaaat aaatctcgat aaaggcgcgg cgcgcgaatg    5100
cagctgatca cgtacgctcc tcgtgttccg ttcaaggacg gtgttatcga cctcagatta    5160
atgtttatcg gccgactgtt ttcgtatccg ctcaccaaac gcgttttgc attaacattg    5220 tatgtcggcg gatgttctat atctaatttg aataaataaa cgataaccgc gttggtttta    5280
gagggcataa taaaagaaat attgttatcg tgttcgccat tagggcagta taaattgacg    5340
ttcatgttgg atattgtttc agttgcaagt tgacactggc ggcgacaagc aattctaatt    5400
ggggtaagtt ttcccgttct tttctgggtt cttcccttt gctcatcctt gctgcactac    5460
cttcaggtgc aagttgagat tcaggccacc atgggagatc ccaccccacc caagaagaag    5520
cgcaaaccgg tcgccaccat ggcctcctcc gagaacgtca tcaccgagtt catgcgcttc    5580
aaggtgcgca tggagggcac cgtgaacggc cacgagttcg agatcgaggg cgagggcgag    5640
ggccgcccct acgagggcca caacaccgtg aagctgaagg tgaccaaggg cggcccctg    5700 ccttcgcct gggacatcct gtcccccag ttccagtacg ctccaaggt gtacgtgaag    5760 caccccgccg acatccccga ctacaagaag ctgtccttcc ccgagggctt caagtgggag    5820
cgcgtgatga acttcgagga cggcggcgtg gcgaccgtga cccaggactc ctccctgcag    5880
gacggctgct tcatctacaa ggtgaagttc atcggcgtga acttcccctc cgacggcccc    5940
```

```
gtgatgcaga agaagaccat gggctgggag gcctccaccg agcgcctgta ccccgcgac      6000
ggcgtgctga agggcgagac ccacaaggcc ctgaagctga aggacggcgg ccactacctg      6060
gtggagttca agtccatcta catggccaag aagcccgtgc agctgcccgg ctactactac      6120
gtggacgcca agctggacat cacctcccac aacgaggact acaccatcgt ggagcagtac      6180
gagcgcaccg agggccgcca ccacctgttc ctgagatctc gacccaagaa aaagcggaag      6240
gtggaggacc cgtaagatcc accggatcta gataactgat cataatcagc cataccacat      6300
ttgtagaggt tttacttgct ttaaaaaacc tcccacacct cccctgaac ctgaaacata       6360
aaatgaatgc aattgttgtt gttaacttgt ttattgcagc ttataatggt tacaaataaa      6420
gcaatagcat cacaaatttc acaaataaag cattttttc actgcattct agttgtggtt       6480
tgtccaaact catcaatgta tcttaacgcg agttaattaa ggccgctcat ttaaatctgg      6540
ccggccgcaa ccattgtggg aaccgtgcga tcaaacaaac gcgagatacc ggaagtactg      6600
aaaaacagtc gctccaggcc agtgggaaca tcgatgtttt gttttgacgg accccttact      6660
ctcgtctcat ataaaccgaa gccagctaag atggtatact tattatcatc ttgtgatgag      6720
gatgcttcta tcaacgaaag taccggtaaa ccgcaaatgg ttatgtatta taatcaaact      6780
aaaggcggag tggacacgct agaccaaatg tgttctgtga tgacctgcag taggaagacg      6840
aataggtggc ctatggcatt attgtacgga atgataaaca ttgcctgcat aaattctttt      6900
attatataca gccataatgt cagtagcaag ggagaaaagg tccaaagtcg caaaaaattt      6960
atgagaaacc tttacatgag cctgacgtca tcgtttatgc gtaagcgttt agaagctcct      7020
actttgaaga gatatttgcg cgataatatc tctaatattt tgccaaatga agtgcctggt      7080
acatcagatg acagtactga agagccagta atgaaaaaac gtacttactg tacttactgc      7140
ccctctaaaa taaggcgaaa ggcaaatgca tcgtgcaaaa aatgcaaaaa agttatttgt      7200
cgagagcata atattgatat gtgccaaagt tgtttctgac tgactaataa gtataatttg      7260
tttctattat gtataagtta agctaattac ttatttata atacaacatg actgttttta     7320
aagtacaaaa taagtttatt tttgtaaaag agagaatgtt taaaagtttt gttactttat      7380
agaagaaatt tgagttttt gtttttttt aataaataaa taaacataaa taaattgttt       7440
gttgaattta ttattagtat gtaagtgtaa atataataaa acttaatatc tattcaaatt      7500
aataaataaa cctcgatata cagaccgata aaacacatgc gtcaatttta cgcatgatta     7560
tctttaacgt acgtcacaat atgattatct ttctagggtt aaataatagt ttctaatttt      7620
tttattattc agcctgctgt cgtgaatacc gtatatctca acgctgtctg tgagattgtc      7680
gtattctagc cttttagtt tttcgctcat cgacttgata ttgtccgaca cattttcgtc       7740
gatttgcgtt ttgatcaaag acttgagcag agacacgtta atcaactgtt caaattgatc      7800
catattaacg atatcaaccc gatgcgtata tggtgcgtaa aatatatttt ttaaccctct      7860
tatactttgc actctgcgtt aatacgcgtt cgtgtacaga cgtaatcatg ttttcttttt      7920
tggataaaac tcctactgag tttgacctca tattagaccc tcacaagttg caaaacgtgg      7980
cattttttac caatgaagaa tttaaagtta ttttaaaaaa tttcatcaca gatttaaaga      8040
agaaccaaaa attaaattat ttcaacagtt taatcgacca gttaatcaac gtgtacacag      8100
acgcgtcggc aaaaaacacg cagcccgacg tgttggctaa aattattaaa tcaacttgtg      8160
ttatagtcac ggatttgccg tccaacgtgt tcctcaaaaa gttgaagacc aacaagttta      8220
cggacactat taattatttg attttgcccc acttcatttt gtgggatcac aattttgtta      8280
tattttaaac aaagcttggc actggccgtc gttttacaac gtcgtgactg ggaaaaccct      8340
```

```
ggcgttaccc aacttaatcg ccttgcagca catccccctt tcgccagctg gcgtaatagc   8400
gaagaggccc gcaccgatcg cccttcccaa cagttgcgca gcctgaatgg cgaatggcgc   8460
ctgatgcggt attttctcct tacgcatctg tgcggtattt cacaccgcat atggtgcact   8520
ctcagtacaa tctgctctga tgccgcatag ttaagccagc cccgacaccc gccaacaccc   8580
gctgacgcgc cctgacgggc ttgtctgctc ccggcatccg cttacagaca agctgtgacc   8640
gtctccggga gctgcatgtg tcagaggttt tcaccgtcat caccgaaacg cgcgagacga   8700
aagggcctcg tgatacgcct attttatag gttaatgtca tgataataat ggtttcttag   8760
acgtcaggtg gcacttttcg gggaaatgtg cgcggaaccc ctatttgttt attttttctaa  8820 atacattcaa atatgtatcc gctcatgaga caataaccct gataaatgct tcaataatat   8880
tgaaaaagga gagtatgag tattcaacat ttccgtgtcg cccttattcc ctttttgcg    8940 gcatttgcc ttcctgtttt tgctcaccca gaaacgctgg tgaaagtaaa agatgctgaa   9000
gatcagttgg gtgcacgagt gggttacatc gaactggatc tcaacagcgg taagatcctt   9060
gagagttttc gccccgaaga acgttttcca atgatgagca cttttaaagt tctgctatgt   9120
ggcgcggtat tatcccgtat tgacgccggg caagagcaac tcggtcgccg catacactat   9180
tctcagaatg acttggttga gtactcacca gtcacagaaa agcatcttac ggatggcatg   9240
acagtaagag aattatgcag tgctgccata accatgagtg ataacactgc ggccaactta   9300
cttctgacaa cgatcggagg accgaaggag ctaaccgctt ttttgcacaa catgggggat   9360
catgtaactc gccttgatcg ttgggaaccg gagctgaatg aagccatacc aaacgacgag   9420
cgtgacacca cgatgcctgt agcaatggca acaacgttgc gcaaactatt aactggcgaa   9480
ctacttactc tagcttcccg gcaacaatta atagactgga tggaggcgga taaagttgca   9540
ggaccacttc tgcgctcggc ccttccggct ggctggttta ttgctgataa atctggagcc   9600
ggtgagcgtg ggtctcgcgg tatcattgca gcactgggc cagatggtaa gccctcccgt    9660
atcgtagtta tctacacgac ggggagtcag gcaactatgg atgaacgaaa tagacagatc   9720
gctgagatag gtgcctcact gattaagcat tggtaactgt cagaccaagt ttactcatat   9780
atactttaga ttgatttaaa acttcatttt taatttaaaa ggatctaggt gaagatcctt   9840
tttgataatc tcatgaccaa aatcccttaa cgtgagtttt cgttccactg agcgtcagac   9900
cccgtagaaa agatcaaagg atcttcttga tccttttt ttctgcgcgt aatctgctgc    9960
ttgcaaacaa aaaaccacc gctaccagcg gtggtttgtt tgccggatca agagctacca  10020 actcttttc cgaaggtaac tggcttcagc agagcgcaga taccaaatac tgtccttcta  10080
gtgtagccgt agttaggcca ccacttcaag aactctgtag caccgcctac atacctcgct  10140
ctgctaatcc tgttaccagt ggctgctgcc agtggcgata gtcgtgtct taccgggttg   10200 gactcaagac gatagttacc ggataaggcg cagcggtcgg gctgaacggg gggttcgtgc  10260
acacagccca gcttggagcg aacgacctac accgaactga gatacctaca gcgtgagcat  10320
tgagaaagcg ccacgcttcc cgaagggaga aaggcggaca ggtatccggt aagcggcagg  10380
gtcggaacag gagagcgcac gagggagctt ccaggggaa acgcctggta tctttatagt   10440
cctgtcgggt ttcgccacct ctgacttgag cgtcgatttt tgtgatgctc gtcagggggg  10500
cggagcctat ggaaaaacgc cagcaacgcg gcctttttac ggttcctggc cttttgctgg  10560
ccttttgctc acatgttctt tcctgcgtta tcccctgatt ctgtggataa ccgtattacc  10620
gcctttgagt gagctgatac cgctcgccgc agccgaacga ccgagcgcag cgagtcagtg  10680
```

```
agcgaggaag cggaagagcg cccaatacgc aaaccgcctc tccccgcgcg ttggccgatt    10740
cattaatgca gctggcacga caggtttccc gactggaaag cgggcagtga gcgcaacgca    10800
attaatgtga gttagctcac tcattaggca ccccaggctt tacactttat gcttccggct    10860
cgtatgttgt gtggaattgt gagcggataa caatttcaca caggaaacag ctatgaccat    10920
gattacgaat tcgacctgca ggcatgcaa gcttgcatgc ctgcaggtcg acgctcgcgc     10980
gacttggttt gccattcttt agcgcgcgtc gcgtcacaca gcttggccac aatgtggttt    11040
ttgtcaaacg aagattctat gacgtgttta agtttaggt cgagtaaagc gcaaatcttt     11100
tttaacccta gaaagatagt ctgcgtaaaa ttgacgcatg cattcttgaa atattgctct    11160
ctctttctaa atagcgcgaa tccgtcgctg tgcatttagg acatctcagt cgccgcttgg    11220
agctcccgtg aggcgtgctt gtcaatgcgg taagtgtcac tgattttgaa ctataacgac    11280
cgcgtgagtc aaaatgacgc atgattatct tttacgtgac ttttaagatt taactcatac    11340
gataattata ttgttatttc atgttctact tacgtgataa cttattatat atatattttc    11400
ttgttataga tatcgtgact aatatataat aaaatgggta gttctttaga cgatgagcat    11460
atcctctctg ctcttctgca aagcgatgac gagcttgttg gtgaggattc tgacagtgaa    11520
atatcagatc acgtaagtga agatgacgtc cagagcgata cagaagaagc gtttatagat    11580
gaggtacatg aagtgcagcc aacgtcaagc ggtagtgaaa tattagacga acaaaatgtt    11640
attgaacaac caggttcttc attggcttct aacagaatct tgaccttgcc acagaggact    11700
attagaggta agaataaaca ttgttggtca acttcaaagt ccacgaggcg tagccgagtc    11760
tctgcactga acattgtcag atcggccc                                      11788
```

<210> SEQ ID NO 52
<211> LENGTH: 13292
<212> TYPE: DNA
<213> ORGANISM: Artificial Sequence
<220> FEATURE:
<223> OTHER INFORMATION: Synthetic construct, pLA3233-Cctra-intron-tTAV2
      construct.

<400> SEQUENCE: 52

```
gggcggccgt ttttcttgaa atattgctct ctctttctaa atagcgcgaa tccgtcgctg      60
tgcatttagg acatctcagt cgccgcttgg agctcccaaa cgcgccagtg gtagtacaca     120
gtactgtggg tgttcagttt gaaatcctct tgcttctcca ttgtctcggt tacctttggt     180
caaatccatg ggttctattg cctatatact cttgcgatta ccagtgattg cgctattagc     240
tattagatgg attgttggcc aaacttgtcg cttaagtggc tgggaattgt aaccgtaggc     300
ccgagtgtaa tgatccccca taaaaagttt tcgcaatgcc tttattttt gttgcaaatc      360 tctctttatt ctgcggtatt cttcattatt gcgggatgg ggaaagtgtt tatatagaag      420
caacttacga ttgaacccaa atgcacctga caagcaaggt caagggcca gattttaaa       480 tatattattt agtcttagga ctctctattt gcaattaaat tactttgcta cctgagggtt     540
aaatcttccc cattgataat aataattcca ctatatgttc aattgggttt caccgcgctt     600
agttacatga cgagccctaa tgagccgtcg gtggtctata aactgtgcct tacaaatact     660
tgcaactctt ctcgttttga agtcagcaga gttattgcta attgctaatt gctaattgct     720
tttaactgat ttcttcgaaa ttggtgctat gtttatggcg ctattaacaa gtatgaatgt     780
caggtttaac caggggatgc ttaattgtgt tctcaacttc aaaggcagaa atgtttactc     840
ttgaccatgg gtttaggtat aatgttatca agctcctcga gttaacgtta cgttaacgtt     900
```

```
aacgttcgag gtcgactcta gacaccggtg ttagccgccg tactcatcga tgcccagggc    960
gtcggtgaac atctgctcga actcgaaatc ggccatatcc agggcgccgt aggggggcgct  1020
atcgtgcggg gtgaatcccg gtcccgggct atcgccatcg cccagcatgt ccaggtcgaa   1080
gtcgtccagg gcatcggcgt gggccatcgc cacatcctcg ccatccaggt gcagctcatc   1140
gcccaggctc acgtcggtcg gcggggcggt cgacaggcgg cgggtgtgtc cggccggcag   1200
gaagctcagg cgcggggcgg ccaggcccgc ctcctccggg gcatcatcat ccggcagatc   1260
cagcaggccc tcgatggtgc tgccgtagtt gttcttggtg cgggcgcggc tgtaggcggg   1320
gcccgagccc gactcgcatt tcagttgctt ttccaatccg cagataatca gctccaagcc   1380
gaacaggaat gccggctcgg ctccttgatg atcgaacagc tcgattgcct gacgcagcag   1440
tgggggcatc gaatcggttg ttgggtctc gcgctcctct tttgcgactt gatgctcttg    1500
gtcctccagc acgcagccca gggtaaagtg accgacggcg ctcagagcgt agagagcatt   1560
ttccaggctg aagccttgct ggcacaggaa cgcgagctgg ttctccagtg tctcgtattg   1620
cttttcggtc gggcgcgtgc cgagatggac tttggcaccg tctcggtggg acagcagagc   1680
gcagcggaac gacttggcgt tattgcggag gaagtcctgc caggactcgc cttccaacgg   1740
gcaaaaatgc gtgtggtggc ggtcgagcat ctcgatggcc agggcatcca gcagcgcccg   1800
cttattcttc acgtgccagt agagggtggg ctgctccacg cccagcttct gcgccaactt   1860
gcgggtcgtc agtccctcaa tgccaacttc gttcaacagc tccaacgcgg agttgatgac   1920
tttggactta tccaggcggc tgacctatag ataccataga tgtatggatt agtatcatat   1980
acatacaaag gctatttttg ggacatatta atattaacaa tttccgtgat agttttcacc   2040
attttgttg aatgttacgt tgaaaattta aatttgtttt aaattaattt taccagtcat    2100
gtgttcttaa aagtttttat gattgaaacg gcataaagtg gttcaaaaat ttatcaagaa   2160
aggctttcct ttttaaaatc ttatctttt ctcttaaaaa tcactagtca attcattatt     2220
aatttgttaa cttgaatttg gaatgtctat ttactttcag ataaattaaa gcaagaaact   2280
taatattcga aaaaaattga ttctaaatgg aatttcactt gatcttcatg tatgcatatc   2340
aattttttatt tacattgtat aataagtttc gagttgattg ttgtaatcca caggtgtccc  2400
agagaattaa attccaaatt acccaagttt attgaatgtt gattgtagtt tcagttgctt   2460
tgttgctgca acaatggctt gttgattgta gatatttttcc ctttccttgg tttacttatt  2520
acatagactg aaaaagaggt ttactttttt gatacttatg aaaaatttct attagtgatt   2580
actaaccaat cgctatatgt ttactagaaa acaaataaac tctttacatt aacattcaat   2640
aatgtttgct ctgtaaccga caattgaagg cgttacagca acagtaatat aactagcttc   2700
ttaaccctca tctattaacc ccatcgttta aaacactatg ttaaatggtc taacaaatct   2760
agatactaat agatgtctta ttacttagca gccacagctg caacatccaa gacaattttt   2820
gaaacttctt attgagctct tggcagcaga aatgttggta tttttcacag ctttctgaaa   2880
gaccggcacc ttcctccggt tcccgtttct gaattcaaga ggatttccga cccccaatta   2940
atcccgaaac aaataaggta tattcaaaat gatggaaaag tcatggctgc tgaccttatt   3000
tttattccta ttgatagaat attattcccc ttttaaatac actgtactaa gaggtccggc   3060
tataatttta ctcacttgtc gattatccca tagaatgttg attgtagttg ttgcttttc    3120
caggtgagag ttgatcaagt cacaaaagtt agcgtgtgtt gattgtagat ttgaaggtaa   3180
aataattttt gcacccattc atcgggtaaa acgttctcca tagaatacat ttccatcgat   3240
aattgataac ttatgaattt caaagaaaaa aatatgcttt taaaattacc atggtggcta   3300
```

-continued

```
gcgcagattg tttagcttgt tcagctgcgc ttgtttattt gcttagcttt cgcttagcga    3360
cgtgttcact ttgcttgttt gaattgaatt gtcgctccgt agacgaagcg cctctattta    3420
tactccggcg ctcgttttcg agtttaccac tccctatcag tgatagagaa aagtgaaagt    3480
cgagtttacc actccctatc agtgatagag aaaagtgaaa gtcgagttta ccactcccta    3540
tcagtgatag agaaaagtga agtcgagtt taccactccc tatcagtgat agagaaaagt    3600
gaaagtcgag tttaccactc cctatcagtg atagagaaaa gtgaaagtcg agtttaccac    3660
tccctatcag tgatagagaa aagtgaaagt cgagtttacc actccctatc agtgatagag    3720
aaaagtgaaa gtcgaaacct ggcgcgcccc ggccatcgag aaagagagag agaagagaag    3780
agagagaaca ttcgagaaag agagagagaa gagaagagag agaacatact ccctatcagt    3840
gatagagaag tccctatcag tgatagagat gtccctatca gtgatagaga gttccctatc    3900
agtgatagag acgtccctat cagtgataga gaagtcccta tcagtgatag agagatccct    3960
atcagtgata gagatttccc tatcagtgat agagaggtcc ctatcagtga tagagacttc    4020
cctatcagtg atagagaaat ccctatcagt gatagagaca tccctatcag tgatagagaa    4080
ctccctatca gtgatagaga cctccctatc agtgatagag atcgatgcgg ccgcatggta    4140
cccattgctt gtcatttatt aatttggatg atgtcatttg tttttaaaat tgaactggct    4200
ttacgagtag aattctacgc gtaaaacaca atcaagtatg agtcataatc tgatgtcatg    4260
ttttgtacac ggctcataac cgaactggct ttacgagtag aattctactt gtaatgcacg    4320
atcagtggat gatgtcattt gtttttcaaa tcgagatgat gtcatgtttt gcacacggct    4380
cataaactcg ctttacgagt agaattctac gtgtaacgca cgatcgattg atgagtcatt    4440
tgttttgcaa tatgatatca tacaatatga ctcatttgtt tttcaaaacc gaacttgatt    4500
tacgggtaga attctacttg taaagcacaa tcaaaaagat gatgtcattt gtttttcaaa    4560
actgaactcg ctttacgagt agaattctac gtgtaaaaca caatcaagaa atgatgtcat    4620
ttgttataaa aataaaagct gatgtcatgt tttgcacatg gctcataact aaactcgctt    4680
tacgggtaga attctacgcg taaaacatga ttgataatta aataattcat ttgcaagcta    4740
tacgttaaat caaacggacg ctcgaggttg cacaacacta ttatcgattt gcagttcggg    4800
acataaatgt ttaaatatat cgatgtcttt gtgatgcgcg cgacattttt gtaggttatt    4860
gataaaatga acgatacgt tgcccgacat tatcattaaa tccttggcgt agaatttgtc    4920
gggtccattg tccgtgtgcg ctagcatgcc cgtaacggac ctcgtacttt tggcttcaaa    4980
ggttttgcgc acagacaaaa tgtgccacac ttgcagctct gcatgtgtgc gcgttaccac    5040
aaatcccaac ggcgcagtgt acttgttgta tgcaaataaa tctcgataaa ggcgcggcgc    5100
gcgaatgcag ctgatcacgt acgctcctcg tgttccgttc aaggacggtg ttatcgacct    5160
cagattaatg tttatcggcc gactgttttc gtatccgctc accaaacgcg ttttttgcatt    5220
aacattgtat gtcggcggat gttctatatc taatttgaat aaataaacga taaccgcgtt    5280
ggttttagag ggcataataa aagaaatatt gttatcgtgt tcgccattag ggcagtataa    5340
attgacgttc atgttggata ttgtttcagt tgcaagttga cactggcggc gacaagcaat    5400
tctaattggg gtaagttttc ccgttctttt ctgggttctt ccccttttgct catccttgct    5460
gcactacctt caggtgcaag ttgagattca ggccaccatg ggagatccca ccccacccaa    5520
gaagaagcga aaaccggtcg ccaccatgga cgaggatggt tcagggggcg ccccgcccct    5580
gttccagagc gacatgacct tcaaaatctt catcgacggc gaggtgaacg gccagaagtt    5640
```

```
caccatcgtg gccgacggca gcagcaagtt cccccacggc gacttcaacg tgcacgccgt    5700
gtgcgagacc ggcaagctgc ccatgagctg gaagcccatc tgccacctga tccagtacgg    5760
cgagcccttc ttcgcccgct accccaacgg catcagccac ttcgcccagg agtgcttccc    5820
cgagggcctg agcatcgacc gcaccgtgcg cttcgagaac gacggcacca tgaccagcca    5880
ccacacctac gagctggacg gcacctgcgt ggtcagccgc atcaccgtga actgcgacgg    5940
cttccagccc gacggcccca tcatgcgcga ccagctggtg gacatcctgc ccaacgagac    6000
ccacatgttc ccccacggcc ccaacgccgt gcgccagctg gccttcatcg gcttcaccac    6060
cgccgacggc ggcctgatga tgggccactt cgacagcaag atgaccttca acggcagccg    6120
cgccatcaag atccccggcc cccacttcgt gaccatcatc accaagcaga tgagggacac    6180
cagcgacaag cgcgaccacg tgtgccagcg cgaggtgacc tacgcccaca gcgtgccccg    6240
catcaccagc gccatcggta cgacgagga ttccggactc agatctcgac ccaagaaaaa    6300
gcggaaggtg gaggacccgt aagatccacc ggatctagat aactgatcat aatcagccat    6360
accacatttg tagaggtttt acttgcttta aaaaacctcc cacacctccc cctgaacctg    6420
aaacataaaa tgaatgcaat tgttgttgtt aacttgttta ttgcagctta taatggttac    6480
aaataaagca atagcatcac aaatttcaca ataaagcat tttttcact gcattctagt    6540 tgtggtttgt ccaaactcat caatgtatct taacgcgagt taattaacac gaaatcgta    6600 attcacggca tcattacaaa atattttgac gttttggacc tcgtccctaa tgacaccata    6660
acggtggcct tgaagtatat ttaaccctag aaagatagtc tgcgtaaaat tgacgcatgc    6720
attcttgaaa tattgctctc tctttctaaa tagcgcgaat ccgtcgctgt gcatttagga    6780
catctcagtc gccgcttgga gctcccgtga ggcgtgcttg tcaatgcggt aagtgtcact    6840
gattttgaac tataacgacc gcgtgagtca aaatgacgca tgattatctt ttacgtgact    6900
tttaagattt aactcatacg ataattatat tgttatttca tgttctactt acgtgataac    6960
ttattatata tatattttct tgttatagat atcgtgacta atatataata aaatgggtag    7020
ttctttagac gatgagcata tcctctctgc tcttctgcaa agcgatgacg agcttgttgg    7080
tgaggattct gacagtgaaa tatcagatca cgtaagtgaa gatgacgtcc aggaaatctg    7140
gccggccgca accattgtgg gaaccgtgcg atcaaacaaa cgcgagatac cggaagtact    7200
gaaaaacagt cgctccaggc cagtgggaac atcgatgttt tgttttgacg gaccccttac    7260
tctcgtctca tataaaccga agccagctaa gatggtatac ttattatcat cttgtgatga    7320
ggatgcttct atcaacgaaa gtaccggtaa accgcaaatg gttatgtatt ataatcaaac    7380
taaaggcgga gtggacacgc tagaccaaat gtgttctgtg atgacctgca gtaggaagac    7440
gaataggtgg cctatggcat tattgtacgg aatgataaac attgcctgca taaattcttt    7500
tattatatac agccataatg tcagtagcaa gggagaaaag gtccaaagtc gcaaaaaatt    7560
tatgagaaac ctttacatga gcctgacgtc atcgtttatg cgtaagcgtt tagaagctcc    7620
tactttgaag agatatttgc gcgataatat ctctaatatt ttgccaaatg aagtgcctgg    7680
tacatcagat gacagtactg aagagccagt aatgaaaaaa cgtacttact gtacttactg    7740
cccctctaaa ataaggcgaa aggcaaatgc atcgtgcaaa aaatgcaaaa aagttatttg    7800
tcgagagcat aatattgata tgtgccaaag ttgtttctga ctgactaata agtataattt    7860
gtttctatta tgtataagtt aagctaatta cttattttat aatacaacat gactgttttt    7920
aaagtacaaa ataagtttat ttttgtaaaa gagagaatgt ttaaaagttt gttactttta    7980
tagaagaaat tttgagtttt tgtttttttt taataaataa ataaacataa ataaattgtt    8040
```

```
tgttgaattt attattagta tgtaagtgta aatataataa aacttaatat ctattcaaat    8100
taataaataa acctcgatat acagaccgat aaaacacatg cgtcaatttt acgcatgatt    8160
atctttaacg tacgtcacaa tatgattatc tttctagggt taaataatag tttctaattt    8220
ttttattatt cagcctgctg tcgtaatac cgtatatctc aacgctgtct gtgagattgt     8280
cgtattctag ccttttagt ttttcgctca tcgacttgat attgtccgac acattttcgt     8340
cgatttgcgt tttgatcaaa gacttgagca gagacacgtt aatcaactgt tcaaattgat    8400
ccatattaac gatatcaacc cgatgcgtat atggtgcgta aaatatattt tttaaccctc    8460
ttatactttg cactctgcgt taatacgcgt tcgtgtacag acgtaatcat gttttctttt    8520
ttggataaaa ctcctactga gtttgacctc atattagacc ctcacaagtt gcaaaacgtg    8580
gcattttta ccaatgaaga atttaaagtt attttaaaaa atttcatcac agatttaaag     8640
aagaaccaaa aattaaatta tttcaacagt ttaatcgacc agttaatcaa cgtgtacaca    8700
gacgcgtcgg caaaaaacac gcagcccgac gtgttggcta aaattattaa atcaacttgt    8760
gttatagtca cggatttgcc gtccaacgtg ttcctcaaaa agttgaagac caacaagttt    8820
acggacacta ttaattattt gattttgccc cacttcattt tgtgggatca caattttgtt    8880
atattttaaa caaagcttgg cactggccgt cgttttacaa cgtcgtgact gggaaaaccc    8940
tggcgttacc caacttaatc gccttgcagc acatccccct ttcgccagct ggcgtaatag    9000
cgaagaggcc cgcaccgatc gcccttccca acagttgcgc agcctgaatg gcgaatggcg    9060
cctgatgcgg tattttctcc ttacgcatct gtgcggtatt tcacaccgca tatggtgcac    9120
tctcagtaca atctgctctg atgccgcata gttaagccag ccccgacacc cgccaacacc    9180
cgctgacgcg ccctgacggg cttgtctgct cccggcatcc gcttacagac aagctgtgac    9240
cgtctccggg agctgcatgt gtcagaggtt ttcaccgtca tcaccgaaac gcgcgagacg    9300
aaagggcctc gtgatacgcc tatttttata ggttaatgtc atgataataa tggtttctta    9360
gacgtcaggt ggcacttttc ggggaaatgt gcgcggaacc cctatttgtt tatttttcta    9420
aatacattca aatatgtatc cgctcatgag acaataaccc tgataaatgc ttcaataata    9480
ttgaaaaagg aagagtatga gtattcaaca tttccgtgtc gcccttattc ccttttttgc    9540
ggcattttgc cttcctgttt ttgctcaccc agaaacgctg gtgaaagtaa aagatgctga    9600
agatcagttg ggtgcacgag tgggttacat cgaactggat ctcaacagcg gtaagatcct    9660
tgagagtttt cgccccgaag aacgttttcc aatgatgagc acttttaaag ttctgctatg    9720
tggcgcggta ttatcccgta ttgacgccgg gcaagagcaa ctcggtcgcc gcatacacta    9780
ttctcagaat gacttggttg agtactcacc agtcacagaa aagcatctta cggatggcat    9840
gacagtaaga gaattatgca gtgctgccat aaccatgagt gataacactg cggccaactt    9900
acttctgaca acgatcggag gaccgaagga gctaaccgct tttttgcaca acatggggga    9960
tcatgtaact cgccttgatc gttgggaacc ggagctgaat gaagccatac caaacgacga   10020
gcgtgacacc acgatgcctg tagcaatggc aacaacgttg cgcaaactat taactggcga   10080
actacttact ctagcttccc ggcaacaatt aatagactgg atggaggcgg ataaagttgc   10140
aggaccactt ctgcgctcgg cccttccggc tggctggttt attgctgata aatctggagc   10200
cggtgagcgt gggtctcgcg gtatcattgc agcactgggg ccagatggta agccctcccg   10260
tatcgtagtt atctacacga cggggagtca ggcaactatg gatgaacgaa atagacagat   10320
cgctgagata ggtgcctcac tgattaagca ttggtaactg tcagaccaag tttactcata   10380
```

```
tatactttag attgatttaa aacttcattt ttaatttaaa aggatctagg tgaagatcct    10440
ttttgataat ctcatgacca aaatcccctta acgtgagttt tcgttccact gagcgtcaga   10500
ccccgtagaa aagatcaaag gatcttcttg agatccttttt tttctgcgcg taatctgctg   10560
cttgcaaaca aaaaaaccac cgctaccagc ggtggtttgt ttgccggatc aagagctacc    10620
aactcttttt ccgaaggtaa ctggcttcag cagagcgcag ataccaaata ctgtccttct    10680
agtgtagccg tagttaggcc accacttcaa gaactctgta gcaccgccta catacctcgc    10740
tctgctaatc ctgttaccag tggctgctgc cagtggcgat aagtcgtgtc ttaccgggtt    10800
ggactcaaga cgatagttac cggataaggc gcagcggtcg ggctgaacgg ggggttcgtg    10860
cacacagccc agcttggagc gaacgaccta caccgaactg agatacctac agcgtgagca    10920
ttgagaaagc gccacgcttc ccgaagggag aaaggcggac aggtatccgg taagcggcag    10980
ggtcggaaca ggagagcgca cgagggagct tccaggggga aacgcctggt atctttatag    11040
tcctgtcggg tttcgccacc tctgacttga gcgtcgattt ttgtgatgct cgtcaggggg    11100
gcggagccta tggaaaaacg ccagcaacgc ggcctttttta cggttcctgg ccttttgctg    11160
gccttttgct cacatgttct ttcctgcgtt atcccctgat tctgtggata accgtattac    11220
cgcctttgag tgagctgata ccgctcgccg cagccgaacg accgagcgca gcgagtcagt    11280
gagcgaggaa gcggaagagc gcccaatacg caaaccgcct ctccccgcgc gttggccgat    11340
tcattaatgc agctggcacg acaggttttcc cgactgaaaa cgggcagtg agcgcaacgc     11400
aattaatgtg agttagctca ctcattaggc accccaggct ttacacttta tgcttccggc    11460
tcgtatgttg tgtggaattg tgagcggata acaatttcac acaggaaaca gctatgacca    11520
tgattacgaa tttcgacctg caggcatgca agcttgcatg cctgcaggtc gacgctcgcg    11580
cgacttggtt tgccattctt tagcgcgcgt cgcgtcacac agcttggcca caatgtggtt    11640
tttgtcaaac gaagattcta tgacgtgttt aaagtttagg tcgagtaaag cgcaaatctt    11700
ttttaaccct agaaagatag tctgcgtaaa attgacgcat gcattcttga aatattgctc    11760
tctcttttcta aatagcgcga atccgtcgct gtgcatttag gacatctcag tcgccgcttg    11820
gagctcccgt gaggcgtgct tgtcaatgcg gtaagtgtca ctgattttga actataacga    11880
ccgcgtgagt caaaatgacg catgattatc tttttacgtga cttttaagat ttaactcata    11940
cgataattat attgttattt catgttctac ttacgtgata acttattata tatatatttt    12000
cttgttatag atatcgtgac taatatataa taaaatgggt agttctttag acgatgagca    12060
tatcctctct gctcttctgc aaagcgatga cgagcttgtt ggtgaggatt ctgacagtga    12120
aatatcagat cacgtaagtg aagatgacgt ccagagcgat acagaagaag cgtttataga    12180
tgaggtacat gaagtgcagc caacgtcaag cggtagtgaa atattagacg aacaaaatgt    12240
tattgaacaa ccaggttctt cattggcttc taacagaatc ttgaccttgc cacagaggac    12300
tattagaggt aagaataaac attgttggtc aacttcaaag tccacgaggc gtagccgagt    12360
ctctgcactg aacattgtca gatcggcccg gcggagtgga cacgctagac caaatgtgtt    12420
ctgtgatgac ctgcagtagg aagacgaata ggtggcctat ggcattattg tacggaatga    12480
taaacattgc ctgcataaat tcttttatta tatacagcca taatgtcagt agcaagggag    12540
aaaaggtcca aagtcgcaaa aaatttatga gaaacctttta catgagcctg acgtcatcgt    12600
ttatgcgtaa gcgtttagaa gctcctactt tgaagagata tttgcgcgat aatatctcta    12660
atattttgcc aaatgaagtg cctggtacat cagatgacag tactgaagag ccagtaatga    12720
aaaaacgtac ttactgtact tactgccccct ctaaaataag gcgaaaggca aatgcatcgt    12780
```

```
gcaaaaaatg caaaaaagtt atttgtcgag agcataatat tgatatgtgc caaagttgtt    12840
tctgactgac taataagtat aatttgtttc tattatgtat aagttaagct aattacttat    12900
tttataatac aacatgactg tttttaaagt acaaaataag tttattttg taaagagag     12960 aatgtttaaa agttttgtta ctttatagaa gaaattttga gtttttgttt ttttttaata    13020
aataaataaa cataaataaa ttgtttgttg aatttattat tagtatgtaa gtgtaaatat    13080
aataaaactt aatatctatt caaattaata ataaacctc gatatacaga ccgataaaac     13140
acatgcgtca attttacgca tgattatctt taacgtacgt cacaatatga ttatctttct    13200
agggttaaaa tgaatgtaag cactttatta acgaaatctt tgggaatatt tcgctcatca    13260
gcattttatt tgagcaggag tccgagatgc cc                                  13292
```

<210> SEQ ID NO 53
<211> LENGTH: 14713
<212> TYPE: DNA
<213> ORGANISM: Artificial Sequence
<220> FEATURE:
<223> OTHER INFORMATION: Synthetic construct, pLA3014-Cctra-intron-Ubiquitin-reaperKR construct.

<400> SEQUENCE: 53

```
cgcgccggac gcggcaagtc tgcgagctta tatttacgtg gatctccggt gtgtccatga      60
ttcggcatca tatcataaac gacgaattcc aataaaaact tgcttgttg ataacacctg      120 atgttcagag atgcccgata aaatcacagc tgttctggtt cacagtcacc agaaataaaa      180
aatattggaa ttgagatgta cacaattaac gatatttata aatatcttcc gatagtctat      240
cgtccggtta atcaaaataa agtgcgacga attaacatat tttcaaaatt aagacgcttt      300
gatagatgta tttgtataga gatagaaatt aaggttaaaa taacataaat gccaaagttt      360
agagcactat tcaataattc tcttgatttc aaattgaaat aatacacaat ataacatttt      420
ctaacactac aaagtcacga tattcttcca ccaaccgata gtatcgcaca cttgccattc      480
gcctcatcac gcacacgccc gcttcacaat tcaaacgaac ggcattttat tttcacagga      540
tcccgggagt cgtgaatgtt ttacccaata tcgactttca ttgttaactg accaaaattg      600
taatctgttc tgttagttgt cgagtgcctg tgccgcgatc gctatgggca tatgttgcca      660
aactctaaac caaatactca ttctgatgtt ttaaatgatt tgccctccca tatgtccttc      720
cgagtgagag acacaaaaaa ttccaacaca ctattgcaat gaaaataaat tcctttatt       780 agccagaagt cagatgctca aggggcttca tgatgtcccc ataatttttg gcagagggaa      840
aaagatctca gtggtatttg tgagccaggg cattggccac accagccacc accttctgat      900
aggcagcctg cacctgagga gtgaattctt tgccaaaatg atgagacagc acaacaacca      960
gcacgttgcc caggagctgt aggaaagaga agaaggcatg aacatggtta gcagaggggc     1020
ccggtttgga ctcagagtat tttatcctca tctcaaacag tgtatatcat tgtaaccata     1080
aagagaaagg caggatgatg accagggtgt agttgtttct accaataaga atatttccac     1140
gccagccaga atttatatgc agaaatattc taccttatca tttaattata acaattgttc     1200
tctaaaactg tgctgaagta caatataata taccctgatt gccttgaaaa aaagtgatt     1260 agagaaagta cttacaatct gacaaataaa caaagtgaa tttaaaaatt cgttacaaat      1320
gcaagctaaa gtttaacgaa aaagttacag aaaatgaaaa gaaataaga ggagacaatg      1380 gttgtcaaca gagtagaaag tgaaagaaac aaaattatca tgagggtcca tggtgataca     1440
agggacatct tcccattcta aacaacaccc tgaaaacttt gccccctcca tataacatga     1500
```

```
attttacaat agcgaaaaag aaagaacaat caagggtccc caaactcacc ctgaagttct    1560
cagctctaga cgcgtttcac tacccaccgt actcgtcaat tccaagggca tcggtaaaca    1620
tctgctcaaa ctcgaagtcg gccatatcca gagcgccgta gggggcggag tcgtgggggg    1680
taaatcccgg acccggggaa tccccgtccc caacatgtc cagatcgaaa tcgtctagcg     1740
cgtcggcatg cgccatcgcc acgtcctcgc cgtctaagtg gagctcgtcc cccaggctga    1800
catcggtcgg gggggccgtc gacagtctgc gcgtgtgtcc cgcggggaga aaggacaggc    1860
gcggagccgc cagccccgcc tcttcggggg cgtcgtcgtc cgggagatcg agcaggccct    1920
cgatggtaga cccgtaattg ttttcgtac gcgcgcggct gtacgcggac ccactttcac     1980
atttaagttg ttttctaat ccgcatatga tcaattcaag gccgaataag aaggctggct     2040
ctgcaccttg gtgatcaaat aattcgatag cttgtcgtaa taatggcggc atactatcag    2100
tagtaggtgt ttccctttct tctttagcga cttgatgctc ttgatcttcc aatacgcaac    2160
ctaaagtaaa atgccccaca gcgctgagtg catataatgc attctctagt gaaaaacctt    2220
gttggcataa aaaggctaat tgattttcga gagtttcata ctgttttct gtaggccgtg     2280 tacctaaatg tacttttgct ccatcgcgat gacttagtaa agcacatcta aaacttttag    2340
cgttattacg taaaaaatct tgccagcttt cccttctaa agggcaaaag tgagtatggt     2400
gcctatctaa catctcaatg gctaaggcgt cgagcaaagc ccgcttattt tttacatgcc    2460
aatacaatgt aggctgctct acacctagct tctgggcgag tttacgggtt gttaaacctt    2520
cgattccgac ctcattaagc agctctaatg cgctgttaat cactttactt ttatctaatc    2580
tcaattccat ggtggcaacc tgcaaggcga atgaataaac aagattgtgg cgaacagtgt    2640
aatgcgaaga acccacctct gctccaattc ccaattccct attcagctcg agcggggatc    2700
cccgggtacc gagctcgaat tcggggccgc ggaggctgga tcggtcccgg tgtcttctat    2760
ggaggtcaaa acagcgtgga tggcgtctcc aggcgatctg acggttcact aaacgagctc    2820
tgcttatata ggcctcccac cgtacacgcc tacctcgacc cgggtaccga gctcgacttt    2880 cactttctc tatcactgat agggagtggt aaactcgact ttcactttc tctatcactg      2940 ataggagtg gtaaactcga cttcacttt tctctatcac tgatagggag tggtaaactc      3000
gactttcact tttctctatc actgataggg agtggtaaac tcgactttca cttttctcta    3060
tcactgatag ggagtggtaa actcgacttt cacttttctc tatcactgat agggagtggt    3120
aaactcgact ttcacttttc tctatcactg atagggagtg gtaaactcga atgtcgact     3180 atgcggaccg agcgccggag tataaataga ggcgcttcgt ctacgagcg acaattcaat     3240 tcaaacaagc aaagtgaaca cgtcgctaag cgaaagctaa gcaaataaac aagcgcagct    3300
gaacaagcta acaatctgc gctagccacc atggttgtta ttaaacgtag atttggtaat    3360
tttaaaagca tatttttc tttgaaattc ataagttatc aattatcgat ggaaatgtat      3420
tctatggaga acgttttacc cgatgaatgg gtgcaaaaat tatttacct tcaaatctac     3480 aatcaacaca cgctaacttt tgtgacttga tcaactctca cctggaaaag caaccaacta    3540
caatcaacat tctatgggat aatcgacaag tgagtaaaat tatagccgga cctcttagta    3600
cagtgtattt aaaaggggaa taatattcta tcaataggaa taaaaataag gtcagcagcc    3660 atgactttc catcatttg aatatacctt atttgtttcg ggattaattg ggggtcggaa      3720
atcctcttga attcagaaac gggaaccgga ggaaggtgcc ggtctttcag aaagctgtga    3780
aaaataccaa catttctgct gccaagagct caataagaag tttcaaaaat tgtcttggat    3840
```

-continued

```
gttgcagctg tggctgctaa gtaataagac atctattagt atctagattt gttagaccat    3900
ttaacatagt gttttaaacg atggggttaa tagatgaggg ttaagaagct agttatatta    3960
ctgttgctgt aacgccttca attgtcggtt acagagcaaa cattattgaa tgttaatgta    4020
aagagtttat ttgttttcta gtaaacatat agcgattggt tagtaatcac taatagaaat    4080
ttttcataag tatcaaaaaa gtaaacctct ttttcagtct atgtaataag taaaccaagg    4140
aaagggaaaa tatctacaat caacaagcca ttgttgcagc aacaaagcaa ctgaaactac    4200
aatcaacatt caataaactt gggtaatttg gaatttaatt ctctgggaca cctgtggatt    4260
acaacaatca actcgaaact tattatacaa tgtaaataaa aattgatatg catacatgaa    4320
gatcaagtga aattccattt agaatcaatt tttttcgaat attaagtttc ttgctttaat    4380
ttatctgaaa gtaaatagac attccaaatt caagttaaca aattaataat gaattgacta    4440
gtgatttta agagaaaaag ataagattta aaaaggaaa gcctttcttg ataaattttt    4500
gaaccacttt atgccgtttc aatcataaaa acttttaaga acacatgact ggtaaaatta    4560
atttaaaaca aatttaaatt ttcaacgtaa cattcaacaa aaatggtgaa aactatcacg    4620
gaaattgtta atattaatat gtcccaaaaa tagcctttgt atgtatatga tactaatcca    4680
tacatctatg gtatctatag gtgaaggctc aaagcctctg atgcagatct ttgtgaagac    4740
tttgaccgga aagaccatca ccctcgaggt agagccatcg acaccattg agaatgtaaa    4800
ggccaagatt caggataagg agggaatccc cccagatcag cagcgtctga tcttcgctgg    4860
caagcaactg gaagacggac gcaccctgtc cgattacaac atccagaagg agtccaccct    4920
tcacttggtc cttcgtctcc gtggtggcgc cgtggccttc tacatcccgg atcaggccac    4980
cctgctgcgc gaggccgagc agcgcgagca gcagatcctg cgcctgcgcg agagccagtg    5040
gcgcttcctg gccaccgtgg tgctggagac cctgcgccag tacaccagct gccaccgcg    5100
caccggccgc cgcagcggcc gttaccgccg tccgagccag taacaccggt gatcataatc    5160
agccatacca catttgtaga ggttttactt gcttttaaaaa acctcccaca cctcccctg    5220
aacctgaaac ataaaatgaa tgcaattgtt gttgttaact tgtttattgc agcttataat    5280
ggttacaaat aaagcaatag catcacaaat ttcacaaata aagcattttt ttcactgcat    5340
tctagttgtg gtttgtccaa actcatcaat gtatcttaac gcgagtttaa acgcgtccgc    5400
atacgtccgc tcacgttaag ttccgcagag agaagttgtt gaaaacataa acagaatcac    5460
ttgttgcact cttttgagaaa actggggcta ttgcggaaaa aaccaactaa aaatattgca    5520
ggttaggggt actacgctcg attggcgtac ggccaccact tttgcgactt cactgttaac    5580
cgctaccttc atagagactt ttacccgata aatgttatgt agtttgactt tctctgttaa    5640
tcacaagaaa aaatattgtg gaaattaaaa ttatctcaaa ctcaataagg aaataataat    5700
atatacacct atgttttata gaagtcaaca gtaaataagt tatttggaaa accattgtag    5760
ccgtttaaat aaatctcctt gagtgtgttt taaataacgg tcattaagta tattacttgg    5820
ccctctgaat ttcttgaatt acaccatttt ttgaaataaa tcaatccaaa agactacttt    5880
ttggtggcaa atgaactgca taaaagtaa caaaagaaat atgttttga ataacagta    5940
tagctgaagt gtattaaaaa ataccgtcat atgagcgacc cgctgttacc gcttcgctgc    6000
gaatgacaaa acgggctgag caagaaaatg gcgtagaagg cgacgaaaat tcgtttcact    6060
cgtgaagaaa acctcgataa ctgaggaata cagctgggat ttaaagagca tattcgaact    6120
acaagcagag atgtttcctg gtggaaacgg aaacgccgat ttgggctaca acaagcatgc    6180
ccacgtccat ggacttggac aacatggcca tgggcacaac cataatcaca atcagttcct    6240
```

```
gcgcagcccc caccaccccc cacacatttt tcactgccct ccggggcgg tcagggcatg    6300 gtgacgccca tggtagccgc cggcctgccg ctcgccatgc agggtggcgt tggcatcgat    6360
tggcgcagct cgcccagcaa tggattaatt aactcgcgtt aagatacatt gatgagtttg    6420
gacaaaccac aactagaatg cagtgaaaaa aatgctttat ttgtgaaatt tgtgatgcta    6480
ttgctttatt tgtaaccatt ataagctgca ataaacaagt taacaacaac aattgcattc    6540
attttatgtt tcaggttcag ggggaggtgt gggaggtttt ttaaagcaag taaaacctct    6600
acaaatgtgg tatggctgat tatgatcagt tatctagatc cggtggatct tacgggtcct    6660
ccaccttccg cttttcttg ggtcgagatc tcaggaacag tggtggcgg ccctcggtgc    6720 gctcgtactg ctccacgatg gtgtagtcct cgttgtggga ggtgatgtcc agcttggcgt    6780
ccacgtagta gtagccgggc agctgcacgg gcttcttggc catgtagatg gacttgaact    6840
ccaccaggta gtggccgccg tccttcagct tcagggcctt gtgggtctcg cccttcagca    6900
cgccgtcgcg ggggtacagg cgctcggtgg aggcctccca gcccatggtc ttcttctgca    6960
tcacggggcc gtcggagggg aagttcacgc cgatgaactt caccttgtag atgaagcagc    7020
cgtcctgcag ggaggagtcc tgggtcacgg tcgccacgcc gccgtcctcg aagttcatca    7080
cgcgctccca cttgaagccc tcggggaagg acagcttctt gtagtcgggg atgtcggcgg    7140
ggtgcttcac gtacaccttg agccgtact ggaactgggg ggacaggatg tcccaggcga    7200
agggcagggg gccgcccttg gtcaccttca gcttcacggt gttgtggccc tcgtaggggc    7260
ggccctcgcc ctcgccctcg atctcgaact cgtggccgtt cacggtgccc tccatgcgca    7320
ccttgaagcg catgaactcg gtgatgacgt tctcggagga ggccatggtg gcgaccggtt    7380
tgcgcttctt cttgggtggg gtgggatccc cgatctgcat tttggattat tctgcgggtc    7440
aaaatagaga tgtggaaaat tagtacgaaa tcaaatgagt ttcgttgaaa ttacaaaact    7500
attgaaacta acttcctggc tggggaataa aatgggaaa cttatttatc gacgccaact    7560
ttgttgagaa accctatta accctctacg aatattggaa caaggaaag cgaagaaaca    7620 ggaacaaagg tagttgagaa acctgttccg ttgctcgtca tcgttttcat aatgcgagtg    7680
tgtgcatgta tatatacaca gctgaaacgc atgcatacac attattttgt gtgtatatgg    7740
tgacgtcaca actactaagc aataagaaat tttccagacg tggctttcgt ttcaagcaac    7800
ctactctatt tcagctaaaa ataagtggat ttcgttggta aaatacttca attaagcaaa    7860
gaactaacta actaataaca tgcacacaaa tgctcgagtg cgttcgtgat ttctcgaatt    7920
ttcaaatgcg tcactgcgaa tttcacaatt tgccaataaa tcttggcgaa aatcaacacg    7980
caagttttat ttatagattt gtttgcgttt tgatgccaat tgattgggaa acaagatgc    8040 gtggctgcca atttcttatt ttgtaattac gtagagcgtt gaataaaaaa aaaatggccg    8100
aacaaagacc ttgaaatgca gttttttcttg aaattactca acgtcttgtt gctcttatta    8160
ctaattggta acagcgagtt aaaaacttac gtttcttgtg actttcgaga atgttctttt    8220
aattgtactt taatcaccaa caattaagta taaattttc gctgattgcg ctttactttc    8280
tgcttgtact tgctgctgca aatgtcaatt ggttttgaag gcgaccgttc gcgaacgctg    8340
tttatatacc ttcggtgtcc gttgaaaatc actaaaaaat accgtagtgt tcgtaacact    8400
ttagtacaga gaaaaaaaat tgtgccgaaa tgttttgat acgtacgaat accttgtatt    8460 aaaattttt atgatttctg tgtatcactt ttttttgtg ttttcgtttt aaactcacca    8520
cagtacaaaa caataaaata tttttaagac aatttcaaat tgagaccttt ctcgtactga    8580
```

```
cttgaccggc tgaatgagga tttctaccta gacgacctac ttcttaccat gacattgaat   8640
gcaatgccac ctttgatcta aacttacaaa agtccaaggc ttgttaggat tggtgtttat   8700
ttagtttgct tttgaaatag cactgtcttc tctaccggct ataattttga aactcgcagc   8760
ttgactggaa atttaaaaag taattctgtg taggtaaagg gtgttttaaa agtgtgatgt   8820
gttgagcgtt gcggcaacga ctgctattta tgtatatatt ttcaaaactt attgttttg   8880 aagtgtttta aatggagcta tctggcaacg ctgcgcataa tcttacacaa gcttttctta   8940
atccattttt aagtgaaatt tgttttact ctttcggcaa ataattgtta aatcgcttta   9000
agtgggctta catctggata agtaatgaaa acctgcatat tataatatta aaacatataa   9060
tccactgtgc tttcccgtg tgtggccata tacctaaaaa agtttatttt cgcagagccc   9120
cgcacggtca cactacggtt cggcgatttt cgattttgga cagtactgat tgcaagcgca   9180
ccgaaagcaa aatggagctg gagattttga acgcgaagaa cagcaagccg tacggcaagg   9240
tgaaggtgcc ctccggcgcc acgcccatcg gcgatctgcg cgccctaatt cacaagaccc   9300
tgaagcagac cccacacgcg aatcgccagt cgcttcgtct ggaactgaag ggcaaaagcc   9360
tgaaagatac ggacacattg gaatctctgt cgctgcgttc cggcgacaag atcggggtac   9420
catgcggccg ctcatttaaa tctggccggc ctggccgatc tgacaatgtt cagtgcagag   9480
actcggctac gcctcgtgga cttgaagtt gaccaacaat gtttattctt acctctaata   9540
gtcctctgtg gcaaggtcaa gattctgtta aagccaatg aagaacctgg ttgtcaata   9600 acatttgtt cgtctaatat ttcactaccg cttgacgttg gctgcacttc atgtacctca   9660
tctataaacg cttcttctgt atcgctctgg acgtcatctt cacttacgtg atctgatatt   9720
tcactgtcag aatcctcacc aacaagctcg tcatcgcttt gcagaagagc agagaggata   9780
tgctcatcgt ctaaagaact acccatttta ttatatatta gtcacgatat ctataacaag   9840
aaaatatata tataatagt tatcacgtaa gtagaacatg aaataacaat ataattatcg   9900
tatgagttaa atcttaaaag tcacgtaaaa gataatcatg cgtcattttg actcacgcgg   9960
tcgttatagt tcaaaatcag tgacacttac cgcattgaca agcacgcctc acgggagctc   10020
caagcggcga ctgagatgtc ctaaatgcac agcgacggat tcgcgctatt tagaaagaga   10080
gagcaatatt tcaagaatgc atgcgtcaat tttacgcaga ctatctttct agggttaaaa   10140
aagatttgcg ctttactcga cctaaacttt aaacacgtca tagaatcttc gtttgacaaa   10200
aaccacattg tggccaagct gtgtgacgcg acgcgcgcta aagaatggca aaccaagtcg   10260
cgcgagcgtc gacctgcagg catgcaagct tgcatgcctg caggtcgaaa ttcgtaatca   10320
tggtcatagc tgtttcctgt gtgaaattgt tatccgctca caattccaca aacatacga   10380 gccgaagcta taagtgtaa agcctggggt gcctaatgag tgagctaact cacattaatt   10440
gcgttgcgct cactgcccgc tttccagtcg ggaaacctgt cgtgccagct gcattaatga   10500
atcggccaac gcgcggggag aggcggtttg cgtattgggc gctcttccgc ttcctcgctc   10560
actgactcgc tgcgctcggt cgttcggctg cggcgagcgg tatcagctca ctcaaaggcg   10620
gtaatacggt tatccacaga atcaggggat aacgcaggaa agaacatgtg agcaaaaggc   10680
cagcaaaagg ccaggaaccg taaaaaggcc gcgttgctgg cgtttttcca taggctccgc   10740
ccccctgacg agcatcacaa aaatcgacgc tcaagtcaga ggtggcgaaa cccgacagga   10800
ctataaagat accaggcgtt tccccctgga agctccctcg tgcgctctcc tgttccgacc   10860
ctgccgctta ccggatacct gtccgccttt ctcccttcgg gaagcgtggc gctttctcaa   10920
tgctcacgct gtaggtatct cagttcggtg taggtcgttc gctccaagct gggctgtgtg   10980
```

```
cacgaacccc ccgttcagcc cgaccgctgc gccttatccg gtaactatcg tcttgagtcc   11040
aacccggtaa gacacgactt atcgccactg gcagcagcca ctggtaacag gattagcaga   11100
gcgaggtatg taggcggtgc tacagagttc ttgaagtggt ggcctaacta cggctacact   11160
agaaggacag tatttggtat ctgcgctctg ctgaagccag ttaccttcgg aaaaagagtt   11220
ggtagctctt gatccggcaa acaaaccacc gctggtagcg gtggttttt tgtttgcaag   11280 cagcagatta cgcgcagaaa aaaggatct caagaagatc ctttgatctt ttctacgggg   11340
tctgacgctc agtggaacga aaactcacgt taagggattt tggtcatgag attatcaaaa   11400
aggatcttca cctagatcct tttaaattaa aaatgaagtt ttaaatcaat ctaaagtata   11460
tatgagtaaa cttggtctga cagttaccaa tgcttaatca gtgaggcacc tatctcagcg   11520
atctgtctat ttcgttcatc catagttgcc tgactcccg tcgtgtagat aactacgata   11580
cgggagggct taccatctgg ccccagtgct gcaatgatac cgcgagaccc acgctcaccg   11640
gctccagatt tatcagcaat aaaccagcca gccggaaggg ccgagcgcag aagtggtcct   11700
gcaactttat ccgcctccat ccagtctatt aattgttgcc gggaagctag agtaagtagt   11760
tcgccagtta atagttttgcg caacgttgtt gccattgcta caggcatcgt ggtgtcacgc   11820
tcgtcgtttg gtatggcttc attcagctcc ggttcccaac gatcaaggcg agttacatga   11880
tcccccatgt tgtgcaaaaa agcggttagc tccttcggtc ctccgatcgt tgtcagaagt   11940
aagttggccg cagtgttatc actcatggtt atggcagcac tgcataattc tcttactgtc   12000
atgccatccg taagatgctt ttctgtgact ggtgagtact caaccaagtc attctgagaa   12060
tagtgtatgc ggcgaccgag ttgctcttgc ccggcgtcaa tacgggataa taccgcgcca   12120
catagcagaa ctttaaaagt gctcatcatt ggaaaacgtt cttcggggcg aaaactctca   12180
aggatcttac cgctgttgag atccagttcg atgtaaccca ctcgtgcacc caactgatct   12240
tcagcatctt ttactttcac cagcgtttct gggtgagcaa aaacaggaag gcaaaatgcc   12300
gcaaaaaagg gaataagggc gacacggaaa tgttgaatac tcatactctt cctttttcaa   12360
tattattgaa gcatttatca gggttattgt ctcatgagcg gatacatatt tgaatgtatt   12420
tagaaaaata aacaaatagg ggttccgcgc acatttcccc gaaaagtgcc acctgacgtc   12480
taagaaacca ttattatcat gacattaacc tataaaaata ggcgtatcac gaggccctt   12540 cgtctcgcgc gtttcggtga tgacggtgaa aacctctgac acatgcagct cccggagacg   12600
gtcacagctt gtctgtaagc ggatgccggg agcagacaag cccgtcaggg cgcgtcagcg   12660
ggtgttggcg ggtgtcgggg ctggcttaac tatgcggcat cagagcagat tgtactgaga   12720
gtgcaccata tatgcggtgt gaaataccgc acagatgcgt aaggagaaaa taccgcatca   12780
ggcgccattc gccattcagg ctgcgcaact gttgggaagg gcgatcggtg cgggcctctt   12840
cgctattacg ccagctggcg aaagggggat gtgctgcaag gcgattaagt tgggtaacgc   12900
cagggttttc ccagtcacga cgttgtaaaa cgacggccag tgccaagctt tgttaaaat   12960 ataacaaaat tgtgatccca caaaatgaag tggggcaaaa tcaaataatt aatagtgtcc   13020
gtaaacttgt tggtcttcaa cttttgagg aacacgttgg acggcaaatc cgtgactata   13080
acacaagtta atttaataat tttagccaac acgtcgggct gcgtgttttt tgccgacgcg   13140
tctgtgtaca cgttgattaa ctggtcgatt aaactgttga ataatttaa ttttggttc   13200 ttctttaaat ctgtgatgaa attttttaaa ataactttaa attcttcatt ggtaaaaat   13260 gccacgtttt gcaacttgtg agggtctaat atgaggtcaa actcagtagg agttttatcc   13320
```

| | | | | |
|---|---|---|---|---|
| aaaaaagaaa | acatgattac | gtctgtacac | gaacgcgtat taacgcagag tgcaaagtat | 13380 |
| aagagggtta | aaaaatatat | tttacgcacc | atatacgcat cggggttgata tcgttaatat | 13440 |
| ggatcaattt | gaacagttga | ttaacgtgtc | tctgctcaag tctttgatca aaacgcaaat | 13500 |
| cgacgaaaat | gtgtcggaca | atatcaagtc | gatgagcgaa aaactaaaaa ggctagaata | 13560 |
| cgacaatctc | acagacagcg | ttgagatata | cggtattcac gacagcaggc tgaataataa | 13620 |
| aaaaattaga | aactattatt | taaccctaga | aagataatca tattgtgacg tacgttaaag | 13680 |
| ataatcatgc | gtaaaattga | cgcatgtgtt | ttatcggtct gtatatcgag gtttatttat | 13740 |
| taatttgaat | agatattaag | ttttattata | tttacactta catactaata ataaattcaa | 13800 |
| caaacaattt | atttatgttt | atttatttat | taaaaaaaaa caaaaactca aaatttcttc | 13860 |
| tataaagtaa | caaaacttttt | aaacattctc | tcttttacaa aaataaactt attttgtact | 13920 |
| ttaaaaacag | tcatgttgta | ttataaaata | agtaattagc ttaacttata cataatagaa | 13980 |
| acaaattata | cttattagtc | agtcagaaac | aactttggca catatcaata ttatgctctc | 14040 |
| gacaaataac | tttttttgcat | tttttgcacg | atgcatttgc ctttcgcctt attttagagg | 14100 |
| ggcagtaagt | acagtaagta | cgttttttca | ttactggctc ttcagtactg tcatctgatg | 14160 |
| taccaggcac | ttcatttggc | aaaatattag | agatatatc gcgcaaatat ctcttcaaag | 14220 |
| taggagcttc | taaacgctta | cgcataaacg | atgacgtcag gctcatgtaa aggtttctca | 14280 |
| taaattttttt | gcgactttgg | accttttctc | ccttgctact gacattatgg ctgtatataa | 14340 |
| taaagaatt | tatgcaggca | atgtttatca | ttccgtacaa taatgccata ggccacctat | 14400 |
| tcgtcttcct | actgcaggtc | atcacagaac | acatttggtc tagcgtgtcc actccgcctt | 14460 |
| tagtttgatt | ataatacata | accatttgcg | gtttaccggt actttcgttg atagaagcat | 14520 |
| cctcatcaca | agatgataat | aagtatacca | tcttagctgg cttcggttta tatgagacga | 14580 |
| gagtaagggg | tccgtcaaaa | caaaacatcg | atgttcccac tggcctggag cgactgtttt | 14640 |
| tcagtacttc | cggtatctcg | cgtttgtttg | atcgcacggt tcccacaatg gttgcggcca | 14700 |
| gcccgggcta | tgg | | | 14713 |

<210> SEQ ID NO 54
<211> LENGTH: 15848
<212> TYPE: DNA
<213> ORGANISM: Artificial Sequence
<220> FEATURE:
<223> OTHER INFORMATION: Synthetic construct, pLA3166-Cctra intron-
      Ubiquitin-reaperKR construct.

<400> SEQUENCE: 54

| | | | |
|---|---|---|---|
| gggcggccgt ttttcttgaa atattgctct ctctttctaa atagcgcgaa tccgtcgctg | 60 |
| tgcatttagg acatctcagt cgccgcttgg agctcccaaa cgcgccagtg gtagtacaca | 120 |
| gtactgtggg tgttcagttt gaaatcctct tgcttctcca ttgtctcggt tacctttggt | 180 |
| caaatccatg ggttctattg cctatatact cttgcgatta ccagtgattg cgctattagc | 240 |
| tattagatgg attgttggcc aaacttgtcg cttaagtggc tgggaattgt aaccgtaggc | 300 |
| ccgagtgtaa tgatcccccca taaaagtttt tcgcaatgcc tttattttttt gttgcaaatc | 360 |
| tctctttatt ctgcggtatt cttcattatt gcggggatgg ggaaagtgtt tatatagaag | 420 |
| caacttacga ttgaacccaa atgcacctga caagcaaggt caagggcca gatttttaaa | 480 |
| tatattattt agtcttagga ctctctattt gcaattaaat tacttttgcta cctgagggtt | 540 |
| aaatcttccc cattgataat aataattcca ctatatgttc aattgggttt caccgcgctt | 600 |

```
agttacatga cgagccctaa tgagccgtcg gtggtctata aactgtgcct tacaaatact    660
tgcaactctt ctcgttttga agtcagcaga gttattgcta attgctaatt gctaattgct    720
tttaactgat ttcttcgaaa ttggtgctat gtttatggcg ctattaacaa gtatgaatgt    780
caggtttaac caggggatgc ttaattgtgt tctcaacttc aaaggcagaa atgtttactc    840
ttgaccatgg gtttaggtat aatgttatca agctcctcga gttaacgtta cgttaacgtt    900
aacgttcgag gtcgactcta gaactaccca ccgtactcgt caattccaag ggcatcggta    960
aacatctgct caaactcgaa gtcggccata tccagagcgc cgtaggggc ggagtcgtgg    1020 ggggtaaatc ccggacccgg ggaatccccg tcccccaaca tgtccagatc gaaatcgtct   1080
agcgcgtcgg catgcgccat cgccacgtcc tcgccgtcta agtggagctc gtcccccagg   1140
ctgacatcgg tcgggggggc cgtcgacagt ctgcgcgtgt gtcccgcggg gagaaaggac   1200
aggcgcggag ccgccagccc cgcctcttcg ggggcgtcgt cgtccgggag atcgagcagg   1260
ccctcgatgg tagacccgta attgtttttc gtacgcgcgc ggctgtacgc ggggcccgag   1320
cccgactcgc atttcagttg cttttccaat ccgcagataa tcagctccaa gccgaacagg   1380
aatgccggct cggctccttg atgatcgaac agctcgattg cctgacgcag cagtgggggc   1440
atcgaatcgg ttgttggggt ctcgcgctcc tcttttgcga cttgatgctc ttggtcctcc   1500
agcacgcagc ccagggtaaa gtgaccgacg gcgctcagag cgtagagagc attttccagg   1560
ctgaagcctt gctggcacag gaacgcgagc tggttctcca gtgtctcgta ttgctttcg    1620 gtcgggcgcg tgccgagatg actttggca ccgtctcggt gggacagcag agcgcagcgg    1680
aacgacttgg cgttattgcg gaggaagtcc tggaaatggg atagatattg gtgttattgt   1740
tcatgtggca tataaggac aagcaacaaa aaacgaacat aacatgagag atggttctga    1800
atcagaactt ctgaatatta tcctcccaaa agggttaaag tttttattaa gcatattacg   1860
ttttatacca cttccttatg taaaattttc ttcgtagttt aatatcatgt gaaatcatat    1920
ataatttcta tcgaacgttt gttcaaattg aatgatgtca ttttttgaat aattggttat    1980
aattttataa catctcccga cttcgacatg tggttggtac taatgattgc gaaatcgccc    2040
tccgagaatg agaacaaccg aggtccaccg tctggtcgag attaaaacac ttgaggagtg   2100
ctttggtgac tcgatcaata ggtacagggc tcgttgccaa caatctggcc agctggacat   2160 ccggacctc gttcccccct gggtatcaa aattttgta gtgtaaatag tagtacactc      2220 ttaaaataa tgaaaattac tgcggacgta attcacatta tgattgaatg acactatcat    2280
tgacatttcc cgaatcagac accatcgtat ttaaaatgtg acacaaattc acctcatttg   2340
gctcgcttct tttatgtgca tccaaaagac gtaaaatcgc atgattttt cggagtgtgt    2400 agtaagattg tcaaatttta atttaaata accagagccc ataaagcaaa gcaacactag    2460 gaaaaaccc acaaactcaa cctgtccaaa aaaaatata acaatcaaag ttgagggaat     2520
cggggtcaaa cgtcatgtaa aaatattttt tgtaaaaacc aaaccaggaa taaatatgaa   2580
tttaatcgga aaaattgca aaatcgcata atttaatcct ccaactgtac tttatccagc    2640
ctgttgcaga aatgatgttt aaaggttcta atctgtaatt gttattagcc ttcaatactg   2700
atgtagtatt tatttcttat tgaaacattg agagctttat tttccaaagt tgtcattttc   2760
tcattcgtat atcgtaatat gtatattcgt aaatggcaag cacaatgata cttagggtag   2820
tcaaggatat ttcaattacg aaaagatcct gaaacgaccg ggaatcgaac ccttcagcat   2880
ggttttgctt tgtagctgct gaatctaacc actaggctga tgaagatccc atttagggt    2940 tgcaagttct caaagagcaa gaatgccaaa atagtgtcaa aagaagccct atttgacgat   3000
```

```
ataccttta  gtctctacgt  taatttgcta  tgataattta  tcatcaatta  attggcaaag   3060
cctgatgcac  gaaaagatct  tcttctaaaa  tttcagttgt  tcttttcaac  acattatgta   3120
atcataaaat  ttaattaata  aaccttttt   ttttgtaact  atccacagtt  gatcaggcat   3180
aattttcttg  gaaagtaaag  tccatattta  ggttgatgtt  gaataaaaaa  actttcaatt   3240
cactcttctg  tttcacttca  gaacttacgt  aatacgacat  tatgcatggt  gcacacggaa   3300
caggataaga  cgttcacaag  ggatcaacat  cacatcggat  cgtaatcact  ggatctggaa   3360
cacatatgac  gccacaagac  agcacatttt  acacgatcac  cagacgtgaa  caaggaactg   3420
gatccacaag  acgtcacagg  aagacggcac  atttccaacg  gcttcgatgg  aacttttctc   3480
gagtctttt   ccaccaatca  taaacaccga  cctgccagga  ctcgccttcc  aacgggcaaa   3540
aatgcgtgtg  gtggcggtcg  agcatctcga  tggccagggc  atccagcagc  gcccgcttat   3600
tcttcacgtg  ccagtagagg  gtgggctgct  ccacgcccag  cttctgcgcc  aacttgcggg   3660
tcgtcagtcc  ctcaatgcca  acttcgttca  acagctccaa  cgcggagttg  atgactttgg   3720
acttatccag  gcggctgccc  atggtggttt  ctaaaggtgt  tataaatcaa  attagttttg   3780
tttttcttg   aaaactttgc  gtttcctttg  atcaacttac  cgccagggta  ccgcagattg   3840
tttagcttgt  tcagctgcgc  ttgtttattt  gcttagcttt  cgcttagcga  cgtgttcact   3900
ttgcttgttt  gaattgaatt  gtcgctccgt  agacgaagcg  cctctattta  tactccggcg   3960
ctcgttttcg  agtttaccac  tccctatcag  tgatagagaa  aagtgaaagt  cgagtttacc   4020
actccctatc  agtgatagag  aaaagtgaaa  gtcgagttta  ccactcccta  tcagtgatag   4080
agaaaagtga  agtcgagtt   taccactccc  tatcagtgat  agagaaaagt  gaaagtcgag   4140
tttaccactc  cctatcagtg  atagagaaaa  gtgaaagtcg  agtttaccac  tccctatcag   4200
tgatagagaa  aagtgaaagt  cgagtttacc  actccctatc  agtgatagag  aaaagtgaaa   4260
gtcgaaacct  ggcgcgcccc  ggccatcgag  aaagagagag  agaagagaag  agagagaaca   4320
ttcgagaaag  agagagagaa  gagaagagag  agaacatact  ccctatcagt  gatagagaag   4380
tccctatcag  tgatagagat  gtccctatca  gtgatagaga  gttccctatc  agtgatagag   4440
acgtccctat  cagtgataga  gaagtcccta  tcagtgatag  agagatccct  atcagtgata   4500
gagatttccc  tatcagtgat  agagaggtcc  ctatcagtga  tagagacttc  cctatcagtg   4560
atagagaaat  ccctatcagt  gatagagaca  tccctatcag  tgatagagaa  ctccctatca   4620
gtgatagaga  cctccctatc  agtgatagag  atcgatgcgg  ccgcatggta  cccattgctt   4680
gtcatttatt  aatttggatg  atgtcatttg  tttttaaaat  tgaactggct  ttacgagtag   4740
aattctacgc  gtaaaacaca  atcaagtatg  agtcataatc  tgatgtcatg  ttttgtacac   4800
ggctcataac  cgaactggct  ttacgagtag  aattctactt  gtaatgcacg  atcagtggat   4860
gatgtcattt  gtttttcaaa  tcgagatgat  gtcatgtttt  gcacacggct  cataaactcg   4920
ctttacgagt  agaattctac  gtgtaacgca  cgatcgattg  atgagtcatt  tgttttgcaa   4980
tatgatatca  tacaatatga  ctcatttgtt  tttcaaaacc  gaacttgatt  tacgggtaga   5040
attctacttg  taaagcacaa  tcaaaaagat  gatgtcattt  gtttttcaaa  actgaactcg   5100
ctttacgagt  agaattctac  gtgtaaaaca  caatcaagaa  atgatgtcat  ttgttataaa   5160
aataaaagct  gatgtcatgt  tttgcacatg  gctcataact  aaactcgctt  tacgggtaga   5220
attctacgcg  taaaacatga  ttgataatta  aataattcat  ttgcaagcta  tacgttaaat   5280
caaacggacg  ctcgaggttg  cacaacacta  ttatcgattt  gcagttcggg  acataaatgt   5340
```

```
ttaaatatat cgatgtctttt gtgatgcgcg cgacattttt gtaggttatt gataaaatga    5400
acggatacgt tgcccgacat tatcattaaa tccttggcgt agaatttgtc gggtccattg    5460
tccgtgtgcg ctagcatgcc cgtaacggac ctcgtacttt tggcttcaaa ggttttgcgc    5520
acagacaaaa tgtgccacac ttgcagctct catgtgtgc gcgttaccac aaatcccaac     5580
ggcgcagtgt acttgttgta tgcaaataaa tctcgataaa ggcgcggcgc gcgaatgcag    5640
ctgatcacgt acgctcctcg tgttccgttc aaggacggtg ttatcgacct cagattaatg    5700
tttatcggcc gactgttttc gtatccgctc accaaacgcg ttttttgcatt aacattgtat   5760 gtcggcggat gttctatatc taatttgaat aaataaacga taaccgcgtt ggttttagag    5820
ggcataataa aagaaatatt gttatcgtgt tcgccattag ggcagtataa attgacgttc    5880
atgttggata ttgtttcagt tgcaagttga cactggcggc gacaagcaat tctaattggg    5940
gtaagttttc ccgttctttt ctgggttctt cccttttgct catccttgct gcactacctt    6000
caggtgcaag ttgagattca ggccaccatg ggagatccca ccccacccaa gaagaagcgc    6060
aaaccggtcg ccaccatgga cgaggatggt tcagagggcg ccccgccct gttccagagc     6120 gacatgacct tcaaaatctt catcgacggc gaggtgaacg ccagaagtt caccatcgtg     6180 gccgacggca gcagcaagtt cccccacggc gacttcaacg tgcacgccgt gtgcgagacc    6240
ggcaagctgc ccatgagctg gaagcccatc tgccacctga tccagtacgg cgagcccttc    6300
ttcgcccgct accccaacgg catcagccac ttcgcccagg agtgcttccc cgagggcctg    6360
agcatcgacc gcaccgtgcg cttcgagaac gacggcacca tgaccagcca ccacctac     6420 gagctggacg gcacctgcgt ggtcagccgc atcaccgtga actgcgacgg cttccagccc    6480
gacggcccca tcatgcgcga ccagctggtg gacatcctgc ccaacgagac ccacatgttc    6540
ccccacggcc ccaacgccgt gcgccagctg gccttcatcg gcttccacca cgccgacggc    6600
ggcctgatga tgggccactt cgacagcaag atgaccttca cggcagccg cgccatcaag    6660 atccccggcc cccacttcgt gaccatcatc accaagcaga tgagggacac cagcgacaag    6720
cgcgaccacg tgtgccagcg cgaggtgacc tacgcccaca gcgtgccccg catcaccagc    6780
gccatcggta gcgacgagga ttccggactc agatctcgac ccaagaaaaa gcggaaggtg    6840
gaggacccgt aagatccacc ggatctagat aactgatcat aatcagccat accacatttg    6900
tagaggtttt acttgcttta aaaaacctcc cacacctccc cctgaacctg aaacataaaa    6960
tgaatgcaat tgttgttgtt aacttgttta ttgcagctta taatggttac aaataaagca    7020
atagcatcac aaatttcaca aataaagcat ttttttcact gcattctagt tgtggtttgt    7080
ccaaactcat caatgtatct taacgcgagt taattaatcc attgctgggc gagctgcgcc    7140
aatcgatgcc aacgccaccc tgcatggcga gcggcaggcc ggcggctacc atgggcgtca    7200
ccatgccctg accgccccg gagggcagtg aaaaatgtgt ggggggtggt ggggctgcg     7260 caggaactga ttgtgattat ggttgtgccc atgccatgt tgtccaagtc catgacgtg     7320 ggcatgcttg ttgtagccca aatcggcgtt tccgttccca ccaggaaaca tctctgcttg    7380
tagttcgaat atgctcttta aatcccagct gtattcctca gttatcgagg ttttcttcac    7440
gagtgaaacg aattttcgtc gccttctacg ccatttttctt gctcagcccg ttttgtcatt   7500
cgcagcgaag cggtaacagc gggtcgctca tatgacggta ttttttaata cacttcagct    7560
atactgttat ttcaaaaaca tatttctttt gttactttttt atgcagttca tttgccacca   7620 aaagtagtc ttttggattg atttatttca aaaaatggtg taattcaaga aattcagagg     7680
gccaagtaat atacttaatg accgttattt aaaacacact caaggagatt tatttaaacg    7740
```

```
gctacaatgg ttttccaaat aacttattta ctgttgactt ctataaaaca taggtgtata    7800
tattattatt tccttattga gtttgagata attttaattt ccacaatatt ttttcttgtg    7860
attaacagag aaagtcaaac tacataacat ttatcgggta aaagtctcta tgaaggtagc    7920
ggttaacagt gaagtcgcaa aagtggtggc cgtacgccaa tcgagcgtag tacccctaac    7980
ctgcaatatt tttagttggt tttttccgca atagccccag ttttctcaaa gagtgcaaca    8040
agtgattctg tttatgtttt caacaacttc tctctgcgga acttaacgtg agcggacgta    8100
tgcggacgcg tttaaactcg cgttaagata cattgatgag tttggacaaa ccacaactag    8160
aatgcagtga aaaaaatgct ttatttgtga aatttgtgat gctattgctt tatttgtaac    8220
cattataagc tgcaataaac aagttaacaa caacaattgc attcatttta tgtttcaggt    8280
tcaggggggag gtgtgggagg ttttttaaag caagtaaaac ctctacaaat gtggtatggc   8340
tgattatgat caccggtgtt actggctcgg acggcggtaa cggccgctgc ggcggccggt    8400
gcgcgggtgg cagctggtgt actggcgcag ggtctccagc accacggtgg ccaggaagcg    8460
ccactggctc tcgcgcaggc gcaggatctg ctgctcgcgc tgctcggcct cgcgcagcag    8520
ggtggcctga tccgggatgt agaaggccac ggcgccacca cggagacgaa ggaccaagtg    8580
aagggtggac tccttctgga tgttgtaatc ggacagggtg cgtccgtctt ccagttgctt    8640
acctatagat accatagatg tatggattag tatcatatac atacaaaggc tattttttggg   8700
acatattaat attaacaatt tccgtgatag ttttcaccat ttttgttgaa tgttacgttg    8760
aaaatttaaa tttgttttaa attaatttta ccagtcatgt gttcttaaaa gtttttatga    8820
ttgaaacggc ataaagtggt tcaaaaattt atcaagaaag ctttcctttt tttaaatctt    8880
atcttttttct cttaaaaatc actagtcaat tcattattaa tttgttaact tgaatttgga   8940
atgtctattt actttcagat aaattaaagc aagaaactta atattcgaaa aaaattgatt    9000
ctaaatggaa tttcacttga tcttcatgta tgcatatcaa tttttatttta cattgtataa   9060
taagtttcga gttgattgtt gtaatccaca ggtgtcccag agaattaaat tccaaattac    9120
ccaagtttat tgaatgttga ttgtagtttc agttgctttg ttgctgcaac aatggcttgt    9180
tgattgtaga tattttccct ttccttggtt tacttattac atagactgaa aaagaggttt    9240
actttttttga tacttatgaa aaatttctat tagtgattac taaccaatcg ctatatgttt   9300
actagaaaac aaataaactc tttacattaa cattcaataa tgtttgctct gtaaccgaca    9360
attgaaggcg ttacagcaac agtaatataa ctagcttctt aaccctcatc tattaacccc    9420
atcgtttaaa acactatgtt aaatggtcta acaaatctag atactaatag atgtcttatt    9480
acttagcagc cacagctgca acatccaaga caatttttga aacttcttat tgagctcttg    9540
gcagcagaaa tgttggtatt tttcacagct ttctgaaaga ccggcacctt cctccggttc    9600
ccgtttctga attcaagagg atttccgacc cccaattaat cccgaaacaa ataaggtata    9660
ttcaaaatga tggaaaagtc atggctgctg accttatttt tattcctatt gatagaatat    9720
tattccccctt ttaaatacac tgtactaaga ggtccggcta aatttttact cacttgtcga   9780
ttatcccata gaatgttgat tgtagttggt tgcttttcca ggtgagagtt gatcaagtca    9840
caaaagttag cgtgtgttga ttgtagattt gaaggtaaaa taattttttgc acccattcat   9900
cgggtaaaac gttctccata gaatacattt ccatcgataa ttgataactt atgaatttca    9960
aagaaaaaaa tatgcttttta aaattaccag cgaagatcag acgctgctga tctgggggga  10020
ttccctcctt atcctgaatc ttggccttta cattctcaat ggtgtccgat ggctctacct   10080
```

```
cgagggtgat ggtctttccg gtcaaagtct tcacaaagat ctgcattttg gattgctagc    10140
gcagattgtt tagcttgttc agctgcgctt gtttatttgc ttagctttcg cttagcgacg    10200
tgttcacttt gcttgtttga attgaattgt cgctccgtag acgaagcgcc tctatttata    10260
ctccggcgct cggtccgcat agtcgacatt tcgagtttac cactccctat cagtgataga    10320
gaaaagtgaa agtcgagttt accactccct atcagtgata gagaaagtg aaagtcgagt     10380 ttaccactcc ctatcagtga tagagaaaag tgaaagtcga gtttaccact ccctatcagt    10440
gatagagaaa agtgaaagtc gagtttacca ctccctatca gtgatagaga aagtgaaag    10500 tcgagtttac cactccctat cagtgataga gaaaagtgaa agtcgagttt accactccct    10560
atcagtgata gagaaaagtg aaagtcgagc tcggtacccg ggtcgaggta ggcgtgtacg    10620
gtgggaggaa atctggccgg ccgcaaccat tgtgggaacc gtgcgatcaa acaaacgcga    10680
gataccggaa gtactgaaaa acagtcgctc caggccagtg ggaacatcga tgttttgttt    10740
tgacggaccc cttactctcg tctcatataa accgaagcca gctaagatgg tatacttatt    10800
atcatcttgt gatgaggatg cttctatcaa cgaaagtacc ggtaaaccgc aaatggttat    10860
gtattataat caaactaaag gcggagtgga cacgctagac caaatgtgtt ctgtgatgac    10920
ctgcagtagg aagacgaata ggtggcctat ggcattattg tacggaatga taaacattgc    10980
ctgcataaat tcttttatta tatacagcca taatgtcagt agcaagggag aaaaggtcca    11040
aagtcgcaaa aaatttatga gaaaccttta catgagcctg acgtcatcgt ttatgcgtaa    11100
gcgtttagaa gctcctactt tgaagagata tttgcgcgat aatatctcta atattttgcc    11160
aaatgaagtg cctggtacat cagatgacag tactgaagag ccagtaatga aaaacgtac     11220 ttactgtact tactgcccct ctaaaataag gcgaaaggca aatgcatcgt gcaaaaaatg    11280
caaaaaagtt atttgtcgag agcataatat tgatatgtgc caaagttgtt tctgactgac    11340
taataagtat aatttgtttc tattatgtat aagttaagct aattacttat tttataatac    11400
aacatgactg ttttttaaagt acaaaataag tttattttg taaaagagag aatgtttaaa    11460
agttttgtta ctttatagaa gaaattttga gttttgttt tttttaata aataaataaa     11520 cataaataaa ttgtttgttg aatttattat tagtatgtaa gtgtaaatat aataaaactt    11580
aatatctatt caaattaata aataaacctc gatatacaga ccgataaaac acatgcgtca    11640
attttacgca tgattatctt taacgtacgt cacaatatga ttatcttttct agggttaaat    11700 aatagtttct aattttttta ttattcagcc tgctgtcgtg aataccgtat atctcaacgc    11760
tgtctgtgag attgtcgtat tctagccttt ttagttttc gctcatcgac ttgatattgt     11820
ccgacacatt ttcgtcgatt tgcgttttga tcaaagactt gagcagagac acgttaatca    11880
actgttcaaa ttgatccata ttaacgtat caacccgatg cgtatatggt gcgtaaaata     11940 tatttttaa ccctcttata ctttgcactc tgcgttaata cgcgttcgtg tacagacgta     12000
atcatgtttt cttttttgga taaaactcct actgagtttg acctcatatt agaccctcac    12060
aagttgcaaa acgtggcatt ttttaccaat gaagaattta agttattttt aaaaaatttc    12120
atcacagatt taagaagaa ccaaaaatta aattatttca acagtttaat cgaccagtta     12180
atcaacgtgt acacagacgc gtcggcaaaa aacacgcagc ccgacgtgtt ggctaaaatt    12240
attaaatcaa cttgtgttat agtcacggat ttgccgtcca acgtgttcct caaaagttg    12300 aagaccaaca agtttacgga cactattaat tatttgattt tgccccactt cattttgtgg   12360
gatcacaatt ttgttatatt ttaaacaaag cttggcactg gccgtcgttt tacaacgtcg    12420
tgactgggaa aaccctggcg ttacccaact taatcgcctt gcagcacatc cccctttcgc    12480
```

-continued

```
cagctggcgt aatagcgaag aggcccgcac cgatcgccct tcccaacagt tgcgcagcct   12540
gaatggcgaa tggcgcctga tgcggtattt tctccttacg catctgtgcg gtatttcaca   12600
ccgcatatgg tgcactctca gtacaatctg ctctgatgcc gcatagttaa gccagccccg   12660
acacccgcca acacccgctg acgcgccctg acgggcttgt ctgctcccgg catccgctta   12720
cagacaagct gtgaccgtct ccgggagctg catgtgtcag aggttttcac cgtcatcacc   12780
gaaacgcgcg agacgaaagg gcctcgtgat acgcctattt ttataggtta atgtcatgat   12840
aataatggtt tcttagacgt caggtggcac ttttcgggga aatgtgcgcg aaccccctat   12900
ttgtttattt ttctaaatac attcaaatat gtatccgctc atgagacaat aaccctgata   12960
aatgcttcaa taatattgaa aaggaagag tatgagtatt caacatttcc gtgtcgccct   13020 tattccctt tttgcggcat tttgccttcc tgttttttgct cacccagaaa cgctggtgaa   13080
agtaaaagat gctgaagatc agttgggtgc acgagtgggt tacatcgaac tggatctcaa   13140
cagcggtaag atccttgaga gttttcgccc cgaagaacgt tttccaatga tgagcacttt   13200
taaagttctg ctatgtggcg cggtattatc ccgtattgac gccgggcaag agcaactcgg   13260
tcgccgcata cactattctc agaatgactt ggttgagtac tcaccagtca cagaaaagca   13320
tcttacggat ggcatgacag taagagaatt atgcagtgct gccataacca tgagtgataa   13380
cactgcggcc aacttacttc tgacaacgat cggaggaccg aaggagctaa ccgcttttt   13440 gcacaacatg gggatcatg taactcgcct tgatcgttgg gaaccggagc tgaatgaagc   13500
cataccaaac gacgagcgtg acaccacgat gcctgtagca atggcaacaa cgttgcgcaa   13560
actattaact ggcgaactac ttactctagc ttcccggcaa caattaatag actggatgga   13620
ggcggataaa gttgcaggac cacttctgcg ctcggccctt ccggctggct ggtttattgc   13680
tgataaatct ggagccggtg agcgtgggtc tcgcggtatc attgcagcac tggggccaga   13740
tggtaagccc tcccgtatcg tagttatcta cacgacgggg agtcaggcaa ctatggatga   13800
acgaaataga cagatcgctg agataggtgc ctcactgatt aagcattggt aactgtcaga   13860
ccaagtttac tcatatatac tttagattga tttaaaactt cattttttaat ttaaaaggat   13920 ctaggtgaag atcctttttg ataatctcat gaccaaaatc ccttaacgtg agttttcgtt   13980
ccactgagcg tcagaccccg tagaaaagat caaaggatct tcttgagatc cttttttct   14040 gcgcgtaatc tgctgcttgc aaacaaaaaa accaccgcta ccagcggtgg tttgtttgcc   14100
ggatcaagag ctaccaactc tttttccgaa ggtaactggc ttcagcagag cgcagatacc   14160
aaatactgtc cttctagtgt agccgtagtt aggccaccac ttcaagaact ctgtagcacc   14220
gcctacatac ctcgctctgc taatcctgtt accagtggct gctgccagtg gcgataagtc   14280
gtgtcttacc gggttggact caagacgata gttaccggat aaggcgcagc ggtcgggctg   14340 aacgggggt tcgtgcacac agcccagctt ggagcgaacg acctacaccg aactgagata   14400
cctacagcgt gagcattgag aaagcgccac gcttcccgaa gggagaaagg cggacaggta   14460
tccggtaagc ggcagggtcg gaacaggaga gcgcacgagg gagcttccag ggggaaacgc   14520
ctggtatctt tatagtcctg tcgggtttcg ccacctctga cttgagcgtc gatttttgtg   14580
atgctcgtca gggggggcgga gcctatggaa aaacgccagc aacgcggcct ttttacggtt   14640
cctggccttt tgctggcctt ttgctcacat gttctttcct gcgttatccc ctgattctgt   14700
ggataaccgt attaccgcct ttgagtgagc tgataccgct cgccgcagcc gaacgaccga   14760
gcgcagcgag tcagtgagcg aggaagcgga agagcgccca atacgcaaac cgcctctccc   14820
```

-continued

| | |
|---|---|
| cgcgcgttgg ccgattcatt aatgcagctg gcacgacagg tttcccgact ggaaagcggg | 14880 |
| cagtgagcgc aacgcaatta atgtgagtta gctcactcat taggcacccc aggctttaca | 14940 |
| ctttatgctt ccggctcgta tgttgtgtgg aattgtgagc ggataacaat ttcacacagg | 15000 |
| aaacagctat gaccatgatt acgaatttcg acgctcgcgc gacttggttt gccattcttt | 15060 |
| agcgcgcgtc gcgtcacaca gcttggccac aatgtggttt ttgtcaaacg aagattctat | 15120 |
| gacgtgttta agtttaggt cgagtaaagc gcaaatcttt tttaacccta gaaagatagt | 15180 |
| ctgcgtaaaa ttgacgcatg cattcttgaa atattgctct ctctttctaa atagcgcgaa | 15240 |
| tccgtcgctg tgcatttagg acatctcagt cgccgcttgg agctcccgtg aggcgtgctt | 15300 |
| gtcaatgcgg taagtgtcac tgattttgaa ctataacgac cgcgtgagtc aaaatgacgc | 15360 |
| atgattatct tttacgtgac ttttaagatt taactcatac gataattata ttgttatttc | 15420 |
| atgttctact tacgtgataa cttattatat atatattttc ttgttataga tatcgtgact | 15480 |
| aatatataat aaaatgggta gttctttaga cgatgagcat atcctctctg ctcttctgca | 15540 |
| aagcgatgac gagcttgttg gtgaggattc tgacagtgaa atatcagatc acgtaagtga | 15600 |
| agatgacgtc cagagcgata cagaagaagc gtttatagat gaggtacatg aagtgcagcc | 15660 |
| aacgtcaagc ggtagtgaaa tattagacga acaaaatgtt attgaacaac caggttcttc | 15720 |
| attggcttct aacagaatct tgaccttgcc acagaggact attagaggta agaataaaca | 15780 |
| ttgttggtca acttcaaagt ccacgaggcg tagccgagtc tctgcactga acattgtcag | 15840 |
| atcggccc | 15848 |

<210> SEQ ID NO 55
<211> LENGTH: 17802
<212> TYPE: DNA
<213> ORGANISM: Artificial Sequence
<220> FEATURE:
<223> OTHER INFORMATION: Synthetic construct, pLA3376-Bztra intron-reaperKR and Bztra-intron-tTAV3.

<400> SEQUENCE: 55

| | |
|---|---|
| gggcggccgt ttttcttgaa atattgctct ctctttctaa atagcgcgaa tccgtcgctg | 60 |
| tgcatttagg acatctcagt cgccgcttgg agctcccaaa cgcgccagtg gtagtacaca | 120 |
| gtactgtggg tgttcagttt gaaatcctct tgcttctcca ttgtctcggt tacctttggt | 180 |
| caaatccatg ggttctattg cctatatact cttgcgatta ccagtgattg cgctattagc | 240 |
| tattagatgg attgttggcc aaacttgtcg cttaagtggc tgggaattgt aaccgtaggc | 300 |
| ccgagtgtaa tgatccccca taaaaagttt tcgcaatgcc tttattttt gttgcaaatc | 360 |
| tctctttatt ctgcggtatt cttcattatt gcggggatgg ggaaagtgtt tatatagaag | 420 |
| caacttacga ttgaacccaa atgcacctga caagcaaggt caaagggcca gatttttaaa | 480 |
| tatattattt agtcttagga ctctctattt gcaattaaat tactttgcta cctgagggtt | 540 |
| aaatcttccc cattgataat aataattcca ctatatgttc aattgggttt caccgcgctt | 600 |
| agttacatga cgagccctaa tgagccgtcg gtggtctata aactgtgcct tacaaatact | 660 |
| tgcaactctt ctcgttttga agtcagcaga gttattgcta attgctaatt gctaattgct | 720 |
| tttaactgat ttcttcgaaa ttggtgctat gtttatggcg ctattaacaa gtatgaatgt | 780 |
| caggtttaac caggggatgc ttaattgtgt tctcaacttc aaaggcagaa atgtttactc | 840 |
| ttgaccatgg gttaggtat aatgttatca agctcctcga gttaacgtta cgttaacgtt | 900 |
| aacgttcgag gtcgactcta gacaccggtg ttagccgccg tactcatcga tgcccagggc | 960 |

-continued

```
gtcggtgaac atctgctcga actcgaaatc ggccatatcc agggcgccgt aggggggcgct    1020 atcgtgcggg gtgaatcccg gtcccgggct atcgccatcg cccagcatgt ccaggtcgaa    1080
gtcgtccagg gcatcggcgt gggccatcgc cacatcctcg ccatccaggt gcagctcatc    1140
gcccaggctc acgtcggtcg gcggggcggt cgacaggcgg cgggtgtgtc cggccggcag    1200
gaagctcagg cgcggggcgg ccaggcccgc ctcctccggg gcatcatcat ccggcagatc    1260
cagcaggccc tcgatggtgc tgccgtagtt gttcttggtg cgggcgcggc tgtaggcggg    1320
gcccgagccc gactcgcatt tcagttgctt ttccaatccg cagataatca gctccaagcc    1380
gaacaggaat gccggctcgg ctccttgatg atcgaacagc tcgattgcct gacgcagcag    1440
tgggggcatc gaatcggttg ttggggtctc gcgctcctct tttgcgactt gatgctcttg    1500
gtcctccagc acgcagccca gggtaaagtg accgacggcg ctcagagcgt agagagcatt    1560
ttccaggctg aagccttgct ggcacaggaa cgcgagctgg ttctccagtg tctcgtattg    1620
cttttcggtc gggcgcgtgc cgagatggac tttggcaccg tctcggtggg acagcagagc    1680
gcagcggaac gacttggcgt tattgcgcag gaagtcctgc caggactcgc cttccaacgg    1740
gcaaaaatgc gtgtggtggc ggtcgagcat ctcgatggcc agggcatcca gcagcgcccg    1800
cttattcttc acgtgccagt agagggtggg ctgctccacg cccagcttct gcgccaactt    1860
gcgggtcgtc agtccctcaa tgccaacttc gttcaacagc tccaacgcgg agttgatgac    1920
tttggactta tccaggcggc tgacctatag ataccataga tgtatggatt agtatcatat    1980
acatacaaag gctattttttg ggacatatta atattaacaa tttccgtgat agttttcacc    2040
atttttgttg aatgttacgt tgaaaattta aatttgtttt aaattaattt taccagtcat    2100
gtgttcttaa aagttttttat gattgaaacg gcataaagtg gttcaaaaat ttatcaagaa    2160
aggctttcct tttttaaatc ttatcttttt ctcttaaaaa tcactagtca attcattatt    2220
aatttgttaa cttgaatttg gaatgtctat ttactttcag ataaattaaa gcaagaaact    2280
taatattcga aaaaaattga ttctaaatgg aatttcactt gatcttcatg tatgcatatc    2340 aattttttatt tacattgtat aataagtttc gagttgattg ttgtaatcca caggtgtccc    2400
agagaattaa attccaaatt acccaagttt attgaatgtt gattgtagtt tcagttgctt    2460
tgttgctgca acaatggctt gttgattgta gatattttcc ctttccttgg tttacttatt    2520
acatagactg aaaagaggt ttacttttttt gatacttatg aaaaatttct attagtgatt    2580
actaaccaat cgctatatgt ttactagaaa acaaataaac tctttacatt aacattcaat    2640
aatgtttgct ctgtaaccga caattgaagg cgttacagca acagtaatat aactagcttc    2700
ttaaccctca tctattaacc ccatcgttta aaacactatg ttaaatggtc taacaaatct    2760
agatactaat agatgtctta ttacttagca gccacagctg caacatccaa gacaattttt    2820
gaaacttctt attgagctct tggcagcaga atgttggta ttttttcacag ctttctgaaa    2880 gaccggcacc ttcctccggt tcccgtttct gaattcaaga ggattccga cccccaatta    2940 atcccgaaac aaataaggta tattcaaaat gatggaaaag tcatggctgc tgaccttatt    3000
tttattccta ttgatagaat attattcccc ttttaaatac actgtactaa gaggtccggc    3060
tataatttta ctcacttgtc gattatccca tagaatgttg attgtagttg ttgcttttc    3120 caggtgagag ttgatcaagt cacaaaagtt agcgtgtgtt gattgtagat ttgaaggtaa    3180 ataattttttt gcacccattc atcgggtaaa acgttctcca tagaatacat ttccatcgat    3240
aattgataac ttatgaattt caagaaaaaa aatatgcttt taaaattacc atggtggcta    3300
gcgcagattg tttagcttgt tcagctgcgc ttgtttattt gcttagcttt cgcttagcga    3360
```

-continued

```
cgtgttcact ttgcttgttt gaattgaatt gtcgctccgt agacgaagcg cctctattta    3420
tactccggcg ctcgttttcg agtttaccac tccctatcag tgatagagaa aagtgaaagt    3480
cgagtttacc actccctatc agtgatagag aaaagtgaaa gtcgagttta ccactcccta    3540
tcagtgatag agaaaagtga aagtcgagtt taccactccc tatcagtgat agagaaaagt    3600
gaaagtcgag tttaccactc cctatcagtg atagagaaaa gtgaaagtcg agtttaccac    3660
tccctatcag tgatagagaa aagtgaaagt cgagtttacc actccctatc agtgatagag    3720
aaaagtgaaa gtcgaaacct cgcgccgtt taaactcgcg ttaagataca ttgatgagtt    3780
tggacaaacc acaactagaa tgcagtgaaa aaatgctttt atttgtgaaa tttgtgatgc    3840
tattgcttta tttgtaacca ttataagctg caataaacaa gttaacaaca acaattgcat    3900
tcattttatg tttcaggttc agggggaggt gtgggaggtt ttttaaagca agtaaaacct    3960
ctacaaatgt ggtatggctg attatgatcg ctctagacac cggtgctacc cgccatactc    4020
atcgatgccc agcgcgtcgg tgaacatttg ctcgaactcg aagtcggcca tgtccagggc    4080
gccgtacggg gcgctatcgt ggggcgtgaa gcccggtccc ggctatctc catcgcccag    4140 catatccagg tcgaaatcgt ccagggcgtc ggcgtgggcc attgccacat cctctccatc    4200
caggtgcagc tcgtcgccca ggctcacatc ggtcggcggg gcggtgctca ggcggcgcgt    4260
gtgtccggcg ggcaggaagc tcaggcgggg ggcggccagg ccggcttcct ccggggcatc    4320
gtcatccggc aggtccagca gtccctcgat ggtgctgcca tagttgttct tggtacgggc    4380
gcggctgtag gcgctgccgc tctcgcactt cagctgcttt tccaggccgc agatgatcag    4440
ctccaggccg aacaggaagg ccggctcggc gccctggtga tcgaacagct cgatggcctg    4500
gcgcagcagc ggcggcatgc tatcggtggt cggggtctcg cgctcctcct tggccacctg    4560
gtgctcctga tcctccagca cacagcccag ggtgaagtgg cccacggcgc tcagggcgta    4620
cagggcgttc tccaggctga agccctgctg gcacaggaag gccagctggt tctccagggt    4680
ctcgtactgc ttctcggtcg ggcgggtgcc caggtgcacc ttggcgccat cgcggtgcga    4740
cagcagggcg cagcggaagc tcttggcgtt gttgcgcagg aaatcctgcc agctctcgcc    4800
ctccagcggg cagaagtggg tgtggtggcg atccagcatt tcgatggcca gggcgtccag    4860
cagggcgcgc ttgttcttca cgtgccagta cagggtcggc tgttccacgc ccagcttctg    4920
ggccagcttg cgggtggtca ggccctcgat accaacttcg ttcagcagct ccagggcgct    4980
gttgatcacc ttgctcttgt ccaggcggct gacctgtgaa tacggttaat gtcactatta    5040
gtgatttata aaataaatt tgatttatat atcaacaatt tttcatcgca gccttcagct    5100
ttttgttgaa taattataat gatatttttt acgattcaaa tcatttaatt gttactcaac    5160
gaaataagtt taattcaaat tttaaaacaa gattatatat taagattaga ataagaaga    5220 actttgttag attatttaat taaaaagatt aaaatttaag tctccagtca ctatttaaag    5280
atcatctttc aaacgttaaa gtgaattcaa acgagacgtt caaatttcga ttaaacagta    5340
attaactcta aatttctatc acgaattaag ttattgaata tgaaggttta tatttattta    5400
catcatctaa taggtttgag ttgattgttg taatccgcat gtgccagaag atatcaattt    5460
ccaaattgtc cgagttcatg gaatgttgat tgttgtttgt gttgctttgt aattgttgca    5520
gggagtattt atggtttgtt gattgtagta taaggctgtt tctaaaggct agaaaataat    5580
tttatttatt tgaaaataag taaatataca taatattact aacaataggt cgtcctattt    5640
tttgatattc tgcacaaatt tttaaaacac aaagattgca atactttag acactaatac    5700
```

```
tgcacactct gaaaaattat taaattattt ttaaaaactt accttaatac tttagagaaa    5760
aatattatac cgcacctttc tactttatac tcactttatt ataccagttg catgttgatt    5820
gtagttcttt gacaagaaaa tattccatat tgctccaaat tatcttggta agttgattgg    5880
tgcgtcattt gagcaagcta acaccttgtc tcatttaagt tcgcctcaag atctcatagc    5940
atttttaaat atcactatat ttagtaagta attagaatta ccatggtggt ttgctagccg    6000
ttctatcaga tgtgctccgg gaaacagaaa tgttcaacta agttctggcg gacgacgcaa    6060
cacctttata tactttgcca agcgcacagg tagaaaggac ctattttggg gattaaaaaa    6120
catctgcctg ttttattgcc atacccgcga aaattcgcga aatccgctac tttacctact    6180
ggggttcctg gaaaatgggc gaagaacggc aaagaactgg tactttccgt caataattgt    6240
ttagaagaga gagaacatac tccctatcag tgatagagaa gtccctatca gtgatagaga    6300
tgtccctatc agtgatagag agttccctat cagtgataga gacgtcccta tcagtgatag    6360
agaagtccct atcagtgata gagagatccc tatcagtgat agagatttcc ctatcagtga    6420
tagagaggtc cctatcagtg atagagactt ccctatcagt gatagagaaa tccctatcag    6480
tgatagagac atccctatca gtgatagaga actccctatc agtgatagag acctccctat    6540
cagtgataga gatcgatgcg gccgcatggt acccattgct tgtcatttat taatttggat    6600
gatgtcattt gttttttaaaa ttgaactggc tttacgagta gaattctacg cgtaaaacac    6660
aatcaagtat gagtcataat ctgatgtcat gttttgtaca cggctcataa ccgaactggc    6720
tttacgagta gaattctact tgtaatgcac gatcagtgga tgatgtcatt tgttttttcaa    6780 atcgagatga tgtcatgttt tgcacacggc tcataaactc gctttacgag tagaattcta    6840
cgtgtaacgc acgatcgatt gatgagtcat ttgttttgca atatgatatc atacaatatg    6900
actcatttgt ttttcaaaac cgaacttgat ttacgggtag aattctactt gtaaagcaca    6960
atcaaaaaga tgatgtcatt tgttttttcaa aactgaactc gctttacgag tagaattcta    7020
cgtgtaaaac acaatcaaga aatgatgtca tttgttataa aaataaaagc tgatgtcatg    7080
ttttgcacat ggctcataac taaactcgct ttacgggtag aattctacgc gtaaaacatg    7140
attgataatt aaataattca tttgcaagct atacgttaaa tcaaacggac gctcgaggtt    7200
gcacaacact attatcgatt tgcagttcgg gacataaatg tttaaatata tcgatgtctt    7260
tgtgatgcgc gcgacatttt tgtaggttat tgataaaatg aacggatacg ttgcccgaca    7320
ttatcattaa atccttggcg tagaatttgt cgggtccatt gtccgtgtgc gctagcatgc    7380
ccgtaacgga cctcgtactt ttggcttcaa aggttttgcg cacagacaaa atgtgccaca    7440
cttgcagctc tgcatgtgtg cgcgttacca caaatcccaa cggcgcagtg tacttgttgt    7500
atgcaaataa atctcgataa aggcgcggcg cgcgaatgca gctgatcacg tacgctcctc    7560
gtgttccgtt caaggacggt gttatcgacc tcagattaat gtttatcggc cgactgtttt    7620
cgtatccgct caccaaacgc gttttttgcat taacattgta tgtcggcgga tgttctatat    7680
ctaatttgaa taaataaacg ataaccgcgt tggttttaga gggcataata aaagaaatat    7740
tgttatcgtg ttcgccatta gggcagtata aattgacgtt catgttggat attgtttcag    7800
ttgcaagttg acactggcgg cgacaagcaa ttctaattgg ggtaagtttt cccgttcttt    7860
tctgggttct tccctttttgc tcatccttgc tgcactacct tcaggtgcaa gttgagattc    7920
aggccaccat gggagatccc accccaccca agaagaagcg caaaccggtc gccaccatgg    7980
agagcgacga gagcggcctg cccgccatgg agatcgagtg ccgcatcacc ggcacccctga    8040 acggcgtgga gttcgagctg gtgggcggcg agagggcac ccccgagcag ggccgcatga    8100
```

| | |
|---|---|
| ccaacaagat gaagagcacc aaaggcgccc tgaccttcag cccctacctg ctgagccacg | 8160 |
| tgatgggcta cggcttctac cacttcggca cctaccccag cggctacgag aaccccttcc | 8220 |
| tgcacgccat caacaacggc ggctacacca cacccgcat cgagaagtac gaggacggcg | 8280 |
| gcgtgctgca cgtgagcttc agctaccgct acgaggccgg ccgcgtgatc ggcgacttca | 8340 |
| aggtgatggg caccggcttc cccgaggaca gcgtgatctt caccgacaag atcatccgca | 8400 |
| gcaacgccac cgtggagcac ctgcacccca tgggcgataa cgatctggat ggcagcttca | 8460 |
| cccgcacctt cagcctgcgc gacggcggct actacagctc cgtggtggac agccacatgc | 8520 |
| acttcaagag cgccatccac cccagcatcc tgcagaacgg ggcccccatg ttcgccttcc | 8580 |
| gccgcgtgga ggaggatcac agcaacaccg agctgggcat cgtggagtac cagcacgcct | 8640 |
| tcaagacccc ggatgcagat gccggtgaag aaagatctcg acccaagaaa agcggaagg | 8700 |
| tggaggaccc gtaagatcca ccggatctag ataactgatc ataatcagcc ataccacatt | 8760 |
| tgtagaggtt ttacttgctt taaaaaacct cccacacctc ccctgaacc tgaaacataa | 8820 |
| aatgaatgca attgttgttg ttaacttgtt tattgcagct tataatggtt acaaataaag | 8880 |
| caatagcatc acaaatttca caaataaagc attttttca ctgcattcta gttgtggttt | 8940 |
| gtccaaactc atcaatgtat cttaacgcga gttatcgcgc tcgcgcgact gacggtcgta | 9000 |
| agcacccgcg tacgtgtcca ccccggtcac aaccccttgt gtcatgtcgg cgaccctacg | 9060 |
| cccccaactg agagaactca aaggttaccc cagttggggc actactcccg aaaaccgctt | 9120 |
| ctgacctggg aaaacgtgaa gccccgggc atccgctgag ggttgccgcc ggggcttcgg | 9180 |
| tgtgtccgtc agtacttaat taacaccgaa atcgtaattc acggcatcat tacaaaatat | 9240 |
| tttgacgttt tggacctcgt ccctaatgac accataacgg tggccttgaa gtatatttaa | 9300 |
| ccctagaaag atagtctgcg taaaattgac gcatgcattc ttgaaatatt gctctctctt | 9360 |
| tctaaatagc gcgaatccgt cgctgtgcat ttaggacatc tcagtcgccg cttggagctc | 9420 |
| ccgtgaggcg tgcttgtcaa tgcggtaagt gtcactgatt ttgaactata acgaccgcgt | 9480 |
| gagtcaaaat gacgcatgat tatctttac gtgactttta agatttaact catacgataa | 9540 |
| ttatattgtt atttcatgtt ctacttacgt gataacttat tatatatata ttttcttgtt | 9600 |
| atagatatcg tgactaatat ataataaaat gggtagttct ttagacgatg agcatatcct | 9660 |
| ctctgctctt ctgcaaagcg atgacgagct tgttggtgag gattctgaca gtgaaatatc | 9720 |
| agatcacgta agtgaagatg acgtccagga aatctggccg gccgcaacca ttgtgggaac | 9780 |
| cgtgcgatca aacaaacgcg agataccgga agtactgaaa acagtcgct ccaggccagt | 9840 |
| gggaacatcg atgttttgtt ttgacggacc ccttactctc gtctcatata aaccgaagcc | 9900 |
| agctaagatg gtatacttat tatcatcttg tgatgaggat gcttctatca acgaaagtac | 9960 |
| cggtaaaccg caaatggtta tgtattataa tcaaactaaa ggcggagtgg acacgctaga | 10020 |
| ccaaatgtgt tctgtgatga cctgcagtag gaagacgaat aggtggccta tggcattatt | 10080 |
| gtacggaatg ataaacattg cctgcataaa ttctttattt atatacagcc ataatgtcag | 10140 |
| tagcaaggga gaaaaggtcc aaagtcgcaa aaaatttatg agaaaccttt acatgagcct | 10200 |
| gacgtcatcg tttatgcgta agcgtttaga agctcctact ttgaagagat atttgcgcga | 10260 |
| taatatctct aatattttgc caaatgaagt gcctggtaca tcagatgaca gtactgaaga | 10320 |
| gccagtaatg aaaaaacgta cttactgtac ttactgcccc tctaaaataa ggcgaaaggc | 10380 |
| aaatgcatcg tgcaaaaaat gcaaaaaagt tatttgtcga gagcataata ttgatatgtg | 10440 |

```
ccaaagttgt ttctgactga ctaataagta taatttgttt ctattatgta taagttaagc    10500
taattactta ttttataata caacatgact gtttttaaag tacaaaataa gtttattttt    10560
gtaaaagaga gaatgtttaa aagttttgtt actttataga agaaattttg agttttgtt     10620 ttttttaat aaataaataa acataaataa attgtttgtt gaatttatta ttagtatgta     10680
agtgtaaata taataaaact taatatctat tcaaattaat aaataaacct cgatatacag    10740
accgataaaa cacatgcgtc aattttacgc atgattatct ttaacgtacg tcacaatatg    10800 attatcttc tagggttaaa taatagtttc taatttttt attattcagc ctgctgtcgt      10860
gaataccgta tatctcaacg ctgtctgtga gattgtcgta ttctagcctt tttagttttt    10920
cgctcatcga cttgatattg tccgacacat tttcgtcgat ttgcgttttg atcaaagact    10980
tgagcagaga cacgttaatc aactgttcaa attgatccat attaacgata tcaacccgat    11040
gcgtatatgg tgcgtaaaat atattttta accctcttat actttgcact ctgcgttaat     11100
acgcgttcgt gtacagacgt aatcatgttt tcttttttgg ataaaactcc tactgagttt    11160
gacctcatat tagaccctca caagttgcaa acgtgtgcat ttttaccaa tgaagaattt     11220 aaagttattt taaaaaattt catcacagat ttaaagaaga accaaaaatt aaattatttc    11280
aacagtttaa tcgaccagtt aatcaacgtg tacacagacg cgtcggcaaa aaacacgcag    11340
cccgacgtgt tggctaaaat tattaaatca acttgtgtta tagtcacgga tttgccgtcc    11400
aacgtgttcc tcaaaagtt gaagaccaac aagtttacgg acactattaa ttatttgatt     11460
ttgccccact tcattttgtg ggatcacaat tttgttatat tttaaacaaa gcttggcact    11520
ggccgtcgtt ttacaacgtc gtgactggga aaaccctggc gttacccaac ttaatcgcct    11580
tgcagcacat ccccctttcg ccagctggcg taatagcgaa gaggcccgca ccgatcgccc    11640
ttcccaacag ttgcgcagcc tgaatggcga atggcgcctg atgcggtatt ttctccttac    11700
gcatctgtgc ggtatttcac accgcatatg gtgcactctc agtacaatct gctctgatgc    11760
cgcatagtta agccagcccc gacacccgcc aacacccgct gacgcgccct gacgggcttg    11820
tctgctcccg gcatccgctt acagacaagc tgtgaccgtc tccgggagct gcatgtgtca    11880
gaggttttca ccgtcatcac cgaaacgcgc gagacgaaag gcctcgtga tacgcctatt      11940 tttataggtt aatgtcatga taataatggt ttcttagacg tcaggtggca cttttcgggg    12000
aaatgtgcgc ggaaccccta tttgtttatt tttctaaata cattcaaata tgtatccgct    12060
catgagacaa taaccctgat aaatgcttca ataatattga aaaggaaga gtatgagtat     12120 tcaacatttc cgtgtcgccc ttattcccct ttttgcggca ttttgccttc ctgttttgc    12180 tcacccagaa acgctggtga agtaaaaga tgctgaagat cagttgggtg cacgagtggg    12240
ttacatcgaa ctggatctca acagcggtaa gatccttgag agttttcgcc ccgaagaacg    12300
ttttccaatg atgagcactt ttaaagttct gctatgtggc gcggtattat cccgtattga    12360
cgccgggcaa gagcaactcg gtcgccgcat acactattct cagaatgact tggttgagta    12420
ctcaccagtc acagaaaagc atcttacgga tggcatgaca gtaagagaat tatgcagtgc    12480
tgccataacc atgagtgata acactgcggc caacttactt ctgacaacga tcggaggacc    12540
gaaggagcta accgcttttt tgcacaacat ggggatcat gtaactcgcc ttgatcgttg     12600
ggaaccggag ctgaatgaag ccataccaaa cgacgagcgt gacaccacga tgcctgtagc    12660
aatggcaaca acgttgcgca aactattaac tggcgaacta cttactctag cttcccggca    12720
acaattaata gactggatgg aggcggataa agttgcagga ccacttctgc gctcggccct    12780
tccggctggc tggtttattg ctgataaatc tggagccggt gagcgtgggt ctcgcggtat    12840
```

```
cattgcagca ctggggccag atggtaagcc ctcccgtatc gtagttatct acacgacggg   12900
gagtcaggca actatggatg aacgaaatag acagatcgct gagataggtg cctcactgat   12960
taagcattgg taactgtcag accaagttta ctcatatata ctttagattg atttaaaact   13020
tcattttaa tttaaaagga tctaggtgaa gatcctttt gataatctca tgaccaaaat     13080
cccttaacgt gagttttcgt tccactgagc gtcagacccc gtagaaaaga tcaaaggatc   13140
ttcttgagat ccttttttc tgcgcgtaat ctgctgcttg caaacaaaaa aaccaccgct    13200
accagcggtg gtttgtttgc cggatcaaga gctaccaact cttttccga aggtaactgg    13260
cttcagcaga gcgcagatac caaatactgt ccttctagtg tagccgtagt taggccacca   13320
cttcaagaac tctgtagcac cgcctacata cctcgctctg ctaatcctgt taccagtggc   13380
tgctgccagt ggcgataagt cgtgtcttac cgggttggac tcaagacgat agttaccgga   13440
taaggcgcag cggtcgggct gaacggggg ttcgtgcaca cagcccagct tggagcgaac    13500
gacctacacc gaactgagat acctacagcg tgagcattga gaaagcgcca cgcttcccga   13560
agggagaaag gcggacaggt atccggtaag cggcagggtc ggaacaggag agcgcacgag   13620
ggagcttcca gggggaaacg cctggtatct ttatagtcct gtcgggtttc gccacctctg   13680
acttgagcgt cgatttttgt gatgctcgtc agggggcgg agcctatgga aaaacgccag    13740
caacgcggcc ttttacggt tcctggcctt ttgctggcct tttgctcaca tgttctttcc   13800
tgcgttatcc cctgattctg tggataaccg tattaccgcc tttgagtgag ctgataccgc   13860
tcgccgcagc cgaacgaccg agcgcagcga gtcagtgagc gaggaagcgg aagagcgccc   13920
aatacgcaaa ccgcctctcc ccgcgcgttg gccgattcat taatgcagct ggcacgacag   13980
gtttcccgac tggaaagcgg gcagtgagcg caacgcaatt aatgtgagtt agctcactca   14040
ttaggcaccc caggctttac actttatgct tccggctcgt atgttgtgtg gaattgtgag   14100
cggataacaa tttcacacag gaaacagcta tgaccatgat tacgaatttc gacctgcagg   14160
catgcaagct tgcatgcctg caggtcgacg ctcgcgcgac ttggtttgcc attctttagc   14220
gcgcgtcgcg tcacacagct tggccacaat gtggttttg tcaaacgaag attctatgac    14280
gtgtttaaag tttaggtcga gtaaagcgca aatctttttt aaccctagaa agatagtctg   14340
cgtaaaattg acgcatgcat tcttgaaata ttgctctctc tttctaaata gcgcgaatcc   14400
gtcgctgtgc atttaggaca tctcagtcgc cgcttggagc tcccgtgagg cgtgcttgtc   14460
aatgcggtaa gtgtcactga ttttgaacta taacgaccgc gtgagtcaaa atgacgcatg   14520
attatctttt acgtgacttt taagatttaa ctcatacgat aattatattg ttatttcatg   14580
ttctacttac gtgataactt attatatata tattttcttg ttatagatat cgtgactaat   14640
atataataaa atgggtagtt ctttagacga tgagcatatc ctctctgctc ttctgcaaag   14700
cgatgacgag cttgttggtg aggattctga cagtgaaata tcagatcacg taagtgaaga   14760
tgacgtccag agcgatacag aagaagcgtt tatagatgag gtacatgaag tgcagccaac   14820
gtcaagcggt agtgaaatat tagacgaaca aaatgttatt gaacaaccag ttcttcatt    14880
ggcttctaac agaatcttga ccttgccaca gaggactatt agaggtaaga ataaacattg   14940
ttggtcaact tcaaagtcca cgaggcgtag ccgagtctct gcactgaaca ttgtcagatc   15000
ggcccggcgg agtggacacg ctagaccaaa tgtgttctgt gatgacctgc agtaggaaga   15060
cgaataggtg gcctatggca ttattgtacg gaatgataaa cattgcctgc ataaattctt   15120
ttattatata cagccataat gtcagtagca agggagaaaa ggtccaaagt cgcaaaaaat   15180
```

```
ttatgagaaa cctttacatg agcctgacgt catcgtttat gcgtaagcgt ttagaagctc    15240
ctactttgaa gagatatttg cgcgataata tctctaatat tttgccaaat gaagtgcctg    15300
gtacatcaga tgacagtact gaagagccag taatgaaaaa acgtacttac tgtacttact    15360
gcccctctaa aataaggcga aaggcaaatg catcgtgcaa aaaatgcaaa aaagttattt    15420
gtcgagagca taatattgat atgtgccaaa gttgtttctg actgactaat aagtataatt    15480
tgtttctatt atgtataagt taagctaatt acttatttta taatacaaca tgactgtttt    15540
taaagtacaa aataagtttta tttttgtaaa agagagaatg tttaaaagtt ttgttacttt    15600
atagaagaaa ttttgagttt ttgttttttt ttaataaata aataaacata aataaattgt    15660
ttgttgaatt tattattagt atgtaagtgt aaatataata aaacttaata tctattcaaa    15720
ttaataaata aacctcgata tacagaccga taaaacacat gcgtcaattt tacgcatgat    15780
tatctttaac gtacgtcaca atatgattat ctttctaggg ttaaaatgaa tgtaagcact    15840
ttattaacga aatctttggg aatatttcgc tcatcagcat tttatttgag caggagtccg    15900
agatgcccgg ccgcgccggc catcgagaaa gagagagaga agagaagaga gagaacattc    15960
gagaaagaga gagagaagag aagagagaga acatactccc tatcagtgat agagaagtcc    16020
ctatcagtga tagagatgtc cctatcagtg atagagagtt ccctatcagt gatagagacg    16080
tccctatcag tgatagagaa gtccctatca gtgatagaga gatccctatc agtgatagag    16140
atttccctat cagtgataga gaggtcccta tcagtgatag agacttccct atcagtgata    16200
gagaaatccc tatcagtgat agagacatcc ctatcagtga tagagaactc cctatcagtg    16260
atagagacct cccctatcagt gatagagatc gatccgtcta cctgagcgat atataaacta    16320
atgcctgttg caattgttca gtcagtcacg agtttgttac cactgcgaca agctagcaac    16380
caccatggcg gtaattctaa ttacttacta aatatagtga tatttaaaaa tgctatgaga    16440
tcttgaggcg aacttaaatg agacaaggtg ttagcttgct caaatgacgc accaatcaac    16500
ttaccaagat aatttggagc aatatggaat attttcttgt caaagaacta caatcaacat    16560
gcaactggta taataaagtg agtataaagt agaaaggtgc ggtataatat ttttctctaa    16620
agtattaagg taagttttta aaaataattt aataattttt cagagtgtgc agtattagtg    16680
tctaaaagta ttgcaatctt tgtgttttaa aaatttgtgc agaatatcaa aaaataggac    16740
gacctattgt tagtaatatt atgtatattt acttattttc aaataaataa aattattttc    16800
tagcctttag aaacagcctt atactacaat caacaaacca taaatactcc ctgcaacaat    16860
tacaaagcaa cacaaacaac aatcaacatt ccatgaactc ggacaatttg gaaattgata    16920
tcttctggca catgcggatt acaacaatca actcaaacct attagatgat gtaaataaat    16980
ataaaccttc atattcaata acttaattcg tgatagaaat ttagagttaa ttactgttta    17040
atcgaaattt gaacgtctcg tttgaattca ctttaacgtt tgaaagatga tctttaaata    17100
gtgactggag acttaaattt taatctttt aattaaataa tctaacaaag ttctttctta    17160
ttctaatctt aatatataat cttgttttaa aatttgaatt aaacttattt cgttgagtaa    17220
caattaaatg atttgaatcg taaaaaatat cattataatt attcaacaaa aagctgaagg    17280
ctgcgatgaa aaattgttga tatataaatc aaatttattt ttataaatca ctaatagtga    17340
cattaaccgt attcacaggt ggccttctac atcccggatc aggccaccct gctgcgcgag    17400
gccgagcagc gcgagcagca gatcctgcgc ctgcgcgaga gccagtggcg cttcctggcc    17460
accgtggtgc tggagaccct gcgccagtac accagctgcc acccgcgcac cggccgccgc    17520
agcggccgtt accgccgtcc gagccagtaa caccggtgat cataatcagc cataccacat    17580
```

```
ttgtagaggt tttacttgct ttaaaaaacc tcccacacct cccctgaac ctgaaacata   17640 aaatgaatgc aattgttgtt gttaacttgt ttattgcagc ttataatggt tacaaataaa   17700
gcaatagcat cacaaatttc acaaataaag catttttttc actgcattct agttgtggtt   17760
tgtccaaact catcaatgta tcttaacgcg agtttaggcg cg                      17802
```

<210> SEQ ID NO 56
<211> LENGTH: 15134
<212> TYPE: DNA
<213> ORGANISM: Artificial Sequence
<220> FEATURE:
<223> OTHER INFORMATION: Synthetic construct, pLA3242-Crtra intron-
      reaperKR construct.

<400> SEQUENCE: 56

```
gggcggccgt ttttcttgaa atattgctct ctctttctaa atagcgcgaa tccgtcgctg     60
tgcatttagg acatctcagt cgccgcttgg agctcccaaa cgcgccagtg gtagtacaca    120
gtactgtggg tgttcagttt gaaatcctct tgcttctcca ttgtctcggt tacctttggt    180
caaatccatg ggttctattg cctatatact cttgcgatta ccagtgattg cgctattagc    240
tattagatgg attgttggcc aaacttgtcg cttaagtggc tgggaattgt aaccgtaggc    300
ccgagtgtaa tgatccccca taaaaagttt tcgcaatgcc tttatttttt gttgcaaatc    360
tctctttatt ctgcggtatt cttcattatt gcggggatgg ggaaagtgtt tatatagaag    420
caacttacga ttgaacccaa atgcacctga caagcaaggt caagggcca gatttttaaa     480 tatattattt agtcttagga ctctctattt gcaattaaat tactttgcta cctgagggtt    540
aaatcttccc cattgataat aataattcca ctatatgttc aattgggttt caccgcgctt    600
agttacatga cgagccctaa tgagccgtcg gtggtctata aactgtgcct tacaaatact    660
tgcaactctt ctcgttttga agtcagcaga gttattgcta attgctaatt gctaattgct    720
tttaactgat ttcttcgaaa ttggtgctat gtttatggcg ctattaacaa gtatgaatgt    780
caggtttaac caggggatgc ttaattgtgt tctcaacttc aaaggcagaa atgtttactc    840
ttgaccatgg gttaggtat aatgttatca agctcctcga gttaacgtta cgttaacgtt     900
aacgttcgag gtcgactcta gaactaccca ccgtactcgt caattccaag gcatcggta    960 aacatctgct caaactcgaa gtcggccata tccagagcgc gtaggggc ggagtcgtgg    1020 ggggtaaatc ccggacccgg ggaatccccg tccccaaca tgtccagatc gaaatcgtct   1080
agcgcgtcgg catgcgccat cgccacgtcc tcgccgtcta agtggagctc gtccccagg   1140 ctgacatcgg tcgggggggc cgtcgacagt ctgcgcgtgt gtcccgcggg gagaaaggac  1200
aggcgcggag ccgccagccc cgcctcttcg ggggcgtcgt cgtccgggag atcgagcagg  1260
ccctcgatgg tagacccgta attgtttttc gtacgcgcgc ggctgtacgc ggggcccgag  1320
cccgactcgc atttcagttg ctttttccaat ccgcagataa tcagctccaa gccgaacagg  1380
aatgccggct cggctccttg atgatcgaac agctcgattg cctgacgcag cagtgggggc  1440
atcgaatcgg ttgttggggt ctcgcgctcc tcttttgcga cttgatgctc ttggtcctcc   1500
agcacgcagc ccagggtaaa gtgaccgacg gcgctcagag cgtagagagc attttccagg   1560
ctgaagcctt gctggcacag gaacgcgagc tggttctcca gtgtctcgta ttgcttttcg   1620
gtcgggcgcg tgccgagatg gactttggca ccgtctcggt gggacagcag agcgcagcgg   1680
aacgacttgg cgttattgcg gaggaagtcc tgccaggact cgccttccaa cgggcaaaaa   1740
tgcgtgtggt ggcggtcgag catctcgatg gccagggcat ccagcagcgc ccgcttattc   1800
```

```
ttcacgtgcc agtagagggt gggctgctcc acgcccagct tctgcgccaa cttgcgggtc    1860
gtcagtccct caatgccaac ttcgttcaac agctccaacg cggagttgat gactttggac    1920
ttatccaggc ggctgaccta tagataccat agatgtatgg attagtatca tatacataca    1980
aaggctattt ttgggacata ttaatattaa caatttccgt gatagttttc accattttg     2040 ttgaatgtta cgttgaaaat ttaaatttgt tttaaattaa ttttaccagt catgtgttct    2100
taaaagtttt tatgattgaa acggcataaa gtggttcaaa aatttatcaa gaaaggcttt    2160
ccttttttaa atcttatctt tttctcttaa aaatcactag tcaattcatt attaatttgt    2220
taacttgaat ttggaatgtc tatttacttt cagataaatt aaagcaagaa acttaatatt    2280
cgaaaaaaat tgattctaaa tggaatttca cttgatcttc atgtatgcat atcaattttt    2340
atttacattg tataataagt ttcgagttga ttgttgtaat ccacaggtgt cccagagaat    2400
taaattccaa attacccaag tttattgaat gttgattgta gtttcagttg ctttgttgct    2460
gcaacaatgg cttgttgatt gtagatattt tccctttcct tggtttactt attacataga    2520
ctgaaaaaga ggtttacttt tttgatactt atgaaaaatt tctattagtg attactaacc    2580
aatcgctata tgtttactag aaaacaaata aactctttac attaacattc aataatgttt    2640
gctctgtaac cgacaattga aggcgttaca gcaacagtaa tataactagc ttcttaaccc    2700
tcatctatta accccatcgt ttaaaacact atgttaaatg gtctaacaaa tctagatact    2760
aatagatgtc ttattactta gcagccacag ctgcaacatc caagacaatt tttgaaactt    2820
cttattgagc tcttggcagc agaaatgttg gtattttca cagctttctg aaagaccggc     2880
accttcctcc ggttcccgtt tctgaattca agaggatttc cgaccccaa ttaatcccga     2940 aacaaataag gtatattcaa aatgatgaa aagtcatggc tgctgacctt attttattc      3000 ctattgatag aatattattc ccctttaaa tacactgtac taagaggtcc ggctataatt     3060
ttactcactt gtcgattatc ccatagaatg ttgattgtag ttggttgctt ttccaggtga    3120
gagttgatca agtcacaaaa gttagcgtgt gttgattgta gatttgaagg taaaataatt    3180
tttgcaccca ttcatcgggt aaaacgttct ccatagaata catttccatc gataattgat    3240
aacttatgaa tttcaaagaa aaaaatatgc ttttaaaatt accatggtgg ctagcgcaga    3300
ttgtttagct tgttcagctg cgcttgttta tttgcttagc tttcgcttag cgacgtgttc    3360
actttgcttg tttgaattga attgtcgctc cgtagacgaa gcgcctctat ttatactccg    3420
gcgctcgttt tcgagtttac cactccctat cagtgataga aaaagtgaa agtcgagttt     3480 accactccct atcagtgata gagaaaagtg aaagtcgagt ttaccactcc ctatcagtga    3540
tagagaaaag tgaaagtcga gtttaccact ccctatcagt gatagagaaa agtgaaagtc    3600
gagtttacca ctccctatca gtgatagaga aagtgaaag tcgagtttac cactccctat     3660
cagtgataga gaaagtgaa agtcgagttt accactccct atcagtgata gagaaaagtg    3720
aaagtcgaaa cctggcgcgc ctaaactcgc gttaagatac attgatgagt ttggacaaac    3780
cacaactaga atgcagtgaa aaaaatgctt tatttgtgaa atttgtgatg ctattgcttt    3840
atttgtaacc attataagct gcaataaaca agttaacaac aacaattgca ttcattttat    3900
gtttcaggtt cagggggagg tgtgggaggt ttttaaagc aagtaaaacc tctacaaatg     3960
tggtatggct gattatgatc accggtgtta ctggctcgga cggcggtaac ggccgctgcg    4020
gcggccggtg cgcgggtggc agctggtgta ctggcgcagg gtctccagca ccacggtggc    4080
caggaagcgc cactggctct cgcgcaggcg caggatctgc tgctcgcgct gctcggcctc    4140
```

```
gcgcagcagg gtggcctgat ccgggatgta gaaggccacc taaagatacc atggatgtat    4200
gaattagtat catatacata taaatgcttt ttttttttggc atattaatgt taaaaatatc    4260
aacaatttcc gtgatagttt ttaccatttt tgttgaatgt ttactttgaa aacttaaata    4320
ttttttaact aattttacca gtcatgtgtt attaaaagta tttatgaata aaactgcaag    4380
taaagcgttt caaaaattta tcaagtaaaa ctttactttt tttaaatctt aactgtcaat    4440
tcattattaa tttattaatt taaatttgca atgtctattt actttaagac aaattaaagc    4500
aagaaactaa atattcgaat caattctttt ttaaatgaaa ttttacttca tcatcatgta    4560
tgtgtgtatc aattttttatt tacattgtat aataagtttc gagttgattg ttgtaatccg    4620
caggtgtccc gaagtattaa attccgaatt cccaagttta ttgaatgttg attgtagttt    4680
cagttgtttt gttattgcaa caatggcttg ttgattggag atattttcct tttccttggt    4740
ttacttacta catagactga aaaagatgtt tgactttttt gatactattg taaaatttct    4800
attagtgatt actaaccaat cgctataagt ttaatagaaa acaaataaac tctttgcatc    4860
cagatatacc tagcttctta acccttatct attaactcca ttgcttgtaa caaatctaga    4920
tattaataga tgtctaatta cttagcaaaa cttcttttttg attaagcagc cacagctgtc    4980
gattttggtc atatttaaag gaaataaatg cgtttaaaat aataattaat ataagttttg    5040
aaacttttta ctaacacttg gcagcaggaa gtaggtgttt ttcacagctt tctgaaccac    5100
cggcaccttc cccggtctcc gttgtcgagt tcagcagga tttccggccc ccaattaacc    5160
ccgaaacaaa acatgtctta ttaataaggt gtattcaaaa tagtgggaat gtcatgactg    5220 ctgacccttat ttttattcct attgtaagtg ttccggctat aattttactc acttgtccat    5280
tatcccatag aatgttatgt tgattgtagt tgtttgcttt tccaggtgag agttgatcaa    5340
gtcgcaaaag ttagcgtgtg ttgattgtag atttgaaggt aaaataattt tgtacacatt    5400
catcaggcaa aacgttctcc atcgaataaa cttccatcga taattgatag cttatgaatt    5460
tcaaaaaaaa atatgctttt aaaattaccg ccatggtggt tgctagcttg tcgcagtggt    5520
aacaaactcg tgactgactg aacaattgca acaggcatta gtttatatat cgctcaggta    5580
gacggatcga tctctatcac tgatagggag gtctctatca ctgataggga gttctctatc    5640
actgataggg atgtctctat cactgatagg gatttctcta tcactgatag ggaagtctct    5700
atcactgata gggaccctctc tatcactgat agggaaatct ctatcactga tgggatctc    5760 tctatcactg ataggggactt ctctatcact gatagggacg tctctatcac tgatagggaa    5820
ctctctatca ctgataggga catctctatc actgataggg acttctctat cactgatagg    5880
gagtatgttc tctctcttct cttctctctc tctttctcga atgttctctc tcttctcttc    5940
tctctctctt tctcgatggc cggcctggct taattaactc gcgttaagat acattgatga    6000
gtttggacaa accacaacta gaatgcagtg aaaaaaatgc tttatttgtg aaatttgtga    6060
tgctattgct ttatttgtaa ccattataag ctgcaataaa caagttaaca acaacaattg    6120
cattcatttt atgtttcagg ttcagggggga ggtgtgggag gttttttaaa gcaagtaaaa    6180
cctctacaaa tgtggtatgg ctgattatga tcagttatct agatccggtg gatcttacgg    6240
gtcctccacc ttccgctttt tcttgggtcg agatctgagt ccggaatcct cgtcgctacc    6300
gatggcgctg gtgatgcggg gcacgctgtg ggcgtaggtc acctcgcgct ggcacacgtg    6360
gtcgcgcttg tcgctggtgt ccctcatctg cttggtgatg atggtcacga agtggggggcc    6420 ggggatcttg atggcgcggc tgccgttgaa ggtcatcttg ctgtcgaagt ggcccatcat    6480
caggccgccg tcggcggtgg tgaagccgat gaaggccagc tggcgcacgg cgttggggcc    6540
```

```
gtgggggaac atgtgggtct cgttgggcag gatgtccacc agctggtcgc gcatgatggg    6600
gccgtcgggc tggaagccgt cgcagttcac ggtgatgcgg ctgaccacgc aggtgccgtc    6660
cagctcgtag gtgtggtggc tggtcatggt gccgtcgttc tcgaagcgca cggtgcggtc    6720
gatgctcagg ccctcgggga agcactcctg ggcgaagtgg ctgatgccgt tggggtagcg    6780
ggcgaagaag ggctcgccgt actggatcag gtggcagatg ggcttccagc tcatgggcag    6840
cttgccggtc tcgcacacgg cgtgcacgtt gaagtcgccg tgggggaact tgctgctgcc    6900
gtcggccacg atggtgaact tctggccgtt cacctcgccg tcgatgaaga ttttgaaggt    6960
catgtcgctc tggaacaggg cggggccgcc ctctgaacca tcctcgtcca tggtggcgac    7020
cggtttgcgc ttcttcttgg gtggggtggg atctcccatg gtggcctgaa tctcaacttg    7080
cacctgaagg tagtgcagca aggatgagca aaagggaaga acccagaaaa gaacgggaaa    7140 acttaccccca attagaattg cttgtcgccg ccagtgtcaa cttgcaactg aaacaatatc    7200
caacatgaac gtcaatttat actgccctaa tggcgaacac gataacaata tttcttttat    7260
tatgccctct aaaaccaacg cggttatcgt ttatttattc aaattagata tagaacatcc    7320
gccgacatac aatgttaatg caaaaacgcg tttggtgagc ggatacgaaa acagtcggcc    7380
gataaacatt aatctgaggt cgataacacc gtccttgaac ggaacacgag gagcgtacgt    7440
gatcagctgc attcgcgcgc cgcgccttta tcgagattta tttgcataca acaagtacac    7500
tgcgccgttg ggatttgtgg taacgcgcac acatgcagag ctgcaagtgt ggcacatttt    7560
gtctgtgcgc aaaaccttg aagccaaaag tacgaggtcc gttacgggca tgctagcgca    7620
cacggacaat ggacccgaca aattctacgc caaggattta atgataatgt cgggcaacgt    7680
atccgttcat tttatcaata acctacaaaa atgtcgcgcg catcacaaag acatcgatat    7740
atttaaacat ttatgtcccg aactgcaaat cgataatagt gttgtgcaac ctcgagcgtc    7800
cgtttgattt aacgtatagc ttgcaaatga attatttaat tatcaatcat gttttacgcg    7860
tagaattcta cccgtaaagc gagtttagtt atgagccatg tgcaaaacat gacatcagct    7920 tttatttta taacaaatga catcatttct tgattgtgtt ttacacgtag aattctactc    7980
gtaaagcgag ttcagttttg aaaaacaaat gacatcatct ttttgattgt gctttacaag    8040
tagaattcta cccgtaaatc aagttcggtt ttgaaaaaca aatgagtcat attgtatgat    8100
atcatattgc aaaacaaatg actcatcaat cgatcgtgcg ttacacgtag aattctactc    8160
gtaaagcgag tttatgagcc gtgtgcaaaa catgacatca tctcgatttg aaaaacaaat    8220
gacatcatcc actgatcgtg cattacaagt agaattctac tcgtaaagcc agttcggtta    8280
tgagccgtgt acaaaacatg acatcagatt atgactcata cttgattgtg ttttacgcgt    8340
agaattctac tcgtaaagcc agttcaattt taaaaacaaa tgacatcatc caaattaata    8400
aatgacaagc aatgggtacc atgcggccgc accgaaatcg taattcacgg catcattaca    8460
aaatattttg acgttttgga cctcgtccct aatgacacca taacggtggc cttgaagtat    8520
atttaaccct agaaagatag tctgcgtaaa attgacgcat gcattcttga atattgctc     8580 tctctttcta aatagcgcga atccgtcgct gtgcatttag dacatctcag tcgccgcttg    8640
gagctcccgt gaggcgtgct tgtcaatgcg gtaagtgtca ctgattttga actataacga    8700
ccgcgtgagt caaatgacg catgattatc ttttacgtga cttttaagat ttaactcata    8760
cgataattat attgttattt catgttctac ttacgtgata acttattata tatatatttt    8820
cttgttatag atatcgtgac taatatataa taaaatgggt agttctttag acgatgagca    8880
```

```
tatcctctct gctcttctgc aaagcgatga cgagcttgtt ggtgaggatt ctgacagtga    8940
aatatcagat cacgtaagtg aagatgacgt ccaggaaatc tggccggccg caaccattgt    9000
gggaaccgtg cgatcaaaca aacgcgagat accggaagta ctgaaaaaca gtcgctccag    9060
gccagtggga acatcgatgt tttgttttga cggacccctt actctcgtct catataaacc    9120
gaagccagct aagatggtat acttattatc atcttgtgat gaggatgctt ctatcaacga    9180
aagtaccggt aaaccgcaaa tggttatgta ttataatcaa actaaaggcg gagtggacac    9240
gctagaccaa atgtgttctg tgatgacctg cagtaggaag acgaataggt ggcctatggc    9300
attattgtac ggaatgataa acattgcctg cataaattct tttattatat acagccataa    9360
tgtcagtagc aagggagaaa aggtccaaag tcgcaaaaaa tttatgagaa accttttacat   9420
gagcctgacg tcatcgttta tgcgtaagcg tttagaagct cctactttga agagatattt    9480
gcgcgataat atctctaata ttttgccaaa tgaagtgcct ggtacatcag atgacagtac    9540
tgaagagcca gtaatgaaaa aacgtactta ctgtacttac tgcccctcta aataaggcg    9600
aaaggcaaat gcatcgtgca aaaatgcaa aaaagttatt tgtcgagagc ataatattga     9660
tatgtgccaa agttgtttct gactgactaa taagtataat ttgtttctat tatgtataag    9720
ttaagctaat tacttatttt ataatacaac atgactgttt ttaaagtaca aaataagttt    9780
attttttgtaa aagagagaat gtttaaaagt tttgttactt tatagaagaa attttgagtt   9840
tttgttttt tttaataaat aaataaacat aaataaattg tttgttgaat ttattattag    9900
tatgtaagtg taaatataat aaaacttaat atctattcaa attaataaat aaacctcgat    9960
atacagaccg ataaaacaca tgcgtcaatt ttacgcatga ttatctttaa cgtacgtcac   10020
aatatgatta tctttctagg gttaaataat agtttctaat ttttttatta ttcagcctgc   10080
tgtcgtgaat accgtatatc tcaacgctgt ctgtgagatt gtcgtattct agccttttta   10140
gtttttcgct catcgacttg atattgtccg acacattttc gtcgatttgc gttttgatca   10200
aagacttgag cagagacacg ttaatcaact gttcaaattg atccatatta acgatatcaa   10260
cccgatgcgt atatggtgcg taaaatatat tttttaaccc tcttatactt tgcactctgc   10320
gttaatacgc gttcgtgtac agacgtaatc atgttttctt ttttggataa aactcctact   10380
gagtttgacc tcatattaga ccctcacaag ttgcaaaacg tggcattttt taccaatgaa   10440
gaatttaaag ttatttttaaa aaatttcatc acagatttaa agaagaacca aaaattaaat   10500
tatttcaaca gtttaatcga ccagttaatc aacgtgtaca cagacgcgtc ggcaaaaaac   10560
acgcagcccg acgtgttggc taaaattatt aaatcaactt gtgttatagt cacggatttg   10620
ccgtccaacg tgttcctcaa aaagttgaag accaacaagt ttacggacac tattaattat   10680
ttgattttgc cccacttcat tttgtgggat cacaattttg ttatatttta aacaaagctt   10740
ggcactggcc gtcgttttac aacgtcgtga ctgggaaaac cctggcgtta cccaacttaa   10800
tcgccttgca gcacatcccc ctttcgccag ctggcgtaat agcgaagagg cccgcaccga   10860
tcgcccttcc caacagttgc gcagcctgaa tggcgaatgg cgcctgatgc ggtatttct    10920
ccttacgcat ctgtgcggta tttcacaccg catatggtgc actctcagta caatctgctc   10980
tgatgccgca tagttaagcc agccccgaca cccgccaaca cccgctgacg cgccctgacg   11040
ggcttgtctg ctcccggcat ccgcttacag acaagctgtg accgtctccg ggagctgcat   11100
gtgtcagagg ttttcaccgt catcaccgaa acgcgcgaga cgaaagggcc tcgtgatacg   11160
cctattttta taggttaatg tcatgataat aatggtttct tagacgtcag gtggcacttt   11220
tcggggaaat gtgcgcggaa cccctatttg tttatttttc taaatacatt caaatatgta   11280
```

```
tccgctcatg agacaataac cctgataaat gcttcaataa tattgaaaaa ggaagagtat    11340
gagtattcaa catttccgtg tcgcccttat tcccttttt gcggcatttt gccttcctgt    11400
ttttgctcac ccagaaacgc tggtgaaagt aaaagatgct gaagatcagt tgggtgcacg    11460
agtgggttac atcgaactgg atctcaacag cggtaagatc cttgagagtt ttcgccccga    11520
agaacgtttt ccaatgatga gcactttta agttctgcta tgtggcgcgg tattatcccg    11580
tattgacgcc gggcaagagc aactcggtcg ccgcatacac tattctcaga atgacttggt    11640
tgagtactca ccagtcacag aaaagcatct tacggatggc atgacagtaa gagaattatg    11700
cagtgctgcc ataaccatga gtgataacac tgcggccaac ttacttctga caacgatcgg    11760
aggaccgaag gagctaaccg cttttttgca acatggggg gatcatgtaa ctcgccttga    11820
tcgttgggaa ccgagctga atgaagccat accaaacgac gagcgtgaca ccacgatgcc    11880
tgtagcaatg gcaacaacgt tgcgcaaact attaactggc gaactactta ctctagcttc    11940
ccggcaacaa ttaatagact ggatggaggc ggataaagtt gcaggaccac ttctgcgctc    12000
ggcccttccg gctggctggt ttattgctga taaatctgga gccggtgagc gtgggtctcg    12060
cggtatcatt gcagcactgg ggccagatgg taagccctcc cgtatcgtag ttatctacac    12120
gacggggagt caggcaacta tggatgaacg aaatagacag atcgctgaga taggtgcctc    12180
actgattaag cattggtaac tgtcagacca agtttactca tatatacttt agattgattt    12240
aaaacttcat ttttaattta aaaggatcta ggtgaagatc ctttttgata atctcatgac    12300
caaaatccct taacgtgagt tttcgttcca ctgagcgtca gacccgtag aaaagatcaa    12360 aggatcttct tgagatcctt ttttttctgcg cgtaatctgc tgcttgcaaa caaaaaaacc    12420
accgctacca gcggtggttt gtttgccgga tcaagagcta ccaactcttt ttccgaaggt    12480
aactggcttc agcagagcgc agataccaaa tactgtcctt ctagtgtagc cgtagttagg    12540
ccaccacttc aagaactctg tagcaccgcc tacatacctc gctctgctaa tcctgttacc    12600
agtggctgct gccagtggcg ataagtcgtg tcttaccggg ttggactcaa gacgatagtt    12660
accggataag gcgcagcggt cgggctgaac ggggggttcg tgcacacagc ccagcttgga    12720
gcgaacgacc tacaccgaac tgagatacct acagcgtgag cattgagaaa gcgccacgct    12780
tcccgaaggg agaaaggcgg acaggtatcc ggtaagcggc agggtcggaa caggagagcg    12840
cacgagggag cttccagggg gaaacgcctg gtatctttat agtcctgtcg ggtttcgcca    12900
cctctgactt gagcgtcgat ttttgtgatg ctcgtcaggg gggcggagcc tatggaaaaa    12960
cgccagcaac gcggcctttt tacggttcct ggccttttg ctggccttttg ctcacatgtt    13020 ctttcctgcg ttatcccctg attctgtgga taaccgtatt accgcctttg agtgagctga    13080
taccgctcgc cgcagccgaa cgaccgagcg cagcgagtca gtgagcgagg aagcggaaga    13140
gcgcccaata cgcaaaccgc ctctccccgc gcgttggccg attcattaat gcagctggca    13200
cgacaggttt cccgactgga aagcgggcag tgagcgcaac gcaattaatg tgagttagct    13260
cactcattag gcaccccagg ctttacactt tatgcttccg gctcgtatgt tgtgtggaat    13320
tgtgagcgga taacaatttc acacaggaaa cagctatgac catgattacg aatttcgacc    13380
tgcaggcatg caagcttgca tgcctgcagg tcgacgctcg cgcgacttgg tttgccattc    13440
tttagcgcgc gtcgcgtcac acagcttggc cacaatgtgg ttttttgtcaa acgaagattc    13500 tatgacgtgt ttaaagttta ggtcgagtaa agcgcaaatc ttttttaacc ctagaaagat    13560
agtctgcgta aaattgacgc atgcattctt gaaatattgc tctctctttc taaatagcgc    13620
```

-continued

```
gaatccgtcg ctgtgcattt aggacatctc agtcgccgct tggagctccc gtgaggcgtg      13680
cttgtcaatg cggtaagtgt cactgatttt gaactataac gaccgcgtga gtcaaaatga      13740
cgcatgatta tcttttacgt gacttttaag atttaactca tacgataatt atattgttat      13800
ttcatgttct acttacgtga taacttatta tatatatatt ttcttgttat agatatcgtg      13860
actaatatat aataaaatgg gtagttcttt agacgatgag catatcctct ctgctcttct      13920
gcaaagcgat gacgagcttg ttggtgagga ttctgacagt gaaatatcag atcacgtaag      13980
tgaagatgac gtccagagcg atacagaaga agcgtttata gatgaggtac atgaagtgca      14040
gccaacgtca agcggtagtg aaatattaga cgaacaaaat gttattgaac aaccaggttc      14100
ttcattggct tctaacagaa tcttgacctt gccacagagg actattagag gtaagaataa      14160
acattgttgg tcaacttcaa agtccacgag gcgtagccga gtctctgcac tgaacattgt      14220
cagatcggcc cggcggagtg gacacgctag accaaatgtg ttctgtgatg acctgcagta      14280
ggaagacgaa taggtggcct atggcattat tgtacggaat gataaacatt gcctgcataa      14340 attctttat tatatacagc cataatgtca gtagcaaggg agaaaaggtc caaagtcgca      14400
aaaaatttat gagaaacctt tacatgagcc tgacgtcatc gtttatgcgt aagcgtttag      14460
aagctcctac tttgaagaga tatttgcgcg ataatatctc taatattttg ccaaatgaag      14520
tgcctggtac atcagatgac agtactgaag agccagtaat gaaaaaacgt acttactgta      14580
cttactgccc ctctaaaata aggcgaaagg caaatgcatc gtgcaaaaaa tgcaaaaaag      14640
ttatttgtcg agagcataat attgatatgt gccaaagttg tttctgactg actaataagt      14700
ataatttgtt tctattatgt ataagttaag ctaattactt attttataat acaacatgac      14760 tgttttaaa gtacaaaata agtttatttt tgtaaaagag agaatgttta aaagttttgt      14820
tactttatag aagaaatttt gagttttgt ttttttttaa taaataaata aacataaata      14880
aattgtttgt tgaatttatt attagtatgt aagtgtaaat ataataaaac ttaatatcta      14940
ttcaaattaa taaataaacc tcgatataca gaccgataaa acacatgcgt caattttacg      15000
catgattatc tttaacgtac gtcacaatat gattatcttt ctagggttaa aatgaatgta      15060
agcactttat taacgaaatc tttgggaata tttcgctcat cagcattta tttgagcagg      15120 agtccgagat gccc                                                        15134
```

<210> SEQ ID NO 57
<211> LENGTH: 1403
<212> TYPE: DNA
<213> ORGANISM: Artificial Sequence
<220> FEATURE:
<223> OTHER INFORMATION: Synthetic construct, partial sequence of a male
    transcript generated in Drosophila melanogaster from LA3077
    transformants that differs to the sequence generated in Medfly
    LA3077 lines.

<400> SEQUENCE: 57

```
ggccagatct gttgttatta aacgtagatt tggtaatttt aaaagcatat ttttttcttt       60
gaaattcata agttatcaat tatcgatgga aatgtattct atggagaacg ttttacccga      120
tgaatgggtg caaaaattat tttaccttca aatctacaat caacacacgc taactttgt      180 gacttgatca actctcacct ggaaaagcaa ccaactacaa tcaacattct atgggataat      240
cgacaagtga gtaaaattat agccggacct cttagtacag tgtatttaaa aggggaataa      300
tattctatca ataggaataa aaataaggtc agcagccatg acttttccat cattttgaat      360
ataccttatt tgtttcggga ttaattgggg gtcggaaatc ctcttgaatt cagaaacggg      420
```

-continued aaccggagga aggtgccggt ctttcagaaa gctgtgaaaa ataccaacat ttctgctgcc 480
aagagctcaa taagaagttt caaaaattgt cttggatgtt gcagctgtgg ctgctaagta 540
ataagacatc tattagtatc tagatttgtt agaccattta acatagtgtt ttaaacgatg 600
gggttaatag atgagggtta agaagctagt tatattactg ttgctgtaac gccttcaatt 660
gtcggttaca gagcaaacat tattgaatgt taatgtaaag agtttatttg ttttctagta 720
aacatatagc gattggttag taatcactaa tagaaatttt tcataagtat caaaaaagta 780
aacctctttt tcagtctatg taataagtaa accaaggaaa gggaaaatat ctacaatcaa 840
caagccattg ttgcagcaac aaagcaactg aaactacaat caacattcaa taaacttggg 900
taatttggaa tttaattctc tgggacacct gtggattaca acaatcaact cgaaacttat 960
tatacaatgt aaataaaaat tgatatgcat acatgaagat caagtgaaat tccatttaga 1020
atcaattttt ttcgaatatt aagtttcttg ctttaattta tctgaaagta aatagacatt 1080
ccaaattcaa gttaacaaat taataatgaa ttgactagtg atttttaaga gaaaaagata 1140
agatttaaaa aaggaaagcc tttcttgata aatttttgaa ccactttatg ccgtttcaat 1200
cataaaaact tttaagaaca catgactggt aaaattaatt taaaacaaat ttaaattttc 1260
aacgtaacat tcaacaaaaa tggtgaaaac tatcacggaa attgttaata ttaatatgtc 1320
ccaaaaatag cctttgtatg tatatgatac taatccatac atctatggta tctataggtg 1380
aaggctcaaa gcctctggct agc 1403

<210> SEQ ID NO 58
<211> LENGTH: 972
<212> TYPE: DNA
<213> ORGANISM: Bactrocera zonata

<400> SEQUENCE: 58
cggtaattct aattacttac taaatatagt gatatttaaa aatgctatga gatcttgagg 60
cgaacttaaa tgagacaagg tgttagcttg ctcaaatgac gcaccaatca acttaccaag 120
ataatttgga gcaatatgga atattttctt gtcaaagaac tacaatcaac atgcaactgg 180
tataataaag tgagtataaa gtagaaaggt gcggtataat atttttctct aaagtattaa 240
ggtaagtttt taaaaataat ttaataattt ttcagagtgt gcagtattag tgtctaaaag 300
tattgcaatc tttgtgtttt aaaaatttgt gcagaatatc aaaaaatagg acgacctatt 360
gttagtaata ttatgtatat ttacttattt tcaaataaat aaaattattt tctagccttt 420
agaaacagcc ttatactaca atcaacaaac cataaatact ccctgcaaca attacaaagc 480
aacacaaaca acaatcaaca ttccatgaac tcggacaatt tggaaattga tatcttctgg 540
cacatgcgga ttacaacaat caactcaaac ctattagatg atgtaaataa atataaacct 600
tcatattcaa taacttaatt cgtgatagaa atttagagtt aattactgtt taatcgaaat 660
ttgaacgtct cgtttgaatt cactttaacg tttgaaagat gatctttaaa tagtgactgg 720
agacttaaat tttaatcttt ttaattaaat aatctaacaa agttctttct tattctaatc 780
ttaatatata atcttgtttt aaaatttgaa ttaaacttat ttcgttgagt aacaattaaa 840
tgatttgaat cgtaaaaaat atcattataa ttattcaaca aaaagctgaa ggctgcgatg 900
aaaaattgtt gatatataaa tcaaatttat ttttataaat cactaatagt gacattaacc 960
gtattcacag gt 972

<210> SEQ ID NO 59
<211> LENGTH: 1312

```
<212> TYPE: DNA
<213> ORGANISM: Ceratitis rosa

<400> SEQUENCE: 59
tggtaatttt aaaagcatat ttttttttga aattcataag ctatcaatta tcgatggaag      60
tttattcgat ggagaacgtt ttgcctgatg aatgtgtaca aaattatttt accttcaaat    120
ctacaatcaa cacacgctaa cttttgcgac ttgatcaact ctcacctgga aaagcaaaca    180
actacaatca acataacatt ctatgggata atggacaagt gagtaaaatt atagccggaa    240
cacttacaat aggaataaaa ataaggtcag cagtcatgac attcccacta ttttgaatac    300
accttattaa taagacatgt tttgtttcgg ggttaattgg gggccggaaa tcctgctgaa    360
ctccgacaac ggagaccggg gaaggtgccg gtggttcaga aagctgtgaa aaacacctac    420
ttcctgctgc caagtgttag taaaaagttt caaaacttat attaattatt attttaaacg    480
catttatttc ctttaaatat gaccaaaatc gacagctgtg gctgcttaat caaaagaag     540
ttttgctaag taattagaca tctattaata tctagatttg ttacaagcaa tggagttaat    600
agataagggt taagaagcta ggtatatctg gatgcaaaga gtttatttgt tttctattaa    660
acttatagcg attggttagt aatcactaat agaaatttta caatagtatc aaaaaagtca    720
aacatctttt tcagtctatg tagtaagtaa accaaggaaa aggaaaatat ctccaatcaa    780
caagccattg ttgcaataac aaaacaactg aaactacaat caacattcaa taaacttggg    840
aattcggaat ttaatacttc gggacacctg cggattacaa caatcaactc gaaacttatt    900
atacaatgta aataaaaatt gatacacaca tacatgatga tgaagtaaaa tttcatttaa    960
aaagaattg attcgaatat ttagtttctt gctttaattt gtcttaaagt aaatagacat   1020
tgcaaattta aattaataaa ttaataatga attgacagtt aagatttaaa aaaagtaaag   1080
ttttacttga taaattttg aaacgctta cttgcagttt tattcataaa tacttttaat    1140
aacacatgac tggtaaaatt agttaaaaaa tatttaagtt ttcaaagtaa acattcaaca   1200
aaaatggtaa aaactatcac ggaaattgtt gatatttta acattaatat gccaaaaaaa   1260
aaagcattta tatgtatatg atactaattc atacatccat ggtatcttta gg           1312

<210> SEQ ID NO 60
<211> LENGTH: 21
<212> TYPE: DNA
<213> ORGANISM: Artificial Sequence
<220> FEATURE:
<223> OTHER INFORMATION: Synthetic construct, spl-agdsx-e3 primer

<400> SEQUENCE: 60
cgagcccaat ggctgttgga g                                                21

<210> SEQ ID NO 61
<211> LENGTH: 22
<212> TYPE: DNA
<213> ORGANISM: Artificial Sequence
<220> FEATURE:
<223> OTHER INFORMATION: Synthetic construct, spl-agdsx-m primer

<400> SEQUENCE: 61
gtcaaggttc agggcccgat cg                                               22

<210> SEQ ID NO 62
<211> LENGTH: 21
<212> TYPE: DNA
<213> ORGANISM: Artificial Sequence
<220> FEATURE:
```

<223> OTHER INFORMATION: Synthetic construct, primer spl-agdsx-e3

<400> SEQUENCE: 62
cgagcccaat ggctgttgga g                                    21

<210> SEQ ID NO 63
<211> LENGTH: 22
<212> TYPE: DNA
<213> ORGANISM: Artificial Sequence
<220> FEATURE:
<223> OTHER INFORMATION: Synthetic construct, spl-agdsx-m primer

<400> SEQUENCE: 63
gtcaaggttc agggcccgat cg                                   22

<210> SEQ ID NO 64
<211> LENGTH: 20
<212> TYPE: DNA
<213> ORGANISM: Artificial Sequence
<220> FEATURE:
<223> OTHER INFORMATION: Synthetic construct, aedesxF1 primer

<400> SEQUENCE: 64
tcaatggctc ctggagaagc                                      20

<210> SEQ ID NO 65
<211> LENGTH: 25
<212> TYPE: DNA
<213> ORGANISM: Artificial Sequence
<220> FEATURE:
<223> OTHER INFORMATION: Synthetic construct, aedesxR5 primer

<400> SEQUENCE: 65
accattcttg cagaagtctt gggac                                25

<210> SEQ ID NO 66
<211> LENGTH: 19
<212> TYPE: DNA
<213> ORGANISM: Artificial Sequence
<220> FEATURE:
<223> OTHER INFORMATION: Synthetic construct, aedesxR2 primer

<400> SEQUENCE: 66
aacattctcc gcgcacagg                                       19

<210> SEQ ID NO 67
<211> LENGTH: 23
<212> TYPE: DNA
<213> ORGANISM: Artificial SeqUence
<220> FEATURE:
<223> OTHER INFORMATION: Synthetic construct, Agexon1 primer

<400> SEQUENCE: 67
gacgctcgct ctggtacagt tcg                                  23

<210> SEQ ID NO 68
<211> LENGTH: 20
<212> TYPE: DNA
<213> ORGANISM: Artificial Sequence
<220> FEATURE:
<223> OTHER INFORMATION: Synthetic construct, Tra (tTAV) seq+ primer

<400> SEQUENCE: 68
cctgccagga ctcgccttcc                                      20

<210> SEQ ID NO 69
<211> LENGTH: 23
<212> TYPE: DNA
<213> ORGANISM: Artificial Sequence
<220> FEATURE:
<223> OTHER INFORMATION: Synthetic construct, Agexon1 primer

<400> SEQUENCE: 69
gacgctcgct ctggtacagt tcg                                     23

<210> SEQ ID NO 70
<211> LENGTH: 26
<212> TYPE: DNA
<213> ORGANISM: Artificial Sequence
<220> FEATURE:
<223> OTHER INFORMATION: Synthetic construct, Exon 3 primer

<400> SEQUENCE: 70
gttgtcgctt tgactggcaa tgtcgc                                  26

<210> SEQ ID NO 71
<211> LENGTH: 632
<212> TYPE: DNA
<213> ORGANISM: Pectinophora gossypiella

<400> SEQUENCE: 71
gaactgccac aaactgctgg aaaagttcca ctactcctgg gaaatgatgc ccctggtgct    60
ggtcattcta aactacgccg gctccgacct cgacgaggct tctagaaaaa ttgatgaagg   120
gaagatgatc atcaacgagt acgcgaggga gcacaatctg aacatcttcg atggccacga   180
gctgaggaac tcgactcgcc agaaaatgct gagcgaaatt aataatataa gtggtgtact   240
atcgtcgtcc atgaagttat tttgcgaatg atactttgtt ttgtatgtgc tgtgtgttgt   300
gtggactttt gctgtgcgtt gctgtttgcg atggaaggac tattgtgtcg tcgccacgct   360
ggactattcg cacattgggt ggtccaccag tggcggatgt acgagcggtc gctgtgctcg   420
ctcctggagc tgcaagcgcg caaagggacg tactcggtgt gctgctcacc ccgctacgtc   480
atcgcgcccg agtacgcgtc acacctgttg cctctgccgc ttaccacgca gagatcatcc   540
ccgccgcccg cgcacttgta gcgatgcgaa cctgcgccgc gggaagcggc gcaagaaccc   600
gccgatgccc cggcgtcgtc gtcgggtgcc ac                                632

<210> SEQ ID NO 72
<211> LENGTH: 222
<212> TYPE: DNA
<213> ORGANISM: Drosophila melanogaster

<400> SEQUENCE: 72
atgcagatct tgtgaagac tttgaccgga aagaccatca ccctcgaggt agagccatcg     60
gacaccattg agaatgtaaa ggccaagatt caggataagg agggaatccc cccagatcag   120
cagcgtctga tcttcgctgg caagcaactg gaagacggac gcaccctgtc cgattacaac   180
atccagaagg agtccaccct tcacttggtc cttcgtctcc gt                      222

<210> SEQ ID NO 73
<211> LENGTH: 74
<212> TYPE: PRT
<213> ORGANISM: Drosophila melanogaster

<400> SEQUENCE: 73

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg
65                  70

<210> SEQ ID NO 74
<211> LENGTH: 34
<212> TYPE: DNA
<213> ORGANISM: Artificial Sequence
<220> FEATURE:
<223> OTHER INFORMATION: Synthetic construct, primer

<400> SEQUENCE: 74
caagcaaagt gaacacgtcg ctaagcgaaa gcta                                   34

<210> SEQ ID NO 75
<211> LENGTH: 22
<212> TYPE: DNA
<213> ORGANISM: Artificial Sequence
<220> FEATURE:
<223> OTHER INFORMATION: Synthetic construct, primer

<400> SEQUENCE: 75
gcgggtggca gctggtgtac tg                                               22

<210> SEQ ID NO 76
<211> LENGTH: 34
<212> TYPE: DNA
<213> ORGANISM: Artificial Sequence
<220> FEATURE:
<223> OTHER INFORMATION: Synthetic construct, primer

<400> SEQUENCE: 76
caagcaaagt gaacacgtcg ctaagcgaaa gcta                                   34

<210> SEQ ID NO 77
<211> LENGTH: 24
<212> TYPE: DNA
<213> ORGANISM: Artificial Sequence
<220> FEATURE:
<223> OTHER INFORMATION: Synthetic construct, primer

<400> SEQUENCE: 77
gcggaacgac ttggcgttat tgcg                                             24

<210> SEQ ID NO 78
<211> LENGTH: 28
<212> TYPE: DNA
<213> ORGANISM: Artificial Sequence
<220> FEATURE:
<223> OTHER INFORMATION: Synthetic construct, primer

<400> SEQUENCE: 78
ggaagggtcc ttacgctata gagcgcag                                         28

<210> SEQ ID NO 79
<211> LENGTH: 31
<212> TYPE: DNA
<213> ORGANISM: Artificial Sequence
<220> FEATURE:

<223> OTHER INFORMATION: Synthetic construct, primer

<400> SEQUENCE: 79
ccaggcgaag ttgttattaa gcgtagattt g                                              31

<210> SEQ ID NO 80
<211> LENGTH: 33
<212> TYPE: DNA
<213> ORGANISM: Artificial Sequence
<220> FEATURE:
<223> OTHER INFORMATION: Synthetic construct, primer

<400> SEQUENCE: 80
cgtcgctttg aaacagaggc tttgagcctt ctc                                            33

<210> SEQ ID NO 81
<211> LENGTH: 48
<212> TYPE: DNA
<213> ORGANISM: Artificial Sequence
<220> FEATURE:
<223> OTHER INFORMATION: Synthetic construct, primer

<400> SEQUENCE: 81
gctagcaacc accatggcgg taattctaat tacttactaa atatagtg                            48

<210> SEQ ID NO 82
<211> LENGTH: 41
<212> TYPE: DNA
<213> ORGANISM: Artificial Sequence
<220> FEATURE:
<223> OTHER INFORMATION: Synthetic construct, primer

<400> SEQUENCE: 82
ccgggatgta gaaggccacc tgtgaatacg gttaatgtca c                                   41

<210> SEQ ID NO 83
<211> LENGTH: 31
<212> TYPE: DNA
<213> ORGANISM: Artificial Sequence
<220> FEATURE:
<223> OTHER INFORMATION: Synthetic construct, primer

<400> SEQUENCE: 83
cagtcagtca cgagtttgtt accactgcga c                                              31

<210> SEQ ID NO 84
<211> LENGTH: 22
<212> TYPE: DNA
<213> ORGANISM: Artificial Sequence
<220> FEATURE:
<223> OTHER INFORMATION: Synthetic construct, primer

<400> SEQUENCE: 84
gcgggtggca gctggtgtac tg                                                        22

<210> SEQ ID NO 85
<211> LENGTH: 21
<212> TYPE: DNA
<213> ORGANISM: Artificial Sequence
<220> FEATURE:
<223> OTHER INFORMATION: Synthetic construct, primer

<400> SEQUENCE: 85
cggagcacat ctgatagaac g                                                         21

```
<210> SEQ ID NO 86
<211> LENGTH: 23
<212> TYPE: DNA
<213> ORGANISM: Artificial Sequence
<220> FEATURE:
<223> OTHER INFORMATION: Synthetic construct, primer

<400> SEQUENCE: 86
cgcggctgta ggcgctgccg ctc                                           23

<210> SEQ ID NO 87
<211> LENGTH: 31
<212> TYPE: DNA
<213> ORGANISM: Artificial Sequence
<220> FEATURE:
<223> OTHER INFORMATION: Synthetic construct, primer

<400> SEQUENCE: 87
ccaggcgaag ttgttattaa gcgtagattt g                                  31

<210> SEQ ID NO 88
<211> LENGTH: 33
<212> TYPE: DNA
<213> ORGANISM: Artificial Sequence
<220> FEATURE:
<223> OTHER INFORMATION: Synthetic construct, primer

<400> SEQUENCE: 88
cgtcgctttg aaacagaggc tttgagcctt ctc                                33

<210> SEQ ID NO 89
<211> LENGTH: 52
<212> TYPE: DNA
<213> ORGANISM: Artificial Sequence
<220> FEATURE:
<223> OTHER INFORMATION: Synthetic construct, primer

<400> SEQUENCE: 89
gctagcaacc accatggcgg taattttaaa agcatatttt ttttttgaaat tc           52

<210> SEQ ID NO 90
<211> LENGTH: 41
<212> TYPE: DNA
<213> ORGANISM: Artificial Sequence
<220> FEATURE:
<223> OTHER INFORMATION: Synthetic construct, primer

<400> SEQUENCE: 90
ccgggatgta gaaggccacc taaagatacc atggatgtat g                       41

<210> SEQ ID NO 91
<211> LENGTH: 31
<212> TYPE: DNA
<213> ORGANISM: Artificial Sequence
<220> FEATURE:
<223> OTHER INFORMATION: Synthetic construct, primer

<400> SEQUENCE: 91
cagtcagtca cgagtttgtt accactgcga c                                  31

<210> SEQ ID NO 92
<211> LENGTH: 22
<212> TYPE: DNA
<213> ORGANISM: Artificial Sequence
<220> FEATURE:
<223> OTHER INFORMATION: Synthetic construct, primer
```

```
<400> SEQUENCE: 92
gcgggtggca gctggtgtac tg                                         22

<210> SEQ ID NO 93
<211> LENGTH: 21
<212> TYPE: DNA
<213> ORGANISM: Artificial Sequence
<220> FEATURE:
<223> OTHER INFORMATION: Synthetic construct, primer

<400> SEQUENCE: 93
gttgcaagtt gacactggcg g                                          21

<210> SEQ ID NO 94
<211> LENGTH: 23
<212> TYPE: DNA
<213> ORGANISM: Artificial Sequence
<220> FEATURE:
<223> OTHER INFORMATION: Synthetic construct, primer

<400> SEQUENCE: 94
aggtgtggga ggttttttaa agc                                        23

<210> SEQ ID NO 95
<211> LENGTH: 52
<212> TYPE: DNA
<213> ORGANISM: Artificial Sequence
<220> FEATURE:
<223> OTHER INFORMATION: Synthetic construct, primer

<400> SEQUENCE: 95
cctgtaatac gactcactat agggcgtttt tttttttttt tttttttttt tt        52

<210> SEQ ID NO 96
<211> LENGTH: 33
<212> TYPE: DNA
<213> ORGANISM: Artificial Sequence
<220> FEATURE:
<223> OTHER INFORMATION: Synthetic construct, primer

<400> SEQUENCE: 96
gcaaacggca atcagacggg cccaggctca gga                             33

<210> SEQ ID NO 97
<211> LENGTH: 28
<212> TYPE: DNA
<213> ORGANISM: Artificial Sequence
<220> FEATURE:
<223> OTHER INFORMATION: Synthetic construct, primer

<400> SEQUENCE: 97
cctgtaatac gactcactat agggcgtt                                   28

<210> SEQ ID NO 98
<211> LENGTH: 37
<212> TYPE: DNA
<213> ORGANISM: Artificial Sequence
<220> FEATURE:
<223> OTHER INFORMATION: Synthetic construct, primer

<400> SEQUENCE: 98
gggatcgagc tagatcggcc tgagccgcca gtggtga                         37

<210> SEQ ID NO 99
<211> LENGTH: 28
```

<210> SEQ ID NO 99
<211> LENGTH: 28
<212> TYPE: DNA
<213> ORGANISM: Artificial Sequence
<220> FEATURE:
<223> OTHER INFORMATION: Synthetic construct, primer

<400> SEQUENCE: 99
cctgtaatac gactcactat agggcgtt				28

<210> SEQ ID NO 100
<211> LENGTH: 32
<212> TYPE: DNA
<213> ORGANISM: Artificial Sequence
<220> FEATURE:
<223> OTHER INFORMATION: Synthetic construct, primer

<400> SEQUENCE: 100
cgctccatgg gatcggcgag ctgcgactcc gt			32

<210> SEQ ID NO 101
<211> LENGTH: 27
<212> TYPE: DNA
<213> ORGANISM: Artificial Sequence
<220> FEATURE:
<223> OTHER INFORMATION: Synthetic construct, primer

<400> SEQUENCE: 101
gcaacaacca gcggtgtccc ttgaaac				27

<210> SEQ ID NO 102
<211> LENGTH: 28
<212> TYPE: DNA
<213> ORGANISM: Artificial Sequence
<220> FEATURE:
<223> OTHER INFORMATION: Synthetic construct, primer

<400> SEQUENCE: 102
cctgtaatac gactcactat agggcgtt				28

<210> SEQ ID NO 103
<211> LENGTH: 28
<212> TYPE: DNA
<213> ORGANISM: Artificial Sequence
<220> FEATURE:
<223> OTHER INFORMATION: Synthetic construct, primer

<400> SEQUENCE: 103
gctagtggag aactgccaca aactgctg				28

<210> SEQ ID NO 104
<211> LENGTH: 34
<212> TYPE: DNA
<213> ORGANISM: Artificial Sequence
<220> FEATURE:
<223> OTHER INFORMATION: Synthetic construct, primer

<400> SEQUENCE: 104
caagcaaagt gaacacgtcg ctaagcgaaa gcta			34

<210> SEQ ID NO 105
<211> LENGTH: 25
<212> TYPE: DNA
<213> ORGANISM: Artificial Sequence
<220> FEATURE:
<223> OTHER INFORMATION: Synthetic construct, primer

<400> SEQUENCE: 105

```
gccctcgatg gtagacccgt aattg                                           25
```

<210> SEQ ID NO 106
<211> LENGTH: 14874
<212> TYPE: DNA
<213> ORGANISM: Artificial Sequence
<220> FEATURE:
<223> OTHER INFORMATION: Synthetic construct, LA1172, including plasmid
      backbone

<400> SEQUENCE: 106

```
gggctggccg caaccattgt gggaaccgtg cgatcaaaca aacgcgagat accggaagta      60
ctgaaaaaca gtcgctccag gccagtggga acatcgatgt tttgttttga cggacccctt    120
actctcgtct catataaacc gaagccagct aagatggtat acttattatc atcttgtgat    180
gaggatgctt ctatcaacga agtaccggt aaaccgcaaa tggttatgta ttataatcaa     240
actaaggcg gagtggacac gctagaccaa atgtgttctg tgatgacctg cagtaggaag    300
acgaatagg ggcctatggc attattgtac ggaatgataa acattgcctg cataaattct    360
tttattatat acagccataa tgtcagtagc aagggagaaa aggtccaaag tcgcaaaaaa    420
tttatgagaa acctttacat gagcctgacg tcatcgttta tgcgtaagcg tttagaagct    480
cctactttga agagatattt gcgcgataat atctctaata ttttgccaaa tgaagtgcct    540
ggtacatcag atgacagtac tgaagagcca gtaatgaaaa aacgtactta ctgtacttac    600
tgcccctcta aaataaggcg aaaggcaaat gcatcgtgca aaaaatgcaa aaaagttatt    660
tgtcgagagc ataatattga tatgtgccaa agttgtttct gactgactaa taagtataat    720
ttgtttctat tatgtataag ttaagctaat tacttatttt ataatacaac atgactgttt    780
ttaaagtaca aaataagttt atttttgtaa aagagagaat gtttaaaagt tttgttactt    840
tatagaagaa attttgagtt tttgtttttt tttaataaat aaataaacat aaataaattg    900
tttgttgaat ttattattag tatgtaagtg taaatataat aaaacttaat atctattcaa    960
attaataaat aaacctcgat atacagaccg ataaaacaca tgcgtcaatt ttacgcatga   1020
ttatctttaa cgtacgtcac aatatgatta tctttctagg gttaaataat agtttctaat   1080
tttttttatta ttcagcctgc tgtcgtgaat accgtatatc tcaacgctgt ctgtgagatt   1140
gtcgtattct agccttttta gttttttcgct catcgacttg atattgtccg acacattttc   1200
gtcgatttgc gttttgatca aagacttgag cagagacacg ttaatcaact gttcaaattg   1260
atccatatta acgatatcaa cccgatgcgt atatggtgcg taaatatat ttttttaaccc    1320
tcttatactt tgcactctgc gttaatacgc gttcgtgtac agacgtaatc atgttttctt   1380
ttttggataa aactcctact gagtttgacc tcatattaga ccctcacaag ttgcaaaacg   1440
tggcattttt taccaatgaa gaatttaaag ttatttttaaa aaatttcatc acagatttaa   1500
agaagaacca aaaattaaat tatttcaaca gtttaatcga ccagttaatc aacgtgtaca   1560
cagacgcgtc ggcaaaaaac acgcagcccg acgtgttggc taaaattatt aaatcaactt   1620
gtgttatagt cacggatttg ccgtccaacg tgttcctcaa aaagttgaag accaacaagt   1680
ttacggacac tattaattat ttgattttgc cccacttcat tttgtgggat cacaattttg   1740
ttatatttta aacaaagctt ggcactggcc gtcgttttac aacgtcgtga ctgggaaaac   1800
cctggcgtta cccaacttaa tcgccttgca gcacatcccc ctttcgccag ctggcgtaat   1860
agcgaagagg cccgcaccga tcgcccttcc caacagttgc gcagcctgaa tggcgaatgg   1920
cgcctgatgc ggtattttct ccttacgcat ctgtgcggta tttcacaccg catatatggt   1980
```

```
gcactctcag tacaatctgc tctgatgccg catagttaag ccagccccga cacccgccaa    2040
cacccgctga cgcgccctga cgggcttgtc tgctcccggc atccgcttac agacaagctg    2100
tgaccgtctc cgggagctgc atgtgtcaga ggttttcacc gtcatcaccg aaacgcgcga    2160
gacgaaaggg cctcgtgata cgcctatttt tataggttaa tgtcatgata ataatggttt    2220
cttagacgtc aggtggcact tttcggggaa atgtgcgcgg aacccctatt tgtttatttt    2280
tctaaataca ttcaaatatg tatccgctca tgagacaata accctgataa atgcttcaat    2340
aatattgaaa aaggaagagt atgagtattc aacatttccg tgtcgccctt attcccwttt    2400
ttgcggcatt ttgccttcct gttttagctc acccagaaac gctggtgaaa gtaaaagatg    2460
ctgaagatca gttgggtgca cgagtgggtt acatcgaact ggatctcaac agcggtaaga    2520
tccttgagag ttttcgcccc gaagaacgtt ttccaatgat gagcactttt aaagttctgc    2580
tatgtggcgc ggtattatcc cgtattgacg ccgggcaaga gcaactcggt cgccgcatac    2640
actattctca gaatgacttg gttgagtact caccagtcac agaaaagcat cttacggatg    2700
gcatgacagt aagagaatta tgcagtgctg ccataaccat gagtgataac actgcggcca    2760
acttacttct gacaacgatc ggaggaccga aggagctaac cgcttttttg cacaacatgg    2820
gggatcatgt aactcgcctt gatcgttggg aaccggagct gaatgaagcc ataccaaacg    2880
acgagcgtga caccacgatg cctgtagcaa tggcaacaac gttgcgcaaa ctattaactg    2940
gcgaactact tactctagct tcccggcaac aattaataga ctggatggag gcggataaag    3000
ttgcaggacc acttctgcgc tcggcccttc cggctggctg gtttattgct gataaatctg    3060
gagccggtga gcgtgggtct cgcggtatca ttgcagcact ggggccagat ggtaagccct    3120
cccgtatcgt agttatctac acgacgggga gtcaggcaac tatggatgaa cgaaatagac    3180
agatcgctga gataggtgcc tcactgatta agcattggta actgtcagac caagtttact    3240
catatatact ttagattgat ttaaaacttc attttaatt taaaaggatc taggtgaaga    3300
tcctttttga taatctcatg accaaaatcc cttaacgtga gttttcgttc cactgagcgt    3360
cagaccccgt agaaaagatc aaaggatctt cttgagatcc ttttttttctg cgcgtaatct    3420 gctgcttgca acaaaaaaa ccaccgctac cagcggtggt ttgtttgccg gatcaagagc    3480
taccaactct tttccgaag gtaactggct tcagcagagc gcagatacca atactgtcc    3540 ttctagtgta gccgtagtta ggccaccact tcaagaactc tgtagcaccg cctacatacc    3600
tcgctctgct aatcctgtta ccagtggctg ctgccagtgg cgataagtcg tgtcttaccg    3660
ggttggactc aagacgatag ttaccggata aggcgcagcg gtcgggctga acggggggtt    3720
cgtgcacaca gcccagcttg gagcgaacga cctacaccga actgagatac ctacagcgtg    3780
agcattgaga aagcgccacg cttcccgaag ggagaaaggc ggacaggtat ccggtaagcg    3840
gcagggtcgg aacaggagag cgcacgaggg agcttccagg gggaaacgcc tggtatcttt    3900
atagtcctgt cgggtttcgc cacctctgac ttgagcgtcg atttttgtga tgctcgtcag    3960
gggggcggag cctatggaaa aacgccagca acgcggcctt tttacggttc ctggcctttt    4020
gctggccttt tgctcacatg ttctttcctg cgttatcccc tgattctgtg ataaccgta    4080 ttaccgcctt tgagtgagct gataccgctc gccgcagccg aacgaccgag cgcagcgagt    4140
cagtgagcga ggaagcggaa gagcgcccaa tacgcaaacc gcctctcccc gcgcgttggc    4200
cgattcatta atgcagctgg cacgacaggt ttcccgactg gaaagcgggc agtgagcgca    4260
acgcaattaa tgtgagttag ctcactcatt aggcacccca ggctttacac tttatgcttc    4320
cggctcgtat gttgtgtgga attgtgagcg gataacaatt tcacacagga aacagctatg    4380
```

| | | | | |
|---|---|---|---|---|
| accatgatta | cgaatttcga | cctgcaggca | tgcaagcttg | catgcctgca ggtcgacgct | 4440 |
| cgcgcgactt | ggtttgccat | tctttagcgc | gcgtcgcgtc | acacagcttg gccacaatgt | 4500 |
| ggttttttgtc | aaacgaagat | tctatgacgt | gtttaaagtt | taggtcgagt aaagcgcaaa | 4560 |
| tctttttttaa | ccctagaaag | atagtctgcg | taaaattgac | gcatgcattc ttgaaatatt | 4620 |
| gctctctctt | tctaaatagc | gcgaatccgt | cgctgtgcat | ttaggacatc tcagtcgccg | 4680 |
| cttggagctc | ccgtgaggcg | tgcttgtcaa | tgcggtaagt | gtcactgatt ttgaactata | 4740 |
| acgaccgcgt | gagtcaaaat | gacgcatgat | tatcttttac | gtgacttttta agatttaact | 4800 |
| catacgataa | ttatattgtt | atttcatgtt | ctacttacgt | gataacttat tatatatata | 4860 |
| ttttcttgtt | atagatatcg | tgactaatat | ataataaaat | gggtagttct ttagacgatg | 4920 |
| agcatatcct | ctctgctctt | ctgcaaagcg | atgacgagct | tgttggtgag gattctgaca | 4980 |
| gtgaaatatc | agatcacgta | agtgaagatg | acgtccagag | cgatacagaa gaagcgttta | 5040 |
| tagatgaggt | acatgaagtg | cagccaacgt | caagcggtag | tgaaatatta gacgaacaaa | 5100 |
| atgttattga | acaaccaggt | tcttcattgg | cttctaacag | aatcttgacc ttgccacaga | 5160 |
| ggactattag | aggtaagaat | aaacattgtt | ggtcaacttc | aaagtccacg aggcgtagcc | 5220 |
| gagtctctgc | actgaacatt | gtcagatcgg | ccaggccggc | cagatttaaa tgagcggccg | 5280 |
| catggtacca | tactcggtgg | cctccccacc | accaactttt | ttgcactgca aaaaaacacg | 5340 |
| cttttgcacg | cgggcccata | catagtacaa | actctacgtt | tcgtagacta ttttacataa | 5400 |
| atagtctaca | ccgttgtata | cgctccaaat | acactaccac | acattgaacc tttttgcagt | 5460 |
| gcaaaaaagt | acgtgtcggc | agtcacgtag | gccggcctta | tcgggtcgcg tcctgtcacg | 5520 |
| tacgaatcac | attatcggac | cggacgagtg | ttgtcttatc | gtgacaggac gccagcttcc | 5580 |
| tgtgttgcta | accgcagccg | gacgcaactc | cttatcggaa | caggacgcgc ctccatatca | 5640 |
| gccgcgcgtt | atctcatgcg | cgtgaccgga | cacgaggcgc | ccgtcccgct tatcgcgcct | 5700 |
| ataaatacag | cccgcaacga | tctggtaaac | acagttgaac | agcatctgtt acagcgacac | 5760 |
| aacatgagcc | ggtccaacaa | cgccaacgcg | cccacgccat | ccaaccgccg ccgcaacctg | 5820 |
| tctctggtgg | atcccacccc | acccaagaag | aagcgcaaac | cggtcgccac catggcctcc | 5880 |
| tccgagaacg | tcatcaccga | gttcatgcgc | ttcaaggtgc | gcatggaggg caccgtgaac | 5940 |
| ggccacgagt | tcgagatcga | gggcgagggc | gagggccgcc | cctacgaggg ccacaacacc | 6000 |
| gtgaagctga | aggtgaccaa | gggcggcccc | ctgcccttcg | cctgggacat cctgtccccc | 6060 |
| cagttccagt | acggctccaa | ggtgtacgtg | aagcaccccg | ccgacatccc cgactacaag | 6120 |
| aagctgtcct | tccccgaggg | cttcaagtgg | gagcgcgtga | tgaacttcga ggacggcggc | 6180 |
| gtggcgaccg | tgacccagga | ctcctccctg | caggacggct | gcttcatcta caaggtgaag | 6240 |
| ttcatcggcg | tgaacttccc | ctccgacggc | cccgtgatgc | agaagaagac catgggctgg | 6300 |
| gaggcctcca | ccgagcgcct | gtaccccgc | gacggcgtgc | tgaagggcga gacccacaag | 6360 |
| gccctgaagc | tgaaggacgg | cggccactac | ctggtggagt | tcaagtccat ctacatggcc | 6420 |
| aagaagcccg | tgcagctgcc | cggctactac | tacgtggacg | ccaagctgga catcaccctc | 6480 |
| cacaacgagg | actacaccat | cgtggagcag | tacgagcgca | ccgagggccg ccaccacctg | 6540 |
| ttcctgagat | ctcgacccaa | gaaaaagcgg | aaggtggagg | acccgtaaga tccaccggat | 6600 |
| ctagataact | gatcataatc | agccatacca | catttgtaga | ggttttactt gctttaaaaa | 6660 |
| acctcccaca | cctcccccty | aacctgaaac | ataaaatgaa | tgcaattgtt gttgttaact | 6720 |

```
tgtttattgc agcttataat ggttacaaat aaagcaatag catcacaaat ttcacaaata    6780
aagcattttt ttcactgcat tctagttgtg gtttgtccaa actcatcaat gtatcttaac    6840
gcgagttaat taatccattg ctgggcgagc tgcgccaatc gatgccaacg ccaccctgca    6900
tggcgagcgg caggccggcg gctaccatgg gcgtcaccat gccctgaccg ccccggagg     6960
gcagtgaaaa atgtgtgggg ggtggtgggg gctgcgcagg aactgattgt gattatggtt    7020
gtgcccatgg ccatgttgtc caagtccatg gacgtgggca tgcttgttgt agcccaaatc    7080
ggcgtttccg tttccaccag gaaacatctc tgcttgtagt tcgaatatgc tctttaaatc    7140
ccagctgtat tcctcagtta tcgaggtttt cttcacgagt gaaacgaatt ttcgtcgcct    7200
tctacgccat tttcttgctc agcccgtttt gtcattcgca gcgaagcggt aacagcgggt    7260
cgctcatatg acggtatttt ttaatacact tcagctatac tgttatttca aaaacatatt    7320
tcttttgtta ctttttatgc agttcatttg ccaccaaaaa gtagtctttt ggattgattt    7380
atttcaaaaa atggtgtaat tcaagaaatt cagagggcca agtaatatac ttaatgaccg    7440
ttatttaaaa cacactcaag gagatttatt taaacggcta caatggtttt ccaaataact    7500
tatttactgt tgacttctat aaaacatagg tgtatatatt attatttcct tattgagttt    7560
gagataattt taatttccac aatatttttt cttgtgatta acagagaaag tcaaactaca    7620
taacatttat cgggtaaaag tctctatgaa ggtagcggtt aacagtgaag tcgcaaaagt    7680
ggtggccgta cgccaatcga gcgtagtacc cctaacctgc aatattttta gttggttttt    7740
tccgcaatag ccccagtttt ctcaaagagt gcaacaagtg attctgttta tgttttcaac    7800
aacttctctc tgcggaactt aacgtgagcg gacgtatgcg gacgcgccat ggtttaaact    7860
cgctagcact gggaagttga cgttgatata gagccgaatt gaacttcacc gctgcttggt    7920
aattactcta caagttcatt taggagaacc ggattcgaaa gatgattttc cagcgtttag    7980
ctttcagatg gccgcataca ttttgcacca ccaaaccgaa actcactagc gtatccaatc    8040
gttcgttttt tggtgccggt gtgttacgaa ctttagctat caagctaaag caatttgctc    8100
tggtcttccg tgctaaaaag aaaaaaaaac tgtttttttt ttggttttga tatttgcgct    8160
attttttactt gggccttaat tgaacaaact tttgaaagtt tccacagcga atcgttttc    8220
gacgatgcca ttttggtaa catttgcatt ttcttgctca aattgcttgc aaaacccgtg    8280
aaagacatta atattcgata gtgtcatcca aaatcacgaa aatgattgtt gcaaaacgtt    8340
gaacaattta cacatgtaaa aaacaaccat cgattaatgt ttattcaaac ttttttacaag   8400
aagggttatt ctgatcaatg tcaccccgct gatgaatgtt accccggatt acacttctcg    8460
aaaagtggtt caaaatgcta cttgagaatt tttatctgtc aaaggaagca aattcgagtc    8520
gaattaaatg gtatagtcct gaattaggtt tccatttact tacaggtatt ccactaaata    8580
gctggaagat ttattttaca caataatgat aattcgtacc ccaaagagtg tagccctact    8640
tttttctctc tttttttttt gtaaattttc atcgctgcgt gccagcttac cgacatgtcg    8700
cgacagcata aagagcctgt caagagatga agaaaaatga caaggagtca gtggtcaggt    8760
ctctgtatca atatttgacg tcctgacttt ccaatatacc tttccttaaa gagtagagat    8820
catgcgatac gtgaataaat atcgtttgga cttcgaaata gaacataatt taaggtagct    8880
gatcagtagt tgaacatctt cagacttctg ggacaagaag tgtttttttg tttgtagaaa    8940
aggttttttgt taaattatat ttgtaagata attcaatgaa tatatctctg attcagtaat    9000
caatccgtac cacgcaccgt ttaagaaaca ccctgtaggt ttgcatcacg tctcagacaa    9060
aagtgtatcg atgtgcgaac actgcatacc ggcgctttgc aaataatgcc aaatttagat    9120
```

-continued

```
atgcattaca ttgtcacttc gcaaaacaca cactcccaaa tgcgtcggaa acctcacccg    9180
aacgcacgat cgtaacgcga tcgatcgccg attgattgat cggaattaac tatctcaatc    9240
gatccttcta tggactgatg catgggccgg cacttccgag tataaaaccc cggtaaaccc    9300
aaggaatcac tcacaatcgg attttgacgc tcgctctggt acagttcgat acggtctagt    9360
gaaccgagg ataacgacga aggttttcc ccattgatcc aggtcggtgt ttatgattgg      9420
tggaaaaga ctcgagaaaa gttccatcga agccgttgga aatgtgccgt cttcctgtga    9480
cgtcttgtgg atccagttcc ttgttcacgt ctggtgatcg tgtaaaatgt gctgtcttgt    9540
ggcgtcatat gtgttccaga tccagtgatt acgatccgat gtgatgttga tcccttgtga    9600
acgtcttatc ctgttccgtg tgcaccatgc ataatgtcgt attacgtaag ttctgaagtg    9660
aaacagaaga gtgaattgaa agttttttta ttcaacatca acctaaatat ggactttact    9720
ttccaagaaa attatgcctg atcaactgtg gatagttaca aaaaaaaag gtttattaat     9780
taaattttat gattacataa tgtgttgaaa agaacaactg aaattttaga agaagatctt    9840
ttcgtgcatc aggctttgcc aattaattga tgataaatta tcatagcaaa ttaacgtaga    9900
gactaaaagg tatatcgtca aatagggctt cttttgacac tattttggca ttcttgctct    9960
ttgagaactt gcaaccctaa aatgggatct tcatcagcct agtggttaga ttcagcagct   10020
acaaagcaaa accatgctga agggttcgat tcccggtcgt ttcaggatct tttcgtaatt   10080
gaaatatcct tgactaccct aagtatcatt gtgcttgcca tttacgaata tacatattac   10140
gatatacgaa tgagaaaatg acaactttgg aaaataaagc tctcaatgtt tcaataagaa   10200
ataaatacta catcagtatt gaaggctaat aacaattaca gattagaacc tttaaacatc   10260
atttctgcaa caggctggat aaagtacagt tggaggatta aattatgcga ttttgcaatt   10320
ttttccgatt aaattcatat ttattcctgg tttggttttt acaaaaaata tttttacatg   10380
acgtttgacc ccgattccct caactttgat tgttatattt tttttggac aggttgagtt    10440
tgtgggtttt ttcctagtgt tgctttgctt tatgggctct ggttatttaa aattaaaatt   10500
tgacaatctt actacacact ccgaaaaaat catgcgattt tacgtctttt ggatgcacat   10560
aaaagaagcg agccaaatga ggtgaatttg tgtcacattt taaatacgat ggtgtctgat   10620
tcgggaaatg tcaatgatag tgtcattcaa tcataatgtg aattacgtcc gcagtaattt   10680
tcattatttt taagagtgta ctactattta cactacaaaa attttgatac ccagggggg    10740
aacgaggtcc cggatgtcca gctggccaga ttgttggcaa cgagccctgt acctattgat   10800
cgagtcacca aagcactcct caagtgtttt aatctcgacc agacggtgga cctcggttgt   10860
tctcattctc ggagggcgat ttcgcaatca ttagtaccaa ccacatgtcg aagtcgggag   10920
atgttataaa attataacca attattcaaa aaatgacatc attcaatttg aacaaacgtt   10980
cgatagaaat tatatatgat ttcacatgat attaaactac gaagaaaatt ttacataagg   11040
aagtggtata aaacgtaata tgcttaataa aactttaac ccttttggga ggataatatt    11100
cagaagttct gattcagaac catctctcat gttatgttcg ttttttgttg cttgtccttt   11160
atatgccaca tgaacaataa caccaatatc tatcccattt ccaggaccta acggaccttg   11220
aagcggcgcc aaaacgtgtg acgatgatgc tggtaccctg gcgtaagtt gatcaaagga    11280
aacgcaaagt tttcaagaaa aaacaaaact aatttgattt ataacacctt tagaaaccac   11340
catgggcagc cgcctggata agtccaaagt catcaactcc gcgttggagc tgttgaacga   11400
agttggcatt gagggactga cgacccgcaa gttggcgcag aagctgggcg tggagcagcc   11460
```

```
caccctctac tggcacgtga agaataagcg ggcgctgctg gatgccctgg ccatcgagat   11520
gctcgaccgc caccacacgc attttttgccc gttggaaggc gagtcctggc aggacttcct   11580
ccgcaataac gccaagtcgt tccgctgcgc tctgctgtcc caccgagacg gtgccaaagt   11640
ccatctcggc acgcgcccga ccgaaaagca atacgagaca ctggagaacc agctcgcgtt   11700
cctgtgccag caaggcttca gcctggaaaa tgctctctac gctctgagcg ccgtcggtca   11760 ctttacccctg ggctgcgtgc tggaggacca agagcatcaa gtcgcaaaag aggagcgcga   11820
gaccccaaca accgattcga tgccccact gctgcgtcag gcaatcgagc tgttcgatca   11880
tcaaggagcc gagccggcat tcctgttcgg cttggagctg attatctgcg gattggaaaa   11940
gcaactgaaa tgcgagtcgg gctcgggccc cgcgtacagc cgcgcgcgta cgaaaaacaa   12000
ttacgggtct accatcgagg gcctgctcga tctcccggac gacgacgccc cgaagaggc   12060 ggggctggcg gctccgcgcc tgtcctttct ccccgcggga cacacgcgca gactgtcgac   12120 ggccccccg accgatgtca gcctggggga cgagctccac ttagacggcg aggacgtggc   12180
gatggcgcat gccgacgcgc tagacgattt cgatctggac atgttggggg acggggattc   12240
cccgggtccg ggatttaccc ccacgactc cgcccctac ggcgctctgg atatggccga   12300
cttcgagttt gagcagatgt ttaccgatgc ccttggaatt gacgagtacg gtgggtagtt   12360
ctagaattgt ccaccgcaag tgcttctaag ccgatcccga ttgtactgat taccataagc   12420
gacattgcca gtgaaagcga caacagcagc atcaaagtac atttgtcata ctgattcggc   12480
tactaccacc atccggaatc agcttgcatc gaacatcaaa tcacgttatt caatgtatct   12540
gtcatccagc tcagacaagt cggagctttt ccagtcgcga aaatctgcga ctccagcgga   12600
aagcaccgaa ccacagagag gactcgtatg aaagccaggg aagaaaccat cattcacctt   12660
gcagcaaata ggaaaaaaaa cggacatctt caacaaacaa aagcccatgc gctaacttgg   12720
tttaggagtt tagtgtgaca ccatgacccc gctgatgatc tttacttagc acaccataac   12780 caccctttatg cgttcgttca tccaaaatct acaggatatc actgcagccg cgagaagaac   12840
tcgtgaacca tcctgttttc ttttttatta tattcttact tttaacttca aattatttc   12900 agtaataaaa cgtctcaaaa taataagttc ataatgagtt taattttacg gaataagaac   12960
aaccatttaa gttattaaat ccttagattt aatggaatta gattgattat atggaaccca   13020
gacttggtaa aaaataaact ccacgttaaa tttctttctg agacttaaaa ttctttcggg   13080
aaagctggga gcaattctcg caccggtgct agggccgcat agtcgacatt tcgagtttac   13140
cactccctat cagtgataga gaaaagtgaa agtcgagttt accactccct atcagtgata   13200
gagaaaagtg aaagtcgagt ttaccactcc ctatcagtga tagagaaaag tgaaagtcga   13260
gtttaccact ccctatcagt gatagagaaa agtgaaagtc gagttaccca ctccctatca   13320
gtgatagaga aagtgaaag tcgagtttac cactccctat cagtgataga gaaaagtgaa   13380
agtcgagttt accactccct atcagtgata gagaaaagtg aaagtcgagc tcggtacccg   13440
ggtcgaggta ggcgtgtacg gtgggaggcc tatataagca gagctcgttt agtgaaccgt   13500
cagatcgcct ggagacgcca tccacgctgt tttgacctcc atagaagaca ccgggaccga   13560
tccagcctcc gcggccccga attcgagctc ggtacccggg gatccccgct cgaccaccat   13620
gggcgctctc ctgggcctgc cgaaagcca acggagctt gataatctta cagaatacaa   13680 cacgcccac aatcggcgca tctcaatgct gggcatcgat gatgtacca atatgcgaaa   13740 gcaaaacgcc ttgaaacagg gacggcgcac tcgaaatgtc acatttaacg atgaggagat   13800
tgtcatcaat cctgaggatg tggatcctaa tgtgggacgc ttcaggaact tggtacaaac   13860
```

```
cactgtggtg cccgccaaga gggctcgctg cgacgtcaac cattagtgat aacgcgtcta    13920
gctagagctg agaacttcag ggtgagtttg gggacccttg attgttcttt cttttcgct    13980 attgtaaaat tcatgttata tggagggggc aaagttttca gggtgttgtt tagaatggga    14040
agatgtccct tgtatcacca tggaccctca tgataatttt gtttctttca ctttctactc    14100
tgttgacaac cattgtctcc tcttattttc ttttcatttt ctgtaacttt ttcgttaaac    14160
tttagcttgc atttgtaacg aatttttaaa ttcacttttg tttatttgtc agattgtaag    14220
tactttctct aatcactttt ttttcaaggc aatcagggta tattatattg tacttcagca    14280
cagttttaga gaacaattgt tataattaaa tgataaggta gaatatttct gcatataaat    14340
tctggctggc gtggaaatat tcttattggt agaaacaact acaccctggt catcatcctg    14400
cctttctctt tatggttaca atgatataca ctgtttgaga tgaggataaa atactctgag    14460
tccaaaccgg gcccctctgc taaccatgtt catgccttct tctctttcct acagctcctg    14520
ggcaacgtgc tggttgttgt gctgtctcat cattttggca aagaattcac tcctcaggtg    14580
caggctgcct atcagaaggt ggtggctggt gtggccaatg ccctggctca caaataccac    14640
tgagatcttt ttccctctgc caaaaattat ggggacatca tgaagcccct tgagcatctg    14700
acttctggct aataaaggaa atttattttc attgcaatag tgtgttggaa tttttttgtgt    14760 ctctcactcg gaaggacata tgggagggca aatcatttaa aacatcagaa tgagtatttg    14820
gtttagagtt tggcaacata tgcccatagc ggccctagcg gcgcgccata gccc          14874
```

EXPRESSION SYSTEMS

CROSS REFERENCE TO RELATED APPLICATIONS

This application is a continuation of U.S. application Ser. No. 11/352,177, filed Feb. 10, 2006, now pending, which is a continuation-in-part of U.S. application Ser. No. 10/566,448, filed Apr. 18, 2006, now pending, which is the national stage entry of International Application No. PCT/GB2004/003263, filed Jul. 28, 2004, which claims the priority from GB 0317656.7, filed Jul. 28, 2003. All applications are hereby incorporated by reference in their entireties for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 750402000401SubSeqList, date recorded: 26 Nov. 9, 2015, size: 434,704 bytes).

INTRODUCTION

The present invention relates to a gene expression system, in combination with splice control sequences, said control sequences providing a mechanism for alternative splicing.

Alternative splicing is also known as pre-mRNA splicing and involves the removal of one or more introns and ligation of the flanking exons. This reaction is catalyzed by the spliceosome, a macromolecular machine composed of five RNAs and hundreds of proteins (Jurica, M. S. & Moore, M. J. (2003) *Mol. Cell* 12, 5-14). Alternative splicing generates multiple mRNAs from a single gene, thus increasing proteome diversity (Graveley, B. R. (2001) *Trends Genet.* 17, 100-107).

Alternative splicing also plays a key role in the regulation of gene expression in many developmental processes ranging from sex determination to apoptosis (Black, D. L. (2003) *Annu. Rev. Biochem.* 72, 291-336), and defects in alternative splicing have been linked to many human disorders (Caceres, J. F. & Kornblihtt, A. R. (2002) *Trends Genet.* 18, 186-193). In general, alternative splicing is regulated by proteins that associate with the pre-mRNA and function to either enhance or repress the ability of the spliceosome to recognize the splice site(s) flanking the regulated exon (Smith, C. W. & Valcarcel, J. (2000) *Trends Biochem. Sci.* 25, 381-388).

Whether a particular alternative exon will be included or excluded from an mRNA in each cell is thought to be determined by the relative concentration of a number of positive and negative splicing regulators and the interactions of these factors with the pre-mRNA and components of the spliceosome (Smith, C. W. & Valcarcel, J. (2000) *Trends Biochem. Sci.* 25, 381-388).

Although at least 74% of human genes encode alternatively spliced mRNAs (Johnson, J. M., Castle, J., Garrett-Engele, P., Kan, Z., Loerch, P. M., Armour C. D., Santos, R., Schadt, E. E., Stoughton, R. & Shoemaker, D. D. (2003) *Science* 302, 2141-2144), relatively few splicing regulators have been identified.

SUMMARY OF THE INVENTION

The present invention provides, in a first aspect, a gene expression system comprising at least one coding sequence to be expressed in an organism, at least one promoter operably linked thereto, and at least one splice control sequence which, in cooperation with a spliceosome, mediates alternative splicing of RNA transcripts of the coding sequence, the mediation being selected from at least one of the group consisting of: sex-specific, stage-specific, germline-specific and tissue-specific mediation.

The gene expression system comprises a gene, capable of expressing a protein of interest, under the control of a promoter therefor, in combination with splice control sequences, preferably intronic sequences that control alternative splicing. Optionally, an enhancer or a transcriptional transactivator protein binding sequence is also present in the gene expression system.

The splice control sequences provide alternative splices of the at least one protein, for instance in a sex-, stage-tissue or germline-specific manner. This differential expression of the at least one protein allows the user to combine two levels of control of expression an, therefore, to express proteins in a previously unobtainable manner.

It is preferred, therefore, that alternative splicing of the RNA transcribed from the gene of interest leads to differential expression of the at least one protein in at least one of the above-mentioned specific manners.

Spliceosomes are large complexes of small nuclear RNA and protein particles (snRNPs) which assemble with pre-mRNA to achieve RNA splicing, by removing introns from eukaryotic nuclear RNAs, thereby producing mRNA which is then translated to protein in ribosomes.

The splice control sequences are preferably substantially intronic. Although it is envisaged that they may comprise a portion of exonic or coding sequence, this is not preferred according to one embodiment of the invention.

The gene expression system is capable of expressing at least one protein of interest. Said at least one protein may have a therapeutic effect or may, preferably, be a marker, for instance DsRed, Green Fluorescent Protein (GFP) or one or more of their mutants or variants, or other markers that are well known in the art.

Most preferably, the at least one protein has a lethal, deleterious or sterilizing effect. Where reference is made herein to a lethal effect, it will be appreciated that this extends to a deleterious or sterilizing effect, such as an effect capable of killing the organism per se or its offspring, or capable of reducing or destroying the function of certain tissues thereof, of which the reproductive tissues are particularly preferred, so that the organism or its offspring are sterile. Therefore, some lethal effects, such as poisons, will kill the organism or tissue in a short time-frame relative to their life-span, whilst others may simply reduce the organism's ability to function, for instance reproductively.

A lethal effect resulting in sterilization is particularly preferred, as this allows the organism to compete in the natural environment ("in the wild") with wild-type organisms, but the sterile insect cannot then produce offspring. In this way, the present invention achieve a similar result to techniques such as the Sterile Insect Technique (SIT) in insects, without the problems associated with SIT, such as the cost, danger to the user, and reduced competitiveness of the irradiated organism.

Preferably, the gene expression system comprises at least one positive feedback mechanism as described herein, namely at least one gene to be expressed and at least one promoter therefor, wherein a product of a gene to be expressed serves as a positive transcriptional control factor for the at least one promoter, and whereby the product, or the expression of the product, is controllable.

Preferably, the at least one protein is an apoptosis-inducing factor, such as the AIF protein described for instance in Candé et al (*Journal of Cell Science* 115, 4727-4734 (2002)) or homologues thereof. AIF homologues are found in mammals and even in invertebrates, including insects, nematodes, fungi, and plants, meaning that the AIF gene has been conserved throughout the eukaryotic kingdom.

Also preferred is Hid, the protein product of the head involution defective gene of *Drosophila melanogaster*, or Reaper (Rpr), the product of the reaper gene of *Drosophila*, or mutants thereof. Use of Hid was described by Heinrichs and Scott (*Proc. Natl Acad. Sci USA* 97, 8229-8232 (2000). Use of a mutant derivative, $Hid^{A1a5}$ was described by Horn and Wimmer (*Nature Biotechnology* 21, 64-70 (2003)). Use of a mutant derivative of Rpr, $Rpr^{KR}$, is described herein (see also White et al 1996, Wing et al., 2001, and Olson et al., 2003).

Both Rpr and Hid are pro-apoptotic proteins, thought to bind to IAP1. IAP1 is a well-conserved anti-apoptotic protein. Hid and Rpr are therefore expected to work across a wide phylogenetic range (Huang et al., 2002, Vernooy et al., 2000) even though their own sequence is not well conserved.

Also preferred is Nipp1Dm, the *Drosophila* homologue of mammalian Nipp1 (Parker et al *Biochemical Journal* 368, 789-797 (2002); Bennett et al., *Genetics* 164, 235-245 (2003)). Nipp1Dm is another example of a protein with lethal effect if expressed at a suitable level, as would be understood by the skilled person. Indeed, many other examples of proteins with a lethal effect will be known to the person skilled in the art.

It is also preferred that the protein of interest is itself a transcriptional transactivator, such as the tTAV system described herein.

It is preferred that the promoter can be activated by environmental conditions, for instance the presence or absence of a particular factor such as tetracycline in the tet system described herein, such that the expression of the gene of interest can be easily manipulated by the skilled person. Alternatively, a preferred example of a suitable promoter is the hsp70 heat shock promoter, allowing the user to control expression by variation of the environmental temperature to which the hosts are exposed in a lab or in the field, for instance. Another preferred example of temperature control is described in Fryxell and Miller (*Journal of Economic Entomology* 88, 1221-1232 (1995)).

Also preferred as a promoter is the sryα embryo-specific promoter (Horn & Wimmer (2003) from *Drosophila melanogaster*, or its homologues, or promoters from other embryo-specific or embryo-active genes, such as that of the *Drosophila* gene slow as molasses, or its homologues from other species.

It is also preferred that the genetic system comprises other upstream, 5' factors and/or downstream 3' factors for controlling expression. Examples include enhancers such as the fat-body enhancers from the *Drosophila* yolk protein genes, and the homology region (hr) enhancers from baculoviruses, for example AcMNPV.

The splice control mechanism allows an additional level of control of protein expression, in addition to the promoter and/or enhancer of the gene. For instance, tissue or sex-specific expression in embryos only would be extremely difficult by conventional methods. Promoters with this specificity are unknown, even in *Drosophila*. However, using combinatorial control according to the present invention, an embryo-specific promoter, for example sryα, can be combined with a suitable alternative splicing system.

It is preferred that any combination of promoter and alternative splicing mechanism is envisaged. The promoter is preferably specific to a particular protein having a short temporal or confined spatial effect.

Alternatively, it is preferred that the promoter may be specific for a broader class of proteins or a specific protein that has a long-term and/or wide system effect, such as a hormone, positive or negative growth factor, morphogen or other secreted or cell-surface signaling molecule. This would allow, for instance, a broader expression pattern so that a combination of a morphogen promoter with a stage-specific alternative splicing mechanism could result in the morphogen being expressed only once a certain life-cycle stage was reached, but the effect of the morphogen would still be felt (i.e. the morphogen can still act and have an effect) beyond that life-cycle stage. Preferred examples would be the morphogen/signaling molecules Hedgehog, Wingless/WNTs, TGFß/BMPs, EGF and their homologues, which are well-known evolutionarily-conserved signaling molecules.

It is also envisaged that a promoter that is activated by a range of protein factors, for instance transactivators, or which has a broad systemic effect, such as a hormone or morphogen, could be used in combination with an alternative splicing mechanism to achieve a tissue and sex-specific control or sex and stage-specific control, or other combinations of stage-, tissue, germ-line- and sex-specific control.

It is also envisaged that more than one promoter, and optionally an enhancer therefor, can be used in the present system, either as alternative means for initiating transcription of the same protein or by virtue of the fact that the genetic system comprises more than one gene expression system (i.e. more than one gene and its accompanying promoter).

In a further aspect, the present invention provides a method of transformation, comprising expressing alternative splices of a protein in an organism by contacting the organism with the gene expression system and preferably inducing expression of the expression system. Methods of introduction or transformation of the gene system and induction of expression are well known in the art with respect to the relevant organism.

Also provided are organisms (i.e. transformants) transformed by the present system.

Where reference to a particular nucleotide or protein or SEQ ID NO is made, it will be understood that this includes reference to any mutant or variant thereof, having substantially equivalent biological activity thereto. Preferably, the mutant or variant has at least 85%, preferably at least 90%, preferably at least 95%, preferably at least 99%, preferably at least 99.9%, and most preferably at least 99.99% sequence identity with the reference sequences or SEQ ID NO.

DESCRIPTION OF THE FIGURES AND SEQUENCE LISTINGS

The present invention will now be described with reference to the following non-limiting Figures and Sequence Listings, wherein.

Figure 19:
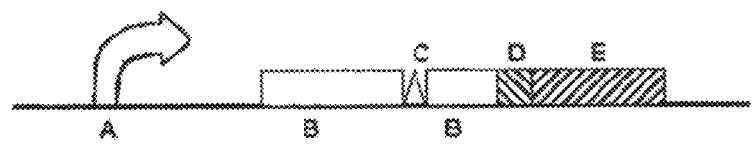

FIG. 19: One use of the P element in generating germline-specific expression of a gene of interest (Gene E). Insertion of the P element IVS3 and flanking exonic sequences upstream of an ubiquitin-Gene E fusion with allow germline-specific expression of Gene E under a germline active promoter. A—Germline active promoter; B—P-element open reading frame; C—P intron 'IVS3'; D—Ubiquitin; E—Coding region for protein of Interest e.g. tTAV.

Figure 20:
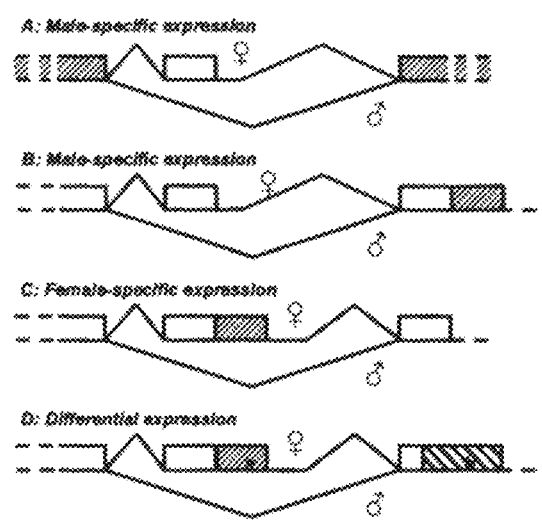

FIG. 20: Sex-specific expression using dsx. A: Intron used as Cctra intron above, but giving male-specific expression. A fragment of dsx (here the *Anopheles* version) is inserted into a heterologous coding region (shaded boxes). The intron is completely removed in males, but in females the coding region is prematurely terminated. B: An alternative approach to male-specific expression, in which a heterologous coding region is fused to a fragment of dsx. C: Female-specific expression: the heterologous coding region is inserted into the female-specific exon, either as an in-frame fusion to a fragment of Dsx, or with its own start and stop codons. D: Differential expression: designs B and C can be combined to give expression of gene a in females and b in males.

Figure 21:
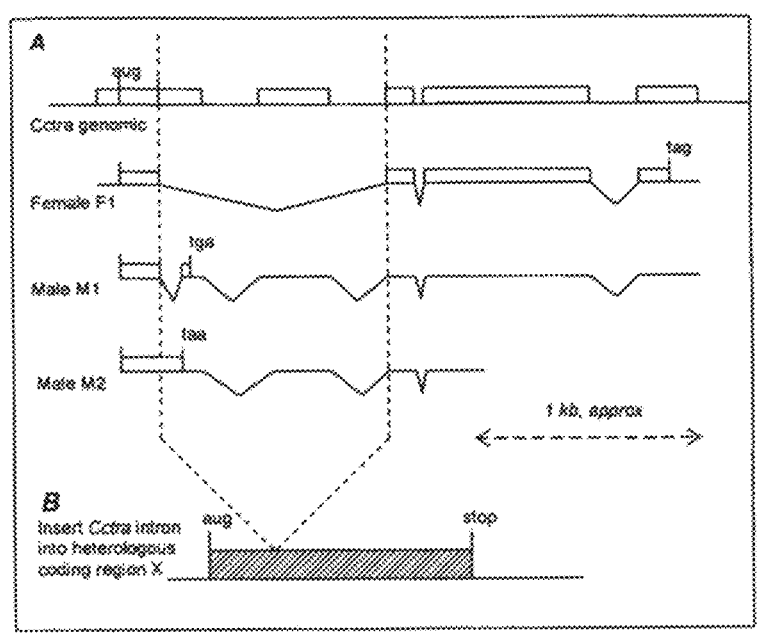

FIG. 21: Sex-specific alternative splicing of Cctra. A: Cctra is spliced in females to produce three transcripts: F1, which encodes functional Tra protein, and M1 and M2, which do not, because they include additional exons with stop codons (redrawn from Pane et al. 2002). Males produce only transcripts M1 and M2 and therefore do not produce functional Tra protein at all. B: If this intron were to function similarly in a heterologous coding region, this would similarly allow females, but not males, to produce functional protein X.

Figure 22:
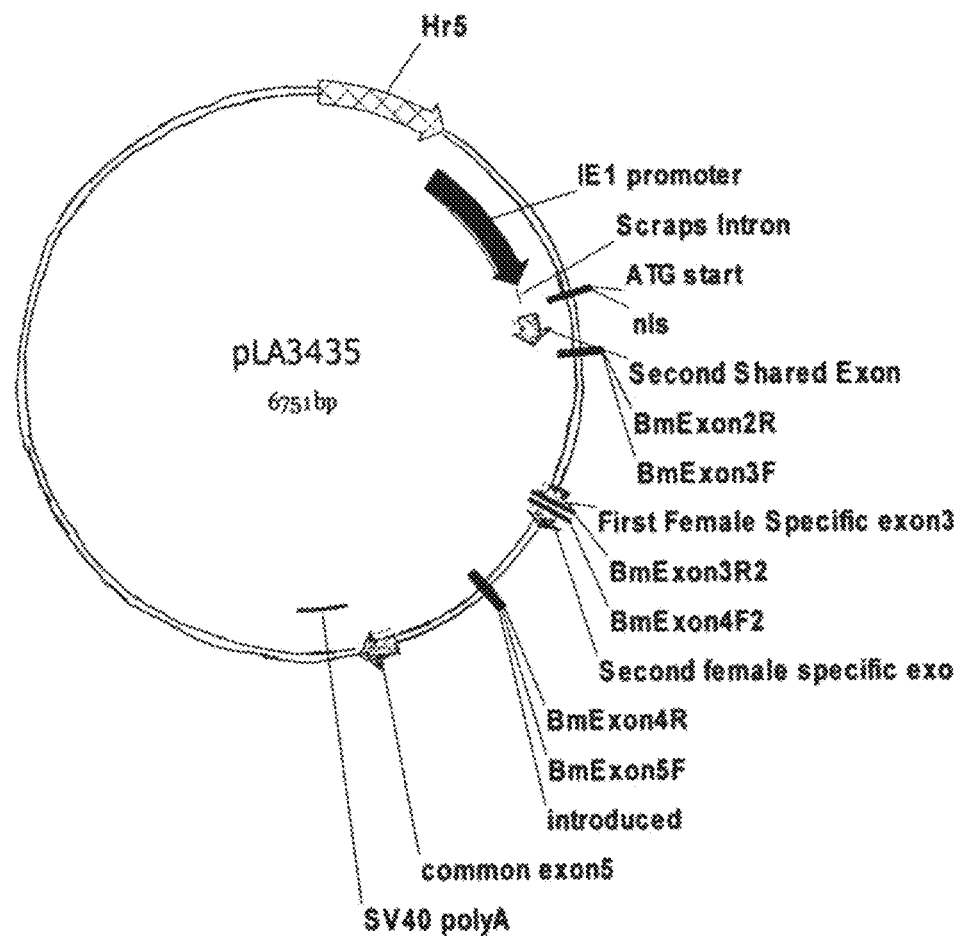

FIG. 22: Diagrammatic representation of pLA3435 construct/plasmid (SEQ ID NO. 46).

Figure 23:
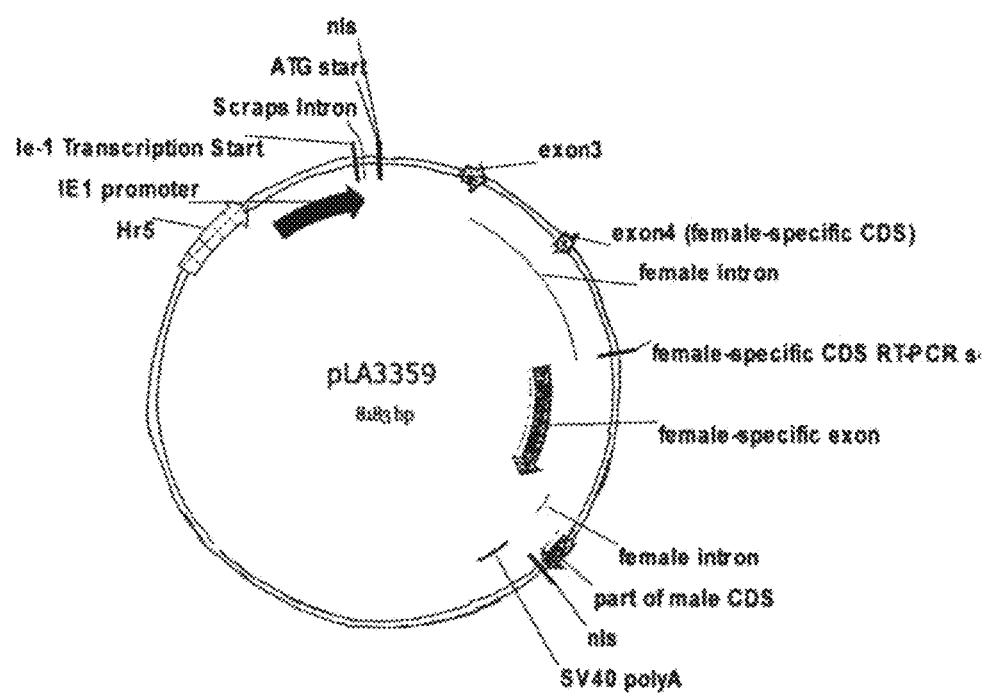

FIG. 23: Plasmid map of pLA3359 *Anopheles gambiae* dsx gene placed under the control of a Hr5-IE1 promoter for assessing splicing via transient expression.

Figure 24:
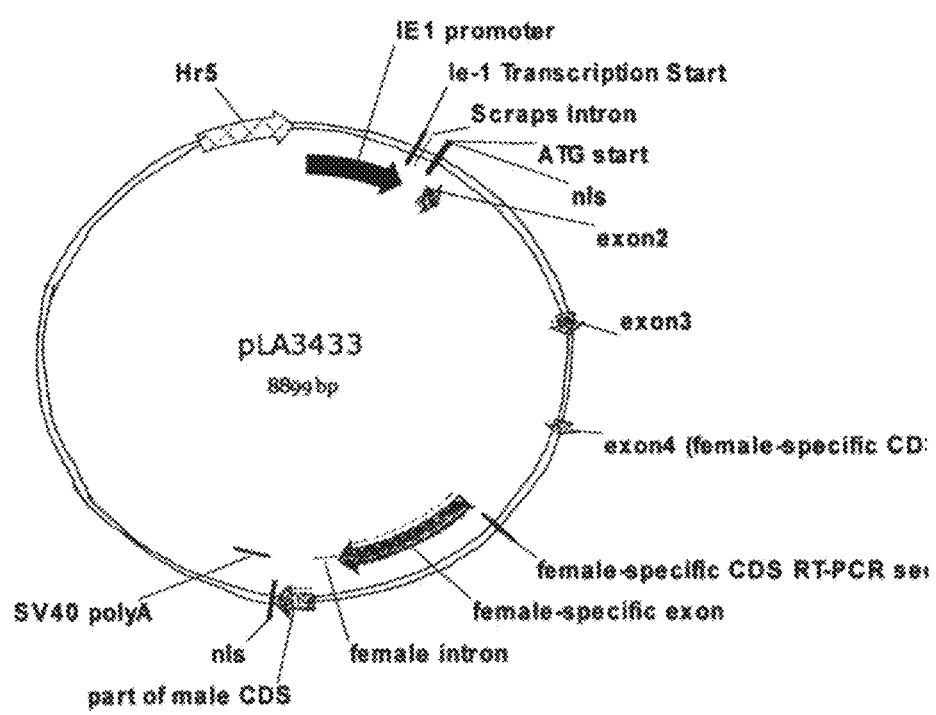

FIG. 24: pLA3433-*Anopheles gambiae* dsx gene placed under the control of a Hr5-IE1 promoter, with the addition of exon 2, for assessing splicing via transient expression.

Figure 25:
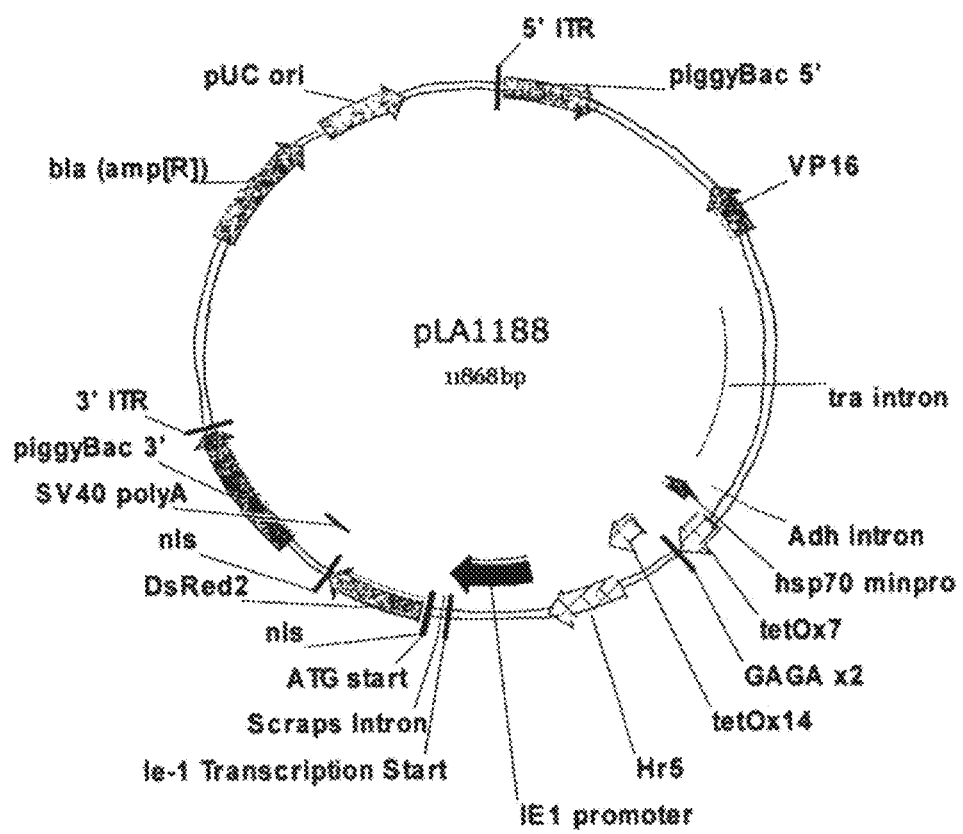

FIG. 25: Schematic representation of pLA1188 construct.

Figure 26:
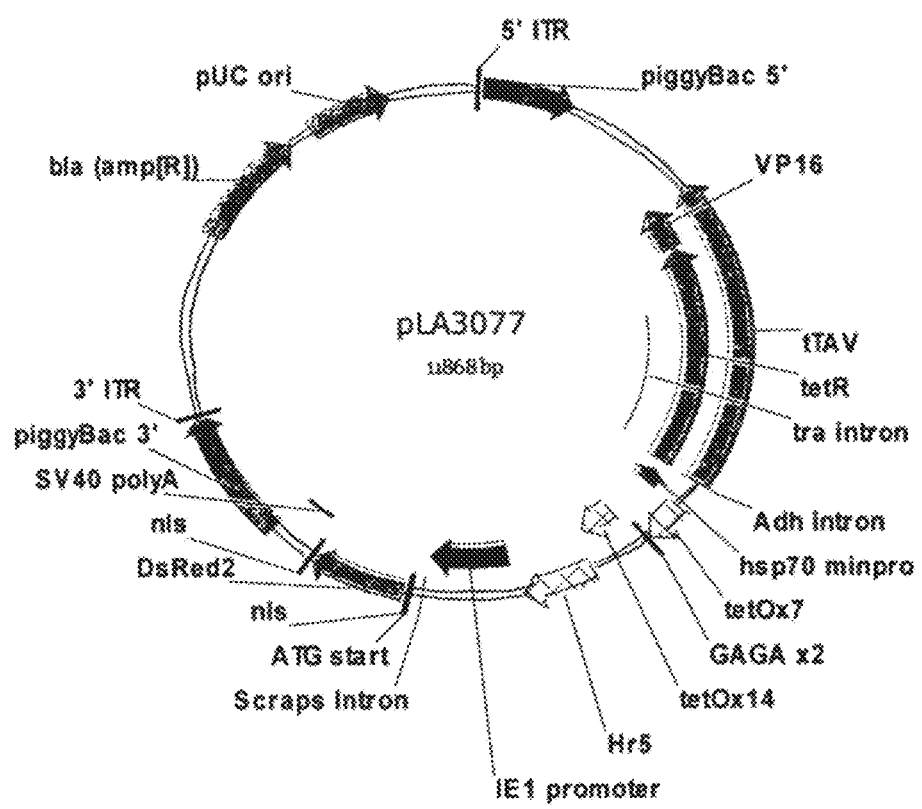

FIG. 26: Schematic diagram of pLA3077 construct.

Figure 27:
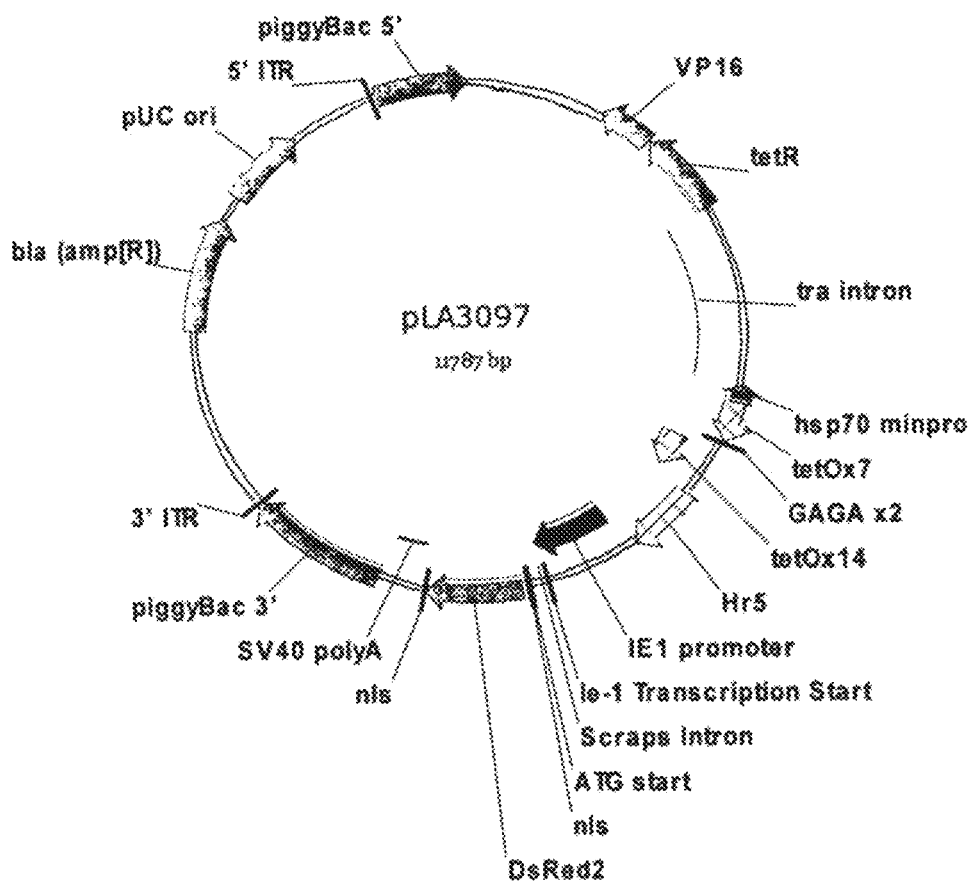

FIG. 27: Schematic diagram of pLA3097 construct.

Figure 28:
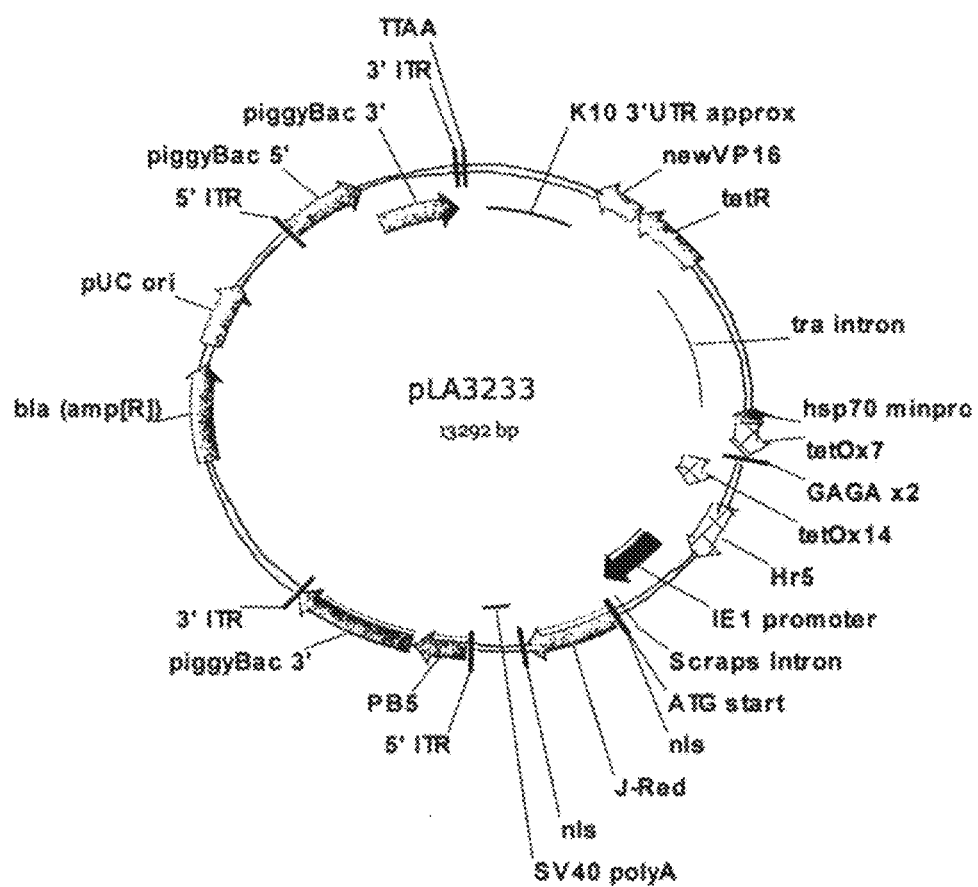

FIG. 28: Schematic diagram of pLA3233 construct.

Figure 29:
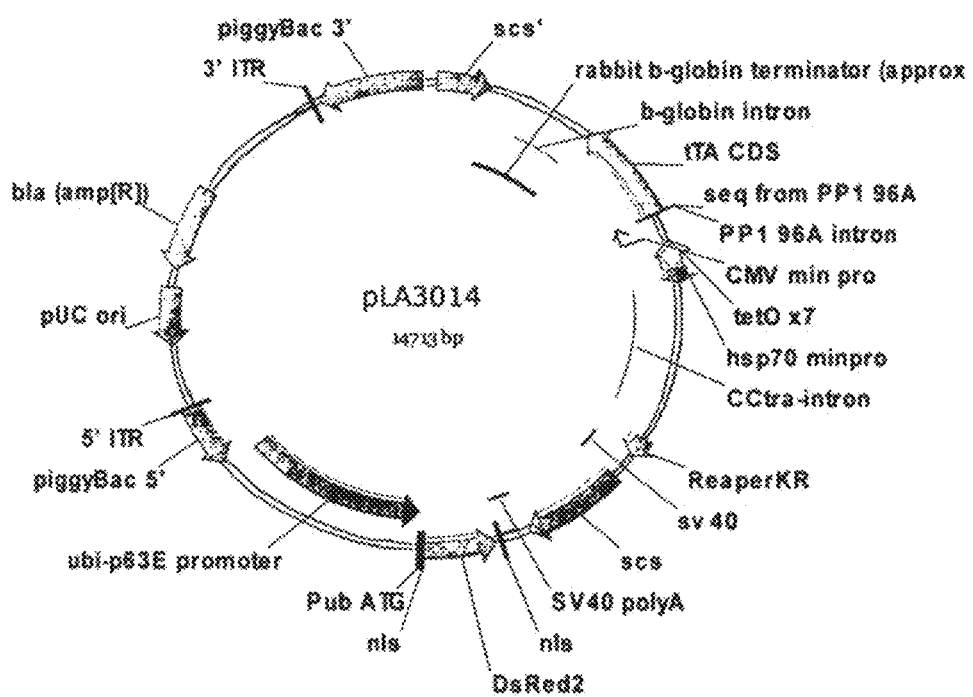

FIG. 29: Schematic diagram of pLA3014 construct.

Figure 30:
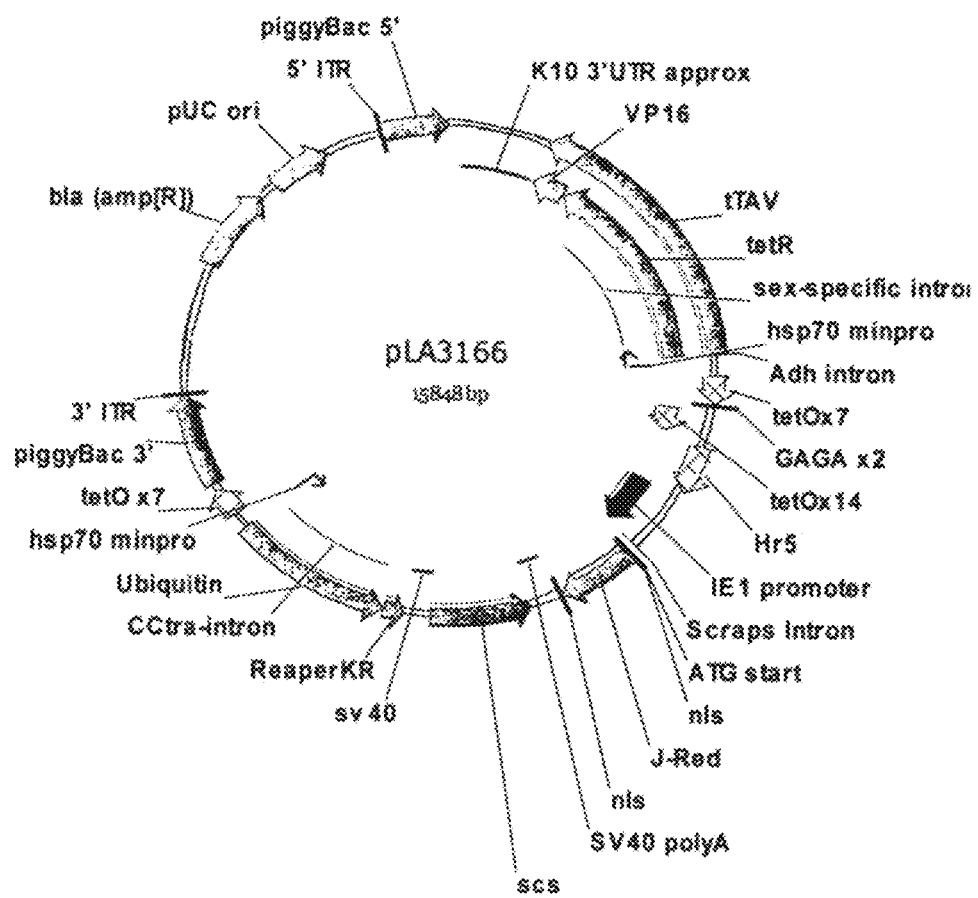

FIG. 30: Schematic diagram of pLA3166 construct.

Figure 31:
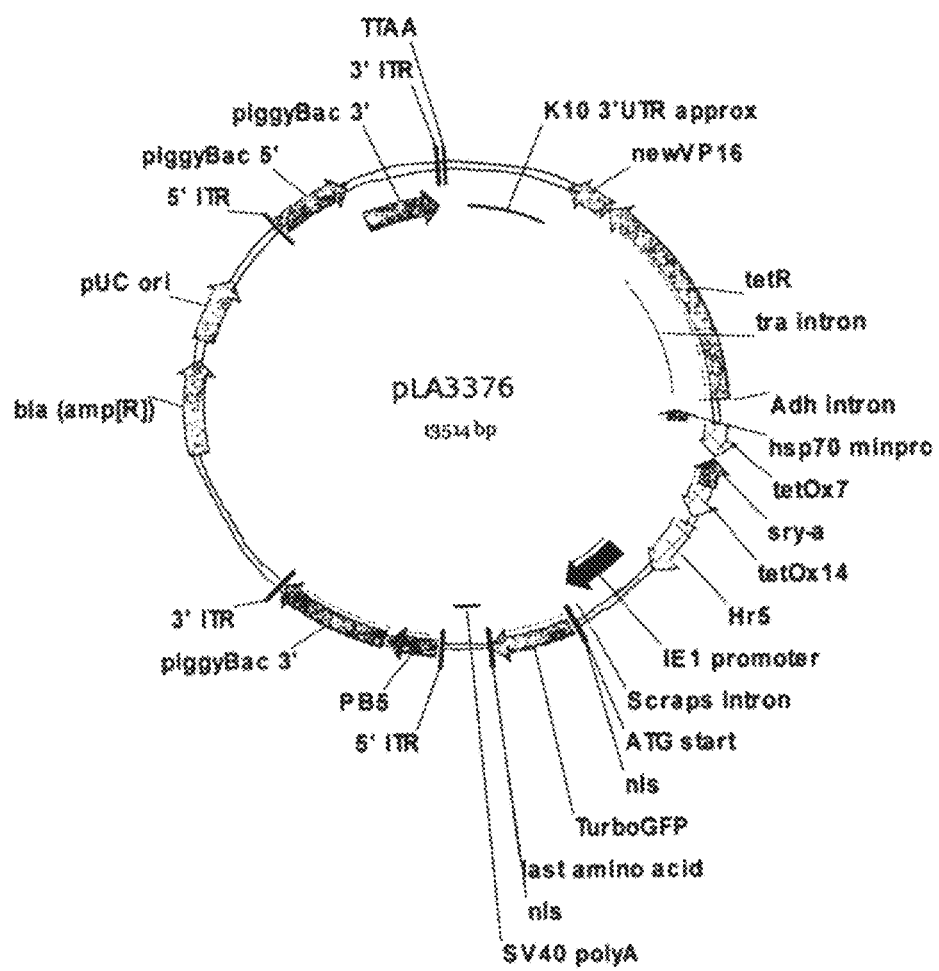

FIG. 31: Schematic diagram of pLA3376 construct.

Figure 32:
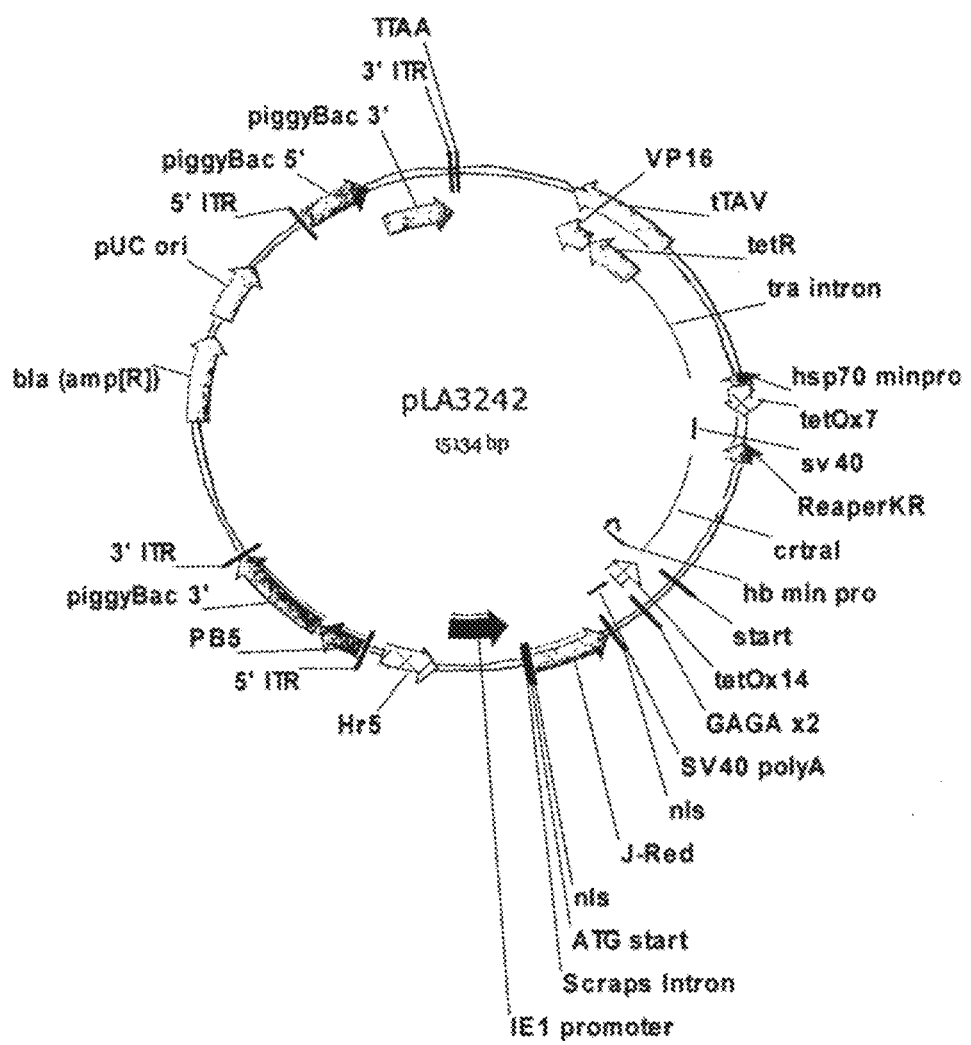

FIG. 32: Schematic diagram of pLA3242 construct.

FIG. 33: Flanking sequence of Cctra. Splicing of the Cctra intron in LA3077 and LA3097 is exactly as you would see in the native Cctra intron. Splicing in LA1188 results in the removal of 4 additional nucleotides. In all cases the introns are flanked by 5' exonic TG and 3' GT.

Figure 34:
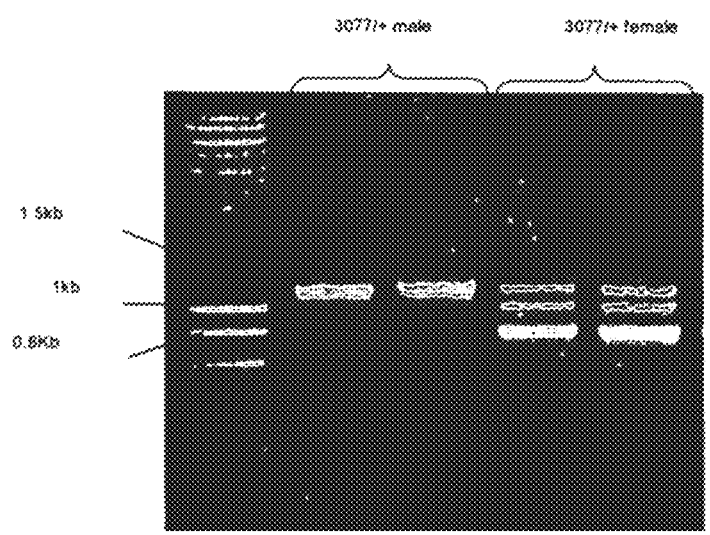

FIG. 34: Gel showing correct sex-specific splicing of intron(s) derived from CcTra (776 bp band in females) in *Ceratitis capitata* transformed with LA3077. Lane 1: Marker (SmartLadder™ from Eurogentec, bands of approx 0.8, 1.0 and 1.5 kb are indicated); Lanes 2 and 3: *Ceratitis capitata* LA3077/+ males; Lanes 4 and 5: *Ceratitis capitata* LA3077/+ females.

FIG. 35: Phenotypic data for transformed female specific constructs in *Ceratitis capitata*. Column 1: Construct designation LA#, e.g. LA3077, LA3097, LA3233, etc, is indicated by number, with independent insertion lines referred to by letter; Columns 2 and 3: Non-tetracycline (NT) results for each transformed line given in total males (2) and total females (3). Columns 4 and 5: Tetracycline (TET) results for each transformed line given in total males (4) and total females (5).

Figure 36:
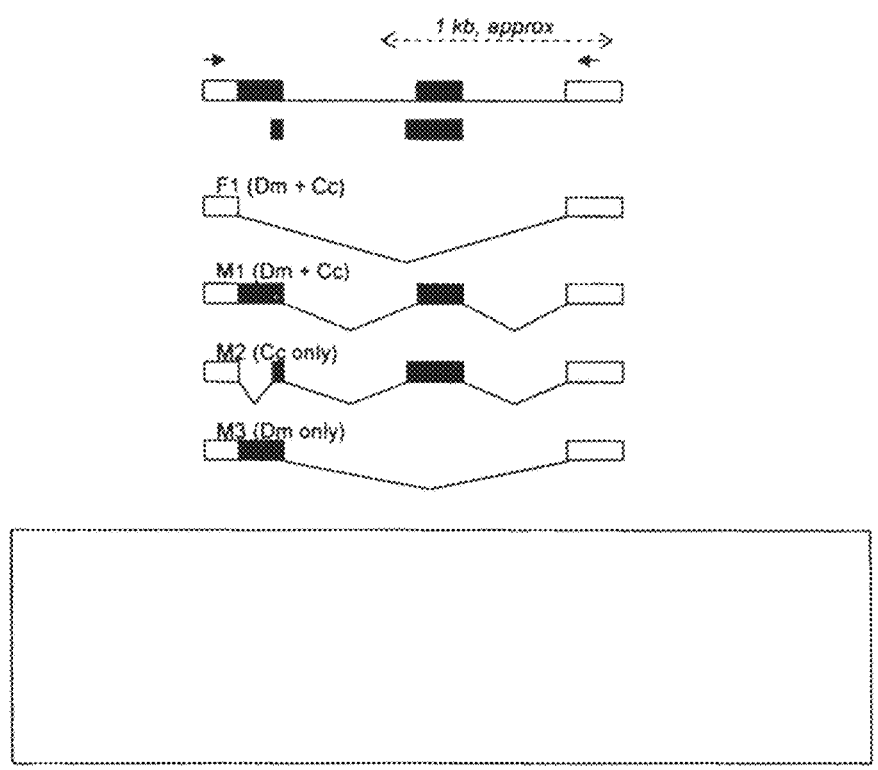

FIG. 36: Transcripts of Cctra intron constructs in *Drosophila* and *Ceratitis capitata*. The top line represents the construct DNA containing tra intron flanked by desired gene (the open box). The red box represents the male specific exons. Introns are represented by solid lines. Arrow above the first line represents the positions of the oligonucleotides used in the RT-PCR experiments. The bar indicates the scale of the figure.

Figure 37:
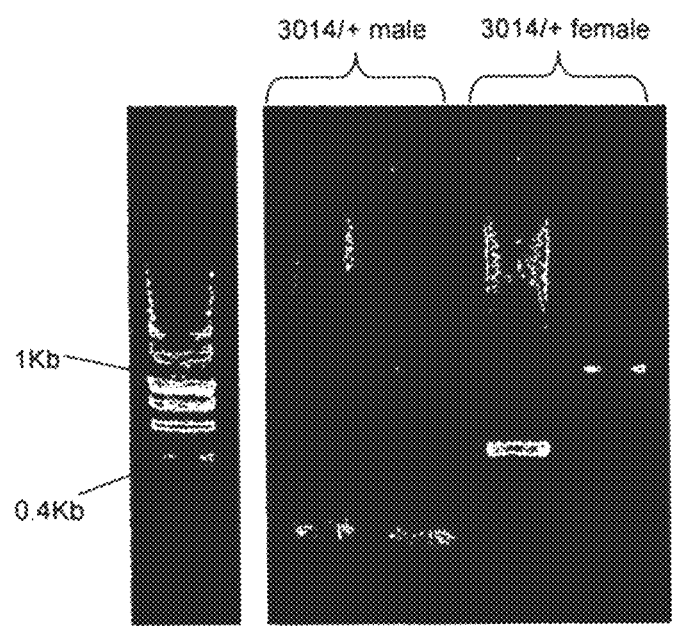

FIG. 37: Gel showing correct female specific splicing of CcTRA-derived sequence (508 bp band) in female *Ceratitis capitata* transformed with LA3014. Lane 1: Marker (SmartLadder™ from Eurogentec, bands of approx 0.4 and 1.0 kb are indicated); Lane 2 *Ceratitis capitata* LA3014/+ male; Lane 4: *Ceratitis capitata* LA3014/+ female; Lanes 3 and 5: no reverse transcriptase negative controls (background bands, probably from genomic DNA, can be seen in lanes 2 and 4).

FIG. 38: Phenotypic data for transgenic *Anastrepha ludens* transformed with LA3097 or LA3233. Column 1: Construct LA# (LA3097 or LA3233) indicated, with independent insertion lines referred to by letter; Columns 2 and 3: Non-tetracycline (NT) results for each transformed line given in total males (2) and total females (3). Columns 4 and 5: Tetracycline (TET) results for each transformed line given in total males (4) and total females (5).

Figure 39:
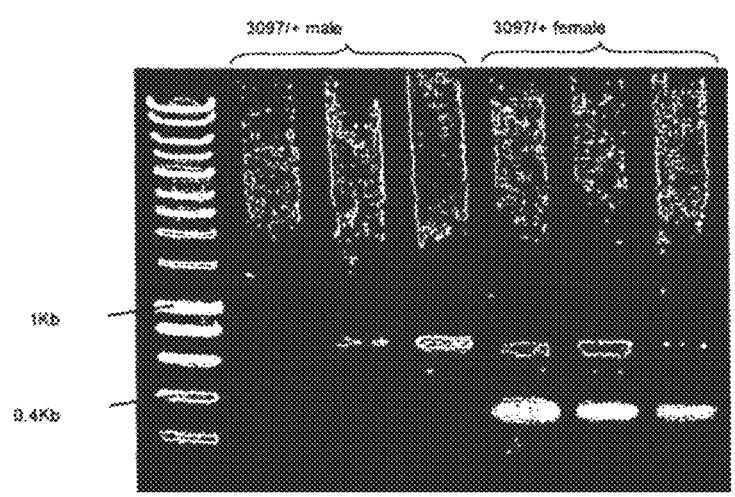

FIG. 39: Gel showing correct sex-specific splicing of CcTRA splicing (348 bp band in females) in *Anastrepha ludens* transformed with LA3097. Lane 1: Marker (SmartLadder™ from Eurogentec, bands of approx 0.4 and 1.0 kb are indicated); Lanes 2, 3 and 4: *A. ludens* LA3097/+ males; Lanes 5, 6 and 7: *A. ludens* LA3097/+ females.

Figure 40:
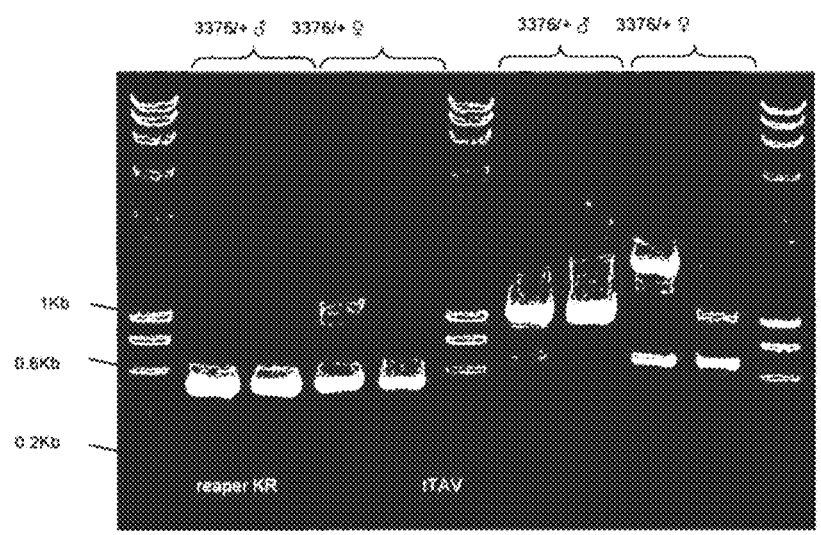

FIG. 40: Gel showing correct sex-specific splicing of BzTRA in reaperKR (200 bp band in females) and tTAV3 (670 bp band in females) regions of LA3376, in *Ceratitis capitata* transformed with LA3376. Lane 1: Marker (SmartLadder™ from Eurogentec, bands of approx 0.2, 0.6 and 1.0 kb are indicated); Lanes 2 and 3: *C. capitata* LA3376/+ males tested for splicing in reaperKR; Lanes 4 and 5: *C. capitata* LA3376/+ females tested for splicing in reaperKR; Lane 6: SmartLadder™; Lanes 7 and 8: *C. capitata* LA3376/+ males tested for splicing in tTAV; Lanes 9 and 10: *C. capitata* LA3376/+ females tested for splicing in tTAV; Lane 11: SmartLadder™.

Figure 41:
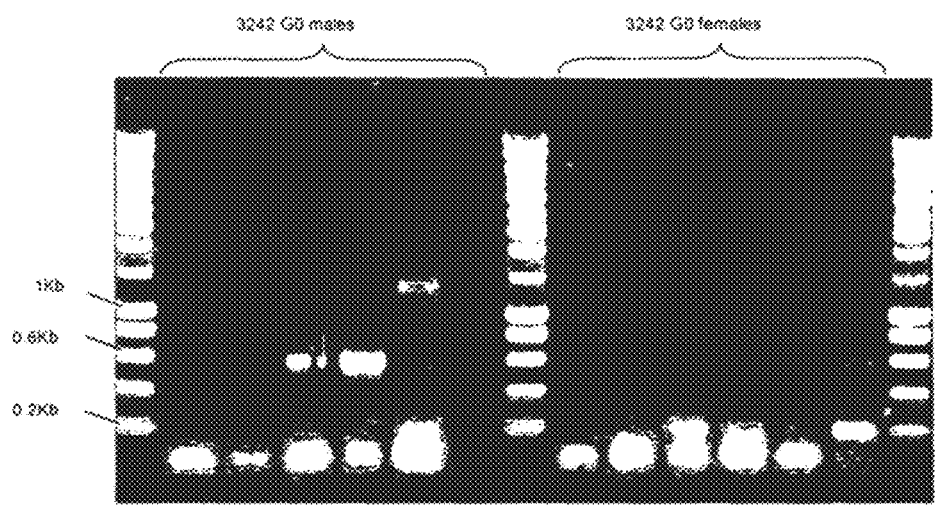

FIG. 41: Gel showing correct sex-specific CrTRA splicing in CrTRA-reaperKR (200 bp band in females) in *Ceratitis capitata* injected with LA3242. Lane 1: Marker (SmartLadder™ from Eurogentec, bands of approx 0.2, 0.6 and 1.0 kb are indicated); Lanes 2-7: *C. capitata* wild type males injected with LA3242; Lane 8: SmartLadder™; Lanes 9-14: *C. capitata* wild type females injected with LA3242; Lane 15: SmartLadder™.

Figure 15:
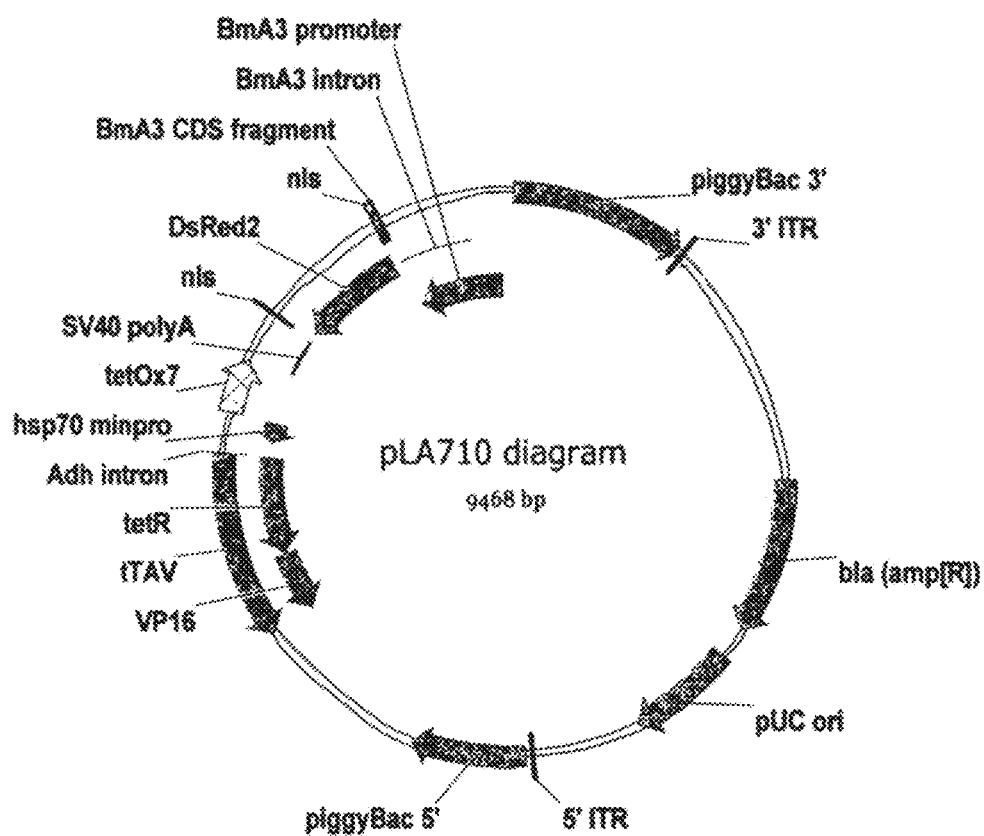
FIG. 15 is a schematic diagram of pLA710.
Figure 42:
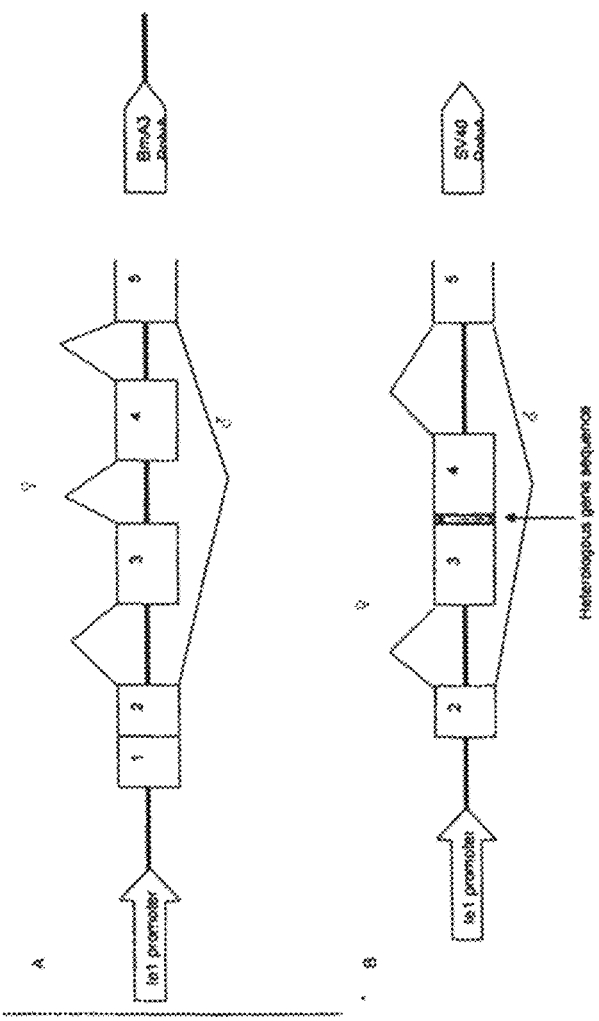

FIG. 42: Schematic representation of Bmdsx minigene constructs. Two minigene constructs derived from the *Bombyx mori* dsx gene are illustrated diagrammatically, together with the predicted alternative splicing of these constructs (female pattern shown above the construct, male pattern below). (A) is the *Bombyx mori* dsx mini-gene construct used in Funaguma et al., 2005) (B) is pLA3435. A and B differ from each other in several ways: (i) Exon 1 is excluded from pLA3435, (ii) the intron between female specific exons 3 and 4 has been removed and a short heterlogous sequence has been inserted in pLA3435 (iii) Funaguma et al., use the ie1 promoter from the baculovirus BmNPV and a BmA3 3'UTR compared with pLA3435 which uses the hr5-IE1 enhancer/promoter from the baculovirus AcNPV and a 3'SV40 3'UTR. (iv) pLA3435 uses slightly longer intron sequences when compared with (A) (see FIG. 15 for sequence). Two minigene constructs derived from the *Bombyx mori* dsx gene are illustrated diagrammatically, together with the predicted alternative splicing of these constructs (female pattern shown above the construct, male pattern below).

Figure 43:
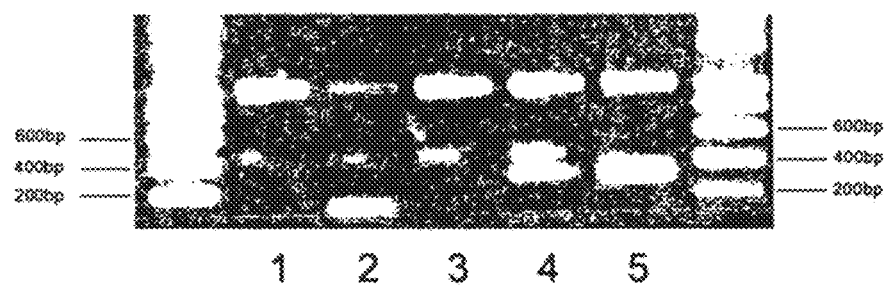

FIG. 43: Sex-specific splicing of BMdsx mini-gene construct in PBW. Analysis of transient expression from pLA3435 using RT-PCR show the presence of a 442 bp fragment (Lanes 1, 2, 3 and 4) in males and a 612 bp fragment in females (Lane 5), showing that the BMdsx mini-gene with a heterologous fragment inserted between exon 3 and 4 is able to splice correctly in the divergent moth, PBW. Markers are SmartLadder™ from Eurogentec; bands of approx 0.2, 0.4 and 0.6 kb are indicated FIG. 44: Sex-specific splicing of *Anopheles gambiae* dsx. *Anopheles* (A) shows the splicing that was reported by Scali et al 2005. However, when RT-PCR was performed using our primers (spl-agdsx-e3 (SEQ ID NO. 60) and spl-agdsx-m (SEQ ID NO. 61)) a different splicing pattern for females was revealed, represented by *Anopheles* (B).

FIG. 45: Identification of male and female *Anopheles gambiae* using dsx primers. RNA was extracted from male and female *Anopheles gambiae* and the dsx transcripts were amplified by RT-PCR using the primers spl-agdsx-e3 (SEQ ID NO. 62) and spl-agdsx-m (SEQ ID NO. 63); the resulting banding pattern is shown in the gel above. The expected bands for the male and female transcripts are indicated by the white arrows, the bands have been cloned and sequenced and are identical to the predicted sequence of our version of the dsx transcript (see SEQ ID NO. 47 (LA3359) and SEQ ID NO. 48 (LA3433)). The molecular weight markers are shown in kb (SmartLadder™ from Eurogentec; sizes are approximate).

Figure 46:
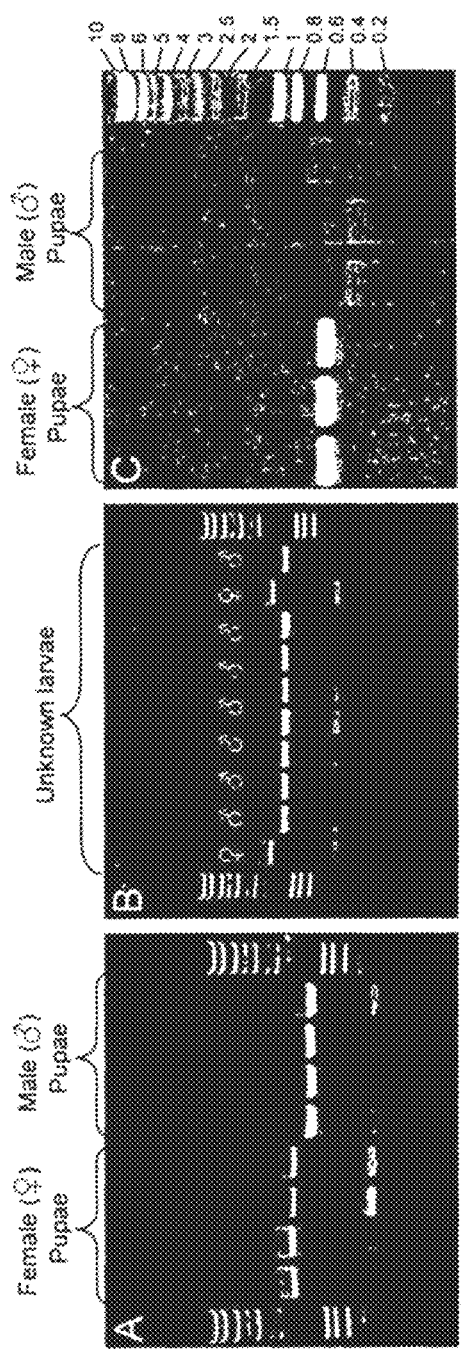

FIG. 46; Identification of male and female *Stegomyia aegypti* using dsx primers. The primers for the *Stegomyia aegypti* RT-PCR for A and B were aedesxF1 (SEQ ID NO. 64) and aedesxR5 (SEQ ID NO. 65) were tested initially on pupae, a life stage of *Stegomyia aegypti* that can be sexed conveniently and accurately; the resulting RT-PCR amplification is shown on gel image (A). The male and female pupae show a distinctive sex specific band. Then the primers were tested on RNA extractions from larvae, which can not be readily sexed by their morphology and the resulting RT-PCR amplification shown on gel image (B). The larvae show a clear banding pattern which distinguishes males from females unambiguously. Gel image (C) shows an approximately 600 bp band from RT-PCR using the primers aedessxF1 and aedesxR2 (SEQ ID NO. 66) from individual male and female pupa. Sequencing of this band showed a female specific splice variant which does not appear to possess the male shared exon to which aedesxR5 is predicted to anneal (exon 7, see FIG. 56). The molecular weight markers are shown in kb (SmartLadder™ from Eurogentec; sizes are approximate).

Figure 47:
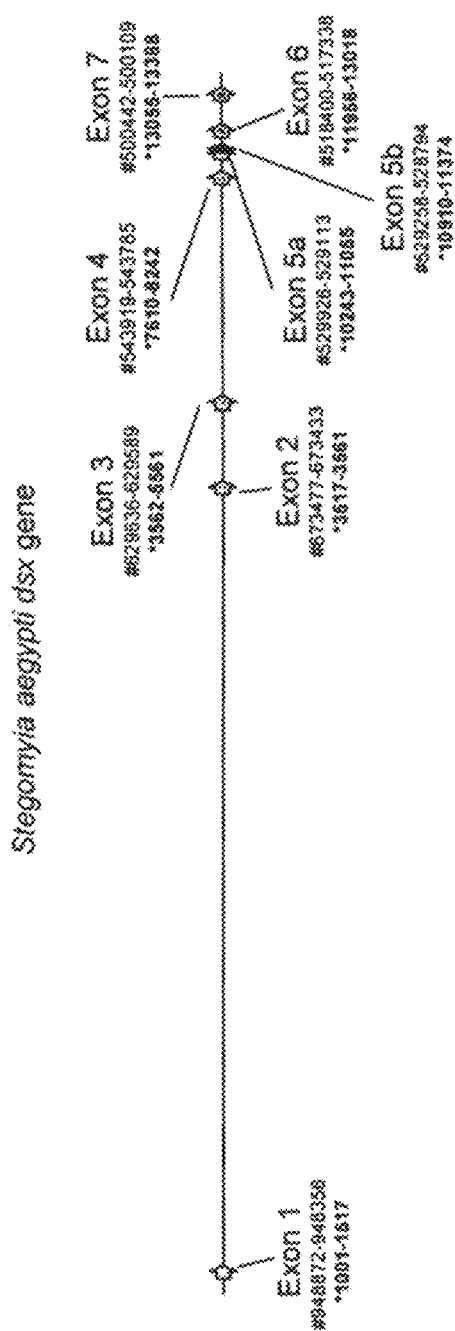

FIG. 47: Diagrammatic representation of part of the *Stegomyia aegypti* dsx gene (not to scale). A fragment of the *Stegomyia aegypti* dsx gene is represented above. Exons 5a and 5b are female specific and exon 6 is a male specific exon. Two female-specific splice variants have been found (F1 and F2) which comprise exons 1-4, 5b, 6 and 7 (F1) or 1-4, 5a (F2); transcripts in males (M1) comprise exons 1-4, 6 and 7 but not exon 5a or 5b and a transcript (C1) of 1-4 and 7 but not exons 5a, 5b or 6 is shown in males and females. The numbers for each of the exons after # relates to contig 1.370 (on the world-wide web, address broad.mit-.edu/annotation/disease_vector/aedes_aegypti/), which reads in the opposite orientation, and after * relate to the nucleotide sequence shown in SEQ ID NO. 43.

Figure 12:
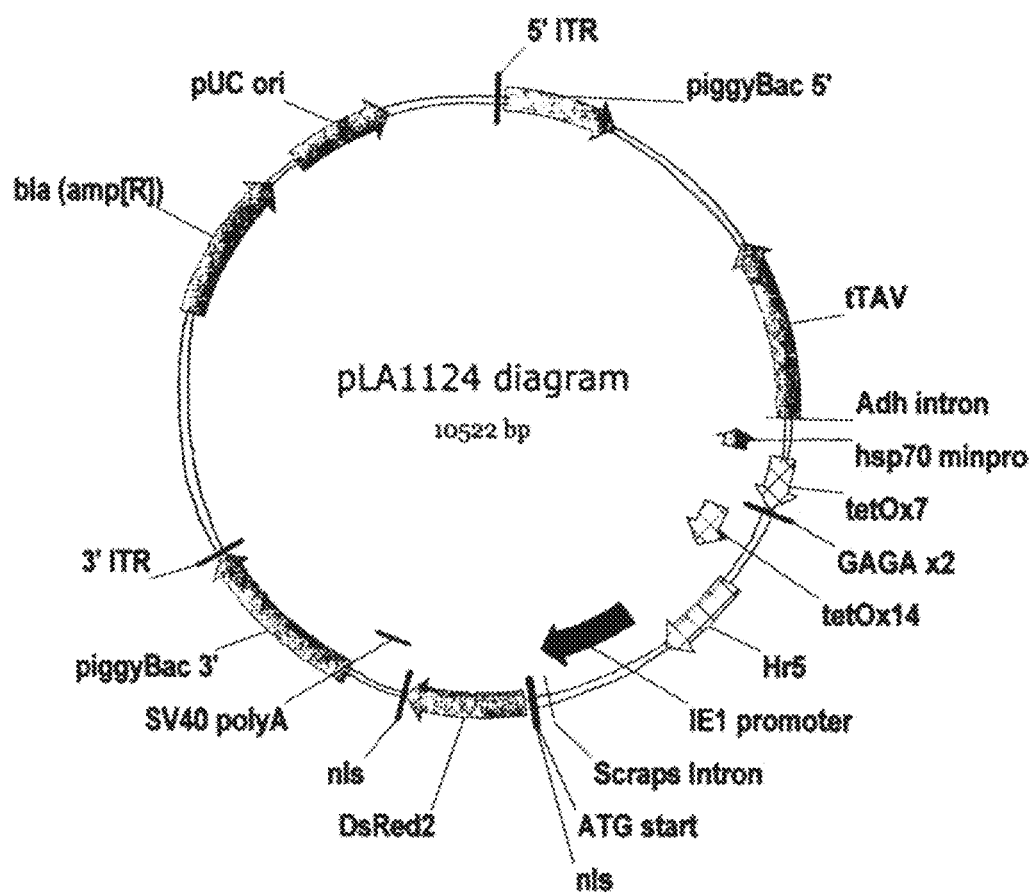
FIG. 12 is a schematic diagram of pLA1124.
Figure 48:
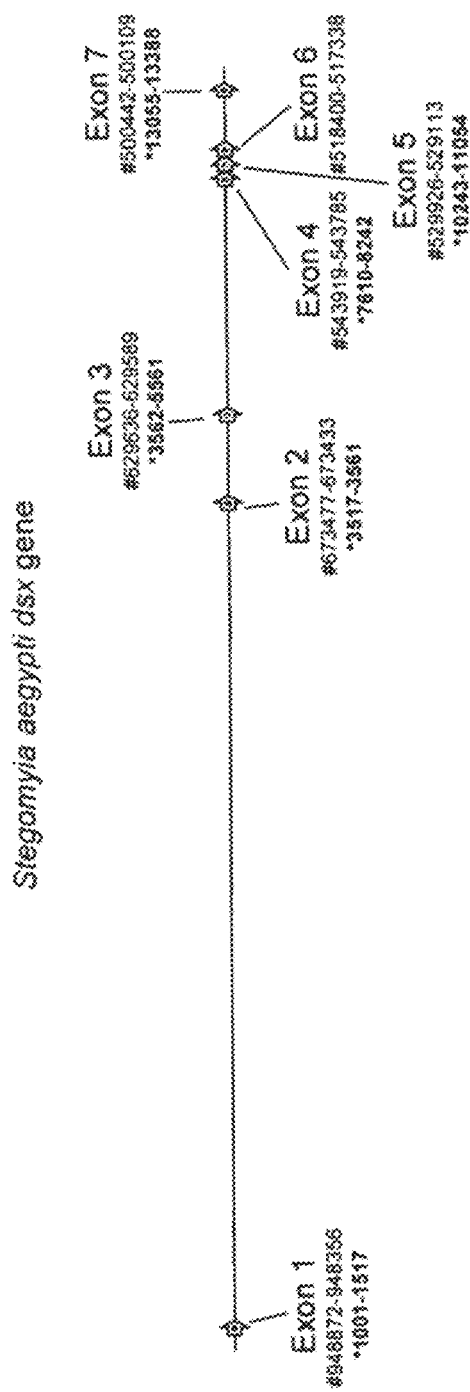

FIG. 48: Diagrammatic representation of the *Stegomyia aegypti* dsx gene. The entire *Stegomyia aegypti* dsx gene is represented above Exon 5 is the female specific exon and exon 6 is a putative male specific exon. In principle, transcripts in females comprise exons 1, 2, 3, 4, 5 and 7, and males comprise exons 1, 2, 3, 4, 6 and 7. The numbers for each of the exons after # relates to contig 1.370 (on the world-wide web, address broad.mit.edu/annotation/disease_vector/aedes_aegypti/) reading in the opposite orientation, and after * relate to FIG. 12.

Figure 49:
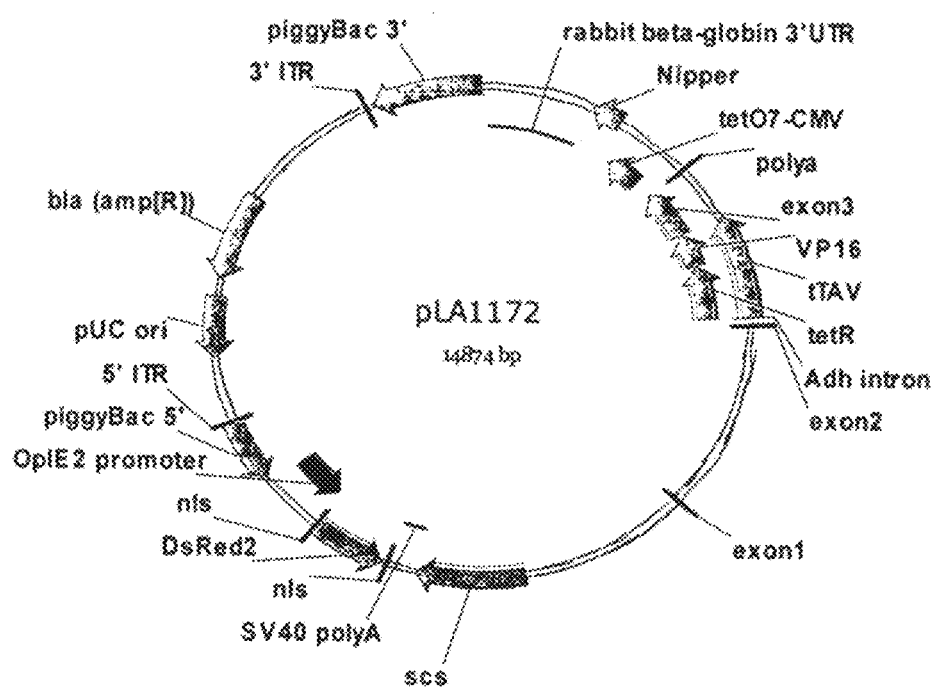

FIG. 49: Plasmid map of pLA 1172. A coding region for tTAV has been placed under the control of a fragment from the *Stegomyia aegypti* actin-4 gene (Munoz et al 2005) which includes the 5' UTR, first intron, and upstream sequences (putative promoter). The construct also contains a tetO$_7$ Nipper sequence. The construct has piggyBac ends and a DsRed2 marker for stable integration into a genome.

Figure 50:
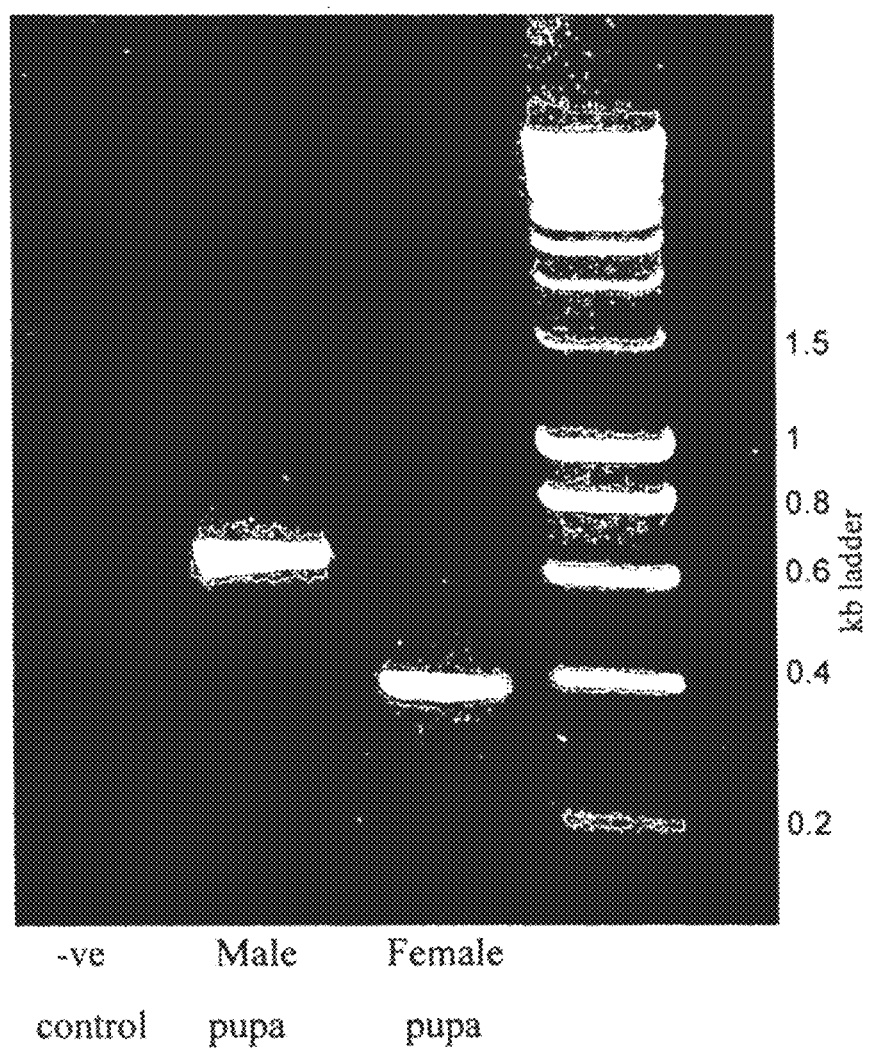

FIG. 50: Sex-specific splicing of tTAV in LA1172 (SEQ ID NO. 106) transformants. Gel image of RT-PCR of RNA extracted from LA1172 line 2 male and female pupa. The primers used were Agexon1 (SEQ ID NO. 67) and Tra (tTAV) seq+ (SEQ ID NO. 68). Sequencing of the RT-PCR bands showed the expected splicing occurring in males and females. The data shown in the above diagram is for LA1172 line 2, line 8 showed exactly the same results (data not shown). Markers are SmartLadder™ from Eurogentec; approximate sizes are indicated, in kb).

Figure 51:

FIG. 51: RT-PCR of wild type samples, showing sex-specific splice variants of the *Stegomyia aegypti* Actin-4 gene. Gel image of RT-PCR of RNA extracted from different developmental stages, and dissections of adults, of LA1172 line 8. The primers used were Agexon1 (SEQ ID NO. 69) and Exon 3 (SEQ ID NO. 70). The gel image shows that strong expression from the Actin-4 gene only occurs at the pupal stage, and that adult expression is generally limited to the female thorax where the flight muscles are found. Table 17, below show the contents of each lane.

TABLE 17

| | |
|---|---|
| E = pool of ~100 embryos | MH = head from male adult |
| L4 = 4$^{th}$ instar larva | MT = thorax from male adult |
| ME = early male pupa (<4 hours old) | MA = abdomen from male adult |
| FE = early female pupa (<4 hours old) | FH = head from female adult |
| MP = male pupa | FT = thorax from female adult |
| FP = female pupae | FA = abdomen from female adult |
| | −ve = water control |

SEQUENCE LISTINGS

SEQ ID NOS. 1-13 and 23-33 are described in Examples 1-12.

JY2004-tTA (SEQ ID NO. 14)—sequence of the tetO$_7$-tTA region only pP[Casper-Act5C-tTA] (SEQ ID NO. 15)

pLA513 (SEQ ID NO. 16)

pLA517 (SEQ ID NO. 17)

pLA656 (SEQ ID NO. 18)

pLA670 (SEQ ID NO. 23)

pLA710 (SEQ ID NO. 19)

pLA928 (SEQ ID NO. 20)

pLA1038 (SEQ ID NO. 24)

pLA1124 (SEQ ID NO. 21)

pLA1188 (SEQ ID NO. 22)

SEQ ID NO. 34: Open reading frame of tTAV

SEQ ID NO. 35: Protein sequence of tTAV

SEQ ID NO. 36: Open reading frame of tTAV2

SEQ ID NO. 37: Protein sequence of tTAV2

SEQ ID NO. 38: Open reading frame of tTAV3

SEQ ID NO. 39: Protein sequence of tTAV3

SEQ ID NO. 40: Pink Bollworm dsx female specific sequence fragment 1

SEQ ID NO. 41: Pink Bollworm (PBW, *Pectinophora gossypiella*) dsx female specific sequence fragment 2

SEQ ID NO. 42: Pink Bollworm (PBW, *Pectinophora gossypiella*) dsx male specific sequence SEQ ID NO. 43: Partial gene sequence of *Aedes aegypti* dsx. All exonic sequence is included, but only partial intronic sequence—see FIGS. 47 and 48 for annotation.

SEQ ID NO. 44: Codling moth (*Cydia pomonella*) dsx female gene sequence: includes a stretch of unknown nucleotides, preferably than then 100, preferably less than 50, more preferably less than 20, more preferably less than 10, and most preferably less than 5.

SEQ ID NO. 45: Codling moth (*Cydia pomonella*) dsx-male sequence.

SEQ ID NO. 46: Sequence of pLA3435-*Bombyx mori*-dsx construct/plasmid.

SEQ ID NO. 47: Sequence of pLA3359-*Anopheles gambiae* dsx construct.

SEQ ID NO. 48: Sequence of pLA3433-Agdsx (*Anopheles gambiae*) construct with exon 2 included.

SEQ ID NO. 49: Sequence of pLA1188-cctra intron construct.

SEQ ID NO. 50: Sequence of pLA3077-a Cctra intron-tTAV construct.

SEQ ID NO. 51: Sequence of pLA3097-a Cctra intron-tTAV construct.

SEQ ID NO. 52: Sequence of pLA3233-Cctra-intron-tTAV2 construct.

SEQ ID NO 53: Sequence of pLA3014-Cctra-intron-Ubiquitin-reaperKR construct.

SEQ ID NO. 54: Sequence of pLA3166-Cctra intron-Ubiquitin-reaperKR construct.

SEQ ID NO. 55: Sequence of pLA3376-Bztra intron-reaperKR and Bztra-intron-tTAV3.

SEQ ID NO. 56: Sequence of pLA3242-Crtra intron-reaperKR construct.

SEQ ID NO. 57: Partial sequence of a male transcript generated in *Drosophila melanogaster* from LA3077 transformants that differs to the sequence generated in Medfly LA3077 lines. This sequence corresponds to the M3 transcript depicted in FIG. 36.

SEQ ID NO. 58: Partial sequence of *Bactrocera zonata* tra homologue. Sequence of intron predicted to be spliced out in a female-specific transcript of *B. zonata* tra (+3 to +970 bp in sequence). Exonic flanking nucleotides are at positions 1-2 and 971-972, i.e. at the 5' and 3' ends of the intronic sequence. In fact, it is worth noting that the intronic sequence is flanked on its 5' end by a Guanine nucleotide, which is thought critical for a clean exit of the intron.

SEQ ID NO 59: Partial sequence of *Ceratitis rosa* tra homologue. Sequence of intron predicted to be spliced out in a female-specific transcript of *C. rosa* tra (+3 to 1311 bp in sequence). Exonic flanking nucleotides are present at positions 1-2 and 1312-3. Again, it is noteworthy that the intronic sequence is flanked on its 5' end by a Guanine nucleotide, which is thought critical for a clean exit of the intron.

SEQ ID NOS. 60-70: Primers as referred to in FIGS. 44-46 and 50-51.

SEQ ID NO. 71: Pink Bollworm (PBW, *Pectinophora gossypiella*) dsx female specific fragment 3.

SEQ ID NO. 72: Open reading frame of *Drosophila melanogaster* ubiquitin.

SEQ ID NO. 73: Protein sequence of *Drosophila melanogaster* Ubiquitin.

SEQ ID NOS. 74-105 are primers as discussed below in the Examples.

SEQ ID NO. 106 is pLA1172.

DETAILED DESCRIPTION OF THE INVENTION

The key tissue for development of filarial worms in their *Culex* mosquito hosts is the adult female in direct flight muscle (IFM). Although it is highly desirable to express an anti-filarial effector molecule in this tissue only, no promoter with this specificity is known. The *Drosophila* IFM Actin gene Act88F is known to be expressed correctly in the IFM's of these mosquitoes (Allen et al, 2004). Therefore, as provided in the present invention, combining the Act88F Actin gene promoter with a suitable alternative splicing mechanism that is sex-specific to the female, allows expression of an effector molecule in this tissue, in females only. Accordingly, such a system is preferred.

Many examples of suitable effector molecules are known to the person skilled in the art, for example pro-apoptotic proteins, e.g. Hid and Reaper and their suitable mutant derivatives, as described above.

The above is an example of a sex-specific alternative splicing mechanism that is capable of exerting a level of male-specific or female-specific control on the expression of a gene of interest, in this case the anti-filarial effecter molecule. Further examples of sex-specific alternative splicing mechanisms are given below, but the invention also extends to tissue-specific, stage-specific, and germ-line-specific alternative splicing mechanisms. Expression with this specificity would be very useful, but extremely difficult to obtain by any other method.

Thus it is also preferred that the at least one protein differentially expressed due to alternative splicing is effective against a pathogen, i.e. is capable of reducing or preventing the transmission of a pathogen, or human, plant or livestock disease, by a non-human transmission vector. Examples are proteins having an effector function capable of preventing transmission of the malarial parasite in mosquitoes or the parasite responsible for sleeping sickness borne by the Tsetse Fly.

Preferably, the protein blocks parasite invasion or entry into the host. Beard et al. (Beard, C. B., Cordon-Rosales, C and Durvasula, R. V. (2002). Bacterial symbionts of the triatominae and their potential use in control of Chagas disease transmission. Ann. Rev. Ent. 47:123-141.) took the bacteria which live in the gut of the Kissing Bug (which transmits Chagas disease), modified it to secrete a peptide and/or protein and re-inserted the bacteria back into the Bug. This was shown to reduce transmission of the parasitic protozoan *Trypanosoma cruzi* and, therefore, the disease.

Therefore, it is envisaged that a similar approach be taken with the malaria parasite. It is known to take bacteria (*E. coli*) which live in the gut of mosquitoes (*Anopheles stephenis*) and engineer them so they express a 'killer' gene such as ricin, and an antibody which is targeted against an essential cell surface molecule of the parasite. When these genetically modified bacteria are reintroduced back into the gut of the mosquito, this resulted in a 95% reduction in the number of oocysts formed (Yoshida, S., Ioka, D., Matsuoka, H., Endo, H. and Ishii, A. (2001). Bacteria expressing single-chain immonotoxin inhibit parasite development in mosquitoes. Mol. Biochem. Parisitol. 113:89-96).

It is also preferred that two or more alternative splicing mechanisms may be combined, to give a further level of combinatorial control. So, for example, a sex-specific alternative splicing mechanism is combined with another splicing system, for example the stage-specific splicing of *Drosophila melanogaster* Mhc exon 18, as described above, to provide a transcript expressed only in embryonic and larval male (or, alternatively, female) muscles.

A wide range of alternative splicing systems will be known to the person skilled in the art. For example, the European Bioinformatics Institute of the European Molecular Biology Organization (EMBL-EBI) hosts a database of alternatively spliced genes and sequences, and computational tools for identifying such (on the world-wide web, address ebi.ac.uk/asd, and Clark and Thanaraj, 2002; Thanaraj et al., 2004). Other examples may readily be found in the literature, for example in (Black, 2003; Burset et al., 2001; Cartegni et al., 2002; Maniatis and Tasic, 2002; Pan et al., 2004; Park et al., 2004; Smith and Valcarcel, 2000; Venables, 2002, Venables, 2004) and references contained therein. Non-limiting, The present invention may use any suitable alternative splicing system, selectable by the skilled person on the basis of the combination of expression required from his common general knowledge including those described in the art discussed herein, which is hereby incorporated by reference.

The system, therefore, preferably comprises splice control sequences derived from, for instance AaActin-4, Dsx, Bztra or Cctra. These and other particularly preferred examples are discussed below.

By "derived" it will be understood that it is meant that the splice control sequence is a sequence from that gene. The splice control sequence itself is a sequence, usually an intron or a substantial part is intronic sequence, which is capable of regulating or mediating the alternative splicing of the pre-mRNA transcript of the coding sequence from that that particular gene.

Tissue-Specific Splicing

Tissue-specific alternative splicing mechanisms are a wide spread phenomena, occurring in both the animal and plant kingdoms. Examples in plants can be found, for instance in The Plant Alternative Splicing Database, on the world-wide web, address pasdb.genomicx.org.cn, incorporated by reference.

Preferred examples of tissue-specific alternative splicing mechanisms are given below.

In rice, the KNOX family class 2 homeobox transcripts undergo tissue-specific alternative splicing. The products of these alternative splicing events are suggested to have different degrees of abilities for activation and repression of transcription of target genes in the different organs in which they are expressed (Ito et al., 2002).

In humans, tissue-specific alternative splicing occurs in the Leukocyte common antigen mRNA. The differential splicing of LCA has a functional importance to T cells, since human T4+ cells are divided into two functionally distinct sub-populations based on expression of LCA isoforms. The sequences controlling this differential splicing can be found within exon 4, which is found in B cell mRNA but not thymocyte mRNA sequences (Streuli and Saito, 1989).

The yellow fever mosquito (*Aedes aegypti*) uses alternative splicing to generate two distinct isoforms of the lipophorin receptor (LpR). This receptor is the main transport vehicle, delivering lipids through the hemolymph to various organs. One isoform (AaLpRov) is expressed exclusively in ovarian germline cells, nurse cells and oocytes throughout the previtellogenic and vitellogenic stages, where it is utilized in yolk protein uptake. In contrast the fat-body specific AaLpRfb transcript is restricted to the post-vittellogenic period where it is important in the storage of lipid, carbohydrate and protein (Seo et al., 2003).

Stage-Specific Splicing

Stage-specific alternative splicing is also known in a range of organisms, and preferred examples are given below.

Stage-specific alternative splicing of the spinach and tobacco chloroplast ascorbate peroxidase (chlAPX) pre-mRNAs, generating distinct isoenzymes are important for changing the ratio and amount of chlAPX isoenzymes during germination and subsequent greening (Yoshimura et al., 2002).

*Drosophila melangaster* exhibits a diversity of functionally distinct muscle types in various tissues at different stages of development. Alternative splicing of muscle-specific contractile proteins such as myosin, actin, tropomyosin, and troponin are key in generating this functional diversity in muscle types. Myosin heavy chain (Mhc) mRNA is predicted to produce up to 480 MHC isoforms (George et al., 1989). It is expressed in not only a tissue-specific manner but also a stage specific manner. Alternative splicing of the penultimate exon18 results in its inclusion in adult indirect flight muscles and other adult muscles mRNAs, exclusion of this exon occurs in all embryonic and larval muscle Mhc mRNA (Kazzaz and Rozek, 1989, Hastings and Emerson, 1991).

Sex-Specific Splicing

Sex-specific splicing is discussed elsewhere, and it will also be appreciated that sex-specific splicing also occurs in plants and examples are well-known. A preferred example is from *Marchantia polymorpha*, a liverwort. This is a sexually heteromorphic plant and displays sex-specific alternative splicing of a calcium-dependent protein kinase, a molecule involved in intracellular signaling events. In addition, tra-2 transcripts are found exclusively in the male sexual organ (Nishiyama et al., 1999 and Nishiyama et al., 2000).

Germline-Specific Splicing.

Preferred examples of germline-specific alternative splicing systems are given below.

Alternative splicing of the Wilms Tumour 1 (WT1) gene results in the incorporation of three amino acids (K, T, and S) which are thought to convert WT1 from a transcription factor to a splicing factor. This splicing factor isoform is essential for male sex determination in mice (Hammes, A et al., 2001) and regulates the expression of the SRY gene.

C3G is a ubiquitously expressed guanine nucleotide-releasing protein that binds to adaptor protein SH3 domains and is involved in the processes of cell growth, differentiation and apoptosis. The germ cell and somatic forms of this molecule are tightly regulated as there is no overlap in their expression pattern (Shivakrupa, et al 1999). The somatically expressed PKCδ is cleaved by caspase 3 resulting in its deregulation. The testes-specific variant contains an extra 78 bp which results in the addition of 26 amino acids that block caspase 3 cleavage.

The *Drosophila* P element taught in Siebel et al, 1992, is particularly preferred. Under the use of this alternative splicing mechanism, a gene of interest, such as an effector molecule or a marker, for instance, can be expressed in the germ line of the host under the control of an appropriate promoter. An example of this is given below and with reference to FIG. 19.

The P transposable element in *Drosophila* is 2907 bp in length and encodes an 87 kDa transposase protein, the 'full-length' canonical form. Variants are also known, especially deletion derivatives. Synthesis of a functional transposase protein is restricted to the germ line. This can only occur when all introns including the third intron (IVS3) are spliced out of pre-mRNA. Splicing of IVS3 is restricted to germ-line cells and in somatic cells is prevented by the binding of a protein complex to 30 bp of regulatory sequence at the 3' end of the second to last exon (exon 2). The presence of this intron, which contains a stop codon, left unspliced, produces a 66 kDa inactive protein which acts as a repressor towards functional transposase protein.

It is preferred to use this P element to generate germline-specific expression of a gene of interest (Gene E) by placing a portion of the P element ORF containing both exonic (at least 30 bp) and intron 3 (IVS3) upstream of a ubiquitin-Gene E fusion (See FIG. 19).

An ubiquitin fusion to the gene of interest is preferred because correct splicing of IVS3 requires exonic sequence. This sequence (P-element exon/IVS3-Ubiquitin-Gene of interest) can then be placed downstream of any promoter having germline activity, or to prevent non-specific expression, a germline-specific promoter.

This germline-specific intron can preferably be used in combination with any germline-active promoter with a desired expression pattern, for example a constitutive, sex-specific or inducible promoter (such as heatshock or Gene-Switch) as described elsewhere. This could alter the expression pattern of these promoters to become germline-specific, thereby providing a level of germ-line control of protein expression in combination with another level of control, such as environmental conditions, the presence of a hormone or inducer of protein transcription and expression.

A simple method for determining whether there is sufficient flanking sequence, or the minimal flanking sequence, required for correct germline-specific splicing is provided as follows:

(1) make a construct of the form promoter-5'flanking sequence-intron-3'flanking sequence.

(2) transfect into suitable cells, e.g. by electroporation, chemical transformation, microinjection or other suitable means known to the person skilled in the art.

(3) after incubation for a suitable period of time, which will depend in part on the species and cell type, extract RNA, RT-PCR the RNA corresponding to the construct and analyse, e.g. by gel electrophoresis and/or sequencing, to determine the splicing pattern.

If this is suitable for the purpose, there is sufficient flanking sequence. If not, more flanking sequence must be included and this can be repeated. If it is desired to determine the minimum suitable flanking sequence, then make a series of deletion derivatives of the construct until this is determined.

It is particularly preferred, however, that the alternative splicing mechanism is sex-specific. This allows expression of a protein of interest in a sex-dependent manner. For instance, if the promoter and/or enhancer of the gene expression system are switched on in muscles, the inclusion of a sex-specific alternative splicing mechanism means that expression of the protein can be either in male muscles only, or, alternatively, in female muscles only.

A particularly preferred example is the sex-specific control of the tetracycline transcriptional transactivator protein, tTA, or suitable variants and mutants thereof, such as tTAV, as described herein in Example 12, and tTAV2 and tTAV3.

For instance, under the control of an alternative splicing mechanism, a functional transcriptional transactivator protein can be produced only in females, with the result that expression of the system is found only in females, such that the females are adversely affected, and may indeed die as a consequence. However, in males, a different splicing combination is achieved, such that the transcriptional transactivator protein is not expressed or is not functional, with the result that the lethal effecter gene is not expressed so that the males survive. In this way, males and females may be easily separated.

Suitable organisms under which the present system can be used include mammals such as mice, rats and farm animals. Also preferred are fish, such as salmon and trout. Plants are also preferred, but it is particularly preferred that the host organism is an insect, preferably a dipteran or tephritid. Preferably, the organism is not a human, preferably non-mammalian, preferably not a bird, preferably an invertebrate, preferably an arthropod.

In particular, it is preferred that the insect is from the Order Diptera, especially higher Diptera and particularly that it is a tephritid fruit fly, preferably Medfly (*Ceratitis capitata*), preferably Mexfly (*Anastrepha ludens*), preferably Oriental fruit fly (*Bactrocera dorsalis*), Olive fruit fly (*Bactrocera oleae*), Melon fly (*Bactrocera cucurbitae*), Natal fruit fly (*Ceratitis rosa*), Cherry fruit fly (*Rhagoletis cerasi*), Queensland fruit fly (*Bactrocera tyroni*), Peach fruit fly (*Bactrocera zonata*) Caribbean fruit fly (*Anastrepha suspensa*) or West Indian fruit fly (*Anastrepha oblique*). It is also particularly preferred that the host organism is a mosquito, preferably from the genera *Stegomyia*, *Aedes*, *Anopheles* or *Culex*. Particularly preferred are *Stegomyia aegyptae*, also known as *Aedes aegypti*, *Stegomyia albopicta* (also known as *Aedes albopictus*), *Anopheles stephensi*, *Anopheles albimanus* and *Anopheles gambiae*.

Within Diptera, another preferred group is Calliphoridae, particularly the New world screwworm (*Cochliomyia hominivorax*), Old world screwworm (*Chrysomya bezziana*) and Australian sheep blowfly (*Lucilia cuprina*). Lepidoptera and Coleoptera are also preferred, especially moths, including codling moth (*Cydia pomonella*), and the silk worm (*Bombyx mori*), the pink bollworm (*Pectinophora gossypiella*), the diamondback moth (*Plutella xylostella*), the Gypsy moth (*Lymantria dispar*), the Navel Orange Worm (*Amyelois transitella*), the Peach Twig Borer (*Anarsia lineatella*) and the rice stem borer (*Tryporyza incertulas*), also the noctuid moths, especially Heliothinae. Among Coleoptera, Japanese beetle (*Popilla japonica*), White-fringed beetle (*Graphognatus* spp.), Boll weevil (*Anthonomous grandis*), corn root worm (*Diabrotica* spp) and Colorado potato beetle (*Leptinotarsa decemlineata*) are particularly preferred.

It is, as mentioned above, particularly preferred that the alternative splicing mechanism is sex-specific. Preferably, this may include the AaActin-4 mechanism, which is a gene from *Stegomyia aegypti* which shows tissue, stage and sex-specific splicing (see Act4-tTAV-LA1172, for instance in Example 20). It is also preferred that the splicing mechanism comprises at least a fragment of the *Drosophila* doublesex gene. However, it is particularly preferred that the alternative splicing mechanism is derived from the Medfly transformer gene Cctra, or from another ortholog or homolog of the *Drosophila* transformer gene, especially one derived from a tephritid fruit fly. This will be discussed in greater detail below and, although these are preferred examples, they are not limiting on the scope of the invention.

Although there a number of recent discussions in the art of combining gene expression systems with alternative splicing mechanisms to result in recombinant gene regulation, none of these groups have actually been successful in providing a construct capable of achieving this end.

In particular, Rafael et al (February 2004) disclose that "a similar approach could be achievable in any insect, including tephritids, provided that species-specific regulatory elements and lethality genes or genetic constructs are isolated. The yolk protein regulatory elements, which have been isolated from *B. tryoni*, may form the basis for female-specific expression of a transgene in this species. Alternately, the regulatory elements which control dsx sex-specific splicing may be manipulated such that the effects of a lethal gene are only observed in females of a line which carries an engineered dsx construct."

Similarly, Crisanti's and Scali's (2005) paper on the Doublesex gene derived from *Anopheles gambiae* hints that "[t]he identification of female- and male-specific transcripts of Agdsx represents an important step towards the understanding of the sex differentiation process in *A. gambiae* and will facilitate the development of genetic tools to induce male sterility or manipulate sex ratios in mosquitoes, for instance by constitutively expressing the female-specific form of dsx in the male gonads or by inducing the sex-specific splicing of a dominant lethal".

Therefore, although there is some discussion in the recent art of the need for effective systems combining alternative splicing with heterologous gene expression, these have been only desiratum and have not led to working examples. Indeed, Scott et al (Scott et al., 2004) try to use a composite system, comprising more than one splicing cassette, including part of *Drosophila* doublesex, but concluded that the constructs spliced in the expected "female-specific" pattern in both males and females. Accordingly, they were not able to achieve sex-specific splicing, as a single splice variant was found in both males and females.

It is preferred that the present system uses a single splicing cassette for reasons of efficiency and to avoid the risk that the function of the alternatively spliced intron is modified or compromised by heterologous sequence placed close to it.

Surprisingly, the present inventor has discovered that it is possible to provide an alternative splicing mechanism that can be used, optionally together with additional splice control sequences, in combination with a gene expression system for at least one gene or protein of interest, whereby the alternative splicing mechanism is capable of providing a level of additional control, for instance in a sex-specific or tissue-specific manner, as discussed elsewhere. Stage-specific and germ-line-specific alternative splicing mechanisms are also preferred. However, sex-specific alternative splicing mechanisms are most preferable.

Whilst it is preferred that the alternative splicing mechanism comprises at least fragments of any of the following genetic elements, selected from the group comprising 5' and/or 3' flanking sequences, exonic sequences, 5' untranslated region (UTR), the 3' untranslated region (3' UTR) and, of course, the intron, it is preferred that the alternative splicing mechanism comprises only short exonic sequences from the flanking regions surrounding the intron in its native context, preferably shorter than 50 nucleotides at each end, and particularly preferred that the alternative splicing mechanism consists entirely of the intron alone or fragments thereof, i.e. without any additional sequences from the flanking regions, the UTR's or exons which would be adjacent to the intron in its native context.

By "native context" it is meant that that the intron, for instance in its wild-type form in nature, is found in association with exon(s) and a promoter, and thus had specific sequences adjacent to it. However, it is preferred to use the intron substantially without these adjacent sequences, i.e. it may be used including only a fragment of these adjacent sequences, but is it preferred that none of the residues of these adjacent sequences are included.

However, when used according to the present invention, the intron will be surrounded by exonic sequences, which will preferably be new or heterologous sequences.

Although the Cctra intron will splice without requiring any specific exonic sequences derived from the Cctra gene, it is not obvious that this is the case for all introns. Exonic splice enhancers (ESEs) and silencers (ESSs) are prevalent in most, if not all, exons and can be important in alternative splicing (Cartegni, et al., 2002). Where exonic sequences are required for efficient operation of the alternative splicing mechanism, it is preferred that the system also include an ubiquitin protein cleavage system (Varshaysky, 2000). The ubiquitin fusion technique greatly increases the ranges and ease of application of alternative splicing as a method for controlling gene expression.

Many proteins will still function with additional amino acids fused to their amino (N) or carboxy (C) termini. This is widely used, for example to fuse an epitope tag, or a fluorescent protein, to a protein of interest, without disrupting its normal function. It is, therefore, preferred to use alternative splicing cassettes which encode one or more amino acids in all alternative splicing variants, by fusing part or all of the alternatively spliced protein to the protein of interest, typically with the alternatively spliced protein at the N-terminus.

FIG. 20 illustrates this, using dsx as example of alternative splicing. Application of this principle to other forms of alternative splicing will be clear to the person skilled in the art.

Of these, version A gives male-specific expression by inserting additional exonic material in the female, disrupting or modifying the function of the protein in females (e.g.) by addition of another protein domain, or premature termination. Version B gives male-specific expression by fusing the protein of interest to the male-specific coding sequence, as can versions C and D, though alternative configurations are also possible. In each case, this would represent the fusion of heterologous sequence to the N-terminus of the protein of interest.

Though the function of many proteins is known not to be affected by such N-terminal fusions, this is not true for all proteins. For example, many secreted or transmembrane proteins have a signal sequence that must form the N-terminus of the coding region. As another example, the proapoptotic protein Reaper is known to have a functional domain, probably involved in binding to dIAP1/Thread, which must be at the N-terminus of the protein. Fusions to the N-terminus, in some cases even of a single amino acid can, therefore, tend to inactivate Reaper (Olson et al., 2003).

However, in order to overcome the limitation of N-terminal fusions, it is particularly preferred to use amino acid or polynucleotide residues coding for at least the cleavage site portion of ubiquitin, more preferably the full protein sequence.

The nucleotide and protein sequences for ubiquitin are SEQ ID NOS 72 and 73, respectively.

It is preferred that the expression system, therefore, comprises nucleotides encoding at least the cleavage site of ubiquitin, and preferably the nucleotide sequence according to SEQ ID NO. 72. This is preferably arranged such that the ubiquitin orp portion thereof is substantially N-terminal to the protein of interest, but more preferably immediately N-terminal (i.e. immediately adjacent) the protein of interest.

This arrangement will reduce the size of, or eliminate, the N-terminal fusion to the post-cleavage (mature) protein. However, in the specific case of a signal peptide, it is known that in some cases, in order to function normally, this signal must be present at the N-terminus of the primary translation product. In such a case it is preferred that the protein be expressed without a fusion N-terminal of the signal sequence.

Ubiquitin proteases will then cleave the protein of interest from the ubiquitin moiety, allowing the correct folding of the N-terminus of the downstream protein. So, if the entire fusion protein is:

Start codon-segment of alternatively spliced gene-ubiquitin-protein of interest the protein of interest will cleaved from the ubiquitin moiety and retain normal folding and function.

Where suitable ubiquitin proteases are not constitutively expressed or expressed at a suitable level, it is preferred that the present invention comprises polynucleotides coding therefor, preferably under the control of a suitable promoter, such that expression of the ubiquitin protease is preferably linked to expression of the fusion protein.

Using this particularly preferred method, alternative splicing can be used, even if the alternative splicing requires exonic signals some distance from the intron itself, and if the specific alternative splicing strategy requires the intron to be in a translated region (and therefore requires the synthetic construct to have a significant amount of coding region derived from the source of the alternative splicing) and if the protein of interest will not tolerate fusions.

If required, several proteins could be controlled by the same regulatory system, by inserting a ubiquitin moiety between each. In such a case, it is preferred that a stabilized mutant derivative of ubiquitin, for example ubiquitin$^{K48R}$ (Rasoulpour et al., 2003; Finley, et al., 1994), be used as the ubiquitin moiety.

Indeed, where reference is made to the term "ubiquitin" is made, it will be understood that it includes ubi$^{K48R}$ and all suitable substrates of ubiquitin. Under some circumstances, a similar effect could be obtained by using a stop codon and an internal ribosome entry sequence (IRES) to separate the coding regions.

It is also preferred to vary the level of control by using alternative splicing, e.g. the as dsx system above, to provide different C-termini for a protein. Specific signals, for instance a prenylation motif (such as—CAAX from Ras) differentially incorporated into these alternate C-termini affect protein function and/or location.

In order to differentially affect protein stability, it is preferred to incorporate signals regulating stability into the genetic system, such as PEST sequences, as are found in many rapidly degraded proteins. These sequences have been suggested to serve as signals for proteolytic degradation. From a survey of the amino acid sequences of 10 short-lived eukaryotic proteins, Rogers et al. [Science. 1986; 234:364-368] found the proteins to contain one or more regions rich in proline (P), glutamic acid (E), serine (S), and threonine (T). These regions are often flanked by positively charged amino acids.

Similarly, it is also preferred to incorporate [polynucleotides encoding RNA stability or instability signals into the genetic system according to the present invention, or signals affecting protein or RNA location, translation, for instance.

The issue of saturation is another generic objection raised in the art to the artificial use of alternative splicing to regulate gene expression. However, this is overcome by a preferred embodiment of the present invention. It is suggested in the att that the factors regulating alternative splicing are thought to be in relatively short supply, so that the alternative splicing pathway or system can be saturated if too much pre-mRNA (primary transcript) is provided (Stoss et al., 1999, Stoss 2001, Yali and Pin Ouyang., 2006).

We have, surprisingly, shown that this is not the case, in Cctra in positive feedback constructs, in that the system is not prevented from functioning as desired. For tra, the default splicing is in the male pattern; female-type splicing to give transcript F1 (FIG. 21) occurs only in the presence of a splicing complex which includes Tra and Tra-2 proteins.

Tra is expressed only in females and so this complex is present only in females. There is no reason to think that these are particularly abundant proteins. For the female-specific positive feedback system to work, i.e. to kill females, very large amounts of tTA need to be produced.

tTA is only produced from transcripts spliced in the female (F1) form, so correspondingly large amounts of this transcript have to be produced. That this is readily accomplished implies that the Tra/Tra2-dependent sex-specific splicing system is not easily saturated.

We have optimized and resynthesized the original tTA sequence for use in *Anopheles gambiae, Bombyx mori* and *Drosophila melanogaster* and generated the variants tTAV (SEQ ID NO. 34-DNA, SEQ ID NO. 35-protein), tTAV2 (SEQ ID NO. 36-DNA, SEQ ID NO. 37-protein) and tTAV3 (SEQ ID NO. 38-DNA and SEQ ID NO. 39-protein).

Thus, in a preferred aspect of the invention, the expression system comprises nucleotides encoding tTA or its functional variants and mutants, in particular those selected from the group consisting of: tTAV (SEQ ID NOS. 34 and 35), tTAV2 (SEQ ID NOS. 36 and 37), and tTAV3 (SEQ ID NOS. 38 and 39), being highly effective tTA variants.

It is, therefore, particularly preferred that the present invention comprises a repressible transactivator protein in combination with the alternative splicing mechanism.

Preferably this is the tet system described herein, and in particular, comprises the tTAV variants described above.

Thus, it is also particularly preferred that the genetic system is used in combination with a further control system. A preferred further control system is the positive feedback system described herein.

AaActin-4

An example of a sex-specific alternative splicing mechanism is AaActin-4. This is a gene from *Stegomyia aegypti* (formerly *Aedes aegypti*), which also shows sex-specific splicing. We have shown that a fragment of this gene, including the intron, a large amount of 5' flanking sequence and a little 3' flanking sequence, splices correctly when reintroduced into this mosquito.

There is a single publication on this gene, which does not mention sex-specific splicing (Muñoz et al., 2004). We've made transgenic mosquitoes (*Stegomyia aegypti*) carrying a fragment of this gene, which is spliced correctly, but a fragment that contained the female intron only was not correctly spliced in Medfly (spliced in the male pattern in both males and females).

It is preferred that Actin-4 is used in combination with the tTAV variant system discussed above.

Dsx and Tra

It is more preferable, however, that the alternative splicing mechanism is dependent on the transformer (tra) gene from insects such as *Drosophila* or Medfly, or its homologues. This protein acts in a complex that also comprises the product of the transformer-2 (tra-2) gene, or its homologues; this complex is involved in the genetic control of sexual differentiation (Pane et al., 2002; Saccone et al., 2002). In particular, these genes and their gene products act on the doublesex genes from *Drosophila*, and its homologues in other species; homologues of dsx are present throughout the insect world, for instance. Tra/tra-2 also act on the Medfly transformer gene which acts as an additional level of control in Medfly and similar insects including *Ceratitis rosa*, *Drosophila melanogaster*, *Bactrocera zonata*, and *Anastrepha ludens*.

When the doublesex alternative splicing mechanism is used, it is preferred that the genetic system is used in Diptera, preferably including those described above.

Particularly in the case of Dipterans, it is preferred that tra and/or tra-2 are expressed in either the male or the female host or organism.

Alternatively, it is also preferred that tra/tra-2 themselves form part of the genetic system and the respective proteins may be encoded by nucleic acids provided in a construct or constructs which form part of the genetic system according to the present invention, under the control of suitable promoters.

In this way, the skilled person will be able to separately control the expression of tra and/or tra-2 and, therefore, allow the user an additional level of spatial or temporal control, i.e. to allow the user to initiate alternative splicing at predetermined point. This could be achieved by linking the tra/tra-2 genes to a promoter, such as the hsp70 heat shock promoter, which can be initiated by high temperatures, thereby leading to expression of the tra and tra-2 proteins, which in turn allow alternative splicing to proceed, at a user-defined time and in an easily controllable manner.

For instance, this allows both and control of, for instance, the Cctra intron in species that have divergent tra (or no tra at all), by expressing tra in a particular stage- or tissue-specific manner. It also allows regulated expression in males, who would not normally express tra. However, to ensure sex-specific expression, by this mechanism, in a species that doesn't have equivalent tra, one may need to arrange differential sex-specific expression of tra, as will be apparent to the skilled person.

When using an alternative splicing mechanism comprising the doublesex mechanism, it is preferred that exonic signals from the doublesex gene are present. In this instance, it is particularly preferred that the following sequences are used:

1) the tra/tra2 binding sites (T/A)C(T/A)(T/A)C(A/G) ATCAACA (Hedley et al., 1991, Hoshijima et al., 1991, Ryner et al., 1991);

2) Medfly dsx mRNA (Genbank ID number AF435087: on the world-wide web, address ncbi.nlm.nih.gov/entrez/viewer.fcgi?db=nucleotide&val=24637185):

3) Pink boll worm dsx female specific 1 exonic sequence (SEQ ID NO. 40);

4) PBW dsx-female specific 2 sequence (SEQ ID NO. 41);

5) PBW male specific sequence (SEQ ID NO. 42);

6) *Anopheles gambiae* dsx gene sequence (Genbank ID number GI19611767);

7) *Aedes aegypti* dsx gene sequence (Supercontig 1.370 (on the world-wide web, address broad.mit.edu/annotation/disease_vector/aedes_aegypti/) and SEQ ID NO. 43);

8) Codling moth dsx gene sequence from females (SEQ ID NO. 44) and males (SEQ ID NO. 45).

Dsx

Where the genetic system of the present invention consists or comprises construct, it is preferred that the construct is selected from the group consisting of: LA3435 (SEQ ID NO. 46 and FIG. 22—vector map), LA3359 (SEQ ID NO. 47 and FIG. 23—vector map) and LA3433 (SEQ ID NO. 48 and FIG. 24—vector map). Dsx is also discussed in more detail elsewhere.

Tra

A particularly preferred example of an alternative splicing mechanism that is sex-specific is the transformer intron from Medfly, referred to as Cctra. This is an example of an "intron-only" alternative splicing mechanism, as it does not necessarily require the presence of exonic, 5' or 3' flanking or untranslated region sequences.

Figure 16:
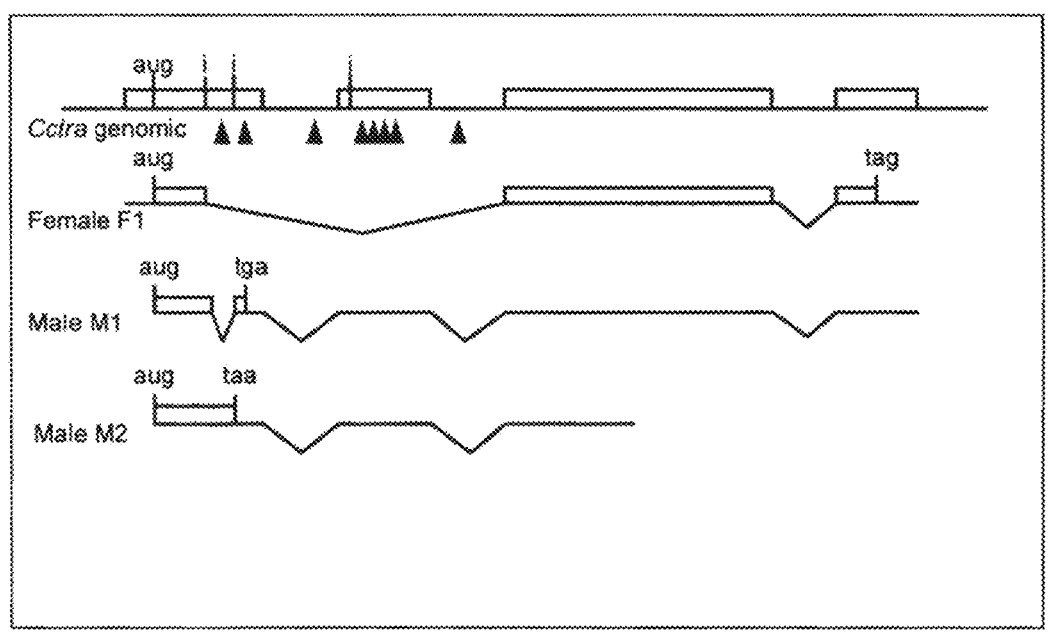
FIG. 16 illustrates the sex-specific splicing of Cctra in medfly.
Figure 17:
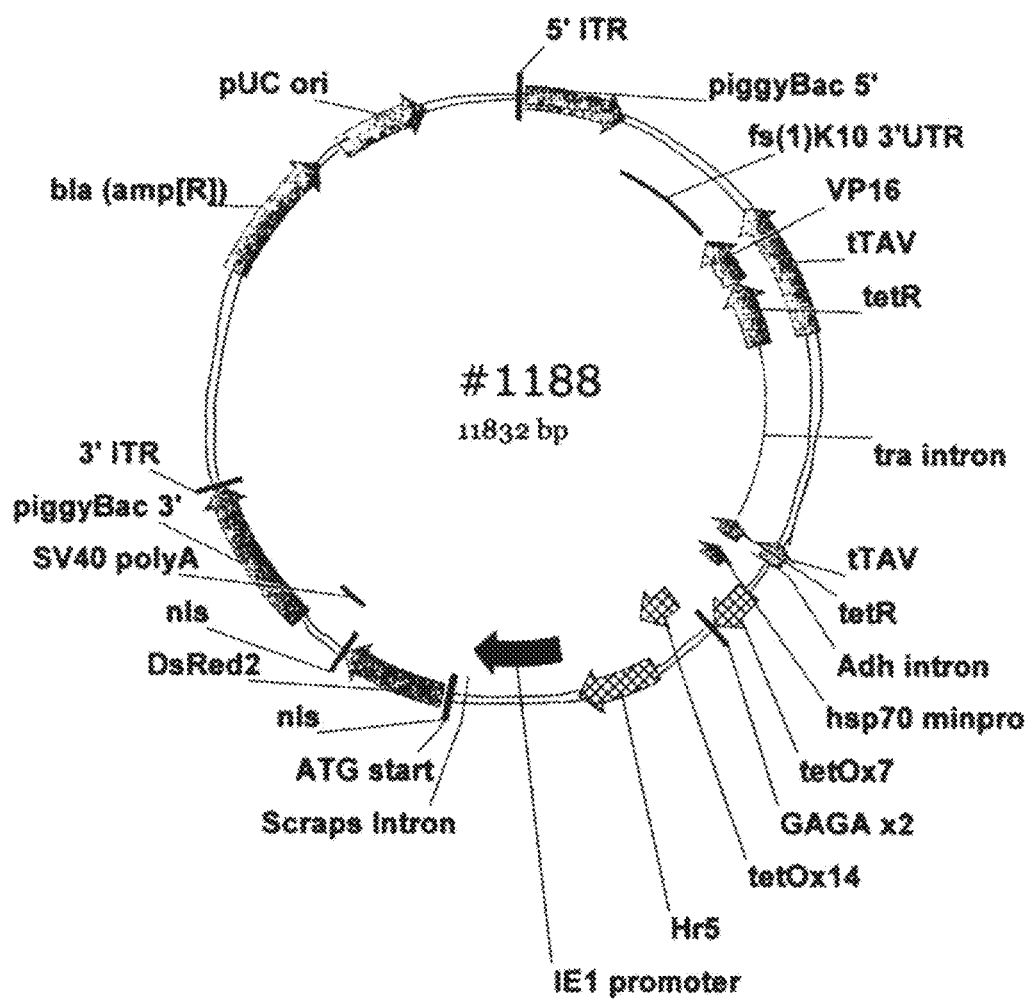
FIG. 17 is a schematic diagram of pLA1188.
Figure 18:
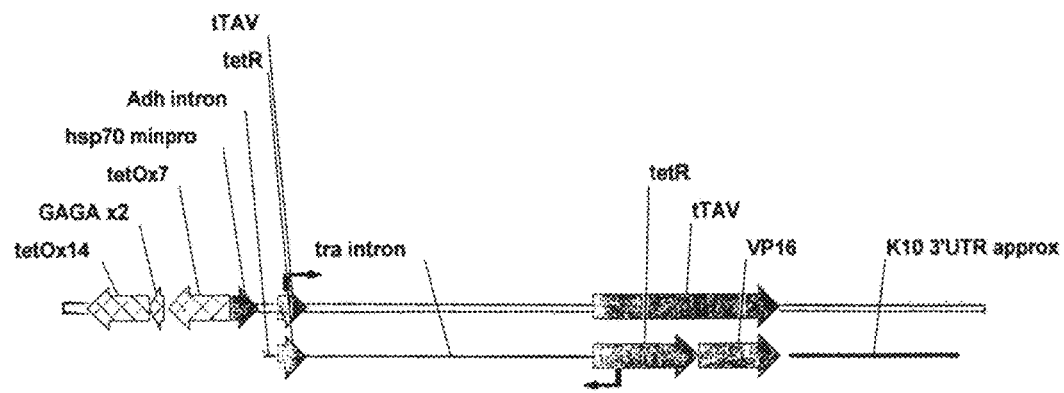
FIG. 18 illustrates sex-specific splicing in medfly.

The splicing mechanism of Cctra was first described in Pane et al (2002) as referred to in Example 12 and accompanying FIG. 16. The disclosure of Pane et al 2002 is hereby incorporated by reference.

This alternative splicing mechanism or cassette produces 3 splice variants in females, one of which is female-specific (called F1). The other two are called M1 and M2 and are also found in males. Thus, F1 is found only in females, whilst M1 and M2 are found in both males and females. Since each of the non-sex-specific transcripts (i.e. M1 and M2) contain additional exonic material with stop codons, only the female splice variant (F1) produces functional protein. Thus, where each genetic system comprises or consists of a construct, it is preferred that said construct is LA1188 and, most preferably, LA3077 or LA3097.

Although LA1188 (SEQ ID NO. 49 and FIG. 25—vector map) is functional, it is not preferred, as it can induce a frame shift.

Thus, it is particularly preferred that the construct comprises LA3077 (SEQ ID NO. 50 and FIG. 26—schematic), LA3097 (SEQ ID NO. 51 and FIG. 27—schematic), LA3233 (SEQ ID NO. 52-sequence and FIG. 28—schematic), LA3014 (Figure SEQ ID NO. 53 and FIG. 29—schematic), LA3166 (SEQ ID NO. 54 and FIG. 30—schematic), LA3376 (SEQ ID NO. 55 and FIG. 31—schematic) and LA3242 (SEQ ID NO. 56 and FIG. 32—schematic).

Other constructs, for instance plasmids, preferably comprise a 5' TG immediately adjacent the intronic sequence, and preferably also comprise a flanking GT sequence immediately 3' to the end of the intronic sequence. In particular, it is preferred that the intron is flanked on both 5' and 3' ends by Guanine nucleotides, in order to ensure a "clean exit" when the intron is spliced out, such that additional nucleotides are not also spliced out which may lead to a frame shift. However, if additional nucleotides are to be excised, in the splicing process, then it is preferred that these are excised in blocks or multiples of 3, so that there is no significant frame shift.

It is most particularly preferred, however, that the intronic sequences flanked on its 5'end by a Guanine nucleotide as this is of greatest importance when seeking to ensure a clean exit. It will be apparent to the person skilled in the art that a flanking G nucleotide can be readily provided without the incorporation of specific flanking exonic sequences from the gene from which the intron is derived, by identifying suitable sequences (e.g. TGGT, 5'G, etc) within the sequence of interest (that into which the intron is to be inserted). The redundancy of the genetic code means that this can readily accomplished.

Since protein coding regions generally begin with the nucleotide sequence 5'-ATG-3', in a particularly preferred embodiment, the TG of this ATG sequence comprise the nucleotides immediately preceding the intron, for example 5'UTR-ATG-intron-GT-3'.

Within this, preferred examples place the coding sequence for either ubiquitin or tTA, or their functional mutants and or variants such as tTAV, tTAV2 or tTAV3, 3' to the intron. These are arranged so that these elements are substantially adjacent to the 3' end of the intron, more preferably the such that the coding region starts within 20 nucleotides or less of the 3' intron boundary), and most preferably, immediately adjacent the 3' end of the intron. Preferred examples of constructs according to the present invention are listed in Table 16, below.

TABLE 16

| Construct NO. (FIGS. #.) | Species tra intron is from | position from ATG | tra intron is fused to- |
|---|---|---|---|
| LA3014 (29) | Medfly | +22 bp | Ubiquitin |
| LA3166 (30) | Medfly | +136 bp | Ubiquitin |
| LA3097 (27) | Medfly | +0 bp | tTAV |
| LA3077 (26) | Medfly | +61 bp | tTAV |
| LA3233 (28) | Medfly | +0 bp | tTAV2 |
| LA3376 (31) | Medfly | +0 bp | tTAV2 |
| LA3376 (31) | B. zonata | +3 bp | Reaper KR |
| LA3376 (31) | B. zonata | +0 bp | tTAV3 |
| LA3242 (32) | C. rosa | +3 bp | reaperKR |

Table 16 shows constructs which contain a tra intron. The introns were derived from *C. capitata*, *B. zonata* or *C. rosa* (column 1). Said intron was inserted within the coding region such that the distance between the putative initiator ATG and the last nucleotide of the exon immediately preceding the tra intron was as should in column 2. Intron is inserted into or adjacent to coding region for either ubiquitin, tTAV or reaper$^{KR}$, as shown in column 3. These were generated and shown to successfully splice, by RT-PCR or phenotypically in Medfly and, in some cases, also either in *Drosophila melanogaster* (LA3077) or *Anastrepha ludensi* (LA3097, LA3233). In addition, the distance between the ATG and the end of the exon immediately preceeding the tra intron (assuming splicing in F1-like form) can range from 0 bp to +228 bp without adverse consequences to splicing (see Table 16, column 3).

As mentioned above when an intron is placed 5' to a protein coding region (ORF-X), it is preferred to position or use ubiquitin 3' to the intron, 5' to ORF-X, thus and providing female-specific regulation of ORF-X, whilst introducing physical separation between that sequence and the tra intron, thereby reducing the chance that sequences within ORF-X will interfere with the splicing of the tra intron.

Composite constructs and sequences are also envisaged, for example of the form:

X-ubi-Y with the alternatively spliced intron inserted between coding region X and the region encoding ubiquitin (ubi), or within the ubiquitin coding region, or between the region encoding ubiquitin and coding region Y. Thus X will be expressed irrespective of the splicing of the intron, while Y will only be expressed when the intron is spliced in a suitable form. Further configurations and arrangements of this general type will be apparent to the person skilled in the art.

Of course, it may be that the skilled person wishes to introduce a frame shift during the splicing process so that the pre-mRNA is spliced into mRNA that is not capable of being transcribed into a functional protein.

The frame-shift may be useful for a number of reasons. Firstly, as discussed above, it may be to introduce a stop codon or may otherwise result in a protein having reduced or no activity.

Alternatively, the frame-shift may be employed, in a manner similar to retro-viruses, for instance, to encode at least two different proteins from the same nucleotide sequence, by using overlapping coding sequences. One can, therefore, introduce a frame shift so that a sequence is read in one frame if the (preceding) intron is spliced in one form and a different frame if spliced in another. This allows one to get two different encoded proteins without tampering with sequence internal to the intron.

It has also been found that it is possible to employ a positive feedback mechanism both to enhance the effect of an insect promoter, as well as to control its expression.

Thus, in a further aspect, the present invention provides a gene expression system, comprising at least one gene to be expressed and at least one promoter therefor, wherein a product of a gene to be expressed serves as a positive transcriptional control factor for the at least one promoter, and whereby the product, or the expression of the product, is controllable. Preferably, the system is for expression in insects.

As used herein, the term "gene" refers to any DNA sequence that may transcribed or translated into a product, at least one such having activity or function in vivo. Such a gene will normally have at least a transcription promoter and a terminator operably associated therewith.

The product capable of positive transcriptional control may act in any suitable manner. In particular, the product may bind to an enhancer located in proximity to the promoter or promoters, thereby serving to enhance polymerase binding at the promoter, for example. Other mechanisms may be employed, such as repressor countering mechanisms, such as the blocking of an inhibitor of transcription or translation. Transcription inhibitors may be blocked, for example, by the use of hairpin RNA's or ribozymes to block translation of the mRNA encoding the inhibitor, for example, or the product may bind the inhibitor directly, thereby preventing inhibition of transcription or translation.

More preferably, the mechanism is a positive feedback mechanism, wherein the product, which may either be RNA or the translation product thereof, acts at a transcription enhancer site, normally by binding the site, thereby enhancing promoter activity. Enhancement of the promoter activity then serves to increase transcription of the gene for the product which, in turn, further serves to either lift inhibition or enhance promotion, thereby leading to a positive feed-back loop.

Control of the product may be by any suitable means, and may be effective at any level. In particular, it is preferred that the control be effective either to block transcription of the control factor gene or to block translation of the RNA product thereof, or to prevent or inhibit action of the translation product of the gene.

For example, the gene product of tTA (tetracycline-repressible transcription activator) acts at the tetO operator sequence (Baron and Bujard, 2000; Gossen et al., 1994; Gossen and Bujard, 1992). Upstream of a promoter, in either orientation, tetO is capable of enhancing levels of transcription from a promoter in close proximity thereto, when bound by the product of the tTA gene. If the tTA gene is part of the cassette comprising the tetO operator together with the promoter, then positive feedback occurs when the tTA gene product is expressed.

Control of this system is readily achieved by exposure to tetracycline, which binds to the gene product and prevents transactivation at tetO.

The tTA system also has the advantage of providing stage-specific toxicity in a number of species. In particular, "squelching" is observed in the development phases of many insects, the precise phase of susceptible insects being species-dependent. Some insects may reach pupation before the larva dies, while others die early on. Susceptibility ranges from 100% fatality to a small reduction in survival rates. In general, though, adult insects appear to be immune to the squelching effect of tTA, so that it is possible to raise insects comprising a tTA positive feedback system in the presence of tetracycline, and then to release the adult insects into the wild. These insects are at little or no competitive disadvantage to the wild type, and will breed with the wild type insects, but larvae carrying the tTA positive feedback cassette will die before reaching maturity.

It is relatively straightforward to modify the tTA sequence to enhance compatibility with the desired insect species, and this has been demonstrated, in the accompanying Examples, with tTAV, which has an additional two amino acids to provide a protease site, but which is encoded by a sequence substantially changed from that of tTA in order to more closely follow *Drosophila* usage.

Accordingly, in a preferred aspect, the present invention provides a system as described, wherein at least one gene is tTA, or is a gene encoding a similar product to tTA effective to up-regulate the tetO promoter.

Thus, the present invention is useful in combination with a dominant lethal gene, allowing selective expression of the dominant lethal gene, or stage specific expression, as desired, of the lethal gene or the lethal phenotype. It will be appreciated that the dominant lethal gene does not need to be an integral part of the positive feedback mechanism, but may be part of a bicistronic cassette, for example. Use of the present invention in association with RIDL (Release of Insects carrying a Dominant Lethal) is particularly preferred.

Control of the feedback mechanism, in the case of tTA or an analogue thereof, is simply effected by the presence or absence of tetracycline, or by modulating tetracycline concentration, when the tTA gene product is used. In the case of another preferred positive feedback system, GAL4, this may be controlled by temperature, for example, thereby suppressing the effective gene, preferably a dominant lethal gene, until release of the insect.

Other mechanisms may also be employed, such as ribozymes or antisense or partially self-complementary RNA molecules, such as hairpin RNA, to inhibit or prevent expression of an activating peptide, or blocking agents that prevent binding of the activator to the enhancer site.

Such blocking agents may be expressed by the insect itself under selective conditions, or may be administered as part of the culture medium, for example.

Where the blocking, or controlling agents are produced by the insect, then it is preferred that their expression be selective, such as being sex specific. Administration of the blocking agent in the culture medium, for example, will enable suppression of the positive feedback cassette under all circumstances until release of the insect, after which stage- or sex-specific selection will occur, preferably in a succeeding generation, particularly preferably the following generation.

More preferably, the cassette comprising the positive feedback mechanism is associated with stage- or sex-specificity. For example, sex specific splicing is observed with the transformer and doublesex mechanisms seen in most insects, and can be employed to limit expression of the feedback system to a particular sex, either by employing sex specific splicing to delete all or part of the effector gene, or to incorporate a frameshift or stop codon, or to modulate RNA stability or mRNA translational efficiency, for example, or otherwise to affect expression so as to differentiate between the sexes. Targeting the females of pest species is particularly preferred.

Although it is possible to provide the effector gene in a separate location and even on a separate chromosome, it is generally preferable to link the effector gene with the feedback gene. This may be achieved either by placing the two genes in tandem, including the possibility of providing the two as a fusion product, or for example by providing each gene with its own promoter in opposite orientations but in juxtaposition to the enhancer site.

An effector gene is the gene whose expression it is desired to enhance. Where a positive feedback product is also effective as a stage-specific lethal, such as tTA in many species, then the effector and the feedback gene may be one and the same, and this is a preferred embodiment.

The effector gene will often be a lethal gene, and it is envisaged that the system of the present invention will most frequently be employed in the control of insect pest populations, particularly in combination with the RIDL technique or related method, as described hereinunder.

It is preferred to include a marker with the systems of the invention, such as DsRed, green fluorescent protein, and variants thereof, as transformation success rates in insects are extremely low, so that it is useful to be able to select in some way.

The promoter may be a large or complex promoter, but these often suffer the disadvantage of being poorly or patchily utilised when introduced into non-host insects. Accordingly, it is preferred to employ minimal promoters, such as the Hsp70 promoter which, while having a naturally somewhat low level of activity, can be substantially enhanced by a positive feedback scenario, such as by the use of tTA and tetO.

A promoter is a DNA sequence, generally directly upstream to the coding sequence, required for basal and/or regulated transcription of a gene. In particular, a promoter has sufficient information to allow initiation of transcription, generally having a transcription initiation start site and a binding site for the polymerase complex. A minimal promoter will generally have sufficient additional sequence to permit these two to be effective. Other sequence information, such as that which determines tissue specificity, for example, is usually lacking, and preferred minimal promoters are, normally as a direct result of this deficiency, substantially inactive in the absence of an active enhancer. Thus, a cistron, or system, the two terms preferably being generally interchangeable herein, of the invention will generally be inactive when the or each promoter is a minimal promoter, until a suitable enhancer or other regulatory element is de-repressed or activated, typically the gene product.

Thus, it will be appreciated that minimal promoters may be obtained directly from known sources of promoters, or derived from larger naturally occurring, or otherwise known, promoters. Suitable minimal promoters and how to obtain them will be readily apparent to those skilled in the art. For example, suitable minimal promoters include a minimal promoter derived from hsp70, a P minimal promoter (exemplified hereinunder as WTP-tTA), a CMV minimal promoter (exemplified hereinunder as JY2004-tTA), an Act5C-based minimal promoter, a BmA3 promoter fragment, and an Adh core promoter (Bieschke, E., Wheeler, J., and Tower, J. (1998). Doxycycline-induced transgene expression during Drosophila development and aging. Mol Gen Genet 258, 571-579). Act5C responds to tTA in transgenic Aedes, for example, and the invention.

Not all minimal promoters will necessarily work in all species of insect, but it is readily apparent to those skilled in the art as to how to ensure that the promoter is active. For example, a plasmid, or other vector, comprising a cistron of the invention with the minimal promoter to be tested further comprises a marker, such a gene encoding a fluorescent protein, under the control of a promoter known to work in that species, the method further comprising assaying putative transgenic individuals for expression of the marker, and wherein individuals expressing the marker are then assayed for expression of the gene under the control of the minimal promoter, such as by assaying transcribed RNA. Presence of the RNA above background levels under induced or de-repressed conditions is indicative that the minimal promoter is active in the species under investigation; absence or presence at low levels only of such RNA in non-induced or repressed conditions is indicative that the minimal promoter has low intrinsic basal activity.

We have used the following marker promoters, by way of example, only, but many more are useful and apparent to those skilled in the art:

mini-white (white promoter): WTP2-tTA, JY2004-tTA
Act5C promoter: LA513 and LA517
ubi-p63E promoter: LA656 and LA1038
BmA3 promoter: LA710
hr enhancer and ie1 promoter: LA928, LA1124 and LA1188 and all of these are useful as, or in the preparation of, minimal promoters.

It will be appreciated that a cistron or system of the invention may comprise two or more cistrons. A system may further comprise non-linked elements, such as where a second gene to be expressed is remote from the positive feedback cistron.

Figure 1:
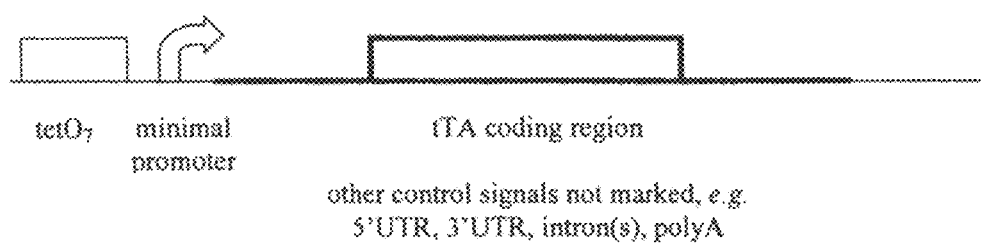
FIG. 1 shows a tetracycline-repressible transcription activator scenario.

Thus, in a preferred aspect, the present invention provides positive feedback constructs of the general form shown in accompanying FIG. 1. In this scenario, the tetracycline-repressible transcription activator (tTA) protein, when expressed, binds to the tetO operator sequence and drives expression from a nearby minimal promoter. In the configuration shown, this then drives expression of tTA, which then binds to tetO, and so on, creating a positive feedback system. This system is inhibited by tetracycline, which binds to tTA and prevents it binding tetO.

Expression is controllable, and this may be achieved by operably linking the promoter to a controllable transcription factor. As illustrated above, this may be tTA (tetracycline-repressible or tetracycline-inducible), or any other factor controllable system, such as GAL4 (which is somewhat cold-sensitive, and can be further controlled by use of GAL80 or mutants thereof), or the streptogrammin regulated expression system, for example. It will be appreciated that other binding sites for the appropriate transcription factor will depend on the transcription factor concerned, such as $UAS_{GAL4}$ (upstream activation sequence) for GAL4, for example.

Preferred systems of the present invention have high levels of induced expression, preferably available at several induced levels, with a low basal level of expression of the regulated gene but also of any other component, and preferably across a range of species. Basal levels are preferably low or substantially non-existent where expression is strongly deleterious, but acceptable levels will depend on the effect of the product. Maximum levels will not generally be an issue, as the positive feedback condition will often provide fatal levels of expression and, even where the expression product is not fatal, or associated with fatal consequences, it is likely to be expressed in far higher concentrations than most gene products.

Where a basal level of expression is desired, then a promoter sequence that does not need the presence of the enhancer may be employed, although there will then, generally, be feedback. Unless there is a cut-off level of feedback, below which the feedback product will not work, then it will be appreciated that it is preferred to keep to a minimum feedback gene expression Different constructs of the invention (described in the accompanying Examples) have varying activity, according to the components of the constructs. For example, in Drosophila:

WTP-tTA gives a low level of induced (non-repressed) expression
JY2004-tTA gives strong expression when not repressed, approximately equivalent to Act5C-tTA
LA513 is lethal when not repressed.

The first two appear to give constitutive expression, as judged by use of a reporter gene (tRE-EGFP), this is difficult to assess for the lethal LA513, although at 10 µg/ml tet, just sufficient for good survival, LA513 in Drosophila drives expression of a $tetO_7$-EGFP reporter gene in both the male and female germline in adults, as well as in somatic cells. This distinguishes it from Act5C, commonly used as a "ubiquitous, constitutive" promoter, which does not, in fact, express well in these cells.

The properties of these constructs are shown in Table 1, below.

TABLE 1

| | Max expression | Minimal promoter | Intron | Optimised coding region? | 3'UTR and polyA |
|---|---|---|---|---|---|
| WTP-tTA | Low | P | PP1α96A | No | fs(1)K10 |
| JY2004-tTA | High | CMV | Rabbit β-globin | No | Rabbit β-globin |
| LA513 | V. high (lethal) | Hsp70 | Adh | Yes | fs(1)K10 |

Accordingly, it will be appreciated that the induced or non-repressed expression level can be modified in a useful and predictable way by adjusting the sequence of the positive feedback system. Toxicity and/or activity of the tTA protein can be modified independently of the transcriptional and translational control signals by several approaches, e.g.

use of a nuclear localisation signal, modification of the activation domain, etc. (see Fussenegger, 2001 for more examples).

The lethality of LA513 is useful, for the reasons given above, and more particularly because:

a) It provides a compact, highly effective repressible lethal gene system;

b) As it uses only simple control elements from *Drosophila* (hsp70 minimal promoter, a small intron and a terminator from fs(1)K10), it, or its expression cassette, functions across a wide phylogenetic range;

c) It has very little, if any, deleterious effect on adults, even in the absence of tetracycline. This is a highly desirable and surprising property for field use, for example in a RIDL-based control programme, as the released adults must be competitive and long-lived for full efficacy of the programme. It will be appreciated that the effect of the system of the invention could be further modified by the incorporation of an adult-effective lethal, for example in the "positive feedback-bi-directional expression" configuration described herein; and d) By its nature, "cross-talk" between various elements is minimised. This is because: (i) the core of the construct is only a single composite element, rather than the normal two in bipartite expression systems; (ii) the principal enhancer of the autoregulatory component, the tTA binding sites, is substantially active only in the absence of tetracycline and (iii) modest expression of tTA under the influence of a nearby enhancer, whether in another part of the construct or in nearby chromatin, is unlikely to be significantly deleterious.

JY2004-tTA is also useful, in the present invention.

Without being bound by theory, the mechanism by which LA513 kills embryos and early larvae, but not adults, appears to be an inherent property of its toxicity. tTA toxicity is believed to derive from "transcriptional squelching", in which high level expression of the transcriptional activator domain (in the case of tTA this is VP16 or a fragment thereof) binds elements of the transcriptional machinery and titrates them, leading to a general effect on transcription, although it may also act to saturate the ubiquitin degradation pathway. Transcriptional squelching is the effect which is thought to lead to deleterious effects in mammalian cell lines expressing tTA at high levels; in the optimised expression context of LA513 positive feedback drives tTA expression to lethal levels. However, developing stages may be more sensitive to disruption of transcription than adults: they have to express genes in a highly coordinated fashion to allow proper development, while adults may be more tolerant of disruption.

The development of LA513 heterozygotes on media with an intermediate level of tet (3 or 10 µg/ml), just sufficient for survival, showed a significant delay, relative to their wild type siblings. Parallel experiments using higher concentrations of tetracycline, e.g. 100 µg/ml, did not show any developmental delay, thereby suggesting that sub-lethal expression of tTA can adversely affect the normal development of the insects.

It is preferred that a positive feedback system show a higher on:off ratio and switch from on to off over a narrower concentration range than a conventional system, thereby allowing the use of a wider range of effector molecules. Lower-toxicity (lower specific activity) effector molecules can be used, as they can be expressed at a high level under active conditions without leading to problems of toxicity at basal levels. Conversely, more toxic (higher specific activity) ones can be used as the necessary low basal level does not preclude high levels of expression when de-repressed or induced. Since basal level of expression is only partly determined by the level of tTA, this advantage is particularly clear in the case of lower-toxicity molecules. tTA is a preferred example of a low specific activity effector molecule that can be used as a lethal in the positive feedback context of LA513, for example. The advantage of switching from on to off over a narrow concentration range is that a modest concentration of repressor can be used without risk of residual (not fully repressed) expression leading to adverse effects and potentially selecting for resistance. Conversely, for an inducible system, modest concentrations of the activator can give full expression.

Activated or de-repressed drivers are useful for expressing effector molecules. Examples of effector molecules include functional RNA's, such as hairpin RNA's, ribozymes etc., and one or more encoded proteins. It will be appreciated that, for different applications, different levels of expression are appropriate. Since the sequence-specific transcription factors used to drive the positive feedback system can also be used to express other genes in a bipartite expression system, this may be achieved by making two separate constructs, one with the driver (normally a promoter-transcription factor construct, here the positive feedback construct), the other with the gene or molecule of interest under the control of a composite promoter (binding site+minimal promoter) responsive to the transcription factor (Bello et al., 1998; Brand et al., 1994). This is also appropriate for these positive feedback drivers. Alternatively, the two elements may be combined on the same construct. This embodiment has significant advantages for most field applications, as it very substantially reduces the risk that the two functional elements can be separated by recombination. Further, the complete expression system can be introduced with only a single transformation event, as well as meaning that insects homozygous for the system are homozygous at only one locus rather than two, which makes them easier to construct by breeding, and tends to reduce the fitness cost due to insertional mutagenesis.

Figure 2:
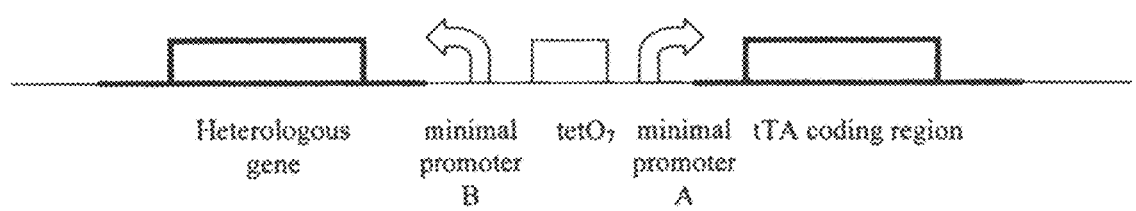
FIG. 2 shows a system of the invention using a bi-directional enhancer.

It is also possible to condense such an expression system into a more compact form, such as is illustrated in accompanying FIG. 2.

This exploits the bi-directional nature of enhancers, in this case the tetO binding site in the presence of tTA. This arrangement further allows, or facilitates, the use of insulator elements to reduce the effect of enhancers or suppressors in the adjacent chromatin: in this arrangement the entire expression cassette can be flanked by insulators. This arrangement also removes the need to duplicate the transcription factor binding sites within the construct. Such duplication is preferably avoided, as it can lead to instability through homologous recombination. For similar reasons, it is generally preferred that non-identical insulators, such as scs and scs' are used, rather than using the same one twice.

Figure 3:
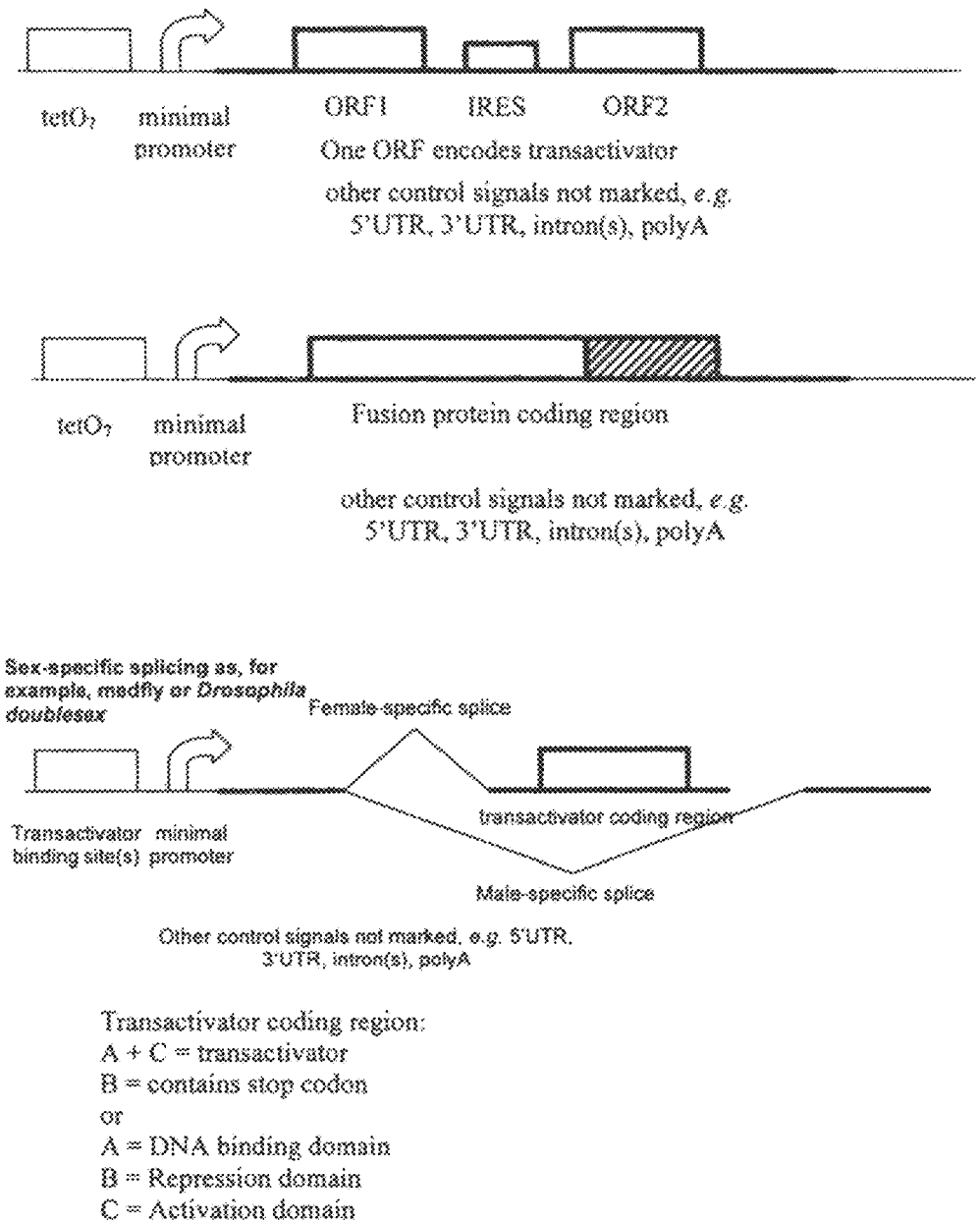
FIG. 3 shows a sex-specific system.

It is further possible to condense the system to provide a single transcript, either bicistronic or expressing a single polypeptide, which may potentially be further processed into more than one protein, for example by use of the ubiquitin fusion technique (Varshavsky, 2000). Each of these approaches (bi-directional expression, bicistronic expression, fusion protein with transactivator) tends to reduce the size of the construct, which in turn will tend to increase the transformation frequency and reduce the mutagenic target. Such condensation can be achieved in several ways, as shown, diagrammatically, in accompanying FIG. 3. Appropriate extensions to and variations of the arrangements shown diagrammatically will be apparent to those skilled in the art.

As an example of the utility of such a system, a general transformation marker might be constructed by using a transactivator system known to function over a wide phylogenetic range, for example those based on tetR, GAL4, lexA or AcNPV ie-1. Such a transactivator, functionally linked to a coding region for a fluorescent protein by any of the above methods (bi-directional expression, bicistronic expression, fusion protein with transactivator), would provide a genetic marker expressed in a wide range of tissues and developmental stages across a broad phylogenetic range. Such a marker would be useful not only for detecting transgenics in transformation and other lab experiments, but also for distinguishing, for example, transgenic flies from wild type flies in the field, or those caught in the field.

Another example is expression of a transposase. Integrated into the chromosomes, this would be a "jump-starter" construct, for example piggyBac transposase integrated into an insect chromosome using mariner/mos1. Such constructs are useful to remobilise piggyBac elements. A widely-applicable jump-starter should be expressed at a significant level across a wide phylogenetic range. The expression system of this invention provides this. Furthermore, such a construct (piggyBac transposase under the control of a positive feedback system of one of the above structures) would also be useful in insect transformation via transient expression (co-expression of a "helper" plasmid, the most widely-used method for insect transformation), and again would be useful and functional across a wide phylogenetic range.

It is advantageous to regulate the action of an expression system at stage-, sex- or other levels, in addition to being able to regulate the expression level by changing environmental conditions. Suitable examples are as follows:

1. Expression of a Repressor Protein.

Repressor proteins are known or can be constructed for the main expression systems, e.g. GAL80 or its mutant derivatives for the GAL4 system, tetR fused to inhibitory proteins for the tet system, etc. Another alternative is gene silencing of the transcription factor using a hairpin RNA directed against part of the expression cassette. Basal expression from the positive feedback system is rather low, therefore it can readily be suppressed by expression of such an inhibitor.

Expression of a suitable inhibitor under suitable control will tend to inhibit expression from the positive feedback expression cassette where the inhibitor is expressed. Female-specific expression, for example, can therefore be achieved by expressing an inhibitor in males.

2. Integrating Specificity into the Positive Feedback System.

Specificity can be integrated into the positive feedback system by using components that are themselves specific. For example, the hsp70 minimal promoter+SV40 intron and polyA signal combination of pUAST is known not to be expressed in the female germline of *Drosophila*, while the P minimal promoter+P intron+fs(1)K10 polyA signal of pUASp is so expressed (Rorth, 1998). Positive feedback expression systems can, therefore, be constructed which specifically do or do not express in this tissue, depending on the use of appropriate regulatory elements.

Figure 4:
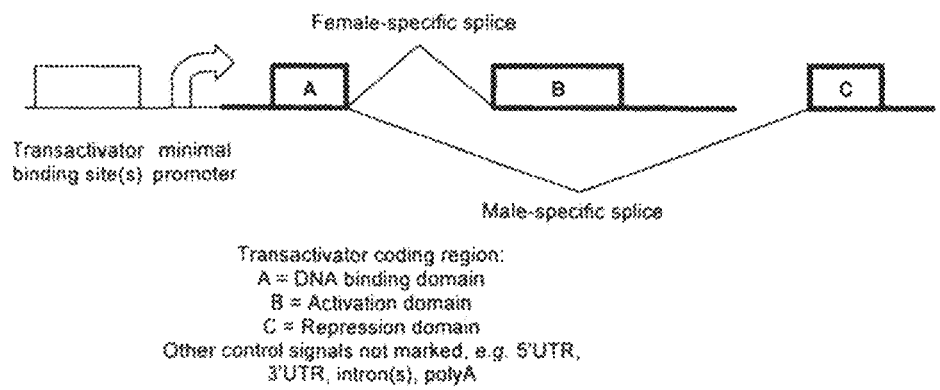
FIG. 4 shows another sex-specific system.

In another embodiment, sex-specificity can be integrated into the system by use of sex-specific splicing. The sex-specific splicing of doublesex and its homologues is a conserved regulatory mechanism and, therefore, available for use in this way across a wide phylogenetic range. Sex-specific splicing of transformer and its homologues is another alternative. The use of sex-specific splicing to integrate specificity into a positive feedback expression system can be achieved in several ways, as shown, diagrammatically, in accompanying FIG. 4. Appropriate extensions to and variations of the arrangements shown diagrammatically will be apparent to those skilled in the art.

In another configuration, a specific splice site can be inserted into the transactivator coding region so that two (or more) alternative proteins are produced in different conditions, e.g. in different cell types or in different sexes. This can be arranged so that a transcriptional activator is produced in one cell type but a transcriptional repressor is produced in another cell type. This arrangement has the advantage that it is relatively robust to inefficient (imperfect) splicing—production of a relatively low proportion of transcriptional activator in the inappropriate cell type, e.g. in male cells, will be less likely to produce the positive feedback amplification as these cells are also producing a larger amount of repressor. Discrimination in output (ratio of levels of transcriptional activator in the two cell types, or ratio of expression of a reporter or other RNA or protein functionally linked to the expression of the transcriptional activator) between the two cell types is thereby enhanced.

It will be readily apparent to those skilled in the art that any of these specific transactivator arrangements can readily be combined with any of the arrangements disclosed herein for expression of an additional protein or RNA, e.g. bi-directional expression, bi- or multi-cistronic expression, expression of a fusion protein, or combined with one or more separate expression cassettes dependent on, or partly dependent on, expression of the transactivator, either combined on the same construct or elsewhere in the genome or cell.

3. Using a Specific Effector Molecule

Specificity in phenotypic consequence can also be introduced by use of a specific effector molecule. Where a molecule, e.g. RNA or protein, expressed under the control of any of the expression systems described herein, has a specific effect only in particular cells, tissues, or sex, etc, then phenotypic specificity can be obtained with broader or less specific expression of the transactivator. For example, in the context of a RIDL-type mass-release insect population control programme, using the system to express a molecule only toxic, or preferentially toxic, to pre-adult stages, results in adults which are fully, or reasonably competitive, relative to wild type. This is desirable as the effectiveness of the programme depends on the competitiveness and longevity of the adult forms, when released into the wild. Since their internal repressor (e.g. tetracycline) concentration is likely to decline in the wild, it would be advantageous to ensure that induction (de-repression) of the expression system, as and when it occurs in adults, has a minimal negative effect on them.

As another example, sex separation, or sex-specific effects, can be achieved by expression in both males and females of a molecule with differential effects in males and females. For example, expression of the Transformer protein in male *Drosophila* will tend to transform them into females, but have no effect on females. Similarly, expression of Male specific lethal-2 (Msl-2) protein in *Drosophila* will tend to kill females, but not males (Gebauer et al., 1998; Kelley et al., 1995; Matsuo et al., 1997; Thomas et al., 2000). Conversely, expression of a partially self-complementary RNA molecule with substantial homology in its self-complementary or double-strand-forming region to ("hairpin RNA against") transformer will tend to transform genetic females into phenotypic males, while not affecting genetic males, and expression of hairpin RNA against msl-2 will tend to be lethal to males but not to females. Expression of hairpin RNA against the male- or female-specific exons of doublesex will tend to affect those sexes only, and simultaneous expression of RNA encoding the other form of doublesex (i.e. Dsx$^M$ in females or Dsx$^F$ in males) will tend to modify or enhance this effect. This simultaneous expression of a protein and a hairpin RNA molecule can readily be accomplished by combining the bicistronic or fusion protein approach described above with expression of a hairpin RNA using the bi-directional expression system also described above. Sex-, stage- or other specificity can be further added to such a system by incorporation of appropriate specific splicing or other transcriptional, translational or other post-translational control signals to either part of the system as will be apparent to the person skilled in the art.

Multi-functional hairpin RNA molecules may be constructed and are envisaged. For example, RNAi against transformer in the Mediterranean fruit fly *Ceratitis capitata* Wiedmann (medfly) will tend to transform genetic females into fertile males. For an area-wide population control program based on mass-release of such insects, it is preferable to sterilise the released flies. This can be accomplished by using a composite RNA molecule that simultaneously disrupts expression of both transformer and a gene required for spermatogenesis or embryonic or larval viability. Many such genes are known in *Drosophila* with homologues in mosquitoes or other animals. With medfly, a suitable homologue can readily be isolated, using techniques known to those skilled in the art. We prefer the use of a gene which allows the production of seminal fluid, and preferably also of sperm, to reduce the tendency of the female to re-mate after insemination by the affected male. We particularly prefer to direct this second part of the hairpin RNAi molecule against a paternal effect lethal, so that no viable progeny can be produced, or against a zygotically expressed gene required for embryonic or larval viability or development, so that progeny inheriting the construct will be affected. Other configurations are envisioned and will be readily apparent to those skilled in the art: for example expression of a female-specific lethal protein by bicistronic expression and a hairpin RNA leading to paternal-effect lethality by bi-directional expression. In common with the composite hairpin RNA against a suitable sex-determination gene and a paternal effect lethal, this allows the generation of a single-sex (male-only) population of insects, all of whose progeny die through the action of the paternal-effect lethal, irrespective of whether their progeny or mates feed on tetracycline. Thus, the present invention provides a controlled promoter, as defined, wherein the promoter is operably linked with DNA encoding an RNAi causing lethality or sterility. In this case, lethality may correspond to low fitness, such as flightless, rather than outright lethality, provided that the likelihood of breeding on is substantially reduced.

4. Using Site-Specific Recombinase(s)

Specificity can also be introduced into the positive feedback system by inserting a "stuffer" fragment which inactivates it. If this "stuffer" fragment is flanked by target sites for a suitable site-specific recombinase, then it will tend to be excised in the presence of active recombinase. Any system for selective expression of active recombinase, for example, expression of the recombinase under the control of a female-specific promoter, will therefore tend to lead to selective expression of the positive feedback system, in this case in females only. If the recombinase is expressed in somatic cells only, for example by using the method described above, then the version transmitted to the next generation includes the stuffer fragment, which can again be daughters but not sons. Conversely, if the recombinase is expressed in the genome only, provision of active recombinase will lead to offspring in which the expression system is active, from parents in which it is inactive. This can be used, for example, to generate gametes containing an active dominant lethal or sterile gene system (e.g. female-specific or non-sex-specific) for use in an insect population control strategy.

In a preferred embodiment, the stuffer fragment encodes the recombinase. This embodiment is particularly compact. In another preferred embodiment, the stuffer fragment encodes a transcriptional repressor which tends to inactivate the positive feedback expression system—this embodiment tends to reduce the basal expression of the system in the presence of the stuffer fragment.

Conversely, the system can be specifically inactivated in certain cells, or clones of cells, by introducing target sites for a suitable site-specific recombinase at suitable positions, and then expressing or introducing the appropriate active recombinase in appropriate cells, such that one or more key functional elements of the expression system are removed or disrupted by recombination between the target sites for the recombinase.

Suitable recombinase systems include cre/lox and Flp/FRT.

The present invention will now be described with reference to the following, non-limiting Examples. All references cited herein are hereby incorporated by reference.

EXAMPLES

A series of constructs was made with tTA in a positive feedback configuration, i.e. with tTA expression regulated by tTA binding to tetO. Transgenic insects carrying these constructs were obtained and their properties analysed.

tTAV

In some cases, the intention was to obtain very high levels of expression of tTA in the absence of tetracycline. In various exemplified constructs described hereinbelow, tTA expression was so high as to be lethal. As part of the process of obtaining strong expression of tTA, part of the tTA open reading frame was redesigned to express a similar protein, but with codon usage closer to the norm for *Drosophila melanogaster*, and lacking some potential cryptic splice sites present in the original nucleotide sequence. This variant tTA sequence was named tTAV (SEQ ID NO. 31, protein sequence SEQ ID NO. 32).

Example 1

WTP-tTA and JY2004-tTA in *Drosophila Melanogaster*

The tTA coding region (SEQ ID NO. 29, tTA protein sequence SEQ ID NO. 30) from pUHD15-1 (SEQ ID NO. 33, Gossen et al., 1994; Gossen and Bujard, 1992) was placed under tetO control, in a positive feedback configuration, by inserting it into pWTP2 (Bello et al., 1998) or pJY2004, a version of pJY2000 that lacks insulators (Stebbins and Yin, 2001). These constructs were named pWTP-tTA and pJY2004-tTA, respectively. A diagram of tetO$_7$-tTA region of pJY2004 is provided as accompanying FIG. 5, and is SEQ ID NO. 14.

Figure 5:
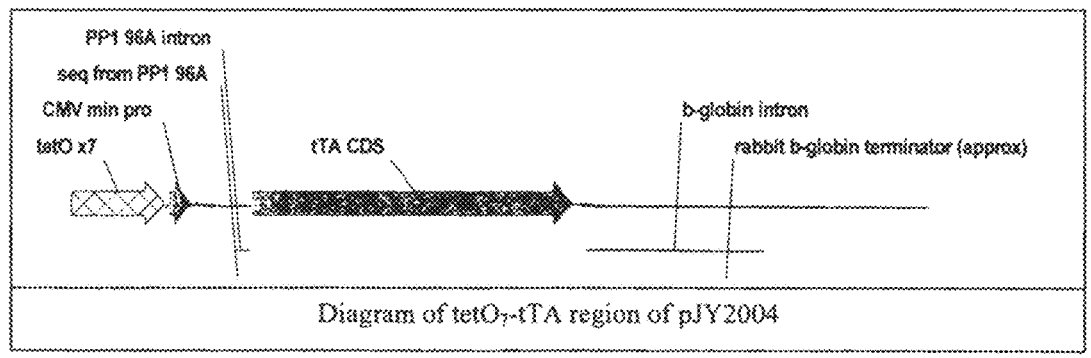
FIG. 5 is a diagram of the $tetO_7$-tTA region of pJY2004.

In pWTP-tTA, the tetO$_7$ binding sites are followed by a minimal promoter from the P element, a leader sequence from *Drosophila* hsp70, a short intron from the *Drosophila* PP1α96A gene, the tTA coding region and a transcription terminator from *Drosophila* hsp70. In pJY2004-tTA, the minimal promoter and leader sequences are from CMV, followed by the tTA coding region and a transcription terminator from rabbit β-globin, as shown in FIG. 5.

Transgenic *Drosophila melanogaster* carrying either of these constructs were fully viable, even without dietary tetracycline. Insects doubly heterozygous for WTP-EGFP and either of these constructs were examined for green fluorescence characteristic of EGFP expression. Insects with WTP-tTA and WTP-EGFP showed very weak fluorescence only slightly above background autofluorescence. In contrast, insects with JY2004-tTA and WTP-EGFP showed strong fluorescence, similar to that seen in insects carrying EGFP under the control of the Actin5C promoter, which is widely used as a strong, constitutive promoter in *Drosophila* (e.g. Reichhart and Ferrandon, 1998). Expression of EGFP was repressed to undetectable levels when the insects were raised on diet supplemented with tetracycline to 100 μg/ml. Control insects heterozygous for either WTP-EGFP, JY2004-tTA or WTP-tTA showed no fluorescence above background whether or not they were raised on a diet containing tetracycline.

We placed tTA under the control of the Actin5C promoter, in plasmid pP [Casper-Act5C-tTA]. Transgenic flies carrying this construct and WTP-EGFP, raised on a diet lacking tetracycline, showed green fluorescence at a comparable intensity to that observed in equivalent flies with JY2004-tTA and WTP-EGFP.

These results show that positive feedback constructs can be used to give strong (JY2004-tTA) or weak (WTP-tTA), tetracycline-repressible expression from a suitable construct (here WTP-EGFP).

EGFP is widely used as a neutral reporter. We further tested JY2004-tTA flies by crossing them to flies with constructs capable of expressing proteins known or predicted to be deleterious. We inserted the central domain of Nipp1Dm (Bennett et al., 2003; Parker et al., 2002) ("nipper"), into pJY2004, to make pJY2004-nipper, and transformed *Drosophila* with this construct. We also used flies carrying tetO-hid (Heinrich and Scott, 2000). In each case, crossing to JY2004-tTA flies gave tetracycline-repressible lethality. Data from two example crosses are presented in Table 2, below.

TABLE 2

Use of positive feedback constructs to drive expression of lethal genes in *Drosophila*.

| JY2004-tTA | CyO | [tetracycline] (μg/ml) |
|---|---|---|
| Male JY2004-tTA/CyO x Female tetO-hid/tetO-hid | | |
| 0 | 15 | 0 |
| 9 | 10 | 100 |
| Male JY2004-tTA/CyO x Female JY2004-nipper/ JY2004-nipper | | |
| 0 | 20 | 0 |
| 16 | 13 | 100 |

Example 2

LA513 in *Drosophila Melanogaster*

Figure 6:
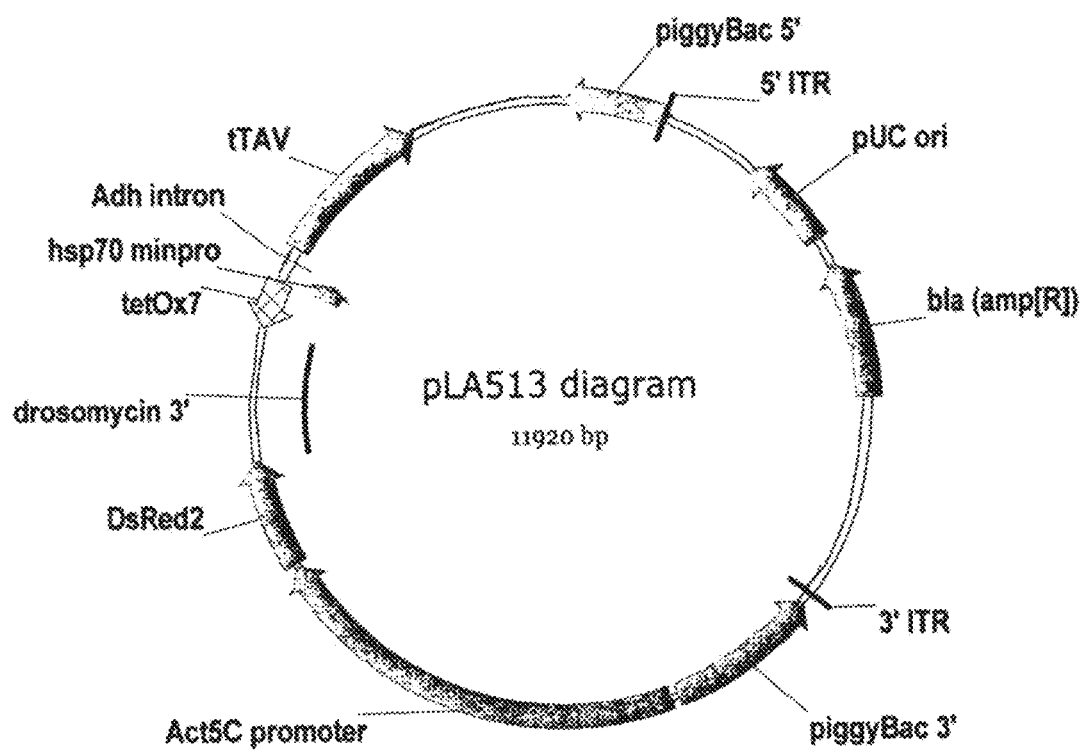
FIG. 6 is a schematic diagram of pLA513.
Figure 7:
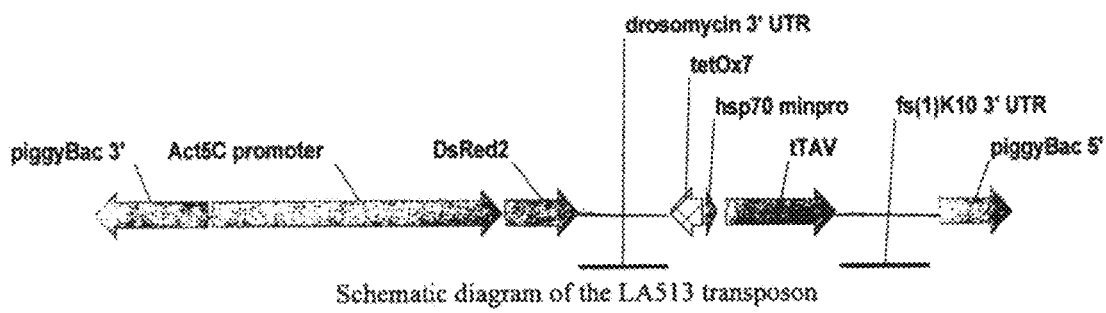
FIG. 7 is a schematic diagram of the LA513 transposon.

We made construct pLA513 (SEQ ID NO. 16, schematic diagram shown in FIG. 6), containing a non-autonomous piggyBac transposon. We generated transgenic *Drosophila melanogaster* carrying this construct by co-injection with a helper plasmid into a white-eyed strain (Handler, 2002; Handler and James, 2000). Potential transgenics were screened for fluorescence characteristic of DsRed2. 5 transgenic lines were recovered, and were designated O513, M8, M13, F23 and F24. A schematic diagram of the LA513 transposon is shown in accompanying FIG. 7.

*Drosophila melanogaster* stocks were maintained at 25° C. on yeast/sugar/maize/tetracycline medium (tetracycline (Sigma) at 100 μg/ml final concentration), unless stated otherwise. All experiments were performed at 25° C.

Survival of LA513/+ Transgenics with and without Tetracycline

Heterozygous transgenics were crossed in at least triplicate to wild type on media with or without Tc (tetracycline). In the absence of any lethality, it would be expected that approximately half the progeny of such a cross would be transgenic. Progeny were scored as young adults for DsRed marker fluorescence [Matz et al., 1999] using an Olympus SZX12 microscope with fluorescence capability, and the ratio of fluorescent (transgenic) to total flies was calculated. The results are shown in Table 3, below. In these experiments, all 5 transgenic lines showed 100% lethality, in the absence of tetracycline, and good survival (i.e. fluorescent: non-fluorescent ratio ~1:1), in the presence of 100 μg/ml tetracycline. Inspection of the vials showed few or no large fluorescent larvae in the absence of Tc, although many very small fluorescent larvae were present, at a time when non-fluorescent (wild type for LA513) larvae were visible at all sizes. This suggests that, in the absence of tetracycline, LA513 causes lethality at an early (embryonic and/or early larval) developmental stage.

TABLE 3

LA513 insertions are tetracycline-repressible dominant lethals

| | 0 μg/ml tetracycline | | 100 μg/ml tetracycline | | |
|---|---|---|---|---|---|
| LA513 line | # Flies | # Fluorescent | # Flies | # Fluorescent | Ratio |
| O513 | 490 | 0 | 1963 | 937 | 0.48 |
| M8 | 74 | 0 | 66 | 25 | 0.38 |
| M13 | 657 | 0 | 1838 | 892 | 0.49 |
| F23 | 473 | 0 | 1914 | 845 | 0.44 |
| F24 | 61 | 0 | 114 | 60 | 0.53 |
| Total | 1755 | 0 | 5895 | 2759 | 0.47 |

Dominant lethality could have several causes. Without being restricted by theory, it seems likely that, in the absence of tetracycline, tTAV accumulates to a relatively high concentration and that this is lethal, possibly due to transcriptional squelching, or interference with protein degradation. An alternative is that, in the absence of tetracycline, tTAV binds to tetO and acts as a long-range enhancer, perturbing the expression of genes near to the LA513 insertion. This appears unlikely, as all 5 transgenic lines gave similar results. Each of these lines was derived from a different G0 injection survivor, and these lines are, therefore, likely to carry LA513 integrated at different genomic sites. We verified this by inverse PCR. Table 4, below, shows the integration sites for 3 of the lines; in each case the LA513 insertion was at a TTAA sequence, as expected from the known insertion site preference of the piggyBac transposon. As expected, the 3 insertions were indeed at 3 different sites in the *Drosophila* genome.

TABLE 4

Insertion sites of LA513 in Drosophila genome

| Line | Sequence Amplified or at Site of Integration | Predicted chromosome arm | Predicted Drosophila cytology | Nearest predicted gene |
|---|---|---|---|---|
| O51 3 | CacagcgcatgatgagcacaTTAAcaaaatgtagtaaaa tagga (SEQ ID NO. 1) | 2L | 25F4-25F5 | CG9171 |
| M8 | GtttcgataaatattgctatTTAAaatgcttattttcaatgcta (SEQ ID NO. 2) | 2L | 36F6-36F6 | CG15160 |
| F24 | TttgttttctaacgttaaagTTAAagagagtccagccacattt t (SEQ ID NO. 3) | 2L | 21C4-21C5 | CG13691 |

Flanking sequence is shown with the TTAA insertion site capitalised. Predicted chromosome locations, and the nearest predicted gene, are also shown; these are based on the published *Drosophila* genome sequence.

Example 3

Reducing the Toxicity of tTAV

Figure 8:
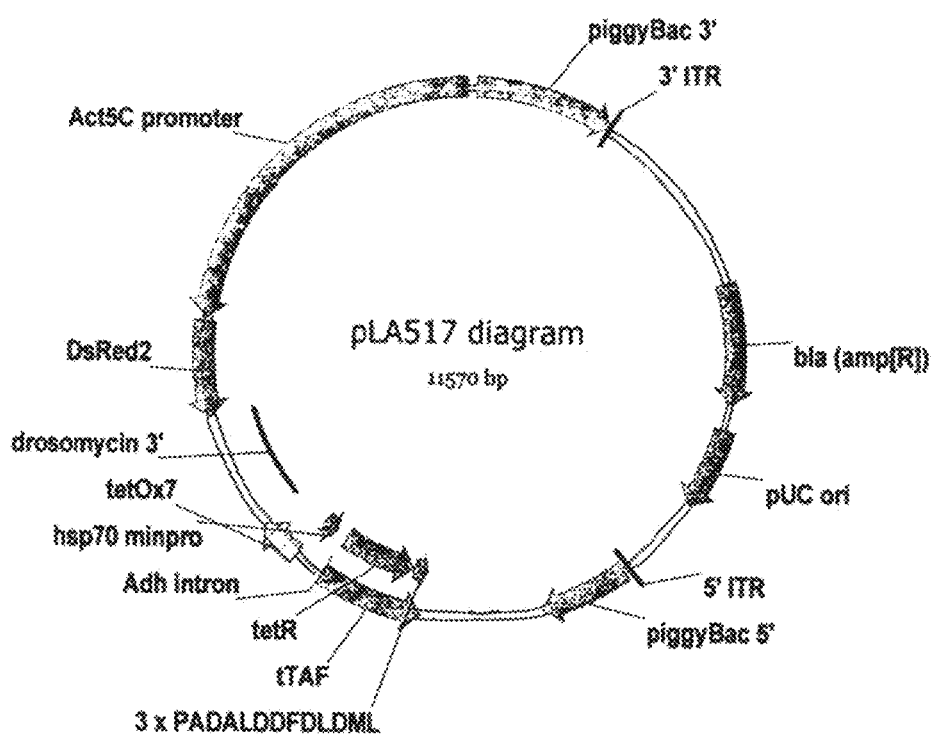
FIG. 8 is a schematic diagram of pLA517.

The toxic effect of high level expression of tTAV is thought to be due to transcriptional squelching and/or interference with ubiquitin-dependent proteolysis, via the VP16-derived section (Gossen and Bujard, 1992; Salghetti et al., 2001). We, therefore, modified tTAV by removing the VP16 section and replacing it with a synthetic sequence which encodes 3 copies of a peptide (PADALDDFDLDML) derived from VP16 (Baron and Bujard, 2000; Baron et al., 1997). This derivative was named tTAF; the resulting plasmid was named pLA517, and is SEQ ID NO. 17, and is shown, diagrammatically, in accompanying FIG. 8.

*Drosophila melanogaster* were transformed with this construct, and one transgenic line was obtained. LA513 heterozygous males were crossed to wild type (for LA513) females and the progeny scored for fluorescence (as adults). If all progeny are equally likely to survive, the expected proportion of the total progeny that are fluorescent is 50%. In the absence of tetracycline, this proportion was 32%, only a modest reduction compared with 48% when parents and progeny were raised on diet supplemented with tetracycline to 100 µg/ml. The results are shown in Table 5, below. We tested whether supplying tetracycline in the diet of the parents but not of the progeny could reduce this lethality. In this case, we observed an intermediate proportion of 0.37, indicating that maternally contributed tetracycline has a modest beneficial effect.

TABLE 5

Effect of tetracycline on the survival of LA517/+ *Drosophila* and their +/+ siblings
LA517

| Parent [Tc] µg/ml | Progeny [Tc] µg/ml | Non-Fluorescent | Fluorescent |
|---|---|---|---|
| 0 | 0 | 165 | 78 |
| 100 | 100 | 524 | 482 |
| 100 | 0 | 502 | 297 |

Since LA517, alone, had little impact on viability, unlike the closely related construct LA513, we tested whether it was capable of driving expression of a heterologous gene under tetO control. For this we used tetO-hid (Heinrich and Scott, 2000). Flies homozygous for tetO-hid were crossed with flies heterozygous for LA517. In the absence of tetracycline, only 3.4% of the adult progeny carried LA517. In the presence of 100 µg/ml tetracycline, this proportion was 42%. LA517 is, therefore, capable of driving effective expression of a heterologous gene.

TABLE 6

Effect of tetracycline on the survival of LA517/+, +/tetO-hid *Drosophila* and their +/+, +/tetO-hid siblings
TetO-Hid x LA517/+

| [Tc] | Non-Fluorescent | Fluorescent |
|---|---|---|
| 0 | 636 | 23 |
| 100 | 174 | 127 |

Example 4

Use of Analogues of Tetracycline

Line F23 was used to determine whether chemical analogues of tetracycline could be used in place of tetracycline to suppress the lethality of LA513. For this purpose we tested 3 analogues at a range of concentrations from 0 to 100 µg/ml (suppliers: tetracycline and doxycycline, Sigma; 4-epi-oxytetracycline, Acros Organics; chlortetracycline Fuzhou Antibiotic Group Corp.). We calculated the concentrations required for half-maximal survival. These are shown in Table 7, below.

TABLE 7

Efficacy of Tc analogues

| Line | Tc/Analogue | Concentration for half-maximal survival, µg/ml |
|---|---|---|
| F23 | Tetracycline | 5.0 |
| F23 | Doxycycline | 3.9 |
| F23 | 7-chlortetracycline | 1.7 |
| F23 | 4-epi-oxytetracycline | 42.0 |

Example 5

Longevity of LA513/+ Adults in the Absence of Tetracycline

LA513 clearly confers dominant lethality, active at an embryonic and/or early larval stage. Larvae were raised on a diet supplemented with 100 µg/ml tetracycline. After eclosion, adults were transferred to a diet lacking tetracycline. The lifespan of these adults was measured, and also of comparable $w^{1118}$ non-transgenic adults. As shown in Table 8, below, the transgenic lines showed good adult survival relative to the non-transgenic control. This suggests that stage-specificity can be obtained in this way—here LA513 is a larval/embryonic lethal, but not an adult lethal.

TABLE 8

Mean adult lifespan of LA513/+ transgenic Drosophila.

| Line | Mean post-eclosion survival time, days | Standard deviation | Number of Flies |
|---|---|---|---|
| O513 | 40.3 | 12.3 | 66 |
| M8 | 26.1 | 2.5 | 9 |
| M13 | 29.5 | 9.9 | 47 |
| F23 | 29.6 | 11.3 | 83 |
| F24 | 19.9 | 10.0 | 9 |
| $w^{1118}$ | 22.2 | 8.6 | 88 |

It is possible to explain these longevity data by postulating that larvae accumulate tetracycline by feeding, and retain this tetracycline into adulthood, so that they survive even in the absence of dietary tetracycline as adults. To examine this, flies heterozygous for LA513/+ (M13 line) were raised as larvae on various concentrations of tetracycline. After eclosion, adults were transferred to diet lacking tetracycline and the lifespan of these adults was measured, as above. As shown in Table 9, below, the concentration of dietary tetracycline as larvae had no obvious effect on subsequent adult longevity in the absence of tetracycline, implying that adult survival is not primarily due to retention of tetracycline from larval feeding. At a concentration of 1 µg/ml, no transgenics survived to adulthood, and at 3 µg/ml only about half of the expected number survived to adulthood, so that this concentration is close to the minimum for larval survival.

TABLE 9

Effect of larval tetracycline on adult longevity

| Larval tetracycline µg/ml | Mean post-eclosion survival time, days | Standard deviation | Number of Flies |
|---|---|---|---|
| 1 | — | — | — |
| 3 | 33.5 | 13.2 | 9 |
| 10 | 28.4 | 9.6 | 17 |
| 30 | 26.3 | 11.3 | 23 |
| 100 | 29.5 | 9.9 | 47 |

Another possible explanation for the survival of LA513/+ adults is that tTAV is inactive in adults, so that the positive feedback cycle does not work, and tTAV does not accumulate. We examined this by measuring the amount of tTAV mRNA by quantitative PCR following a reverse transcriptase reaction (quantitative rt-PCR, or qPCR). We used Taqman chemistry and reagents (ABI), and an ABI Prism 7000 qPCR instrument. Each sample was assayed in triplicate; data are the mean of these three assays. The 18S primers anneal to Drosophila melanogaster, Ceratitis capitata and Aedes aegypti 18S RNA, so these primers were used for all three species.
Primers Used:

| 18S RNA | SEQ ID NO. |
|---|---|
| Forward Primer: ACGCGAGAGGTGAAATTCTTG | 4 |
| Reverse Primer: GAAAACATCTTTGGCAAATGCTT | 5 |

| 18S RNA | SEQ ID NO. |
|---|---|
| TaqMan MGB Probe: 6-Fam-CCGTCGTAAGACTAAC-MGB | 6 |
| tTAV | |
| Forward Primer: CATGCCGACGCGCTAGA | 7 |
| Reverse Primer: GTAAACATCTGCTCAAACTC-GAAGTC | 8 |
| TaqMan MGB Probe: VIC-TCGATCTGGACATGTTGG-MGB | 9 |

We found that O513 raised on 100 µg/ml tetracycline had a tTA:18S ratio of 0.00016 (larvae) and 0.00013 (adult). Adults raised as larvae on 100 µg/ml tetracycline, but then transferred to non-tetracycline diet as adults had ratios of 0.0061, 0.0047, 0.0087 and 0.011 after 1, 2, 4 and 8 days without tetracycline, respectively. This 28- to 64-fold increase in expression relative to the tetracycline-fed control indicates that the tTAV-based positive feedback expression system is functional in adults.

Example 6

LA513 in Aedes Aegypti

Aedes aegypti (the yellow fever mosquito, also the major vector of urban dengue fever) were transformed with LA513. Two independent insertion lines, LA513A and LA513B, were obtained.

Males heterozygous for LA513A (reared as larvae on 30 µg/ml tetracycline) were allowed to mate with wild type females. Eggs were collected and the resulting larvae raised in normal media, or in media supplemented with tetracycline (Tc) to 30 µg/ml. The number of transgenic and non-transgenic adults resulting from these eggs was determined. Data are the sum of at least 5 experiments. Larvae were reared at a density of ≤250 individuals per liter; all the eggs in "no tetracycline" experiments were washed twice before submergence to avoid transferring tetracycline. For the "with tetracycline" experiments, the parental blood and sugar-water was supplemented with tetracycline to 30 µg/ml; for the "no tetracycline" experiments it was not. $\chi^2$ test for differentiation in ratio of the transgene and wild types for survival to adult: "with tetracycline", either orientation: P>0.05; "without tetracycline, either orientation P<0.001 (null hypothesis: genotype with respect to LA513 has no effect on survival).

LA513A is, therefore, a repressible dominant lethal, with a penetrance in these experiments of 95-97%. LA513B is also a repressible dominant lethal, with a penetrance in these experiments of 100%. The results are shown in Table 10, below.

TABLE 10

Effect of tetracycline on the survival of LA513/+ *Aedes aegypti* and their +/+ siblings.

| Parents | | | | Progeny | | | | | | |
|---|---|---|---|---|---|---|---|---|---|---|
| Male | Female | Egg | Tc as larvae | Genotype | 1<sup>st</sup> instar larvae | $2^{nd}$ | $3^{rd}$ | $4^{th}$ | Pupae | Adults |
| LA513A/+ | +/+ | 1000 | Yes | LA513A/+ | 489 | 468 | 446 | 442 | 437 | 434 |
| | | | | Wild type | 444 | 431 | 403 | 400 | 396 | 392 |
| +/+ | LA513A/+ | 1000 | Yes | LA513A/+ | 442 | 420 | 404 | 399 | 393 | 383 |
| | | | | Wild type | 466 | 444 | 428 | 417 | 412 | 404 |
| LA513A/+ | +/+ | 540 | No | LA513A/+ | 274 | 265 | 235 | 208 | 155 | 7 |
| | | | | Wild type | 233 | 225 | 214 | 212 | 209 | 206 |
| +/+ | LA513A/+ | 497 | No | LA513A/+ | 216 | 205 | 181 | 168 | 131 | 9 |
| | | | | Wild type | 241 | 225 | 216 | 214 | 211 | 207 |
| LA513B/+ | +/+ | 377 | Yes | LA513B/+ | 161 | 153 | 147 | 141 | 139 | 131 |
| | | | | Wild type | 178 | 171 | 165 | 160 | 157 | 153 |
| +/+ | LA513B/+ | 442 | Yes | LA513B/+ | 189 | 181 | 170 | 166 | 161 | 153 |
| | | | | Wild type | 203 | 198 | 185 | 182 | 180 | 176 |
| LA513B/+ | +/+ | 188 | No | LA513B/+ | 69 | 19 | 0 | 0 | 0 | 0 |
| | | | | Wild type | 85 | 84 | 83 | 83 | 82 | 81 |
| +/+ | LA513B/+ | 240 | No | LA513B/+ | 91 | 60 | 0 | 0 | 0 | 0 |
| | | | | Wild type | 107 | 104 | 99 | 98 | 95 | 93 |

We examined the survival of LA513A/+ males that had been raised on tetracycline (30 μg/ml), as larvae, but not given tetracycline as adults. We found that all males tested survived for three weeks, irrespective of genotype (LA513A/LA513A, LA513A/+ or +/+) or the presence or absence of tetracycline in their diet (n≥140 for each genotype).

We investigated the induction kinetics of tTAV in adult LA513B/+ mosquitoes after withdrawal of tetracycline, using qPCR. As shown in Table 11, below, tTAV increased in males and females following withdrawal of tetracycline. Induction of tTA expression is fairly rapid after removal of Tc, as with *Drosophila*. In each case, shifting between diets containing different levels of tetracycline provides a level of control over the expression level of genes controlled by tTA (here exemplified by tTA itself), using such a positive feedback system.

TABLE 11

Induction of tTA expression in LA513B/+ males following withdrawal of tetracycline

| Sex | Time (days) without tetracycline | tTA:18S expression ratio | tTA:18S expression relative to male with tetracycline |
|---|---|---|---|
| Male | 0 | 0.00036 | 1 |
| Female | 0 | 0.00060 | 1.7 |
| Male | 3 | 0.0043 | 12 |
| Female | 3 | 0.014 | 38 |
| Male | 4 | 0.054 | 150 |
| Female | 4 | 0.019 | 530 |
| Male | 8 | 0.012 | 34 |
| Female | 8 | 0.52 | 1500 |
| Male | 16 | 0.10 | 280 |
| Female | 16 | 0.032 | 88 |

Example 7

Tetracycline-Repressible Enhancement of a Nearby Promoter by tTAV in a Positive Feedback Configuration We observed that the fluorescent marker in LA513A and LA513B transgenic mosquitoes showed a different pattern of fluorescence in the absence of tetracycline, compared with the pattern in the presence of tetracycline. Fluorescence in the presence of tetracycline was typical of Actin5C-driven expression in mosquitoes (Catteruccia et al., 2000; Pinkerton et al., 2000), and limited largely to the swollen part of the thorax. In contrast, in the absence of tetracycline, expression was much stronger and evident substantially throughout the body of transgenic individuals. In each case, assessment of fluorescence intensity and expression pattern was made by visual observation using fluorescence microscopy.

Elevated expression of tTAV in this positive feedback situation appears, therefore, to be stimulating expression from the nearby Actin5C promoter. This is illustrated, diagrammatically, in FIG. 9. We also found that intermediate concentrations of tetracycline, just sufficient substantially to suppress the lethality of LA513, did not suppress this broader expression pattern of fluorescence. At these intermediate concentrations of tetracycline, tTAV accumulates to an intermediate level—sub-lethal, but higher than in 30 μg/ml tetracycline, and which still influences the expression of DsRed2. This again exemplifies the additional control available by modulating tetracycline concentration.

Figure 9:
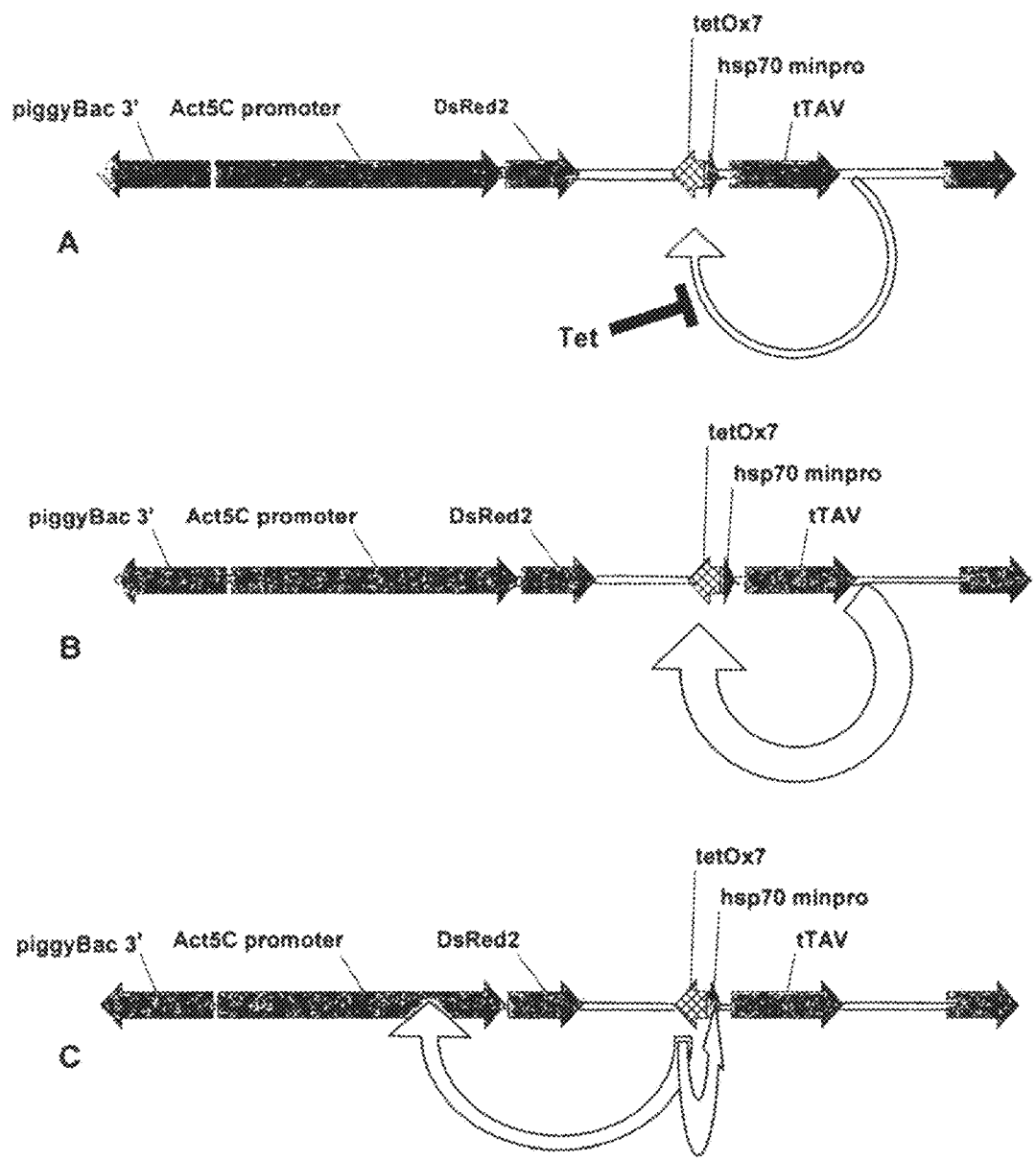
FIG. 9 illustrates the bidirectional action of tetO$_7$ in 513A and 513B mosquitoes.

FIG. 9 illustrates the bidirectional action of tetO$_7$ in 513A and 513B mosquitoes. In 513, DsRed2 is under the transcriptional control of the *Drosophila* Actin5C promoter.

(A) In the presence of tetracycline, relatively little tTAV is produced, this binds tetracycline and has little or no effect on DsRed2 expression. DsRed2 is seen in a pattern typical of Actin5C expression in mosquitoes.

(B) In the absence of tetracycline, tTAV stimulates its own expression in a positive feedback loop.

(C) tTAV binding to the tetO sites enhances expression of both the hsp70 minimal promoter, and hence tTAV, but also the Actin5C promoter, and hence DsRed2.

Example 8

LA656, LA928 and LA1124 in *Ceratitis Capitata*

Figure 10:
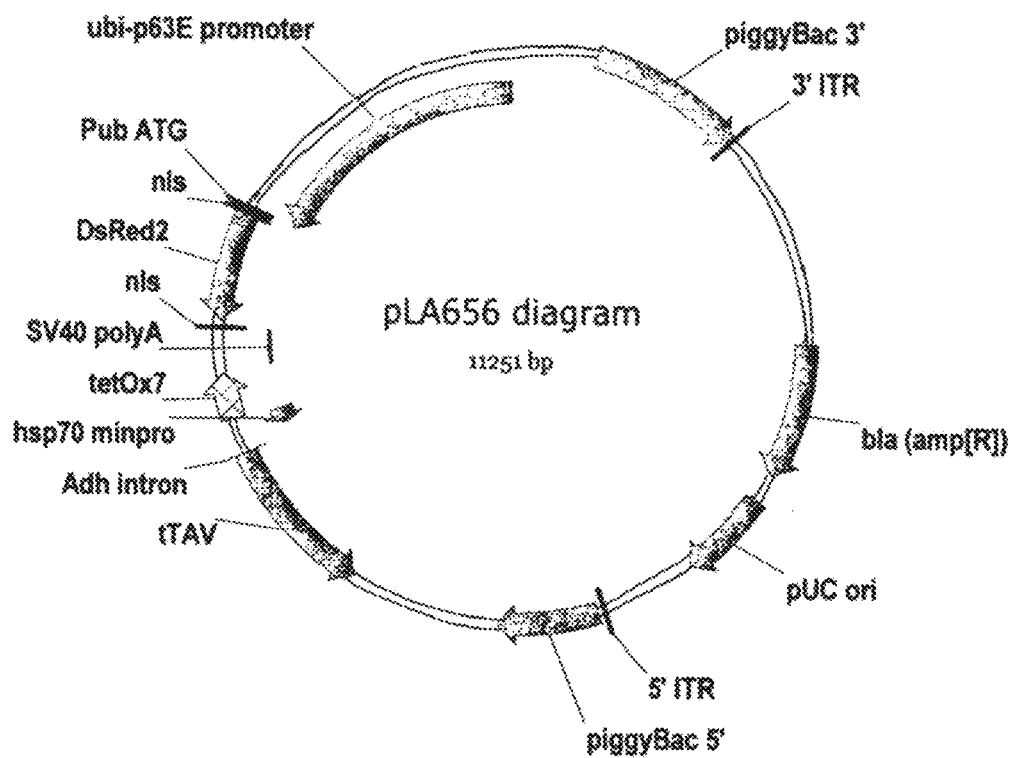
FIG. 10 is a schematic diagram of pLA656.
Figure 11:
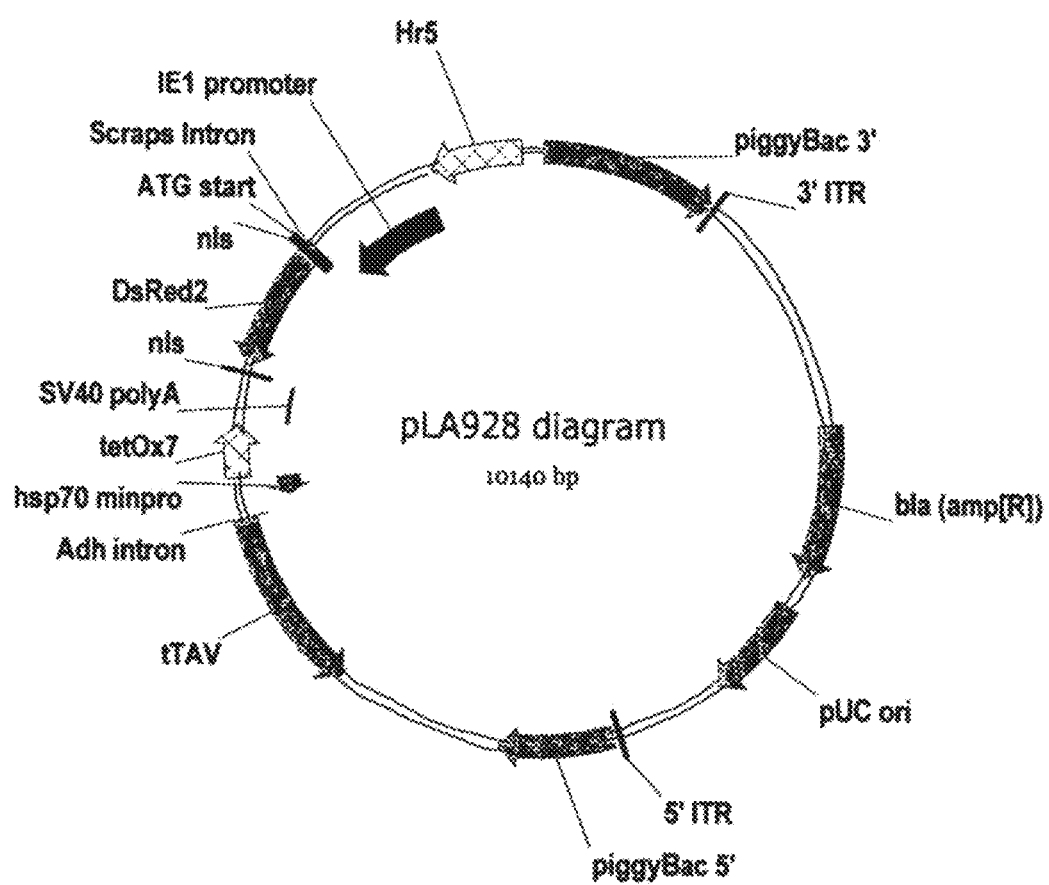
FIG. 11 is a schematic diagram of pLA928.

No transgenic lines of the Mediterranean fruit fly (medfly, *Ceratitis capitata* Wiedmann) were obtained, using pLA513, probably indicating that the Actin5C-based marker of pLA513 is inappropriate for use in medfly. This emphasises the desirability of expression constructs with a wide species range. We, therefore, modified the construct to include a polyubiquitin (ubi-p63E)-based marker instead of the Actin5C-based one of pLA513. One such construct is pLA656. We also made two additional constructs, pLA928 and pLA1124 (SEQ ID NO's 18, 20 and 21, respectively, and shown, diagrammatically, in FIGS. 10, 11 and 12), using a marker based on the hr5 enhancer and ie1 promoter from a baculovirus (*Autographica californica* nuclear polyhedrosis virus, AcMNPV). These differ in the orientation of the marker with respect to the tetO-tTAV cassette. The hr enhancer is closer to the tetO-tTAV cassette in pLA1124 than in pLA928. Furthermore, pLA1124 has 21, rather than 7, copies of tetO and additionally has a putative GAGA-factor binding region related to that of pUASp (Rorth, 1998).

One transgenic line was obtained from pLA656, three for pLA928, and three for pLA1124. These lines are assumed to have independent insertions, as they were derived from different G0 injection survivors.

The results of these crosses are shown in Table 12, below. In each case, in the absence of tetracycline, survival of the heterozygous transgenics was less than 2% relative to their wild type siblings. The survival of these wild type siblings is a good control, as they are genetically similar, and raised in the same environment. In each case, this highly penetrant dominant lethality was substantially repressed by the addition of tetracycline to 100 µg/ml. In the case of LA656 and LA928, the survival rates on intermediate concentrations of tetracycline indicated that 0.1 µg/ml was insufficient for significant viability, and that viability increased in the range 1 µg/ml to 100 µg/ml. Thus, varying the concentration of dietary tetracycline provides a convenient level of control over the expression level of genes controlled by tTAV (here exemplified by tTAV itself), using such a positive feedback system. Three additional methods, shifting between diets containing different levels of tetracycline, modifying the construct, and using position effect, are discussed elsewhere herein.

TABLE 12

Effect of tetracycline on the survival of transgenic medfly heterozygous for various constructs, and their +/+ siblings

| | Progeny [Tc] (µg/ml) | F/NF pupae | Pupal survival ratio (%) | F male | F female | NF male | NF female | Adult survival ratio (%) |
|---|---|---|---|---|---|---|---|---|
| LA656 | 0 | 84/1161 | 7 | 6 | 2 | 530 | 551 | 0.7 |
| | 0.1 | 16/423 | 4 | 0 | 0 | 205 | 177 | 0 |
| | 1 | 124/384 | 32 | 34 | 12 | 155 | 174 | 14 |
| | 3 | 258/370 | 70 | 84 | 53 | 165 | 133 | 46 |
| | 10 | 249/252 | 99 | 91 | 98 | 107 | 127 | 81 |
| | 100 | 330/307 | 107 | 151 | 150 | 134 | 148 | 107 |
| LA928m1 | 0 | 28/1499 | 1.87 | 5 | 1 | 661 | 639 | 0.46 |
| | 0.1 | 0/765 | 0 | 0 | 0 | 347 | 246 | 0 |
| | 1 | 190/256 | 74 | 62 | 59 | 119 | 101 | 55 |
| | 3 | 290/302 | 96 | 133 | 98 | 143 | 107 | 92 |
| | 10 | nd | nd | nd | nd | nd | nd | nd |
| | 100 | 222/286 | 77 | 117 | 84 | 146 | 126 | 74 |
| LA928m3 | 0 | 68/1026 | 6.6 | 13 | 4 | 489 | 449 | 1.8 |
| | 0.1 | 0/265 | 0 | 0 | 0 | 117 | 91 | 0 |
| | 1 | 358/446 | 80 | 154 | 100 | 228 | 164 | 65 |
| | 3 | 105/105 | 100 | 39 | 35 | 42 | 38 | 93 |
| | 10 | nd | nd | nd | nd | nd | nd | nd |
| | 100 | 245/245 | 100 | 109 | 121 | 117 | 108 | 100 |
| LA928f1 | 0 | 17/1331 | 1.3 | 2 | 0 | 639 | 599 | 0.16 |
| | 0.1 | 2/254 | 0.8 | 0 | 0 | 100 | 84 | 0 |
| | 1 | 461/567 | 81 | 218 | 146 | 244 | 181 | 85 |
| | 3 | 520/527 | 99 | 214 | 182 | 249 | 202 | 88 |
| | 10 | 350/399 | 91 | 139 | 112 | 131 | 159 | 87 |
| | 100 | 126/117 | 108 | 63 | 57 | 57 | 49 | 113 |
| LA1124f1 | 0 | 104/213 | 51 | 0 | 3 | 95 | 62 | 1.9 |
| | 100 | 478/536 | 89 | 218 | 208 | 205 | 203 | 104 |
| LA1124m1 | 0 | 337/437 | 77 | 2 | 1 | 176 | 207 | 0.78 |
| | 100 | 84/90 | 93 | 35 | 31 | 30 | 26 | 118 |
| LA1124m2 | 0 | 104/145 | 72 | 0 | 1 | 46 | 34 | 1.3 |
| | 100 | 77/77 | 100 | 24 | 14 | 19 | 13 | 119 |

F: fluorescent;
NF: non-fluorescent.

Males heterozygous for each line were crossed to wild type females. The progeny were raised on standard yeast/sugar/wheatgerm or yeast/sugar/maize *Drosophila* diet, supplemented with tetracycline as appropriate. The parents were raised on the same diet, supplemented with tetracycline to 100 µg/ml in the case of the transgenic males. The wild type females to which these males were mated were raised without tetracycline, to eliminate any potential maternal contribution of tetracycline. The number of transgenic and non-transgenic pupae and adults obtained from each cross was determined by scoring for DsRed2 by fluorescence microscopy.

Pupae were collected and scored for fluorescence (column 3), then allowed to eclose. Surviving adults were scored for sex and fluorescence (columns 5-8). From these data on adults, the ratio of fluorescent to non-fluorescent survivors was calculated, presented in column 9 as the percentage of fluorescent adults observed relative to non-fluorescent. It is to be expected that these crosses give, on average, equal numbers of transgenic and non-transgenic individuals; if an equal proportion of transgenic and non-transgenic individuals were to survive to adulthood, then this would give an "adult survival ratio" of 100%.

We further investigated the expression of tTA in these transgenic lines by quantitative (real-time) rt-PCR (qPCR). The results are given in Table 13, below.

TABLE 13

Expression levels of tTA in wild type and transgenic medfly

| Sample | tTA/18S ratio | NT/T ratio |
|---|---|---|
| Larvae | | |
| WT tet | 3.13E-06 | |
| WT NT | 2.81E-06 | |
| 656 tet | 5.80E-06 | 1.00 |
| 656 NT | 2.06E-04 | 36 |
| 670A tet | 2.71E-06 | 1.00 |
| 670A NT | 1.10E-04 | 41 |
| 670e tet | 9.70E-06 | 1.00 |
| 670e NT | 8.40E-05 | 8.7 |
| Adults | | |
| WT female | 2.83E-06 | |
| WT male | 2.16E-07 | |
| Heterozygous | | |
| 656 tet M 0 d | 5.52E-06 | 1.00 |
| 656 tet M 8 d | 1.12E-05 | 2.0 |
| 656 NT M 0 d | 4.49E-05 | 8.1 |
| 656 NT M 2 d | 2.77E-04 | 50 |
| 656 NT M 4 d | 2.22E-04 | 40 |
| 656 NT M 8 d | 9.71E-05 | 18 |
| 656 NT M 16 d | 1.49E-04 | 27 |
| 670 M tet | 4.21E-06 | 1.00 |
| 670 F tet | 2.86E-06 | 0.68 |
| 670 M NT S | 6.93E-05 | 16.45 |
| 670 F NT S | 1.92E-04 | 45.57 |
| 928Am1 F tet | 7.17E-06 | 1.00 |
| 928Am1 M tet | 8.56E-06 | 1.19 |
| 928Am1 M NT 2 d | 1.71E-04 | 23.81 |
| 928Am1 M NT 4 d | 5.36E-04 | 74.72 |
| 928Am1 M NT 8 d | 1.91E-04 | 26.66 |
| 928Am1 M NT 16 d | 1.01E-05 | 1.41 |
| 928Am1 M tet 8 d | 1.11E-06 | 0.16 |
| 928Am1 M NT S | 2.22E-04 | 31.02 |
| 928Am1 M NT S | 1.51E-04 | 21.11 |
| 928Am3 F tet | 9.09E-07 | 1.00 |
| 928Am3 M tet | 9.09E-07 | 1.00 |
| 928Am3 F NT S | 3.62E-05 | 39.85 |
| 928Am3 F NT S | 8.74E-04 | 962.07 |
| 928Am3 F NT S | 2.99E-04 | 329.32 |
| 928Am3 M NT S | 5.53E-05 | 60.83 |
| 928Am3 M NT S | 9.18E-04 | 1009.90 |
| 1124fl F tet | 2.86E-05 | 1.00 |
| 1124fl F NT 7 d | 4.11E-04 | 14.35 |
| 1124m1 M tet | 1.62E-05 | 1.00 |
| 1124m1 F NT S | 9.30E-04 | 57.55 |
| 1124m2 F tet | 8.98E-05 | 1.00 |
| 1124m2 F NT 7 d homozygous | 7.90E-04 | 8.79 |
| 656 tet 8 d | 1.49E-05 | 1.00 |
| 656 NT 0 d | 9.23E-05 | 6.2 |
| 656 NT 2 d | 3.90E-03 | 262 |
| 656 NT 4 d | 1.92E-03 | 129 |
| 656 NT 8 d | 4.70E-03 | 316 |
| 656 NT 16 d | 8.58E-04 | 58 |

M: male;
F: female;
tet: raised on diet supplemented with tetracycline to 100 µg/ml;
NT S: raised on standard diet (0 µg/ml tetracycline);
d: days post-eclosion;
NT (n)d: raised on tet diet, then held as adults on non-tet (NT) diet for n days, as indicated;
tet (n)d: raised on tet diet, then held as adults on tet diet for n days, as indicated.

Example 9

LA670 in *Ceratitis Capitata*

Figure 13:
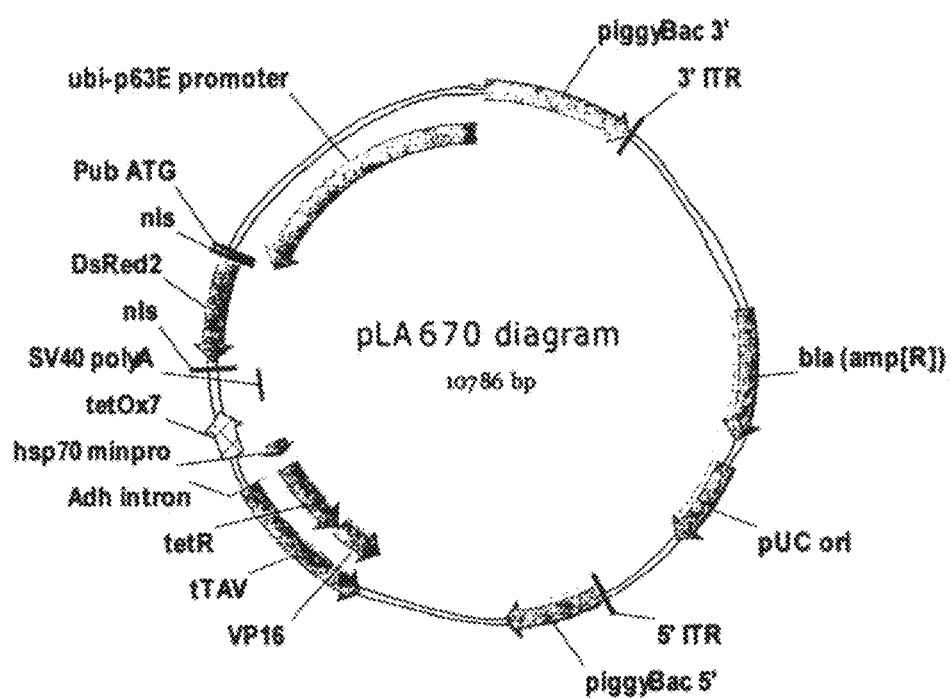
FIG. 13 is a schematic diagram of pLA670.

We obtained a single transgenic line of medfly by transformation with pLA670, a construct which closely resembles pLA656. This plasmid is illustrated in accompanying FIG. 13, and is SEQ ID NO. 23.

However, this transgenic line gave a significant number of adult transgenic progeny, even when raised as larvae on diet lacking tetracycline (Table 14). However, this LA670 insertion line does produce a readily detectable amount of tTAV mRNA in the absence of tetracycline, and this is substantially reduced by dietary tetracycline (assessed by qPCR, results shown in Table 13, above). LA670, therefore, represents a useful regulatable source of tTAV with which to drive the expression of tTAV-responsive genes. The difference in phenotype between LA656 and LA670, which are extremely similar in structure, is probably due to position effect, which is the variation in expression of transgenes depending on where they have inserted in the genome. Such variation is also shown by the variation in phenotype and tTAV expression levels between different transgenic lines with the same construct, as shown in Table 13, above. A simple method for obtaining transgenic lines carrying positive feedback constructs with different expression levels and phenotypic consequences is therefore provided, comprising generating a panel of insertion lines and screening for suitable basal and de-repressed expression levels and patterns.

TABLE 14

Effect of tetracycline on the survival of transgenic medfly heterozygous for LA670, and their +/+ siblings

| | Progeny [Tc] (µg/ml) | F/NF pupae | Pupal survival ratio (%) | F male | F female | NF male | NF female | Adult survival ratio (%) |
|---|---|---|---|---|---|---|---|---|
| LA670 | 0 | 182/220 | 83 | 72 | 35 | 102 | 103 | 52 |
| | 100 | 10/8 | 125 | 5 | 3 | 5 | 3 | 100 |

F: fluorescent;
NF: non-fluorescent.

Pupae were collected and scored for fluorescence (column 3), then allowed to eclose. Surviving adults were scored for sex and fluorescence (columns 5-8). From these data on adults, the ratio of fluorescent to non-fluorescent survivors was calculated, presented in column 9 as the percentage of fluorescent adults observed relative to non-fluorescent. It is to be expected that these crosses give, on average, equal numbers of transgenic and non-transgenic individuals; if an equal proportion of transgenic and non-transgenic individuals survived to adulthood, this would give an "adult survival ratio" of 100%.

Figure 14:
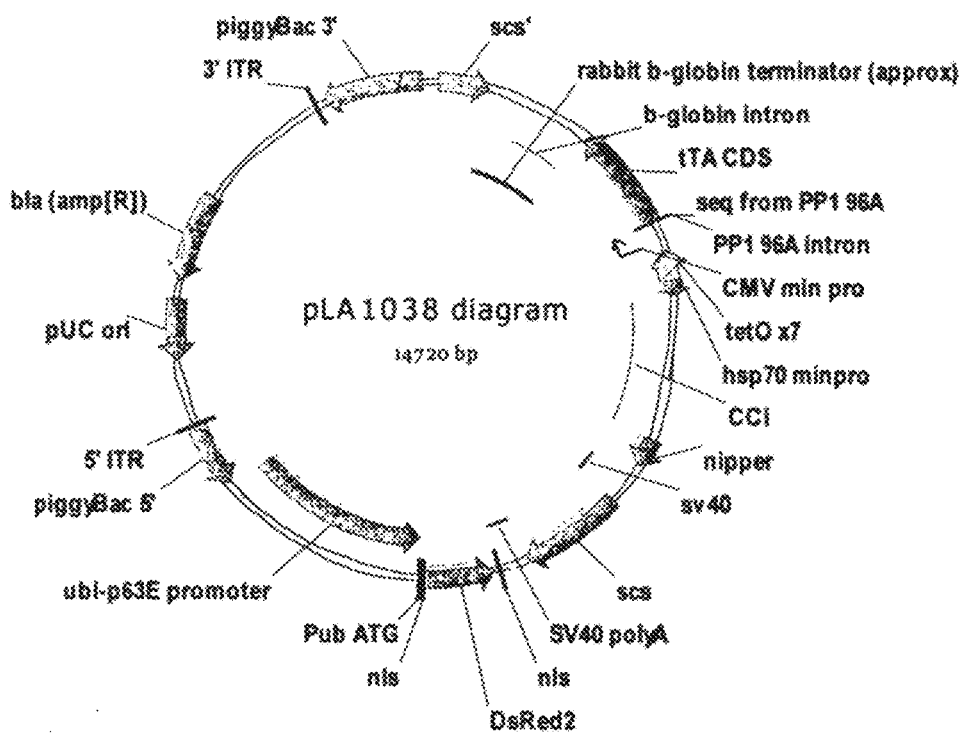
FIG. 14 is a schematic diagram of pLA1038.

We tested the ability of LA670 to drive expression of sequences placed under the transcriptional control of tetO. We analysed the expression of two potential mRNAs from pLA1038 (FIG. 14, SEQ ID NO. 24), which contains two potential tTA-responsive transcription units, divergently transcribed. These are CMV-tTA and hsp70-Cctra-nipper. PCR analysis, with controls, was performed on the expression of these transcription units in the presence and absence of pLA670. Both transcription units are expressed in the presence of pLA670. CMV-tTA is expressed at a lower, but detectable, level in LA1038/+ transgenics in the absence of LA670. hsp70-Cctra-nipper is not detectably expressed in the absence of pLA670, showing that expression is indeed driven by, and dependent on, tTAV supplied by pLA670.

Example 10

LA710 in *Pectinophora Gossypiella*

*Pectinophora gossypiella* (pink bollworm, a lepidopteran) was transformed with LA710 (FIG. 15, SEQ ID NO. 19) by standard methods (Peloquin et al., 2000). Four transgenic lines were recovered. Males of these lines were crossed with females wild type for LA710. Newly hatched larvae were placed in individual 1.7 ml vials with diet, either with or without 7-chlortetracycline (40 μg/ml), and scored for fluorescence. No significant difference was observed in the numbers of transgenics surviving to adulthood relative to numbers of their wild type siblings, either with or without chlortetracycline. We conclude that LA710 does not typically lead to the accumulation of lethal levels of tTAV, even in the absence of dietary chlortetracycline.

We examined the expression of tTAV mRNA in LA710 transgenics by PCR following a reverse transcriptase reaction (rt-PCR). We found that tTAV mRNA was not detectable in chlortetracycline-fed larvae, but was detectable in larvae which had not received chlortetracycline (data not shown). This positive feedback construct LA710, therefore, provides, in these moths, a source of tTAV that can be regulated by supplying dietary chlortetracycline, and for which de-repressed expression, though readily detectable, is non-lethal. We also observed significant variation in the intensity of the band corresponding to tTAV mRNA in samples from different lines.

Example 11

LA1124 in *Pectinophora Gossypiella*

*Pectinophora gossypiella* (pink bollworm, a lepidopteran) was transformed with LA1124 (FIG. 12, SEQ ID NO. 21) by standard methods (Peloquin et al., 2000). A single transgenic line was recovered. Males of this line were crossed with females wild type for LA1124. Newly hatched larvae were placed in individual 1.7 ml vials with diet, either with or without 7-chlortetracycline (40 μg/ml), and scored for fluorescence. These larvae were screened again when they had had time to develop to a late larval stage. All larvae survived, except for the fluorescent (LA1124/+) larvae on diet lacking chlortetracycline, as shown in Table 15, below.

TABLE 15

Pink bollworm: survival from early to late larval stage of LA1124/+ or their wild type siblings, on diet with or without chlortetracycline

| 100 μg/ml chlortetracycline | | 0 μg/ml chlortetracycline | |
|---|---|---|---|
| LA1124/+ | Wild-type | LA1124/+ | Wild-type |
| 3 (0 dead) | 11 (0 dead) | 8 (8 dead) | 7 (0 dead) |

We examined the expression of tTAV mRNA in LA1124 pink bollworm by PCR following a reverse transcriptase reaction (rt-PCR). We found that tTAV mRNA was readily detectable in chlortetracycline-fed larvae, but considerably elevated in larvae which had not received chlortetracycline (data not shown). The significant basal expression of tTAV mRNA in this construct is probably due to the inclusion in LA1124 of the hr enhancer, which was included for this reason. Comparison of the structure and function of LA1124 with that of LA710 clearly illustrates that basal and maximum levels of the gene product can readily be selected by appropriate modification of the expression construct, this principle being demonstrated, here, by regulating levels of expression of a tTAV-dependent RNA (in this case the tTAV mRNA).

Example 12

Sex-Specific Expression Using Positive Feedback

It is preferred to control, by design, the expression of tTAV from a positive feedback construct, so that it can be differentially expressed in different tissues, or different developmental stages, or different sexes, for example. One application for this is in genetic sexing, in which a sexual dimorphism is induced between the two sexes and this is used as a basis for separating the two sexes. In the context of the Sterile Insect Technique, e.g. for medfly, this preferably means killing the females, most preferably at an early stage in their development. No early-acting female-specific promoters are known for medfly, which limits the potential of the two-component repressible dominant lethal system exemplified for *Drosophila* using promoters or enhancers from yolk protein genes (Heinrich and Scott, 2000; Thomas et al., 2000). It would clearly be advantageous to be able to combine the beneficial characteristics of a conditional positive feedback system with a mechanism conferring female specificity.

We, therefore, modified a non-sex-specific positive feedback construct by inserting a sex-specific intronic region from Cctra, the medfly homologue of the *Drosophila melanogaster* gene transformer (Pane et al., 2002). The sex-specific splicing of Cctra is illustrated diagrammatically in FIG. 16, which is adapted from (Pane et al., 2002) supra. FIG. 16 shows the genomic organisation of the medfly tra gene. The top line represents the genomic Cctra locus. Exons are shown as blocks; aug marks the shared start codon. The alternate splice junctions are marked i. Putative tra/tra-2 binding sites are marked with arrowheads. Transcript F1, the only one to encode functional Cctra protein, is specific to females. Transcripts M1 and M2 are found in both males and females.

Three main transcripts are produced: M1, M2 and F1. Transcript F1 is found only in females, and is the only one to encode full-length, functional Cctra protein. Transcripts M1 and M2 are found in both males and females, and include additional exonic sequence, which inserts one or more stop codons relative to transcript F1, leading to truncation of the open reading frame.

We inserted the Cctra intron into the open reading frame of tTAV, so that excision by splicing of the complete intron, in the manner of transcript F1, would reconstitute an intact tTAV coding region, but splicing in the manner of either M1 or M2 would result in a truncated protein incapable of acting as a transcriptional enhancer. The resulting plasmid, pLA1188 (FIG. 17, SEQ ID NO. 22), was injected into medfly embryos. Surviving larvae were recovered, and extracts from these larvae were analysed by rt-PCR to determine the splicing pattern of the tTAV transcript.

Female larvae yielded PCR products corresponding to the expected sizes that would result from splicing in the pattern of the endogenous Cctra gene, in other words corresponding to splicing in the M1, M2 and F1 patterns. These data indicate that the Cctra intron can splice correctly in a heterologous context and, therefore, provides a suitable method for introducing sex-specificity into a positive feedback construct. Furthermore, since tra function is conserved across a wide phylogenetic range (Saccone et al., 2002), and other sex-specific introns are known, e.g. in the *Drosophila melanogaster* gene double-sex (dsx), which is also well conserved, this provides a general method for manipulating the expression of genes. It will be apparent to the person skilled in the art that such manipulations can alternatively, or additionally, be applied to other genes responsive to a transcriptional activator, so that sex-specific expression of a target gene can be achieved by combining non-sex-specific expression of a transcriptional activator with sex-specific expression, e.g. through splicing, of a functional RNA under the transcriptional control of the transcriptional activator. Furthermore, it will also be apparent that this provides a simple mechanism for differential expression of two, or more, different target genes, or gene products, such that one, or one group, is expressed in both sexes and the other, or other group, in only one sex. This is illustrated for medfly in FIG. 18.

The primers used were:

```
                                        (SEQ ID NO. 12)
Tra(tTAV)Seq+: 5'-CCTGCCAGGACTCGCCTTCC;
and (SEQ ID NO. 13)
Tra(tTAV)Seq-: 5'-GTCATCAACTCCGCGTTGGAGC.
```

RT-PCR products of ~600 and ~200 bp were produced when cDNA derived from female medflies 1 and 2 was used as a template, representing "male" (M1 and M2) and female-specific (F1) spliced forms of mRNA respectively (data not shown). The ~200 bp product could have been produced due to contamination with tTAV DNA—the female spliced form completely removes the Cctra intron an so leads to a PCR product that is identical to that which would be obtained from any of several tTAV-containing plasmids or samples handled in the same laboratory. The ~600 bp band, in contrast, retains ~400 bp of Cctra sequence and is diagnostic of correct splicing of the construct.

In another experiment (data not shown), expression of transcripts from LA1038 in response to tTAV from LA670 was analysed by gel chromatography (data not shown), using:

A: rt-PCR for expression of CMV-tTA from LA1038 in extracts from LA1038/+, LA670/+ double heterozygotes;

B: rt-PCR for expression of hsp70-Cctra-nipper in extracts from LA1038/+, LA670/+ double heterozygotes; and C: rt-PCR for expression of CMV-tTA from LA1038 in extracts from LA1038/+ heterozygotes without LA670.

All flies were raised in the absence of dietary tetracycline. In A and C, two bands were present between 200 bp and 400 bp and represent cDNA from spliced mRNA (lower molecular weight band) and genomic DNA or cDNA from unspliced message (higher molecular weight band) respectively. In B, a band at approximately 200 bp represents cDNA from mRNA spliced in the pattern of the Cctra female-specific F1 transcript, an upper band of approximately 1500 bp representing genomic DNA or cDNA from unspliced message, and bands of intermediate size representing cDNA spliced in the pattern of the Cctra non-sex-specific M1 and M2 transcripts, or non-specific bands.

Primer sequences used were:

```
hsp70-Cctra-nipper:
NIP: 5'-CATCGATGCCCAGCATTGAGATG
and

HSP: 5'-CAAGCAAAGTGAACACGTCGCTAAGCGAAAGCTA;

CMV-tTA: CMV: 5'-GCCATCCACGCTGTTTTGACCTCCATAG
and

TTA: 5'-GCCAATACAATGTAGGCTGCTCTACAC.
```

These data (not shown) demonstrate that the hsp-Cctra-nipper section of LA1038 is shown to be correctly spliced in the female form in 6/6 females, and in the male form in 6/6 males.

Transformer

Example 13

*Ceratitis Capitata* Tra Intron

We have prepared an insertion of a Cctra intron cassette into a synthetic open reading frame (ORF). Two versions of this splice correctly in Medfly, in other words the splicing of the Cctra intron cassette faithfully recapitulates what it would normally do in the context of the endogenous Cctra gene. This is to produce 3 (major or only) splice variants in females, one of which is female-specific (called F1), while the other two are found in both males and females (called M1 and M2). Since each of the non-sex-specific transcripts contain additional exonic material with stop codons, we have also arranged this so that only the female splice variant produces functional protein.

Each of these constructs (LA3077 and LA3097) has the Cctra intron flanked by TG and GT (to give 5' . . . TG¦intron¦GT . . . 3'. An older construct, which does not work perfectly, is LA1188. LA1188 is quite well characterized—splicing is exactly as above except that an additional 4 nucleotides are removed. The intron is in the context 5' . . . TGGCAC¦intron¦GT . . . 3'; splicing removes an additional 4 bases, i.e. 5' . . . TG¦GCACintron¦GT . . . 3' (FIG. 33).

In all cases the intron is invariant, and is simply the complete Cctra intron sequence. As is normal for introns, it begins GT and ends AG. Almost all introns start with GT, so the use of the rare alternative GC in LA1188 is surprising [GC-AG introns are a known alternative—in one large-scale survey, 0.5% of all introns were reported to use GC-AG (Burset et al., 2001), though this may be an underestimate, particularly for alternatively spliced introns, of which perhaps 5% might use GC-AG (Thanaraj and Clark, 2001)].

RT-PCR analysis was performed on LA3077, (a positive feedback construct with the CcTRA intron in the tTAV open reading frame). Transformed adult flies of both sexes were reared on diet substantially free of tetracycline ("off tetracycline") for 7 days. Flies were then collected for RNA extraction and RT PCR using primers (HSP—SEQ ID NO. 104 and VP16 SEQ ID NO. 105) were used to analyse the splicing pattern of the CcTRA intron (FIG. 34). In two female samples we found the correct splice pattern of the Cctra (776 bp, corresponding to precise removal of the Cctra intron) and saw no such band in males.

We found that LA3077 and LA3097 correspondingly gave repressible female-specific lethality. LA3077 was tested phenotypically through crossing flies heterozygous for LA3077 to wild type, on and off tetracycline. Female lethality ranged from 50 to 70%. LA3097 (a modified version of LA3077 whereby the Cctra intron immediately follows the start codon in the tTAV ORF), demonstrated a much higher level of female specific lethality, peaking at 100% (FIG. 35). The Cctra intron was also inserted in tTAV2 at the same position as LA3097, in construct LA3233, and this gave a similar phenotypic result as LA3097 (FIG. 35).

We have also prepared transformants of LA3077 in Drosophila. Phenotypically, the construct works perfectly, which is to say it is a highly effective female-specific lethal. However, sequencing of the splice variants of one of these insertions has shown that the splicing of this construct in Drosophila is not quite the same as it is in Medfly (SEQ ID NO. 57). The critical transcript, the female-specific one, is the same in both, but at least one of the non-sex-specific transcripts is different. It still incorporates extra exonic sequence, with stop codons, but the splice junctions are not quite the same (FIG. 36). This observation is extremely important in that it shows that this method (regulation of gene expression by use of alternatively spliced introns) can be used across quite a wide phylogenetic range.

A simple test to determine whether an as yet uncharacterized exonic splice regulator (such as enhancers and suppressors) may be modifying the function of the alternatively spliced intron, could include making the construct and introducing it into a target tissue, then examining its splice pattern. In many cases this will not require germline transformation, so the test can be quite rapid, for instance by transient expression in suitable tissue culture cells or in vivo. For instance, in vivo testing in insects could be achieved by delivering the DNA by microinjection. However, as the skilled person will appreciate, microinjection coupled with electroporation, or electroporation, chemical transformation, ballistic methods, for instance, have all been used in a number of various contexts and such methods of plasmid introduction and protein expression therefrom are will known in the art.

We have also recently made, and have obtained transgenics with, the Cctra intron in a different gene (LA3014) (all the above examples are in tTAV). LA3014 contains a ubiquitin-reaper$^{KR}$ fusion downstream of a Cctra intron. Phenotypic data (FIG. 35) shows that LA3014 transgenic Medfly gave repressible female-specific lethality. RT-PCR analysis on RNA extracted from adult males and females raised off tetracycline, using primers (HSP, SEQ ID NO 74) and ReaperKR (SEQ ID NO. 75), demonstrate that correct splicing was occurring in females (508 bp band) and no such band was found in males (FIG. 37). LA3166 is another construct with the Cctra intron placed inside the ubiquitin coding region fused to reaper$^{KR}$, but placed in a different position in ubiquitin. LA3166 also produces a dominant repressible female-specific lethal effect in Medfly (FIG. 35).

We have also recently made, and have obtained transgenics with, 'intron-only' Cctra-based constructs with the intron in a different gene (all the above examples are in tTAV or one of its variants, i.e. tTAV2 or tTAV3). These constructs work as predicted. This is an important result, thus showing that there are not essential exonic sequences in Cctra that we have simply duplicated (in function, if not necessarily in sequence) by chance, in tTAV. We also have ubi-rpr$^{KR}$ constructs of this type (LA3014 and LA3166), which also validates the ubiquitin fusion method described above.

In order to demonstrate the phylogenetic range of the Cctra intron we generated transgenic LA3097 and LA3233 Anastrepha ludens. LA3097 and LA3233 were selected for injection into Anastrepha ludens as they demonstrated the best female specific lethality in Ceratitis capitata (see Example 13). Phenotypic data was generated for 4 independent LA3097 lines and 1 LA3233 line (see FIG. 38). Female specific lethality was generally somewhat lower in Anastrepha ludens when compared to C. capitata but reached 100% in one line.

Anastrepha ludens transformed with LA3097 and raised on tetracycline until eclosion were isolated and maintained off tetracycline for 7 days. RNA was then extracted and RT-PCR analysis was performed using primers HSP (SEQ ID NO. 76) and TETRR1 (SEQ ID NO. 77). The correct female specific (F1-like) splice pattern was observed RNA isolated from in females (348 bp) but not from males demonstrating the function of the Cctra intron in a different species (FIG. 39)

The brightest male band and the female specific band were purified and precipitated for sequencing. The female specific transcript was found to be correctly spliced in Mexfly females as expected for LA3097:

LA3097: AGCCACCATG ☐☐ GT. . .intron. . .AG ☐
GTCAGCCGCC

Example 14

Bactocera Zonata Tra Intron

We isolated the tra intron from Bactocera zonata (B. zonata) (SEQ ID NO. 58) using primers ROSA1 (SEQ ID NO. 78), ROSA2 (SEQ ID NO. 79), and ROSA3 (SEQ ID NO. 80).

These primer sequences were designed based on conserved coding sequence of Ceratitis capitata and Bactrocera oleae tra homologs. Using ROSA2 and ROSA3 or ROSA1 and ROSA3 as primers, the tra intron and its flanking coding region were amplified from Bactrocera zonata genomic DNA. Then we used these PCR products as a template and amplified the tra intron fragment to make the construct-LA3376 (FIG. 31 and SEQ ID NO. 55). The primers (BZNHE—SEQ ID NO. 81 and BZR—SEQ ID NO. 82) were used for making the constructs; these primers contain additional sequences for cloning purposes. The Bztra intron in LA3376 is cloned into the ORF of tTAV3 and also of reaper$^{KR}$. Medfly transformants were generated and RNA extracted from male and female flies.

RT-PCR was then performed on both the reaper$^{KR}$ (HB—SEQ ID NO. 83) and Reaper KR—SEQ ID NO. 84) and tTAV3 (SRY—SEQ ID NO. 85) and AV3F—SEQ ID NO. 86) splice. The expected fragments of 200 bp for reaper$^{KR}$ and 670 bp for tTAV3, corresponding to splicing in a pattern equivalent to the F1 transcript of Cctra (Pane et al., 2002), were generated in females (FIG. 40).

Example 15

Isolation and Splicing of the *Ceratitis Rosa* (*C. Rosa*, Natal Fruit Fly) Tra Intron Primers ROSA2 (SEQ ID NO. 87) and ROSA3 (SEQ ID NO. 88) were designed based on conserved coding sequence of *Ceratitis capitata* and *Bactrocera oleae*. Using ROSA2 and ROSA3 as primers, the tra intron and its flanking coding region were amplified from *Ceratitis rosa* genomic DNA (SEQ ID NO. 59). We then used the PCR products as a template and amplified the tra intron fragment to make constructs. The primers (CRNHE—SEQ ID NO 89 and CRR SEQ ID NO 90) were used during the construction of LA3242 (SEQ ID NO. 56 and FIG. 32. LA3242 contains the *C. rosa* intron at the 5' end of the reaper$^{KR}$ ORF. *Ceratitis capitata* embryos were injected with DNA of LA3242, injected embryos were raised to adulthood on a diet substantially free of tetracycline. RNA was extracted from adult males and females; this was used as a template for RT PCR using primers HB (SEQ ID NO. 91) and ReaperKR (SEQ ID NO. 92). The expected female-specific splice band (200 bp), corresponding to splicing in the equivalent pattern to that of transcript F1 of Cctra, was observed in females and not males (FIG. 41).
Double-Sex Example 16

*Bombyx Mori* Dsx in PBW

The sequence of a *Bombyx mori* (silk moth) homolog of *Drosophila* Dsx (Bmdsx) has been previously described and a male- and a female-specific splice product have been identified (Suzuki et al, 2001). Both males and females use the same 3' polyA, and there are two female specific exons. One paper has suggested that the sex-specific splicing is not dependent on tra/tra2, in other words even though the pattern looks the same, the underlying mechanism may be different (Suzuki et al., 2001), though their data, principally the lack of recognisable tra-tra2 binding sites, however, is not compelling. In addition, a *B. mori* dsx mini-gene construct (containing exonic sequence and truncated intronic sequence) has been transformed into *B. mori* and the germline transformants show sex-specific splicing (Funaguma et al., 2005).

We have generated a Bmdsx minigene based on the sequence used in the Funaguma et al paper, with some significant changes, and injected this into the moth Pink Bollworm to ascertain if one can obtain sex-specific splicing in a divergent species. The mini-gene construct we generated does not included exon 1, which is present in both males and females. In addition, we removed the intron between exon 3 and 4 (the two female specific exons), included a heterologous sequence (containing multiple cloning sites, MCS), used the Hr5-IE1 enhancer/promoter sequence from the baculovirus AcNPV and used a 3' transcriptional termination sequence derived from SV40 (see FIG. 42 for a schematic). The individual exon/flanking intron fragments used were amplified and recombined together by PCR and ligated into a construct carrying a Hr5/IE1 enhancer promoter fragment and SV40 3'UTR (FIG. 22 and SEQ ID NO. 22).

LA3435 was injected into pink bollworm (*Pectinophora gossypiella*) embryos. First instar larvae were collected after 5-7 days and analysed individually by RT-PCR (using primers IE1 transcr—SEQ ID NO. 93 and SV40-RT-P2—SEQ ID NO. 94) to determine if BMdsx can undergo male and female specific splicing (FIG. 43). Our analysis detected the male specific band (predicted to be 442 bp) in 4 samples (Lanes 1, 2, 3 and 4) and the female specific band (predicted to be 612 bp) in 1 sample (Lane 5).

The correct splicing of *B. mori* dsx in PBW demonstrates that we can achieve (have achieved) sex-specific expression of a heterologous sequence (here, the MCS) in a Lepidopteran by utilizing an alternative splicing system. Furthermore, since this splicing system was derived from a heterologous species, this suggests that such constructs might work over a wide phylogenetic range. However, the identification of alternative splicing systems in the species of interest is also envisioned, and methods for identifying such alternative splicing systems are provided herein or will be known to the person skilled in the art. By providing a MCS in our Example (see FIG. 42), the expression of a sequence of interest, for example a coding region for a protein of interest could readily be achieved by inserting said sequence. If said sequence encoded a suitable protein, a sex-specific phenotype, for example conditional sex-specific lethality, could thereby be introduced, for example into pink bollworm.

Example 17

Isolation of Codling Moth Dsx

The dsx gene from Codling moth (*Cydia pomonella*) was isolated by performing 3' RACE using primers which were based on sequence alignments from *B. oleae, B. tyroni, C. capitata, D. melanogaster, B. mori*, and *A. gambiae*. RNA was isolated from a male and female codling moth and 3' RACE, to generate cDNA, was performed using the TT7T25 primer (SEQ ID NO. 95).

PCR was performed using the primers ds1c (SEQ ID NO. 96) and TT7 (SEQ ID NO. 97). Two rounds of nested PCR were then performed on the product of the first PCR using the primers codling2a (SEQ ID NO. 98) and TT7 (SEQ ID NO. 99) and the product of the second round of PCR using Codling2b (SEQ ID NO. 100) and TT7. The isolated male and female specific sequences share sequence similarity to previously isolated dsx homologues (Male—SEQ ID NO. 43 and Female—SEQ ID NO. 42).

Example 18

Isolation of PBW Dsx

The dsx gene from pink bollworm was isolated by performing 3' RACE using primers which were based on sequence alignments from *B. oleae, B. tyroni, C. capitata, D. melanogaster, B. mori*, and *A. gambiae*. RNA was isolated from a male and female codling moth and 3' RACE, to generate cDNA, was performed using TT7T25 (sequence defined herein). PCR was performed using the primers Pbwdsx2 (SEQ ID NO. 101) and TT7 (SEQ ID NO. 102). Nested PCR was then performed on the product of the first PCR using the primers Pbwdsx3 (SEQ ID NO. 103) and TT7. Three female specific sequences were isolated: PBWdsx-F1 (SEQ ID NO. 40), PBWdsx-F2 (FIG. 10), and PBWdsx-F3 (SEQ ID NO. 71) and one male specific sequence (SEQ ID NO. 42). The isolated male and female specific sequences share sequence similarity to previously isolated dsx homologues.

Example 19

Dsx in *Anopheles Gambiae*

Figure 44:
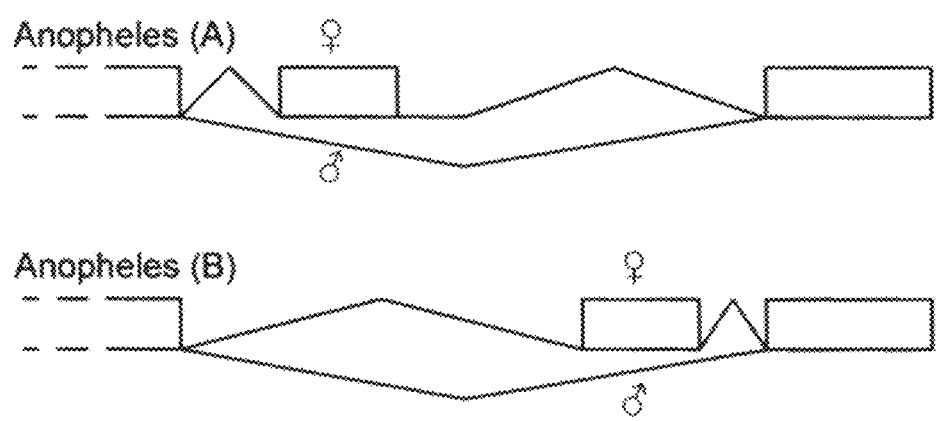
Figure 43:
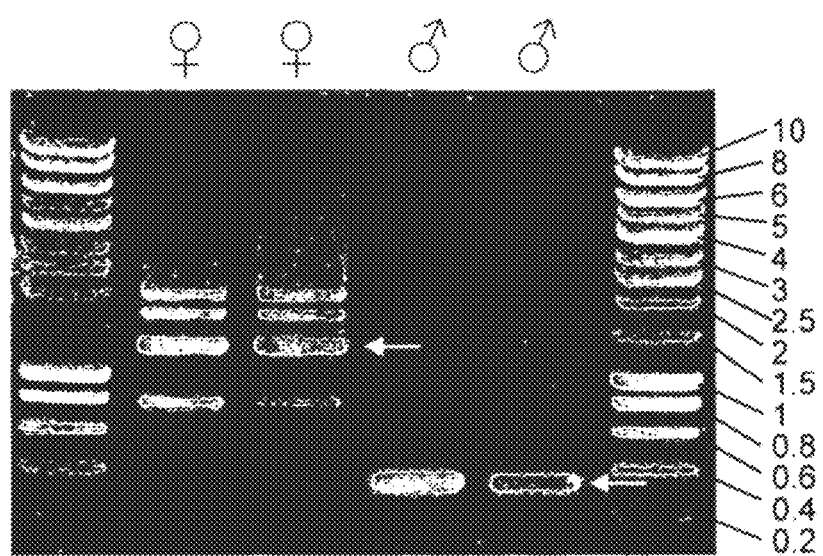

The sequence of the dsx gene of *Anopheles gambiae* has previously been described (Scali et al 2005). However, when we have tried to repeat the work described in the paper we find that there are some differences in the splicing that occurs. When we tried to repeat the amplification of the female specific transcript using primers designed from the mRNA sequence (Accession; AY903308 for female coding sequence and AY903307 for male coding sequence), the amplification failed. However, when Scali and colleagues showed that there was a shared exon, which had previously not been described, we designed primers to amplify the entire dsx transcript and gene. Using these primers and primers designed from genomic DNA sequence (Accession; GI:19611767) we find that the splicing of the female transcript is different from that described by Scali et al 2005 (FIG. 44). The transcript showed that the female exon was in a different position. There are several explanations for these differences, but the most likely are either some sort of strain difference in the *Anopheles* that we used to get the data from, or the published sequence is not from *Anopheles gambiae*, or there is more than one female isoform as shown for *Stegomyia aegypti* in Example 20.

We have also successfully used primers, designed around our version of the *Anopheles gambiae* dsx splicing, that are able to distinguish between males and females of *Anopheles gambiae* (FIG. 45). This provides good evidence that the system will be functional as a sex-specific splicing mechanism when fused to a protein of interest, such as tTAV or a killer.

The *Anopheles gambiae* dsx gene that we have isolated from genomic DNA, which has several changes in nucleotide sequence compared to the reported genomic sequence, was cloned into LA3359 (SEQ ID NO. 47) and LA3433 (SEQ ID NO. 48), schematics can be found in FIG. 23 and FIG. 24, respectively.

Example 20

Dsx in *Stegomyia Aegypti*

The splicing of the gene appears to be similar to *Anopheles gambiae* dsx (Scali et al 2005). The *Stegomyia aegypti* dsx gene is illustrated diagrammatically in FIG. 47 or 48. A male-specific transcript (M1) is produced which does not include exons 5a or 5b. Two female specific splice variants (F1 and F2) have the following structure; F1 comprises exons 1-4, 5a, 6 and 7 but not 5b, F2 comprises exons 1-4 and 5b (FIG. 46). In addition, a further transcript (C1) is present in both males and females; this comprises exons 1-4 and 7, but not exons 5a, 5b or 6.

The splicing of the gene appears to be similar to *Anopheles gambiae* dsx (Scali et al 2005). The *Stegomyia aegypti* dsx gene is illustrated diagrammatically in FIG. 47 or 48.

Actin 4

Example 21

*Stegomyia Aegypti* Actin-4 Gene

One way to get sex-, tissue- and stage-specific expression of a gene of interest is to link it with the *Stegomyia aegypti* Actin-4 (AeAct-4) gene. This gene is only expressed in the developing flight muscles of female *Stegomyia aegypti* (Munoz et al 2004). They used in-situ hybridisation to an RNA to detect the expression profile of AeAct-4. We have taken a fragment of the *Stegomyia aegypti* Actin-4 gene, comprising a putative promoter region, an alternatively spliced intron, and a section of 5' untranslated region (UTR) and placed it in front of sequence coding for tTAV (FIG. 49) to test the function of the sex specific splicing when fused to tTAV.

We integrated LA1172 into the *Stegomyia aegypti* genome using piggyBac. Two independent lines were generated (lines 2 and 8). Both of these lines show the correct splicing of the Actin-4-tTAV gene (FIGS. 50 and 51). The Actin-4 promoter and alternatively spliced intron can therefore be used successfully to provide sex-, tissue- and stage-specific splicing of a gene of interest in *Stegomyia aegypti*.

REFERENCES PART 1

Alphey, L. (2002). Re-engineering the Sterile Insect Technique. Insect Biochem Mol Biol 32, 1243-1247.

Alphey, L., and Andreasen, M. H. (2002). Dominant lethality and insect population control. Mol Biochem Parasitol 121, 173-178.

Alphey, L., Beard, B., Billingsley, P., Coetzee, M., Crisanti, A., Curtis, C. F., Eggleston, P., Godfray, C., Hemingway, J., Jacobs-Lorena, M., et al. (2002). Malaria control with genetically modified vectors. Science 298, 119-121.

Baron, U., and Bujard, H. (2000). Tet repressor-based system for regulated gene expression in eukaryotic cells: principles and advances. Meth Enzymol 327.

Baron, U., Gossen, M., and Bujard, H. (1997). Tetracycline-controlled transcription in eukaryotes: novel transactivators with graded transactivation potential. Nucl Acids Res 25, 2723-2729.

Bello, B., Resendez-Perez, D., and Gehring, W. (1998). Spatial and temporal targeting of gene expression in *Drosophila* by means of a tetracycline-dependent transactivator system. Development 125, 2193-2202.

Benedict, M., and Robinson, A. (2003). The first releases of transgenic mosquitoes: an argument for the sterile insect technique. Trends Parasitol 19, 349-355.

Bennett, D., Szoor, B., Gross, S., Vereshchagina, N., and Alphey, L. (2003). Ectopic expression of inhibitors of Protein Phosphatase type 1 (PP1) can be used to analyse roles of PP1 in *Drosophila* development. Genetics 164, 235-245.

Berger, S. L., Cress, W. D., Cress, A., Triezenberg, S. J., and Guarente, L. (1990). Selective inhibition of activated but not basal transcription by the acidic activation domain of VP16: evidence for transcriptional adaptors. Cell 61, 1199-1208.

Berghammer, A. J., Klingler, M., and Wimmer, E. A. (1999). A universal marker for transgenic insects. Nature 402, 370-371.

Brand, A., Manoukian, A., and Perrimon, N. (1994). Ectopic expression in *Drosophila*. Meth Cell Biol 44, 635-654.

Catteruccia, F., Nolan, T., Loukeris, T., Blass, C., Savakis, C., Kafatos, F., and Crisanti, A. (2000). Stable germline transformation of the malaria mosquito *Anopheles stephensi*. Nature 405, 959-962.

Coates, C., Jasinskiene, N., Miyashiro, L., and James, A. (1998). Mariner transposition and transformation of the yellow fever mosquito, *Aedes aegypti*. Proc Natl Acad Sci USA 95, 3748-3751.

Damke, H., Gossen, M., Freundlieb, S., Bujard, H., and Schmid, S. (1995). Tightly regulated and inducible expression of dominant interfering dynamin mutant in stably transformed HeLa cells. Meth Enz 257, 209-220.

Fussenegger, M. (2001). The impact of mammalian gene regulation concepts on functional genomic research, metabolic engineering, and advanced gene therapies. Biotechnol Prog 17, 1-51.

Fussenegger, M., Mazur, X., and Bailey, J. (1998a). pTRIDENT, a novel vector family for tricistronic expression in mammalian cells. Biotech Bioeng 57, 1-10.

Fussenegger, M., Moser, S., and Bailey, J. (1998b). pQuattro vectors allow one-step transfection and auto-selection of quattrocistronic artificial mammalian operons. Cytotechnology 28, 229-235.

Gebauer, F., Merendino, L., Hentze, M. W., and Valcarcel, J. (1998). The *Drosophila* splicing regulator sex-lethal directly inhibits translation of male-specific-lethal 2 mRNA. RNA 4, 142-150.

Gill, G., and Ptashne, M. (1988). Negative effect of the transcriptional activator GAL4. Nature 334, 721-724.

Gossen, M., Bonin, A., Freundlieb, S., and Bujard, H. (1994). Inducible gene expression systems for higher eukaryotic cells. Curr Opin Biotechnol 5, 516-520.

Gossen, M., and Bujard, H. (1992). Tight control of gene expression in mammalian cells by tetracycline-responsive promoters. Proc Natl Acad Sci USA 89, 5547-5551.

Handler, A. (2002). Use of the piggyBac transposon for germ-line transformation of insects. Insect Biochem Mol Biol 32, 1211-1220.

Handler, A., and James, A. (2000). Insect transgenesis: methods and applications (Boca Raton, CRC Press).

Heinrich, J., and Scott, M. (2000). A repressible female-specific lethal genetic system for making transgenic insect strains suitable for a sterile-release program. Proc Nat'l Acad Sci (USA) 97, 8229-8232.

Horn, C., Schmid, B., Pogoda, F., and Wimmer, E. (2002). Fluorescent transformation markers for insect transgenesis. Insect Biochem Mol Biol 32, 1221-1235.

Jasinskiene, N., Coates, C., Benedict, M., Cornel, A., Rafferty, C., James, A., and Collins, F. (1998). Stable transformation of the yellow fever mosquito, *Aedes aegypti*, with the Hermes element from the housefly. Proc Natl Acad Sci USA 95, 3743-3747.

Kelley, R. L., Solovyeva, I., Lyman, L. M., Richman, R., Solovyev, V., and Kuroda, M. I. (1995). Expression of msl-2 causes assembly of dosage compensation regulators on the X chromosomes and female lethality in *Drosophila*. Cell 81, 867-877.

Lobo, N., Hua-Van, A., Li, X., Nolen, B., and Fraser, M. (2002). Germ line transformation of the yellow fever mosquito, *Aedes aegypti*, mediated by transpositional insertion of a piggyBac vector. Insect Molecular Biology 11, 133-139.

Lozovsky, E., Nurminsky, D., Wimmer, E., and Hartl, D. (2002). Unexpected stability of mariner transgenes in *Drosophila*. Genetics 160, 527-535.

Matsuo, T., Takahashi, K., Kondo, S., Kaibuchi, K., and Yamamoto, D. (1997). Regulation of cone cell formation by Canoe and Ras in the developing *Drosophila* eye. Development 124, 2671-2680.

McCombs, S., and Saul, S. (1995). Translocation-based genetic sexing system for the oriental fruit-fly (Diptera, Tephritidae) based on pupal color dimorphism. Ann Ent Soc Am 88, 695-698.

Moreira, L., Wang, J., Collins, F., and Jacobs-Lorena, M. (2004). Fitness of anopheline mosquitoes expressing transgenes that inhibit *Plasmodium* development. Genetics 166, 1337-1341.

Pane, A., Salvemini, M., Delli Bovi, P., Polito, C., and Saccone, G. (2002). The transformer gene in *Ceratitis capitata* provides a genetic basis for selecting and remembering the sexual fate. Development 129, 3715-3725.

Parker, L., Gross, S., Beullens, M., Bollen, M., Bennett, D., and Alphey, L. (2002). Functional interaction between NIPP1 and PP1 in *Drosophila*: lethality of over-expression of NIPP1 in flies and rescue by the over-expression of PP1. Biochem J 368, 789-797.

Peloquin, J. J., Thibault, S. T., Staten, R., and Miller, T. A. (2000). Germ-line transformation of pink bollworm (Lepidoptera: gelechiidae) mediated by the piggyBac transposable element. Insect Mol Biol 9, 323-333.

Perera, O., Harrell, R., and Handler, A. (2002). Germ-line transformation of the South American malaria vector, *Anopheles albimanus*, with a piggyBac-EGFP tranposon vector is routine and highly efficient. Insect Molecular Biology 11, 291-297.

Pinkerton, A., Michel, K., O'Brochta, D., and Atkinson, P. (2000). Green fluorescent protein as a genetic marker in transgenic *Aedes aegypti*. Insect Molecular Biology 9, 1-10.

Reichhart, J., and Ferrandon, D. (1998). Green balancers. *Drosophila* Information Service 81, 201-202.

Rorth, P. (1998). Gal4 in the *Drosophila* female germline. Mech Dev 78, 113-118.

Saccone, G., Pane, A., and Polito, C. (2002). Sex determination in flies, fruitfles and butterflies. Genetica 116, 15-23.

Salghetti, S., Caudy, A., Chenoweth, J., and Tansey, W. (2001). Regulation of transcriptional activation domain function by ubiquitin. Science 293, 1651-1653.

Scott, M., Heinrich, J., and Li, X. (2004). Progress towards the development of a transgenic strain of the Australian sheep blowfly (*Lucilia cuprina*) suitable for a male-only sterile release program. Insect Biochem Mol Biol 34, 185-192.

Shockett, P., Difilippantonio, M., Hellman, N., and Schatz, D. (1995). A modified tetracycline-regulated system provides autoregulatory, inducible gene expression in cultured cells and transgenic mice. Proc Nat'l Acad Sci (USA) 92, 6522-6526.

Stebbins, M., and Yin, J. (2001). Adaptable doxycycline-regulated gene expression systems for *Drosophila*. Gene 270, 103-111.

Thomas, D., Donnelly, C., Wood, R., and Alphey, L. (2000). Insect population control using a dominant, repressible, lethal genetic system. Science 287, 2474-2476.

Varshaysky, A. (2000). Ubiquitin fusion technique and its descendants. Meth Enz 327.

REFERENCES, PART 2

Allen M L, Christensen B M. Related 2004 Flight muscle-specific expression of act88F: GFP in transgenic *Culex quinquefasciatus* Say (Diptera: Culicidae). Parasitol Int. 53(4)307-14.

Bennett D, Szoor B, Gross S, Vereshchagina N, Alphey L. 2003 Ectopic expression of inhibitors of protein phosphatase type 1 (PP1) can be used to analyze roles of PP1 in *Drosophila* development. Genetics. 164(1):235-45.

Black, D. (2003). Mechanisms of alternative pre-messenger RNA splicing. Annu Rev Biochem 72, 291-336.

Burset, M., Seledtsov, I., and Solovyev, V. (2001). SpliceDB: database of canonical and non-canonical splice sites in mammalian genomes. Nucleic Acids Research 29, 255-259.

Caceres J F, Kornblihtt A R. 2002 Alternative splicing: multiple control mechanisms and involvement in human disease. Trends Genet. 18(4)186-93.

Cande C, Cecconi F, Dessen P, Kroemer G. 2002 Apoptosis-inducing factor (AIF): key to the conserved caspase-independent pathways of cell death? J Cell Sci. 115(24): 4727-34.

Cartegni, L., Chew, S., and Krainer, A. (2002). Listening to silence and understanding nonsense: exonic mutations that affect splicing. Nature Reviews Genetics 3, 285-298.

Clark, F., and Thanaraj, T. (2002). Categorization and characterization of transcript-confirmed constitutively and alternatively spliced introns and exons from human. Human Molecular Genetics 11, 451-464.

Funaguma, S., Suzuki, M., Tamura, T., and Shimada, T. (2005). The Bmdsx transgene including trimmed introns is sex-specifically spliced in tissues of the silkworm, *Bombyx mori*. J Insect Sci 5, 17.

George, E. L., Ober, M. B. and Emerson Jr, C. P. (1989). Functional domains of the *Drosophila melanogaster* muscle myosin heavy-chain gene are encoded by alternatively spliced exons. Mol. Cell Biol. 9:2957-2974.

Graveley B R. 2001 Alternative splicing: increasing diversity in the proteomic world. Trends Genet. 17(2)100-7.

Hammes, A., Guo, J. K., Lutsch, G., Leheste, J. R., Landrock, D., Zeigler, U., Gubler, M. C. and Schedl, A. (2001). Two splice variants of the Wilms' Tumour 1 gene have distinct functions during sex determination and nephron formation. Cell 106:319-329.

Hastings, G. A. and Emerson Jr, C. P (1991). Myosin functional domains encoded by alternative exons are expressed in specific thoracic muscles of *Drosophila*. J. Cell Biol. 114: 263-276.

Hedley, M. L. and Maniatis (1991). Sex-specific splicing and polyadenylation of dsx pre-mRNA requires a sequence that binds specifically to a tra-2 protein in vivo. Cell 65:579-586.

Heinrich J. C. and Scott M. J. 2000 A repressible female-specific lethal genetic system for making transgenic insect strains suitable for a sterile-release program PNAS 97 (15): 8229-8232

Horn C, Wimmer E A. 2003 A transgene-based, embryo-specific lethality system for insect pest management. Nat Biotechnol. 21(1):64-70.

Hoshijima, K. K, Inoue, L., Higuchi, I., Sakamoto, H. and Shimura, Y. (1991). Control of doublesex alternative splicing by transformer and transformer-2 in *Drosophila*. Science 252:833-836.

Huang, Q., Deveraux, Q. L., Maeda, S., Salvesen, G. S., Stennicke, H. R., Hammock, B. D. and Reed, J. C. (2002). Evolutionary conservation of apoptosis mechanisms: Lepidopteran and baculoviral inhibitor of apoptosis proteins are inhibitor of mammalian caspase-9. Agricultural Sciences 97(4):1427-1432.

Ito, Y., Hirochicka, H. and Kurata, N. (2002). Organ-specific alternative transcripts of KNOX family class 2 homeobox genes of rice. Gene 288:41-47.

Johnson J M, Castle J, Garrett-Engele P, Kan Z, Loerch P M, Armour C D, Santos R, Schadt E E, Stoughton R, Shoemaker D D. 2003 Genome-wide survey of human alternative pre-mRNA splicing with exon junction microarrays. Science. 302(5653):2141-4.

Jurica M S, Moore M J. 2003 Pre-mRNA splicing: awash in a sea of proteins. Mol Cell. 12(1):5-14.

Kazzaz J A, Rozek C E. 1989 Tissue-specific expression of the alternately processed *Drosophila* myosin heavy-chain messenger RNAs. Dev Biol. 133(2):550-61.

Maniatis, T., and Tasic, B. (2002). Alternative pre-mRNA splicing and proteome expansion in metazoans. Nature 418, 236-243.

Muñoz, D., Jimenez, A., Marinotti, O., and James, A. (2004). The AeAct-4 gene is expressed in the developing flight muscles of females *Aedes aegypti*. Insect Molecular Biology 13, 563-568.

Nishiyama, R., Mizuno, H., Okada, S., Yamaguchi, T., Takenaka, M., Fukuzawa, H. and Ohyama, K. (1999). Two mRNA species encoding calcium-dependent protein kinases are differentially expressed in sexual organs of *Marchantia polymorpha* through alternative splicing. Plant Cell Physiol. 40(2):205-212.

Nishiyama, R., Yamato, K. T., Miura, K., Sakida, M., Okada, S., Kono, K., Takahama, M., Sone, T., Takenaka, M., Fukuzawa, H. and Ohyama, K. (2000). Comparison of expressed sequence tags from male and female sexual organs of *Marchantia polymorpha*. DNA Res. 7:165-174.

Olson, M. R., Holley, C. L., Ji Yoo, S., Huh, J. R, Hay, B. A. and Kornbluth, S. (2003). Reaper is regulated by IAP-mediated Ubiquitination. J. Biol. Chem., 278(6): 4028-4034.

Olson, M. R., Holley, C. L., Gan, E. C., Colon-Ramos, D. A., Kaplan, B. and Kornbluth, S. (2003). A GH3-like domain in reaper is required for mitochondrial localization and induction of IAP degradation. J. Biol. Chem. 278(45): 44758-44768.

Pan, Q., Shai, O., Misquitta, C., Zhang, W., Saltzman, A., Mohammad, N., Babak, T., Siu, H., Hughes, T., Morris, Q., et al. (2004). Revealing global regulatory features of mammalian alternative splicing using a quantitative microarray platform. Mol Cell 16, 929-941.

Pane, A., Salvemini, M., Delli Bovi, P., Polito, C., and Saccone, G. (2002). The transformer gene in *Ceratitis capitata* provides a genetic basis for selecting and remembering the sexual fate. Development 129, 3715-3725.

Park, J., Parisky, K., Celotto, A., Reenan, R., and Graveley, B. (2004). Identification of alternative splicing regulators by RNA interference in *Drosophila*. Proc Nat'l Acad Sci (USA) 101, 15974-15979.

Parker L, Gross S, Beullens M, Bollen M, Bennett D, Alphey L. 2002 Functional interaction between nuclear inhibitor of protein phosphatase type 1 (NIPP1) and protein phosphatase type 1 (PP1) in *Drosophila*: consequences of over-expression of NIPP1 in flies and suppression by co-expression of PP1. Biochem J. 368(3): 789-97.

Raphael, K. A., Whyard, S., Shearman, D., An, X. and Frommer, M. (2004). *Bactrocera tyroni* and closely related pest-tephritids-molecular analysis and prospects for transgenic control strategies. Insect Biochem. Mol. Biol. 34:167-176.

Ryner, L. and Baker, B. S. (1991). Regulation of doublesex pre-mRNA processing occurs by 3'-splice site activation. Genes Dev. 5:2071-2085.

Saccone, G., Pane, A., and Polito, C. (2002). Sex determination in flies, fruitflies and butterflies. Genetica 116, 15-23.

Scali, C., Catteruccia, F., Li, Q., and Crisanti, A. (2005). Identification of sex-specific transcripts of the *Anopheles gambiae* doublesex gene. J Exp Biol 208, 3701-3709.

Scott, M., Heinrich, J., and Li, X. (2004). Progress towards the development of a transgenic strain of the Australian sheep blowfly (*Lucilia cuprina*) suitable for a male-only sterile release program. Insect Biochem Mol Biol 34, 185-192.

Seo, S-J., Cheon, H-M., Sun, J., Sappington, T. W. and Raikhel, A. S. (2003). Tissue- and stage-specific expression of two lipophorin receptor variants with seven and eight ligand-binding repeats in the adult mosquito. J. Biol. Chem. 278(43):41954-41962.

Siebel C W, Fresco L D, Rio D C. 1992 The mechanism of somatic inhibition of Drosophila P-element pre-mRNA splicing: multiprotein complexes at an exon pseudo-5' splice site control U1 snRNP binding. Genes Dev. 6(8): 1386-401.

Shivikrupa, Singh., R and Swarup, G. (1999). Identification of a novel splice variant of C3G which shows tissue-specific expression. DNA Cell Biol. 18: 701-708.

Smith, C., and Valcarcel, J. (2000). Alternative pre-mRNA splicing: the logic of combinatorial control. Trends Biochem Sci 25, 381-388.

Stoss, O., Stoilov, P., Hartmann, A. M., Nayler, O., and Stamm, S. (1999). The in vivo minigene approach to analyze tissue-specific splicing. Brain Research Protocols 4, 383-394.

Stoss, O., Olbrich, M, Hartmann, A. M., Konig, H., Memmott, J., Andreadis, A and Stamm, S. (2001). The STAR/GSG family protein rSLM-2 regulates the selection of alternative splice sites. J. Biol. Chem. 276(12):8665-8673.

Streuli, M. and Saito, H. (1989). Regulation of tissue-specific alternative splicing: exon-specific cis-elements govern the splicing of leukocyte common antigen pre-mRNA. EMBO J. 8(3): 787-796.

Suzuki, M., Ohbayashi, F., Mita, K., and Shimada, T. (2001). The mechanism of sex-specific splicing at the doublesex gene is different between Drosophila melanogaster and Bombyx mori. Insect Biochem Mol Biol 31, 1201-1211.

Thanaraj, T., and Clark, F. (2001). Human GC-AG alternative intron isoforms with weak donor sites show enhanced consensus at acceptor exon positions. Nucleic Acids Research 29, 2581-2593.

Thanaraj, T., Stamm, S., Clark, F., Reithoven, J., Le Texier, V., and Muilu, J. (2004). ASD: the Alternative Splicing Database. Nucleic Acids Research 32, D64-D69.

Varshaysky, A. (2000). Ubiquitin fusion technique and its descendants. Meth Enz 327.

Venables, J. (2002). Alternative splicing in the testes. Curr Opin Genet Dev 12, 615-619.

Venables J P. 2004 Aberrant and alternative splicing in cancer. Cancer Res. 64(21):7647-54.

Vernooy, S. Y., Copeland, J., Ghaboosi, N., Griffin, E. E., Yoo, S. J. and Hay, B. A. (2000). J. Cell Biol. 150(2): F69-F75.

White, K., Tahoaglu, E. and Steller, H. (1996). Cell killing by the Drosophila gene reaper. Science 271 (5250): 805-807.

Wing, J. P., Zhou, L., Schwartz, L. M. and Nambu, J. R. (2001) Distinct cell killing properties of the Drosophila reaper, head involution defective, and grim genes. Cell Death Diffn 5(11): 930-939

Yali Chiu A., and Pin Ouyang, A. B., (2006). Loss of Pnn expression attenuates expression levels of SR family splicing factors and modulates alternative pre-mRNA splicing in vivo. Bioch. Biophys. Res. Comm.341:663-671.

Yoshimura, K., Yabuta, Y., Ishikawa, T. and Shigeoka, S. (2002). Idenitification of a cis element for tissue-specific alternative splicing of chloroplast Ascorbate Peroxidase pre-mRNA in higher plants. J. Biol. Chem 277 (43): 40623-40632.

---

The invention claimed is:

1. A gene expression system comprising a coding sequence to be expressed in an organism, a promoter operably linked thereto, and an intronic splice control sequence,
    wherein the intronic splice control sequence is flanked on its 5' end by a guanine (G) nucleotide, and, in cooperation with a spliceosome, mediates alternative splicing of RNA transcripts of the coding sequence, the mediation being selected from at least one of the group consisting of sex specific, developmental stage specific, germline specific, and tissue specific mediation,
    wherein the coding sequence is not a sequence associated with or linked to the intronic splice control sequence in a native context,
    wherein the intronic splice control sequence is derived from Actin-4, dsx, or tra, and
    wherein the coding sequence comprises a sequence encoding a protein having a lethal, deleterious, or sterilizing effect.

2. The gene expression system of claim 1, wherein the coding sequence comprises a sequence encoding a marker.

3. The gene expression system of claim 1, wherein the coding sequence comprises a sequence encoding an apoptosis-inducing factor.

4. The gene expression system of claim 3, wherein the apoptosis-inducing factor is selected from the group consisting of apoptosis-inducing factor (AIF), an AIF homolog, Hid, and Reaper (Rpr).

5. The gene expression system of claim 1, wherein the coding sequence comprises a sequence encoding Nipp1, Nipp1Dm, or nipper.

6. The gene expression system of claim 1, wherein the coding sequence comprises a sequence encoding a transcriptional transactivator protein.

7. The gene expression system of claim 6, further comprising a binding sequence for the transcriptional transactivator protein.

8. The gene expression system of claim 1, wherein the coding sequence comprises a sequence encoding tTA or a functional variant or mutant thereof.

9. The gene expression system of claim 8, wherein the tTA or functional variant or mutant is selected from the group consisting of tTAV (SEQ ID NO. 34), tTAV2 (SEQ ID NO. 36), and tTAV3 (SEQ ID NO. 38).

10. The gene expression system of claim 1, wherein the coding sequence comprises a sequence encoding a ubiquitin or a functional variant or mutant thereof.

11. The gene expression system of claim 1, wherein the intronic splice control sequence is flanked on its 3' end by a Guanine (G) nucleotide.

12. The gene expression system of claim 1, further comprising an enhancer.

13. The gene expression system of claim 1, wherein the organism is an insect, arthropod, mammal, fish, or plant.

14. The gene expression system of claim 13, wherein the organism is an insect, and the insect is of the Order Diptera, Calliphoridae, Lepidoptera, or Coleoptera.

15. The gene expression system of claim 14, wherein the insect is of the Order Diptera and is selected from the group consisting of Medfly (*Ceratitis capitata*), Mexfly (*Anastrepha ludens*), Oriental fruit fly (*Bactrocera dorsalis*), Olive fruit fly (*Bactrocera oleae*), Melon fly (*Bactrocera cucurbitae*), Natal fruit fly (*Ceratitis rosa*), Cherry fruit fly (*Rhagoletis cerasi*), Queensland fruit fly (*Bactrocera tyroni*), Peach fruit fly (*Bactrocera zonata*), Caribbean fruit fly (*Anastrepha suspensa*), and West Indian fruit fly (*Anastrepha oblique*).

16. The gene expression system of claim 1, wherein the intronic splice control sequence is derived from AaActin-4

(*Aedes aegypti* Actin-4), Aadsx (*Aedes aegypti* dsx), Agdsx (*Anopheles gambiae* dsx), Bmdsx (*Bombyx mori* dsx), *Cydia pomonella* dsx, *Pectinophora gossypiella* dsx, Bztra (*Bactrocera zonata* tra), Cctra (*Ceratitis rosa* tra), or Cctra (*Ceratitis capitata* tra).

17. The gene expression system of claim 1, wherein the intronic splice control sequence is derived from dsx and the expression system comprises a sequence selected from the group consisting of SEQ ID NO. 40, SEQ ID NO. 41, SEQ ID NO. 42, SEQ ID NO. 43, SEQ ID NO. 44, SEQ ID NO. 45, and SEQ ID NO. 71.

18. The gene expression system of claim 1, wherein the intronic splice control sequence is derived from dsx and the expression system comprises a construct selected from the group consisting of pLA3435 (SEQ ID NO. 46), pLA3359 (SEQ ID NO. 47), and pLA3433 (SEQ ID NO. 48).

19. The gene expression system of claim 1, wherein the intronic splice control sequence is derived from Cctra (*Ceratitis capitata* tra) and the expression system comprises a construct selected from the group consisting of pLA1188 (SEQ ID NO. 49), pLA3077 (SEQ ID NO. 50), pLA3097 (SEQ ID NO. 51), pLA3233 (SEQ ID NO. 52), pLA3014 (SEQ ID NO 53), pLA3166 (SEQ ID NO. 54), and pLA3242 (SEQ ID NO. 56).

20. The gene expression system of claim 1, wherein the intronic splice control sequence is derived from Bztra (*Bactrocera zonata* tra) and the expression system comprises a construct according to pLA3376 (SEQ ID NO. 55).

21. A construct selected from the group consisting of: pLA3435 (SEQ ID NO. 46), pLA3359 (SEQ ID NO. 47), pLA3433 (SEQ ID NO. 48), pLA1188 (SEQ ID NO. 49), pLA3077 (SEQ ID NO. 50), pLA3097 (SEQ ID NO. 51), pLA3233 (SEQ ID NO. 52), pLA3014 (SEQ ID NO 53), pLA3166 (SEQ ID NO. 54), pLA3376 (SEQ ID NO. 55), pLA3242 (SEQ ID NO. 56), and pLA1172 (SEQ ID NO 106).

22. The gene expression system of claim 1, wherein the intronic splice control sequence is derived from Actin-4.

23. The gene expression system of claim 1, wherein the intronic splice control sequence is derived from dsx.

24. The gene expression system of claim 23, wherein the intronic splice control sequence is derived from Aadsx (*Aedes aegypti* dsx), Agdsx (*Anopheles gambiae* dsx), Bmdsx (*Bombyx mori* dsx), *Cydia pomonella* dsx, or *Pectinophora gossypiella* dsx.

25. The gene expression system of claim 1, wherein the intronic splice control sequence is derived from tra.

26. The gene expression system of claim 25, wherein the intronic splice control sequence is derived from Bztra (*Bactrocera zonata* tra), Cctra (*Ceratitis rosa* tra), or Cctra (*Ceratitis capitata* tra).

* * * * *